(12) United States Patent
Saavedra et al.

(10) Patent No.: US 8,329,726 B2
(45) Date of Patent: Dec. 11, 2012

(54) INHIBITORS OF VEGF RECEPTOR AND HGF RECEPTOR SIGNALING

(75) Inventors: Oscar Mario Saavedra, Montreal (CA); Stephen William Claridge, Montreal (CA); Lijie Zhan, Montreal (CA); Franck Raeppel, Montreal (CA); Arkadii Vaisburg, Kirkland (CA); Stephane Raeppel, Peirrefonds (CA); Michael Mannion, Cuthbert (CA); Frederic Gaudette, Verdun (CA); Ljubomir Isakovic, Montreal (CA); Marie-Claude Granger, Laprairie (CA); Naomy Bernstein, Cote Saint-Luc (CA)

(73) Assignee: MethylGene Inc., Montreal (CA)

( * ) Notice: Subject to any disclaimer, the term of this patent is extended or adjusted under 35 U.S.C. 154(b) by 0 days.

(21) Appl. No.: 13/314,362

(22) Filed: Dec. 8, 2011

(65) Prior Publication Data

US 2012/0083482 A1 Apr. 5, 2012

Related U.S. Application Data

(62) Division of application No. 11/438,133, filed on May 19, 2006, now Pat. No. 8,093,264.

(60) Provisional application No. 60/683,036, filed on May 20, 2005, provisional application No. 60/754,902, filed on Dec. 29, 2005, provisional application No. 60/785,054, filed on Mar. 22, 2006.

(51) Int. Cl.
*A01N 43/42* (2006.01)
*A61K 31/44* (2006.01)

(52) U.S. Cl. ............ 514/301; 514/210.18; 514/249; 514/253.04; 514/233.8; 546/114

(58) Field of Classification Search ............ 514/301, 514/210.18, 249, 253.04, 233.8; 546/114
See application file for complete search history.

(56) References Cited

U.S. PATENT DOCUMENTS

| | | | |
|---|---|---|---|
| 5,578,716 A | 11/1996 | Szyf et al. | |
| 5,919,772 A | 7/1999 | Szyf et al. | |
| 6,020,318 A | 2/2000 | Szyf et al. | |
| 6,054,439 A | 4/2000 | Szyf et al. | |
| 6,066,625 A | 5/2000 | MacLeod | |
| 6,184,211 B1 | 2/2001 | Szyf | |
| 6,221,849 B1 | 4/2001 | Szyf et al. | |
| 6,232,320 B1 | 5/2001 | Stewart et al. | |
| 6,268,137 B1 | 7/2001 | Szyf et al. | |
| 6,448,261 B1 | 9/2002 | Bakthavatchalam et al. | |
| 6,492,383 B1 | 12/2002 | Munchhof et al. | |
| 6,506,735 B1 | 1/2003 | MacLeod | |
| 6,833,456 B2 | 12/2004 | Romines, III et al. | |
| 6,897,220 B2 | 5/2005 | Delorme et al. | |
| 6,953,783 B1 | 10/2005 | Besterman et al. | |
| 6,995,171 B2 | 2/2006 | Autry et al. | |
| 2002/0004511 A1 | 1/2002 | Luzzio et al. | |
| 2004/0138251 A1 | 7/2004 | Boschelli et al. | |
| 2005/0116028 A1 | 6/2005 | Cohen et al. | |
| 2005/0239820 A1 | 10/2005 | Borzilleri et al. | |
| 2005/0245547 A1 | 11/2005 | Kim et al. | |
| 2005/0288282 A1 | 12/2005 | Delorme et al. | |
| 2005/0288290 A1 | 12/2005 | Borzilleri et al. | |
| 2006/0004006 A1 | 1/2006 | Borzilleri et al. | |
| 2006/0058298 A1 | 3/2006 | Delorme et al. | |
| 2006/0074056 A1 | 4/2006 | Vaisburg et al. | 514/151 |
| 2006/0211695 A1 | 9/2006 | Borzilleri et al. | |
| 2007/0197537 A1 | 8/2007 | Blake et al. | |
| 2008/0207647 A1 | 8/2008 | Hoelzemann et al. | |
| 2008/0312232 A1 | 12/2008 | Kim et al. | 514/235.2 |
| 2009/0137580 A1 | 5/2009 | Imamura et al. | |

FOREIGN PATENT DOCUMENTS

| | | |
|---|---|---|
| WO | WO99/24440 | 5/1999 |
| WO | WO99/62908 | 12/1999 |
| WO | WO00/56738 | 9/2000 |
| WO | WO 00/71703 | 11/2000 |
| WO | WO00/75145 | 12/2000 |
| WO | WO 01/38322 | 5/2001 |
| WO | WO 01/70675 | 9/2001 |
| WO | WO01/94353 | 12/2001 |
| WO | WO03/000194 | 1/2003 |
| WO | WO03/000688 | 1/2003 |
| WO | WO 03/006652 | 1/2003 |
| WO | WO 03/024448 | 3/2003 |

(Continued)

OTHER PUBLICATIONS

Medicine Net.com—cancer definition 2004.*
Wolff, Manfred E. "Burger's Medicinal Chemistry, 5ed, Part I", John Wiley & Sons, 1995, pp. 975-977.
Banker et al, "Modern Pharmaceutics, 3ed.", Marcel Dekker, New York, 1996, pp. 451 and 596.

(Continued)

*Primary Examiner* — Yong Chu
*Assistant Examiner* — Valerie Rodriguez-Garcia
(74) *Attorney, Agent, or Firm* — Wood, Phillips, Katz, Clark & Mortimer

(57) ABSTRACT

The invention relates to the inhibition of VEGF receptor signaling and HGF receptor signaling. The invention provides compounds of general formula (A)

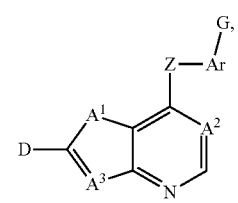

wherein $A^1$ is sulfur, $A^3$ is CH, $A^2$ is CH, D is heterocycle, Z is oxygen, $SO_{0-2}$ or NR, Ar is phenyl and G is not a ring, and methods for inhibiting VEGF receptor signaling and HGF receptor signaling. The invention also provides compositions and methods for treating cell proliferative diseases and conditions.

13 Claims, No Drawings

FOREIGN PATENT DOCUMENTS

| | | |
|---|---|---|
| WO | WO03/074529 | 9/2003 |
| WO | WO 2004/035525 | 4/2004 |
| WO | WO2004/048386 | 6/2004 |
| WO | WO 2004/069823 | 8/2004 |
| WO | WO2005/021554 | 3/2005 |
| WO | WO 2005/030705 | 4/2005 |
| WO | WO2005/073224 | 8/2005 |
| WO | WO 2005/092899 | 10/2005 |
| WO | WO2005/117867 | 12/2005 |
| WO | WO2005/121125 | 12/2005 |
| WO | WO2006/004636 | 1/2006 |
| WO | WO2006/004833 | 1/2006 |
| WO | WO 2006/010264 | 2/2006 |
| WO | WO2006/030266 | 4/2006 |
| WO | WO 2006/078752 | 7/2006 |
| WO | WO2006/104161 | 10/2006 |
| WO | WO2006/116713 | 11/2006 |
| WO | WO2007/072179 | 6/2007 |
| WO | WO2007/107005 | 9/2007 |
| WO | W02008/063202 | 5/2008 |

OTHER PUBLICATIONS

Dörwald, F. Zaragoza. Side Reactions in Organic Synthesis: A Guide to Successful Synthesis Design, Weinheim: Wiley-VCH Verlag GmbH & Co. KGaA, 2005, Preface.

Jordan, V. C. Nature Reviews: Drug Discovery, 2, 2003, pp. 205-213).

Volonterio et al.; "Synthesis of Partially Modified Retro and Retroinverso ψ[NHCH(CF3)]-Peptides"; Org. Lett. 2:1827, 2000.

Volonterio et al.; "Solution/solid-phase synthesis of partically modified retro- ψ [NHCH(CF3)]-peptidyl hydroxamates"; Tet. Lett, 42:3141, 2001.

Black et al.; "Trifluoroethylamines as amide isosteres in inhibitors of cathepsin K"; Bioorg. Med. Chem. Lett., 15:4741, 2005.

Li et al.; "Identification of a Potent and Selective Non-Basic Cathepsin K Inhibitor" Bioorg. Med. Chem. Lett., 16:1985, 2006.

Zanda et al.; "Trifluoromethyl group: an effective xenobiotic function for peptide backbone modificaton"; New J. Chem., 28:1401, 2004.

Quinn et al., J. Clin. Oncology, "Phase II Trial of Temozolomide in Patients with Progressive Low-Grade Glioma", 21(4):646-651 (2003).

Doff et al., "Phase I Clinical Trial of Imexon: A mitochondrial Thiol Oxidant", Proc. Amer. Soc. Clin. Oncology, 23, Abstract 3181 (2004).

Wood et al., Curr. Opin. Pharm., "Past and Future of the Mitotic Spindle as an Oncology Target", 1:370-377 (2001).

Raymond et al., Drugs, "Epidermal Growth Factor Receptor Tyrosine Kinase as a Target for Anticancer Therapy". 60(supp 1): 15-23 (2000).

Harari et al., Oncogene, "Molecular Mechanisms Underlying ErbB2/HER2 Action in Breast Cancer", 19:6102-6114 (2000).

Baselga et al., Drugs, "ZD1839 ('Iressa')[1,2] as an Anticancer Agent", 60(supp. 1): 33-40 (2000).

Pollack et al., J. Pharm. Exp. Ther., "Inhibition of Epidermal Growth Factor Receptor-Associated With Tyrosine Phosphorylation in Human Carcinomas with CP-358,774: Dynamics of Receptor Inhibition in Situ and Antitumor Effects in Athymic Mice", 291(2):739-748 (1999).

Bridges et al., Curr. Med. Chem., "The Rationale and Strategy Used to develop a Series of Highly Potent, Irreversible, Inhibitors of the Epidermal Growth Factor Receptor Family of Tyrosine Kinases", 6:825-843 (1999).

Lackey et al., "The Discovery of a New Anti-Cancer Agent GW2016: A Potent Dual EGFR/ErbB-2 Tyrosine Kinase Inhibitor", 92nd AACR Meeting, New Orleans, Mar. 24-28, Abstract 4582 (2001).

Jani et al., "Discovery and Development of CP-724714, a Selective HER2 Receptor Tyrosine Kinase Inhibitor", Proceedings of the American Society for Clinical Oncology, 23, Abstract 3122 (2004).

Rabindran et al., Cancer Res., "Antitumor Activity of HKI-272, an orally Active, Irreversible Inhibitor of the HER-2 Tyrosine Kinase", 64:3958-3965 (2004).

Greenberger et al., "EKB-569: A new Irreversible Inhibitor of Epidermal Growth Factor Receptor Tyrosine Kinase for the Treatment of Cancer", 11th NCI-EORTC-AACR Syinposiuni of New Drugs in Cancer Therapy, Amsterdam, Nov. 7-10, Abstract 388 (2000).

Oulton et al., "Telomeres, Telomerase, and Cancer: Life on the Edge of Genomic Stability", Curr. Opin. Oncol., 12:74-81 (2000).

Wood et al., Cancer Res. PTK787/ZK 222584, A Novel Potent Inhibitor of Vascular Endothelial Growth Factor Receptor Tyrosine Kinases, Impairs Vascular Endothelial Growth Factor-Induced Responses and Tumor Growth After Oral Administration, 60:2178-2189 (2000).

Demetri et al., Proc. Amer. Soc. Clin. Oncology, SU11248, A Multi-Targeted Tyrosine Kinase Inhibitor, Can overcome Imatinib (IM) Resistance Caused by Diverse Genomic Mechanisms in Patients (pts) With Metastatic Gastrointestinal Stromal Tumor (GIST), 23, Abstract 3001 (2004).

Hennequin et al., "ZD6474: Design, Synthesis and Structure Activity Relationship of a Novel, Orally Active VEGF Receptor Tyrosine Kinase Inhibitor", 92nd AACR Meeting, New Orleans, Mar. 24-28, Abstract 3152 (2001).

Herbst et al., "Targeting the Epidermal Growth Factor Receptor in Non-Small Cell Lung Cancer", Clinical Cancer Research, 9:5813-5824 (2003).

Taguchi et al., "A Novel Orally Active Inhibitor of VEGF Receptor Tyrosine Kinases KRN951: Anti-Angiogenic and Anti-Tumor Activity Against Human Solid Tumors" 95th AACR Meeting, Orlando, Fla., Abstract 2575 (2004).

Beebe et al., "Pharmacological Characterization of CP-547,632, a Novel Vascular Endothelial Growth Factor Receptor-2 Tyrosine Kinase Inhibitor for Cancer Therapy [1]", Cancer Res. 63:7301-7309 (2003).

Roberts et al., Proceedings of the American Association of Cancer Research, "Anti-Angiogenic and Anti-Tumor Activity of a Selective PDGFR Tyrosine Kinase Inhibitor, CP-673,451", 45, Abstract 3989 (2004).

Lee et al., "Durable in Vivo Target Modulation with CHIR258, A Small Molecule Inhibitor of Growth Factor Tyrosine Kinase Receptors, is Associated With Potent Antitumor Efficacy Using Various Dosing Schedules", Proceedings of the American Association of Cancer Research, 45, Abstract 2130 (2004).

Shen et al., Blood, "Effects of MLN519 (CT53518), a Dual Flt3 and Kit Inhibitor, on Normal and Malignant Hematopoiesis", 102, 11, Abstract 476 (2003).

Hennequin et al., Proceedings of the American Associate of Cancer Research, Structure-Activity Relationship, Physicochemical and Pharmacokinetic Properties of AZD2171: A Highly Potent Inhibitor of VEGF Receptor Tyrosine Kinases, 45, Abstract 4539 (2004).

Avruch et al., Recent Prog. Horm, Res., "Ras Activation of the Raf Kinase: Tyrosine Kinase Recruitment of the MAP Kinase Cascade", 56:127-155 (2001).

Lawlor et al., "PKB/Akt: A Key Mediator of Cell Proliferation, Survival and Insulin Responses", J. cell Sci., 114:2903-2910 (2001).

Sebolt-Leopold et al., Proceedings of the American Association of Cancer Research, "The Biological Profile of PD 0325901: A Second Generation Analog of Cl-1040 With Improved Pharmaceutical Potential", 45, Abstract 4003 (2004).

Wallace et al., Proceedings of the American Association of Cancer Research, "Preclinical Development of ARRY-142886, A Potent and Selective MEK Inhibitor", 45, Abstract 3891 (2004).

Ottmann et al., Proceedings of the American Society for Clinical Oncology, "A Phase I, Pharmacokinetic (PK) and Pharmacodynamic (PD) Study of a Novel Histone Deacetylase Inhibitor LAQ824 in Patients with Hematologic Malignancies", 23, Abstract 3024 (2004).

Beck et al., Proceedings of the American Society for Clinical Oncology, "Phase I Pharmacokinetic (PK) and Pharmacodynamic (PD) Study of LBH589A: A Novel Histone Deacetylase Inhibitor", 23, Abstract 3025 (2004).

Ryan et al., Proceedings of the American Association of Cancer Research, "A First Human Trial of an Oral Histone Deacetylase Inhibitor, MS-275, in Advanced Solid Tumor and Lymphoma Patients", 45, Abstract 2452 (2004).

Piekarz et al., Proceedings of the American Society for Clinical Oncology, "Update on the Phase II Trial and Correlative Studies of Depsipeptide in Patients With Cutaneous T-Cell Lymphoma and Relapsed Peripheral T-Cell Lymphoma", 23, Abstract 3028 (2004).

Mackay et al., Proceedings of the American Society for Clinical Oncology, "A Phase II Trial of the Proteosome Inhibitor PS-341 in Patients with Metastatic Colorectal Cancer", 23, Abstract 3109 (2004).
Wu et al., Proceedings of the American Association of Cancer Research, "Effects of the mTOR Inhibitor CCI-779 Used Alone or During Motherapy on Human Prostate Cancer Xenografts", 45, Abstract 3849 (2004).
Danishefsky et al., "A Highly Activated Cyclopropane for Homoconjugate Reactions", JACS, 97:3239-3241 (1975).
A. Janowski, "Penicillins", Chem. Abstracts, 88, Abstract 6873a (1975).
Rigo et al., Tetrahedron Lett., "Reaction of Trimethylsilyl Derivatives With Meldrum's Acid: A New and Easy Monofunction of Malonic Acid", 30(23):3073-3076 (1989).
McCallum et al., Aust. J. Chem., "Reaction of Imidazoles with Cyanogen Bromide: Cyanation at N1 or Bromination at C2?", 52:159-166 (1999).
Begtrup et al., Acta Chem. Scand., "Alkylation, Acylation and Silylation of Azoles", 44:1050-1057 (1990).
Begtrup et al., "Introduction of Substitutes Into 5-Membered AZA-Heteroamatics", Bull. Soc. Chem. Belg., 98(8-9):573-598 (1988).
Ohba et al., Chem. Pharm. Bull., "Preparatory Study for the Synthesis of the Starfish Alkaloid Imbricatine, Syntheses of 5-Arylthio-3-Methyl-L-Histidines", 42(9):1784-1790 (1994).
Ryu et al., Tet. Lett., "Self-Condensation of Activated Malonic Acid half Esters: a Model for the Decarboxylative Claisen Condensation in Polyketide Biosynthesis", 44:7499-7502 (2003).
Tsou et al., J. Med. Chem., "6-Substituted-4-(3-Bromophenylamino)Quinazolines as Putative Irreversible Inhibitors of the Epidermal Growth Factor Receptor (EGFR) and Human Epidermal Growth Factor Receptor (HER-2)Tyrosine Kinases with Enhanced Antitumor Activity", 44:2719-2734 (2001).
Mewshaw et al., J. Med. Chem., New Generation Dopaminergic Agents. 6. Structure- Activity Relationship Studies of a Series of 4-(Aminoethoxy)Indole and 4-(Aminoethoxy)Indolone Derivatives Based on the Newly Discovered 3-Hydroxyphenoxyethylamine $D_2$ Template, 42:2007-2020 (1999).
Mayer et al., J. Med. Chem., "New Substituted 1-(2,3-Dihydrobenzo[1,4]Dioxin-2-ylmethyl)Piperidin-4-yl Derivatives with $\alpha_2$-Adrenoceptor Antagonist Activity", 43:3653-3664 (2000).
Su et al., J. Chem. Res. Synop., "The Preparation of 3-Substituted 1 Chlorocarbonyl-Imidazolidin-2-Ones Using Bis(Trichloromethyl) Carbonate", 9:440-441 (2000).
Drinkuth et al., Eur. J. Org. Chem., "1-Methyl-Azacyclohexa-2,3-Diene(N-β)Borane—Generation and Interception of an Unsymmetrical Isodihydropyridine", 14:2665-2670 (2001).
He et al., Tet. Lett., "A Convenient Synthesis of 1,4-Disubstituted Imidazoles", 45:5529-5532 (2004).
Panosyan et al., Can. J. Chem., "An Efficient Route to 5-Iodo-1-Methylimidazole: Synthesis of Xestomanzamine A", 79:1110-1114 (2001).
Smith et al., J. org. Chem., "Convenient Syntheses of 1,2,3,4-Tetrahydroquinoxalines", 24:205-207 (1959).
Wolfe et al., J. org. Chem., "Simple, Efficient Catalyst System for the Palladium-Catalyzed Amination of Aryl Chlorides, Bromides, and Triflates", 65:1158-1174 (2000).
Klapars et al., J. Am. Chem. Soc., "A General and Efficient Copper Catalyst for the Amidation of Aryl Halides and the N-Arylation of Nitrogen Heterocycles", 123:7727-7729 (2001).
Ragan et al., Org. Proc. Res. Dev., "Cross-Coupling Methods for the Large-Scale Preparation of an Imidazole-Thienopyridine: Synthesis of [2-(3-Methyl-3H-Imidazol-4-yl)-Thieno[3,2-*b*]Pyridin-7-yl]-2(Methyl-1H-Indol-5-yl)-Amine", 7:676-683 (2003).
Harris et al., J. Org. Chem., "Sequential N-Arylation of Primary Amines as a Route to Alkyldiarylamines", 64:6019-6022 (1999).
Remington's Pharmaceuticals Sciences, 19th Edition, ed., A. Gennaro, Mack Publishing Co., Easton, PA, 1990.
Wells et al., Cell Motil Cytoskeleton, "Rho Family GTPases are Activated During HGF-Stimulated Prostate Cancer-Cell Scattering", 62:180-194 (2005).

Miura et al., Urology, "Effects of Hepatocyte Growth Factor on E-Cadherin-Mediated Cell-Cell Adhesion in DU145 Prostate Cancer Cells", 58:1064-1069 (2001).
Nishimura et al., "Regulation of Invasive Potential of Human Prostate Cancer Cell Lines by Hepatocyte Growth Factor", Int. J. Urol., 5:276-281 (1998).
Wang et al., "Potent and Selective Inhibitors of the Met [Hepatocyte Growth Factor/Scatter Factor (HGF/SF) Receptor] Tyrosine Kinase Block HGF/SF-Induced Tumor Cell Growth and Invasion", Mol. Cancer Ther., 2:1085-1092 (2003).
Christensen et al., "A Selective Small Molecule Inhibitor of c-Met Kinase Inhibits c-Met-Dependent Phenotypes In Vitro and Exhibits Cytoreductive Antitumor Activity In Vivo", Cancer Res., 63:7345-7355 (2003).
Fan et al., "Controlling the Vasculature: Angiogenesis, Anti-Angiogenesis, and Vascular Targeting of Gene Therapy", Trends Pharmacol. Sci., 16:57-66 (1995).
Folkman et al., "Angiogenesis in Cancer, Vascular, Rheumatoid and Other Disease", Nat. Med., 1:27-31 (1995).
Jakeman et al., "Developmental Expression of Binding Sites and Messenger Ribonucleic Acid for Vascular Endothelial Growth Factor Suggests a Role for This Protein in Vasculogenesis and Angiogenesis", Endocrinology, 133(2):848-859 (1993).
Connolly et al., "Human Vascular Permeability Factor, Isolation from U937 Cells", J. Biol. Chem., 264(33):20017-20024 (1989).
Plowman, et al., "Receptor Tyrosine Kinases as Targets for Drug Intervention", Drug News Perspect, 7(6):324-339 (1994).
Strawn et al., "Tyrosine Kinases in Disease: Overview of Kinase Inhibitors as Therapeutic Agents and Current Drugs in Clinical Trials", Exp. Opin. Invest. Drugs, 7:553-573 (1998).
Shawver et al., "Receptor Tyrosine Kinases as Targets for Inhibition of Angiogenesis", Drug. Discov. Today, 2(2):50-63 (1997).
DeVries et al., "The FMS-Like Tyrosine Kinase, a Receptor for Vascular Endothelial Growth Factor", Science, 255:989-991 (1992).
Terman et al., "Identification of the KDR Tyrosine Kinase as a Receptor for Vascular Endothelial Cell Growth Factor", Biocehm. Biophys. Res. Commun., 187(3):1579-1586 (1992).
Plate et al., "Vascular Endothelial Growth Factor and Glioma Angiogenesis: Coordinate Induction of VEGF Receptors, Distribution of VEGF Protein and Possible In Vivo Regulatory Mechanisms", Int. J. Cancer, 59:520-529 (1994).
Fuh et al., "Requirements for Binding and Signaling of the Kinase Domain Receptor for Vascular Endothelial Growth Factor", J. Biol. Chem., 273 (18):11197-11204 (1998).
Wheeler-Jones et al., "Vascular Endothelial Growth Factor Stimulates Prostacyclin Production and Activation of Cytosolic Phospholipase $A_2$ in Endothelial Cells Via p42/p44 Mitogen-Activated Protein Kinase", FEBS Lett., 420:28-32 (1997).
Kim et al., "Inhibition of Vascular Endothelial Growth Factor-Induced Angiogenesis Suppresses Tumour Growth In Vivo", Nature (Lond.), 362:841-844 (1993).
Kanai et al., "Anti-Tumour and Anti-Metastatic Effects of Human-Vascular-Endothelial-Growth-Factor-Neutralizing Antibody on Human Colon and Gastric Carcinoma Xenotransplanted Orthotopically Into Nude Mice", Int. J. Cancer., 77:933-936 (1998).
Zhu et al., "Inhibition of Vascular Endothelial Growth Factor-Induced Receptor Activation with Anti-Kinase Insert Domain-Containing Receptor Single Chain Antibodies from a Phage Display Library", Cancer Res., 58:3209-3214 (1998).
Siemeister et al., "An Antagonistic Vascular Endothelial Growth Factor (VEGF) Variant Inhibits VEGF-Stimulated Receptor Autophosphorylation and Proliferation of Human Endothelial Cells", Proc. Natl. Acad. Sci. USA, 95:4625-4629 (1998).
Lin et al., "Inhibition of Tumor Growth by Targeting Tumour Endothelium Using a Soluble Vascular Endothelial Growth Factor Receptor", Cell Growth Differ., 9:49-58 (1998).
Cheng et al., "Suppression of Glioblastoma Angiogenicity and Tumorigenicity by Inhibition of Endogenous Expression of Vascular Endothelial Growth Factor", Proc. Natl. Acad. Sci. USA, 93:8502-8507 (1996).
Millauer et al., "Dominant-Negative Inhibition of Flk-1 Suppresses the Growth of Many Tumour Types In Vivo", Cancer Res., 56:1615-1620 (1996).

Pennacchietti et al, "hypoxia Promotes Invasive Growth by Transcriptional Activation of the MET Protooncogene", Cancer Cell., 3(4):347-361 (2003).

Camps et al., "Fibroblast-Mediated Acceleration of Human Epithelial Tumor Growth In Vivo", proc. Natl. Acad. Sci. USA, 87:75-79 (1990).

Nakamura et al., "Induction of Hepatocyte Growth Factor in Fibroblasts by Tumor-Derived Factors Affects Invasive Growth of Tumor Cells: In Vitro Analysis of Tumor-Stromal Interactions", Cancer Res., 57:3305-3313 (1997).

Bae-Jump et al., "Hepatocyte Growth Factor (HGF) Induces Invasion of Endometrial Carcinoma Cell Lines in Vitro", Gynecol. Oncol., 73:265-272 (1999).

Nakamura et al., "Partial Purification and Characterization of Hepatocyte Growth Factor From Serum of Hepatectomized Rats", Biocehm. Biophys. Res. Commun., 122(3):1450-1459 (1984).

Nakamura et al., "Molecular Cloning and Expression of Human Hepatocyte Growth Factor", Nature, 342:440-443 (1989).

Ebert et al., "Coexpression of the C-Met Proto-Oncogene and Hepatocyte Growth Factor in Human Pancreatic Cancer", Cancer Res., 54:5775-5778 (1994).

DiRenzo et al., "Expression of the Met/HGF Receptor in Normal and Neoplastic Human Tissues", Oncogene, 6:1997-2003 (1991).

DiRenzo et al., "Expression of the Met/Hepatocyte Growth Factor Receptor in Human Pancreatic Cancer", Cancer Res., 55:1129-1138 (1995).

Delehedde et al., "Hepatocyte Growth Factor/Scatter Factor Stimulates Migration of Rat Mammary Fibroblasts Through Both Mitogen-Activated Protein Kinase and Phosphatidylinositol 3-Kinase/Akt Pathways", Eur. J. Biochem., 269:4423-4429 (2001).

Bardelli et al., "Concomitant Activation of Pathways Downstream of Grb2 and PI 3-Kinase is Required for MET-Mediated Metastasis", Oncogene, 18:1139-1146 (1999).

Saucier et al., "The Shc Adaptor Protein is Critical for VEGF Induction by Met/HGF and ErB2 Receptors and for Early Onset of Tumor Angiogenesis", Proc. Natl. Acad. Sci. USA, 101(8):2345-2350 (2004).

The Merck Manual, Eighteenth Ed., 2006.

$13^{th}$ Edition of the Merck Index, 2001.

Goodman and Gilman's The Pharmacological Basis of Therapeutics (Ninth Ed. 1996, McGraw-Hill).

U.S. Appl. No. 11/393,380, filed Mar. 30, 2006.

* cited by examiner

INHIBITORS OF VEGF RECEPTOR AND HGF RECEPTOR SIGNALING

RELATED APPLICATIONS

This application is a divisional of U.S. patent application Ser. No. 11/438,133, filed on May 19, 2006, which claims the benefit of U.S. Provisional Patent Application Ser. No. 60/683,036, filed on May 20, 2005, U.S. Provisional Patent Application Ser. No. 60/754,902, filed on Dec. 29, 2005, and U.S. Provisional Patent Application Ser. No. 60/785,054, filed on Mar. 22, 2006, the contents of which are incorporated herein by reference in their entirety.

BACKGROUND OF THE INVENTION

1. Field of the Invention

This invention relates to the inhibition of VEGF receptor signaling and HGF receptor signaling. More particularly, the invention relates to compounds and methods for the inhibition of VEGF receptor signaling and HGF receptor signaling.

2. Summary of the Related Art

Angiogenesis is an important component of certain normal physiological processes such as embryogenesis and wound healing, but aberrant angiogenesis contributes to some pathological disorders and in particular to tumor growth.[1,2] VEGF-A (vascular endothelial growth factor A) is a key factor promoting neovascularization (angiogenesis) of tumors.[3-7] VEGF induces endothelial cell proliferation and migration by signaling through two high affinity receptors, the fms-like tyrosine kinase receptor, Flt-1, and the kinase insert domain-containing receptor, KDR.[8,9,10] These signaling responses are critically dependent upon receptor dimerization and activation of intrinsic receptor tyrosine kinase (RTK) activity. The binding of VEGF as a disulfide-linked homodimer stimulates receptor dimerization and activation of the RTK domain[11]. The kinase activity autophosphorylates cytoplasmic receptor tyrosine residues, which then serve as binding sites for molecules involved in the propagation of a signaling cascade. Although multiple pathways are likely to be elucidated for both receptors, KDR signaling is most extensively studied, with a mitogenic response suggested to involve ERK-1 and ERK-2 mitogen-activated protein kinases [12].

Disruption of VEGF receptor signaling is a highly attractive therapeutic target in cancer, as angiogenesis is a prerequisite for all solid tumor growth, and that the mature endothelium remains relatively quiescent (with the exception of the female reproductive system and wound healing). A number of experimental approaches to inhibiting VEGF signaling have been examined, including use of neutralizing antibodies[13,14,15], receptor antagonists [16], soluble receptors[17], antisense constructs[18] and dominant-negative strategies[19].

Despite the attractiveness of anti-angiogenic therapy by VEGF inhibition alone, several issues may limit this approach. VEGF expression levels can themselves be elevated by numerous diverse stimuli and perhaps most importantly, the hypoxic state of tumors resulting from VEGFr inhibition, can lead to the induction of factors that themselves promote tumor invasion and metastasis thus, potentially undermining the impact of VEGF inhibitors as cancer therapeutics[20].

The HGF (hepatocyte growth factor) and the HGF receptor, c-met, are implicated in the ability of tumor cells to undermine the activity of VEGF inhibition[20]. HGF derived from either stromal fibroblasts surrounding tumor cells or expressed from the tumor itself has been suggested to play a critical role in tumor angiogenesis, invasion and metastasis[21,22]. For example, invasive growth of certain cancer cells is drastically enhanced by tumor-stromal interactions involving the HGF/c-Met (HGF receptor) pathway[23,24,25]. HGF, which was originally identified as a potent mitogen for hepatocytes[26,27] is primarily secreted from stromal cells, and the secreted HGF can promote motility and invasion of various cancer cells that express c-Met in a paracrine manner[28,29,30]. Binding of HGF to c-Met leads to receptor phosphorylation and activation of Ras/mitogen-activated protein kinase (MAPK) signaling pathway, thereby enhancing malignant behaviors of cancer cells[30,31]. Moreover, stimulation of the HGF/c-met pathway itself can lead to the induction of VEGF expression, itself contributing directly to angiogenic activity[32].

Thus, anti-tumor anti-angiogenic strategies or approaches that target both VEGF/VEGFr signaling and HGF/c-met signaling may circumvent the ability of tumor cells to overcome VEGF inhibition alone and may represent improved cancer therapeutics.

Here we describe small molecules that are potent inhibitors of both the VEGF receptor KDR and the HGF receptor c-met.

BRIEF SUMMARY OF THE INVENTION

The present invention provides new compounds and methods for treating cell proliferative diseases. The compounds of the invention are dual function inhibitors, capable of inhibiting both VEGF and HGF receptor signaling. Accordingly, the invention provides new inhibitors of VEGF receptor signaling and HGF receptor signaling, including the VEGF receptor KDR and the HGF receptor c-met.

In a first aspect, the invention provides compounds of formula A that are useful as inhibitors of VEGF receptor signaling and HGF receptor signaling and, therefore, are useful research tools for the study of the role of VEGF and HGF in both normal and disease states.

In a second aspect, the invention provides compounds of formula B that are useful as inhibitors of VEFG receptor signaling and HGF receptor signaling and, therefore, are useful research tools for the study of the role of VEGF and HGF in both normal and disease states.

In a third aspect, the invention provides compositions comprising a compound that is an inhibitor of VEGF receptor signaling and HUE receptor signaling, or a pharmaceutically acceptable salt thereof, and a pharmaceutically acceptable carrier, excipient, or diluent.

The fourth aspect of the invention provides a method of inhibiting VEGF receptor signaling and HGF receptor signaling, the method comprising contacting the receptor with a compound according to the present invention, or with a composition according to the present invention. Inhibition of VEGF and HGF activity can be in a cell or a multicellular organism. If in a multicellular organism, the method according to this aspect of the invention comprises administering to the organism a compound according to the present invention, or a composition according to the present invention. Preferably the organism is a mammal, more preferably a human.

The foregoing merely summarizes certain aspects of the invention and is not intended to be limiting in nature. These aspects and other aspects and embodiments are described more fully below.

DETAILED DESCRIPTION OF THE PREFERRED EMBODIMENTS

The invention provides compounds and methods for inhibiting the VEGF receptor KDR and the HGF receptor c-met.

The invention also provides compositions and methods for treating cell proliferative diseases and conditions. The patent and scientific literature referred to herein establishes knowledge that is available to those with skill in the art. The issued patents, applications, and references that are cited herein are hereby incorporated by reference to the same extent as if each was specifically and individually indicated to be incorporated by reference. In the case of inconsistencies, the present disclosure will prevail.

For purposes of the present invention, the following definitions will be used (unless expressly stated otherwise):

The terms "inhibitor of VEGF receptor signaling" and "inhibitor of HGF receptor signaling" are used to identify a compound having a structure as defined herein, which is capable of interacting with a HGF receptor and a VEGF receptor and inhibiting the activity of HGF and VEGF. In some preferred embodiments, such reduction of activity is at least about 50%, more preferably at least about 75%, and still more preferably at least about 90%.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g. $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene.) All atoms are understood to have their normal number of valences for bond formation (i.e., 4 for carbon, 3 for N, 2 for O, and 2, 4, or 6 for S, depending on the oxidation state of the S). On occasion a moiety may be defined, for example, as $(A)_a$-B—, wherein a is 0 or 1. In such instances, when a is 0 the moiety is B— and when a is 1 the moiety is A-B—. Also, a number of moieties disclosed herein exist in multiple tautomeric forms, all of which are intended to be encompassed by any given tautomeric structure.

The term "hydrocarbyl" as employed herein refers to a straight, branched, or cyclic alkyl, alkenyl, or alkynyl, each as defined herein. A "$C_0$" hydrocarbyl is used to refer to a covalent bond. Thus, "$C_0$-$C_3$-hydrocarbyl" includes a covalent bond, methyl, ethyl, ethenyl, ethynyl, propyl, propenyl, propynyl, and cyclopropyl.

The term "alkyl" as employed herein refers to straight and branched chain aliphatic groups having from 1 to 12 carbon atoms, preferably 1-8 carbon atoms, and more preferably 1-6 carbon atoms, which is optionally substituted with one, two or three substituents. Preferred alkyl groups include, without limitation, methyl, ethyl, propyl, isopropyl, butyl, isobutyl, sec-butyl, tert-butyl, pentyl, and hexyl. A "$C_0$" alkyl (as in "$C_0$-$C_3$-alkyl") is a covalent bond (like "$C_0$" hydrocarbyl).

The term "alkenyl" as employed herein means an unsaturated straight or branched chain aliphatic group with one or more carbon-carbon double bonds, having from 2 to 12 carbon atoms, preferably 2-8 carbon atoms, and more preferably 2-6 carbon atoms, which is optionally substituted with one, two or three substituents. Preferred alkenyl groups include, without limitation, ethenyl, propenyl, butenyl, pentenyl, and hexenyl.

The term "alkynyl" as employed herein means an unsaturated straight or branched chain aliphatic group with one or more carbon-carbon triple bonds, having from 2 to 12 carbon atoms, preferably 2-8 carbon atoms, and more preferably 2-6 carbon atoms, which is optionally substituted with one, two or three substituents. Preferred alkynyl groups include, without limitation, ethynyl, propynyl, butynyl, pentynyl, and hexynyl.

An "alkylene," "alkenylene," or "alkynylene" group is an alkyl, alkenyl, or alkynyl group, as defined hereinabove, that is positioned between and serves to connect two other chemical groups. Preferred alkylene groups include, without limitation, methylene, ethylene, propylene, and butylene. Preferred alkenylene groups include, without limitation, ethenylene, propenylene, and butenylene. Preferred alkynylene groups include, without limitation, ethynylene, propynylene, and butynylene.

The term "carbocycle" as employed herein is intended to mean an optionally substituted cycloalkyl or aryl moiety. The term "carbocycle" also includes a cycloalkenyl moiety having at least one carbon-carbon double bond.

The term "cycloalkyl" as employed herein includes saturated and partially unsaturated cyclic hydrocarbon groups having 3 to 12 carbons, preferably 1 to 8 carbons, and more preferably 3 to 6 carbons, wherein the cycloalkyl group additionally is optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroalkyl" as employed herein refers to an alkyl group, as defined hereinabove, wherein one or more carbon atoms in the chain are replaced by a heteroatom selected from the group consisting of O, S, NH, N-alkyl, SO, $SO_2$, $SO_2NH$, or $NHSO_2$.

An "aryl" group is a $C_6$-$C_{14}$ aromatic moiety comprising one to three aromatic rings, which is optionally substituted. Preferably, the aryl group is a $C_6$-$C_{10}$ aryl group. Preferred aryl groups include, without limitation, phenyl, naphthyl, anthracenyl, and fluorenyl. An "aralkyl" or "arylalkyl" group comprises an aryl group covalently linked to an alkyl group, either of which may independently be optionally substituted or unsubstituted. Preferably, the aralkyl group is ($C_1$-$C_6$)alk($C_6$-$C_{10}$)aryl, including, without limitation, benzyl, phenethyl, and naphthylmethyl. A "lower arylalkyl" refers to an arylalkyl where the "alkyl" portion of the group has one to six carbons A "heterocyclyl" or "heterocyclic" group is a ring structure having from about 3 to about 12 atoms, wherein one or more atoms are selected from the group consisting of N, O, S, SO, and $SO_2$. The heterocyclic group is optionally substituted on carbon at one or more positions. The heterocyclic group is also independently optionally substituted on nitrogen with alkyl, aryl, aralkyl, alkylcarbonyl, alkylsulfonyl, arylcarbonyl, arylsulfonyl, alkoxycarbonyl, or aralkoxycarbonyl. Preferred heterocyclic groups include, without limitation, epoxy, aziridinyl, tetrahydrofuranyl, pyrrolidinyl, piperidinyl, piperazinyl, thiazolidinyl, oxazolidinyl, oxazolidinonyl, and morpholino. In certain preferred embodiments, the heterocyclic group is fused to an aryl, heteroaryl, or cycloalkyl group. Examples of such fused heterocycles include, without limitation, tetrahydroquinoline and dihydrobenzofuran. Specifically excluded from the scope of this term are compounds where an annular O or S atom is adjacent to another O or S atom.

As used herein, the term "heteroaryl" refers to groups having 5 to 14 ring atoms, preferably 5, 6, 9, or 10 ring atoms; having 6, 10, or 14 π-electrons shared in a cyclic array; and having, in addition to carbon atoms, from one to three heteroatoms per ring selected from the group consisting of N, O, and S. The term "heteroaryl" is also meant to encompass monocyclic and bicyclic groups. For example, a heteroaryl group may be pyrimidinyl, pyridinyl, benzimidazolyl, thienyl, benzothiazolyl, benzofuranyl and indolinyl. A "heteroaralkyl" or "heteroarylalkyl" group comprises a heteroaryl group covalently linked to an alkyl group, either of which is independently optionally substituted or unsubstituted. Preferred heteroalkyl groups comprise a $C_1$-$C_6$ alkyl group and a heteroaryl group having 5, 6, 9, or 10 ring atoms. Specifically excluded from the scope of this term are compounds having adjacent annular O and/or S atoms. Examples of preferred heteroaralkyl groups include pyridylmethyl, pyridylethyl, pyrrolylmethyl, pyrrolylethyl, imidazolylmethyl, imidazolylethyl, thiazolylmethyl, and thiazolylethyl. Specifically excluded from the scope of this term are compounds having adjacent annular O and/or S atoms.

For simplicity, reference to a "$C_n$-$C_m$" heterocyclyl or heteroaryl means a heterocyclyl or heteroaryl having from "n" to "m" annular atoms, where "n" and "m" are integers. Thus, for example, a $C_5$-$C_6$-heterocyclyl is a 5- or 6-membered ring having at least one heteroatom, and includes pyrrolidinyl ($C_5$) and piperidinyl ($C_6$); $C_6$-hetoaryl includes, for example, pyridyl and pyrimidyl.

An "arylene," "heteroarylene," or "heterocyclylene" group is an aryl, heteroaryl, or heterocyclyl group, as defined hereinabove, that is positioned between and serves to connect two other chemical groups.

The term "azolyl" as employed herein is intended to mean a five-membered saturated or unsaturated heterocyclic group containing two or more hetero-atoms, as ring atoms, selected from the group consisting of nitrogen, sulfur and oxygen, wherein at least one of the hetero-atoms is a nitrogen atom. An azolyl group as used in the present invention may be optionally substituted. Preferred azolyl groups include, but are not limited to, optionally substituted imidazolyl, oxazolyl, thiazolyl, pyrazolyl, isoxazolyl, isothiazolyl, 1,3,4-thiadiazolyl, 1,2,4-thiadiazolyl, 1,2,4-oxadiazolyl, and 1,3,4-oxadiazolyl.

A heteroalicyclic group refers specifically to a non-aromatic heterocyclyl radical. A heteroalicyclic may contain unsaturation, but is not aromatic.

A heterocyclylalkyl group refers to a residue in which a heterocyclyl is attached to a parent structure via one of an alkylene, alkylidene, or alkylidyne radical. Examples include (4-methylpiperazin-1-yl)methyl, (morpholin-4-yl)methyl, (pyridine-4-yl)methyl, 2-(oxazolin-2-yl)ethyl, 4-(4-methylpiperazin-1-yl)-2-butenyl, and the like. Both the heterocyclyl and the corresponding alkylene, alkylidene, or alkylidyne radical portion of a heterocyclylalkyl group may be optionally substituted. A "lower heterocyclylalkyl" refers to a heterocyclylalkyl where the "alkyl" portion of the group has one to six carbons.

A heteroalicyclylalkyl group refers specifically to a heterocyclylalkyl where the heterocyclyl portion of the group is non-aromatic.

Preferred heterocyclyls and heteroaryls include, but are not limited to, acridinyl, azocinyl, benzimidazolyl, benzofuranyl, benzothiophenyl, benzoxazolyl, benzthiazolyl, benztriazolyl, pyridotriazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,3,4-triazolyl, and xanthenyl.

As employed herein, when a moiety (e.g., cycloalkyl, hydrocarbyl, aryl, heteroaryl, heterocyclic, urea, etc.) is described as "optionally substituted" it is meant that the group optionally has from one to four, preferably from one to three, more preferably one or two, non-hydrogen substituents. Suitable substituents include, without limitation, halo, hydroxy, oxo an annular —CH— substituted with oxo is —C(O)—) nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Preferred substituents, which are themselves not further substituted (unless expressly stated otherwise) are:

(a) halo, hydroxy, cyano, oxo, carboxy, formyl, nitro, amino, amidino, guanidino, (b) $C_1$-$C_5$ alkyl or alkenyl or arylalkyl imino, carbamoyl, azido, carboxamido, mercapto, hydroxy, hydroxyalkyl, alkylaryl, arylalkyl, $C_1$-$C_8$ alkyl, $C_1$-$C_8$ alkenyl, $C_1$-$C_8$ alkoxy, $C_1$-$C_8$ alkoxycarbonyl, aryloxycarbonyl, $C_2$-$C_8$ acyl, $C_2$-$C_8$ acylamino, $C_1$-$C_8$ alkylthio, arylalkylthio, arylthio, $C_1$-$C_8$ alkylsulfinyl, arylalkylsulfinyl, arylsulfinyl, $C_1$-$C_8$ alkylsulfonyl, arylalkylsulfonyl, arylsulfonyl, $C_0$-$C_6$ N alkyl carbamoyl, $C_2$-$C_{15}$ N,N-dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$ heterocycle, $C_5$-$C_{14}$ heteroaryl, or any of these rings fused or spiro-fused to a cycloalkyl, heterocyclyl, or aryl, wherein each of the foregoing is further optionally substituted with one more moieties listed in (a), above; and (c) —(CH$_2$)$_s$—NR$^{31}$R$^{32}$, wherein s is from 0 (in which case the nitrogen is directly bonded to the moiety that is substituted) to 6, and R$^{31}$ and R$^{32}$ are each independently hydrogen, cyano, oxo, carboxamido, amidino, $C_1$-$C_8$ hydroxyalkyl, $C_1$-$C_3$ alkylaryl, aryl-$C_1$-$C_3$ alkyl, $C_1$-$C_8$ alkyl, $C_1$-$C_8$ alkenyl, $C_1$-$C_8$ alkoxy, $C_1$-$C_8$ alkoxycarbonyl, aryloxycarbonyl, aryl-$C_1$-$C_3$ alkoxycarbonyl, $C_2$-$C_8$ acyl, $C_1$-$C_8$ alkylsulfonyl, arylalkylsulfonyl, arylsulfonyl, aroyl, aryl, cycloalkyl, heterocyclyl, or heteroaryl, wherein each of the foregoing is further optionally substituted with one more moieties listed in (a), above; or R$^{30}$ and R$^{31}$ taken together with the N to which they are attached form a heterocyclyl or heteroaryl, each of which is optionally substituted with from 1 to 3 substituents from (a), above.

Especially preferred substituents on alkyl groups include halogen and hydroxy.

Especially preferred substituents on ring groups, such as aryl, heteroaryl, cycloalkyl and heterocyclyl, include halogen, alkoxy and alkyl.

A "halohydrocarbyl" as employed herein is a hydrocarbyl moiety, in which from one to all hydrogens have been replaced with one or more halo.

The term "halogen" or "halo" as employed herein refers to chlorine, bromine, fluorine, or iodine. As herein employed, the term "acyl" refers to an alkylcarbonyl or arylcarbonyl substituent. The term "acylamino" refers to an amide group attached at the nitrogen atom (i.e., R—CO—NH—). The term "carbamoyl" refers to an amide group attached at the carbonyl carbon atom (i.e., $NH_2$—CO—). The nitrogen atom of an acylamino or carbamoyl substituent is additionally substituted. The term "sulfonamido" refers to a sulfonamide substituent attached by either the sulfur or the nitrogen atom. The term "amino" is meant to include $NH_2$, alkylamino, arylamino, and cyclic amino groups. The term "ureido" as employed herein refers to a substituted or unsubstituted urea moiety.

The term "radical" as employed herein means a chemical moiety comprising one or more unpaired electrons.

A moiety that is substituted is one in which one or more hydrogens have been independently replaced with another chemical substituent. As a non-limiting example, substituted phenyls include 2-fluorophenyl, 3,4-dichlorophenyl, 3-chloro-4-fluoro-phenyl, 2-fluoro-3-propylphenyl. As another non-limiting example, substituted n-octyls include 2,4-dimethyl-5-ethyl-octyl and 3-cyclopentyl-octyl. Included within this definition are methylenes (—$CH_2$—) substituted with oxygen to form carbonyl —CO—).

An "unsubstituted" moiety as defined above (e.g., unsubstituted cycloalkyl, unsubstituted heteroaryl, etc.) means that moiety as defined above that does not have any of the optional substituents for which the definition of the moiety (above) otherwise provides. Thus, for example, while an "aryl" includes phenyl and phenyl substituted with a halo, "unsubstituted aryl" does not include phenyl substituted with a halo.

A saturated or unsaturated three- to eight-membered carbocyclic ring is preferably a four- to seven-membered, more preferably five- or six-membered, saturated or unsaturated carbocyclic ring. Examples of saturated or unsaturated three- to eight-membered carbocyclic rings include phenyl, cyclopropyl, cyclobutyl, cyclopentyl, cyclohexyl, and cycloheptyl.

A saturated or unsaturated three- to eight-membered heterocyclic ring contains at least one heteroatom selected from oxygen, nitrogen, and sulfur atoms. The saturated or unsaturated three- to eight-membered heterocyclic ring preferably contains one or two heteroatoms with the remaining ring-constituting atoms being carbon atoms. The saturated or unsaturated three- to eight-membered heterocyclic ring is preferably a saturated or unsaturated four- to seven-membered heterocyclic ring, more preferably a saturated or unsaturated five- or six-membered heterocyclic ring. Examples of saturated or unsaturated three- to eight-membered heterocyclic groups include thienyl, pyridyl, 1,2,3-triazolyl, imidazolyl, isoxazolyl, pyrazolyl, piperazinyl, piperazino, piperidyl, piperidino, morpholinyl, morpholino, homopiperazinyl, homopiperazino, thiomorpholinyl, thiomorpholino, tetrahydropyrrolyl, and azepanyl.

A saturated or unsaturated carboxylic and heterocyclic group may condense with another saturated or heterocyclic group to form a bicyclic group, preferably a saturated or unsaturated nine- to twelve-membered bicyclic carbocyclic or heterocyclic group. Bicyclic groups include naphthyl, quinolyl, 1,2,3,4-tetrahydroquinolyl, 1,4-benzoxanyl, indanyl, indolyl, and 1,2,3,4-tetrahydronaphthyl.

When a carbocyclic or heterocyclic group is substituted by two $C_{1-6}$ alkyl groups, the two alkyl groups may combine together to form an alkylene chain, preferably a $C_{1-3}$ alkylene chain. Carbocyclic or heterocyclic groups having this crosslinked structure include bicyclo[2.2.2]octanyl and norbornanyl.

The term "therapeutically effective amount" as employed herein is an amount of a compound of the invention, that when administered to a patient, ameliorates a symptom of a disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art.

The term "patient" as employed herein for the purposes of the present invention includes humans and other animals, particularly mammals, and other organisms. Thus the compounds, compositions and methods of the present invention are applicable to both human therapy and veterinary applications. In a preferred embodiment the patient is a mammal, and in a most preferred embodiment the patient is human.

The terms "treating" or "treatment" as used herein covers the treatment of a disease-state in a mammal, which disease-state is characterized by abnormal cellular proliferation, and invasion and includes at least one of: (i) preventing the disease-state from occurring in a mammal, in particular, when such mammal is predisposed to the disease-state but has not yet been diagnosed as having it; (ii) inhibiting the disease-state, i.e., arresting its development; and (iii) relieving the disease-state, i.e., causing regression of the disease-state. In a preferred embodiment of the present invention the mammal is a human. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

Throughout the specification, preferred embodiments of one or more chemical substituents are identified. Also preferred are combinations of preferred embodiments. For example, paragraph [0054] describes preferred embodiments of $R^7$ in the compounds of the present invention and paragraph [0114] describes preferred embodiments of G in the compounds of the present invention. Thus, also contemplated as within the scope of the invention are compounds in which $R^7$ is as described in paragraph [0054] and G is as described in paragraph [0114]. Furthermore, compounds excluded from any one particular genus of compounds (e.g., through a proviso clause) are intended to be excluded from the scope of the invention entirely, including from other disclosed genera, unless expressly stated to the contrary.

Compounds

In the first and second aspects, the invention comprises compounds of formula (A) and formula (B), that are inhibitors of VEGF receptor signaling and HGF receptor signaling:

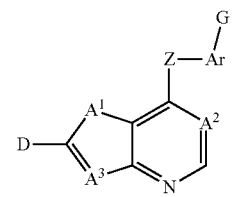

A

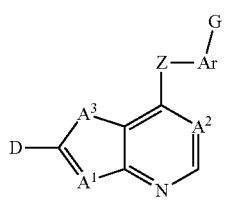

and pharmaceutically acceptable salts and complexes thereof, wherein,

D is selected from the group consisting of $R^7$, $R^1$ and $R^{21}$, wherein $R^7$ is selected from the group consisting of —H, halogen, nitro, azido, $C_1$-$C_6$ alkyl, $C_3$-$C_{10}$ cycloalkyl, —C(O)$NR^{42}R^{43}$, —Y—$NR^{42}R^{43}$, —$NR^{42}$C(=O)$R^{43}$, —$SO_2R^{42}$, —$SO_2NR^{42}R^{43}$, —$NR^{37}SO_2R^{42}$, —$NR^{37}SO_2NR^{42}R^{43}$, —C(=N—O$R^{42}$)$R^{43}$, —C(=$NR^{42}$)$R^{43}$, —$NR^{37}$C(=$NR^{42}$)$R^{43}$, —C(=$NR^{42}$)$NR^{37}R^{43}$, —$NR^{37}$C(=$NR^{42}$)$NR^{37}R^{43}$, —C(O)$R^{42}$, —$CO_2R^{42}$, —C(O)(heterocyclyl), —C(O)($C_6$-$C_{10}$ aryl), —C(O)(heteroaryl), —Y—($C_6$-$C_{10}$ aryl), —Y-(heteroaryl), —Y-(5-10 membered heterocyclyl), —$NR^{6a}R^{6b}$, —$NR^{6a}SO_2R^{6b}$, —$NR^{6a}$C(O)$R^{6b}$, —OC(O)$R^{6b}$, —$NR^{6a}$C(O)O$R^{6b}$, —OC(O)$NR^{6a}R^{6b}$, —O$R^{6a}$, —S$R^{6a}$, —S(O) $R^{6a}$, —$SO_2R^{6a}$, $SO_3R^{6a}$, —$SO_2NR^{6a}R^{6b}$, —$SO_2NR^{42}R^{43}$, —CO$R^{6a}$, —$CO_2R^{6a}$, —CON$R^{6a}R^{6b}$, —($C_1$-$C_4$)fluoroalkyl, —($C_1$-$C_4$)fluoroalkoxy, —(CZ$^3$Z$^4$)$_a$CN, wherein n is an integer ranging from 0 to 6, and the aforementioned $R^7$ groups other than —H and halogen are optionally substituted by 1 to 5 $R^{38}$, or $R^7$ is a moiety selected from the group consisting of —(CZ$^3$Z$^4$)$_a$-aryl, —(CZ$^3$Z$^4$)$_a$-heterocycle, ($C_2$-$C_6$)alkynyl, —(CZ$^3$Z$^4$)$_a$—($C_3$-$C_6$)cycloalkyl, —(CZ$^3$Z$^4$)$_a$—($C_5$-$C_6$)cycloalkenyl, ($C_2$-$C_6$) alkenyl and ($C_1$-$C_6$)alkyl, wherein said moiety is optionally substituted with 1 to 3 independently selected $Y^2$ groups, where a is 0, 1, 2, or 3, and wherein when a is 2 or 3, the CZ$^3$Z$^4$ units may be the same or different; wherein each $R^{6a}$ and $R^{6b}$ is independently selected from the group consisting of hydrogen and a moiety selected from the group consisting of —(CZ$^5$Z$^6$)$_u$—($C_3$-$C_6$)cycloalkyl, —(CZ$^5$Z$^6$)$_u$—($C_5$-$C_6$)cycloalkenyl, —(CZ$^5$Z$^6$)$_u$-aryl, —(CZ$^5$Z$^6$)$_u$-heterocycle, ($C_2$-$C_6$)alkenyl, and ($C_1$-$C_6$) alkyl, wherein said moiety is optionally substituted with 1 to 3 independently selected $Y^3$ groups, where u is 0, 1, 2, or 3, and wherein when u is 2 or 3, the CZ$^5$Z$^6$ units may be the same or different, or $R^{6a}$ and $R^{6b}$ taken together with adjacent atoms form a heterocycle;

each $Z^3$, $Z^4$, $Z^5$ and $Z^6$ is independently selected from the group consisting of H, F and ($C_1$-$C_6$)alkyl, or each $Z^3$ and $Z^4$, or $Z^5$ and $Z^6$ are selected together to form a carbocycle, or two $Z^3$ groups on adjacent carbon atoms are selected together to optionally form a carbocycle;

each $Y^2$ and $Y^3$ is independently selected from the group consisting of halogen, cyano, nitro, tetrazolyl, guanidino, amidino, methylguanidino, azido, —C(O)$Z^7$, —OC(O)$NH_2$, —OC(O) $NHZ^7$, —OC(O)$NZ^7Z^8$, —NHC(O)$Z^7$, —NHC(O)$NH_2$, —NHC(O)$NHZ^7$, —NHC(O)$NZ^7Z^8$, —C(O)OH, —C(O)O$Z^7$, —C(O)$NH_2$, —C(O)$NHZ^7$, —C(O)$NZ^7Z^8$, —P(O)$_3H_2$, —P(O)$_3(Z^7)_2$, —S(O)$_3$H, —S(O)$Z^7$, —S(O)$_2Z^7$, —S(O)$_3Z^7$, —$Z^7$, —O$Z^7$, —OH, —$NH_2$, —$NHZ^7$, —$NZ^7Z^8$, —C(=NH)$NH_2$, —C(=NOH)$NH_2$, —N-morpholino, ($C_2$-$C_6$)alkenyl, ($C_2$-$C_6$)alkynyl, ($C_1$-$C_6$)haloalkyl, ($C_2$-$C_6$)haloalkenyl, ($C_2$-$C_6$)haloalkynyl, ($C_1$-$C_6$)haloalkoxy, —(CZ$^9$Z$^{10}$)$_r$$NH_2$, —(CZ$^9$Z$^{10}$)$_r$NH$Z^3$, —(CZ$^9$Z$^{10}$)$_r$N$Z^7Z^8$, —$X^6$(CZ$^9$Z$^{10}$)$_r$—($C_3$-$C_8$)cycloalkyl, —$X^6$(CZ$^9$Z$^{10}$)$_r$—($C_5$-$C_8$) cycloalkenyl, —$X^6$(CZ$^9$Z$^{10}$)$_r$-aryl and —$X^6$(CZ$^9$Z$^{10}$)$_r$-heterocycle, wherein r is 1, 2, 3 or 4;

$X^6$ is selected from the group consisting of O, S, NH, —C(O)—, —C(O)NH—, —C(O)O—, —S(O)—, —S(O)$_2$— and —S(O)$_3$—;

$Z^7$ and $Z^8$ are independently selected from the group consisting of an alkyl of 1 to 12 carbon atoms, an alkenyl of 2 to 12 carbon atoms, an alkynyl of 2 to 12 carbon atoms, a cycloalkyl of 3 to 8 carbon atoms, a cycloalkenyl of 5 to 8 carbon atoms, aryl of 6 to 14 carbon atoms, a heterocycle of 5 to 14 ring atoms, an aralkyl of 7 to 15 carbon atoms, and a heteroaralkyl of 5 to 14 ring atoms, or $Z^7$ and $Z^8$ together may optionally form a heterocycle;

$Z^9$ and $Z^{10}$ are independently selected from the group consisting of H, F, a ($C_1$-$C_{12}$)alkyl, a ($C_6$-$C_{14}$)aryl, a ($C_5$-$C_{14}$) heteroaryl, a ($C_7$-$C_{15}$)aralkyl and a ($C_5$-$C_{14}$)heteroaralkyl, or $Z^9$ and $Z^{10}$ are taken together form a carbocycle, or two $Z^9$ groups on adjacent carbon atoms are taken together to form a carbocycle; or any two $Y^2$ or $Y^3$ groups attached to adjacent carbon atoms may be taken together to be —O[C(Z$^9$)(Z$^{10}$)]$_r$O or —O[C(Z$^9$)(Z$^{10}$)]$_{r+1}$, or any two $Y^2$ or $Y^3$ groups attached to the same or adjacent carbon atoms may be selected together to form a carbocycle or heterocycle; and wherein any of the above-mentioned substituents comprising a $CH_3$ (methyl), $CH_2$ (methylene), or CH (methine) group which is not attached to a halogen, SO or $SO_2$ group or to a N, O or S atom optionally bears on said group a substituent selected from hydroxy, halogen, ($C_1$-$C_4$)alkyl, ($C_1$-$C_4$) alkoxy and an —N[($C_1$-$C_4$)alkyl][($C_1$-$C_4$)alkyl];

$R^1$ is —C≡CH or —C≡C—(CR$^{45}R^{45}$)$_n$—$R^{46}$;

each $R^{45}$ is independently selected from the group consisting of H, a ($C_1$-$C_6$)alkyl and a ($C_3$-$C_8$)cycloalkyl;

$R^{46}$ is selected from the group consisting of heterocyclyl, —N($R^{47}$)—C(O)—N($R^{47}$)($R^{48}$), —N($R^{47}$)—C(S)—N($R^{47}$)($R^{48}$), —N($R^{47}$)—C(O)—O$R^{48}$, —N($R^{47}$)—C(O)—(CH$_2$)$_n$—$R^{48}$, —N($R^{47}$)—SO$_2R^{47}$, —(CH$_2$)$_n$NR$^{47}R^{48}$, —(CH$_2$)$_n$OR$^{48}$, —(CH$_2$)$_n$SR$^{49}$, —(CH$_2$)$_n$S(O)R$^{49}$, —(CH$_2$)$_n$S(O)$_2R^{49}$, —OC(O)R$^{49}$, —OC(O)OR$^{49}$, —C(O)NR$^{47}R^{48}$, heteroaryl optionally substituted with one or more substituents selected from the group consisting of halo, —CF$_3$, (C$_1$-C$_6$)alkoxy, —NO$_2$, (C$_1$-C$_6$)alkyl, —CN, —SO$_2R^{50}$ and —(CH$_2$)$_n$NR$^{50}R^{51}$, and aryl optionally substituted with one or more substituents selected from the group consisting of halo, —CF$_3$, (C$_1$-C$_6$)alkoxy, —NO$_2$, (C$_1$-C$_6$)alkyl, —CN, —SO$_2R^{50}$ and —(CH$_2$)$_n$NR$^{50}R^{51}$;

$R^{47}$ and $R^{48}$ are independently selected from the group consisting of H, (C$_1$-C$_6$)alkyl, (C$_3$-C$_8$)cycloalkyl, heterocyclyl, —(CH$_2$)$_n$NR$^{50}R^{51}$, —(CH$_2$)$_n$OR$^{50}$, —(CH$_2$)$_n$C(O)R$^{49}$, —C(O)$_2R^{49}$, —(CH$_2$)$_n$SR$^{49}$, —(CH$_2$)$_n$S(O)R$^{49}$, —(CH$_2$)$_n$S(O)$_2R^{49}$, —(CH$_2$)$_n$R$^{49}$, —(CH$_2$)$_n$CN, aryl optionally substituted with one or more substituents selected from the group consisting of halo, —CF$_3$, (C$_1$-C$_6$) alkoxy, —NO$_2$, (C$_1$-C$_6$)alkyl, —CN, —(CH$_2$)$_n$OR$^{49}$, —(CH$_2$)$_n$heterocyclyl, —(CH$_2$)$_n$heteroaryl, —SO$_2R^{50}$ and —(CH$_2$)$_n$NR$^{50}R^{51}$, and heteroaryl optionally substituted with one or more substituents selected from the group consisting of halo, —CF$_3$, (C$_1$-C$_6$)alkoxy, —NO$_2$, (C$_1$-C$_6$)

alkyl, —CN, —(CH$_2$)$_n$OR$^{49}$, —(CH$_2$)$_n$heterocyclyl, —(CH$_2$)$_n$heteroaryl, —SO$_2$R$^{50}$ and —(CH$_2$)$_n$NR$^{50}$R$^{51}$, or R$^{47}$ and R$^{48}$, together with the atom to which they are attached, form a 3-8 membered carbo- or hetero-cyclic ring;

R$^{49}$ is selected from the group consisting of (C$_1$-C$_6$)alkyl, (C$_3$-C$_8$)cycloalkyl, heterocyclyl(C$_1$-C$_6$)alkylene, aryl(C$_1$-C$_6$)alkylene wherein the aryl is optionally substituted with one or more substituents selected from the group consisting of halo, —CF$_3$, (C$_1$-C$_6$)alkoxy, —NO$_2$, (C$_1$-C$_6$)alkyl, —CN, —SO$_2$R$^{50}$ and —(CH$_2$)$_n$—NR$^{50}$R$^{51}$, heteroaryl (C$_1$-C$_6$)alkylene wherein the heteroaryl is optionally substituted with one or more substituents selected from the group consisting of halo, —CF$_3$, (C$_1$-C$_6$)alkoxy, —NO$_2$, (C$_1$-C$_6$)alkyl, —CN, —SO$_2$R$^{50}$ and —(CH$_2$)$_n$NR$^{50}$R$^{51}$, aryl optionally substituted with one or more substituents selected from the group consisting of halo, —CF$_3$, (C$_1$-C$_6$) alkoxy, —NO$_2$, (C$_1$-C$_6$)alkyl, —CN, —SO$_2$R$^{50}$ and —(CH$_2$)$_n$NR$^{50}$R$^{51}$, and heteroaryl optionally substituted with one or more substituents selected from the group consisting of halo, —CF$_3$, (C$_1$-C$_6$)alkoxy, —NO$_2$, (C$_1$-C$_6$) alkyl, —CN, —SO$_2$R$^{50}$ and —(CH$_2$)$_n$NR$^{50}$R$^{51}$;

R$^{50}$ and R$^{51}$ are independently selected from the group consisting of H, (C$_1$-C$_6$)alkyl, (C$_3$-C$_8$)cycloalkyl and —C(O) R$^{45}$, or R$^{50}$ and R$^{51}$, together with the atom to which they are attached, form a 3-8 membered carbo- or hetero-cyclic ring; and R$^{21}$ is the group defined by —(Z$^{11}$)—(Z$^{12}$)$_m$—(Z$^{13}$)$_{m1}$, wherein Z$^{11}$ is heterocyclyl, when m and m1 are 0, or heterocyclylene, when either m or m1 are 1, Z$^{12}$ is selected from the group consisting of OC(O), OC(S) and C(O);

Z$^{13}$ is selected from the group consisting of heterocyclyl, aralkyl, N(H)R$^{52}$, (C$_1$-C$_3$)alkyl, —OR$^{52}$, halo, S(O)$_2$R$^{56}$, (C$_1$-C$_3$)hydroxyalkyl and (C$_1$-C$_3$)haloalkyl;

m is 0 or 1;

m1 is 0 or 1;

R$^{52}$ is selected from the group consisting of H, —(CH$_2$)$_q$S (O)$_2$R$^{54}$, —(C$_1$-C$_6$) alkyl-NR$^{53}$R$^{53}$ (C$_1$-C$_3$)alkyl, —(CH$_2$)$_q$OR$^{53}$, —C(O)R$^{54}$ and —C(O)OR$^{53}$;

q is 0, 1, 2, 3 or 4;

each R$^{53}$ is independently (C$_1$-C$_3$)alkyl;

R$^{54}$ is (C$_1$-C$_3$)alkyl or N(H)R$^{53}$;

R$^{56}$ is selected from the group consisting of NH$_2$, (C$_1$-C$_3$) alkyl and OR$^{52}$;

A$^1$ is selected from the group consisting of —CH$_2$—, —O—, —S—, —N(H)—, —N(C$_1$-C$_6$ alkyl)-, —N—(Y-aryl)-, —N-OMe, —NCH$_2$OMe and N-Bn;

Y is a bond or —(C(R$^{11}$)(H))$_t$—, wherein t is an integer from 1 to 6; and

R$^{11}$ at each occurrence is independently selected from the group consisting of H and C$_1$-C$_6$ alkyl, wherein the C$_1$-C$_6$ alkyl is optionally substituted;

A$^2$ is selected from the group consisting of N and CR, wherein R is selected from the group consisting of —H, halogen, —CN, C$_1$-C$_6$ alkyl, C$_2$-C$_6$ alkenyl, and C$_2$-C$_6$ alkynyl, wherein the C$_1$-C$_6$ alkyl, C$_2$-C$_6$ alkenyl, and C$_2$-C$_6$ alkynyl are optionally substituted;

A$^3$ is selected from the group consisting of C-D and N;

Ar is a group of the formula C,

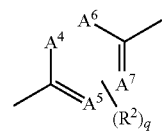

C wherein,

A$^4$, A$^5$, A$^6$ and A$^7$ are independently selected from the group consisting of N and —CH$_2$—, with the proviso that no more than two of A$^4$, A$^5$, A$^6$ and A$^7$ can be N;

R$^2$ at each occurrence is independently selected from the group consisting of —H, halogen, trihalomethyl, —CN, —NO$_2$, —NH$_2$, —OR$^3$, —NR$^3$R$^4$, —S(O)$_{0-2}$R$^3$, —S(O)$_2$ NR$^3$R$^3$, —C(O)OR$^3$, —C(O)NR$^3$R$^3$, —N(R$^3$)SO$_2$R$^3$, —N(R$^3$)C(O)R$^3$, —N(R$^3$)CO$_2$R$^3$, —C(O)R$^3$, alkoxy, C$_1$-C$_4$ alkylthio, —O(CH$_2$)$_n$aryl, —O(CH$_2$)$_n$heteroaryl, —(CH$_2$)$_{0-5}$(aryl), —(CH$_2$)$_{0-5}$(heteroaryl), C$_1$-C$_6$ alkyl, C$_2$-C$_6$ alkenyl, C$_2$-C$_6$ alkynyl, —CH$_2$(CH$_2$)$_{0-4}$-T$^2$, wherein T$^2$ is selected from the group consisting of —OH, —OMe, —OEt, —NH$_2$, —NHMe, —NMe$_2$, —NHEt and —NEt$_2$, and wherein the aryl, heteroaryl, C$_1$-C$_6$ alkyl, C$_2$-C$_6$ alkenyl, and C$_2$-C$_6$ alkynyl are optionally substituted; and q is an integer from 0 to 4;

G is a group B-L-T, wherein

B is selected from the group consisting of absent, —N(R$^{13}$)—, —N(SO$_2$R$^{13}$)—, —O—, —S(O)$_{0-2}$ and —C(=O)—;

L is selected from the group consisting of absent, —C(=S) N(R$^{13}$)—, —C(=NR$^{14}$)N(R$^{13}$)—, —SO$_2$N(R$^{13}$)—, —SO$_2$—, —C(=O)N(R$^{13}$)—, —N(R$^{13}$)—, —C(=O) C$_{1-2}$alkyl-N(R$^{13}$)—, —N(R$^{13}$)C$_{1-2}$alkyl-C(=O)—, —C(=O)C$_{0-1}$alkyl-C(=O)N(R$^{13}$)—, —C$_{0-4}$alkylene, —C(=O)C$_{0-1}$alkyl-C(=O)OR$^3$—, —C(=NR$^{14}$)— C$_{0-1}$alkyl-C(=O)—, —C(=O)—, —C(=O)C$_{0-1}$ alkyl-C(=O)— and an optionally substituted four to six-membered heterocyclyl containing between one and three annular heteroatoms including at least one nitrogen; and T is selected from the group consisting of —H, —R$^{13}$, —C$_{0-4}$alkyl, —C$_{0-4}$alkyl-Q, —O—C$_{0-4}$alkyl-Q, —C$_{0-4}$ alkyl-O-Q, —N(R$^{13}$)C$_{0-4}$alkyl-Q, —SO$_2$C$_{0-4}$alkyl-Q, —C(=O)C$_{0-4}$alkyl-Q, —C$_{0-4}$alkyl-N(R$^{13}$)Q and —C(=O)N(R$^{13}$)—C$_{0-4}$alkyl-Q, wherein each C$_{0-4}$alkyl is optionally substituted;

R$^{13}$ is selected from the group consisting of —H, —CN, —NO$_2$, —NH$_2$, —OR$^3$, —NR$^3$R$^4$, —S(O)$_{0-2}$R$^3$, —S(O)$_2$ NR$^3$R$^3$, —C(O)OR$^3$, —C(O)NR$^3$R$^3$, —N(R$^3$)SO$_2$R$^3$, —N(R$^3$)C(O)R$^3$, —N(R$^3$)CO$_2$R$^3$, —C(O)R$^3$, —C(O) SR$^3$, C1-C$_4$ alkoxy, C$_1$-C$_4$ alkylthio, —O(CH$_2$)$_n$aryl, —O(CH$_2$)$_n$heteroaryl, —(CH$_2$)$_{0-5}$(aryl), —(CH$_2$)$_{0-5}$(heteroaryl), C$_1$-C$_6$ alkyl, C$_2$-C$_6$ alkenyl, C$_2$-C$_6$ alkynyl, —CH$_2$(CH$_2$)$_{0-4}$-T$^2$, an optionally substituted C$_{1-4}$ alkyl-carbonyl, and a saturated or unsaturated three- to seven-membered carboxyclic or heterocyclic group, wherein T$^2$ is selected from the group consisting of —OH, —OMe, —OEt, —NH$_2$, —NHMe, —NMe$_2$, —NHEt and —NEt$_2$, and wherein the aryl, heteroaryl, C$_1$-C$_6$ alkyl, C$_2$-C$_6$ alkenyl, and C$_2$-C$_6$ alkynyl are optionally substituted;

two R$^{13}$, together with the atom or atoms to which they are attached, can combine to form a heteroalicyclic optionally substituted with between one and four of R$^{60}$, wherein the heteroalicyclic can have up to four annular heteroatoms, and the heteroalicyclic can have an aryl or heteroaryl fused thereto, in which case the aryl or heteroaryl is optionally substituted with an additional one to four of $R^{60}$;

$R^{14}$ is selected from the group —H, —NO$_2$, —NH$_2$, —N(R$^3$)R$^4$, —CN, —OR$^3$, an optionally substituted (C$_1$-C$_6$)alkyl, an optionally substituted heteroalicyclylalkyl, an optionally substituted aryl, an optionally substituted arylalkyl and an optionally substituted heteroalicyclic, each $R^3$ is independently selected from the group consisting of —H and $R^4$;

$R^4$ is selected from the group consisting of a (C$_1$-C$_6$)alkyl, an aryl, a lower arylalkyl, a heterocyclyl and a lower heterocyclylalkyl, each of which is optionally substituted, or $R^3$ and $R^4$, taken together with a common nitrogen to which they are attached, form an optionally substituted five- to seven-membered heterocyclyl, the optionally substituted five- to seven-membered heterocyclyl optionally containing at least one additional annular heteroatom selected from the group consisting of N, O, S and P;

$R^{60}$ is selected from the group consisting of —H, halogen, trihalomethyl, —CN, —NO$_2$, —NH$_2$, —OR$^3$, —NR$^3$R$^4$, —S(O)$_{0-2}$R$^3$, —SO$_2$NR$^3$R$^3$, —CO$_2$R$^3$, —C(O)NR$^3$R$^3$, —N(R$^3$)SO$_2$R$^3$, —N(R$^3$)C(O)R$^3$, —N(R$^3$)CO$_2$R$^3$, —C(O)R$^3$, an optionally substituted (C$_1$-C$_6$)alkyl, an optionally substituted aryl, an optionally substituted heteroarylalkyl and an optionally substituted arylalkyl;

two $R^{60}$, when attached to a non-aromatic carbon, can be oxo;

Q is a five- to ten-membered ring system, optionally substituted with between zero and four of $R^{20}$;

$R^{20}$ is selected from the group consisting of —H, halogen, trihalomethyl, —CN, —NO$_2$, —NH$_2$, —OR$^3$, —OCF$_3$, —NR$^3$R$^4$, —S(O)$_{0-2}$R$^3$, —S(O)$_2$NR$^3$R$^3$, —C(O)OR$^3$, —C(O)NR$^3$R$^3$, —N(R$^3$)SO$_2$R$^3$, —N(R$^3$)C(O)R$^3$, —N(R$^3$)C(O)OR$^3$, —C(O)R$^3$, —C(O)SR$^3$, alkoxy, C$_1$-C$_4$ alkylthio, —O(CH$_2$)$_n$aryl, —O(CH$_2$)$_n$heteroaryl, —(CH$_2$)$_{0-5}$(aryl), —(CH$_2$)$_{0-5}$(heteroaryl), C$_1$-C$_6$ alkyl, C$_2$-C$_6$ alkenyl, C$_2$-C$_6$ alkynyl, —CH$_2$(CH$_2$)$_{0-4}$-T$^2$, an optionally substituted C$_{1-4}$ alkylcarbonyl, C$_{1-4}$ alkoxy, an amino optionally substituted by C$_{1-4}$ alkyl optionally substituted by C$_{1-4}$ alkoxy and a saturated or unsaturated three- to seven-membered carboxylic or heterocyclic group, wherein T$^2$ is selected from the group consisting of —OH, —OMe, —OEt, —NH$_2$, —NHMe, —NMe$_2$, —NHEt and —NEt$_2$, and wherein the aryl, heteroaryl, C$_1$-C$_6$ alkyl, C$_2$-C$_6$ alkenyl, and C$_2$-C$_6$ alkynyl are optionally substituted;

each $R^{38}$ is independently selected from halo, cyano, nitro, trifluoromethoxy, trifluoromethyl, azido, —C(O)R$^{40}$, —C(O)OR$^{40}$, —OC(O)R$^{40}$, —OC(O)OR$^{40}$, —NR$^{36}$C(O)R$^{39}$, —C(O)NR$^{36}$R$^{39}$, —NR$^{36}$R$^{39}$, —OR$^{37}$, —SO$_2$NR$^{36}$R$^{39}$, C$_1$-C$_6$ alkyl, —(CH$_2$)$_n$O(CH$_2$)$_i$NR$^{36}$R$^{39}$, —(CH$_2$)$_n$O(CH$_2$)$_i$OR$^{37}$, —(CH$_2$)$_n$OR$^{37}$, —S(O)$_j$(C$_1$-C$_6$ alkyl), —(CH$_2$)$_n$(C$_6$-C$_{10}$ aryl), —(CH$_2$)$_n$(5-10 membered heterocyclyl); —C(O)(CH$_2$)$_n$(C$_6$-C$_{10}$ aryl), —(CH$_2$)$_n$O(CH$_2$)$_j$(C$_6$-C$_{10}$ aryl), —(CH$_2$)$_n$—O(CH$_2$)$_i$(5-10 membered heterocyclyl), —C(O)(CH$_2$)$_n$(5-10 membered heterocyclyl), —(CH$_2$)$_j$NR$^{39}$(CH$_2$)$_i$NR$^{36}$R$^{39}$, —(CH$_2$)$_j$NR$^{39}$CH$_2$C(O)NR$^{36}$R$^{39}$, —(CH$_2$)NR$^{39}$(CH$_2$)$_i$NR$^{37}$C(O)R$^{40}$, —(CH$_2$)$_j$NR$^{39}$(CH$_2$)$_n$—O(CH$_2$)$_i$OR$^{37}$, —(CH$_2$)$_j$NR$^{39}$(CH$_2$)$_i$S(O)$_j$(C$_1$-C$_6$ alkyl), —(CH$_2$)$_j$NR$^{39}$(CH$_2$)$_n$R$^{36}$, —SO$_2$(CH$_2$)$_n$(C$_6$-C$_{10}$ aryl), —SO$_2$(CH$_2$)$_n$(5-10 membered heterocyclyl), —(CH$_2$)$_n$NR$^{36}$R$^{39}$, —NR$^{37}$SO$_2$NR$^{36}$R$^{39}$, SO$_2$R$^{36}$, C$_2$-C$_6$ alkenyl, C$_3$-C$_{10}$ cycloalkyl and C$_1$-C$_6$ alkylamino, wherein j is an integer ranging from 0 to 2, n is an integer ranging from 0 to 6, i is an integer ranging from 2 to 6, the —(CH$_2$)$_i$— and —(CH$_2$)$_n$— moieties of the foregoing R$^{38}$ groups optionally include a carbon-carbon double or triple bond where n is an integer between 2 and 6, and the alkyl, aryl and heterocyclyl moieties of the foregoing $R^{38}$ groups are optionally substituted by one or more substituents independently selected from halo, cyano, nitro, trifluoromethyl, azido, —OH, —C(O)R$^{40}$, —C(O)OR$^{40}$, —OC(O)R$^{40}$, —OC(O)OR$^{40}$, —NR$^{36}$C(O)R$^{39}$, —C(O)NR$^{36}$R$^{39}$, —(CH$_2$)$_n$NR$^{36}$R$^{39}$, C$_1$-C$_6$ alkyl, C$_3$-C$_{10}$ cycloalkyl, —(CH$_2$)$_n$(C$_6$-C$_{10}$ aryl), —(CH$_2$)$_n$(5-10 membered heterocyclyl), —(CH$_2$)$_n$O(CH$_2$)$_i$OR$^{37}$, and —(CH$_2$)$_n$OR$^{37}$, wherein n is an integer ranging from 0 to 6 and i is an integer ranging from 2 to 6;

each $R^{36}$ and $R^{39}$ is independently selected from the group consisting of H, —OH, C$_1$-C$_6$ alkyl, C$_3$-C$_{10}$ cycloalkyl, —(CH$_2$)$_n$(C$_6$-C$_{10}$ aryl), —(CH$_2$)$_n$(5-10 membered heterocyclyl), —(CH$_2$)$_n$O(CH$_2$)$_i$OR$^{37}$, —(CH$_2$)$_n$CN(CH$_2$)$_n$—OR$^{37}$, —(CH$_2$)$_n$CN(CH$_2$)$_n$R$^{37}$, and —(CH$_2$)$_n$OR$^{37}$, wherein n is an integer ranging from 0 to 6 and i is an integer ranging from 2 to 6, and the alkyl, aryl and heterocyclyl moieties of the foregoing R$^{36}$ and R$^{39}$ groups are optionally substituted by one or more substituents independently selected from —OH, halo, cyano, nitro, trifluoromethyl, azido, —C(O)R$^{40}$, —C(O)OR$^{40}$, —CO(O)R$^{40}$, —OC(O)OR$^{40}$, —NR$^{37}$C(O)R$^{41}$, —C(O)NR$^{37}$R$^{41}$, —NR$^{37}$R$^{41}$, —C$_1$-C$_6$ alkyl, —(CH$_2$)$_n$(C$_6$-C$_{10}$ aryl), —(CH$_2$)$_n$(5 to 10 membered heterocyclyl), —(CH$_2$)$_n$O(CH$_2$)$_i$OR$^{37}$, and —(CH$_2$)$_n$OR$^{37}$, wherein n is an integer ranging from 0 to 6 and i is an integer ranging from 2 to 6, with the proviso that when R$^{36}$ and R$^{39}$ are both attached to the same nitrogen, then R$^{36}$ and R$^{39}$ are not both bonded to the nitrogen directly through an oxygen;

each $R^{40}$ is independently selected from H, C$_1$-C$_{10}$ alkyl, —(CH$_2$)$_n$(C$_6$-C$_{10}$ aryl), C$_3$-C$_{10}$ cycloalkyl, and —(CH$_2$)$_n$) 5-10 membered heterocyclyl), wherein n is an integer ranging from 0 to 6;

each $R^{37}$ and $R^{41}$ is independently selected from H, OR$^{36}$, C$_1$-C$_6$ alkyl and C$_3$-C$_{10}$ cycloalkyl;

each $R^{42}$ and $R^{43}$ is independently selected from the group consisting of H, C$_1$-C$_6$ alkyl, —Y—(C$_3$-C$_{10}$ cycloalkyl), —Y—(C$_6$-C$_{10}$ aryl), —Y—(C$_6$-C$_{10}$ heteroaryl), —Y-(5-10 membered heterocyclyl), —Y—O—Y$^1$—OR$^{37}$, —Y$^1$—CO$_2$—R$^{37}$, and —Y—OR$^{37}$, wherein, Y is a bond or is —(C(R$^{37}$)(H))$_n$, wherein n is an integer ranging from 1 to 6, Y$^1$ is —(C(R$^{37}$)(H))$_n$, and the alkyl, cycloalkyl, aryl, heteroaryl and heterocyclyl moieties of the foregoing R$^{42}$ and R$^{43}$ groups are optionally substituted by 1 or more substituents independently selected from R$^{44}$; or $R^{42}$ and $R^{43}$ taken together with the nitrogen to which they are attached form a C$_5$-C$_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring, wherein said C$_5$-C$_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring are optionally substituted by 1 to 5 R$^{44}$ substituents, with the proviso that R$^{42}$ and R$^{43}$ are not both bonded to the nitrogen directly through an oxygen;

each $R^{44}$ is independently selected from the group consisting of halo, cyano, nitro, trifluoromethoxy, trifluoromethyl, azido, —C(O)R$^{40}$, —C(O)OR$^{40}$, —OC(O)R$^{40}$, —OC(O)OR$^{40}$, —NR$^{36}$C(O)R$^{39}$, —C(O)NR$^{36}$R$^{39}$, —NR$^{36}$R$^{39}$, —OR$^{37}$, —SO$_2$NR$^{36}$R$^{39}$, —SO$_2$R$^{36}$, —NR$^{36}$SO$_2$R$^{39}$, —NR$^{36}$SO$_2$NR$^{37}$R$^{41}$, C1-C$_6$ alkyl, C$_2$-C$_6$ alkenyl, C$_2$-C$_6$ alkynyl, C$_3$-C$_{10}$ cycloalkyl, —C$_1$-C$_6$ alkylamino, —(CH$_2$)$_j$O(CH$_2$)$_i$NR$^{36}$R$^{39}$, —(CH$_2$)$_n$O(CH$_2$)$_i$OR$^{37}$, —(CH$_2$)$_n$OR$^{37}$, —S(O)$_j$(C$_1$-C$_6$ alkyl), —(CH$_2$)$_n$(C$_6$-C$_{10}$ aryl), —(CH$_2$)$_n$(5-10 membered heterocyclyl), —C(O)(CH$_2$)$_n$ ($C_6$-$C_{10}$ aryl), —($CH_2$)$_n$O($CH_2$)$_j$($C_6$-$C_{10}$ aryl), —($CH_2$)$_n$O($CH_2$)$_i$(5 to 10 membered heterocyclyl), —C(O)($CH_2$)$_n$(5 to 10 membered heterocyclyl), —($CH_2$)$_j$NR$^{39}$($CH_2$)$_i$NR$^{36}$R$^{39}$, —($CH_2$)$_j$NR$^{39}$CH$_2$C(O)NR$^{36}$R$^{39}$, —($CH_2$)$_j$NR$^{39}$($CH_2$)$_i$NR$^{37}$C(O)R$^{40}$, —($CH_2$)$_j$NR$^{39}$($CH_2$)$_n$O($CH_2$)$_i$OR$^{37}$, —($CH_2$)$_j$NR$^{39}$($CH_2$)$_i$S(O)$_j$($C_1$-$C_6$ alkyl), —($CH_2$)$_j$NR$^{39}$($CH_2$)$_n$R$^{36}$, —SO$_2$($CH_2$)$_n$($C_6$-$C_{10}$ aryl), and —SO$_2$($CH_2$)$_n$(5 to 10 membered heterocyclyl) wherein, j is an integer from 0 to 2, n is an integer from 0 to 6 and i is an integer ranging from 2 to 6, the —($CH_2$)$_i$— and —($CH_2$)$_{n1}$— moieties of the foregoing R$^{44}$ groups optionally include a carbon-carbon double or triple bond wherein n is an integer from 2 to 6, and the alkyl, aryl and heterocyclyl moieties of the foregoing R$^{44}$ groups are optionally substituted by 1 or more substituents independently selected from the group consisting of halo, cyano, nitro, trifluoromethyl, azido, —OH, —C(O)R$^{40}$, —C(O)OR$^{40}$, —OC(O)R$^{40}$, —OC(O)OR$^{40}$, —NR$^{36}$C(O)R$^{39}$, —C(O)NR$^{36}$R$^{39}$, —($CH_2$)$_n$NR$^{36}$R$^{39}$, —SO$_2$R$^{36}$, —SO$_2$NR$^{36}$R$^{39}$, $C_1$-$C_6$ alkyl, $C_3$-$C_{10}$ cycloalkyl, —($CH_2$)$_n$($C_6$-$C_{10}$ aryl), —($CH_2$)$_n$(5 to 10 membered heterocyclyl), —($CH_2$)$_n$O($CH_2$)$_i$OR$^{37}$ and —($CH_2$)$_n$OR$^{37}$, wherein n is an integer from 0 to 6 and i is an integer from 2 to 6; and Z is selected from the group consisting of —O—, —S— and —NR$^5$—, wherein R$^5$ is selected from the group consisting of H, an optionally substituted ($C_1$-$C_5$)acyl and $C_1$-$C_6$ alkyl-O—C(O), wherein $C_1$-$C_6$ alkyl is optionally substituted;

with the proviso that when G is NR$^{13}$(C=$Z_p$)NR$^{13}$C(O)(C(X)(X$^1$))-Q, wherein $Z_p$ is O, S or NH, X and X$^1$ independently represent H, $C_1$-$C_6$ alkyl, halo, cyano or nitro, wherein the $C_1$-$C_6$ alkyl is optionally substituted, or X and X$^1$ taken together with the atom to which they are attached, form a $C_3$-$C_7$ cylcoalkyl, Q is selected from the group consisting of cycloalkyl, heterocyclyl, aryl and heteroaryl, wherein each of said cycloalkyl, heterocyclyl, aryl and heteroaryl is optionally substituted with 1 to 3 R$^{20}$, Ar is phenyl optionally substituted with 1 to 4 moieties independently selected from the group consisting of hydrogen, halo, trihalomethyl, —CN, —NO$_2$, —NH$_2$, —OR$^3$, —NR$^3$R$^4$, —C(O)OR$^3$, —C(O)R$^3$, $C_1$-$C_4$ alkoxy, $C_1$-$C_6$ alkylthio, $C_1$-$C_6$ alkyl, $C_2$-$C_6$ alkenyl or $C_2$-$C_6$ alkynyl, wherein $C_1$-$C_6$ alkyl, $C_2$-$C_6$ alkenyl and $C_2$-$C_6$ alkynyl are optionally substituted, and Z is O, S or NH, then D is not R$^7$, R$^1$ or R$^{21}$;

when D is selected from the group consisting of —H, halogen, nitro, azido, —NR$^{6a}$R$^{6b}$, —NR$^{6a}$SO$_2$R$^{6b}$; —NR$^{6a}$C(O)R$^{6b}$; —OC(O)R$^{6b}$, —NR$^{6a}$C(O)OR$^{6b}$, —OC(O)NR$^{6a}$R$^{6b}$, —OR$^{6a}$, —SR$^{6a}$, —S(O)R$^{6a}$, —SO$_2$R$^{6a}$, —SO$_3$R$^{6a}$, —SO$_2$NR$^{6a}$R$^{6b}$, —COR$^{6a}$, —CO$_2$R$^{6a}$, —CONR$^{6a}$R$^{6b}$, —($C_1$-$C_4$)fluoroalkyl, —($C_1$-$C_4$)fluoroalkoxy, —(CZ$^3$Z$^4$)$_a$CN, and a moiety selected from the group consisting of —(CZ$^3$Z$^4$)$_a$-aryl, —(CZ$^3$Z$^4$)$_a$-heterocycle, ($C_2$-$C_6$)alkynyl, —(CZ$^3$Z$^4$)$_a$—($C_3$-$C_6$)cycloalkyl, —(CZ$^3$Z$^4$)$_a$—($C_5$-$C_6$)cycloalkenyl, ($C_2$-$C_6$) alkenyl and ($C_1$-$C_6$)alkyl, wherein said moiety is optionally substituted with 1 to 3 independently selected Y$^2$ groups, where a is 0, 1, 2, or 3, and wherein when a is 2 or 3, the CZ$^3$Z$^4$ units may be the same or different, A$^1$ is —S—, A$^2$ is —N— or —CR—, wherein R is H, F, Cl, CF$_3$, CH$_3$, OCH$_3$ or OCF$_3$, A$^3$ is —CH—, Z is —O— or —S—, A$^6$ and A$^7$ are —CH$_2$—, then B-L-T is not —X$^3$—C(O)—NH—R$^{33}$, wherein X$^3$ is O or CR$^{2a}$R$^{2b}$, each of R$^{2a}$ and R$^{2b}$ is independently selected from the group consisting of H, halogen, or a moiety, optionally substituted with 1 to 3 independently selected X$^4$ groups, selected from the group consisting of ($C_1$-$C_6$)alkoxy, ($C_1$-$C_6$)alkylamine and ($C_1$-$C_6$)alkyl, wherein any number of the hydrogen atoms on the ($C_1$-$C_6$)alkyoxy and ($C_1$-$C_6$)alkyl groups may be optionally replaced with F, or R$^{2a}$ and R$^{2b}$ together can be oxo or a moiety, optionally substituted with 1 to 3 independently selected X$^4$ groups, selected from the group consisting of ($C_3$-$C_6$)cycloalkyl, 3 to 6 membered heterocycloalkyl and =CH—($C_1$-$C_5$)alkyl, R$^{33}$ is H or a moiety, optionally substituted with 1 to 3 independently selected Y$^2$ groups, selected from the group consisting of —(CZ$^1$Z$^2$)$_s$CN, —(CZ$^1$Z$^2$), —($C_3$-$C_8$)cycloalkyl, —(CZ$^1$Z$^2$), —($C_5$-$C_8$)cycloalkenyl, ($C_2$-$C_6$)alkenyl, ($C_2$-$C_6$)alkynyl, —(CZ$^1$Z$^2$)$_s$-aryl, —(CZ$^1$Z$^2$)$_s$-heterocycle and ($C_1$-$C_8$)alkyl, where s is 0, 1, 2 or 3, and wherein when s is 2 or 3, the CZ$^1$Z$^2$ units may be the same or different, and wherein Z$^1$ and Z$^2$ are each independently selected from the group consisting of H, F, and ($C_1$-$C_6$)alkyl or each Z$^1$ and Z$^2$ are selected together to form a carbocycle or two Z$^1$ or Z$^2$ groups on adjacent carbon atoms are selected together to optionally form a carbocycle;

when D is selected from the group consisting of H, $C_1$-$C_6$ alkyl, $C_3$-$C_{10}$ cycloalkyl, —C(O)NR$^{42}$R$^{43}$, —C(O)($C_6$-$C_{10}$ aryl), —($CH_2$)$_n$($C_6$-$C_{10}$ aryl), —($CH_2$)$_n$(5 to 10 membered heterocyclyl), —($CH_2$)$_n$NR$^{42}$R$^{43}$, —SO$_2$NR$^{42}$R$^{43}$ and —CO$_2$R$^{42}$, wherein n is an integer from 0 to 6, and wherein said $C_1$-$C_6$ alkyl, —C(O)($C_6$-$C_{10}$ aryl), —($CH_2$)$_n$($C_6$-$C_{10}$ aryl), —($CH_2$)$_n$(5 to 10 membered heterocyclyl) moieties are unsubstituted or substituted by one or more substituents selected from R$^{38}$, with the proviso that R$^{38}$ is not —($CH_2$)$_{3-6}$NR$^{36}$R$^{39}$, —NR$^{37}$SO$_2$NR$^{36}$R$^{39}$, SO$_2$R$^{36}$, or $C_2$-$C_6$ alkenyl, A$^1$ is —S—, A$^2$ is —N— or —CH—, A$^3$ is —CH—, and Z is —O—, —S— or —NH—, then Ar-G is not unsubstituted $C_6$ aryl or 6-membered heterocyclyl group or $C_6$ aryl or 6-membered heterocyclyl group substituted with 1 to 5 substituents selected from R$^{38}$, with the proviso that R$^{38}$ is not —($CH_2$)$_{3-6}$NR$^{36}$R$^{39}$, —NR$^{37}$SO$_2$NR$^{36}$R$^{39}$, SO$_2$R$^{36}$, or $C_2$-$C_6$ alkenyl;

when D is selected from the group consisting of imidazolyl, oxazolyl, oxadiazolyl, isoxazolyl, thiazolyl and thiadiazolyl, wherein said imidazolyl, oxazolyl, oxadiazolyl, isoxazolyl, thiazolyl and thiadiazolyl are optionally substituted by 1 to 5 substituents selected from R$^{38}$, with the proviso that R$^{38}$ is not nitro, azido, —C(O)OR$^{40}$, —OC(O)R$^{40}$, —OC(O)OR$^{40}$, —C(O)($CH_2$)$_n$$C_6$-$C_{10}$ aryl), —($CH_2$)$_n$O($CH_2$)$_j$($C_6$-$C_{10}$ aryl), $C_3$-$C_{10}$ cycloalkyl or $C_1$-$C_6$ alkylamino, R$^{36}$ and R$^{39}$ are not —OH, $C_3$-$C_5$ cycloalkyl, —($CH_2$)$_n$CN($CH_2$)$_n$OR$^{37}$ or —($CH_2$)$_n$CN($C_2$)R$^{37}$, R$^{37}$ and R$^{41}$ are not —OR$^{36}$ or $C_3$-$C_{10}$ cycloalkyl, and R$^{40}$ is not $C_3$-$C_{10}$ cycloalkyl, A$^1$ is —S—, A$^2$ is N, CH or C—CN, A$^3$ is —CH—, and Z is —NH—, then Ar-G is not unsubstituted 6-membered heterocyclyl or 6-membered heterocyclyl optionally substituted by 1 to 5 substituents selected from R$^{38}$, with the proviso that R$^{38}$ is not nitro, azido, —C(O)OR$^{40}$, —OC(O)R$^{40}$, —OC(O)OR$^{40}$, —C(O)($CH_2$)$_n$($C_6$-$C_{10}$ aryl), —($CH_2$)$_n$O($CH_2$)$_j$($C_6$-$C_{10}$ aryl), $C_3$-$C_{10}$ cycloalkyl or $C_1$-$C_6$ alkylamino, R$^{36}$ and R$^{39}$ are not —OH, $C_3$-$C_5$ cycloalkyl, —($CH_2$)$_n$CN($CH_2$)$_n$OR$^{37}$ or —($CH_2$)$_n$CN($CH_2$)R$^{37}$, R$^{37}$ and R$^{41}$ are not —OR$^{36}$ or $C_3$-$C_{10}$ cycloalkyl, and R$^{40}$ is not $C_3$-$C_{10}$ cycloalkyl;

when D is selected from the group consisting of H, $C_1$-$C_6$ alkyl, —C(O)NR$^{36}$R$^{39}$, —C(O)($C_6$-$C_{10}$ aryl), —($CH_2$)$_n$($C_6$-$C_{10}$ aryl), and —($CH_2$)$_n$(5 to 10 membered heterocyclyl), wherein said groups, other than H, are unsubstituted or substituted by one to five substituents selected from R$^{38}$, with the proviso that R$^{38}$ is not —($CH_2$)$_{3-6}$NR$^{36}$R$^{39}$, —NR$^{37}$SO$_2$NR$^{36}$R$^{39}$, SO$_2$R$^{36}$, $C_2$-$C_6$ alkenyl, $C_3$-$C_{10}$ cycloalkyl or $C_1$-$C_6$ alkylamino, R$^{36}$ and R$^{39}$ are not —OH, $C_3$-$C_{10}$ cycloalkyl, —($CH_2$)$_n$CN($CH_2$)$_n$OR$^{37}$ or —($CH_2$)$_n$ $CN(CH_2)_nR^{37}$, $R^{37}$ and $R^{41}$ are not $OR^{36}$ or $C_3$-$C_{10}$ cycloalkyl and $R^{40}$ is not $C_3$-$C_{10}$ cycloalkyl, $A^1$ is —S— when $A^3$ is —CH— or $A^1$ is —CH— when $A^3$ is —S—, $A^2$ is —N— or —CH—, and Z is —NH— or N—($C_1$-$C_6$ alkyl), then Ar-G is not unsubstituted $C_6$ aryl or 6-membered heterocyclyl or $C_6$ aryl or 6-membered heterocyclyl substituted with 1 to 5 substituents selected from the group $R^{38}$, with the proviso that $R^{38}$ is not —$(CH_2)_{3-6}NR^{36}R^{39}$, —$NR^{37}SO_2NR^{36}R^{39}$, $SO_2R^{36}$, $C_2$-$C_6$ alkenyl, $C_3$-$C_{10}$ cycloalkyl or $C_1$-$C_6$ alkylamino, $R^{36}$ and $R^{39}$ are not —OH, $C_3$-$C_{10}$ cycloalkyl, —$(CH_2)_nCN(CH_2)_nOR^{37}$ or —$(CH_2)_n$ $CN(CH_2)_nR^{37}$, $R^{37}$ and $R^{41}$ are not $OR^{36}$ or $C_3$-$C_{10}$ cycloalkyl and $R^{40}$ is not $C_3$-$C_{10}$ cycloalkyl;

when D is selected from the group consisting of —C(O) $NR^{42}R^{43}$, —$(CH_2)_nNR^{42}R^{43}$, —$NR^{42}C(=O)R^{43}$, —$SO_2R^{42}$, —$SO_2R^{42}$, —$SO_2NR^{42}R^{43}$, —$NR^{37}SO_2NR^{42}R^{43}$, —$C(=N-OR^{42})R^{43}$, —$C(=NR^{42})R^{43}$, —$NR^{37}C(=NR^{42})R^{43}$, —$C(=NR^{42})$ $NR^{37}R^{43}$, —$NR^{37}C(=NR^{42})NR^{37}R^{43}$, —$C(O)R^{42}$ and —$CO_2R^{42}$, wherein the alkyl, aryl and heterocyclyl moieties of the foregoing $R^{42}$ and $R^{43}$ groups are optionally substituted with 1 to 3 substituents independently selected from the group $R^{44}$, with the proviso that $R^{44}$ is not nitro, azido, —C(O)$OR^{40}$, —OC(O)$R^{40}$, OC(O)$OR^{40}$, $C_3$-$C_{10}$ cycloalkyl or $C_1$-$C_6$ alkylamine, $A^1$ is —S—, $A^2$ is N, CH or C(CN), $A^3$ is CH, and Z is NH or N—($C_1$-$C_6$)alkyl, then Ar-G is not 6-membered heterocyclyl, wherein the 6-membered heterocyclyl is optionally substituted by 1 to 5 substituents from the group $R^{44}$, with the proviso that $R^{44}$ is not nitro, azido, —C(O)$OR^{40}$, —OC(O)$R^{40}$, OC(O)$OR^{40}$, $C_3$-$C_{10}$ cycloalkyl or $C_1$-$C_6$ alkylamine;

when D is —C≡CH or —C≡C—$(CR^{45}R^{45})_n$—$R^{46}$, $A^1$ is —S— and $A^3$ is —CH— or $A^1$ is —CH— and $A^3$ is —S—, $A^2$ is N, and Z is NH or N—($C_1$-$C_6$)alkyl, then Ar-G is not selected from the group consisting of aryl optionally substituted with one or more substituents selected from the group consisting of halo, alkynyl, —$CF_3$, —$(CH_2)_nOR^{57}$, —$(CH_2)_nSR^{57}$, —$NO_2$, $C_1$-$C_6$ alkyl, —CN, —$SO_2R^{50}$, —$(CH_2)_n$aryl and —$(CH_2)_nNR^{50}R^{51}$, and heteroaryl optionally substituted with one or more substituents selected from the group consisting of halo, alkynyl, —$CF_3$, —$(CH_2)_nOR^{57}$, —$(CH_2)_nSR^{57}$, —$NO_2$, $C_1$-$C_6$alkyl, —CN, —$SO_2R^{50}$, —$(CH_2)_n$aryl and —$(CH_2)_nNR^{50}R^{51}$, wherein $R^{57}$ is selected from the group consisting of H, $C_1$-$C_6$ alkyl, —$(CH_2)_nNR^{50}R^{51}$, —$(CH_2)_n$heterocyclyl, —$(CH_2)_n$aryl in which aryl is optionally substituted with one or more substitutents selected from the group consisting of halo, —$CF_3$, $C_1$-$C_6$alkoxy, —$NO_2$, $C_1$-$C_6$alkyl, —CN, —$SO_2R^{50}$, and —$(CH_2)_nNR^{50}R^{51}$, aryl$C_1$-$C_6$alkenylene in which aryl is optionally substituted with one or more substituents selected from the group consisting of halo, —$CF_3$, $C_1$-$C_6$alkoxy, —$NO_2$, $C_1$-$C_6$alkyl, —CN, —$SO_2R^{50}$, and —$(CH_2)_nNR^{50}R^{51}$, heteroaryl$C_1$-$C_6$alkenylene in which heteroaryl is optionally substituted with one or more substituents selected from the group consisting of halo, —$CF_3$, $C_1$-$C_6$alkoxy, —$NO_2$, $C_1$-$C_6$alkyl, —CN, —$SO_2R^{50}$, and —$(CH_2)_nNR^{50}R^{51}$, and —$(CH_2)_n$heteroaryl in which heteroaryl is optionally substituted with one or more substituents selected from the group consisting of halo, —$CF_3$, $C_1$-$C_6$alkoxy, —$NO_2$, $C_1$-$C_6$alkyl, —CN, —$SO_2R^{50}$, and —$(CH_2)_nNR^{50}R^{51}$; and when D is the group defined by —$(Z^{11})$—$(Z^{12})_m$—$(Z^{13})_{m1}$, $A^1$ is —S— and $A^3$ is CH, or $A^1$ is CH and $A^3$ is S, $A^2$ is N, and Z is NH, N—($C_1$-$C_3$alkyl) or N—C(O)$R^{53}$, then Ar-G is not the group defined by $(Q^1)$-$(Q^2)_{0-1}$-$(Q^3)_{0-1}$, wherein $Q^1$ is arylene, heteroarylene, aryl or aralkyl, $Q^2$ is O, S(O)$_2$, or S, and $Q^3$ is aralkyl, heteroary, or aryl.

In a preferred embodiment of the compounds according to the present invention, D is defined by the group $R^7$, wherein $R^7$ is selected from the group consisting of —H, halogen, $C_1$-$C_6$ alkyl, $C_3$-$C_{10}$ cycloalkyl, —C(O)$NR^{42}R^{43}$, —C(O) ($C_6$-$C_{10}$ aryl), —C(O)(heterocyclyl), —C(O)(heteroaryl), —Y—($C_6$-$C_{10}$ aryl), —Y-(5-10 membered heterocyclyl), —Y-(heteroaryl), —S-aryl, —S—$C_1$-$C_6$ alkyl, —SO—$C_1$-$C_6$ alkyl, —$SO_2$—$C_1$-$C_6$ alkyl, —Y—$NR^{42}R^{43}$, —$SO_2$ $NR^{42}R^{43}$ and —C(O)$OR^{6a}$, wherein the aforementioned $R^7$ groups other than —H and halogen are optionally substituted by 1 to 5 $R^{38}$.

In a preferred embodiment of the compounds according to the present invention, D is defined by the group $R^7$, wherein $R^7$ is selected from the group consisting of —H, —C(O) $NR^{42}R^{43}$, —Y-(5 to 10 membered heterocyclyl), —Y—($C_6$-$C_{10}$ aryl), —Y-(heteroaryl), —Y—$NR^{42}R^{43}$, $SO_2NR^{42}R^{43}$ and C(O)$OR^{42}$, wherein the aforementioned $R^7$ groups other than —H are optionally substituted by 1 to 5 $R^{38}$.

In a preferred embodiment of the compounds according to the present invention, $R^7$ is selected from the group consisting of —$(CH_2)_n$(5 to 10 membered heterocyclyl), —C(O) $NR^{42}R^{43}$, —$SO_2NR^{42}R^{43}$ and —$CO_2R^{42}$, wherein said $R^7$ group —$(CH_2)_n$(5 to 10 membered heterocyclyl) is unsubstituted or substituted by one or more $R^{38}$ groups.

In a preferred embodiment of the compounds according to the present invention, $R^7$ is selected from the group consisting of —$(CH_2)_n$(5 to 10 membered heterocyclyl), and —C(O) $NR^{42}R^{43}$.

In a preferred embodiment of the compounds according to the present invention, $R^7$ is —C(O)$NR^{42}R^{43}$, wherein $R^{42}$ and $R^{43}$ are independently selected from H, ($C_1$-$C_6$)alkyl, ($C_3$-$C_{10}$)cycloalkyl, —$(CH_2)_n(C_3$-$C_{10}$ cycloalkyl), —$(CH_2)_n(C_6$-$C_{10}$ aryl), —$(CH_2)_n$(5 to 10 membered heterocyclyl), —$(CH_2)_nO(CH_2)_iOR^{37}$, —$(CH_2)_nOR^{37}$, wherein n is an integer from 0 to 6, i is an integer from 2 to 6, and the alkyl, aryl and heterocyclyl moieties of said $R^{42}$ and $R^{43}$ groups are unsubstituted or substituted with one or more substituents independently selected from $R^{38}$, or $R^{42}$ and $R^{43}$ are taken together with the nitrogen to which they are attached to form a $C_5$-$C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring, wherein said $C_5$-$C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring are unsubstituted or substituted with 1 to 5 $R^{38}$ substituents, where $R^{42}$ and $R^{43}$ are not both bonded to the nitrogen directly through an oxygen.

In a preferred embodiment of the compounds according to the present invention, $R^7$ is —C(O)$NR^{42}R^{43}$, wherein $R^{42}$ and $R^{43}$ are taken together with the nitrogen to which they are attached to form a $C_5$-$C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring, wherein said $C_5$-$C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring are unsubstituted or substituted with 1 to 5 $R^{38}$ substituents.

In a preferred embodiment of the compounds according to the present invention. $R^7$ is —C(O)$NR^{42}R^{43}$, wherein $R^{42}$ and $R^{43}$ are taken together with the nitrogen to which they are attached to form a pyrrolidinyl, piperidinyl, piperazinyl, morpholinyl, thiomorpholinyl, isoquinolinyl, or dihydroisoquinolinyl ring, wherein said pyrrolidinyl, piperidinyl, piperazinyl, morpholinyl, thiomorpholinyl, isoquinolinyl, or dihydroisoquinolinyl ring are unsubstituted or substituted with 1 to 5 $R^{38}$ substituents.

In a preferred embodiment of the compounds according to the present invention, $R^7$ is —C(O)$NR^{42}R^{43}$, wherein $R^{42}$ and $R^{43}$ are taken together with the nitrogen to which they are attached to form a pyrrolidinyl, piperidinyl, piperazinyl, morpholinyl, or thiomorpholinyl ring, wherein said pyrrolidinyl, piperidinyl, piperazinyl, morpholinyl, or thiomorpholinyl rings are unsubstituted or substituted with 1 to 5 $R^{38}$ substituents.

In a preferred embodiment of the compounds according to the present invention, $R^7$ is —C(O)$NR^{42}R^{43}$, wherein $R^{42}$ and $R^{43}$ are taken together with the nitrogen to which they are attached to form a pyrrolidinyl or piperidinyl ring, wherein said pyrrolidinyl or piperidinyl ring are unsubstituted or substituted with 1 to 5 $R^{38}$ substituents.

In a preferred embodiment of the compounds according to the present invention, $R^7$ is —C(O)$NR^{42}R^{43}$, wherein $R^{42}$ and $R^{43}$ are taken together with the nitrogen to which they are attached to form a pyrrolidinyl ring, wherein said pyrrolidinyl is unsubstituted or substituted with 1 to 5 $R^{38}$ substituents.

In a preferred embodiment of the compounds according to the present invention, $R^7$ is —C(O)$NR^{42}R^{43}$, wherein $R^{42}$ and $R^{43}$ are taken together with the nitrogen to which they are attached to form a pyrrolidin-1-yl ring, wherein said pyrrolidin-1-yl is unsubstituted or substituted by 1 to 5 $R^{38}$ substituents.

In a preferred embodiment of the compounds according to the present invention, $R^7$ is —$(CH_2)_n$(5 to 10 membered heterocyclyl) group, wherein said —$(CH_2)_n$(5 to 10 membered heterocyclyl) group is unsubstituted or substituted by 1 to 5 $R^{38}$ groups.

In a preferred embodiment of the compounds according to the present invention, $R^7$ is —$(CH_2)_n$(5-8 membered heterocyclyl) group, said —$(CH_2)_n$(5-8 membered heterocyclyl) group is unsubstituted or substituted by 1 to 5 $R^{38}$ groups.

In a preferred embodiment of the compounds according to the present invention, $R^7$ is —$(CH_2)_n$(5 or 6 membered heterocyclyl) group, said —$(CH_2)_n$(5 or 6 membered heterocyclyl) group is unsubstituted or substituted by 1 to 5 $R^{38}$ groups.

In a preferred embodiment of the compounds according to the present invention, $R^7$ is —$(CH_2)_n$(5 membered heterocyclyl) group, said —$(CH_2)_n$(5 membered heterocyclyl) group is unsubstituted or substituted by 1 to 5 $R^{38}$ groups.

In a preferred embodiment of the compounds according to the present invention, $R^7$ is —$(CH_2)_n$thiazolyl, wherein n is an integer from 0 to 6, said —$(CH_2)_n$thiazolyl is unsubstituted or substituted by 1 to 5 $R^{38}$ groups.

In a preferred embodiment of the compounds according to the present invention, $R^7$ is a thiazolyl, said thiazolyl is unsubstituted or substituted by 1 to 5 $R^{38}$ groups.

In a preferred embodiment of the compounds according to the present invention, $R^7$ is an imidazolyl, said imidazolyl is unsubstituted or substituted by 1 to 5 $R^{38}$ groups.

In a preferred embodiment of the compounds according to the present invention, $R^7$ is selected from the group consisting of imidazolyl, oxazolyl, oxadiazolyl, isoxazolyl, thiazolyl and thiadiazolyl, wherein the imidazolyl, oxazolyl, oxadiazolyl, isoxazolyl, thiazolyl and thiadiazolyl, each of which is optionally substituted by 1 to 5 $R^{38}$ groups.

In a preferred embodiment of the compounds according to the present invention, $R^7$ is selected from the group consisting of halo, —$CO_2H$, —$CONH_2$ and —$CSNH_2$.

In a preferred embodiment of the compounds according to the present invention, $R^7$ is a heteroaryl group optionally substituted by one or more moiety selected from the group consisting of halo, cyano, nitro, trifluoromethoxy, trofluoromethyl, azido, —C(O)$R^{40}$, —C(O)O$R^{40}$, —OC(O)$R^{40}$, —OC(O)O$R^{40}$, —$NR^{36}$C(O)$NR^{36}R^{39}$, —$NR^{36}R^{37}$, —O$R^{37}$, —$SO_2NR^{36}R^{39}$, ($C_1$-$C_6$)alkyl, ($C_3$-$C_{10}$)cycloalkyl, —$(CH_2)_n$O$(CH_2)_i$$NR^{36}R^{39}$, —$(CH_2)_n$O$(CH_2)_i$O$R^{37}$, —$(CH_2)_n$O$R^{37}$, —S(O)$_j$($C_1$-$C_6$ alkyl), —$(CH_2)_n$($C_6$-$C_{10}$ aryl), —$(C_2)_n$(5 to 10 membered heterocyclyl), —C(O)$(CH_2)_n$($C_6$-$C_{10}$aryl), —$(CH_2)_n$O$(CH_2)_i$($C_6$-$C_{10}$ aryl), —$(CH_2)_n$O$(CH_2)_i$(5 to 10 membered heterocyclyl), —C(O)$(CH_2)_n$(5 to 10 membered heterocyclyl), —$(CH2)_n$$NR^{39}$$(CH_2)_i$$NR^{36}R^{39}$, —$(CH_2)_n$$NR^{39}CH_2C(O)NR^{36}R^{39}$, —$(CH_2)_j$$NR^{39}(CH_2)_i$$NR^{37}C(O)R^{40}$, $(CH_2)_n$$NR^{39}(CH_2)_n$O$(CH_2)_i$O$R^{37}$, —$(CH_2)_n$$NR^{39}(CH_2)_i$S(O)$_j$($C_1$-$C_6$ alkyl), —$(CH_2)_j$$NR^{39}$, —$(CH_2)_n$$R^{36}$, —$SO_2(CH_2)_n$($C_6$-$C_{10}$ aryl), and —$SO_2(CH_2)_n$(5 to 10 membered heterocyclyl), wherein j is an integer from 0 to 2, n is an integer from 0 to 6, i is an integer from 2 to 6, the —$(CH_2)_i$— and —$(CH_2)_n$— moieties of the said substituent groups optionally include a carbon-carbon double or triple bond where n is an integer between 2 and 6, and the alkyl, aryl and heterocyclyl moieties of the substituent groups are unsubstituted or substituted with one or more substituents independently selected from halo, cyano, nitro, trifluoromethyl, azido, —OH, —C(O)$R^{40}$, —C(O)O$R^{40}$, —OC(O)$R^{40}$, —OC(O)O$R^{40}$, —$NR^{36}C(O)R^{39}$, —C(O)$NR^{36}R^{39}$, —$(CH_2)_n$$NR^{36}R^{39}$, ($C_1$-$C_6$)alkyl, ($C_3$-$C_{10}$)cycloalkyl, —$(CH_2)_n$($C_6$-$C_{10}$ aryl), —$(CH_2)_n$(5 to 10 membered heterocyclyl), —$(CH_2)_n$O$(CH_2)_i$O$R^{37}$, and —$(CH_2)_n$O$R^{37}$, wherein n is an integer from 0 to 6 and i is an integer from 2 to 6, and wherein $R^{36}$ and $R^{39}$ are independently selected from the group consisting of H, —OH, ($C_1$-$C_6$)alkyl, ($C_3$-$C_{10}$)cycloalkyl, —$(CH_2)_n$($C_6$-$C_{10}$ aryl), —$(CH_2)_n$(5 to 10 membered heterocyclyl), —$(CH_2)_n$O$(CH_2)_i$O$R^{37}$ and —$(CH_2)_n$O$R^{37}$, wherein n is an integer from 0 to 6 and i is an integer from 2 to 6, and the alkyl, aryl and heterocyclyl moieties of the $R^{36}$ and $R^{39}$ groups are unsubstituted or substituted with one or more substituents independently selected from hydroxy, halo, cyano, nitro, trifluoromethyl, azido, —C(O)$R^{40}$, —C(O)O$R^{40}$, —CO(O)$R^{40}$, —OC(O)O$R^{40}$, —$NR^{37}C(O)R^{41}$, —C(O)$NR^{37}R^{41}$, —$NR^{37}R^{41}$, ($C_1$-$C_6$) alkyl, —$(CH_2)_n$($C_6$-$C_{10}$ aryl), —$(CH_2)_n$(5 to 10 membered heterocyclyl), —$(CH_2)_n$O$(CH_2)_i$O$R^{37}$, and —$(CH_2)_n$O$R^{37}$, wherein n is an integer from 0 to 6 and i is an integer from 2 to 6, where when $R^{36}$ and $R^{39}$ are both attached to the same nitrogen, then $R^{36}$ and $R^{39}$ are not both bonded to the nitrogen directly through an oxygen.

In a preferred embodiment of the compounds according to the present invention, $R^7$ is selected from the group consisting of H, —($C_1$-$C_6$)alkyl, —C(O)$NR^{36}R^{37}$, —C(O)($C_6$-$C_{10}$ aryl), —$(CH_2)_n$($C_6$-$C_{10}$ aryl) and —$(CH_2)_n$(5 to 10 membered heterocyclyl), wherein the $R^7$ groups other than H are optionally substituted by 1 to 5 $R^{38}$ groups. Preferably $R^7$ is —$(CH_2)_n$($C_6$-$C_{10}$ aryl) and —$(CH_2)_n$(5 to 10 membered heterocyclyl), optionally substituted by 1 to 5 $R^{38}$ groups, more preferably phenyl or pyridyl, optionally substituted by 1 to 5 $R^{38}$ groups.

In a preferred embodiment of the compounds according to the present invention, $R^7$ is selected from the group consisting of H, —($C_1$-$C_6$)alkyl, —C(O)$NR^{36}R^{37}$, —C(O)($C_6$-$C_{10}$ aryl), —$(CH_2)_n$($C_6$-$C_{10}$ aryl) and —$(CH_2)_n$(5 to 10 membered heterocyclyl), wherein the $R^7$ groups other than H are optionally substituted by tert-butyl-dimethyl-silanyl and 1 to 3 $R^{38}$ groups.

In a preferred embodiment of the compounds according to the present invention, $R^7$ is selected from the group consisting of —C(O)$NR^{42}R^{43}$, —$(CH_2)_n$$NR^{42}R^{43}$, —$NR^{42}C(=O)R^{43}$, —$SO_2R^{42}$), —$SO_2NR^{42}R^{43}$, —$NR^{37}SO_2R^{42}$, —NR$^{37}$SO$_2$NR$^{42}$R$^{43}$, —C(=N—OR$^{42}$)R$^{43}$, —C(=NR$^{42}$)R$^{43}$, —NR$^{37}$C(=NR$^{42}$)R$^{43}$, —C(=NR$^{42}$)NR$^{37}$R$^{43}$, —NR$^{37}$C(=NR$^{42}$)NR$^{37}$R$^{43}$, —C(O)R$^{42}$, —CO$_2$R$^{42}$, wherein each R$^{42}$ and R$^{43}$ is independently selected from the group consisting of H, (C$_1$-C$_6$)alkyl, —(CH$_2$)$_n$C$_3$-C$_{10}$cycloalkyl), —(CH$_2$)$_n$(C$_6$-C$_{10}$ aryl), —(CH$_2$)$_n$(5 to 10 membered heterocyclyl), —(CH$_2$)$_n$O(CH$_2$)$_i$OR$^{37}$, —(CH$_2$)$_n$OR$^{37}$, wherein n is an integer from 0 to 6 and i is an integer from 2 to 6, and the alkyl, aryl and heterocyclyl moieties of the foregoing R$^{42}$ and R$^{43}$ groups are optionally substituted by 1 to 3 substituents independently from R$^{38}$, or R$^{42}$ and R$^{43}$ are taken together with the nitrogen to which they are attached to form a C$_5$-C$_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring, wherein said C$_5$-C$_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring are unsubstituted or substituted with 1 to 5 R$^{38}$ substituents, with the proviso that R$^{42}$ and R$^{43}$ are not both bonded to the nitrogen directly through an oxygen.

In a preferred embodiment of the compounds according to the present invention, R$^7$ is selected from the group consisting of —C(O)NR$^{42}$R$^{43}$, —SO$_2$R$^{42}$, —SO$_2$NR$^{42}$R$^{43}$, —C(=N—OR$^{42}$)R$^{43}$ and —C(=NR$^{42}$)R$^{43}$.

In a preferred embodiment of the compounds according to the present invention, R$^7$ is —C(O)NR$^{42}$R$^{43}$, wherein each R$^{42}$ and R$^{43}$ is independently selected from the group consisting of H, (C$_1$-C$_6$)alkyl, —(CH$_2$)$_n$OR$^{37}$, wherein n is an integer from 0 to 6 and the alkyl moiety of the foregoing R$^{42}$ and R$^{43}$ groups are optionally substituted by 1 to 3 substituents independently from halo, cyano, trifluoromethyl, —C(O)R$^{40}$, —NR$^{37}$C(O)R$^{41}$, —C(O)NR$^{37}$R$^{41}$, —NR$^{37}$R$^{41}$, (C$_1$-C$_6$)alkyl, —(CH$_2$)$_n$(C$_6$-C$_{10}$ aryl), —(CH$_2$)$_n$(5 to 10 membered heterocyclyl), —(CH$_2$)$_n$O(CH$_2$)$_i$OR$^{37}$ and —(CH$_2$)$_n$OR$_{37}$, wherein n is an integer from 0 to 6 and i is an integer from 2 to 6, or R$^{42}$ and R$^{43}$ are taken together with the nitrogen to which they are attached to form a C$_5$-C$_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring, wherein said C$_5$-C$_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring are unsubstituted or substituted with 1 to 5 R$^{38}$ substituents, with the proviso that R$^{42}$ and R$^{43}$ are not both bonded to the nitrogen directly through an oxygen.

In a preferred embodiment of the compounds according to the present invention, R$^7$ is —C(O)NR$^{42}$R$^{43}$, wherein R$^{42}$ and R$^{43}$ are taken together with the nitrogen to which they are attached to form a C$_5$-C$_9$ azabicyclic, aziridinyl, azetidinyl, pyrrolidinyl, piperidinyl, piperazinyl or morpholinyl ring, wherein said C$_5$-C$_9$ azabicyclic, aziridinyl, azetidinyl, pyrrolidinyl, piperidinyl, piperazinyl or morpholinyl ring are unsubstituted or substituted with 1 to 5 R$^{38}$ substituents.

In a preferred embodiment of the compounds according to the present invention, R$^7$ is —C(O)NR$^{42}$R$^{43}$, wherein R$^{42}$ and R$^{43}$ are taken together with the nitrogen to which they are attached to form a C$_5$-C$_9$ azabicyclic, aziridinyl, azetidinyl or pyrrolidinyl ring, wherein said C$_5$-C$_9$ azabicyclic, aziridinyl, azetidinyl or pyrrolidinyl ring are unsubstituted or substituted with 1 to 5 R$^{38}$ substituents.

In a preferred embodiment of the compounds according to the present invention, R$^7$ is —C(O)NR$^{42}$R$^{43}$, wherein R$^{42}$ and R$^{43}$ are taken together with the nitrogen to which they are attached to form a C$_5$-C$_9$ azabicyclic, azetidinyl or pyrrolidinyl ring, wherein said C$_5$-C$_9$ azabicyclic, azetidinyl or pyrrolidinyl ring are unsubstituted or substituted with 1 to 5 R$^{38}$ substituents.

In a preferred embodiment of the compounds according to the present invention, R$^7$ is —C(O)NR$^{42}$R$^{43}$, wherein R$^{42}$ and R$^{43}$ are taken together with the nitrogen to which they are attached to form a C$_5$-C$_9$ azabicyclic ring, wherein said C$_5$-C$_9$ azabicyclic ring is unsubstituted or substituted with 1 to 5 R$^{38}$ substituents.

In a preferred embodiment of the compounds according to the present invention, R$^7$ is —C(O)NR$^{42}$R$^{43}$, wherein R$^{42}$ and R$^{43}$ are taken together with the nitrogen to which they are attached to form a azetidinyl ring, wherein said azetidinyl ring is unsubstituted or substituted with 1 to 5 R$^{38}$ substituents.

In a preferred embodiment of the compounds according to the present invention, R$^7$ is —C(O)NR$^{42}$R$^{43}$, wherein R$^{42}$ and R$^{43}$ are taken together with the nitrogen to which they are attached to form a pyrrolidinyl ring, wherein said pyrrolidinyl ring is unsubstituted or substituted with 1 to 5 R$^{38}$ substituents.

In a preferred embodiment of the compounds according to the present invention, R$^7$ is selected from the group consisting of —H, halogen, nitro, azido, —NR$^{6a}$R$^{6b}$, —NR$^{6a}$SO$_2$R$^{6b}$, —NR$^{6a}$C(O)R$^{6b}$, —OC(O)R$^{6b}$, —NR$^{6a}$C(O)OR$^{6b}$, —OC(O)NR$^{6a}$R$^{6b}$, —OR$^{6a}$, —SR$^{6a}$, —S(O)R$^{6a}$, —SO$_2$R$^{6a}$, —SO$_3$R$^{6a}$, —SO$_2$NR$^{6a}$R$^{6b}$, —COR$^{6a}$, —CO$_2$R$^{6a}$, —CONR$^{6a}$R$^{6b}$, —(C$_1$-C$_4$)fluoroalkyl, —(C$_1$-C$_4$)fluoroalkoxy, —(CZ$^3$Z$^4$)$_a$CN, and a moiety selected from the group consisting of —(CZ$^3$Z$^4$)$_a$-aryl, —(CZ$^3$Z$^4$)$_a$-heterocycle, (C$_2$-C$_6$)alkynyl, —(CZ$^3$Z$^4$)$_a$—(C$_3$-C$_6$)cycloalkyl, —(CZ$^3$Z$^4$), —(C$_5$-C$_6$)cycloalkenyl, (C$_2$-C$_6$) alkenyl and (C$^1$-C$^6$)alkyl, wherein said moiety is optionally substituted with 1 to 3 independently selected Y$^2$ groups, where a is 0, 1, 2, or 3, and wherein when a is 2 or 3, the CZ$^3$Z$^4$ units may be the same or different; wherein each R$^{6a}$ and R$^{6h}$ is independently selected from the group consisting of hydrogen and a moiety selected from the group consisting of —(CZ$^5$Z$^6$)$_u$—(C$_3$-C$_6$)cycloalkyl, —(CZ$^5$Z$^6$)$_u$—(C$_5$-C$_6$)cycloalkenyl, —(CZ$^5$Z$^6$)$_u$-aryl, —(CZ$^5$Z$^6$)$_u$-heterocycle, (C$_2$-C$_6$)alkenyl, and (C$_1$-C$_6$) alkyl, wherein said moiety is optionally substituted with 1 to 3 independently selected Y$^3$ groups, where u is 0, 1, 2, or 3, and wherein when u is 2 or 3, the CZ$^5$Z$^6$ units may be the same or different, or R$^{6a}$ and R$^{6b}$ taken together with adjacent atoms form a atoms form a heterocycle;

each Z$^3$, Z$^4$, Z$^5$ and Z$^6$ is independently selected from the group consisting of H, F and (C$_1$-C$_6$)alkyl, or each Z$^3$ and Z$^4$, or Z$^5$ and Z$^6$ are selected together to form a carbocycle, or two Z$^3$ groups on adjacent carbon atoms are selected together to optionally form a carbocycle;

each Y$^2$ and Y$^3$ is independently selected from the group consisting of halogen, cyano, nitro, tetrazolyl, guanidino, amidino, methylguanidino, azido, —C(O)Z$^7$, —OC(O)NH$_2$, —OC(O) NHZ$^7$, —OC(O)NZ$^7$Z$^8$, —NHC(O)Z$^7$, —NHC(O)NH$_2$, —NHC(O)NHZ$^7$, —NHC(O)NZ$^7$Z$^8$, —C(O)OH, —C(O)OZ$^7$, —C(O)NH$_2$, —C(O)NHZ$^7$, —C(O)NZ$^7$Z$^8$, —P(O)$_3$H$_2$, —P(O)$_3$(Z$^7$)$_2$, —S(O)$_3$H, —S(O)Z$^7$, —S(O)$_2$Z$^7$, —S(O)$_3$Z$^7$, —Z$^7$, —OZ$^7$, —OH, —NH$_2$, —NHZ$^7$, —NZ$^7$Z$^8$, —C(=NH)NH$_2$, —C(=NOH)NH$_2$, —N-morpholino, (C$_2$-C$_6$)alkenyl, (C$_2$-C$_6$)alkynyl, (C$_1$-C$_6$)haloalkyl, (C$_2$-C$_6$)haloalkenyl, (C$_2$-C$_6$)haloalkynyl, (C$_1$-C$_6$)haloalkoxy, —(CZ$^9$Z$^{10}$)$_r$NH$_2$, —(CZ$^9$Z$^{10}$)$_r$—NHZ$^3$, —(CZ$^9$Z$^{10}$)$_r$NZ$^7$Z$^8$, —X$^6$ $(CZ^9Z^{10})_r$—$(C_3$-$C_8)$cycloalkyl, —$X^6(CZ^9Z^{10})_r$—$(C_5$-$C_8)$cycloalkenyl, —$X^6(CZ^9Z^{10})_r$-aryl and —$X^6(CZ^9Z^{10})_r$-heterocycle, wherein r is 1, 2, 3 or 4;

$X^6$ is selected from the group consisting of O, S, NH, —C(O)—, —C(O)NH—, —C(O)O—, —S(O)—, —S(O)$_2$— and —S(O)$_3$—;

$Z^7$ and $Z^8$ are independently selected from the group consisting of an alkyl of 1 to 12 carbon atoms, an alkenyl of 2 to 12 carbon atoms, an alkynyl of 2 to 12 carbon atoms, a cycloalkyl of 3 to 8 carbon atoms, a cycloalkenyl of 5 to 8 carbon atoms, an aryl of 6 to 14 carbon atoms, a heterocycle of 5 to 14 ring atoms, an aralkyl of 7 to 15 carbon atoms, and a heteroaralkyl of 5 to 14 ring atoms, or $Z^7$ and $Z^8$ together may optionally form a heterocycle;

$Z^9$ and $Z^{10}$ are independently selected from the group consisting of H, F, a $(C_1$-$C_{12})$alkyl, a $(C_6$-$C_{14})$aryl, a $(C_5$-$C_{14})$heteroaryl, a $(C_7$-$C_{15})$aralkyl and a $(C_5$-$C_{14})$heteroaralkyl, or $Z^9$ and $Z^{10}$ are taken together form a carbocycle, or two $Z^9$ groups on adjacent carbon atoms are taken together to form a carbocycle; or any two $Y^2$ or $Y^3$ groups attached to adjacent carbon atoms may be taken together to be —O[C($Z^9$)($Z^{10}$)]$_r$O or —O[C($Z^9$)($Z^{10}$)]$_{r+1}$, or any two $Y^2$ or $Y^3$ groups attached to the same or adjacent carbon atoms may be selected together to form a carbocycle or heterocycle; and wherein any of the above-mentioned substituents comprising a $CH_3$ (methyl), $CH_2$ (methylene), or CH (methine) group which is not attached to a halogen, SO or $SO_2$ group or to a N, O or S atom optionally bears on said group a substituent selected from hydroxy, halogen, $(C_1$-$C_4)$alkyl, $(C_1$-$C_4)$alkoxy and an —N [$(C_1$-$C_4)$alkyl][$(C_1$-$C_4)$alkyl].

In a preferred embodiment of the compounds according to the present invention $R^7$ is selected from the group consisting of —H, —Y-(aryl), —Y-(heteroaryl) and C(O)-heterocyclyl, each of which, except for —H, is optionally substituted with 1 to 5 $R^{38}$.

In a preferred embodiment of the compounds according to the present invention, $R^7$ is selected from the group consisting of

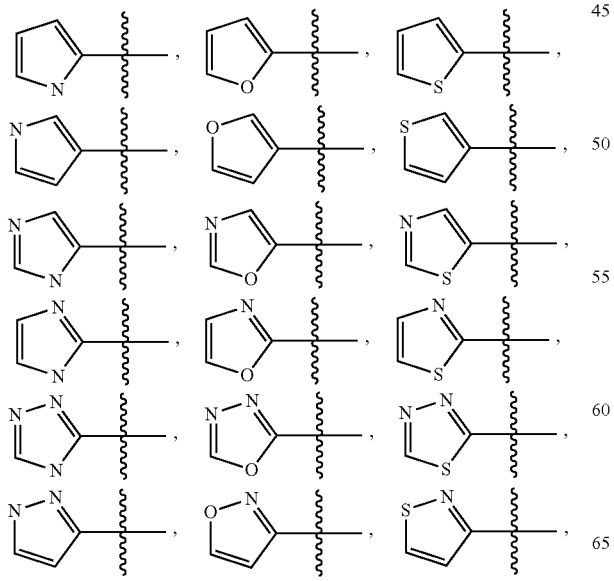

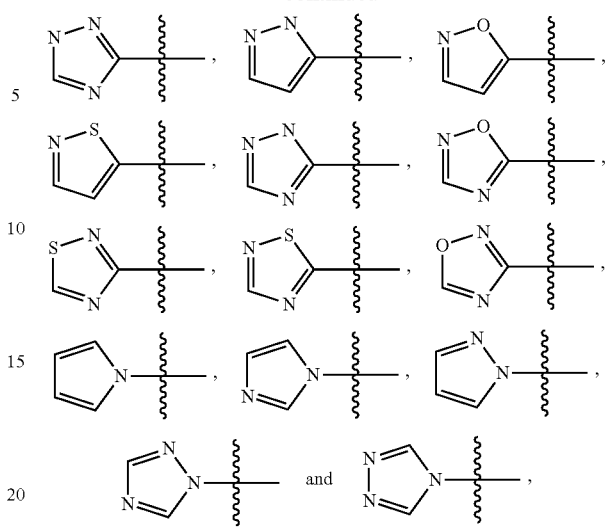

wherein the members of said group are optionally substituted by 1 to 3 $R^{38}$.

In a preferred embodiment of the compounds according to the present invention, $R^7$ is selected from the group consisting of

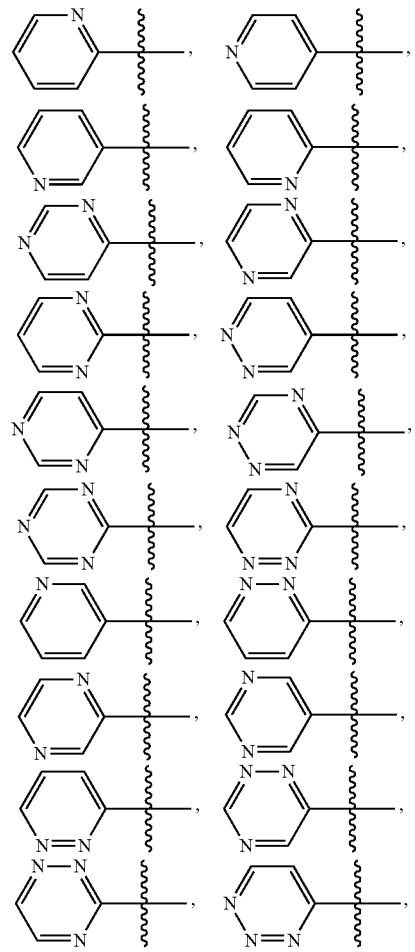

-continued
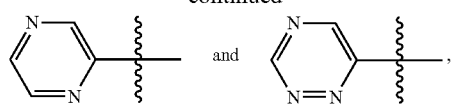
wherein the members of said group are optionally substituted with 1 to 3 $R^{38}$.
In a preferred embodiment of the compounds according to the present invention, $R^7$ is selected from the group consisting of
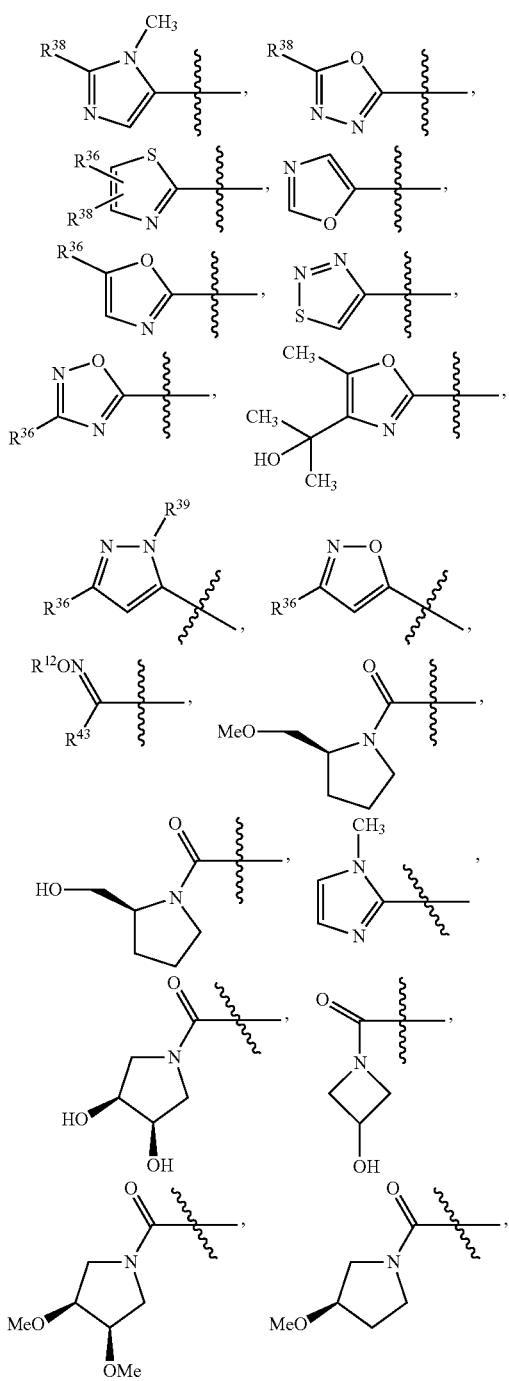
-continued
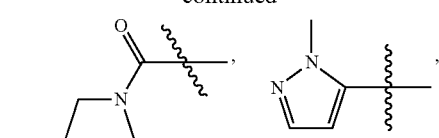
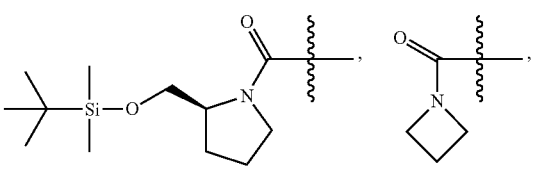
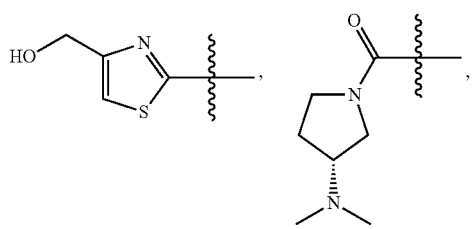
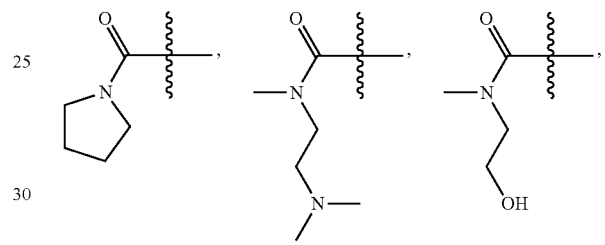
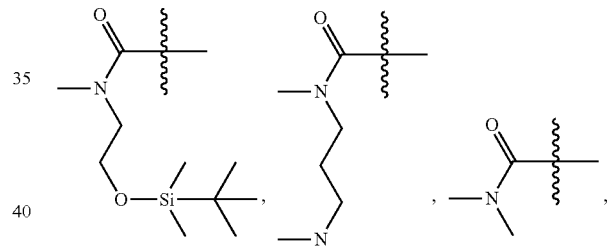
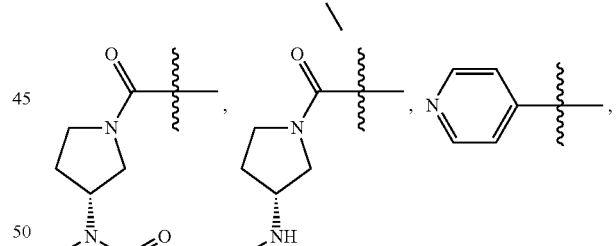
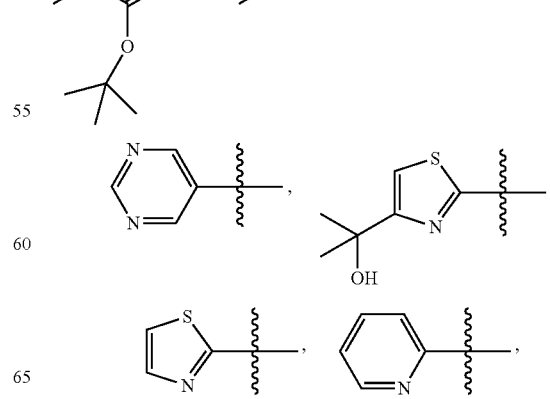

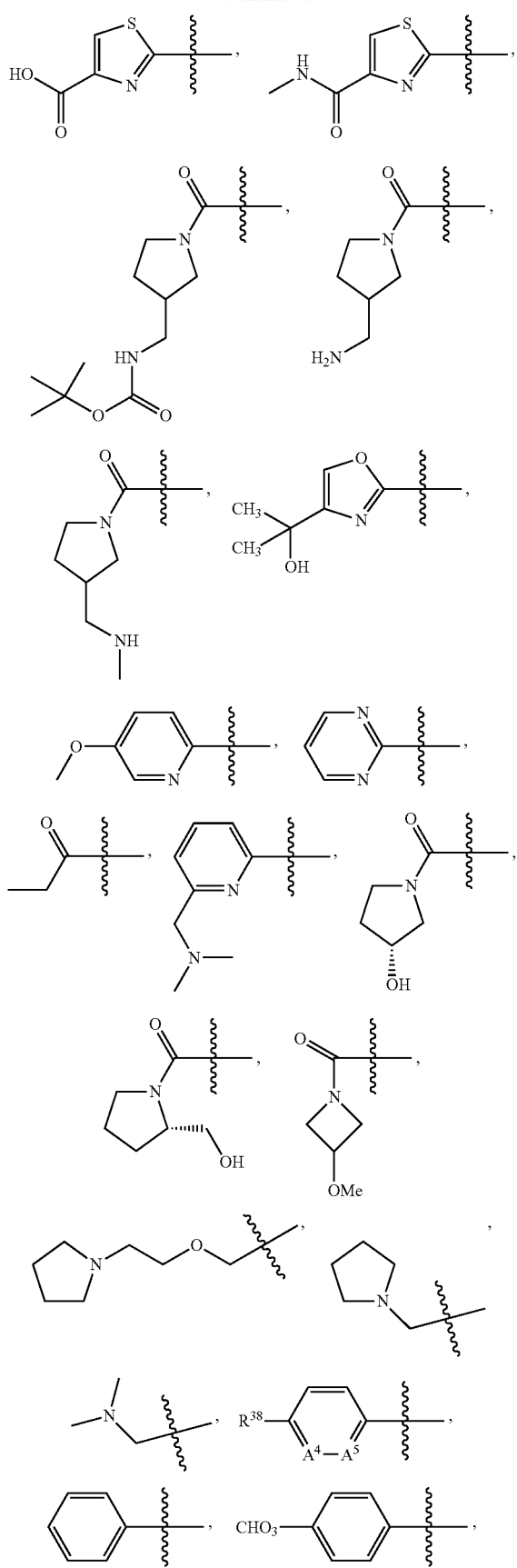
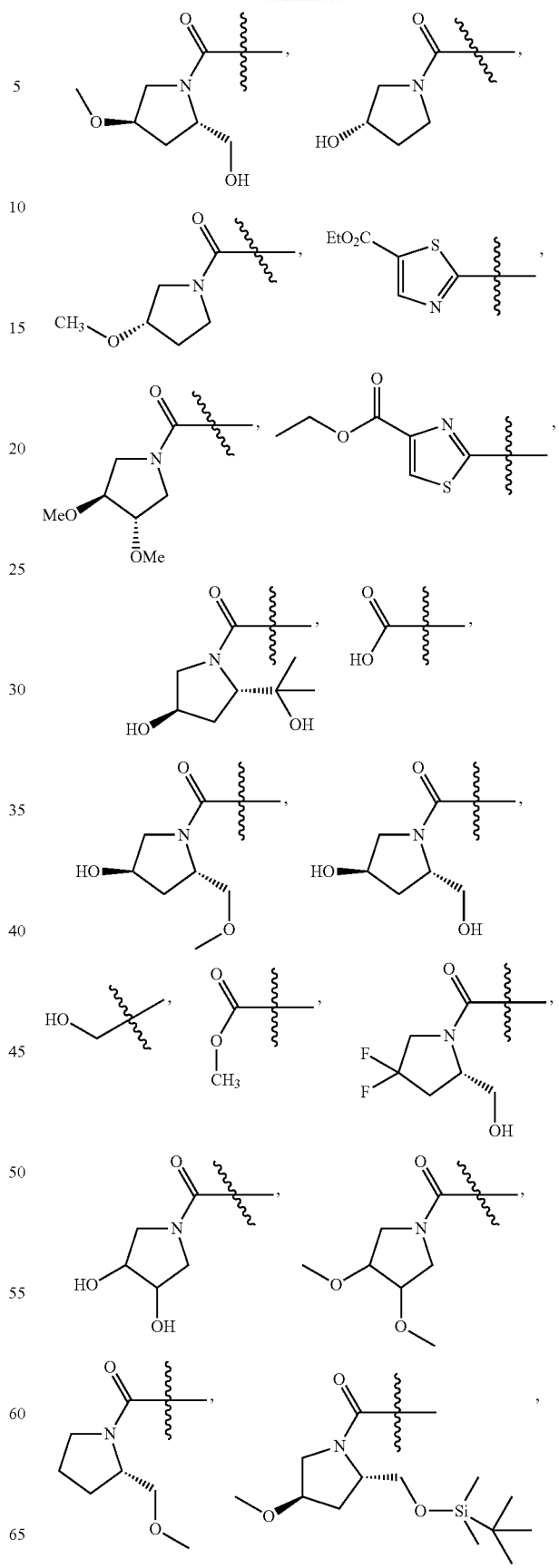

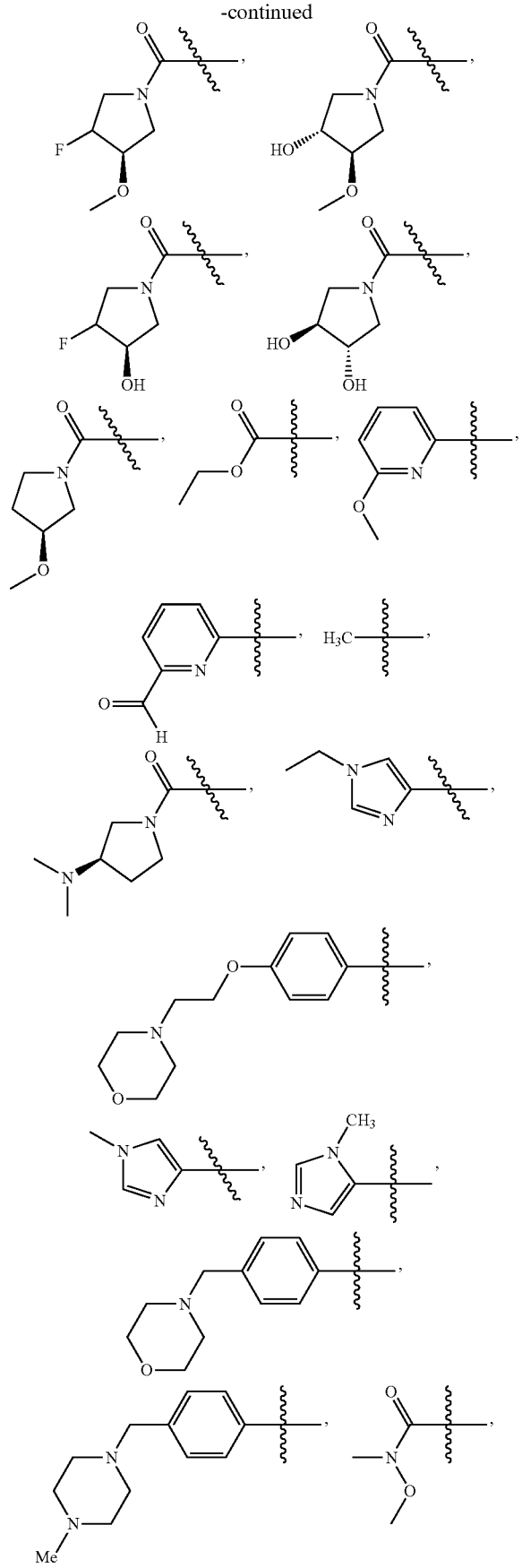
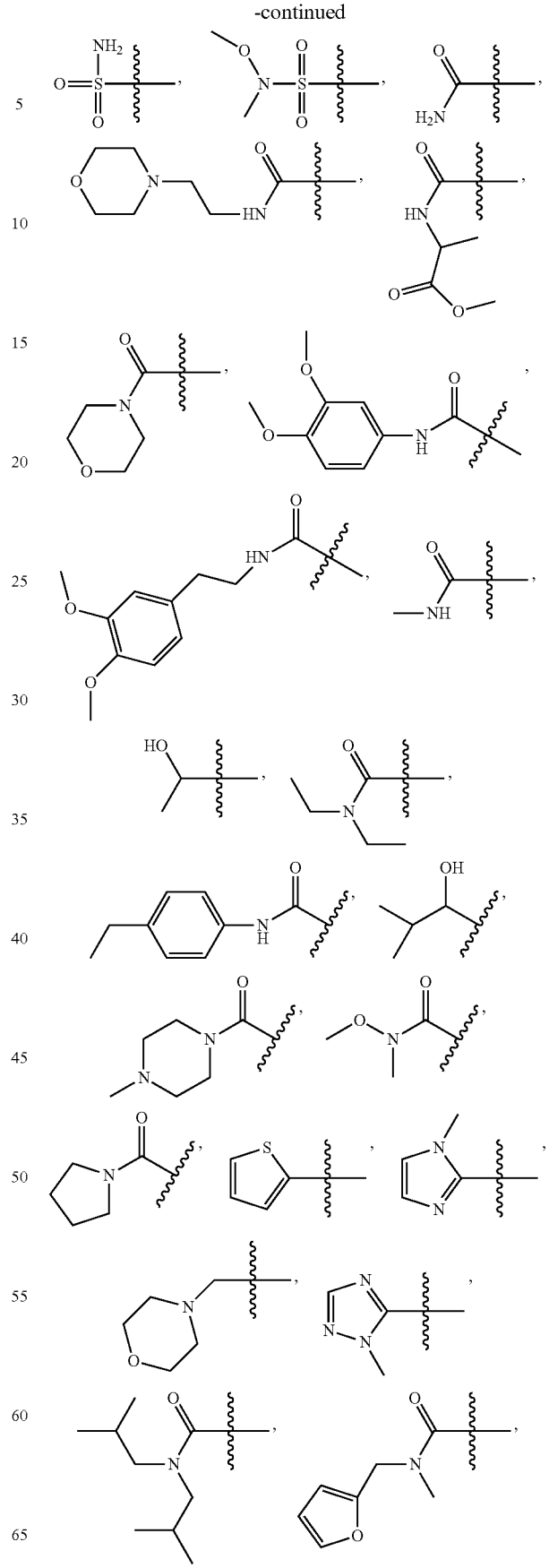

-continued

-continued
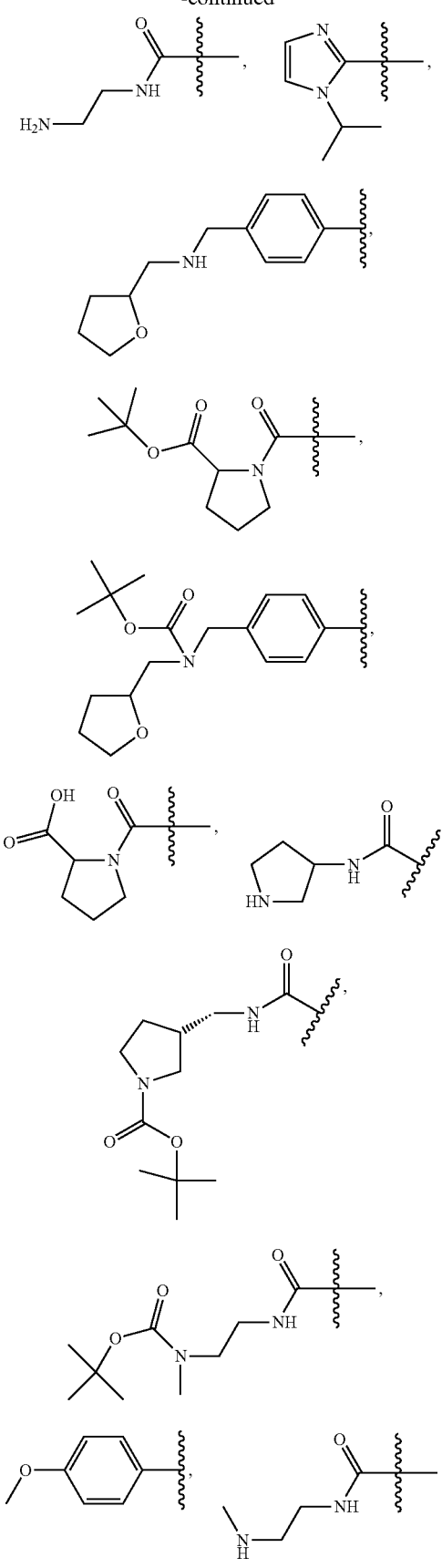
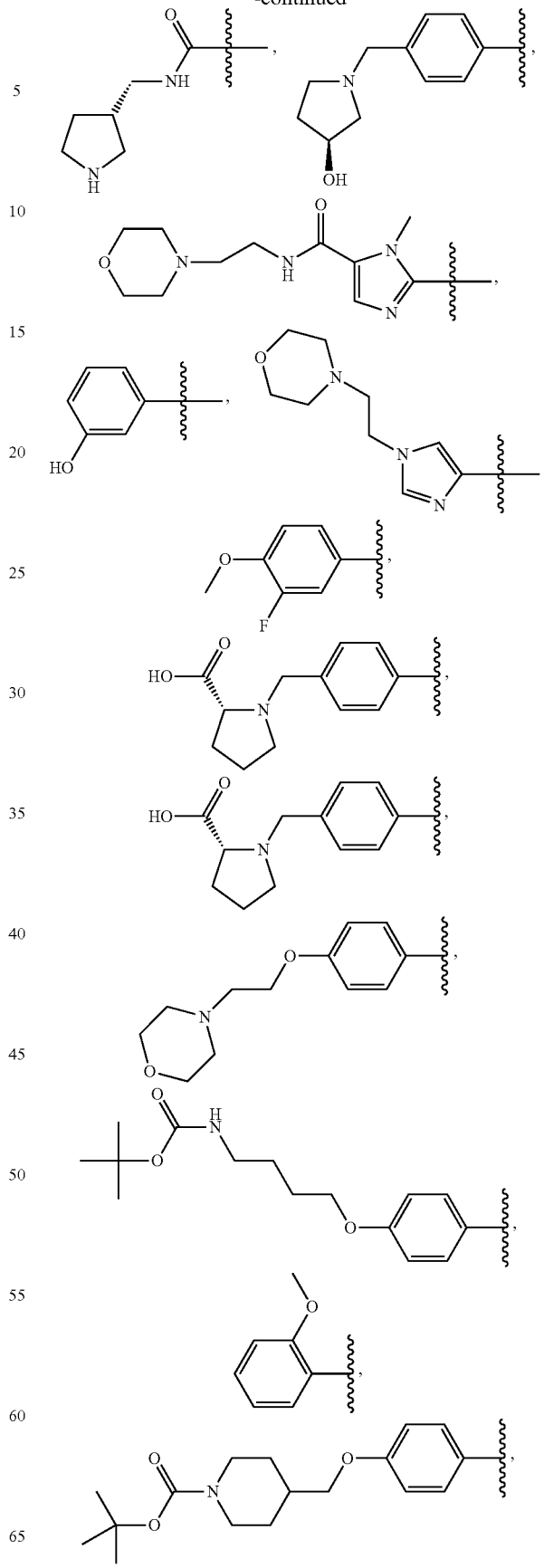

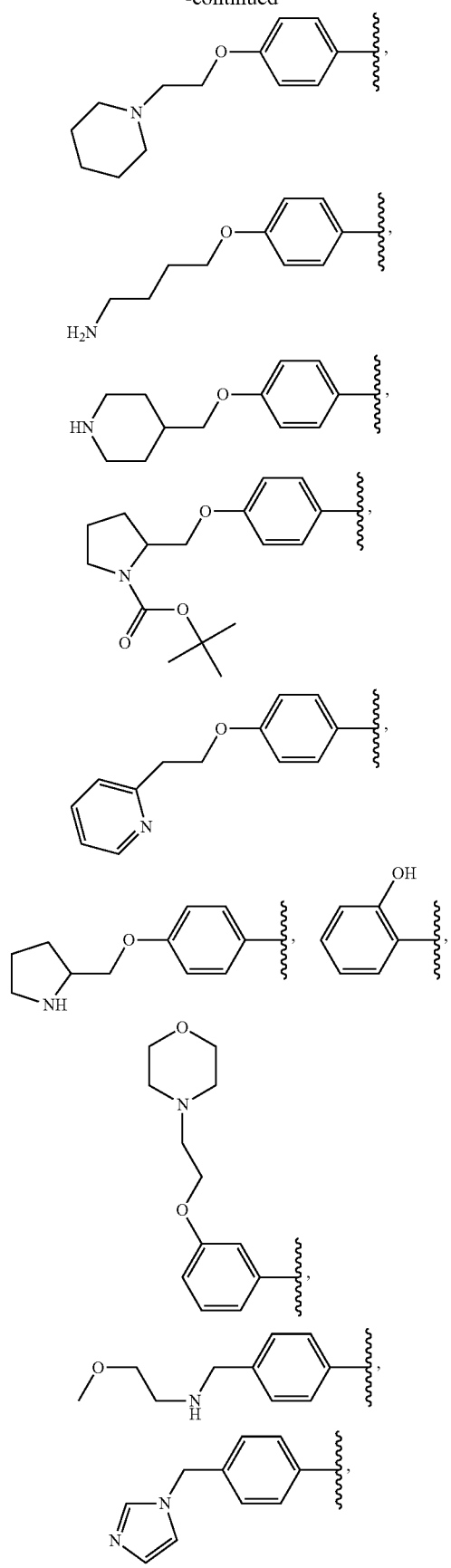
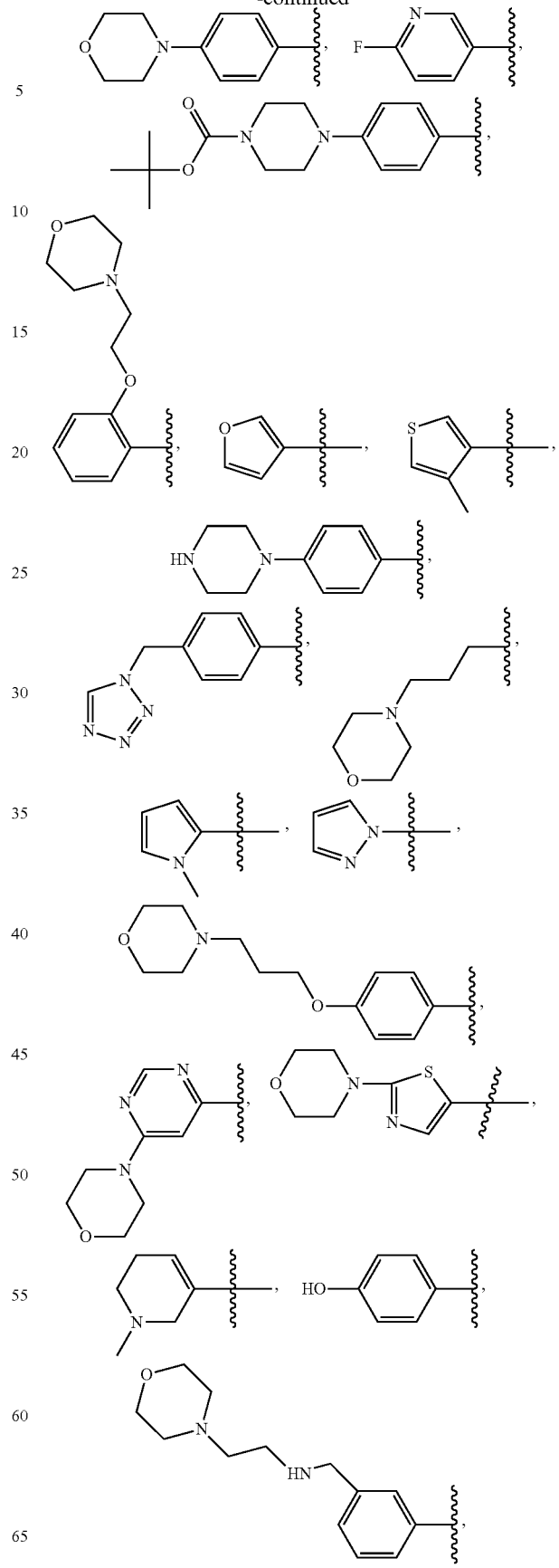

-continued

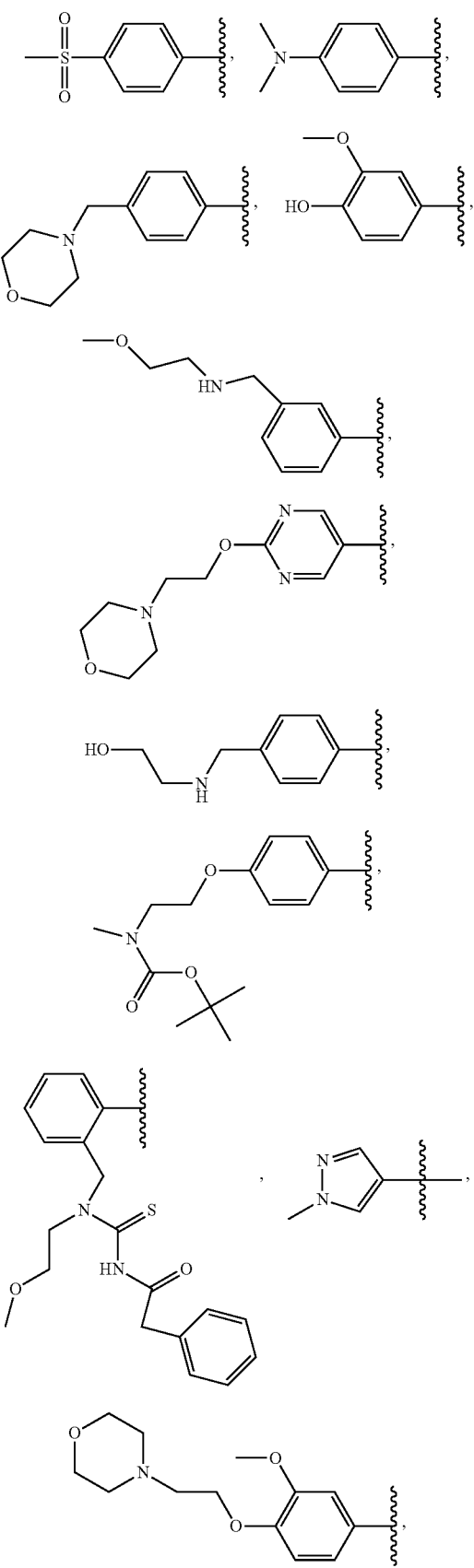
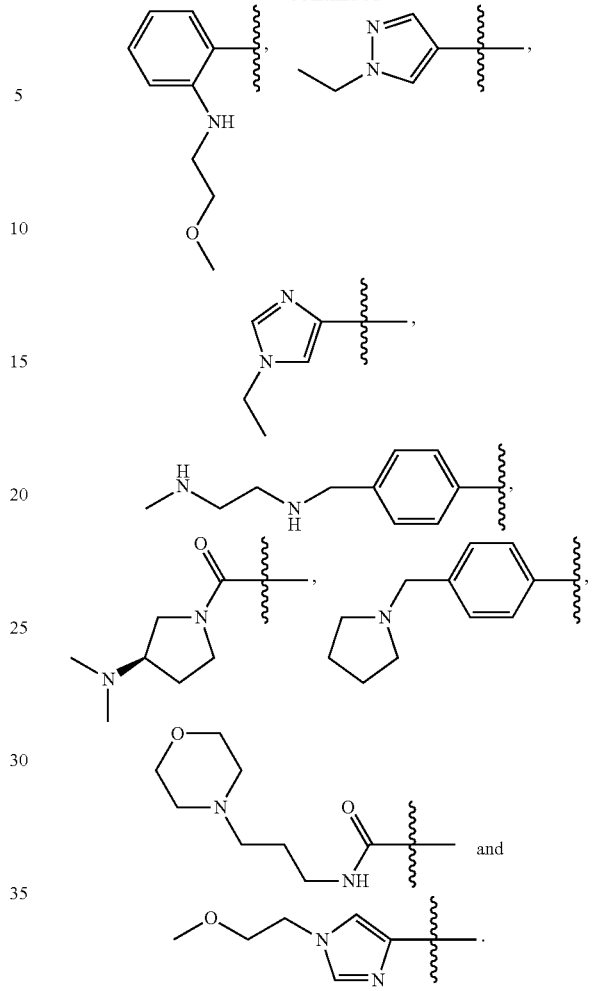

In a preferred embodiment of the compounds according to the present invention, $R^7$ is selected from the group consisting of phenyl and pryidyl, which are optionally substituted by 1 to 5 $R^{38}$.

In a preferred embodiment of the compounds according to the present invention, D is defined by the group $R^1$, wherein $R^1$ is —C≡CH or —C≡C—$(CR^{45}R^{45})_n$—$R^{46}$; wherein each $R^{45}$ is independently selected from the group consisting of H, a $(C_1\text{-}C_6)$alkyl and a $(C_3\text{-}C_8)$cycloalkyl;

$R^{46}$ is selected from the group consisting of heterocyclyl, —N($R^{47}$)—C(O)—N($R^{47}$)($R^{48}$), —N($R^{47}$)—C(S)—N($R^{47}$)($R^{48}$), —N($R^{47}$)—C(O)—O$R^{48}$, —N($R^{47}$)—C(O)—$(CH_2)_n$—$R^{48}$, —N($R^{47}$)—SO$_2R^{47}$, —$(CH_2)_n$NR$^{47}R^{48}$, —$(CH_2)_n$OR$^{48}$, —$(C_2)_n$SR$^{49}$, —$(CH_2)_n$S(O)R$^{49}$, —$(CH_2)_n$S(O)$_2R^{49}$, —OC(O)R$^{49}$, —OC(O)OR$^{49}$, —C(O)NR$^{47}R^{48}$, heteroaryl optionally substituted with one or more substituents selected from the group consisting of halo, —CF$_3$, $(C_1\text{-}C_6)$alkoxy, —NO$_2$, $(C_1\text{-}C_6)$alkyl, —CN, —SO$_2R^{50}$ and —$(CH_2)_n$NR$^{50}R^{51}$, and aryl optionally substituted with one or more substituents selected from the group consisting of halo, —CF$_3$, $(C_1\text{-}C_6)$alkoxy, —NO$_2$, $(C_1\text{-}C_6)$alkyl, —CN, —SO$_2R^{50}$ and —$(CH_2)_n$NR$^{50}R^{51}$;

$R^{47}$ and $R^{48}$ are independently selected from the group consisting of H, $(C_1\text{-}C_6)$alkyl, $(C_3\text{-}C_8)$cycloalkyl, heterocyclyl, —$(CH_2)_n$NR$^{50}R^{51}$, —$(CH_2)_n$OR$^{50}$, —$(CH_2)_n$C(O)R$^{49}$, —C(O)$_2R^{49}$, —$(CH_2)_n$SR$^{49}$, —$(CH_2)_n$S(O)R$^{49}$, —(CH$_2$)$_n$S(O)$_2$R$^{49}$, —(CH$_2$)$_n$R$^{49}$, —(CH$_2$)$_n$CN, aryl optionally substituted with one or more substituents selected from the group consisting of halo, —CF$_3$, (C$_1$-C$_6$) alkoxy, —NO$_2$, (C$_1$-C$_6$)alkyl, —CN, —(CH$_2$)$_n$OR$^{49}$, —(CH$_2$)$_n$heterocyclyl, —(CH$_2$)$_n$heteroaryl, —SO$_2$R$^{50}$ and —(CH$_2$)$_n$NR$^{50}$R$^{51}$, and heteroaryl optionally substituted with one or more substituents selected from the group consisting of halo, —CF$_3$, (C$_1$-C$_6$)alkoxy, —NO$_2$, (C$_1$-C$_6$) alkyl, —CN, —(CH$_2$)$_n$OR$^{49}$, —(CH$_2$)$_n$heterocyclyl, —(CH$_2$)$_n$heteroaryl, —SO$_2$R$^{50}$ and —(CH$_2$)$_n$NR$^{50}$R$^{51}$, or R$^{47}$ and R$^{48}$, together with the atom to which they are attached, form a 3-8 membered carbo- or hetero-cyclic ring;

R$^{49}$ is selected from the group consisting of (C$_1$-C$_6$)alkyl, (C$_3$-C$_8$)cycloalkyl, heterocyclyl(C$_1$-C$_6$)alkylene, aryl(C$_1$-C$_6$)alkylene wherein the aryl is optionally substituted with one or more substituents selected from the group consisting of halo, —CF$_3$, (C$_1$-C$_6$)alkoxy, —NO$_2$, (C$_1$-C$_6$)alkyl, —CN, —SO$_2$R$^{50}$ and —(CH$_2$)$_n$NR$^{50}$R$^{51}$ heteroaryl(C$_1$-C$_6$)alkylene wherein the heteroaryl is optionally substituted with one or more substituents selected from the group consisting of halo, —CF$_3$, (C$_1$-C$_6$)alkoxy, —NO$_2$, (C$_1$-C$_6$) alkyl, —CN, —SO$_2$R$^{50}$ and —(CH$_2$)$_n$NR$^{50}$R$^{51}$, aryl optionally substituted with one or more substituents selected from the group consisting of halo, —CF$_3$, (C$_1$-C$_6$) alkoxy, —NO$_2$, (C$_1$-C$_6$)alkyl, —CN, —SO$_2$R$^{50}$ and —(CH$_2$)$_n$NR$^{50}$R$^{51}$, and heteroaryl optionally substituted with one or more substituents selected from the group consisting of halo, —CF$_3$, (C$_1$-C$_6$)alkoxy, —NO$_2$, (C$_1$-C$_6$) alkyl, —CN, —SO$_2$R$^{50}$ and —(CH$_2$)$_n$NR$^{50}$R$^{51}$;

R$^{50}$ and R$^{51}$ are independently selected from the group consisting of H, (C$_1$-C$_6$)alkyl, (C$_3$-C$_8$)cycloalkyl and —C(O)R$^{45}$, or R$^{50}$ and R$^{51}$, together with the atom to which they are attached, form a 3-8 membered carbo- or hetero-cyclic ring.

In a preferred embodiment of the compounds according to the present invention,

R$^{46}$ is selected from the group consisting of —N(R$^{47}$)—C(O)—N(R$^{47}$)(R$^{48}$), —N(R$^{47}$)—C(O)—(CH$_2$)$_n$—R$^{48}$ and —(CH$_2$)$_n$NR$^{47}$R$^{48}$; wherein R$^{47}$ and R$^{48}$ are independently selected from the group consisting of H, (C$_1$-C$_6$)alkyl, (C$_3$-C$_8$)cycloalkyl, heterocyclyl, —(CH$_2$)$_n$NR$^{50}$R$^{51}$, —(CH$_2$)$_n$OR$^{50}$, —(CH$_2$)$_n$S(O)$_2$R$^{49}$ and —(CH$_2$)$_n$CN, or R$^{47}$ and R$^{48}$, together with the atom to which they are attached, form a 3-8 membered carbo- or hetero-cyclic ring; and R$^{50}$ and R$^{51}$ are independently selected from the group consisting of H and (C$_1$-C$_6$)alkyl, or R$^{50}$ and R$^{51}$, together with the atom to which they are attached, form a 3-8 membered carbo- or hetero-cyclic ring.

In a preferred embodiment of the compounds according to the present invention, R$^1$ is selected from the group consisting of

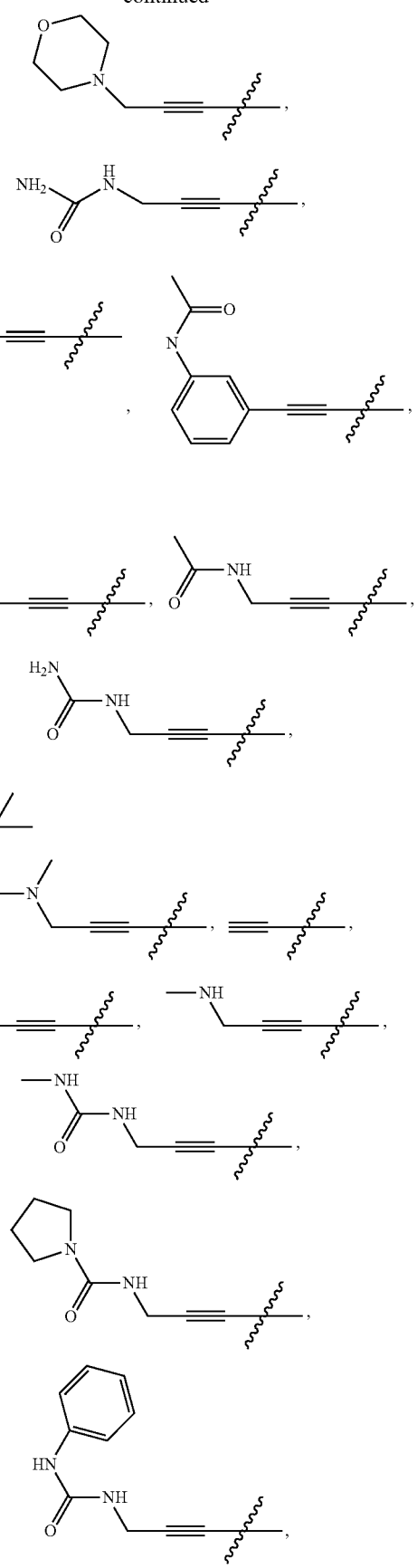

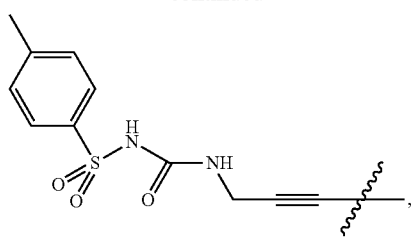
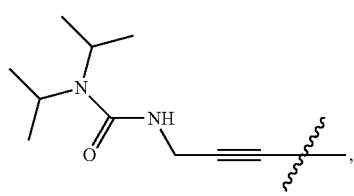
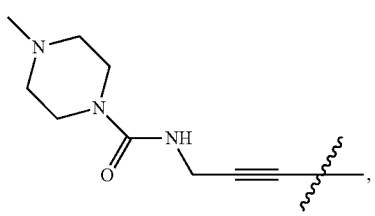
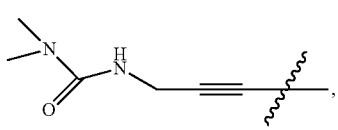
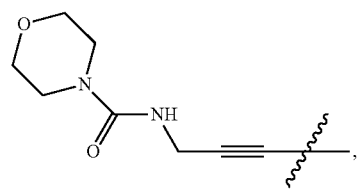
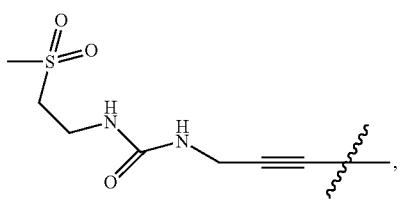
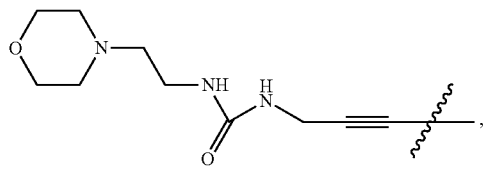
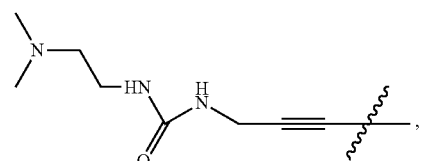
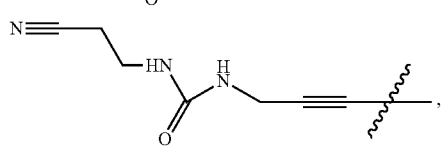
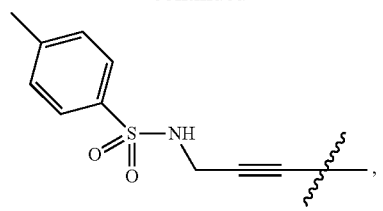
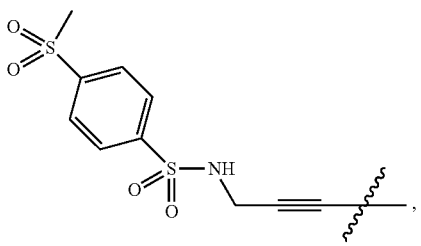
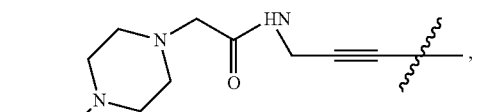
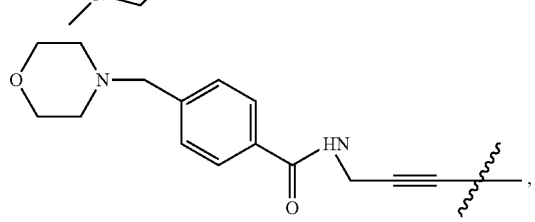
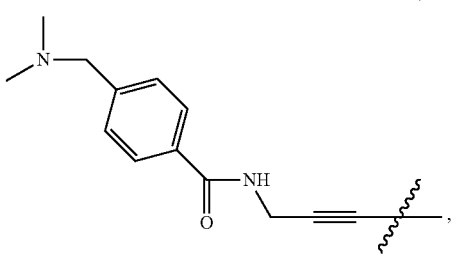
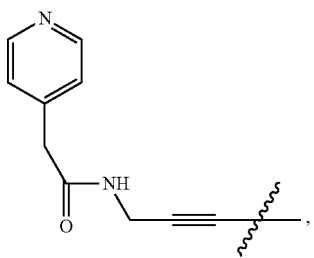
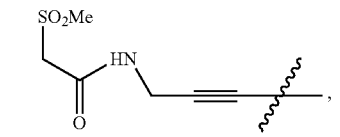
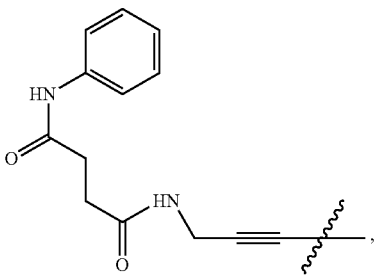

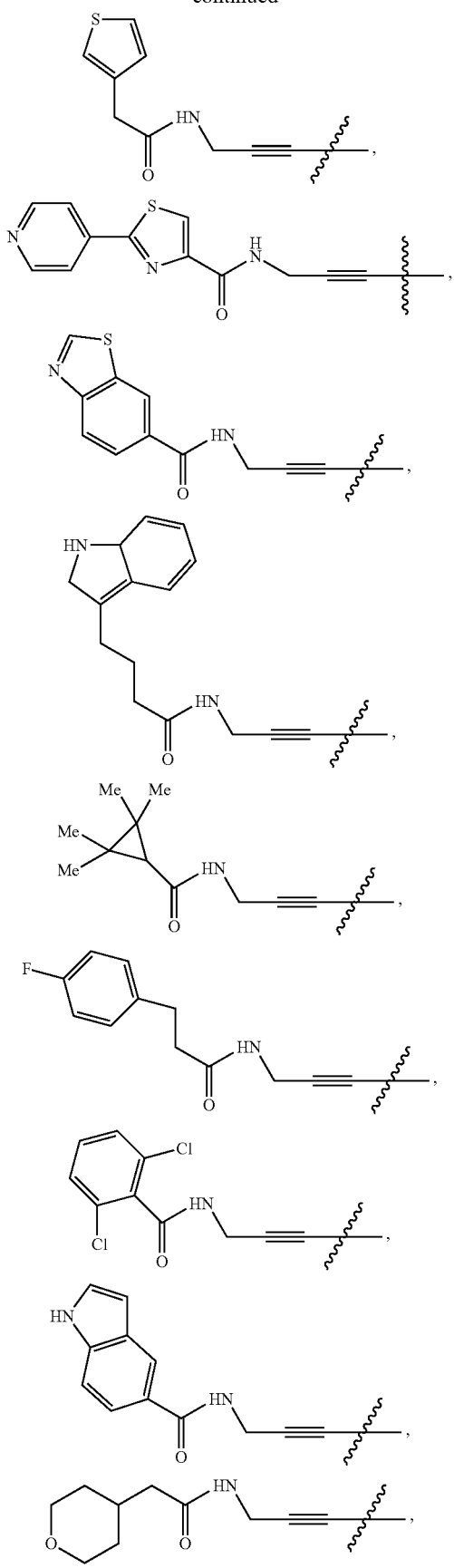
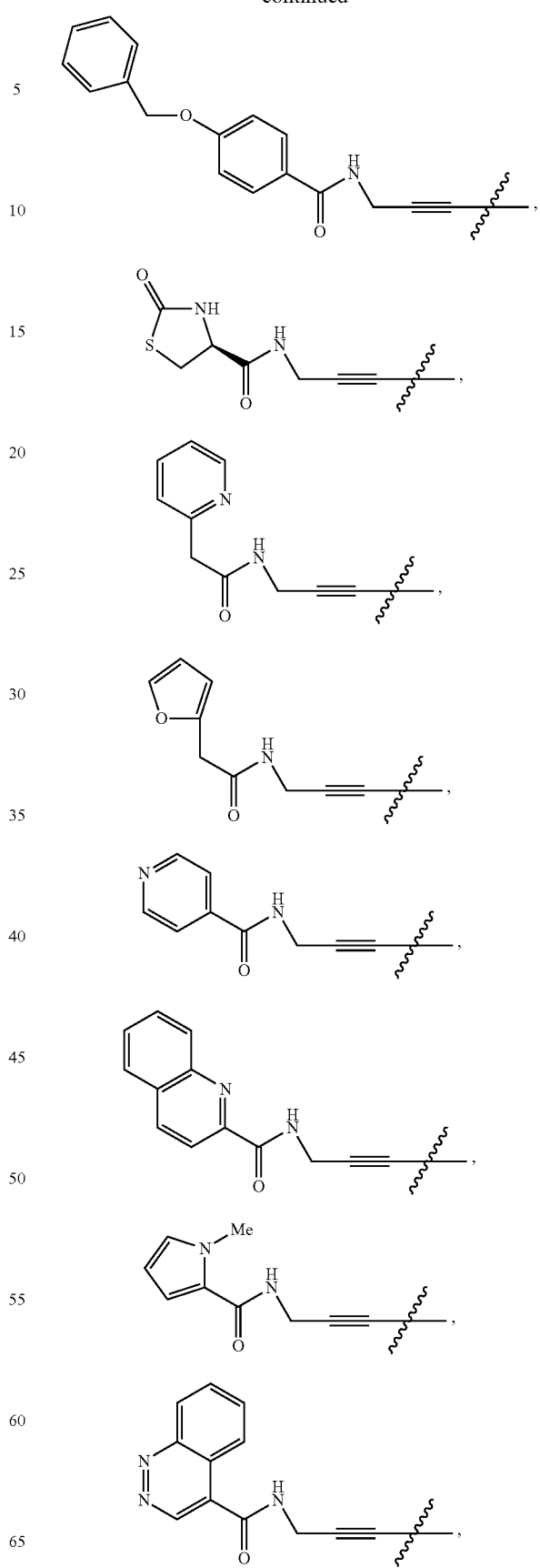

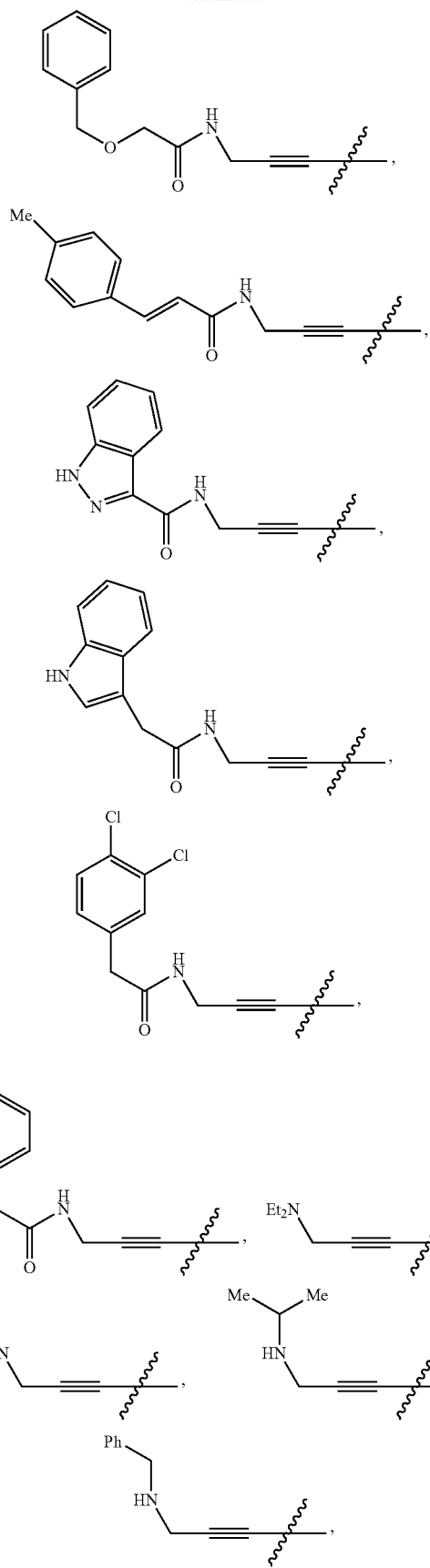
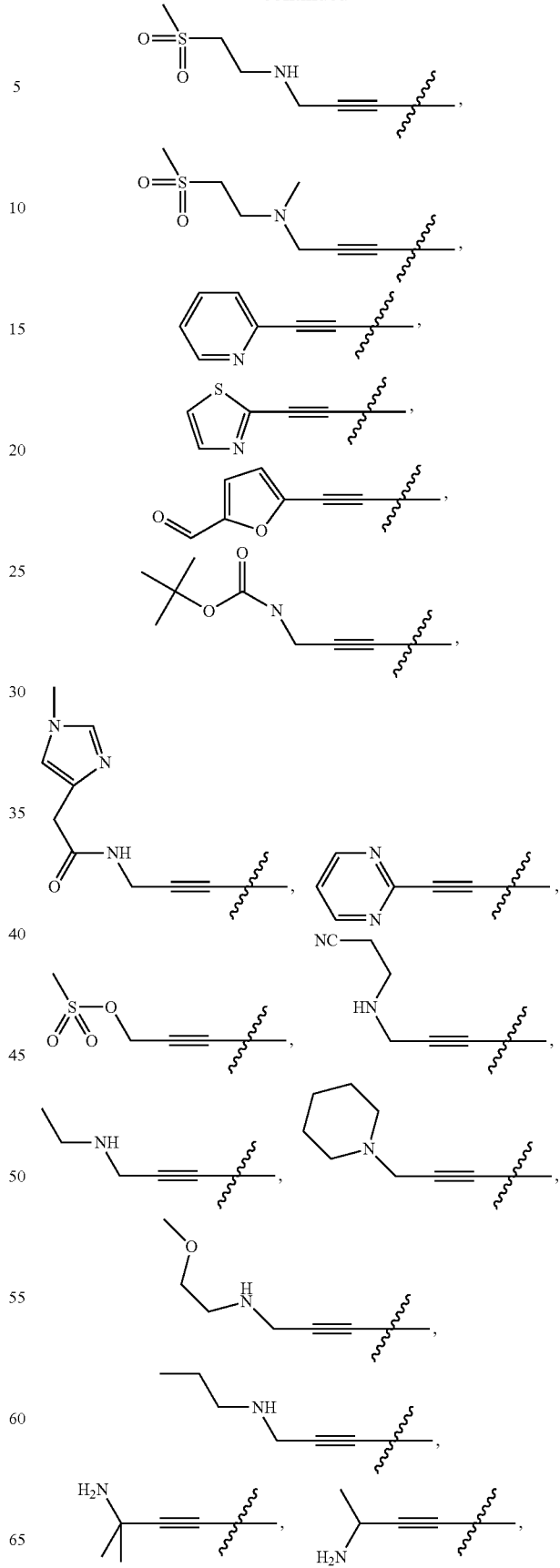

q is 0, 1, 2, 3 or 4;

each $R^{53}$ is independently $(C_1-C_3)$alkyl;

$R^{54}$ is $(C_1-C_3)$alkyl or $N(H)R^{53}$; and $R^{56}$ is selected from the group consisting of $NH_2$, $(C_1-C_3)$alkyl and $OR^{52}$.

In a preferred embodiment of the compounds according to the present invention, $Z^{11}$ is a heterocyclyl and m and m1 are each 0.

In a preferred embodiment of the compounds according to the present invention, $Z^{11}$ is a heterocyclyl and m is 0 and n is 0, where the heterocyclyl group is selected from the group consisting of In a preferred embodiment of the compounds according to the present invention, $Z^{11}$ is heterocyclylene, $Z^{12}$ is OC(O), m is 1, m1 is 1 and $Z^{13}$ is heterocyclyl.

In a preferred embodiment of the compounds according to the present invention, $Z^{11}$ is $Z^{12}$ is OC(O), and $Z^{13}$ is In a preferred embodiment of the compounds according to the present invention, D is defined by the group $R^{21}$, wherein $R^{21}$ is defined by $—(Z^{11})—(Z)_m—(Z^{13})_{m1}$, wherein $Z^{11}$ is heterocyclyl, when m and m1 are 0, or heterocyclylene, when either m or m1 are 1;

$Z^{12}$ is selected from the group consisting of OC(O), OC(S) and C(O);

$Z^{13}$ is selected from the group consisting of heterocyclyl, aralkyl, $N(H)R^{52}$, $(C_1-C_3)$alkyl, $—OR^{52}$, halo, $S(O)_2R^{56}$, $(C_1-C_3)$hydroxyalkyl and $(C_1-C_3)$haloalkyl;

m is 0 or 1;

m1 is 0 or 1;

$R^{52}$ is selected from the group consisting of H, $—(CH_2)_qS(O)_2R^{54}$, $—(C_1-C_6)$ alkyl-$NR^{53}R^{53}$, $(C_1-C_3)$alkyl, $—(CH_2)_qOR^{53}$, $—C(O)R^{54}$ and $—C(O)OR^{53}$;

or $Z^{13}$ is $N(H)R^{52}$, wherein $R^{52}$ is $(C_1-C_3)$alkyl.

In a preferred embodiment of the compounds according to the present invention $Z^{11}$ is heterocyclylene, $Z^{12}$ is C(O) and m is 1, m1 is 1 and $Z^{13}$ is $(C_1-C_3)$haloalkyl.

In a preferred embodiment of the compounds according to the present invention, $Z^{11}$ is

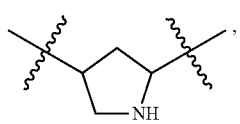

$Z^{12}$ is C(O), and $Z^{13}$ is $(C_1-C_3)$haloalkyl, preferably —$CF_3$.

In a preferred embodiment of the compounds according to the present invention, $Z^{11}$ is heterocyclylene, m is 0, m1 is 1 and $Z^{13}$ is heterocyclyl.

In a preferred embodiment of the compounds according to the present invention, $Z^{11}$ is

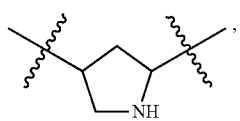

m is 0, and $Z^{13}$ is

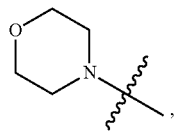

or $Z^{13}$ is $(C_1-C_3)$alkyl, or $Z^{13}$ is —OH, or $Z^{13}$ is —$OR^{52}$, wherein $R^{52}$ is $(C_1-C_3)$alkyl, preferably —$CH_3$ or $Z^{13}$ is halo, preferably —F, or $Z^{13}$ is $(C_1-C_3)$hydroxyalkyl, preferably —$CH_3OH$.

In a preferred embodiment of the compounds according to the present invention, $R^{21}$ is selected from the group consisting of

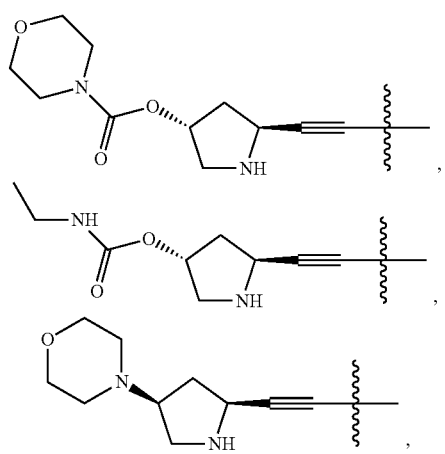

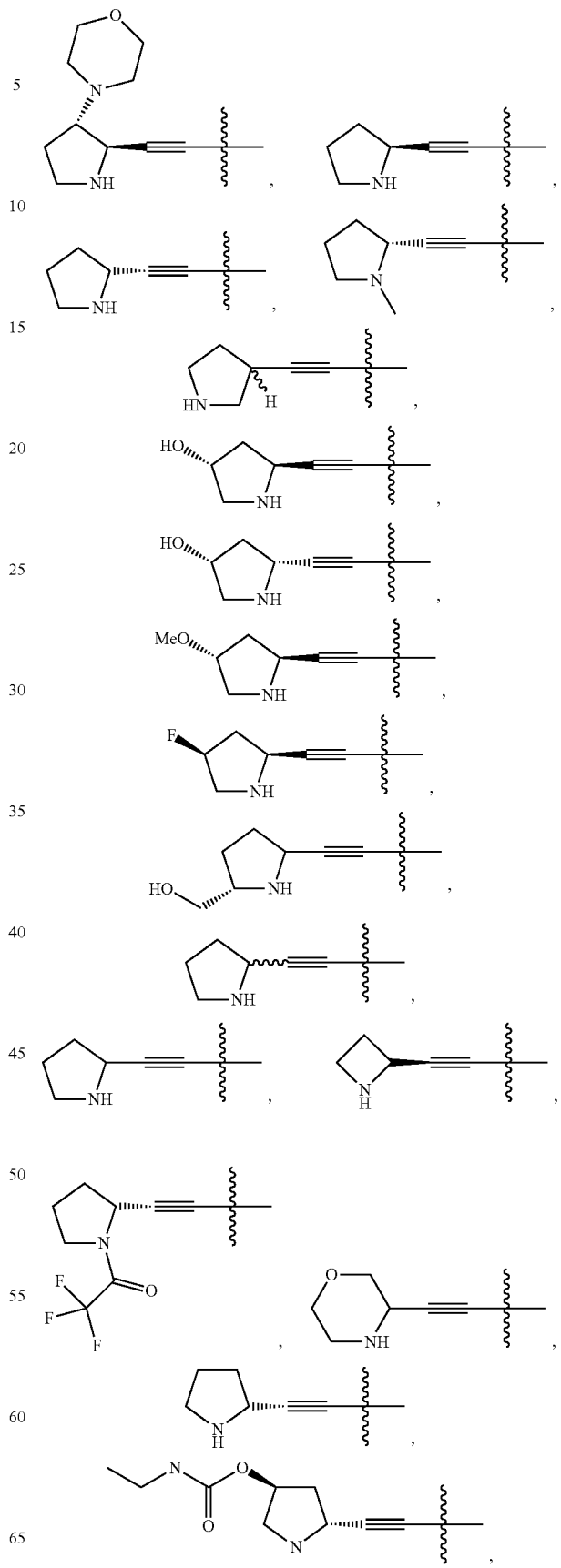

-continued

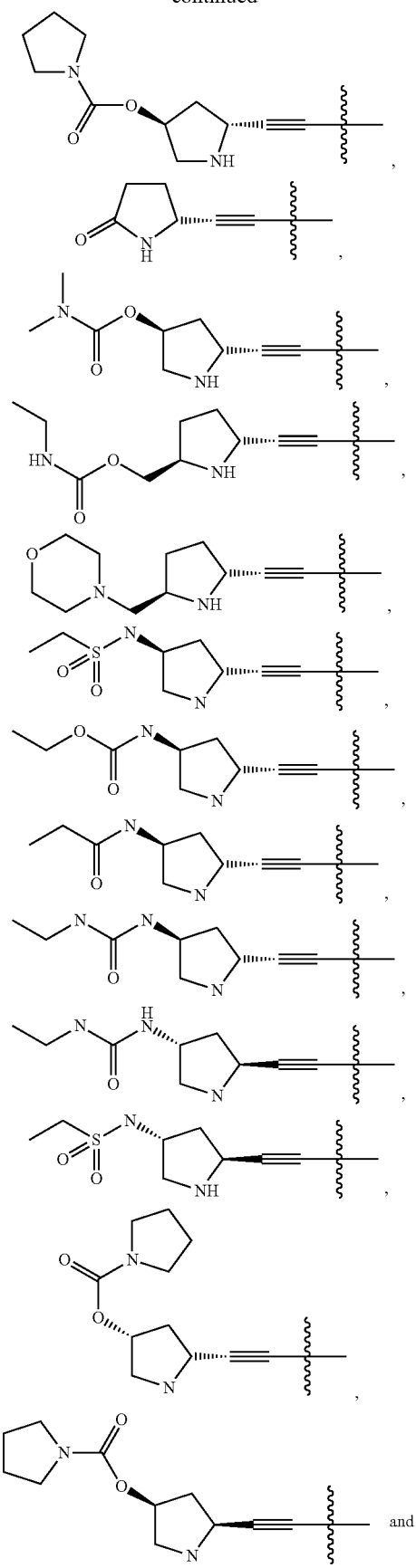

-continued

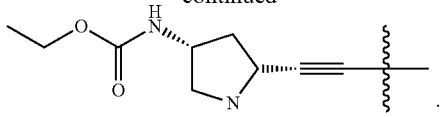

In a preferred embodiment of the compounds according to the present invention wherein D is defined by the group $R^{21}$, the heterocyclic or heterocyclyl group is optionally substituted with a substituent selected from the group consisting of $(C_1-C_6)$alkyl, $(C_1-C_6)$alkoxy, $(C_1-C_6)$alkylsufanyl, $(C_1-C_6)$alkylsulfenyl, $(C_1-C_6)$alkylsulfonyl, oxo, hydroxyl, mercapto, amino optionally substituted by alkyl, carboxy, carbamoyl optionally substituted by alkyl, alkylcarboxyamide, carboxyamide, aminosulfonyl optionally substituted by alkyl, ureido, arylurea, arylthiourea, alkylurea, cycloalkylurea, sulfonylurea, nitro, cyano, halo, aryl, aralkyl, heteroaryl and $(C_1-C_6)$perfluoroalkyl. Such a ring may be optionally fused to one or more other "heterocyclic" ring or cycloalkyl ring. Preferred examples of "heterocyclic" moieties include, but are not limited to, tetrahydrofuranyl, pyranyl, 1,4-dioxaneyl, 1,3-dioxanyl, piperidinyl, piperazinyl, 2,4-piperazinedionyl, pyrrolidinyl, pyrrolidinon-2-yl, pyrrolidinon-3-yl, pyrrolidinon-4-yl, pyrrolidinon-5-yl, imidazolidinyl, pyrazolidinyl, morpholinyl, thiomorpholinyl, tetrahydrothiopyranyl, tetrahydrothiophenyl, and the like In a preferred embodiment of the compounds according to the present invention wherein D is defined by the group $R^{21}$, the heterocyclylene group is optionally substituted with substituents selected from the group consisting of $(C_1-C_6)$alkyl, $(C_1-C_6)$alkoxy, $(C_1-C_6)$alkylsufanyl, $(C_1-C_6)$alkylsulfenyl, $(C_1-C_6)$alkylsulfonyl, oxo, hydroxyl, mercapto, amino optionally substituted by alkyl, carboxy, carbamoyl optionally substituted by alkyl, alkylcarboxyamide, carboxyamide, aminosulfonyl optionally substituted by alkyl, ureido, arylurea, arylthiourea, alkylurea, cycloalkylurea, sulfonylurea, nitro, cyano, halo and $(C_1-C_6)$perfluoroalkyl, multiple degrees of substitution being allowed. Such a ring may be optionally fused to one or more benzene rings or to one or more of another "heterocyclic" rings or cycloalkyl rings. Preferred examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, pyrrolidinon-2,3-diyl, pyrrolidinon-2,4-diyl, pyrrolidinon-2,5-diyl, pyrrolidinon-3,4-diyl, pyrrolidinon-3,5-diyl, pyrrolidinon-4,5-diyl, morpholine-2,4-diyl, and the like.

In a preferred embodiment of the present invention, D is selected from the group consisting of

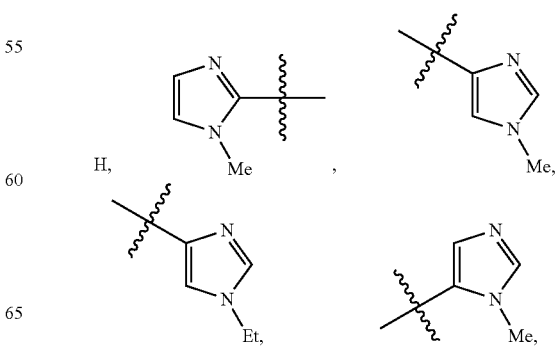

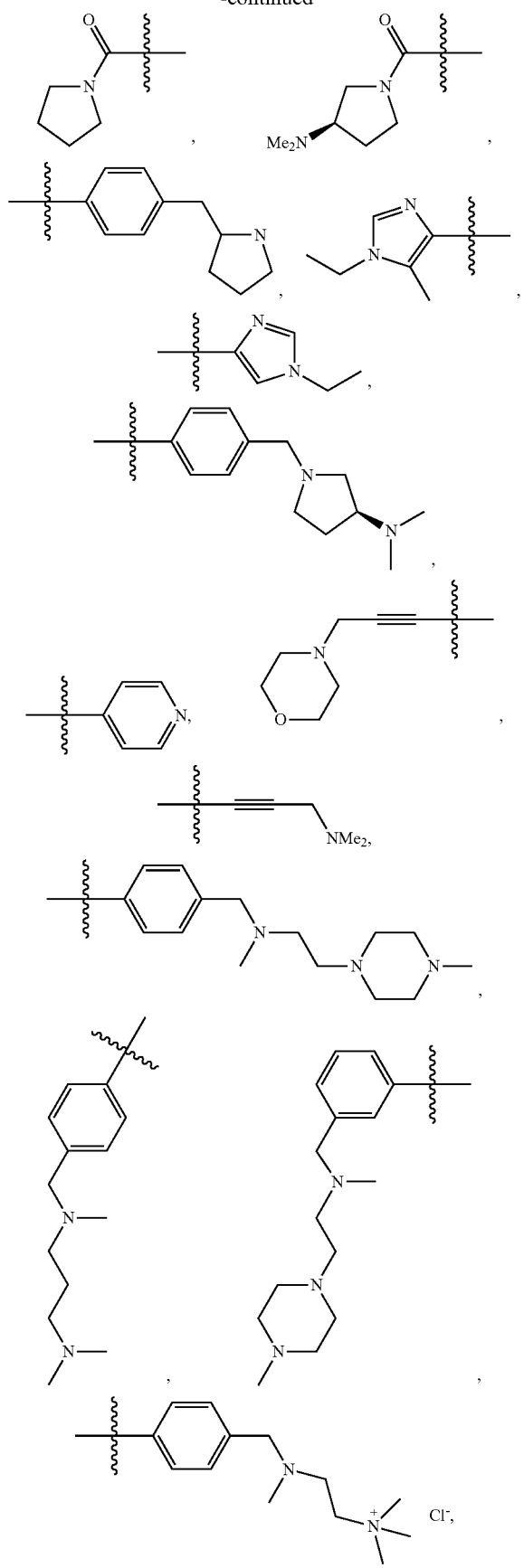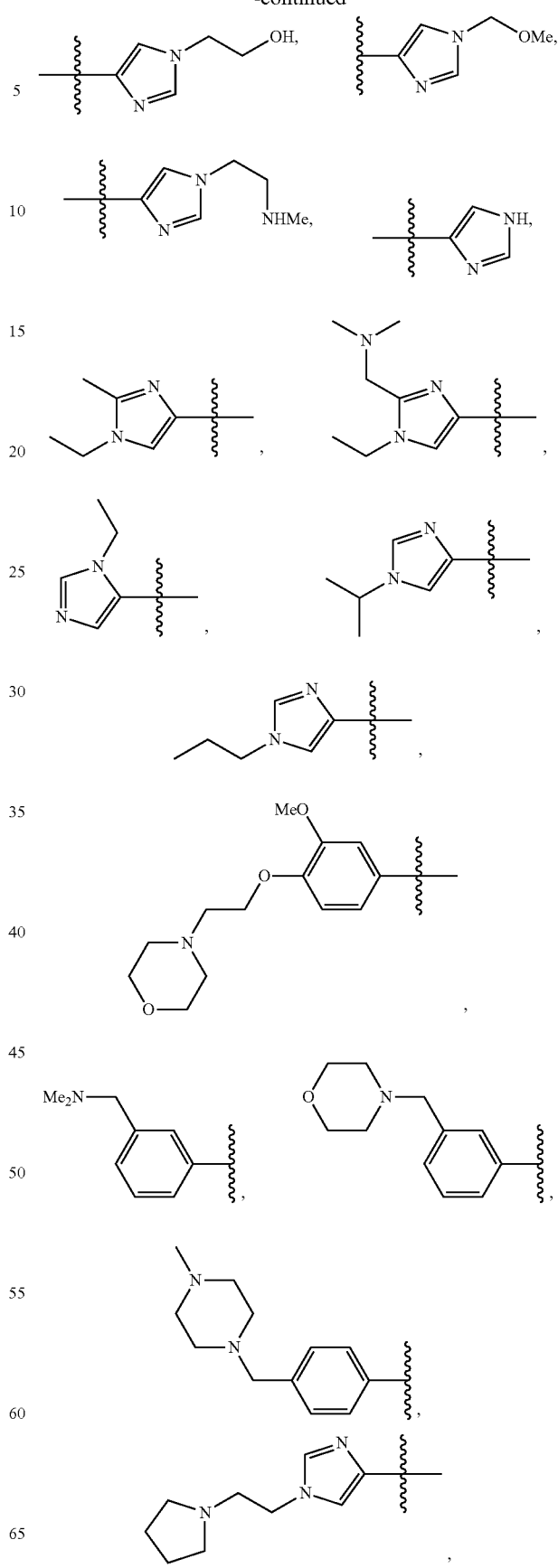

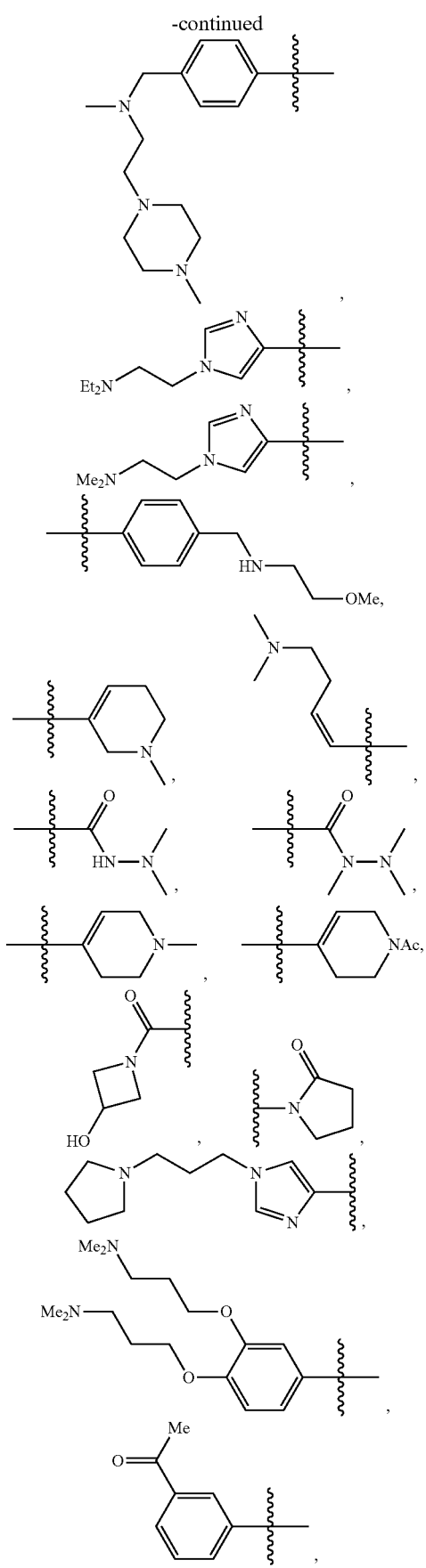

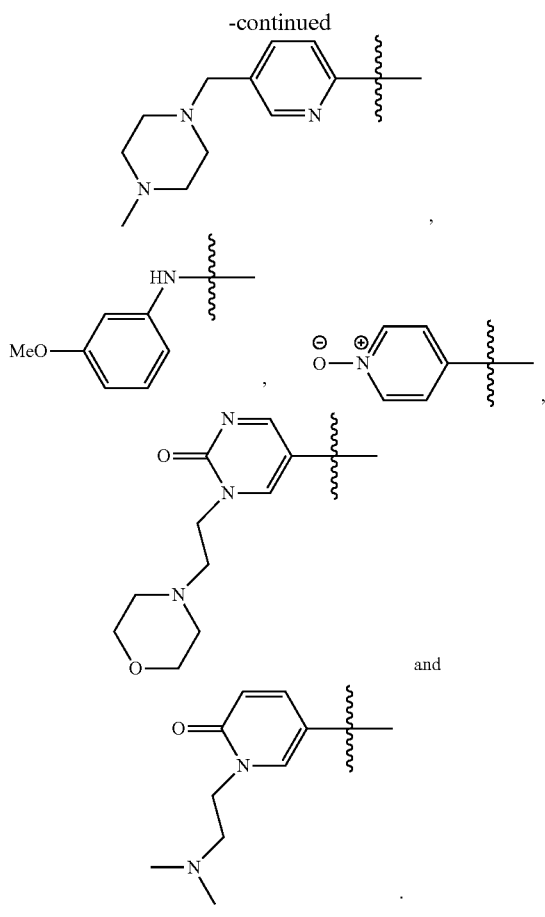

In a preferred embodiment of the compounds according to the present invention, Z is selected from the group consisting of —O—, —S—, —S(O)$_{0-2}$ and —NR$^5$—, wherein R$^5$ is selected from the group consisting of H, an optionally substituted (C$_1$-C$_5$)acyl and C$_1$-C$_6$ alkyl-O—C(O), wherein C$_1$-C$_6$ alkyl is optionally substituted.

In a preferred embodiment of the compounds according to the present invention, Z is —O—.

In a preferred embodiment of the compounds according to the present invention, Ar is a group of the formula C,

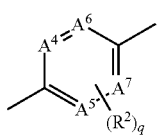

wherein,

A$^4$, A$^5$, A$^6$ and A$^7$ are independently selected from the group consisting of N and —CH$_2$—, with the proviso that no more than two of A$^4$, A$^5$, A$^6$ and A$^7$ can be N;

R$^2$ at each occurrence is independently selected from the group consisting of —H, halogen, trihalomethyl, —CN, —NO$_2$, —NH$_2$, —OR$^3$, —NR$^3$R$^4$, —S(O)$_{0-2}$R$^3$, —S(O)$_2$NR$^3$R$^3$, —C(O)OR$^3$, —C(O)NR$^3$R$^3$, —N(R$^3$)SO$_2$R$^3$, —N(R$^3$)C(O)R$^3$, —N(R$^3$)CO$_2$R$^3$, alkoxy, C$_1$-C$_4$ alkylthio, —O(CH$_2$)$_n$aryl, —O(CH$_2$)$_n$heteroaryl, —(CH$_2$)$_{0-5}$(aryl), —(CH$_2$)$_{0-5}$(heteroaryl), C$_1$-C$_6$ alkyl, C$_2$-C$_6$ alkenyl, C$_2$-C$_6$ alkynyl, —CH$_2$(CH$_2$)$_{0-4}$-T$^2$, wherein T$^2$ is selected from the group consisting of —OH, —OMe, —OEt, —NH$_2$, —NHMe, —NMe$_2$, —NHEt and —NEt$_2$, and wherein the aryl, heteroaryl, C$_1$-C$_6$ alkyl, C$_2$-C$_6$ alkenyl, and C$_2$-C$_6$ alkynyl are optionally substituted; and R$^3$ selected from the group consisting of —H and R$^4$;

R$^4$ is selected from the group consisting of a (C$_1$-C$_6$)alkyl, an aryl, a lower arylalkyl, a heterocyclyl and a lower heterocyclylalkyl, each of which is optionally substituted, or R$^3$ and R$^4$, taken together with a common nitrogen to which they are attached, form an optionally substituted five- to seven-membered heterocyclyl, which optionally contains at least one additional annular heteroatom selected from the group consisting of N, O, S and P; and q is an integer from 0 to 4.

In a preferred embodiment of the compounds according to the present invention, Ar is selected from the group consisting of phenyl, pyrazine, pyridazine, pryimidine and pyridine, wherein each of said phenyl, pyrazine, pyridazine, pryimidine and pyridine are optionally substituted with between zero and four R$^2$.

In a preferred embodiment of the compounds according to the present invention, Ar is phenyl, optionally substituted with between zero and four R$^2$.

In a preferred embodiment of the compounds according to the present invention. Ar is phenyl, substituted with between zero and four halo.

In a preferred embodiment of the compounds according to the present invention, G is a group B-L-T, wherein B is selected from the group consisting of absent, —N(R$^{13}$)—, —N(SO$_2$R$^{13}$)—, —O—, —S(O)$_{0-2}$ and —C(=O)—;

L is selected from the group consisting of absent, —C(=S) N(R$^{13}$)—, —C(=NR$^{14}$)N(R$^{13}$)—, —SO$_2$N(R$^{13}$)—, —SO$_2$—, —C(=O)N(R$^{13}$)—, —N(R$^{13}$)—, —C(=O) C$_{1-2}$alkyl-N(R$^{13}$)—, —N(R$^{13}$)C$_{1-2}$alkyl-C(=O)—, —C(=O)C$_{0-1}$alkyl-C(=O)N(R$^{13}$)—, —C$_{0-4}$alkylene, —C(=O)C$_{0-4}$alkyl-C(=O)OR$^3$—, —C(=NR$^{14}$)—C$_{0-1}$ alkyl-C(=O)—, —C(=O)—, —C(=O)CO$_{0-1}$alkyl-C (=O)— and an optionally substituted four to six-membered heterocyclyl containing between one and three annular heteroatoms including at least one nitrogen, wherein an alkyl of the aforementioned L groups is optionally independently substituted with one or two of H, (C$_1$-C$_6$)alkyl, halo, cyano or nitro, wherein the (C$_1$-C$_6$)alkyl is optionally substituted; and T is selected from the group consisting of —H, —R$^{13}$, —C$_{0-4}$ alkyl, —C$_{0-4}$alkyl-Q, —O—C$_{0-4}$alkyl-Q, —C$_0$-4-alkyl-O- Q, —N(R$^{13}$)C$_{0-4}$alkyl-Q, —SO$_2$C$_{0-4}$alkyl-Q, —C(=O) C$_{0-4}$alkyl-Q, —C$_{0-4}$alkyl-N(R$^{13}$)Q and —C(=O)N (R$^{13}$)—C$_{0-4}$alkyl-Q, wherein each C$_{0-4}$alkyl is optionally substituted;

R$^{13}$ is selected from the group consisting of —H, —CN, —NO$_2$, —NH$_2$, —OR$^3$, —NR$^3$R$^4$, —S(O)$_{0-2}$R$^3$, —S(O)$_2$ NR$^3$R$^3$, —C(O)OR$^3$, —C(O)NR$^3$R$^3$, —N(R$^3$)SO$_2$R$^3$, —N(R$^3$)C(O)R$^3$, —N(R$^3$)CO$_2$R$^3$, —C(O)R$^3$, —C(O) SR$^3$, C1-C$_4$ alkoxy, C$_1$-C$_4$ alkylthio, —O(CH$_2$)$_n$aryl, —O(CH$_2$)$_n$heteroaryl, —(CH$_2$)$_{0-5}$(aryl), —(CH$_2$)$_{0-5}$(heteroaryl), C$_1$-C$_6$ alkyl, C$_2$-C$_6$ alkenyl, C$_2$-C$_6$ alkynyl, —CH$_2$(CH$_2$)$_{0-4}$-T$^2$, an optionally substituted C$_{1-4}$ alkylcarbonyl, and a saturated or unsaturated three- to seven-membered carboxylic or heterocyclic group, wherein T$^2$ is selected from the group consisting of —OH, —OMe, —OEt, —NH$_2$, —NHMe, —NMe$_2$, —NHEt and —NEt$_2$, and wherein the aryl, heteroaryl, C$_1$-C$_6$ alkyl, C$_2$-C$_6$ alkenyl, and C$_2$-C$_6$ alkynyl are optionally substituted;

two $R^{13}$, together with the atom or atoms to which they are attached, can combine to form a heteroalicyclic optionally substituted with between one and four of $R^{60}$, wherein the heteroalicyclic can have up to four annular heteroatoms, and the heteroalicyclic can have an aryl or heteroaryl fused thereto, in which case the aryl or heteroaryl is optionally substituted with an additional one to four of $R^{60}$;

$R^{14}$ is selected from the group —H, —$NO_2$, —$NH_2$, —$N(R^3)R^4$, —CN, —$OR^3$, an optionally substituted ($C_1$-$C_6$)alkyl, an optionally substituted heteroalicylylalkyl, an optionally substituted aryl, an optionally substituted arylalkyl and an optionally substituted heteroalicyclic, each $R^3$ is independently selected from the group consisting of —H and $R^4$;

$R^4$ is selected from the group consisting of a ($C_1$-$C_6$)alkyl, an aryl, a lower arylalkyl, a heterocyclyl and a lower heterocyclylalkyl, each of which is optionally substituted, or $R^3$ and $R^4$, taken together with a common nitrogen to which they are attached, form an optionally substituted five- to seven-membered heterocyclyl, the optionally substituted five- to seven-membered heterocyclyl optionally containing at least one additional annular heteroatom selected from the group consisting of N, O, S and P;

$R^{60}$ is selected from the group consisting of —H, halogen, trihalomethyl, —CN, —$NO_2$, —$NH_2$, —$OR^3$, —$NR^3R^4$, —$S(O)_{0-2}R^3$, —$SO_2NR^3R^3$, —$CO_2R^3$, —$C(O)NR^3R^3$, —$N(R^3)SO_2R^3$, —$N(R^3)C(O)R^3$, —$N(R^3)CO_2R^3$, —$C(O)R^3$, an optionally substituted ($C_1$-$C_6$)alkyl, an optionally substituted aryl, an optionally substituted heteroarylalkyl and an optionally substituted arylalkyl;

two $R^{60}$, when attached to a non-aromatic carbon, can be oxo;

Q is a five- to ten-membered ring system, optionally substituted with between zero and four of $R^{20}$; and $R^{20}$ is selected from the group consisting of —H, halogen, trihalomethyl, —CN, —$NO_2$, —$NH_2$, —$OR^3$, —$OCF_3$, —$NR^3R^4$, —$S(O)_{0-2}R^3$, —$S(O)_2NR^3R^3$, —$C(O)OR^3$, —$C(O)NR^3R^3$, —$N(R^3)SO_2R^3$, —$N(R^3)C(O)R^3$, —$N(R^3)C(O)OR^3$, —$C(O)R^3$, —$C(O)SR^3$, $C_1$-$C_4$ alkoxy, $C_1$-$C_4$ alkylthio, —$O(CH_2)_n$aryl, —$O(CH_2)_n$heteroaryl, —$(CH_2)_{0-5}$(aryl), —$(CH_2)_{0-5}$(heteroaryl), $C_1$-$C_6$ alkyl, $C_2$-$C_6$ alkenyl, $C_2$-$C_6$ alkynyl, —$CH_2(CH_2)_{0-4}$-$T^2$, an optionally substituted $C_{1-4}$ alkylcarbonyl, $C_{1-4}$ alkoxy, an amino optionally substituted by $C_{1-4}$ alkyl optionally substituted by $C_{1-4}$ alkoxy and a saturated or unsaturated three- to seven-membered carboxyclic or heterocyclic group, wherein $T^2$ is selected from the group consisting of —OH, —OMe, —OEt, —$NH_2$, —NHMe, —$NMe_2$, —NHEt and —$NEt_2$, and wherein the aryl, heteroaryl, $C_1$-$C_6$ alkyl, $C_2$-$C_6$ alkenyl, and $C_2$-$C_6$ alkynyl are optionally substituted.

In a preferred embodiment of the compounds according to the present invention, G is selected from the group consisting of

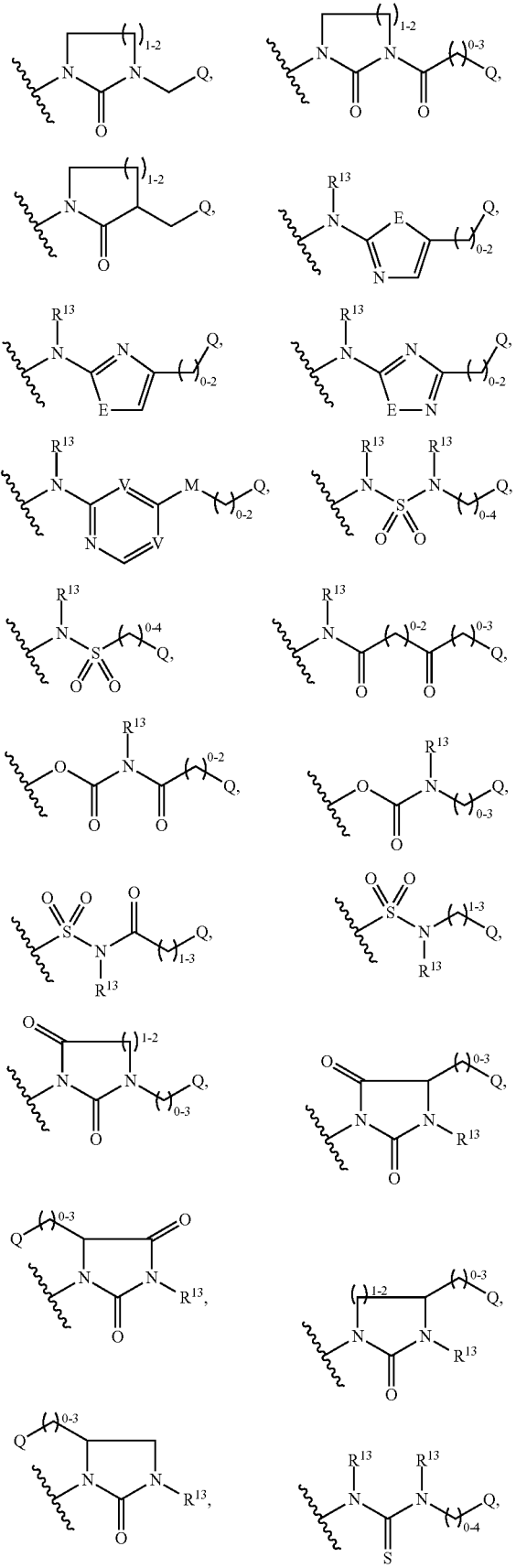

-continued
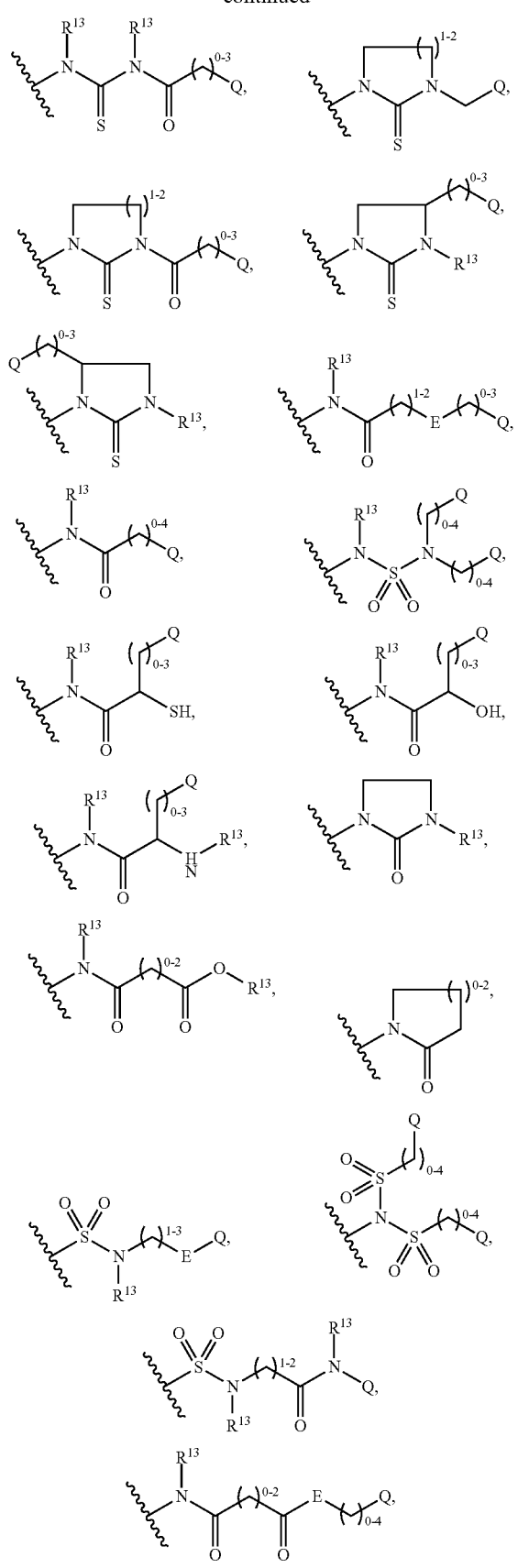
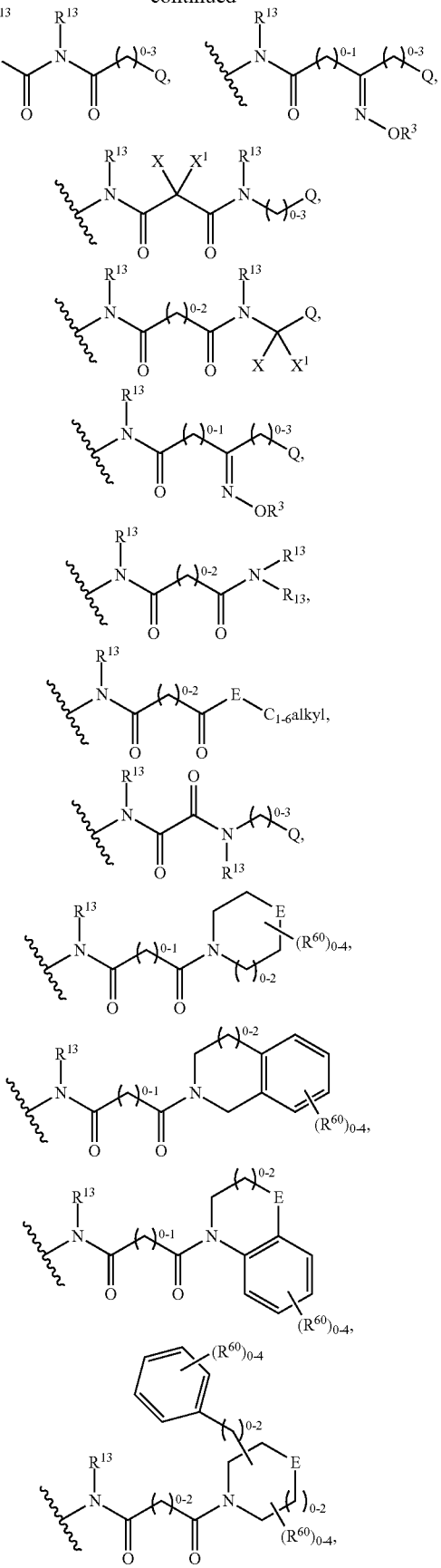

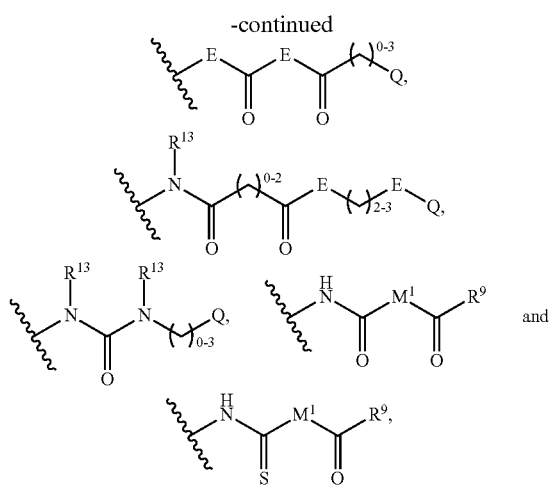

wherein $R^{13}$, $R^{14}$, Q and $R^3$ are as defined above;

any methylene group is independently optionally substituted with $R^{25}$, wherein $R^{25}$ is selected from the group consisting of halogen, trihalomethyl, —CN, —NO$_2$, —NH$_2$, —OR$^3$, —NR$^3$R$^4$, —S(O)$_{0-2}$R$^3$, —SO$_2$NR$^3$R$^3$, —CO$_2$R$^3$, —C(O)NR$^3$R$^3$, —N(R$^3$)SO$_2$R$^3$, —N(R$^3$)C(O)R$^3$, —N(R$^3$)CO$_2$R$^3$, —C(O)R$^3$, an optionally substituted aryl, an optionally substituted arylalkyl, an optionally substituted heteroarylalkyl, and an optionally substituted (C$_1$-C$_6$)alkyl, two $R^{25}$, together with the carbon or carbons to which they are attached, can combine to form a three- to seven-membered alicyclic or heteroalicyclic, and two $R^{25}$, on a single carbon can be oxo;

$R^9$ is selected from the group consisting of a $C_{1-6}$ alkyl on which one or more hydrogen atoms are optionally substituted by —R$^{24}$, -T$^1$-R$^{15}$, or —NR$^{16}$R$^{17}$, a —N(R$^{18}$)(R$^{19}$) moiety and a saturated or unsaturated three- to eight-membered carbocyclic or heterocyclic group which is optionally substituted by a $C_{1-6}$ alkyl, a $C_{1-6}$ alkoxy, a halogen atom, nitro, a trifluoromethyl, a $C_{1-6}$ alkoxy carbonyl, cyano, a cyano $C_{1-6}$ alkyl, a $C_{1-6}$ alkylthio, a phenoxy, an acetyl, or a saturated or unsaturated five- or six-membered heterocyclyl ring wherein, when the three- to eight-membered carbocyclic or heterocyclic group is substituted by two $C_{1-6}$ alkyl groups, the two alkyl groups may combine together to form an alkylene chain, or the three- to eight-membered carbocyclic or heterocyclic group may be a bicyclic group condensed with another saturated or unsaturated three- to eight-membered carbocyclic or heterocyclic group, wherein $T^1$ is selected from the group consisting of —O—, —S— and —NH—;

$R^{21}$ represents a saturated or unsaturated three- to eight-membered carbocyclic or heterocyclic group;

$R^{15}$, $R^{16}$, and $R^{17}$, which may be the same or different, represent a $C_{1-6}$ alkyl or a saturated or unsaturated three- to eight-membered carbocyclic or heterocyclic group; wherein the three- to eight-membered carbocyclic or heterocyclic group represented by $R^{21}$, $R^{15}$, $R^{16}$, and $R^{17}$ is optionally substituted by a $C_{1-6}$ alkyl, a $C_{1-6}$ alkoxy, a halogen atom, nitro, a trifluoromethyl, a $C_{1-6}$ alkoxy carbonyl, a cyano, a cyano $C_{1-6}$ alkyl, a $C_{1-6}$ alkylthio, a phenoxy, an acetyl, or a saturated or unsaturated five- or six-membered heterocyclyl ring; and wherein when the three- to eight-membered carbocyclic or heterocyclic group is substituted by two $C_{1-6}$ alkyl groups, the two alkyl groups may combine together to form an alkylene chain; and wherein the three- to eight-membered carbocyclic or heterocyclic group may be a bicyclic group condensed with another saturated or unsaturated three- to eight-membered carbocyclic or heterocyclic group; and $R^{18}$ and $R^{19}$, which may be the same or different, represent (1) a hydrogen atom, (2) a $C_{1-6}$ alkyl which is optionally substituted by a $C_{1-6}$ alkoxy, a $C_{1-6}$ alkylthio, or a saturated or unsaturated three- to eight-membered carbocyclic or heterocyclic group in which the three- to eight-membered carbocyclic or heterocyclic group is optionally substituted by a $C_{1-6}$ alkyl, a $C_{1-6}$ alkoxy, a halogen atom, nitro, a trifluoromethyl, a $C_{1-6}$ alkoxy carbonyl, cyano, a cyano $C_{1-6}$ alkyl, a $C_{1-6}$ alkylthio, a phenoxy, an acetyl, or a saturated or unsaturated five- or six-membered heterocyclyl ring and wherein when the three- to eight-membered carbocyclic or heterocyclic group is substituted by two $C_{1-6}$ alkyl groups, the two alkyl groups may combine together to form an alkylene chain, or the three- to eight-membered carbocyclic or heterocyclic group may be a bicyclic group condensed with another saturated or unsaturated three- to eight-membered carbocyclic or heterocyclic group, or (3) a saturated or unsaturated three- to eight-membered carbocyclic or heterocyclic group which is optionally substituted by a $C_{1-6}$ alkyl, a $C_{1-6}$ alkoxy, a halogen atom, nitro, a trifluoromethyl, a $C_{1-6}$ alkoxy carbonyl, cyano, a cyano $C_{1-6}$ alkyl, a $C_{1-6}$ alkylthio, a phenoxy, an acetyl, or a saturated or unsaturated five- or six-membered heterocyclyl ring and in which, when the three to eight-membered carbocyclic or heterocyclic group is substituted by two $C_{1-6}$ alkyl groups, the two alkyl groups may combine together to form an alkylene chain, or the three- to eight-membered carbocyclic or heterocyclic group may be a bicyclic group condensed with another saturated or unsaturated three- to eight-membered carbocyclic or heterocyclic group;

X and $X^1$ are each independently selected from the group consisting of —H, halogen, cyano, nitro, $C_1$-$C_6$ alkyl, or X and $X^1$ together with the atom to which they are attached form a $C_3$-$C_4$ cycloalkyl;

E is selected from the group consisting of —O—, —N(R$^{13}$)—, —CH$_2$— and —S(O)$_{0-2}$—;

M is selected from the group consisting of —O—, —N(R$^{13}$)—, —CH$_2$— and —C(=O)N(R$^{13}$);

$M^1$ represents —C(R$^{26}$)(R$^{27}$)—, wherein $R^{26}$ and $R^{27}$ are independently selected from the group consisting of a hydrogen atom, a $C_{1-4}$ alkyl, a $C_{1-4}$ alkoxy and —N(R$^{12}$), wherein $R^{12}$ is a hydrogen atom or a $C_{1-4}$ alkyl; and each V is independently selected from the group consisting of =N— and =C(H)—.

In a preferred embodiment of the compounds according to the present invention, G is selected from the group consisting of

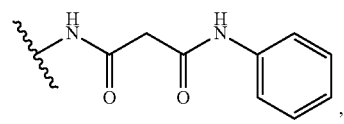

,

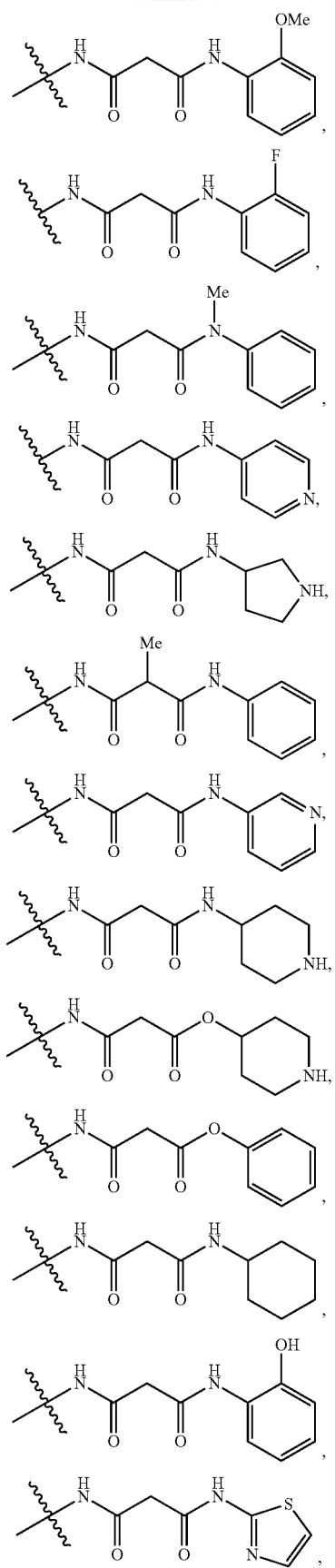
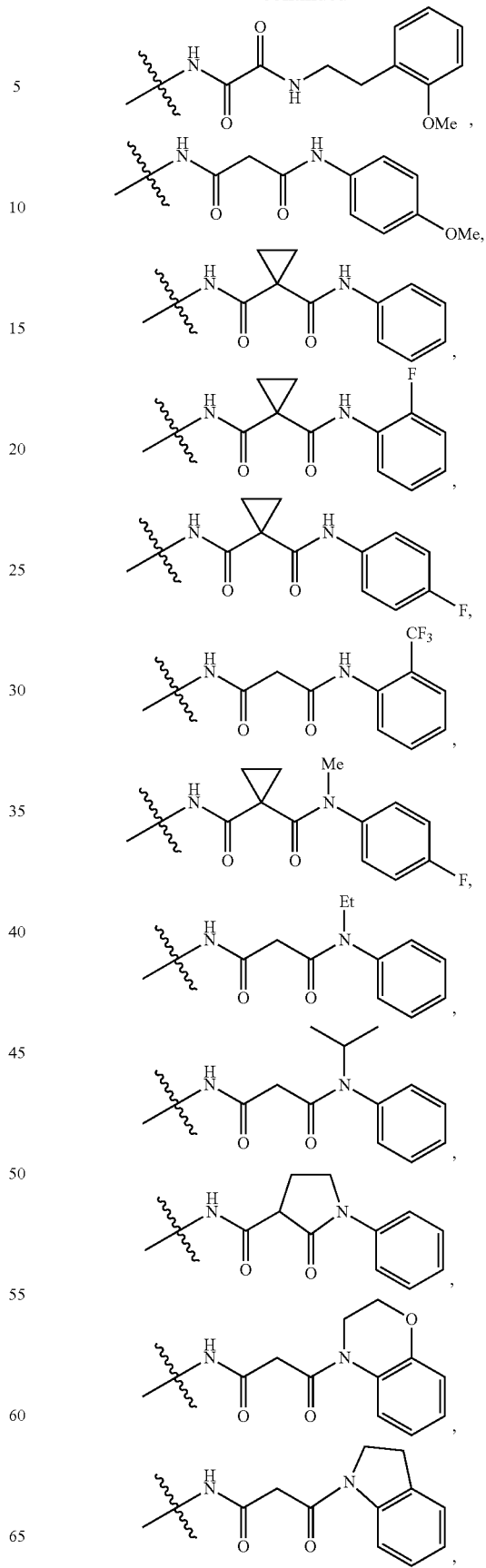

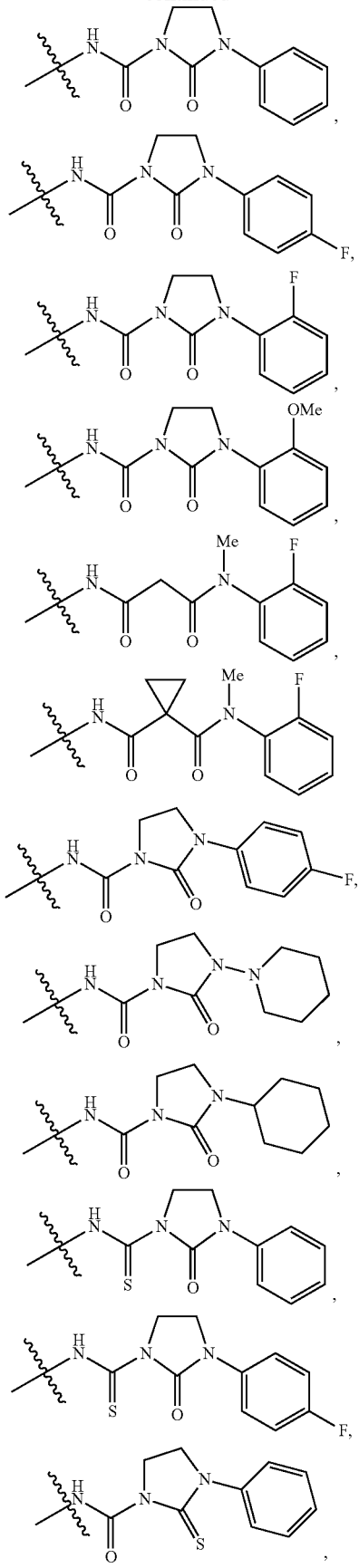
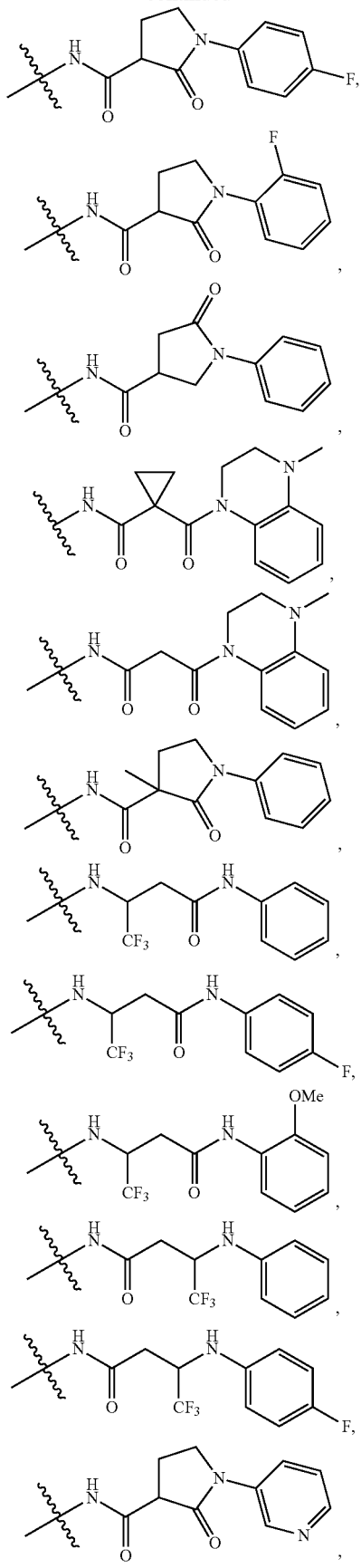

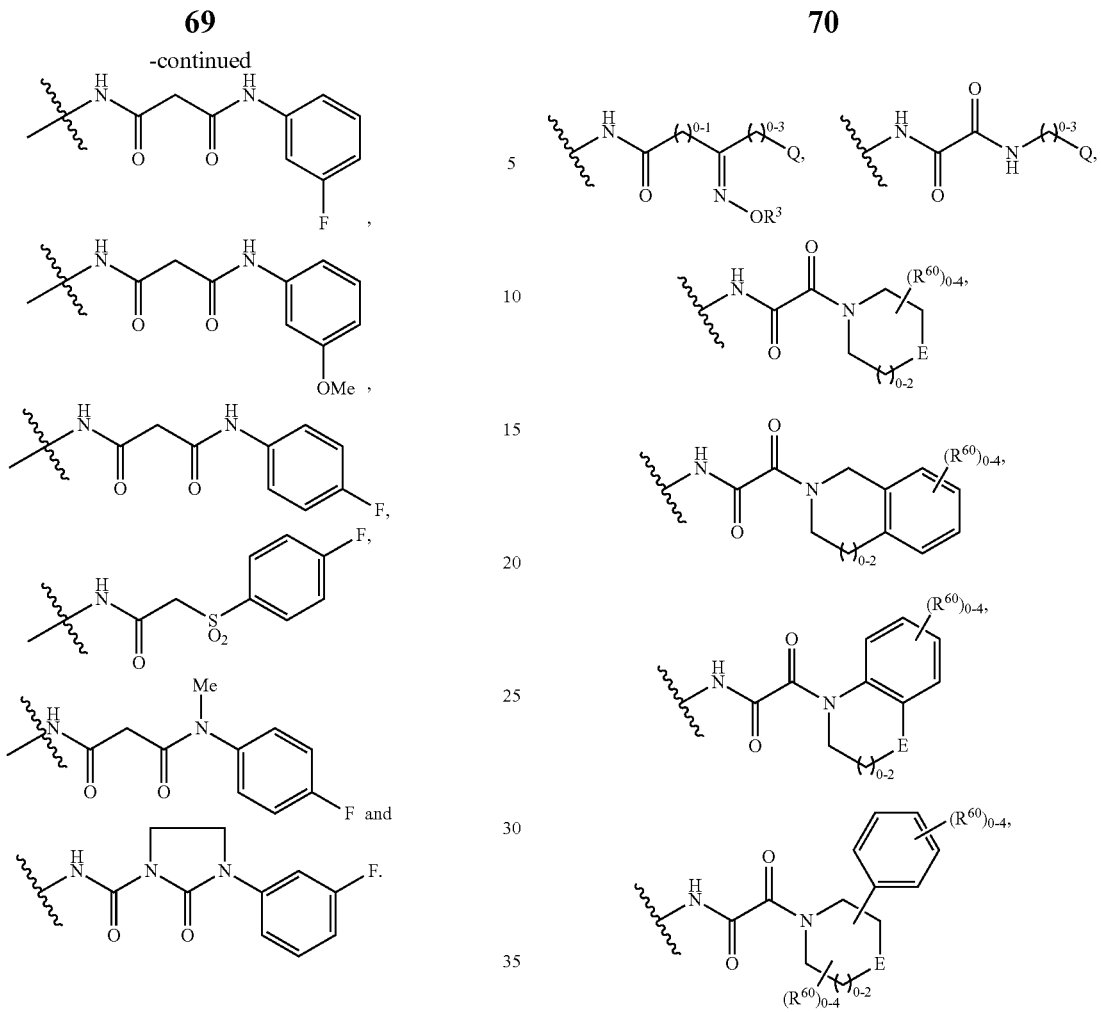

In a preferred embodiment of the compounds according to the present invention, the optionally substituted alkyl group represented by $R^9$ preferably represents —$(CH_2)p$—$R^{24}$, —$(CH_2)p$-T-$R^{15}$, or —$(CH_2)p$—$NR^{16}R^{17}$ wherein p is an integer of 1 to 6 and $R^{24}$, $R^{15}$, $R^{16}$, and $R^{17}$ are as defined above.

In a preferred embodiment of the compounds according to the present invention in —$N(R^{18})(R^{19})$ represented by $R^9$, preferably, $R^{18}$ represents a hydrogen atom or $C_{1-6}$ alkyl, and $R^{19}$ represents $C_{1-6}$ alkyl which is optionally substituted by an optionally substituted saturated or unsaturated five- or six-membered carbocyclic or heterocyclic group; or an optionally substituted saturated or unsaturated five- or six-membered carbocyclic or heterocyclic group.

In a preferred embodiment of the compounds according to the present invention, preferred examples of $R^9$ include, but are not limited to, benzyl, fluorobenzyl, difluorobenzyl, chlorobenzyl, methylbenzyl, methoxybenzyl, aniline, fluoroanilino, difluoroanilino, chloroanilino, methylanilino, methoxyanilino, naphthyl, thienyl-2-yl-methyl, and thienyl-3-yl-methyl.

In a preferred embodiment of the compounds according to the present invention, examples of $R^{19}$ include phenyl, fluorophenyl, difluorophenyl, chlorophenyl, methylphenyl, methoxyphenyl, pyridyl, isoxazolyl and quinolyl.

In a preferred embodiment of the compounds according to the present invention, G is selected from the group consisting of:

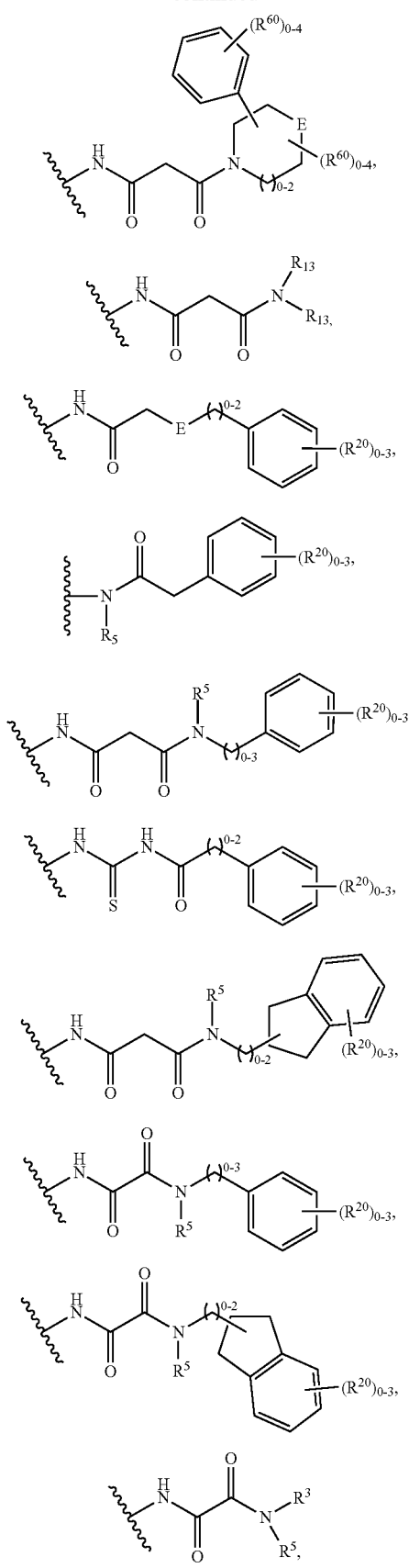
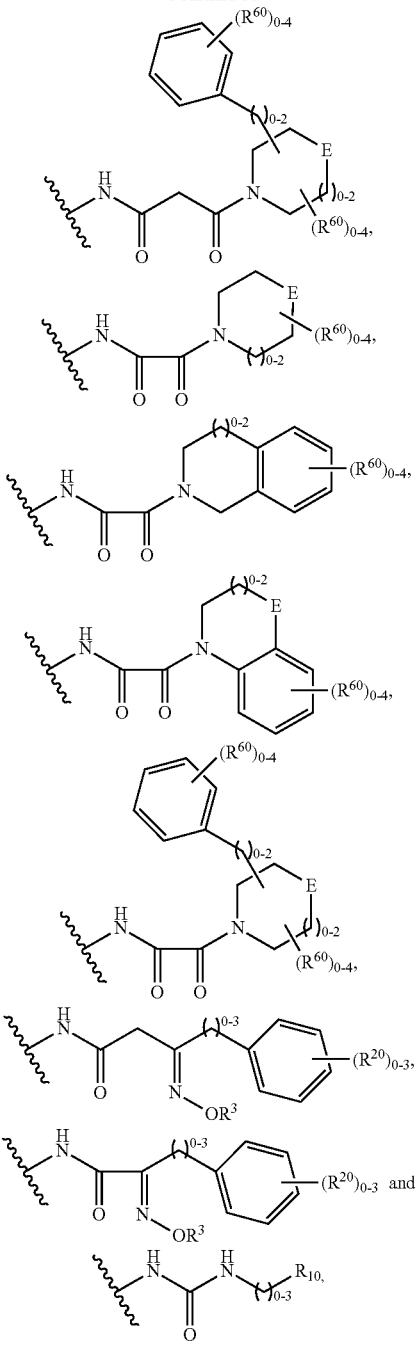

wherein each methylene in any of the above formulae, other than those in a depicted ring, is independently optionally substituted with $R^{25}$;

$R^{25}$ is selected from the group consisting of halogen, trihalomethyl, —CN, —NO$_2$, —OR$^3$, —NR$^3$R$^4$, —S(O)$_{0-2}$R$^3$, —SO$_2$NR$^3$R$^3$, —CO$_2$R$^3$, —C(O)NR$^3$R$^3$, —N(R$^3$)SO$_2$R$^3$, —N(R$^3$)C(O)R$^3$, —N(R$^3$)CO$_2$R$^3$, —C(O)R$^3$, an optionally substituted aryl, an optionally substituted arylalkyl, an optionally substituted heteroarylalkyl, and an optionally substituted (C$_1$-C$_6$)alkyl, two $R^{25}$, together with the carbon or carbons to which they are attached, can combine to form a three- to seven-membered alicyclic or heteroalicyclic;

$R^5$ is —H or an optionally substituted (C$_1$-C$_6$)alkyl;

R¹⁰ is an azolyl, wherein one or more hydrogen atoms are optionally substituted by a moiety selected from the group consisting of a halogen, $C_{1-4}$ alkyl, $C_{1-4}$ alkoxy, $C_{1-4}$ alkylthio, trihalomethyl, nitro, amino optionally independently substituted by one or two of $C_{1-4}$ alkyl, a $C_{1-4}$ alkoxycarbonyl $C_{1-4}$ alkyl, a $C_{1-4}$ alkylcarbonyl and a $C_{3-5}$ cyclic alkyl;

X and X¹ are independently selected from the group consisting of —H, halogen, cyano, nitro, $C_1$-$C_6$ alkyl, or X and X¹ taken together with the atom to which they are attached, form a $C_3$-$C_7$ cycloalkyl;

E is selected from the group consisting of —O—, —N(R¹³)—, —CH₂— and —S(O)₀₋₂—.

In a preferred embodiment of the compounds according to the present invention, a methylene group between two carbonyl groups is mono- or di-substituted with either an optionally substituted ($C_1$-$C_6$)alkyl or an optionally substituted spirocycle.

In a preferred embodiment of the compounds according to the present invention, R¹⁰ is selected from the group consisting of

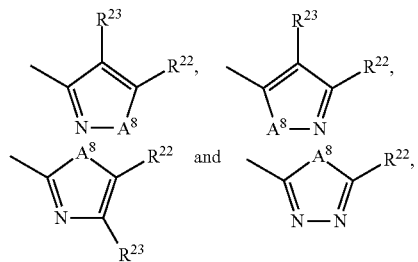

wherein A⁸ is selected from the group consisting of —O—, —S— and —NH—; and

R²² and R²³ are independently selected from the group consisting of —H, halogen, $C_{1-4}$ alkyl, $C_{1-4}$ alkoxy, $C_{1-4}$ alkylthio, trihalomethyl, nitro, amino optionally independently substituted by one or two of $C_{1-4}$ alkyl, a $C_{1-4}$ alkoxycarbonyl $C_{1-4}$ alkyl, a $C_{1-4}$ alkylcarbonyl and a $C_{3-5}$ cyclic alkyl.

In a preferred embodiment of the compounds according to the present invention, R¹⁰ is an optionally substituted azolyl selected from the group consisting of imidazolyl, oxazolyl, thiazolyl, pyrazolyl, isoxazolyl, isothiazolyl, 1,3,4-thiadiazolyl, 1,2,4-thiadiazolyl, 1,2,4-oxadiazolyl, and 1,3,4-oxadiazolyl.

In a preferred embodiment of the compounds according to the present invention, Q is selected from the group consisting of

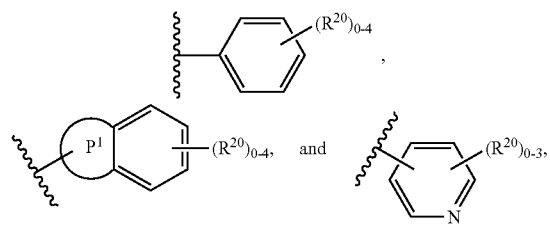

wherein P¹ is a five- to seven-membered ring, including the two shared carbon atoms of the aromatic ring to which P¹ is fused, and wherein P¹ optionally contains between one and three heteroatoms.

In a preferred embodiment of the compounds according to the present invention, Q is selected from the group consisting of phenyl, napthyl, 1,2,3,4-tetrahydronaphthyl, indanyl, benzodioxanyl, benzofuranyl, phenazinyl, phenothiazinyl, phenoxazinyl, tetrahydroisoquinolyl, pyrrolyl, pyrazolyl, pyrazolidinyl, imidazolyl, imidazolinyl, imidazolidinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, thiazolyl, thiazolinyl, thiazolidinyl, isothiazolyl, isothiazolidinyl, indolyl, isoindolyl, indolinyl, isoindolinyl, octahydroindolyl, octahydroisoindolyl, quinolyl, isoquinolyl, benzimidazolyl, thiadiazolyl, benzopyranyl, benzothiazolyl, benzoxazolyl, furyl, thienyl, benzothieliyl, and oxadiazolyl; each optionally substituted with between one and four of R²⁰, wherein each R²⁰ is selected from the group consisting of —H, halogen, trihalomethyl, —CN, —NO₂, —NH₂, —OR³, —OCF₃, —NR³R⁴, —S(O)₀₋₂R³, —S(O)₂NR³R³, —C(O)OR³, —C(O)NR³R³, —N(R³)SO₂R³, —N(R³)C(O)R³, —N(R³)C(O)OR³, —C(O)R³, —C(O)SR³, alkoxy, $C_1$-$C_4$ alkylthio, —O(CH₂)ₙaryl, —O(CH₂)ₙheteroaryl, —(CH₂)₀₋₅(aryl), —(CH₂)₀₋₅(heteroaryl), $C_1$-$C_6$ alkyl, $C_2$-$C_6$ alkenyl, $C_2$-$C_6$ alkynyl, —CH₂(CH₂)₀₋₄-T², an optionally substituted $C_{1-4}$ alkylcarbonyl, $C_{1-4}$ alkoxy, an amino optionally substituted by $C_{1-4}$ alkyl optionally substituted by $C_{1-4}$ alkoxy and a saturated or unsaturated three- to seven-membered carboxyclic or heterocyclic group, wherein T² is selected from the group consisting of —OH, —OMe, —OEt, —NH₂, —NHMe, —NMe₂, —NHEt and —NEt₂, and wherein the aryl, heteroaryl, $C_1$-$C_6$ alkyl, $C_2$-$C_6$ alkenyl, and $C_2$-$C_6$ alkynyl are optionally substituted.

In a preferred embodiment of the compounds according to the present invention, the compounds are represented by the formulas A-1 and B-1:

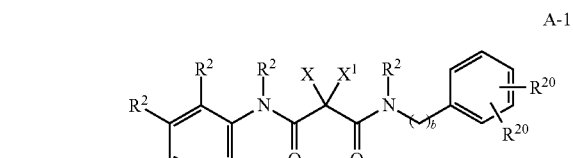

A-1

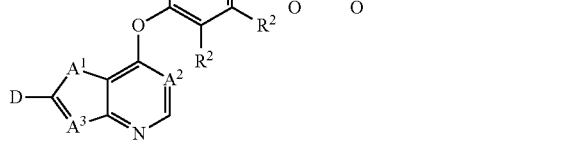

B-1

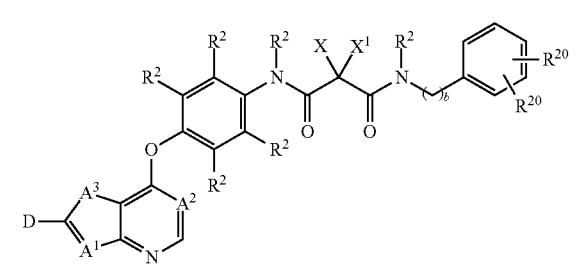

and pharmaceutically acceptable salts and complexes thereof, wherein

D is selected from the group consisting of R⁷, R¹ and R²¹, wherein

R⁷ is selected from the group consisting of —H, halogen, nitro, azido, $C_1$-$C_6$ alkyl, $C_3$-$C_{10}$ cycloalkyl, —C(O)

NR$^{42}$R$^{43}$, —Y—NR$^{42}$R$^{43}$, —NR$^{42}$C(=O)R$^{43}$, —SO$_2$R$^{42}$, —SO$_2$NR$^{42}$R$^{43}$, —NR$^{37}$SO$_2$R$^{42}$, —NR$^{37}$SO$_2$NR$^{42}$R$^{43}$, —C(=N—OR$^{42}$)R$^{43}$, —C(=NR$^{42}$)R$^{43}$, —NR$^{37}$C(=NR$^{42}$)R$^{43}$, —C(=NR$^{42}$)NR$^{37}$R$^{43}$, —NR$^{37}$C(=NR$^{42}$)NR$^{37}$R$^{43}$, —C(O)R$^{42}$, —CO$_2$R$^{42}$, —C(O)(heterocyclyl), —C(O)(C$_6$-C$_{10}$ aryl), —C(O)(heteroaryl), —Y—(C$_6$-C$_{10}$ aryl), —Y-(heteroaryl), —Y-(5-10 membered heterocyclyl), —NR$^{6a}$R$^{6b}$, —NR$^{6a}$SO$_2$R$^{6b}$, —NR$^{6a}$C(O)R$^{6b}$, —OC(O)R$^{6b}$, —NR$^{6a}$C(O)OR$^{6b}$, —OC(O)NR$^{6a}$R$^{6b}$, —OR$^{6a}$, —SR$^{6a}$, —S(O)R$^{6a}$, —SO$_2$R$^{6a}$, —SO$_3$R$^{6a}$, —SO$_2$NR$^{6a}$R$^{6b}$, —SO$_2$NR$^{42}$R$^{43}$, —COR$^{6a}$, —CO$_2$R$^{6a}$, —CONR$^{6a}$R$^{6b}$, —(C$_1$-C$_4$)fluoroalkyl, —(C$_1$-C$_4$)fluoroalkoxy, —(CZ$^3$Z$^4$)$_a$CN, wherein n is an integer ranging from 0 to 6, and the aforementioned R$^7$ groups other than —H and halogen are optionally substituted by 1 to 5 R$^{38}$, or R$^7$ is a moiety selected from the group consisting of —(CZ$^3$Z$_4$)$_a$-aryl, —(CZ$^3$Z$^4$)$_a$-heterocycle, (C$_2$-C$_6$)alkynyl, —(CZ$^3$Z$^4$)$_a$—(C$_3$-C$_6$)cycloalkyl, —(CZ$^3$Z$^4$), —(C$_5$-C$_6$)cycloalkenyl, (C$_2$-C$_6$) alkenyl and (C$^1$-C$^6$)alkyl, wherein said moiety is optionally substituted with 1 to 3 independently selected Y$^2$ groups, where a is 0, 1, 2, or 3, and wherein when a is 2 or 3, the CZ$^3$Z$^4$ units may be the same or different; wherein each R$^{6a}$ and R$^{6b}$ is independently selected from the group consisting of hydrogen and a moiety selected from the group consisting of —(CZ$^5$Z$^6$)$_u$—(C$_3$-C$_6$)cycloalkyl, —(CZ$^5$Z$^6$)$_u$—(C$_5$-C$_6$)cycloalkenyl, —(C$^5$Z$^6$)$_u$-aryl, —(CZ$^5$Z$^6$)$_u$-heterocycle, (C$_2$-C$_6$)alkenyl, and (C$_1$-C$_6$) alkyl, wherein said moiety is optionally substituted with 1 to 3 independently selected Y$^3$ groups, where u is 0, 1, 2, or 3, and wherein when u is 2 or 3, the CZ$^5$Z$^6$ units may be the same or different, or R$^{6a}$ and R$^{6b}$ taken together with adjacent atoms form a heterocycle;

each Z$^3$, Z$^4$, Z$^5$ and Z$^6$ is independently selected from the group consisting of H, F and (C$_1$-C$_6$)alkyl, or each Z$^3$ and Z$^4$, or Z$^5$ and Z$^6$ are selected together to form a carbocycle, or two Z$^3$ groups on adjacent carbon atoms are selected together to optionally form a carbocycle;

each Y$^2$ and Y$^3$ is independently selected from the group consisting of halogen, cyano, nitro, tetrazolyl, guanidino, amidino, methylguanidino, azido, —C(O)Z$^7$, —OC(O) NH$_2$, —OC(O) NHZ$^7$, —OC(O)NZ$^7$Z$^8$, —NHC(O)Z$^7$, —NHC(O)NH$_2$, —NHC(O)NHZ$^7$, —NHC(O)NZ$^7$Z$^8$, —C(O)OH, —C(O)OZ$^7$, —C(O)NH$_2$, —C(O)NHZ$^7$, —C(O)NZ$^7$Z$^8$, —P(O)$_3$H$_2$, —P(O)$_3$(Z$^7$)$_2$, —S(O)$_3$H, —S(O)Z$^7$, —S(O)$_2$Z$^7$, —S(O)$_3$Z$^7$, —Z$^7$, —OZ$^7$, —OH, —NH$_2$, —NHZ$^7$, —NZ$^7$Z$^8$, —C(=NH)NH$_2$, —C(=NOH)NH$_2$, —N-morpholino, (C$_2$-C$_6$)alkenyl, (C$_2$-C$_6$)alkynyl, (C$_1$-C$_6$)haloalkyl, (C$_2$-C$_6$)haloalkenyl, (C$_2$-C$_6$)haloalkynyl, (C$_1$-C$_6$)haloalkoxy, —(CZ$^9$Z$^{10}$)$_r$NH$_2$, —(CZ$^9$Z$^{10}$)$_r$NHZ$^3$, —(CZ$^9$Z$^{10}$)$_r$NZ$^7$Z$^8$, —X$^6$ (CZ$^9$Z$^{10}$)$_r$—(C$_3$-C$_8$)cycloalkyl, —X$^6$(CZ$^9$Z$^{10}$)$_r$—(C$_5$-C$_8$) cycloalkenyl, —X$^6$(CZ$^9$Z$^{10}$)$_r$-aryl and —X$^6$(CZ$^9$Z$^{10}$)$_r$-heterocycle, wherein r is 1, 2, 3 or 4;

X$^6$ is selected from the group consisting of O, S, NH, —C(O)—, —C(O)NH—, —C(O)O—, —S(O)—, —S(O)$_2$— and —S(O)$_3$—;

Z$^7$ and Z$^8$ are independently selected from the group consisting of an alkyl of 1 to 12 carbon atoms, an alkenyl of 2 to 12 carbon atoms, an alkynyl of 2 to 12 carbon atoms, a cycloalkyl of 3 to 8 carbon atoms, a cycloalkenyl of 5 to 8 carbon atoms, an aryl of 6 to 14 carbon atoms, a heterocycle of 5 to 14 ring atoms, an aralkyl of 7 to 15 carbon atoms, and a heteroaralkyl of 5 to 14 ring atoms, or Z$^7$ and Z$^8$ together may optionally form a heterocycle;

Z$^9$ and Z$^{10}$ are independently selected from the group consisting of H, F, a (C$_1$-C$_{12}$)alkyl, a (C$_6$-C$_{14}$)aryl, a (C$_5$-C$_{14}$) heteroaryl, a (C$_7$-C$_{15}$)aralkyl and a (C$_5$-C$_{14}$)heteroaralkyl, or Z$^9$ and Z$^{10}$ are taken together form a carbocycle, or two Z$^9$ groups on adjacent carbon atoms are taken together to form a carbocycle; or any two Y$^2$ or Y$^3$ groups attached to adjacent carbon atoms may be taken together to be —O[C(Z$^9$)(Z$^{10}$)$_r$O or —O[C (Z$^9$)(Z$^{10}$)]$_{r+1}$, or any two Y$^2$ or Y$^3$ groups attached to the same or adjacent carbon atoms may be selected together to form a carbocycle or heterocycle; and wherein any of the above-mentioned substituents comprising a CH$_3$ (methyl), CH$_2$ (methylene), or CH (methine) group which is not attached to a halogen, SO or SO$_2$ group or to a N, O or S atom optionally bears on said group a substituent selected from hydroxy, halogen, (C$_1$-C$_4$)alkyl, (C$_1$-C$_4$) alkoxy and an —N[(C$_1$-C$_4$)alkyl][(C$_1$-C$_4$)alkyl];

R$^1$ is —C≡CH or —C≡C—(CR$^{45}$R$^{45}$)$_n$—R$^{46}$;

each R$^{45}$ is independently selected from the group consisting of H, a (C$_1$-C$_6$)alkyl and a (C$_3$-C$_8$)cycloalkyl;

R$^{46}$ is selected from the group consisting of heterocyclyl, —N(R$^{47}$)—C(O)—N(R$^{47}$)(R$^{48}$), —N(R$^{47}$)—C(S)—N (R$^{47}$)(R$^{48}$), —N(R$^{47}$)—C(O)—OR$^{48}$, —N(R$^{47}$)—C(O)—(CH$_2$)$_n$—R$^{48}$, —N(R$^{47}$)—SO$_2$R$^{47}$, —(CH$_2$)$_n$NR$^{47}$R$^{48}$, —(CH$_2$)$_n$OR$^{48}$, —(CH$_2$)$_n$SR$^{49}$, —(CH$_2$)$_n$S(O)R$^{49}$, —(CH$_2$)$_n$S(O)$_2$R$^{49}$, —OC(O)R$^{49}$, —OC(O)OR$^{49}$, —C(O)NR$^{47}$R$^{48}$, heteroaryl optionally substituted with one or more substituents selected from the group consisting of halo, —CF$_3$, (C$_1$-C$_6$)alkoxy, —NO$_2$, (C$_1$-C$_6$)alkyl, —CN, —SO$_2$R$^{50}$ and —(CH$_2$)$_n$NR$^{50}$R$^{51}$, and aryl optionally substituted with one or more substituents selected from the group consisting of halo, —CF$_3$, (C$_1$-C$_6$)alkoxy, —NO$_2$, (C$_1$-C$_6$)alkyl, —CN, —SO$_2$R$^{50}$ and —(CH$_2$)$_n$NR$^{50}$R$^{51}$;

R$^{47}$ and R$^{48}$ are independently selected from the group consisting of H, (C$_1$-C$_6$)alkyl, (C$_3$-C$_8$)cycloalkyl, heterocyclyl, —(CH$_2$)$_n$NR$^{50}$R$^{51}$, —(CH$_2$)$_n$OR$^{50}$, —(CH$_2$)$_n$C(O) R$^{49}$, —C(O)$_2$R$^{49}$, —(CH$_2$)$_n$SR$^{49}$, —(CH$_2$)$_n$S(O)R$^{49}$, —(CH$_2$)$_n$S(O)$_2$R$^{49}$, —(CH$_2$)$_n$R$^{49}$, —(CH$_2$)$_n$CN, aryl optionally substituted with one or more substituents selected from the group consisting of halo, —CF$_3$, (C$_1$-C$_6$) alkoxy, —NO$_2$, (C$_1$-C$_6$)alkyl, —CN, —(CH$_2$)$_n$OR$^{49}$, —(CH$_2$)$_n$heterocyclyl, —(CH$_2$)$_n$heteroaryl, —SO$_2$R$^{50}$ and —(CH$_2$)$_n$NR$^{50}$R$^{51}$, and heteroaryl optionally substituted with one or more substituents selected from the group consisting of halo, —CF$_3$, (C$_1$-C$_6$)alkoxy, —NO$_2$, (C$_1$-C$_6$) alkyl, —CN, —(CH$_2$)$_n$OR$^{49}$, —(CH$_2$)$_n$heterocyclyl, —(CH$_2$)$_n$heteroaryl, —SO$_2$R$^{50}$ and —(CH$_2$)$_n$NR$^{50}$R$^{51}$, or R$^{47}$ and R$^{48}$, together with the atom to which they are attached, form a 3-8 membered carbo- or heterocyclic ring;

R$^{49}$ is selected from the group consisting of (C$_1$-C$_6$)alkyl, (C$_3$-C$_8$)cycloalkyl, heterocyclyl(C$_1$-C$_6$)alkylene, aryl(C$_1$-C$_6$)alkylene wherein the aryl is optionally substituted with one or more substituents selected from the group consisting of halo, —CF$_3$, (C$_1$-C$_6$)alkoxy, —NO$_2$, (C$_1$-C$_6$)alkyl, —CN, —SO$_2$R$^{50}$ and —(CH$_2$)$_n$NR$^{50}$R$^{51}$, heteroaryl(C$_1$-C$_6$)alkylene wherein the heteroaryl is optionally substituted with one or more substituents selected from the group consisting of halo, —CF$_3$, (C$_1$-C$_6$)alkoxy, —NO$_2$, (C$_1$-C$_6$) alkyl, —CN, —SO$_2$R$^{50}$ and —(CH$_2$)$_n$NR$^{50}$R$^{51}$, aryl optionally substituted with one or more substituents selected from the group consisting of halo, —CF$_3$, (C$_1$-C$_6$)

alkoxy, —NO$_2$, (C$_1$-C$_6$)alkyl, —CN, —SO$_2$R$^{50}$ and —(CH$_2$)$_n$NR$^{50}$R$^{51}$, and heteroaryl optionally substituted with one or more substituents selected from the group consisting of halo, —CF$_3$, (C$_1$-C$_6$)alkoxy, —NO$_2$, (C$_1$-C$_6$) alkyl, —CN, —SO$_2$R$^{50}$ and —(CH$_2$)$_n$NR$^{50}$R$^{51}$;

R$^{50}$ and R$^{51}$ are independently selected from the group consisting of H, (C$_1$-C$_6$)alkyl, (C$_3$-C$_8$)cycloalkyl and —C(O)R$^{45}$, or R$^{50}$ and R$^{51}$, together with the atom to which they are attached, form a 3-8 membered carbo- or hetero-cyclic ring; and R$^{21}$ is the group defined by —(Z$^{11}$)—(Z$^{12}$)$_m$(Z$^{13}$)$_{m1}$, wherein Z$^{11}$ is heterocyclyl, when m and m1 are 0, or heterocyclylene, when either m or m1 are 1;

Z$^{12}$ is selected from the group consisting of OC(O), OC(S) and C(O);

Z$^{13}$ is selected from the group consisting of heterocyclyl, aralkyl, N(H)R$^{52}$, (C$_1$-C$_3$)alkyl, —OR$^{52}$, halo, S(O)$_2$R$^{56}$, (C$_1$-C$_3$)hydroxyalkyl and (C$_1$-C$_3$)haloalkyl;

m is 0 or 1;

m1 is 0 or 1;

R$^{52}$ is selected from the group consisting of H, —(CH$_2$)$_q$S(O)$_2$R$^{54}$, —(C$_1$-C$_6$) alkyl-NR$^{53}$R$^{53}$ (C$_1$-C$_3$)alkyl, —(CH$_2$)$_q$OR$^{53}$, —C(O)R$^{54}$ and —C(O)OR$^{53}$;

q is 0, 1, 2, 3 or 4;

each R$^{53}$ is independently (C$_1$-C$_3$)alkyl;

R$^{54}$ is (C$_1$-C$_3$)alkyl or N(H)R$^3$;

R$^{56}$ is selected from the group consisting of NH$_2$, (C$_1$-C$_3$) alkyl and OR$^{52}$;

A$^1$ is selected from the group consisting of —CH$_2$—, —O—, —S—, —N(H)—, —N(C$_1$-C$_6$ alkyl)-, —N—(Y-aryl)-, —N-OMe, —NCH$_2$OMe and N-Bn;

Y is a bond or —(C(R$^{11}$)(H))$_t$—, wherein t is an integer from 1 to 6; and

R$^{11}$ at each occurrence is independently selected from the group consisting of H and C$_1$-C$_6$ alkyl, wherein the C$_1$-C$_6$ alkyl is optionally substituted;

A$^2$ is selected from the group consisting of N and CR, wherein R is selected from the group consisting of —H, halogen, —CN, C$_1$-C$_6$ alkyl, C$_2$-C$_6$ alkenyl, and C$_2$-C$_6$ alkynyl, wherein the C$_1$-C$_6$ alkyl, C$_2$-C$_6$ alkenyl, and C$_2$-C$_6$ alkynyl are optionally substituted;

A$^3$ is selected from the group consisting of C-D and N;

R$^2$ at each occurrence is independently selected from the group consisting of —H, halogen, trihalomethyl, —CN, —NO$_2$, —NH$_2$, —OR$^3$, —NR$^3$R$^4$, —S(O)$_{0-2}$R$^3$, —S(O)$_2$NR$^3$R$^3$, —C(O)OR$^3$, —C(O)NR$^3$R$^3$, —N(R$^3$)SO$_2$R$^3$, —N(R$^3$)C(O)R$^3$, —N(R$^3$)CO$_2$R$^3$, —C(O)R$^3$, alkoxy, C$_1$-C$_4$ alkylthio, —O(CH$_2$)$_n$aryl, —O(CH$_2$)$_n$heteroaryl, —(CH$_2$)$_{0-5}$(aryl), —(CH$_2$)$_{0-5}$(heteroaryl), C$_1$-C$_6$ alkyl, C$_2$-C$_6$ alkenyl, C$_2$-C$_6$ alkynyl, —CH$_2$(CH$_2$)$_{0-4}$-T$^2$, wherein T$^2$ is selected from the group consisting of —OH, —OMe, —OEt, —NH$_2$, —NHMe, —NMe$_2$, —NHEt and —NEt$_2$, and wherein the aryl, heteroaryl, C$_1$-C$_6$ alkyl, C$_2$-C$_6$ alkenyl, and C$_2$-C$_6$ alkynyl are optionally substituted; and each R$^3$ is independently selected from the group consisting of —H and R$^4$;

R$^4$ is selected from the group consisting of a (C$_1$-C$_6$)alkyl, an aryl, a lower arylalkyl, a heterocyclyl and a lower heterocyclylalkyl, each of which is optionally substituted, or R$^3$ and R$^4$, taken together with a common nitrogen to which they are attached, form an optionally substituted five- to seven-membered heterocyclyl, which optionally contains at least one additional annular heteroatom selected from the group consisting of N, O, S and P;

X and X$^1$ are each independently selected from the group consisting of —H, halogen, cyano, nitro, C$_1$-C$_6$ alkyl, or X and X$^1$ taken together with the atom to which they are attached, form a C$_3$-C$_7$ cycloalkyl;

b is 0, 1, 2, 3 or 4;

R$^{20}$ is selected from the group consisting of —H, halogen, trihalomethyl, —CN, —NO$_2$, —NH$_2$, —OR$^3$, —OCF$_3$, —NR$^3$R$^4$, —S(O)$_{0-2}$R$^3$, —S(O)$_2$NR$^3$R$^3$, —C(O)OR$^3$, —C(O)NR$^3$R$^3$, —N(R$^3$)SO$_2$R$^3$, —N(R$^3$)C(O)R$^3$, —N(R$^3$)C(O)OR$^3$, —C(O)R$^3$, —C(O)SR$^3$, alkoxy, C$_1$-C$_4$ alkylthio, —O(CH$_2$)$_n$aryl, —O(CH$_2$)$_n$heteroaryl, —(CH$_2$)$_{0-5}$(aryl), —(CH$_2$)$_{0-5}$(heteroaryl), C$_1$-C$_6$ alkyl, C$_2$-C$_6$ alkenyl, C$_2$-C$_6$ alkynyl, —CH$_2$(CH$_2$)$_{0-4}$-T$^2$, an optionally substituted C$_{1-4}$ alkylcarbonyl, C$_{1-4}$ alkoxy, an amino optionally substituted by C$_{1-4}$ alkyl optionally substituted by C$_{1-4}$ alkoxy and a saturated or unsaturated three- to seven-membered carboxyclic or heterocyclic group, wherein T$^2$ is selected from the group consisting of —OH, —OMe, —OEt, —NH$_2$, —NHMe, —NMe$_2$, —NHEt and —NEt$_2$, and wherein the aryl, heteroaryl, C$_1$-C$_6$ alkyl, C$_2$-C$_6$ alkenyl, and C$_2$-C$_6$ alkynyl are optionally substituted;

In another preferred embodiment of the compounds according to the present invention, D is defined by the group R$^7$, wherein R$^7$ is selected from the group consisting of —H, halogen, C$_1$-C$_6$ alkyl, —C(O)NR$^{42}$R$^{43}$, —C(O)(C$_6$-C$_{10}$ aryl), —C(O)(heterocyclyl), —C(O)(heteroaryl), —Y—(C$_6$-C$_{10}$ aryl), —Y-(5-10 membered heterocyclyl), —Y-(heteroaryl), —S-aryl, —S—C$_1$-C$_6$ alkyl, —SO—C$_1$-C$_6$ alkyl, —SO$_2$—C$_1$-C$_6$ alkyl, —NR$^{42}$R$^{43}$, —SO$_2$NR$^{42}$R$^{43}$ and —CO$_2$R$^{6a}$, wherein the aforementioned R$^7$ groups other than —H and halogen are optionally substituted by 1 to 5 R$^{38}$.

In another preferred embodiment of the compounds according to the present invention, D is defined by the group R$^7$, wherein R$^7$ is selected from the group consisting of —H, —C(O)NR$^{42}$R$^{43}$, —Y—(C$_6$-C$_{10}$ aryl), —Y-(heteroaryl), —C(O)(heterocyclyl) and —Y—NR$^{42}$R$^{43}$, wherein the aforementioned R$^7$ groups other than —H are optionally substituted by 1 to 5 R$^{38}$.

In another preferred embodiment of the compounds according to the present invention, D is defined by the group R$^7$, wherein R$^7$ is selected from the group consisting of —H, —C(O)NR$^{42}$R$^{43}$, —Y—(C$_6$-C$_{10}$ aryl), —Y-(heteroaryl), —C(O)(heterocyclyl) and —Y—NR$^{42}$R$^{43}$, wherein the aforementioned R$^7$ groups other than —H are optionally substituted by 1 to 5 R$^{38}$.

In another preferred embodiment of the compounds according to the present invention, D is defined by the group R$^7$, wherein R$^7$ is selected from the group consisting of —H, —Y—(C$_6$-C$_{10}$ aryl), —Y-(heteroaryl) and —C(O)(heterocyclyl), wherein the aforementioned R$^7$ groups other than —H are optionally substituted by 1 to 5 R$^{38}$.

Preferred compounds according to formulas A-1 and B-1 have groups as defined in the preferred embodiments of the present invention.

In preferred embodiment of the compounds according to the present invention, the compounds are represented by the formulas A-2 and B-2:

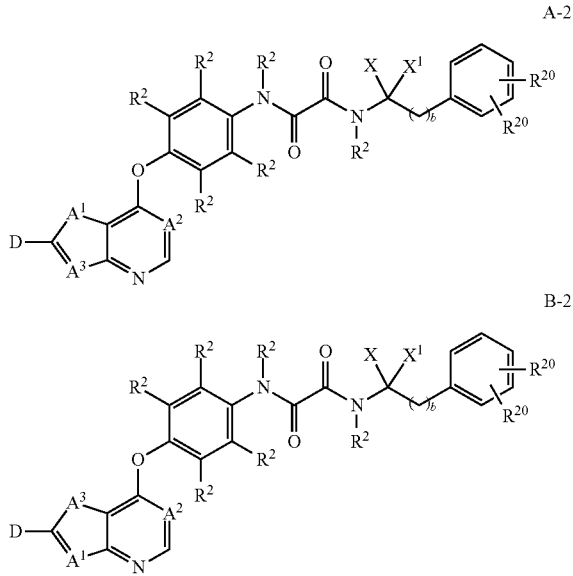

and pharmaceutically acceptable salts and complexes thereof, wherein

D is selected from the group consisting of $R^7$, $R^1$ and $R^{21}$, wherein $R^7$ is selected from the group consisting of —H, halogen, nitro, azido, $C_1$-$C_6$ alkyl, $C_3$-$C_{10}$ cycloalkyl, —C(O)NR$^{42}$R$^{43}$, —Y—NR$^{42}$R$^{43}$, —NR$^{42}$C(O)R$^{43}$, —SO$_2$R$^{42}$, SO$_2$NR$^{42}$R$^{43}$, —NR$^{37}$SO$_2$R$^{42}$, —NR$^{37}$SO$_2$NR$^{42}$R$^{43}$, —C(=N—OR$^{42}$)R$^{43}$, —C(=NR$^{42}$)R$^{43}$, —NR$^{37}$C(=NR$^{42}$)R$^{43}$, —C(=NR$^{42}$)NR$^{37}$R$^{43}$, —NR$^{37}$C(=NR$^{42}$)NR$^{37}$R$^{43}$, —C(O)R$^{42}$, —CO$_2$R$^{42}$, —C(O)(heterocyclyl), —C(O)($C_6$-$C_{10}$ aryl), —C(O)(heteroaryl), —Y—($C_6$-$C_{10}$ aryl), —Y-(heteroaryl), —Y-(5-10 membered heterocyclyl), —NR$^{6a}$R$^{6b}$ NR$^{6a}$SO$_2$R$^{6b}$, —NR$^{6a}$C(O)R$^{6b}$, —OC(O)R$^{6b}$, —NR$^{6a}$C(O)OR$^{6b}$, —OC(O)NR$^{6a}$R$^{6b}$, —OR$^{6a}$, —SR$^{6a}$, —S(O)R$^{6a}$, —SO$_2$R$^{6a}$, —SO$_3$R$^{6a}$, —SO$_2$NR$^{6a}$R$^{6b}$, —SO$_2$NR$^{42}$R$^{43}$, —COR$^{6a}$, —CO$_2$R$^{6a}$, —CONR$^{6a}$R$^{6b}$, ($C_1$-$C_4$)fluoroalkyl, —($C_1$-$C_4$)fluoroalkoxy, —(CZ$^3$ Z$^4$)$_a$CN, wherein n is an integer ranging from 0 to 6, and the aforementioned R groups other than —H and halogen are optionally substituted by 1 to 5 R$^{38}$, or $R^7$ is a moiety selected from the group consisting of —(CZ$^3$Z$_4$)$_a$-aryl, —(CZ$^3$Z$^4$)$_a$-heterocycle, ($C_2$-$C_6$)alkynyl, —(CZ$^3$Z$^4$), —($C_3$-$C_6$)cycloalkyl, —(CZ$^3$Z$^4$), —($C_5$-$C_6$)cycloalkenyl, ($C_2$-$C_6$) alkenyl and ($C^1$—$C^6$)alkyl, wherein said moiety is optionally substituted with 1 to 3 independently selected $Y^2$ groups, where a is 0, 1, 2, or 3, and wherein when a is 2 or 3, the CZ$^3$Z$^4$ units may be the same or different; wherein each R$^{6a}$ and R$^{6b}$ is independently selected from the group consisting of hydrogen and a moiety selected from the group consisting of —(CZ$^5$Z$^6$)$_u$—($C_3$-$C_6$)cycloalkyl, —(CZ'Z$^6$)$_u$—($C_5$-$C_6$)cycloalkenyl, —(CZ$^5$Z$^6$)$_u$-aryl, —(CZ$^3$Z$^6$)$_u$-heterocycle, ($C_2$-$C_6$)alkenyl, and ($C_1$-$C_6$) alkyl, wherein said moiety is optionally substituted with 1 to 3 independently selected $Y^3$ groups, where u is 0, 1, 2, or 3, and wherein when u is 2 or 3, the CZ$^5$Z$^6$ units may be the same or different, or R$^{6a}$ and R$^{6b}$ taken together with adjacent atoms form a heterocycle;

each Z$^3$, Z$^4$, Z$^5$ and Z$^6$ is independently selected from the group consisting of H, F and ($C_1$-$C_6$)alkyl, or each Z$^3$ and Z$^4$, or Z$^5$ and Z$^6$ are selected together to form a carbocycle, or two Z$^3$ groups on adjacent carbon atoms are selected together to optionally form a carbocycle;

each $Y^2$ and $Y^3$ is independently selected from the group consisting of halogen, cyano, nitro, tetrazolyl, guanidino, amidino, methylguanidino, azido, —C(O)Z$^7$, —OC(O)NH$_2$, —OC(O) NHZ$^7$, —OC(O)NZ$^7$Z$^8$, —NHC(O)Z$^7$, —NHC(O)NH$_2$, —NHC(O)NHZ$^7$, —NHC(O)NZ$^7$Z$^8$, —C(O)OH, —C(O)OZ$^7$, —C(O)NH$_2$, —C(O)NHZ$^7$, —C(O)NZ$^7$Z$^8$, —P(O)$_3$H$_2$, —P(O)$_3$(Z$^7$)$_2$, —S(O)$_3$H, —S(O)Z$^7$, —S(O)$_2$Z$^7$, —S(O)$_3$Z$^7$, —Z$^7$, —OZ$^7$, —OH, —NH$_2$, —NHZ$^7$, —NZ$^7$Z$^8$, —C(=NH)NH$_2$, —C(=NOH)NH$_2$, —N-morpholino, ($C_2$-$C_6$)alkenyl, ($C_2$-$C_6$)alkynyl, ($C_1$-$C_6$)haloalkyl, ($C_2$-$C_6$)haloalkenyl, ($C_2$-$C_6$)haloalkynyl, ($C_1$-$C_6$)haloalkoxy, —(CZ$^9$Z$^{10}$)$_r$—NH$_2$, —(CZ$^9$Z$^{10}$)$_r$NHZ$^3$, —(CZ$^9$Z$^{10}$)$_r$NZ$^7$Z$^8$, —X$^6$(CZ$^9$Z$^{10}$)$_r$—($C_3$-$C_8$)cycloalkyl, —X$^6$(CZ$^9$Z$^{10}$)$_r$—($C_5$-$C_8$)cycloalkenyl, —X$^6$(CZ$^9$Z$^{10}$)$_r$-aryl and —X$^6$(CZ$^9$Z$^{10}$)$_r$-heterocycle, wherein r is 1, 2, 3 or 4;

X$^6$ is selected from the group consisting of O, S, NH, —C(O)—, —C(O)NH—, —C(O)O—, —S(O)—, —S(O)$_2$— and —S(O)$_3$—;

Z$^7$ and Z$^8$ are independently selected from the group consisting of an alkyl of 1 to 12 carbon atoms, an alkenyl of 2 to 12 carbon atoms, an alkynyl of 2 to 12 carbon atoms, a cycloalkyl of 3 to 8 carbon atoms, a cycloalkenyl of 5 to 8 carbon atoms, an aryl of 6 to 14 carbon atoms, a heterocycle of 5 to 14 ring atoms, an aralkyl of 7 to 15 carbon atoms, and a heteroaralkyl of 5 to 14 ring atoms, or Z$^7$ and Z$^8$ together may optionally form a heterocycle;

Z$^9$ and Z$^{10}$ are independently selected from the group consisting of H, F, a ($C_1$-$C_{12}$)alkyl, a ($C_6$-$C_{14}$)aryl, a ($C_5$-$C_{14}$) heteroaryl, a ($C_7$-$C_{15}$)aralkyl and a ($C_5$-$C_{14}$)heteroaralkyl, or Z$^9$ and Z$^1$ are taken together form a carbocycle, or two Z$^9$ groups on adjacent carbon atoms are taken together to form a carbocycle; or any two $Y^2$ or $Y^3$ groups attached to adjacent carbon atoms may be taken together to be —O[C(Z$^9$)(Z$^{10}$)]$_r$O or —O[C(Z$^9$)(Z$^{10}$)]$_{r+1}$, or any two $Y^2$ or $Y^3$ groups attached to the same or adjacent carbon atoms may be selected together to form a carbocycle or heterocycle; and wherein any of the above-mentioned substituents comprising a CH$_3$ (methyl), CH$_2$ (methylene), or CH (methine) group which is not attached to a halogen, SO or SO$_2$ group or to a N, O or S atom optionally bears on said group a substituent selected from hydroxy, halogen, ($C_1$-$C_4$)alkyl, ($C_1$-$C_4$) alkoxy and an —N[($C_1$-$C_4$)alkyl][($C_1$-$C_4$)alkyl];

$R^1$ is —C≡CH or —C≡C—(CR$^{45}$R$^{45}$)$_n$—R$^{46}$;

each R$^{45}$ is independently selected from the group consisting of H, a ($C_1$-$C_6$)alkyl and a ($C_3$-$C_8$)cycloalkyl;

R$^{46}$ is selected from the group consisting of heterocyclyl, —N(R$^{47}$)—C(O)—N(R$^{47}$)(R$^{48}$), —N(R$^{47}$)—C(S)—N(R$^{47}$)(R$^{48}$), —N(R$^{47}$)—C(O)—OR$^{48}$, —N(R$^{47}$)—C(O)—(CH$_2$)$_n$—R$^{48}$, —N(R$^{47}$)—SO$_2$R$^{47}$, —(CH$_2$)$_n$NR$^{47}$R$^{48}$, —(CH$_2$)$_n$OR$^{48}$, —(CH$_2$)$_n$SR$^{49}$, —(CH$_2$)$_n$S(O)R$^{49}$, —(CH$_2$)$_n$S(O)$_2$R$^{49}$, —OC(O)R$^{49}$, —OC(O)OR$^{49}$, —C(O)NR$^{47}$R$^{48}$, heteroaryl optionally substituted with one or more substituents selected from the group consisting of halo, —CF$_3$, ($C_1$-$C_6$)alkoxy, —NO$_2$, ($C_r$—$C_6$)alkyl, —CN, —SO$_2$R$^{50}$ and —(CH$_2$)$_n$NR$^{50}$R$^{51}$, and aryl optionally substituted with one or more substituents selected from the group consisting of halo, —CF$_3$, (C$_1$-C$_6$)alkoxy, —NO$_2$, (C$_1$-C$_6$)alkyl, —CN, —SO$_2$R$^{50}$ and —(CH$_2$)$_n$NR$^{50}$R$^{51}$;

R$^{47}$ and R$^{48}$ are independently selected from the group consisting of H, (C$_1$-C$_6$)alkyl, (C$_3$-C$_8$)cycloalkyl, heterocyclyl, —(CH$_2$)$_n$NR$^{50}$R$^{51}$, —(CH$_2$)$_n$OR$^{50}$, —(CH$_2$)$_n$C(O)R$^{49}$, —C(O)$_2$R$^{49}$, —(CH$_2$)$_n$SR$^{49}$, —(CH$_2$)$_n$S(O)R$^{49}$, —(CH$_2$)$_n$S(O)$_2$R$^{49}$, —(CH$_2$)$_n$R$^{49}$, —(CH$_2$)$_n$CN, aryl optionally substituted with one or more substituents selected from the group consisting of halo, —CF$_3$, (C$_1$-C$_6$)alkoxy, —NO$_2$, (C$_1$-C$_6$)alkyl, —CN, —(CH$_2$)$_n$OR$^{49}$, —(CH$_2$)$_n$heterocyclyl, —(CH$_2$)$_n$heteroaryl, —SO$_2$R$^{50}$ and —(CH$_2$)$_n$NR$^{50}$R$^{51}$, and heteroaryl optionally substituted with one or more substituents selected from the group consisting of halo, —CF$_3$, (C$_1$-C$_6$)alkoxy, —NO$_2$, (C$_1$-C$_6$)alkyl, —CN, —(CH$_2$)$_n$OR$^{49}$, —(CH$_2$)$_n$heterocyclyl, —(CH$_2$)$_n$heteroaryl, —SO$_2$R$^{50}$ and —(CH$_2$)$_n$NR$^{50}$R$^{51}$, or R$^{47}$ and R$^{48}$, together with the atom to which they are attached, form a 3-8 membered carbo- or heterocyclic ring;

R$^{49}$ is selected from the group consisting of (C$_1$-C$_6$)alkyl, (C$_3$-C$_8$)cycloalkyl, heterocyclyl(C$_1$-C$_6$)alkylene, aryl(C$_1$-C$_6$)alkylene wherein the aryl is optionally substituted with one or more substituents selected from the group consisting of halo, —CF$_3$, (C$_1$-C$_6$)alkoxy, —NO$_2$, (C$_1$-C$_6$)alkyl, —CN, —SO$_2$R$^{50}$ and —(CH$_2$)$_n$NR$^{50}$R$^{51}$, heteroaryl(C$_1$-C$_6$)alkylene wherein the heteroaryl is optionally substituted with one or more substituents selected from the group consisting of halo, —CF$_3$, (C$_1$-C$_6$)alkoxy, —NO$_2$, (C$_1$-C$_6$)alkyl, —CN, —SO$_2$R$^{50}$ and —(CH$_2$)$_n$NR$^{50}$R$^{51}$, aryl optionally substituted with one or more substituents selected from the group consisting of halo, —CF$_3$, (C$_1$-C$_6$)alkoxy, —NO$_2$, (C$_1$-C$_6$)alkyl, —CN, —SO$_2$R$^{50}$ and —(CH$_2$)$_n$NR$^{50}$R$^{51}$, and heteroaryl optionally substituted with one or more substituents selected from the group consisting of halo, —CF$_3$, (C$_1$-C$_6$)alkoxy, —NO$_2$, (C$_1$-C$_6$)alkyl, —CN, —SO$_2$R$^{50}$ and —(CH$_2$)$_n$NR$^{50}$R$^{51}$;

R$^{50}$ and R$^{51}$ are independently selected from the group consisting of H, (C$_1$-C$_6$)alkyl, (C$_3$-C$_8$)cycloalkyl and —C(O)R$^{45}$, or R$^{50}$ and R$^{51}$, together with the atom to which they are attached, form a 3-8 membered carbo- or hetero-cyclic ring; and R$^{21}$ is the group defined by —(Z$^{11}$)—(Z$^{12}$)$_m$—(Z$^{13}$)$_{m1}$, wherein Z$^{11}$ is heterocyclyl, when m and m1 are 0, or heterocyclylene, when either m or m1 are 1;

Z$^{12}$ is selected from the group consisting of OC(O), OC(S) and C(O);

Z$^{13}$ is selected from the group consisting of heterocyclyl, aralkyl, N(H)R$^{52}$, (C$_1$-C$_3$)alkyl, —OR$^{52}$, halo, S(O)$_2$R$^{56}$, (C$_1$-C$_3$)hydroxyalkyl and (C$_1$-C$_3$)haloalkyl;

m is 0 or 1;

m1 is 0 or 1;

R$^{52}$ is selected from the group consisting of H, —(CH$_2$)$_q$S(O)$_2$R$^{54}$, —(C$_1$-C$_6$) alkyl-NR$^{53}$R$^{53}$ (C$_1$-C$_3$)alkyl, —(CH$_2$)$_q$OR$^{53}$, —C(O)R$^{54}$ and —C(O)OR$^{53}$;

q is 0, 1, 2, 3 or 4;

each R$^{53}$ is independently (C$_1$-C$_3$)alkyl;

R$^{54}$ is (C$_1$-C$_3$)alkyl or N(H)R$^{53}$;

R$^{56}$ is selected from the group consisting of NH$_2$, (C$_1$-C$_3$)alkyl and OR$^{52}$;

A$^1$ is selected from the group consisting of —CH$_2$—, —O—, —S—, —N(H)—, —N(C$_1$-C$_6$ alkyl)-, —N—(Y-aryl)-, —N-OMe, —NCH$_2$OMe and N-Bn;

Y is a bond or —(C(R$^{11}$)(H))$_t$—, wherein t is an integer from 1 to 6; and

R$^{11}$ at each occurrence is independently selected from the group consisting of H and C$_1$-C$_6$ alkyl, wherein the C$_1$-C$_6$ alkyl is optionally substituted;

A$^2$ is selected from the group consisting of N and CR, wherein R is selected from the group consisting of —H, halogen, —CN, C$_1$-C$_6$ alkyl, C$_2$-C$_6$ alkenyl, and C$_2$-C$_6$ alkynyl, wherein the C$_1$-C$_6$ alkyl, C$_2$-C$_6$ alkenyl, and C$_2$-C$_6$ alkynyl are optionally substituted;

A$^3$ is selected from the group consisting of C-D and N;

R$^2$ at each occurrence is independently selected from the group consisting of —H, halogen, trihalomethyl, —CN, —NO$_2$, —NH$_2$, —OR$^3$, —NR$^3$R$^4$, —S(O)$_{0-2}$R$^3$, —S(O)$_2$NR$^3$R$^3$, —C(O)OR$^3$, —C(O)NR$^3$R$^3$, —N(R$^3$)SO$_2$R$^3$, —N(R$^3$)C(O)R$^3$, —N(R$^3$)CO$_2$R$^3$, —C(O)R$^3$, C$_1$-C$_4$ alkoxy, C$_1$-C$_4$ alkylthio, —O(CH$_2$)$_n$aryl, —O(CH$_2$)$_n$heteroaryl, —(CH$_2$)$_{0-5}$(aryl), —(CH$_2$)$_{0-5}$(heteroaryl), C$_1$-C$_6$ alkyl, C$_2$-C$_6$ alkenyl, C$_2$-C$_6$ alkynyl, —CH$_2$(CH$_2$)$_{0-4}$-T$^2$, wherein T$^2$ is selected from the group consisting of —OH, —OMe, —OEt, —NH$_2$, —NHMe, —NMe$_2$, —NHEt and —NEt$_2$, and wherein the aryl, heteroaryl, C$_1$-C$_6$ alkyl, C$_2$-C$_6$ alkenyl, and C$_2$-C$_6$ alkynyl are optionally substituted; and R$^3$ selected from the group consisting of —H and R$^4$;

R$^4$ is selected from the group consisting of a (C$_1$-C$_6$)alkyl, an aryl, a lower arylalkyl, a heterocyclyl and a lower heterocyclylalkyl, each of which is optionally substituted, or R$^3$ and R$^4$, taken together with a common nitrogen to which they are attached, form an optionally substituted five- to seven-membered heterocyclyl, which optionally contains at least one additional annular heteroatom selected from the group consisting of N, O, S and P;

X and X$^1$ are each independently selected from the group consisting of —H, halogen, cyano, nitro, C$_1$-C$_6$ alkyl, or X and X$^1$ taken together with the atom to which they are attached form a C$_3$-C$_7$ cycloalkyl;

R$^{20}$ is selected from the group consisting of —H, halogen, trihalomethyl, —CN, —NO$_2$, —NH$_2$, —OR$^3$, —OCF$_3$, —NR$^3$R$^4$, —S(O)$_{0-2}$R$^3$, —S(O)$_2$NR$^3$R$^3$, —C(O)OR$^3$, —C(O)NR$^3$R$^3$, —N(R$^3$)SO$_2$R$^3$, —N(R$^3$)C(O)R$^3$, —N(R$^3$)C(O)OR$^3$, —C(O)R$^3$, —C(O)SR$^3$, C$_1$-C$_4$ alkoxy, C$_1$-C$_4$ alkylthio, —O(CH$_2$)$_n$aryl, —O(CH$_2$)$_n$heteroaryl, —(CH$_2$)$_{0-5}$(aryl), —(CH$_2$)$_{0-5}$(heteroaryl), C$_1$-C$_6$ alkyl, C$_2$-C$_6$ alkenyl, C$_2$-C$_6$ alkynyl —CH$_2$(CH$_2$)$_{0-4}$-T$^2$, an optionally substituted C$_{1-4}$ alkylcarbonyl, C$_{1-4}$ alkoxy, an amino optionally substituted by C$_{1-4}$ alkyl optionally substituted by C$_{1-4}$ alkoxy and a saturated or unsaturated three- to seven-membered carboxylic or heterocyclic group, wherein T$^2$ is selected from the group consisting of —OH, —OMe, —OEt, —NH$_2$, —NHMe, —NMe$_2$, —NHEt and —NEt$_2$, and wherein the aryl, heteroaryl, C$_1$-C$_6$ alkyl, C$_2$-C$_6$ alkenyl, and C$_2$-C$_6$ alkynyl are optionally substituted.

In another preferred embodiment of the compounds according to the present invention, D is defined by the group R$^7$, wherein R$^7$ is selected from the group consisting of —H, —C(O)NR$^{42}$R$^{43}$, —Y—(C$_6$-C$_{10}$ aryl), —Y-(heteroaryl) and —Y—NR$^{42}$R$^{43}$, wherein the aforementioned R$^7$ groups other than —H are optionally substituted by 1 to 5 R$^{38}$.

Preferred compounds according to formulas A-2 and B-2 have groups as defined in the preferred embodiments of the present invention.

In another preferred embodiment of the compounds according to the present invention, the compounds are represented by the formulas A-3 and B-3:

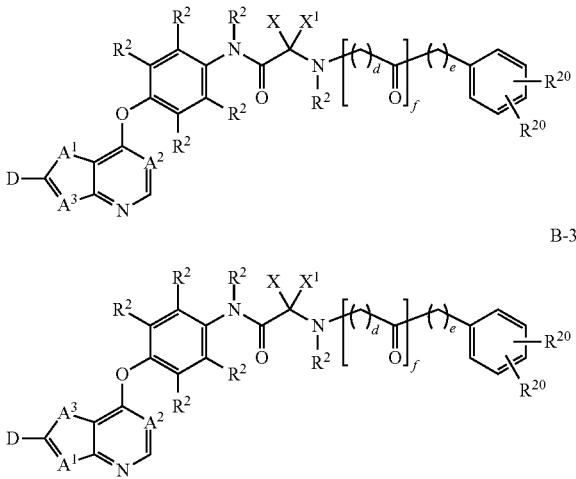

and pharmaceutically acceptable salts and complexes thereof, wherein

D is selected from the group consisting of $R^7$, $R^1$ and $R^{21}$, wherein $R^7$ is selected from the group consisting of —H, halogen, nitro, azido, $C_1$-$C_6$ alkyl, $C_3$-$C_{10}$ cycloalkyl, —C(O)$NR^{42}R^{43}$, —Y—$NR^{42}R^{43}$, —$NR^{42}$C(=O)$R^{43}$, —$SO_2R^{42}$, —$SO_2NR^{42}R^{43}$, —$NR^{37}SO_2R^{42}$, —$NR^{37}SO_2NR^{42}R^{43}$, —C(=N—$OR^{42}$)$R^{43}$, —C(=$NR^{42}$)$R^{43}$, —$NR^{37}$C(=$NR^{42}$)$R^{43}$, —C(=$NR^{42}$)$NR^{37}R^{43}$, —$NR^{37}$C(=$NR^{42}$)$NR^{37}R^{43}$, —C(O)$R^{42}$, —$CO_2R^{42}$, —C(O)(heterocyclyl), —C(O)($C_0$-$C_{10}$ aryl), —C(O)(heteroaryl), —Y—($C_6$-$C_{10}$ aryl), —Y-(heteroaryl), —Y-(5-10 membered heterocyclyl), —$NR^{6a}R^{6b}$, $NR^{6a}SO_2R^{6b}$C(O)$R^{6b}$, —OC(O)$R^{6b}$, —$NR^{6a}$C(O)$OR^{6b}$, —OC(O)$NR^{6a}R^{6b}$, —$OR^{6a}$, —$SR^{6a}$, S(O)$R^{6a}$, —$SO_2R^{6a}$, —$SO_3R^{6a}$, —$SO_2NR^{6a}R^{6b}$, —$SO_2NR^{42}R^{43}$, —$COR^{6a}$, —$CO_2R^{6a}$, —$CONR^{6a}R^{6b}$, —($C_1$-$C_4$)fluoroalkyl, —($C_1$-$C_4$)fluoroalkoxy, —($CZ^3Z^4$)$_a$CN, wherein n is an integer ranging from 0 to 6, and the aforementioned $R^7$ groups other than —H and halogen are optionally substituted by 1 to 5 $R^{38}$, or $R^7$ is moiety selected from the group consisting of —($CZ^3Z_4$)$_a$-aryl, —($CZ^3Z^4$)$_a$-heterocycle, ($C_2$-$C_6$) alkynyl, —($CZ^3Z^4$)$_a$—($C_3$-$C_6$)cycloalkyl, —($CZ^3Z^4$)$_a$— ($C_5$-$C_6$)cycloalkenyl, ($C_2$-$C_6$) alkenyl and ($C^1$—$C^6$)alkyl, wherein said moiety is optionally substituted with 1 to 3 independently selected $Y^2$ groups, where a is 0, 1, 2, or 3, and wherein when a is 2 or 3, the $CZ^3Z^4$ units may be the same or different; wherein each $R^{6a}$ and $R^{6b}$ is independently selected from the group consisting of hydrogen and a moiety selected from the group consisting of —($CZ^5Z^6$)$_u$—($C_3$-$C_6$)cycloalkyl, —($CZ^5Z^6$)$_u$—($C_5$-$C_6$)cycloalkenyl, —($CZ^5Z^6$)$_u$-aryl, —($CZ^5Z^6$)$_u$-heterocycle, ($C_2$-$C_6$)alkenyl, and ($C_1$-$C_6$) alkyl, wherein said moiety is optionally substituted with 1 to 3 independently selected $Y^3$ groups, where u is 0, 1, 2, or 3, and wherein when u is 2 or 3, the $CZ^5Z^6$ units may be the same or different, or $R^{6a}$ and $R^{6b}$ taken together with adjacent atoms form a heterocycle;

each $Z^3$, $Z^4$, $Z^5$ and $Z^6$ is independently selected from the group consisting of H, F and ($C_1$-$C_6$)alkyl, or each $Z^3$ and $Z^4$, or $Z^5$ and $Z^6$ are selected together to form a carbocycle, or two $Z^3$ groups on adjacent carbon atoms are selected together to optionally form a carbocycle;

each $Y^2$ and $Y^3$ is independently selected from the group consisting of halogen, cyano, nitro, tetrazolyl, guanidino, amidino, methylguanidino, azido, —C(O)$Z^7$, —OC(O) $NH_2$, —OC(O) $NHZ^7$, —OC(O)$NZ^7Z^8$, —NHC(O)$Z^7$, —NHC(O)$NH_2$, —NHC(O)$NHZ^7$, —NHC(O)$NZ^7Z^8$, —C(O)OH, —C(O)$OZ^7$, —C(O)$NH_2$, —C(O)$NHZ^7$, —C(O)$NZ^7Z^8$, —P(O)$_3H_2$, —P(O)$_3$($Z^7$)$_2$, —S(O)$_3$H, —S(O)$Z^7$, —S(O)$_2Z^7$, —S(O)$_3Z^7$, —$Z^7$, —$OZ^7$, —OH, —$NH_2$, —$NHZ^7$, —$NZ^7Z^8$, —C(=NH)$NH_2$, —C(=NOH)$NH_2$, —N-morpholino, ($C_2$-$C_6$)alkenyl, ($C_2$-$C_6$) alkynyl, ($C_1$-$C_6$)haloalkyl, ($C_2$-$C_6$)haloalkenyl, ($C_2$-$C_6$) haloalkynyl, ($C_1$-$C_6$)haloalkoxy, —($CZ^9Z^{10}$)$_r$$NH_2$, —($CZ^9Z^{10}$)$_r$$NHZ^3$, —($CZ^9Z^{10}$)$_r$$NZ^7Z^8$, —$X^6$($CZ^9Z^{10}$)$_r$— ($C_3$-$C_8$)cycloalkyl, —$X^6$($CZ^9Z^{10}$)$_r$—($C_5$-$C_8$)cycloalkenyl, —$X^6$($CZ^9Z^{10}$)$_r$-aryl and —$X^6$($CZ^9Z^{10}$)$_r$-heterocycle, wherein r is 1, 2, 3 or 4;

$X^6$ is selected from the group consisting of O, S, NH, —C(O)—, —C(O)NH—, —C(O)O—, —S(O)—, —S(O)$_2$— and —S(O)$_3$—;

$Z^7$ and $Z^8$ are independently selected from the group consisting of an alkyl of 1 to 12 carbon atoms, an alkenyl of 2 to 12 carbon atoms, an alkynyl of 2 to 12 carbon atoms, a cycloalkyl of 3 to 8 carbon atoms, a cycloalkenyl of 5 to 8 carbon atoms, an aryl of 6 to 14 carbon atoms, a heterocycle of 5 to 14 ring atoms, an aralkyl of 7 to 15 carbon atoms, and a heteroaralkyl of 5 to 14 ring atoms, or $Z^7$ and $Z^8$ together may optionally form a heterocycle;

$Z^9$ and $Z^{10}$ are independently selected from the group consisting of H, F, a ($C_1$-$C_{12}$)alkyl, a ($C_6$-$C_{14}$)aryl, a ($C_5$-$C_{14}$) heteroaryl, a ($C_7$-$C_{15}$)aralkyl and a ($C_5$-$C_{14}$)heteroaralkyl, or $Z^9$ and $Z^{10}$ are taken together form a carbocycle, or two $Z^9$ groups on adjacent carbon atoms are taken together to form a carbocycle; or any two $Y^2$ or $Y^3$ groups attached to adjacent carbon atoms may be taken together to be —O[C($Z^9$)($Z^{10}$)]$_r$O or —O[C($Z^9$)($Z^{10}$)]$_{r+1}$, or any two $Y^2$ or $Y^3$ groups attached to the same or adjacent carbon atoms may be selected together to form a carbocycle or heterocycle; and wherein any of the above-mentioned substituents comprising a $CH_3$ (methyl), $CH_2$ (methylene), or CH (methine) group which is not attached to a halogen, SO or $SO_2$ group or to a N, O or S atom optionally bears on said group a substituent selected from hydroxy, halogen, ($C_1$-$C_4$)alkyl, ($C_1$-$C_4$) alkoxy and an —N[($C_1$-$C_4$)alkyl][($C_1$-$C_4$)alkyl];

$R^1$ is —C≡CH or —C≡C—($CR^{45}R^{45}$)$_n$—$R^{46}$;

each $R^{45}$ is independently selected from the group consisting of H, a ($C_1$-$C_6$)alkyl and a ($C_3$-$C_8$)cycloalkyl;

$R^{46}$ is selected from the group consisting of heterocyclyl, —N($R^{47}$)—C(O)—N($R^{47}$)($R^{48}$), —N($R^{47}$)—C(S)—N ($R^{47}$)($R^{48}$), —N($R^{47}$)—C(O)—$OR^{48}$, —N($R^{47}$)—C(O)— ($CH_2$)$_n$—$R^{48}$, —N($R^{47}$)—$SO_2R^{47}$, —($CH_2$)$_n$$NR^{47}R^{48}$, —($CH_2$)$_n$$OR^{48}$, —($C_2$)$_n$$SR^{49}$, —($CH_2$)$_n$S(O)$R^{49}$, —($CH_2$)$_n$S(O)$_2R^{49}$, —OC(O)$R^{49}$, —OC(O)$OR^{49}$, —C(O)$NR^{47}R^{48}$, heteroaryl optionally substituted with one or more substituents selected from the group consisting of halo, —$CF_3$, ($C_1$-$C_6$)alkoxy, —$NO_2$, ($C_1$-$C_6$)alkyl, —CN, —$SO_2R^{50}$ and —($CH_2$)$_n$$NR^{50}R^{51}$, and aryl optionally substituted with one or more substituents selected from the group consisting of halo, —$CF_3$, ($C_1$-$C_6$)alkoxy, —$NO_2$, ($C_1$-$C_6$)alkyl, —CN, —$SO_2R^{50}$ and —($CH_2$)$_n$$NR^{50}R^{51}$;

$R^{47}$ and $R^{48}$ are independently selected from the group consisting of H, $(C_1-C_6)$alkyl, $(C_3-C_8)$cycloalkyl, heterocyclyl, $-(CH_2)_nNR^{50}R^{51}$, $-(CH_2)_nOR^{50}$, $-(CH_2)_nC(O)R^{49}$, $-C(O)_2R^{49}$, $-(CH_2)_nSR^{49}$, $-(CH_2)_nS(O)R^{49}$, $-(CH_2)_nS(O)_2R^{49}$, $-(CH_2)_nR^{49}$, $-(CH_2)_nCN$, aryl optionally substituted with one or more substituents selected from the group consisting of halo, $-CF_3$, $(C_1-C_6)$alkoxy, $-NO_2$, $(C_1-C_6)$alkyl, $-CN$, $-(CH_2)_nOR^{49}$, $-(CH_2)_n$heterocyclyl, $-(CH_2)_n$heteroaryl, $-SO_2R^{50}$ and $-(CH_2)_nNR^{50}R^{51}$, and heteroaryl optionally substituted with one or more substituents selected from the group consisting of halo, $-CF_3$, $(C_1-C_6)$alkoxy, $-NO_2$, $(C_1-C_6)$alkyl, $-CN$, $-(CH_2)_nOR^{49}$, $-(CH_2)_n$heterocyclyl, $-(CH_2)_n$heteroaryl, $-SO_2R^{50}$ and $-(CH_2)_nNR^{50}R^{51}$, or $R^{47}$ and $R^{48}$, together with the atom to which they are attached, form a 3-8 membered carbo- or hetero-cyclic ring;

$R^{49}$ is selected from the group consisting of $(C_1-C_6)$alkyl, $(C_3-C_8)$cycloalkyl, heterocyclyl$(C_1-C_6)$alkylene, aryl$(C_1-C_6)$alkylene wherein the aryl is optionally substituted with one or more substituents selected from the group consisting of halo, $-CF_3$, $(C_1-C_6)$alkoxy, $-NO_2$, $(C_1-C_6)$alkyl, $-CN$, $-SO_2R^{50}$ and $-(CH_2)_nNR^{50}R^{51}$, heteroaryl$(C_1-C_6)$alkylene wherein the heteroaryl is optionally substituted with one or more substituents selected from the group consisting of halo, $-CF_3$, $(C_1-C_6)$alkoxy, $-NO_2$, $(C_1-C_6)$alkyl, $-CN$, $-SO_2R^{50}$ and $-(CH_2)_nNR^{50}R^{51}$, aryl optionally substituted with one or more substituents selected from the group consisting of halo, $-CF_3$, $(C_1-C_6)$alkoxy, $-NO_2$, $(C_1-C_6)$alkyl, $-CN$, $-SO_2R^{50}$ and $-(CH_2)_nNR^{50}R^{51}$, and heteroaryl optionally substituted with one or more substituents selected from the group consisting of halo, $-CF_3$, $(C_1-C_6)$alkoxy, $-NO_2$, $(C_1-C_6)$alkyl, $-CN$, $-SO_2R^{50}$ and $-(CH_2)_nNR^{50}R^{51}$;

$R^{50}$ and $R^{51}$ are independently selected from the group consisting of H, $(C_1-C_6)$alkyl, $(C_3-C_8)$cycloalkyl and $-C(O)R^{45}$, or $R^{50}$ and $R^{51}$, together with the atom to which they are attached, form a 3-8 membered carbo- or hetero-cyclic ring; and $R^{21}$ is the group defined by $-(Z^{11})-(Z^{12})_m-(Z^{13})_{m1}$, wherein $Z^{11}$ is heterocyclyl, when m and m1 are 0, or heterocyclylene, when either m or m1 are 1;

$Z^{12}$ is selected from the group consisting of OC(O), OC(S) and C(O);

$Z^{13}$ is selected from the group consisting of heterocyclyl, aralkyl, $N(H)R^{52}$, $(C_1-C_3)$alkyl, $-OR^{52}$ halo, $S(O)_2R^{56}$, $(C_1-C_3)$hydroxyalkyl and $(C_1-C_3)$haloalkyl;

m is 0 or 1;

m1 is 0 or 1;

$R^{52}$ is selected from the group consisting of H, $-(CH_2)_nS(O)_2R^{54}$, $-(C_1-C_6)$ alkyl-$NR^{53}R^{53}$ $(C_1-C_3)$alkyl, $-(CH_2)_nOR^{53}$, $-C(O)R^{54}$ and $-C(O)OR^{53}$;

q is 0, 1, 2, 3 or 4;

each $R^{53}$ is independently $(C_1-C_3)$alkyl;

$R^{54}$ is $(C_1-C_3)$alkyl or $N(H)R^{53}$;

$R^{56}$ is selected from the group consisting of $NH_2$, $(C_1-C_3)$ alkyl and $OR^{52}$;

$A^1$ is selected from the group consisting of $-CH_2-$, $-O-$, $-S-$, $-N(H)-$, $-N(C_1-C_6$ alkyl)-, $-N-(Y$-aryl)-, $-N$-OMe, $-NCH_2$OMe and N-Bn;

Y is a bond or $-(C(R^{11})(H))_t-$, wherein t is an integer from 1 to 6; and $R^{11}$ at each occurrence is independently selected from the group consisting of H and $C_1-C_6$ alkyl, wherein the $C_1-C_6$ alkyl is optionally substituted;

$A^2$ is selected from the group consisting of N and CR, wherein R is selected from the group consisting of $-H$, halogen, $-CN$, $C_1-C_6$ alkyl, $C_2-C_6$ alkenyl, and $C_2-C_6$ alkynyl, wherein the $C_1-C_6$ alkyl, $C_2-C_6$ alkenyl, and $C_2-C_6$ alkynyl are optionally substituted;

$A^3$ is selected from the group consisting of C-D and N;

$R^2$ at each occurrence is independently selected from the group consisting of $-H$, halogen, trihalomethyl, $-CN$, $-NO_2$, $-NH_2$, $-OR^3$, $-NR^3R^4$, $-S(O)_{0-2}R^3$, $-S(O)_2NR^3R^3$, $-C(O)OR^3$, $-C(O)NR^3R^3$, $-N(R^3)SO_2R^3$, $-N(R^3)C(O)R^3$, $-N(R^3)CO_2R^3$, $-C(O)R^3$, $C_1-C_4$ alkoxy, alkylthio, $-O(CH_2)_n$aryl, $-O(CH_2)_n$heteroaryl, $-(CH_2)_{0-5}$(aryl), $-(CH_2)_{0-5}$(heteroaryl), $C_1-C_6$ alkyl. $C_2-C_6$ alkenyl, $C_2-C_6$ alkynyl, $-CH_2(CH_2)_{0-4}-T^2$, wherein r is selected from the group consisting of $-OH$, $-OMe$, $-OEt$, $-NH_2$, $-NHMe$, $-NMe_2$, $-NHEt$ and $-NEt_2$, and wherein the aryl, heteroaryl, $C_1-C_6$ alkyl, $C_2-C_6$ alkenyl, and $C_2-C_6$ alkynyl are optionally substituted; and $R^3$ selected from the group consisting of $-H$ and $R^4$;

$R^4$ is selected from the group consisting of a $(C_1-C_6)$alkyl, an aryl, a lower arylalkyl, a heterocyclyl and a lower heterocyclylalkyl, each of which is optionally substituted, or $R^3$ and $R^4$, taken together with a common nitrogen to which they are attached, form an optionally substituted five- to seven-membered heterocyclyl, which optionally contains at least one additional annular heteroatom selected from the group consisting of N, O, S and P;

X and $X^1$ are each independently selected from the group consisting of $-H$, halogen, cyano, nitro, $C_1-C_6$ alkyl, or X and $X^1$ taken together with the atom to which they are attached, form a $C_3-C_7$ cycloalkyl;

d is 0, 1, 2 or 3;

e is 0, 1, 2 or 3;

f is 0 or 1;

$R^{20}$ is selected from the group consisting of $-H$, halogen, trihalomethyl, $-CN$, $-NO_2$, $-NH_2$, $-OR^3$, $-OCF_3$, $-NR^3R^4$, $-S(O)_{0-2}R^3$, $-S(O)_2NR^3R^3$, $-C(O)OR^3$, $-C(O)NR^3R^3$, $-N(R^3)SO_2R^3$, $-N(R^3)C(O)R^3$, $-N(R^3)C(O)OR^3$, $-C(O)R^3$, $-C(O)SR^3$, $C_1-C_4$ alkoxy, $C_1-C_4$ alkylthio, $-O(CH_2)_n$aryl, $-O(CH_2)_n$heteroaryl, $-(CH_2)_{0-5}$(aryl), $-(CH_2)_{0-5}$(heteroaryl), $C_1-C_6$ alkyl, $C_2-C_6$ alkenyl, $C_2-C_6$ alkynyl, $-CH_2(CH_2)_{0-4}-T^2$, an optionally substituted $C_{1-4}$ alkylcarbonyl, $C_{1-4}$ alkoxy, an amino optionally substituted by $C_{1-4}$ alkyl optionally substituted by $C_{1-4}$ alkoxy and a saturated or unsaturated three- to seven-membered carboxyclic or heterocyclic group, wherein $T^2$ is selected from the group consisting of $-OH$, $-OMe$, $-OEt$, $-NH_2$, $-NHMe$, $-NMe_2$, $-NHEt$ and $-NEt_2$, and wherein the aryl, heteroaryl, $C_1-C_6$ alkyl, $C_2-C_6$ alkenyl, and $C_2-C_6$ alkynyl are optionally substituted;

In another preferred embodiment of the compounds according to the present invention, D is defined by the group $R^7$, wherein $R^7$ is selected from the group consisting of $-H$, halogen, $C_1-C_6$ alkyl, $-C(O)NR^{42}R^{43}$, $-C(O)(C_6-C_{10}$ aryl), $-C(O)$(heterocyclyl), $-C(O)$(heteroaryl), $-Y-(C_6-C_{10}$ aryl), $-Y$-(5-10 membered heterocyclyl), $-Y$-(heteroaryl), $-S$-aryl, $-S-C_1-C_6$ alkyl, $-SO-C_1-C_6$ alkyl, $-SO_2-C_1-C_6$ alkyl, $-Y-NR^{42}R^{43}$, $-SO_2NR^{42}R^{43}$ and $-CO_2R^{6a}$, wherein the aforementioned $R^7$ groups other than $-H$ and halogen are optionally substituted by 1 to 5 $R^{38}$.

Preferred compounds according to formulas A-3 and B-3 have groups as defined in the preferred embodiments of the present invention.

In the third aspect, the invention provides a composition comprising a compound according to the present invention together with a pharmaceutically acceptable excipient. In a preferred embodiment of this aspect, the composition further comprises an additional therapeutic agent.

The fourth aspect of the invention provides a method of inhibiting VEGF receptor signaling and HGF receptor signaling, the method comprising contacting the receptor with a compound according to the present invention, or with a composition according to the present invention. Inhibition of VEGF and HGF activity can be in a cell or a multicellular organism. If in a multicellular organism, the method according to this aspect of the invention comprises administering to the organism a compound according to the present invention, or a composition according to the present invention. Preferably the organism is a mammal, more preferably a human.

Examples of kinases that are inhibited by the compounds and compositions described herein and against which the methods described herein are useful include, but are not limited to, c-Met and KDR.

Depending on the particular condition, or disease, to be treated, additional therapeutic agents, which could be normally administered to treat that condition, may also be present in the compositions of this invention. In other words, compounds of this invention can be administered as the sole pharmaceutical agent or in combination with one or more other additional therapeutic (pharmaceutical) agents where the combination causes no unacceptable adverse effects. This may be of particular relevance for the treatment of hyper-proliferative diseases such as cancer. In this instance, the compound of this invention can be combined with known cytotoxic agents, signal transduction inhibitors, or with other anti-cancer agents, as well as with admixtures and combinations thereof. As used herein, additional therapeutic agents that are normally administered to treat a particular disease, or condition, are known as "appropriate for the disease, or condition, being treated". As used herein, "additional therapeutic agents" is meant to include chemotherapeutic agents and other anti-proliferative agents.

For example, chemotherapeutic agents or other anti-proliferative agents may be combined with the compounds of this invention to treat proliferative disease or cancer. Examples of chemotherapeutic agents or other anti-proliferative agents include HDAC inhibitors including, but are not limited to, SAHA, MS-275, MG0103, and those described in WO 2006/010264, WO 03/024448, WO 2004/069823, US 2006/0058298, US 2005/0288282, WO 00/71703, WO 01/38322, WO 01/70675, WO 03/006652, WO 2004/035525, WO 2005/030705, WO 2005/092899, and demethylating agents including, but not limited to, 5-aza-dC, Vidaza and Decitabine and those described in U.S. Pat. No. 6,268,137, U.S. Pat. No. 5,578,716, U.S. Pat. No. 5,919,772, U.S. Pat. No. 6,054,439, U.S. Pat. No. 6,184,211, U.S. Pat. No. 6,020,318, U.S. Pat. No. 6,066,625, U.S. Pat. No. 6,506,735, U.S. Pat. No. 6,221, 849, U.S. Pat. No. 6,953,783, U.S. Ser. No. 11/393,380 and PCT/US2006/001791.

In another embodiment of the present invention, for example, chemotherapeutic agents or other anti-proliferative agents may be combined with the compounds of this invention to treat proliferative diseases and cancer. Examples of known chemotherapeutic agents include, but are not limited to, for example, other therapies or anticancer agents that may be used in combination with the inventive anticancer agents of the present invention and include surgery, radiotherapy (in but a few examples, gamma-radiation, neutron beam radiotherapy, electron beam radiotherapy, proton therapy, brachytherapy, and systemic radioactive isotopes, to name a few), endocrine therapy, taxanes (taxol, taxotere etc), platinum derivatives, biologic response modifiers (interferons, interleukins, and tumor necrosis factor (TNF), TRAIL receptor targeting agents, to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate, Pemetrexed etc), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), Cell cycle inhibitors (KSP mitotic kinesin inhibitors, CENP-E and CDK inhibitors), enzymes (Asparaginase), and hormones (Tamoxifen, Leuprolide, Flutamide, and Megestrol), Gleevec™, adriamycin, dexamethasone, and cyclophosphamide. Antiangiogenic agents (Avastin and others). Kinase inhibitors (Imatinib (Gleevec), Sutent, Nexavar, Erbitux, Herceptin, Tarceva, Iressa and others). Agents inhibiting or activating cancer pathways such as the mTOR, HIF (hypoxia induced factor) pathways and others. For a more comprehensive discussion of updated cancer therapies see, http://www.nci.nih.gov/, a list of the FDA approved oncology drugs at http://www.fda.gov/cder/cancer/druglistframe.htm, and The Merck Manual, Eighteenth Ed. 2006, the entire contents of which are hereby incorporated by reference.

In another embodiment, the compounds of the present invention can be combined with cytotoxic anti-cancer agents. Examples of such agents can be found in the 13th Edition of the Merck Index (2001) These agents include, by no way of limitation, asparaginase, bleomycin, carboplatin, carmustine, chlorambucil, cisplatin, colaspase, cyclophosphamide, cytarabine, dacarbazine, dactinomycin, daunorubicin, doxorubicin (adriamycins), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other cytotoxic drugs suitable for use with the compounds of the invention include, but are not limited to, those compounds acknowledged to be used in the treatment of neoplastic diseases, such as those for example in Goodman and Gilman's The Pharmacological Basis of Therapeutics (Ninth Edition, 1996, McGraw-Hill). These agents include, by no way of limitation, aminoglutethimide, L-asparaginase, azathioprine, 5-azacytidine cladribine, busulfan, diethylstilbestrol, 2',2'-difluorodeoxycytidine, docetaxel, erythrohydroxynonyladenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other cytotoxic anti-cancer agents suitable for use in combination with the compounds of the invention also include newly discovered cytotoxic principles such as oxaliplatin, gemcitabine, capecitabine, epothilone and its natural or synthetic derivatives, temozolomide (Quinn et al., J. Clin. Oncology 2003, 21(4), 646-651), tositumomab (Bexxar), trabedectin (Vidal et al., Proceedings of the American Society for Clinical Oncology 2004, 23, abstract 3181), and the inhibitors of the kinesin spindle protein Eg5 (Wood et al., Curr. Opin. Pharmacol. 2001, 1, 370-377).

In another embodiment, the compounds of the present invention can be combined with other signal transduction inhibitors. Of particular interest are signal transduction inhibitors which target the EGFR family, such as EGFR, HER-2, and HER-4 (Raymond et al., Drugs 2000, 60 (Suppl.1), 15-23; Harari et al., Oncogene 2000, 19 (53), 6102-6114), and their respective ligands. Examples of such agents include, by no way of limitation, antibody therapies such as Herceptin (trastuzumab), Erbitux (cetuximab), and pertuzumab. Examples of such therapies also include, by no way of limitation, small-molecule kinase inhibitors such as ZD-1839/Iressa (Baselga et al., Drugs 2000, 60 (Suppl. 1), 33-40), OSI-774/Tarceva (Pollack et al. J. Pharm. Exp. Ther. 1999, 291(2), 739-748), CI-1033 (Bridges, Curr. Med. Chem. 1999, 6, 825-843), GW-2016 (Lackey et al., 92nd AACR Meeting, New Orleans, Mar. 24-28, 2001, abstract 4582), CP-724,714 (Jain et al. Proceedings of the American Society for Clinical Oncology 2004, 23, abstract 3122), HKI-272 (Rabindran et al., Cancer Res. 2004, 64, 3958-3965), and EKB-569 (Greenberger et al., 11th NCI-EORTC-AACR Symposium on New Drugs in Cancer Therapy, Amsterdam, Nov. 7-10, 2000, abstract 388).

In another embodiment, the compounds of the present invention can be combined with other signal transduction inhibitors targeting receptor kinases of the split-kinase domain families (VEGFR, FGFR, PDGFR, flt-3, c-kit, c-fms, and the like), and their respective ligands. These agents include, by no way of limitation, antibodies such as Avastin (bevacizumab). These agents also include, by no way of limitation, small-molecule inhibitors such as STI-571/Gleevec (Zvelebil, Curr. Opin. Oncol., Endocr. Metab. Invest. Drugs 2000, 2(1), 74-82), PTK-787 (Wood et al., Cancer Res. 2000, 60(8), 2178-2189), SU-11248 (Demetri et al. Proceedings of the American Society for Clinical Oncology 2004, 23, abstract 3001), ZD-6474 (Hennequin et al., 92nd AACR Meeting, New Orleans, Mar. 24-28, 2001, abstract 3152), AG-13736 (Herbst et al., Clin. Cancer Res. 2003, 9, 16 (suppl 1), abstract C253), KRN-951 (Taguchi et al., 95<th> AACR Meeting, Orlando, Fla., 2004, abstract 2575), CP-547,632 (Beebe et al. Cancer Res. 2003, 63, 7301-7309), CP-673,451 (Roberts et al., Proceedings of the American Association of Cancer Research 2004, 45, abstract 3989), CHIR-258 (Lee et al., Proceedings of the American Association of Cancer Research 2004, 45, abstract 2130), MLN-518 (Shen et al., Blood 2003, 102, 11, abstract 476), and AZD-2171 (Hennequin et al., Proceedings of the American Association of Cancer Research 2004, 45, abstract 4539).

In another embodiment, the compounds of the present invention can be combined with inhibitors of the Raf/MEK/ERK transduction pathway (Avruch et al., Recent Prog. Horm. Res. 2001, 56, 127-155), or the PKB (akt) pathway (Lawlor et al., J. Cell Sci. 2001, 114, 2903-2910). These include, by no way of limitation, PD-325901 (Sebolt-Leopold et al., Proceedings of the American Association of Cancer Research 2004, 45, abstract 4003), and ARRY-142886 (Wallace et al., Proceedings of the American Association of Cancer Research 2004, 45, abstract 3891).

In another embodiment, the compounds of the present invention can be combined with inhibitors of histone deacetylase. Examples of such agents include, by no way of limitation, suberoylanilide hydroxamic acid (SAHA), LAQ-824 (Ottmann et al., Proceedings of the American Society for Clinical Oncology 2004, 23, abstract 3024), LBH-589 (Beck et al., Proceedings of the American Society for Clinical Oncology 2004, 23, abstract 3025), MS-275 (Ryan et al. Proceedings of the American Association of Cancer Research 2004, 45, abstract 2452), FR-901228 (Piekarz et al., Proceedings of the American Society for Clinical Oncology 2004, 23, abstract 3028) and MGCD0103 (U.S. Pat. No. 6,897,220).

In another embodiment, the compounds of the present invention can be combined with other anti-cancer agents such as proteasome inhibitors, and m-TOR inhibitors. These include, by no way of limitation, bortezomib (Mackay et al., Proceedings of the American Society for Clinical Oncology 2004, 23, Abstract 3109), and CCI-779 (Wu et al., Proceedings of the American Association of Cancer Research 2004, 45, abstract 3849). The compounds of the present invention can be combined with other anti-cancer agents such as topoisomerase inhibitors, including but not limited to camptothecin.

Those additional agents may be administered separately from the compound-containing composition, as part of a multiple dosage regimen. Alternatively, those agents may be part of a single dosage form, mixed together with the compound of this invention in a single composition. If administered as part of a multiple dosage regimen, the two active agents may be submitted simultaneously, sequentially or within a period of time from one another which would result in the desired activity of the agents.

The amount of both the compound and the additional therapeutic agent (in those compositions which comprise an additional therapeutic agent as described above) that may be combined with the carrier materials to produce a single dosage form will vary depending upon the host treated and the particular mode of administration.

In those compositions which comprise an additional therapeutic agent, that additional therapeutic agent and the compound of this invention may act synergistically.

The data presented herein demonstrate the inhibitory effects of the VEGF and HGF inhibitors of the invention. These data lead one to reasonably expect that the compounds of the invention are useful not only for inhibition of VEGF receptor signaling and HGF receptor signaling, but also as therapeutic agents for the treatment of proliferative diseases, including cancer and tumor growth.

Preferred compounds according to the invention include those described in the examples below. Compounds were named using Chemdraw Ultra version 6.0.2 or version 8.0.3, which are available through Cambridgesoft.com, 100 Cambridge Park Drive, Cambridge, Mass. 02140, Namepro version 5.09, which is available from ACD labs, 90 Adelaide Street West, Toronto, Ontario, M5H, 3V9, Canada, or were derived therefrom.

Synthetic Schemes and Experimental Procedures

The compounds of the invention can be prepared according to the reaction schemes or the examples illustrated below utilizing methods known to one of ordinary skill in the art. These schemes serve to exemplify some procedures that can be used to make the compounds of the invention. One skilled in the art will recognize that other general synthetic procedures may be used. The compounds of the invention can be prepared from starting components that are commercially available. Any kind of substitutions can be made to the starting components to obtain the compounds of the invention according to procedures that are well known to those skilled in the art.

Thieno[3,2-b]pyridine based compounds of formula A-1 may be prepared according to a general procedure shown in the scheme A, via an amide coupling reaction between N-aryl (heteroaryl)-malonamic acids [3-oxo-3-(arylamino)- or 3-oxo-3-(heteroarylamino)-propanoic acids] (I) and thieno[3,2-b]pyridine derivatives bearing an amino-group (II).

Scheme A

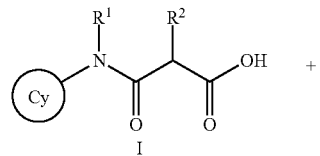

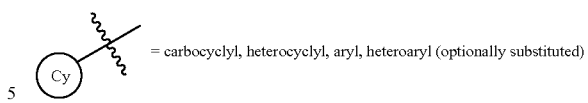

Acids I typically could be prepared according to the scheme B by reacting the amines IV either with 3-chloro-3-oxopropanoate (V) via the intermediate amino esters VI which have to be hydrolized (two-step procedure), or with 2,2-dimethyl-[1,3]dioxane-4,6-dione (Meldrum's acid) (VII) in the presence of TMSCl, to form the desired acid I in one step.

Scheme B

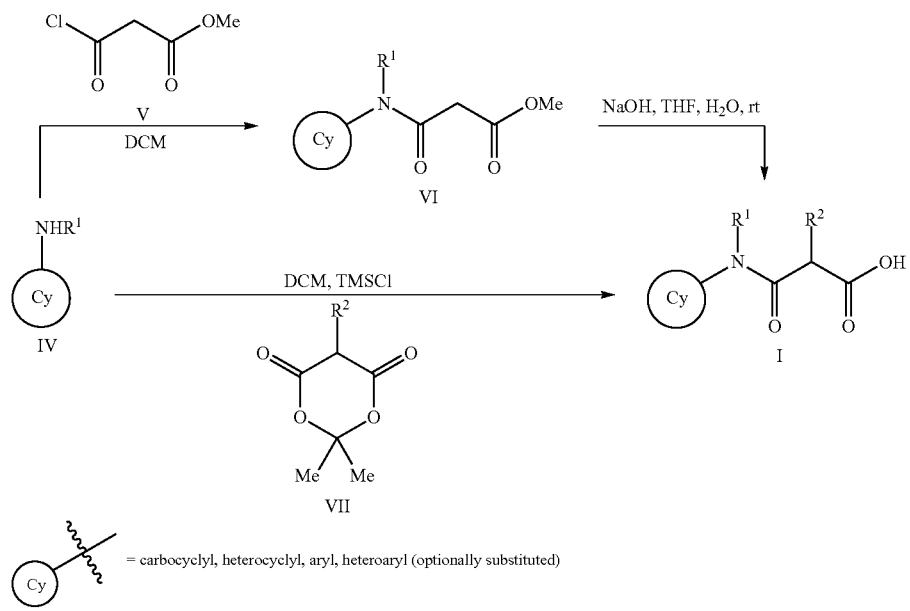

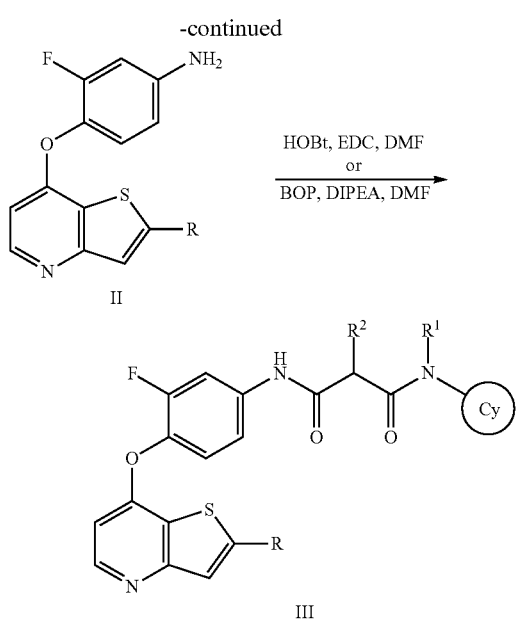

Thieno[3,2-b]pyridine derivatives bearing an amino-group (II) could be prepared in different ways depending on the nature of the substituent R on the thiophene ring of the thienopyridine bicyclic ring system. For example, when R is an amide moiety synthetic sequence shown in the Scheme C, can be employed.

Scheme C

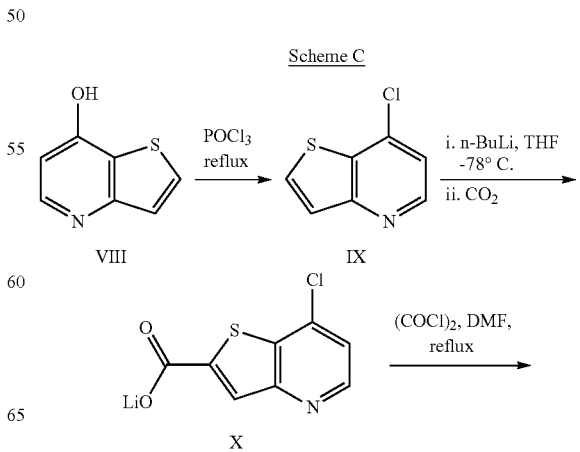

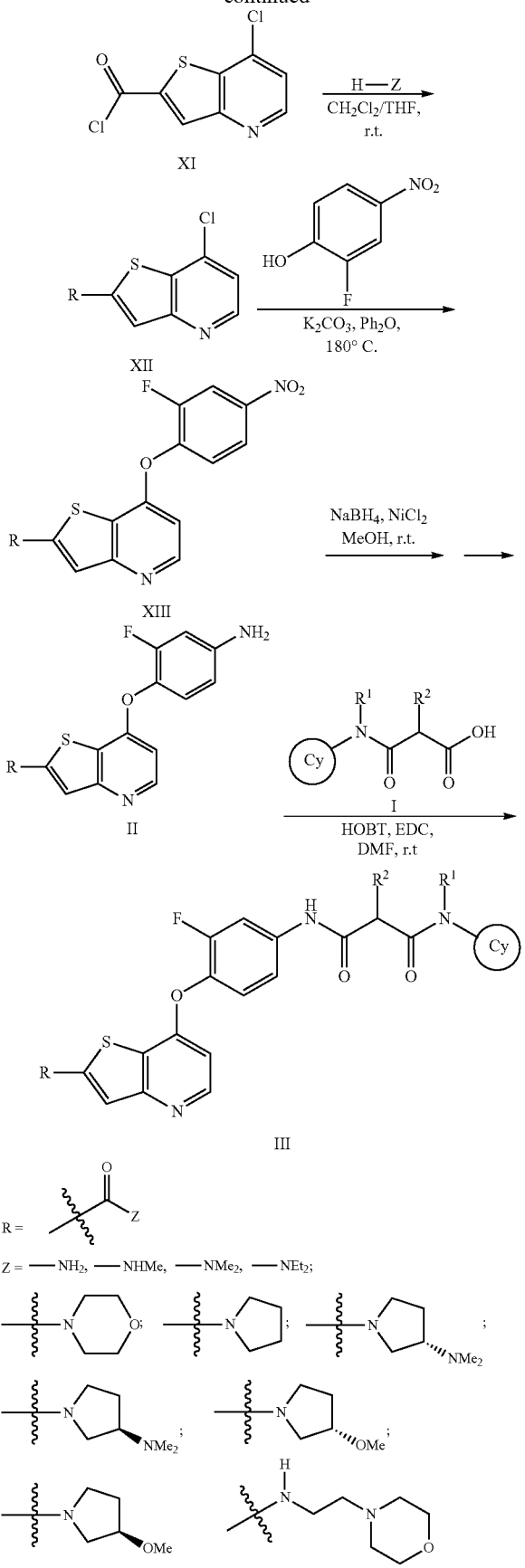
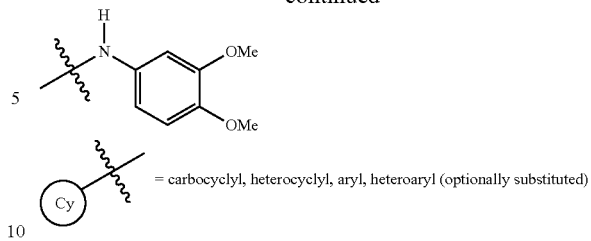

Thus, thieno[3,2-b]pyridine-7-ol (VIII) reacting with POCl₃ is converted to the chloride XI. Treatment of this material with a strong base such as n-BuLi followed by the addition of carbon dioxide affords the carboxylate X which is used without purification in the next step, providing the acyl chloride XI upon its reaction with oxalyl chloride. The acyl chloride XI is used for the next step without further purification as well: upon its reaction with different primary or secondary amines the compound XI is converted to a variety of primary and secondary amides XII which can further be derivatized via a substitution of the chlorine atom of the pyridine ring. Thus, XII reacting with 2-fluoro-4-nitrophenol in a high boiling point solvent, such as diphenyl ether in the presence of a base such as potassium carbonate, produced the nitro derivatives XIII which are then reduced to the amines II upon treatment with a mixture NiCl₂/NaBH₄. The amines H (could be used for the next step without further purification) upon treatment with N-aryl(heteroaryl)-malonamic acids (I) afford malonamides III bearing the amido-substituents on the thiophene ring such as the ones shown in the scheme C.

Scheme D

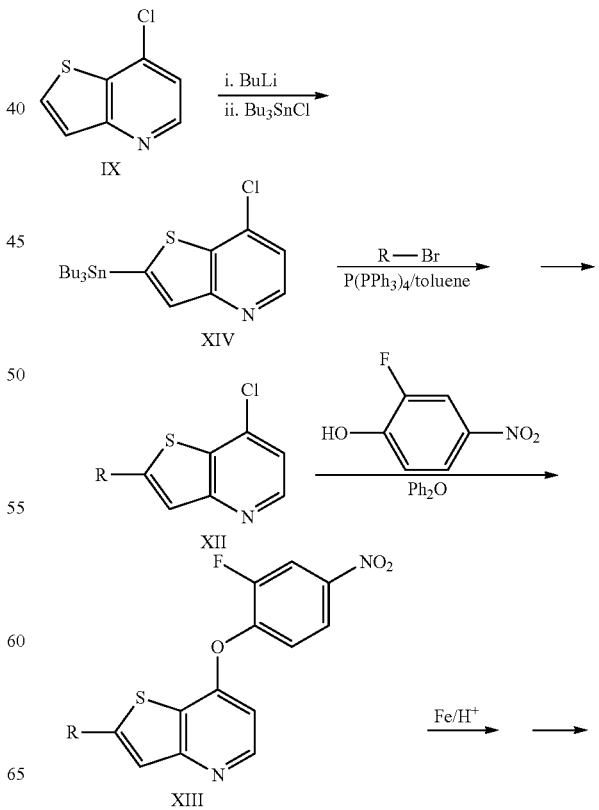

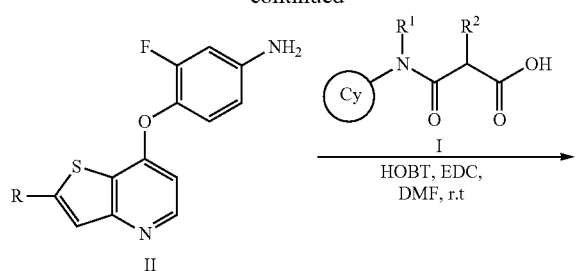

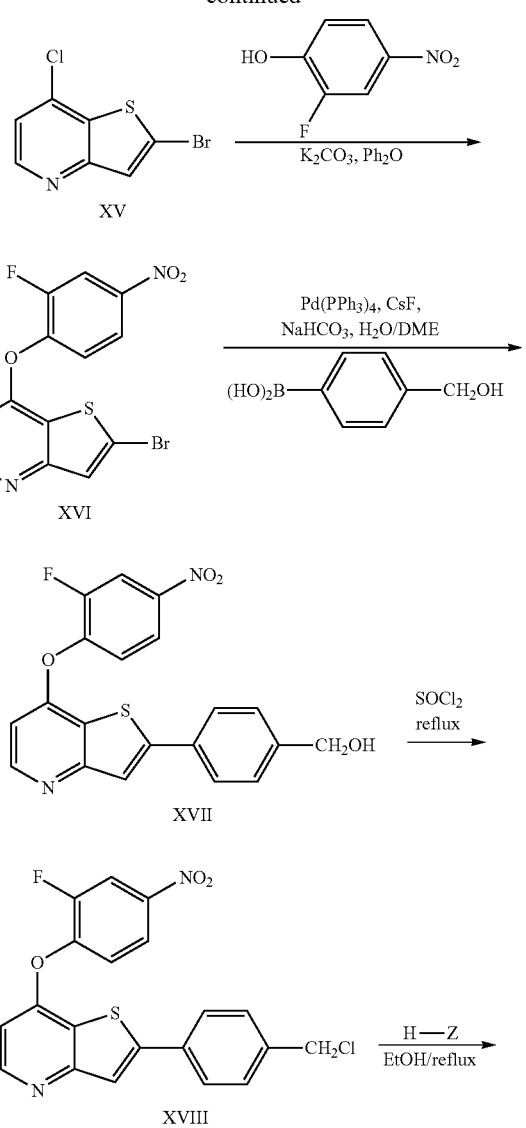

Thieno[3,2-b]pyridine based malonamides of formula A-1 bearing heteroaryl substituents instead of the amido moieties may be prepared using procedures illustrated in the Scheme D. Thus, treatment of the chloride IX with a strong base such as n-BuLi followed by an addition tributyltin chloride affords the tributylstannyl derivative XIV. This material reacting with different heteroaryl bromides in the presence of a Pd-catalyst (Stille coupling reaction) produces heteroaryl-substituted thienopyridines XII (R=heteroaryl) which can further be derivatized via a substitution of the chlorine atom of the pyridine ring of the thienopyridine ring system.

Scheme E

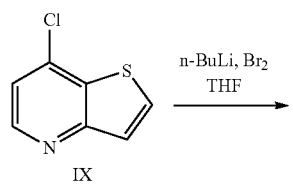

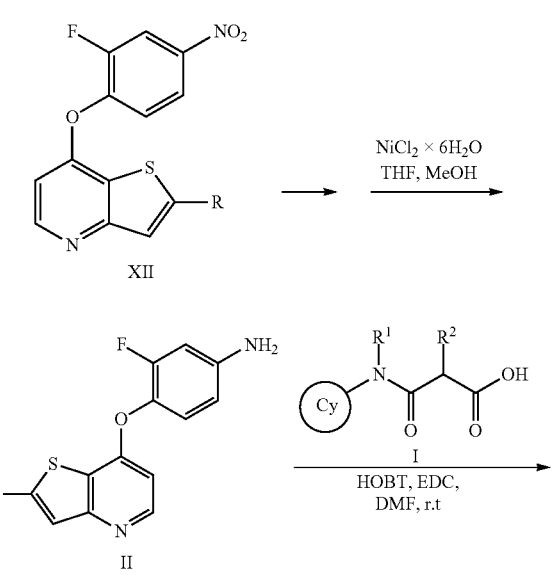

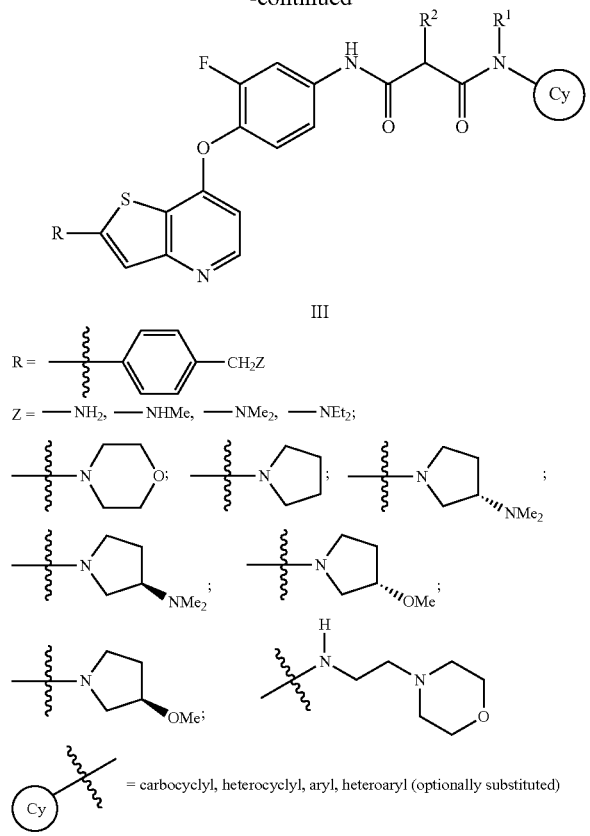

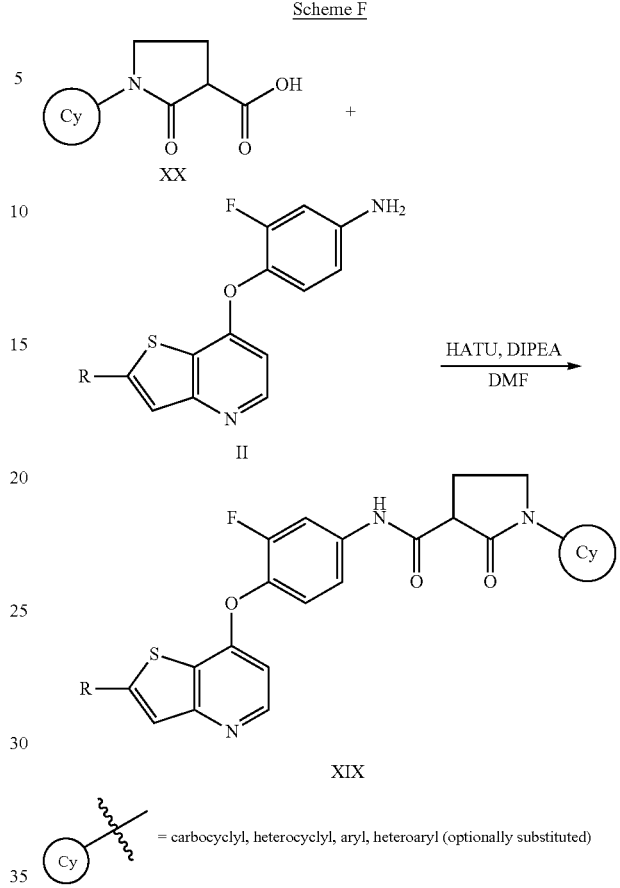

Thus, XIV reacting with 2-fluoro-4-nitrophenol in a high boiling point solvent, such as diphenyl ether in the presence of a base such as potassium carbonate, produced the nitro derivatives XIII which are then reduced to the amines II upon treatment with iron in an acidic medium. The amines II (could be used for the next step without further purification) upon treatment with N-aryl(heteroaryl)-malonamic acids (I) afford malonamides III bearing heteroaryl substituents on the thiophene ring such as the ones shown in the Scheme D.

Thieno[3,2-b]pyridine based malonamides of formula A-1 bearing aryl substituents on the thiophene ring, particularly aryl substituents with basic moieties, may be prepared using procedures illustrated in the Scheme E. Thus, treatment of the chloride IX with a strong base such as n-BuLi followed by bromination (for instance, with elemental bromine) affords the bromide XV. This material reacting with 2-fluoro-4-nitrophenol in a high boiling point solvent, such as diphenyl ether in the presence of a base such as potassium carbonate, produced the nitro derivative XVI which underwent a reaction with 4-(hydroxymethyl)phenylboronic acid in the presence of a base and a Pd-catalyst (Suzuki coupling reaction) to provide aryl-substituted derivative XVII with a free hydroxyl group. The hydroxyl group was replaced by a halogen (for example, chloride using the thionyl chloride) to form the compound XVIII which upon treatment with secondary and primary amines was converted into a variety of aryl-substituted compounds XII (R=substituted aryl). The nitro group of these basic entities was reduced with $NaBH_4/NiCl_2$ to form the amines II. These intermediates (could be used for the next step without further purification) upon treatment with N-aryl (heteroaryl)-malonamic acids (I) afford malonamides III bearing aryl substituents with basic moieties, attached to the thiophene ring such as the ones shown in the Scheme E.

Thieno[3,2-b]pyridine based compounds of formula XIX may be prepared according to a general procedure shown in the scheme F, via an amide coupling reaction between 2-oxo-1-aryl(heteroaryl)pyrrolidine-3-carboxylic acids (XX) and thieno[3,2-b]pyridine derivatives bearing an amino-group (II). Acids XX could be prepared following the literature procedure [S. Danishefsky. R. K. Singh. JACS, 1975, 97, 3239-3241] or purchased if commercially available.

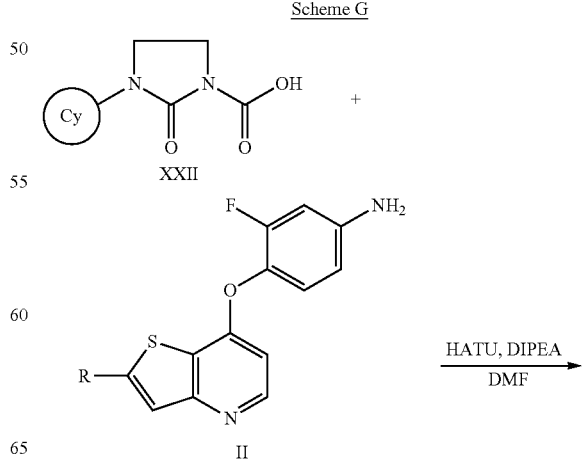

-continued

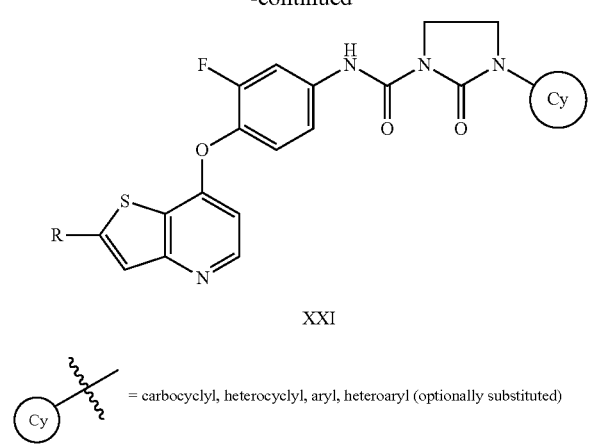

Thieno[3,2-b]pyridine based compounds of formula XXI could be prepared via a condensation reaction (scheme G) between amines II and 2-oxo-3-aryl(heteroaryl)-1-carbonyl chlorides of a general formula XXII. Acyl chlorides XXII could be prepared following the literature procedure (*Chem. Abstr.*; 88; 6873 and P. Mayer, et al.; *J. Med. Chem.*; 2000, 43, 3653-3664) while the reaction could be carried out in aprotic solvents such as DCM, CHCl$_3$, toluene, ethylene glycol dimethyl ether, MeCN, DMF, DMSO, THF, dioxane and like, in the presence of organic bases such as DIPEA, Et$_3$N, DBU, DMAP, N-methylmorpholine, N-methylpiperidine, and like.

Scheme H

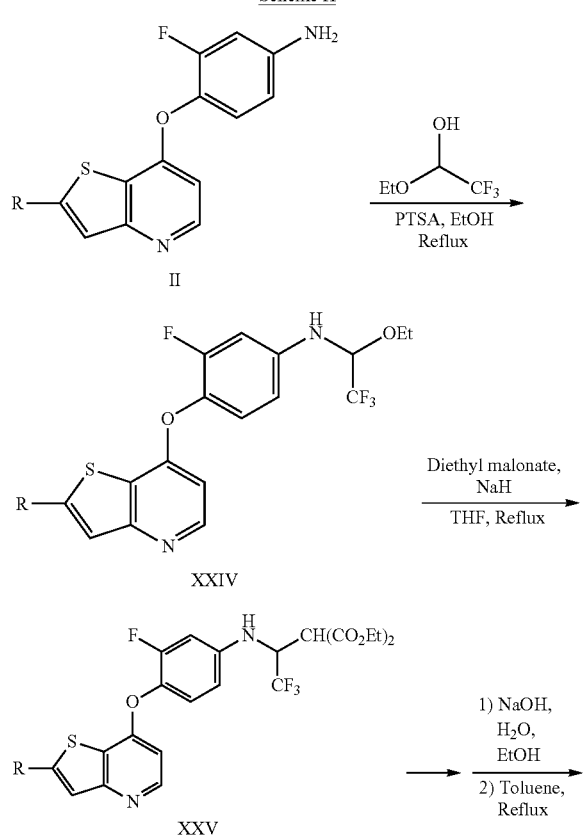

-continued

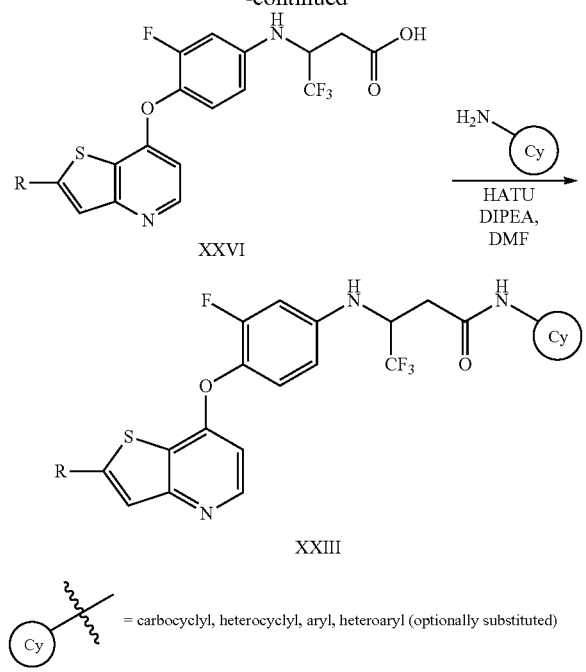

4,4,4-Trifluoro-N-aryl(heteroaryl)-3-(amino)butanamides of the general formula XXIII may be obtained via a short reaction sequence starting from the amines II. Amines II upon treatment with trifluoroacetaldehyde ethyl hemiacetal under acidic conditions (e.g. in the presence of 4-toluenesulfonic acid) in polar solvents such as ethanol are transformed into N-(1-ethoxy-2,2,2-trifluoroethyl)amines of the general structure XXIV. Compounds XXIV reacting with malonates under basic conditions form 2-(2,2,2-trifluoro-1-(amino)ethyl)malonates such as XXV. The amino di-esters XXV undergo alkaline hydrolysis to form the intermediate malonic acids (not shown in the scheme A), which are further decarboxylated, to afford 4,4,4-trifluoro-3-(amino)butanoic acids XXVI. Acids XXVI are coupled to different primary or secondary amines using standard techniques, to produce title compounds XXIII.

Scheme I

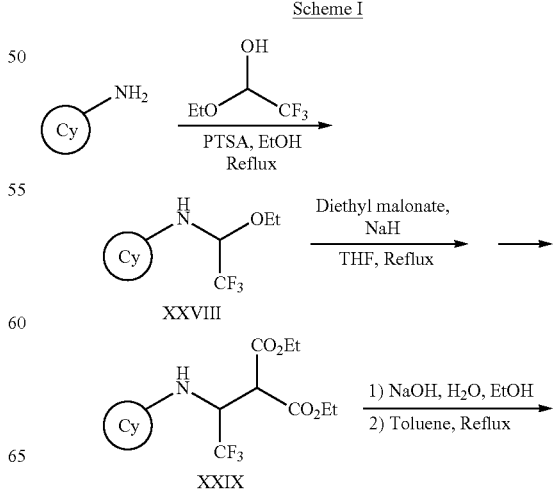

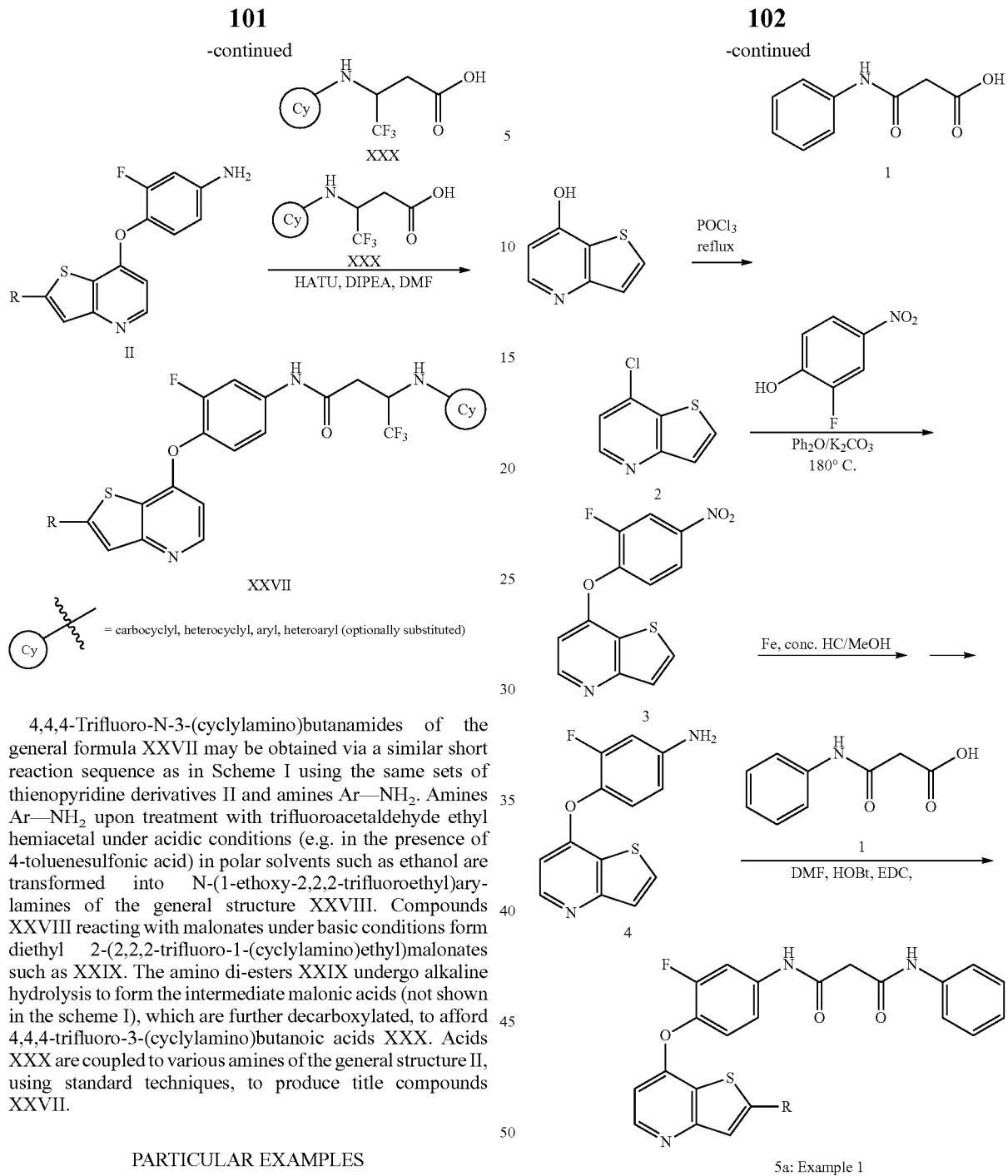

4,4,4-Trifluoro-N-3-(cyclylamino)butanamides of the general formula XXVII may be obtained via a similar short reaction sequence as in Scheme I using the same sets of thienopyridine derivatives II and amines Ar—NH$_2$. Amines Ar—NH$_2$ upon treatment with trifluoroacetaldehyde ethyl hemiacetal under acidic conditions (e.g. in the presence of 4-toluenesulfonic acid) in polar solvents such as ethanol are transformed into N-(1-ethoxy-2,2,2-trifluoroethyl)arylamines of the general structure XXVIII. Compounds XXVIII reacting with malonates under basic conditions form diethyl 2-(2,2,2-trifluoro-1-(cyclylamino)ethyl)malonates such as XXIX. The amino di-esters XXIX undergo alkaline hydrolysis to form the intermediate malonic acids (not shown in the scheme I), which are further decarboxylated, to afford 4,4,4-trifluoro-3-(cyclylamino)butanoic acids XXX. Acids XXX are coupled to various amines of the general structure II, using standard techniques, to produce title compounds XXVII.

PARTICULAR EXAMPLES

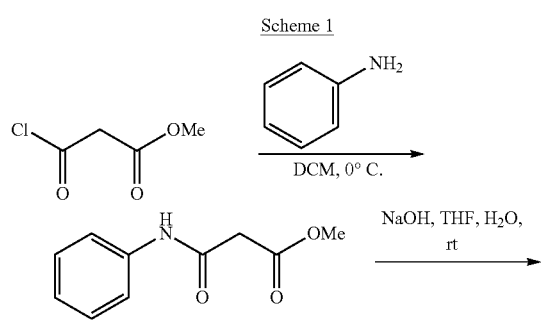

Scheme 1 a: R = H;

Example 1

N$^1$-(3-Fluoro-4-(thieno[3,2-b]pyridin-7-yloxy)phenyl)-N$^3$-phenylmalonamide (5a)

Step 1. 3-Oxo-3-(phenylamino)propanoic acid (1) (two-step procedure)

To a solution of methyl 3-chloro-3-oxopropanoate (2.0 g, 14.7 mmol) in dry DCM (100 ml) was added aniline (2.68 g, 3.6 mmol) and the reaction mixture was stirred at 0° C. for 1 hr, evaporated then dissolved in EtOAc, washed with dilute HCl, NaHCO₃, and brine. The organic phase was collected, dried over sodium sulfate, filtered and the solvent was evaporated to afford methyl 3-oxo-3-(phenylamino)propanoate as a brown oil which was used without further purification (2.8 g, 100%, crude). To a solution of this material (2.8 g, 14.5 mmol) in THF (40 ml) and water (20 ml) was added NaOH (1.16 g, 29 mmol) and the reaction mixture was stirred overnight, evaporated (to remove the THF) and then extracted with Et₂O. The aqueous phase was acidified to pH 1 and extracted with EtOAc. The extract was dried over Na₂SO₄, filtered and evaporated to afford the title compound 1 as a brown solid, which was used without further purification (2.0 g, 77% yield). MS (m/z): 18.0 (100%) (M+H), 202.0 (44%) (M+Na).

Step 2. 7-Chlorothieno[3,2-b]pyridine (2)

A stirred suspension of thieno[3,2-b]pyridin-7-ol (5.0 g, 33.1 mmol) in POCl₃ (15 mL) was heated at 105° C. in an oil bath for 4 hrs. The resultant solution was cooled to room temperature and the POCl₃ was removed under reduced pressure. The residue was cooled in an ice/water bath and cold water was added. The mixture was made basic with concentrated NH₄OH solution and extracted with EtOAc. The organic extract was dried over anhydrous sodium sulfate and concentrated to produce oil, which was purified by column chromatography (eluent EtOAc-hexane, 1:4) to afford the title compound as a brown solid (4.5 g, 72% yield). ¹H NMR (400 MHz, CDCl₃) δ (ppm): 8.60 (d, J=4.9 Hz, 1H), 7.80 (d, J=5.5 Hz, 1H), 7.60 (d, J=5.5 Hz, 1H), 7.30 (d, J=4.9 Hz, 1H).

Step 3.
7-(2-Fluoro-4-nitrophenoxy)thieno[3,2-b]pyridine (3)

A mixture of 2 (500 mg, 2.95 mmol), potassium carbonate (1.62 g, 11.8 mmol) and 2-fluoro-4-nitrophenol (603 mg, 3.85 mmol) were heated to 170° C. in diphenyl ether (10 ml) for 5 hrs. The mixture was cooled to room temperature, diluted with EtOAc and washed with water. The organic phase was collected, dried over anhydrous sodium sulfate and the solvents were removed under reduced pressure. The residue was purified by column chromatography, eluent gradient EtOAc-hexane (9:1) to EtOAc, to afford the title compound 3 (660 mg, 76% yield). ¹H NMR (400 MHz, CDCl₃) δ (ppm) 8.60 (d, J=5.54 Hz, 1H), 8.14 (m, 3H), 7.80 (d, J=5.47 Hz, 1H), 7.61 (d, J=5.48 Hz, 1H), 7.36 (t, J=7.63 Hz), 6.65 (m, 1H).

Step 4. N¹-(3-Fluoro-4-(thieno[3,2-b]pyridin-7-yloxy)phenyl)-N³-phenylmalonamide (5a)

To a solution of 3 (660 mg, 2.27 mmol) in MeOH (10 ml) was added conc. HCl (1 ml) and Fe (1.91 g, 34.8 mmol), and the reaction mixture was stirred at 0° C. for 3 hrs, neutralized with aqueous NaHCO₃ solution and extracted with EtOAc, producing 3-fluoro-4-(thieno[3,2-b]pyridin-7-yloxy)-phenylamine (4) as a dark oil (500 mg, 83%), which was used directly in the next step. To a solution of the amine 4 (200 mg, 0.69 mmol) in DMF (10 ml) was added 3-oxo-3-(phenylamino)propanoic acid (1, 155 mg, 0.89 mmol), HOBT (121 mg, 0.89 mmol) and EDC (198 mg, 1.035 mmol). The reaction mixture was stirred at room temperature overnight, evaporated to dryness and the residue was dissolved in EtOAc and washed with water. The organic phase was dried over sodium sulfate, filtered and evaporated under reduced pressure. The residue was purified by column chromatography (eluent EtOAc:hexane 3:1) to afford the title compound 5a (30 mg, 10% yield) as a white solid (after trituration with Et₂O). ¹H NMR (400 MHz, DMSO-d₆) δ (ppm): 10.5 (s, 1H), 10.2 (s, 1H), 8.49 (d, J=5.48 Hz, 1H), 8.14 (d, J=5.48 Hz, 1H), 7.85 (dd, J=2.35 and 13.01 Hz, 1H), 7.59 (m, 3H), 7.42 (m, 2H), 7.30 (dt, J=1.96 and 7.43 Hz, 2H), 7.05 (t, J=7.24 Hz, 1H), 6.65 (d, J=5.28 Hz, 1H), 3.51 (s, 2H).

Scheme 2

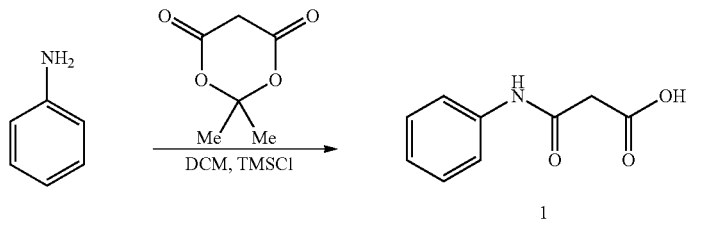

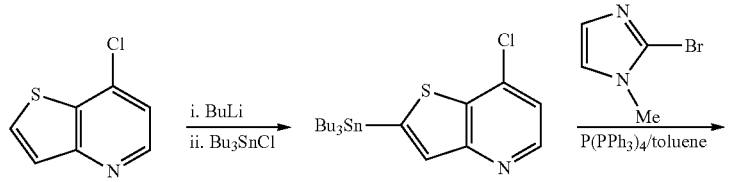

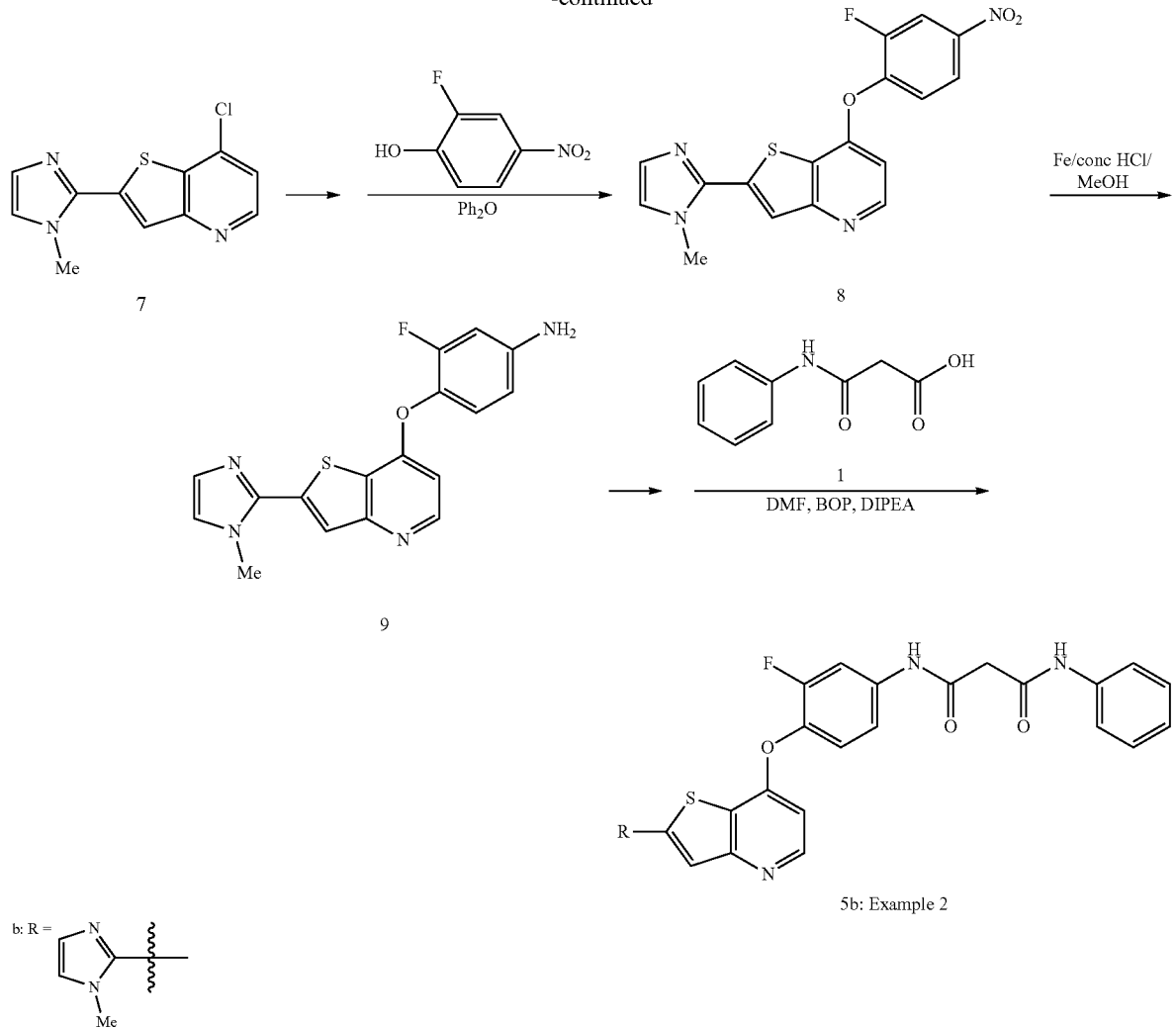

Example 2

N$^1$-(3-Fluoro-4-(2-(1-methyl-1H-imidazol-2-yl)thieno[3,2-b]pyridin-7-yloxy)phenyl)-N$^3$-phenylmalonamide (5b)

Step 1. 3-Oxo-3-(phenylamino)propanoic acid (1) (one-step procedure)

To a solution of aniline (13 mL, 143 mmol) in DCM (290 mL) was added TMSCl (18.2 mL, 143 mmol) at room temperature and the reaction mixture was stirred for 1 hour. [Rigo, B.; Fasseur, D.; Cauliez, P. and Couturier, D. *Tetrahedron Lett.;* 30; 23; 1989; 3073-3076.]. 2,2-Dimethyl-1,3-dioxane-4,6-dione (20.6 g, 143 mmol) was added and combined reaction mixture was stirred overnight at room temperature, poured into saturated NaHCO$_3$ solution and extracted with EtOAc. The aqueous phase was collected, acidified with conc. HCl to pH~3 by addition of 2N HCl and extracted with DCM. The organic phase was dried over anhydrous Na$_2$SO$_4$, filtered and concentrated under reduced pressure affording 3-oxo-3-(phenylamino)propanoic acid (1, 16.82 g, 65% yield) as a white solid. MS (m/z): 180.0 (25%) (M+H), 202.0 (100%) (M+Na).

Step 2: 7-Chloro-2-(tributylstannyl)thieno[3,2-b]pyridine (6)

To a solution of 7-chlorothieno[3,2-b]pyridine 2 (9.82 g, 57.89 mmol) in THF (290 mL) BuLi (2.5 N, 25 mL) was added at −78° C. and the mixture stirred for 20 min at the same temperature. Tributyltin chloride (63.68 mmol, 17.3 mL) was added dropwise and the mixture stirred for 2 h at −78° C. The homogeneous mixture thus obtained was poured in water (200 mL) and extracted with EtOAc (2×200 mL). The organic phase was collected, dried over anhydrous Na$_2$SO$_4$ and concentrated under reduced pressure. The residue was purified by flash chromatography (eluent EtOAc/Hex 1:4) to afford 7-chloro-2-(tributylstannyl)thieno[3,2-b]pyridine (6, 24.79 g, 93% yield) as a syrup. MS (m/z): cluster of signals centered around 460.1 (M+1).

Step 3: 7-Chloro-2-(1-methyl-1H-imidazol-2-yl)thieno[3,2-b]pyridine (7)

To a solution of the tin derivative 6 (24.79 g, 54.05 mmol) and 2-bromo-1-methyl-1H-imidazole (10.4 g, 64.86 mmol) [McCallum, P. W.; Weavers, R. T.; Grimmet, M. R.; Blackman, A. G.; *Aust. J. Chem.;* 52; 3; 1999; 159-166.] in toluene (180 mL) Pd[PPh$_3$]$_4$ (5 g, 4.32 mmol) was added and the mixture was refluxed under nitrogen for 2 days, cooled to room temperature. A precipitate was formed which was collected by filtration, washed with Et$_2$O and dried, to afford the title compound 7 as a grey solid (12.72 g, 94% yield). MS (m/z): 250.0 (M+H).

Step 4: 7-(2-Fluoro-4-nitrophenoxy)-2-(1-methyl-1H-imidazol-2-yl)thieno[3,2-b]pyridine (8)

A mixture of 7-chloro-2-(1-methyl-1H-imidazol-2-yl)thieno[3,2-b]pyridine (7) (1.0 g, 4 mmol), 2-fluoro-4-nitrophenol (0.942 g, 6 mmol) and K$_2$CO$_3$ (1.1 g, 8 mmol) in Ph$_2$O (20 mL) was stirred at 200° C. for 24 h. The cooled reaction mixture was diluted with DCM (200 mL) and extracted with 1M HCl (200 mL). The aqueous phase was filtered through paper filter, basified (pH~10) with conc. NH$_4$OH to produce a cloudy mixture that was extracted with DCM. The organic phase was dried over anhydrous Na$_2$SO$_4$ and concentrated under pressure to give title compound 8 as an orange solid (0.667 g, 45% yield). MS (m/z): 371.0 (M+H).

Step 5: 3-Fluoro-4-(2-(1-methyl-1H-imidazol-2-yl)thieno[3,2-b]pyridin-7-yloxy)benzenamine (9)

To a solution of the nitro compound 8 (1.50 g, 4.05 mmol) and NiCl$_2$.6H$_2$O (2.02 g, 8.52 mmol) in MeOH/THF (45 mL/68 mL) at 0° C. was added NaBH$_4$ (0.618 g, 16.3 mmol) portion wise with vigorous stirring. The reaction mixture was stirred for 30 minutes at 0° C. and concentrated under reduced pressure. The resultant black residue was suspended in 1M HCl (10 mL) and the mixture was basified (pH~11) with conc. NH$_4$OH. The cloudy suspension was filtered; the solid residue was separated, washed with water and dried under reduced pressure to afford the title compound 9 as a brown solid (0.73 g, 52% yield), which was used in the next step without further purification. MS (m/z): 341.1 (M+H).

Step 6: N$^1$-(3-Fluoro-4-(2-(1-methyl-1H-imidazol-2-yl)thieno[3,2-b]pyridin-7-yloxy)phenyl)-N$^3$-phenyl-malonamide (5b)

To a solution of the amine 9 (80 mg, 0.235 mmol), 3-oxo-3-(phenylamino)propanoic acid (1) (42 mg, 0.235 mmol) and BOP (114.6 mg, 0.259 mmol) in DMF (2.4 mL), DIPEA (0.164 mL, 0.941 mmol) was added and the mixture was stirred at room temperature for 2 h. The reaction mixture was partitioned between EtOAc and water. Organic phase was collected, washed with H$_2$O and brine, dried over anhydrous Na$_2$SO$_4$ and concentrated. The residue was purified by flash chromatography (EtOAc/MeOH 95:5) followed by crystallization (MeOH) to afford the title compound 5b (11 mg, 9% yield). $^1$H NMR (DMSO-d$_6$) δ (ppm): 10.55 (s, 1H), 10.19 (s, 1H), 8.5 (d, J=5.4 Hz, 1H), 7.86 (m, 2H), 7.59 (m, 2H), 7.49 (t, J=8.8 Hz, 1H), 7.41 (m, 2H), 7.30 (m, 2H), 7.05 (m, 2H), 6.69 (d, J=5.4 Hz, 1H), 3.99 (s, 3H), 3.52 (s, 2H). MS (m/z): 502.2 (M+H).

Scheme 3

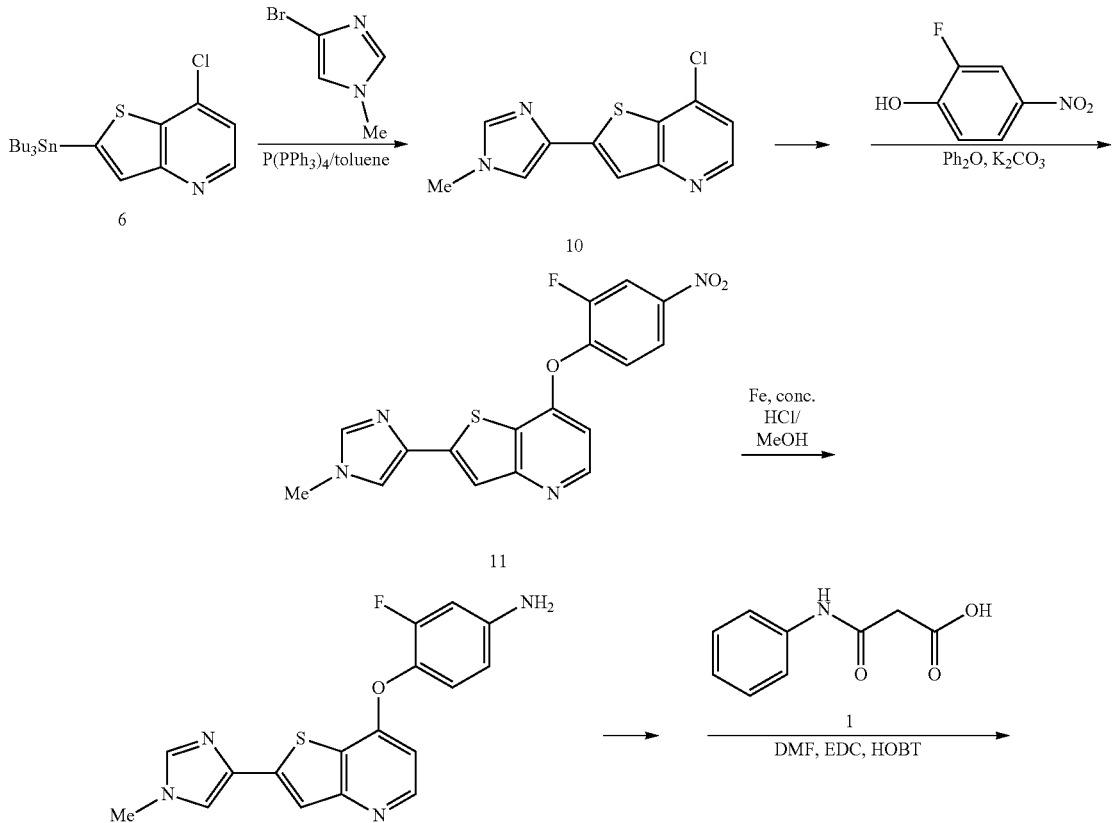

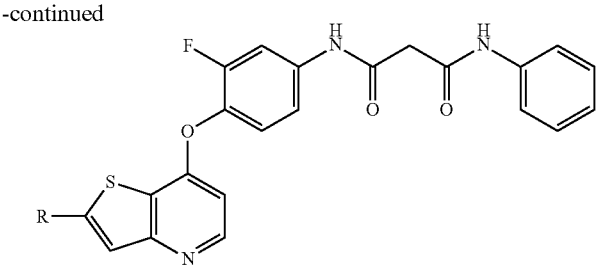

5c: Example 3

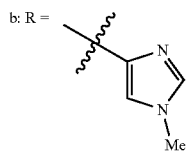

b: R =

Example 3

N[1]-{3-Fluoro-4-[2-(1-methyl-1H-imidazol-4-yl)thieno[3,2-b]pyridin-7-yloxy]-phenyl}-N[3]-phenyl-malonamide (5c)

Step 1: 7-Chloro-2-(1-methyl-1H-imidazol-4-yl)thieno[3,2-b]pyridine (10)

Following the procedure described for compound 7 (example 2, step 3) but substituting 2-bromo-1-methyl-1H-imidazole for 4-bromo-1-methyl-1H-imidazole [a) Begtrup, M.; Larsen, P.; *Acta Chem. Scand.* 44, 10:1990:1050-1057, b) Begtrup, M.; *Bull. Soc. Chim. Belg.;* 97; 8-9; 1988; 573-598, c) Begtrup, M.; Larsen, P.; *Chem. Pharm. Bull.* 42, 9; 1994; 1784-1790.], title compound 10 was obtained as an off-white solid (29% yield). MS (m/z): 250.1 (M+H).

Step 2: 7-(2-Fluoro-4-nitrophenoxy)-2-(1-methyl-1H-imidazol-4-yl)thieno[3,2-b]pyridine (11)

Following the procedure described for the nitro compound 8 (example 2, step 4) but substituting compound 7 for the compound 10, title compound II was obtained as a red solid (46% yield). MS (m/z): 371.1 (M+H).

Step 3: 3-Fluoro-4-(2-(1-methyl-1H-imidazol-4-yl)thieno[3,2-b]pyridin-7-yloxy)benzenamine (12)

Following the procedure described for the amine 9 (example 2, step 5) but substituting nitro-compound 8 for compound II, title compound 12 was obtained as a red solid (82% yield). MS (m/z): 341.1 (M+H).

Step 4: N[1]-(3-fluoro-4-(2-(1-methyl-1H-imidazol-4-yl)thieno[3,2-b]pyridin-7-yloxy)phenyl)-N[3]-phenyl-malonamide (5c)

Following the procedure described for compound 5a (example 1, step 5) but substituting amine 9 for compound 12, title compound 5c was obtained as a white solid (78% yield). MS (m/z): 502.0 (M+H).

Scheme 4

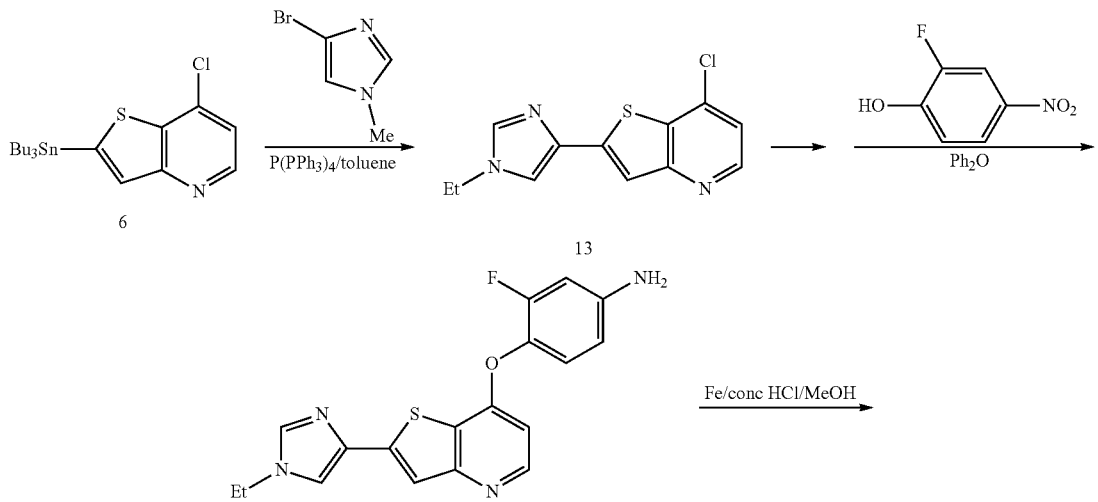

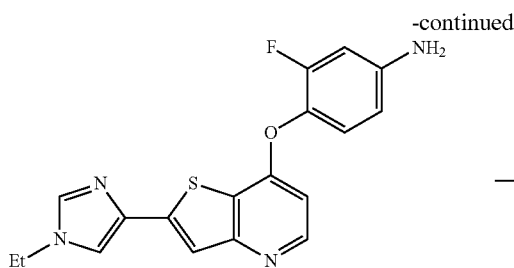

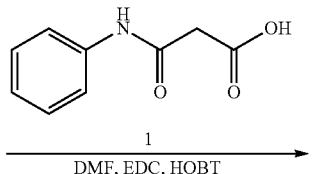

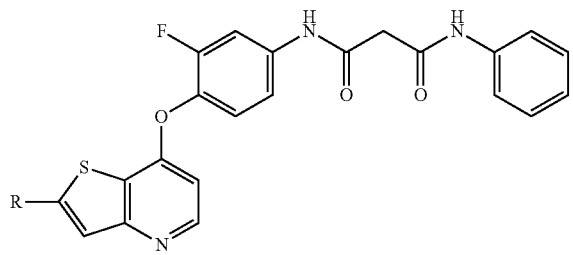

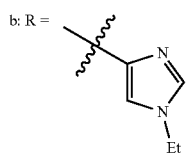

Example 4

N¹-(4-(2-(1-Ethyl-1H-imidazol-4-yl)thieno[3,2-b]pyridin-7-yloxy)-3-fluorophenyl)-N³-phenylmalonamide (5d)

Step 1: 7-Chloro-2-(1-ethyl-1H-imidazol-4-yl)thieno[3,2-b]pyridine (13)

Following the procedure described for compound 7 (example 2, step 3) but substituting 2-bromo-1-methyl-1H-imidazole for 4-bromo-1-ethyl-1H-imodazole [a) Begtrup, M.; Larsen, P.; *Acta Chem. Scand.* 44, 10; 1990; 1050-1057, b) Begtrup, M.; *Bull. Soc. Chim. Belg.;* 97: 8-9; 1988; 573-598, c) Begtrup, M.; Larsen, P.; *Chem. Pharm. Bull.* 42, 9; 1994; 1784-1790.], title compound 13 was obtained as a yellow solid (30% yield). MS (m/z): 263.9 (M+H).

Step 2: 2-(1-Ethyl-1H-imidazol-4-yl)-7-(2-fluoro-4-nitrophenoxy)thieno[3,2-b]pyridine (14)

Following the procedure described for 8 (example 2, step 4) but substituting compound 7 for compound 10, title compound 14 was obtained as a yellow solid (76% yield). MS (m/z): 384.9 (M+H).

Step 3: 4-(2-(1-Ethyl-1H-imidazol-4-yl)thieno[3,2-b]pyridin-7-yloxy)-3-fluorobenzenamine (15)

Following the procedure described for compound 9 (example 2, step 5) but substituting nitro compound 8 for the compound 14, title compound 15 was obtained as a yellow solid (86% yield). MS (m/z): 402.1 (M+H).

Step 4. N¹-(4-(2-(1-ethyl-1H-imidazol-4-yl)thieno[3,2-b]pyridin-7-yloxy)-3-fluorophenyl)-N³-phenylmalonamide (5d)

Following the procedure described for compound 5a (example 1, step 5) but substituting amine 9 for compound 15, title compound 5d was obtained in 57% yield. MS (m/z): 516.0 (M+H).

Scheme 5

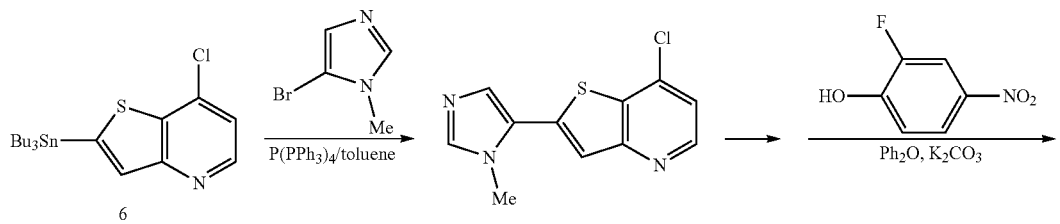

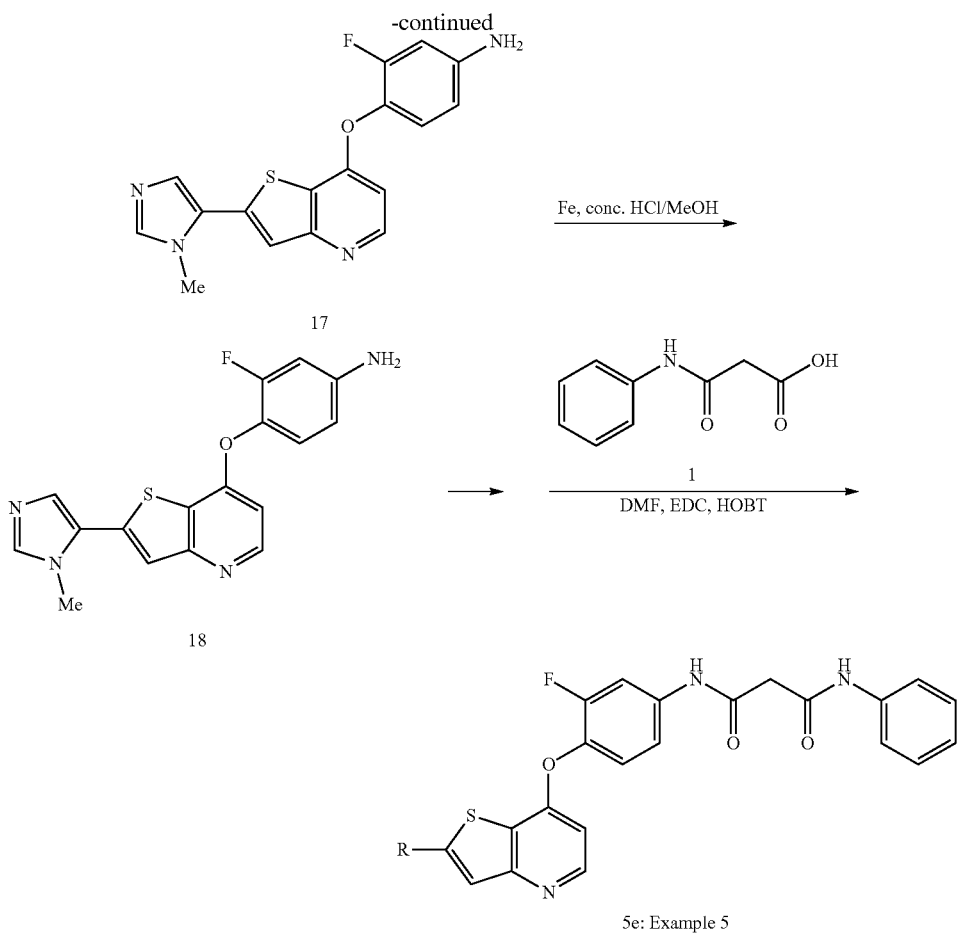

Example 5

N[1]-(3-Fluoro-4-(2-(1-methyl-1H-imidazol-5-yl)thieno[3,2-b]pyridin-7-yloxy)phenyl)-N[3]-phenylmalonamide (5e)

Step 1: 7-Chloro-2-(1-methyl-1H-imidazol-5-yl)thieno[3,2-b]pyridine (16)

Nitrogen was bubbled through a mixture of the tin derivative 6 (7.19 g, 15.7 mmol) and 5-bromo-1-methyl-1H-imidazole (2.02 g, 12.5 mmol) [a) Begtrup, M.; Larsen, P.; *Acta Chem. Scand.* 44, 10; 1990; 1050-1057, b) Begtrup, M.; *Bull. Soc. Chim. Belg.;* 97; 8-9; 1988; 573-598, c) Begtrup, M.; Larsen, P.; *Chem. Pharm. Bull.* 42, 9; 1994; 1784-1790.] in toluene (20 mL) for 5 minutes. Pd(PPh$_3$)$_4$ (1.50 g, 1.30 mmol) was added and nitrogen was bubbled for additional 5 minutes. Finally, the mixture was refluxed under nitrogen overnight, the resultant yellow suspension was concentrated under reduced pressure and then purified with flash chromatography (eluent EtOAc/MeOH 90:10), to afford title compound 16 as a yellow solid (2.48 g, 79% yield). MS (m/z): 250.0 (M+H).

Step 2: 7-(2-Fluoro-4-nitrophenoxy)-2-(1-methyl-1H-imidazol-5-yl)thieno[3,2-b]pyridine (17)

A mixture of the compound 16 (1.52 g, 6.09 mmol), 2-fluoro-4-nitrophenol (3.87 g, 24.6 mmol) and K$_2$CO$_3$ (4.31 g, 31.2 mmol) in Ph$_2$O (20 mL) was heated at 190° C. overnight. DCM (250 mL) was added to the resultant dark-brown mixture, which was then extracted with aqueous 1M HCl. The aqueous layer was collected, washed with DCM and basified with NH$_4$OH. The resultant cloudy mixture was extracted with DCM. The organic phase was combined, filtered; the filtrate was washed with water, dried over anhydrous Na$_2$SO$_4$ and concentrated under reduced pressure. The resultant yellow solid was purified by flash chromatography, eluent EtOAc/MeOH (80:20) to afford title compound 17 as a yellow solid (0.96 g, 43% yield). MS (m/z): 371.0 (M+H).

Step 3: 3-Fluoro-4-(2-(1-methyl-1H-imidazol-5-yl)thieno[3,2-b]pyridin-7-yloxy)benzenamine (18)

To a stirring mixture of the nitro compound 17 (0.96 g, 2.59 mmol) and NiCl$_2$.6H$_2$O (1.24 g, 5.22 mmol) in MeOH/THF (26 mL/39 mL) at 0° C. NaBH$_4$ (0.341 g, 9.01 mmol) was added portion wise. The reaction mixture was stirred for 15 minutes, quenched with 1M HCl (10 mL) and concentrated under reduced pressure to form a green residue, which was then dissolved in 1M HCl (250 mL) and basified with NH$_4$OH. The cloudy suspension was extracted with EtOAc, the organic layer was collected, filtered, washed with water and then dried over anhydrous Na$_2$SO$_4$. Evaporation of this solution afforded title compound 18 as brown solid (0.46 g, 52% yield), which was used in the next step without additional purification. MS (m/z): 341.1 (M+H).

Step 4. N$^1$-(3-Fluoro-4-(2-(1-methyl-1H-imidazol-5-yl)thieno[3,2-b]pyridin-7-yloxy)phenyl)-N$^3$-phenyl-malonamide (5e)

Following the procedure described for compound 5b (example 2, step 6) but substituting amine 9 for compound 18, title compound 5e was obtained in 5% yield. MS (m/z): 502.0 (M+H).

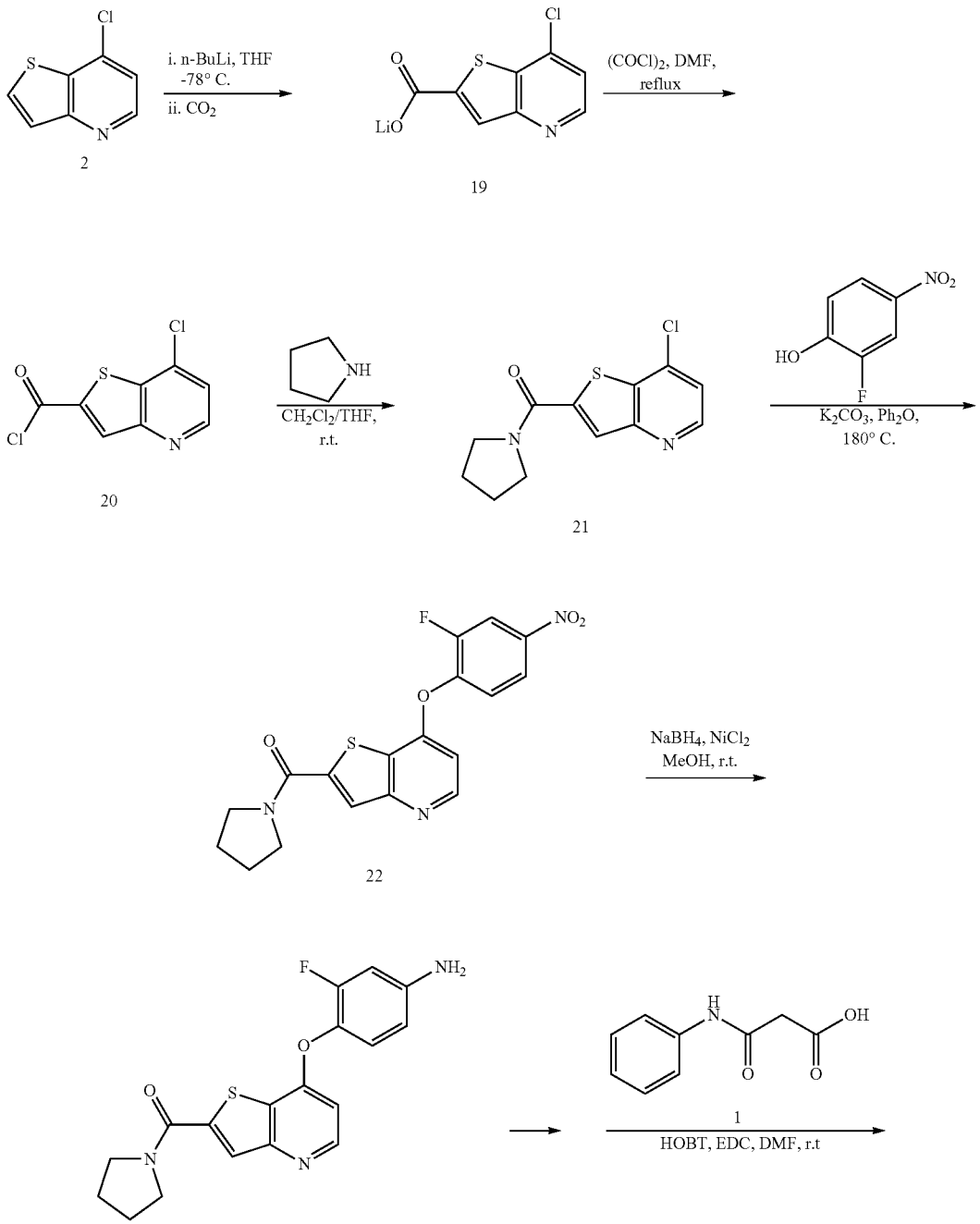

Scheme 6

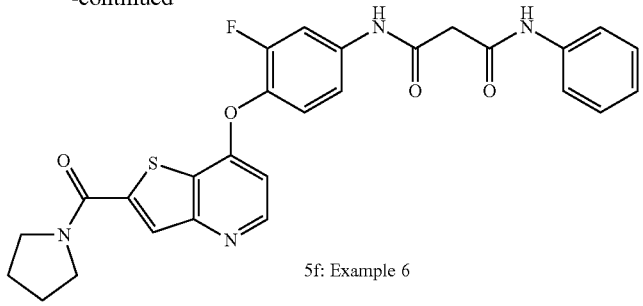

5f: Example 6

Example 6

N[1]-(3-Fluoro-4-(2-(pyrrolidine-1-carbonyl)thieno[3,2-b]pyridin-7-yloxy)phenyl)-N[3]-phenylmalonamide (5f)

Steps 1-3: (7-Chlorothieno[3,2-b]pyridin-2-yl)(pyrrolidin-1-yl)methanone (21)

To a stirred solution of 2 (11.91 g, 70.22 mmol) in dry THF (200 mL) at −78° C. was added n-BuLi (33.70 mL, 84.26 mmol, 2.5 M solution in hexanes) and the resultant suspension was stirred for 1 h. Solid carbon dioxide (excess) was added and the mixture was allowed to warm to room temperature over a period of 1 hour. The solvent was removed under reduced pressure and the resultant lithium carboxylate 19 was used without further purification (16.43 g, quantitative). To a stirred suspension of 19 (15.41 g, 70.22 mmol) in dry DCM (150 mL) was added (COCl)$_2$ (12.25 mL, 140.44 mmol) and dry DMF (5 drops). The reaction mixture was heated to reflux for 3 hrs. The solvents were evaporated to produce 20, which was used directly in the next step. Acyl chloride 20 (8.14 g, 35.11 mmol) was suspended in dry DCM (300 mL) at 0° C., pyrrolidine (3.22 mL, 38.62 mmol) was added and the reaction mixture was stirred overnight. The solvent was removed under reduced pressure and the residue was dissolved in EtOAc and washed with water. The organic phase was collected and dried over anhydrous sodium sulfate, then filtered and concentrated under reduced pressure to produce a residue, which was purified by column chromatography (eluent MeOH—CH$_2$Cl$_2$, 2:98, 5:95) to afford the title compound 21 as a brown solid (16.07 g, 86% yield). MS (m/z): 267.1 (M+H).

Step 4: (7-(2-Fluoro-4-nitrophenoxy)thieno[3,2-b]pyridin-2-yl)(pyrrolidin-1-yl)methanone (22)

A mixture of 21 (2.4 g, 8.89 mmol), K$_2$CO$_3$ (4.97 g, 35.96 mmol) and 2-fluoro-4-nitrophenol (1.55 g, 9.89 mmol) were heated at 150° C. in diphenyl ether (40 mL) for 2 days. The mixture was purified by column chromatography (eluents EtOAc-hexane 5:95, 2:8, then MeOH-EtOAc 2:98, 5:95) to give the title compound 22 as a yellow solid (3.23 g, 93% yield). MS (m/z): 388.2 (M+H).

Step 4: (7-(4-Amino-2-fluorophenoxy)thieno[3,2-b]pyridin-2-yl)(pyrrolidin-1-yl)methanone (23)

To a solution of 22 (3.23 g, 8.33 mmol) and NiCl$_2$.6H$_2$O (3.96 g, 16.66 mmol) in MeOH/THF (100/100 mL) was added NaBH$_4$ (1.24 g, 33.32 mmol). The reaction mixture was stirred for 1 hr, concentrated to dryness and the resultant solid was dissolved in 10% HCl. The aqueous solution was then made basic with concentrated. NH$_4$OH solution and extracted with EtOAc. The organic phase was collected, dried over anhydrous sodium sulfate and concentrated under reduced pressure to afford 23 as a black solid (2.72 g, 91% yield). MS (m/z): 358.2 (M+H).

Step 5: N[1]-(3-Fluoro-4-(2-(pyrrolidine-1-carbonyl)thieno[3,2-b]pyridin-7-yloxy)phenyl)-N[3]-phenylmalonamide (5l)

To a solution of 23 (100 mg, 0.28 mmol), HOBT (49 mg, 0.36 mmol) and EDC (80 mg, 0.41 mmol) in DMF (5 mL) was added 3-oxo-3-(phenylamino)propanoic acid (1) (65 mg, 0.36 mmol). The reaction mixture was stirred for 1 day and was diluted with EtOAc. The resultant solution was washed with water and brine, dried over anhydrous sodium sulfate and concentrated to provide a residue, which was purified by column chromatography (eluents MeOH—CH$_2$Cl$_2$, 2:98, 5:95) to produce a solid material, which after trituration with EtOAc/hexane afforded 5f as a white solid (74 mg, 51% yield). MS (m/z): 519.2 (M+H).

Scheme 7

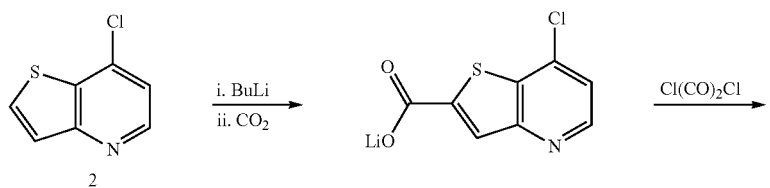

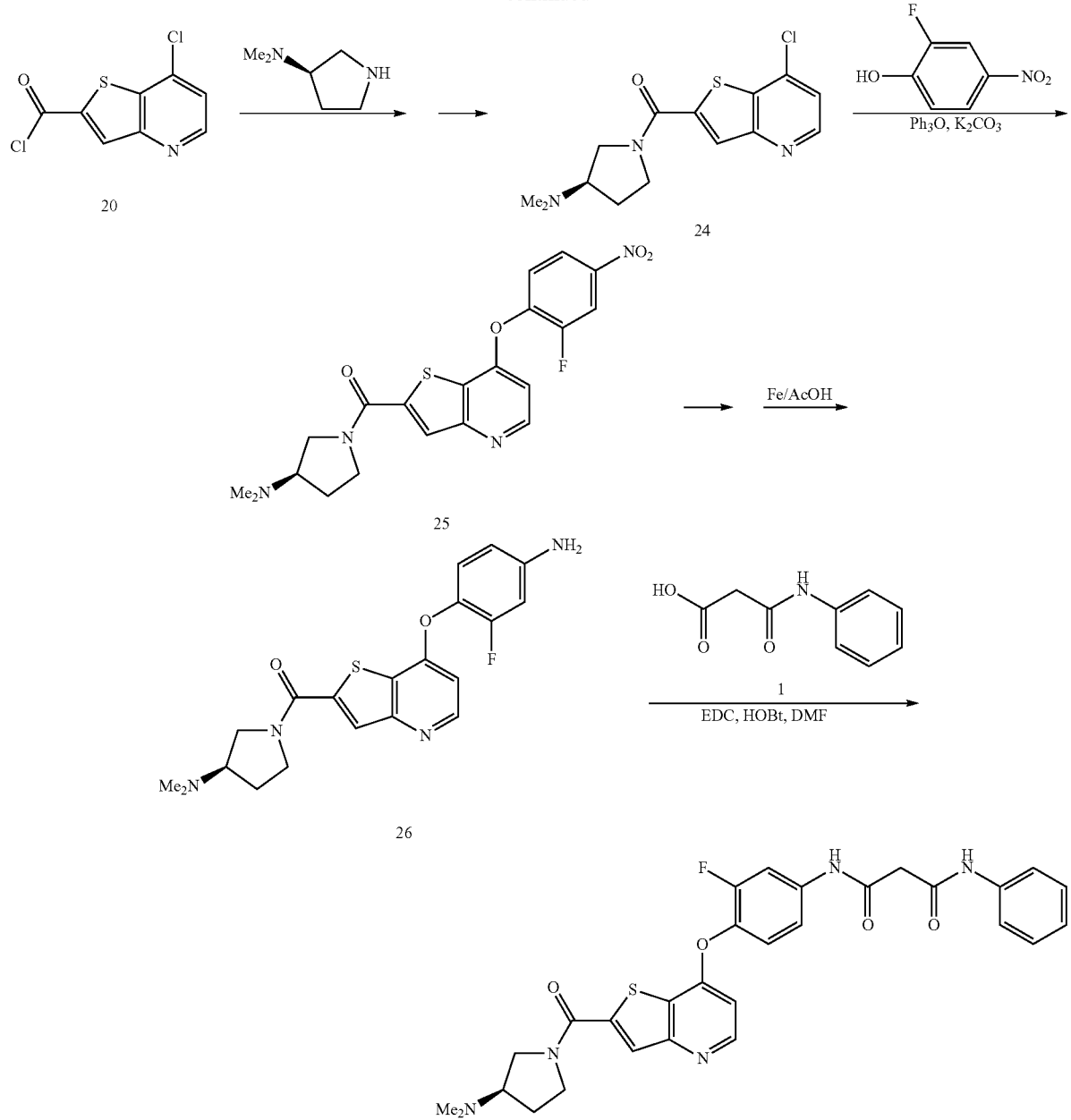

5g: Example 7

Example 7

(R)—N¹-(4-(2-(3-(Dimethylamino)pyrrolidine-1-carbonyl)thieno[3,2-b]pyridin-7-yloxy)-3-fluorophenyl)-N³-phenylmalonamide (5g)

Steps 1-3: (R)-(7-Chlorothieno[3,2-b]pyridin-2-yl)(3-(dimethylamino)pyrrolidin-1-yl)methanone (24)

Following the procedures described above for the compound 21 (example 5f, steps 1-3) but substituting pyrrolidine in the step 3 for (R)—N,N-dimethylpyrrolidin-3-amine, title compound 24 was obtained as a white solid (58% yield). MS (m/z): 310.0 (M+H).

Step 4: (R)-(3-(Dimethylamino)pyrrolidin-1-yl)(7-(2-fluoro-4-nitrophenoxy)thieno[3,2-b]pyridin-2-yl)methanone (25)

A mixture of the amide 24 (1.44 g, 4.65 mmol), 2-fluoro-4-nitrophenol (2.21 g, 14.1 mmol) and K₂CO₃ (2.56 g, 18.5 mmol) in Ph₂O (5.0 mL) was heated at 190° C. for 3 hrs. CHCl₃ (100 mL) was added to the resultant dark brown mixture and then the mixture was extracted with 1M HCl. The aqueous phase was washed with CHCl₃ and basified with NH₄OH (pH 11). The resultant cloudy mixture was extracted with CHCl₃ and the organic phase was collected, washed with water, dried over anhydrous Na₂SO₄ then concentrated under reduced pressure. The remaining yellow solid material was purified by flash chromatography, eluent CHCl₃/MeOH (95:

5, then 80:20) to afford title compound 25 as a white solid (1.41 g, 3.28 mmol, 71% yield). MS (m/z): 431.0 (M+H).

Step 5: (R)-(7-(4-Amino-2-fluorophenoxy)thieno[3,2-b]pyridin-2-yl)(3-(dimethylamino) pyrrolidin-1-yl)methanone (26)

To a solution of the nitro compound 25 (708 mg, 1.64 mmol) in AcOH (16 mL) at 90° C., was added iron powder (928 mg, 16.6 mmol) and the reaction mixture was stirred vigorously for 20 min. The grey suspension was dissolved in 1N HCl (50 mL) and washed with CHCl$_3$ (50 mL). The aqueous phase was basified with NH$_4$OH to pH~10, extracted with CHCl$_3$. The organic phase was collected, dried over anhydrous Na$_2$SO$_4$ and concentrated under reduced pressure to give the title compound 26 (506 mg, 77%) as a white solid. MS (m/z): 401.1 (M+H).

Step 6. (R)—N$^1$-(4-(2-(3-(Dimethylamino)pyrrolidine-1-carbonyl)thieno[3,2-b]pyridin-7-yloxy)-3-fluorophenyl)-N$^3$-phenylmalonamide (5g)

Following the procedure described above for the compound 5a (step 5, example 1) but replacing the amine 9 with the compound 26, title compound 5g was obtained in 38% yield. MS (m/z): 562.0 (M+H).

TABLE 1

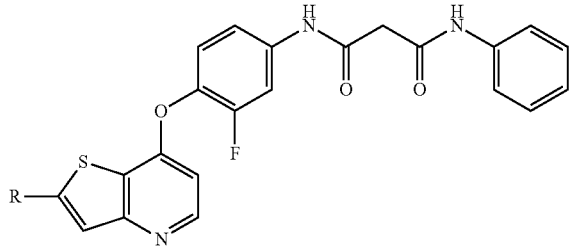

5c-f: Examples 3-7

| Cpd | Ex. | R | Name | Characterization |
|---|---|---|---|---|
| 5c | 3 | (1-methyl-1H-imidazol-4-yl) | N-(3-Fluoro-4-(2-(1-methyl-1H-imidazol-4-yl)thieno[3,2-b]pyridin-7-yloxy)phenyl)-3-oxo-3-phenylpropanamide | $^1$H NMR (DMSO-d$_6$) δ (ppm): 10.78 (s, 1H), 10.31 (s, 1H), 8.64 (d. 1H), 8.23 (broad, s, 1H), 8.20 (s, 1H), 7.93 (dd, 1H), 7.92 (s, 1H) 7.61-7.48 (m, 4H), 7.30 (t, 2H), 7.05 (t, 1H), 6.95 (d, 1H), 3.78 (s, 3H), 3.55 (s, 2H). MS (m/z): 501.1 (M + H). |
| 5d | 4 | (1-ethyl-1H-imidazol-4-yl) | N$^1$-(4-(2-(1-Ethyl-1H-imidazol-4-yl)thieno[3,2-b]pyridin-7-yloxy)-3-fluorophenyl)-N$^3$-phenylmalonamide | $^1$H NMR (DMSO-d$_6$) δ (ppm): 10.82 (s, 1H), 10.34 (s, 1H), 8.67 (d. 1H), 8.38 (broad, s, 1H), 8.34 (dd, 1H), 7.96 (s, 1H), 7.93 (dd, 1H), 7.62-7.51 (m, 4H), 7.30 (t, 2H), 7.05 (t, 1H), 6.98 (d, 1H), 6.96 (d, 1H), 4.13 (q, 2H), 3.54 (s, 2H), 1.43 (t, 3H). MS (m/z): 516.0 (M + H). |
| 5e | 5 | (1-methyl-1H-imidazol-5-yl) | N$^1$-(3-Fluoro-4-(2-(1-methyl-1H-imidazol-5-yl)thieno[3,2-b]pyridin-7-yloxy)phenyl)-N$^3$-(pyridine-3-yl)malonamide | $^1$H NMR (DMSO-d$_6$) δ (ppm): 10.52 (s, 1H), 10.16 (s, 1H), 8.45 (d, 1H), 7.92 (broad, s, 1H), 7.27 (dd, 1H), 7.74 (s, 1H), 7.56 (s, 1H), 7.54 (s, 1H), 7.41 (m, 3H), 7.26 (t, 2H), 7.00 (t, 1H), 6.59 (d, 1H), 3.84 (s, 3H), 3.46 (s, 2H). MS (m/z): 502.4 (M + H). |
| 5f | 6 | (pyrrolidin-1-yl carbonyl) | N$^1$-(3-Fluoro-4-(2-(pyrrolidine-1-carbonyl)thieno[3,2-b]pyridin-7-yloxy)phenyl)-N$^3$-phenylmalonamide | $^1$H NMR (DMSO-d$_6$) δ (ppm): 10.65 (s, 1H), 10.25 (s, 1H), 8.61 (d, J = 5.6 Hz, 1H), 8.03 (s, 1H), 7.92-7.86 (m, 1H), 7.60 (d, J = 8.4 Hz, 2H), 7.50 (t, J = 8.4 Hz, 1H), 7.47-7.20 (m, 1H), 7.30 (t, J = 8.0 Hz, 2H), 7.04 (t, J = 7.2 Hz, 1H), 6.83 (d, J = 5.6 Hz, 1H), 3.54 (t, J = 6.4 Hz, 2H), 3.53 (s, 2H), 1.97 (quin, J = 6.4 Hz, 2H), 1.89 (quin, J = 6.4 Hz, 2H). MS (m/z): (M + 1) 519.2 (100%). |
| 5g | 7 | (3-dimethylamino-pyrrolidin-1-yl carbonyl) | (R)-N$^1$-(4-(2-(3-Dimethylamino)pyrrolidine-1-carbonyl)thieno[3,2-b]pyridin-7-yloxy)-3-fluorophenyl)-N$^3$-phenylmalonamide | $^1$H NMR (DMSO-d$_6$) δ (ppm): 10.57 (s, 1H), 10.20 (s, 1H), 8.57 (dd, 1H), 8.06 (d, 1H), 7.87 (dd, 1H), 7.60 (m, 2H), 7.49 (t, 1H.), 7.42 (dd, 1H), 7.31 (m, 2H)), 7.05 (m, 1H), 6.76 (d, 1H), 4.02 (m, 1H), 3.91-3.76 (m, 1H), 3.64 (m, 1H), 3.50 (s, 2H), 3.47 (m, 1H), 2.82 (m, 1H), 2.23 (s, 3H), 2.21 (s, 3H), 2.10 (m, 1H), 1.80 (m, 1H). MS (m/z): 562.1 (M + H). |

Scheme 8

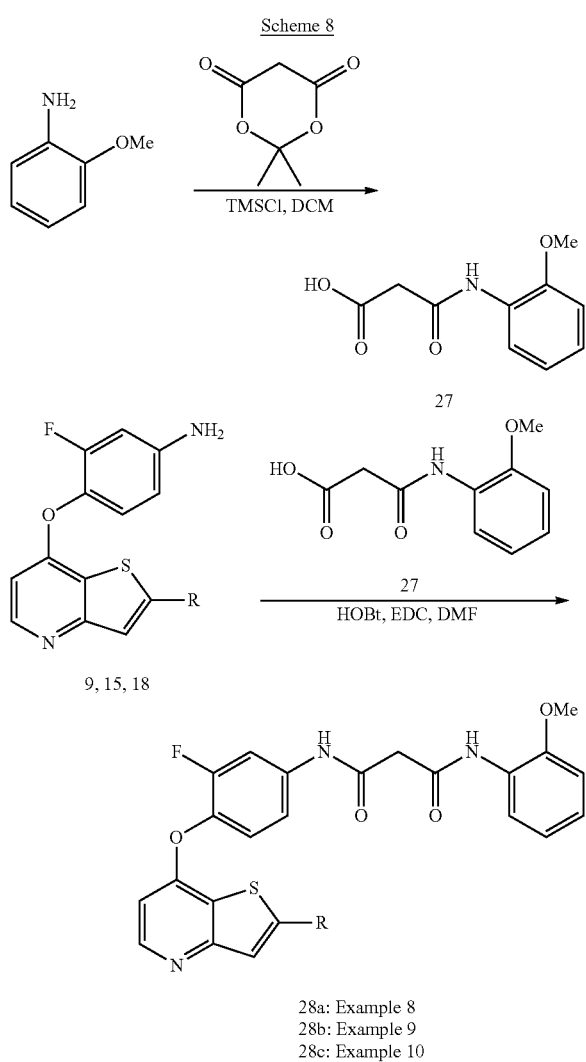

28a: Example 8
28b: Example 9
28c: Example 10

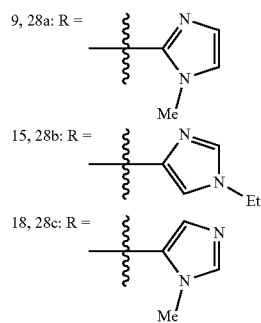

Example 8

N¹-(3-Fluoro-4-(2-(1-methyl-1H-imidazol-2-yl)thieno[3,2-b]pyridin-7-yloxy)phenyl)-N³-(2-methoxyphenyl)malonamide (28a)

Step 1: 3-(2-Methoxyphenylamino)-3-oxopropanoic acid (27)

To a solution of 2-methoxybenzeneamine (1.1 g, 8.93 mmol) in DCM (90 mL) was added TMSCl (1.1 mL, 8.93 mmol) at room temperature [Rigo, B.; Fasseur, D.; Cauliez, P. and Couturier, D. *Tetrahedron Lett.;* 30; 23; 1989; 3073-3076.]. The reaction mixture was stirred for 30 mins before the addition of 2,2-dimethyl-1,3-dioxane-4,6-dione (1.29 g, 8.93 mmol) and then stirring was continued mixture for additional 2 hours. Water (1 mL) was added, and the reaction mixture was concentrated under reduced pressure. The residue was poured into saturated NaHCO₃ solution, and extracted with EtOAc. The aqueous phase was collected, acidified with conc. HCl to pH~4, extracted with EtOAc, the extract was dried over anhydrous Na₂SO₄ and concentrated. The residue was purified by flash chromatography (eluent CHCl₃/MeOH/AcOH 9:1:0.1) to afford the compound 27 (0.56 g, 30% yield) as a white solid. $^1$H NMR (DMSO-d$_6$) δ (ppm): 12.62 (bs, 1H), 9.52 (s, 1H), 8.02 (dd, 1H), 7.03 (m, 2H), 6.88 (m, 1H), 3.82 (s, 3H), 3.46 (s, 2H). MS (m/z): 210.1 (M+H).

Step 2: N¹-(3-Fluoro-4-(2-(1-methyl-1H-imidazol-2-yl)thieno[3,2-b]pyridin-7-yloxy)phenyl)-N³-(2-methoxyphenyl)malonamide (28a)

To a solution of the acid (27) (75 mg, 0.36 mmol) and HOBt (54 mg, 0.40 mmol) in DMF (6 mL), was added amine 9 (135 mg, 0.40 mmol). After stirring for 5 min, EDC (84 mg, 0.42 mmol) was added and the reaction mixture was stirred for additional 4 hrs at room temperature. The reaction mixture was poured into NaHCO₃ solution, extracted with EtOAc; the organic phase was collected, dried over anhydrous Na₂SO₄ and concentrated. The residue was purified by preparative HPLC (Aquasil C-18 column, gradient MeOH/water from 60:40 to 95:5) to afford 28a (105 mg, 55% yield) as a white solid. $^1$H NMR (DMSO-d$_6$) δ (ppm): 10.80 (s, 1H), 9.62 (s, 1H), 8.66 (d, 1H), 8.33 (s, 1H), 8.04 (d, 1H), 7.90 (d, 1H), 7.82 (s, 1H), 7.68 (s, 1H), 7.54-7.49 (m, 2H), 7.06 (m, 2H), 6.89 (m, 2H), 4.03 (s, 3H), 3.84 (s, 3H), 3.66 (s, 2H). MS (m/z): 532.0 (M+H).

Example 9

N¹-(4-(2-(1-Ethyl-1H-imidazol-4-yl)thieno[3,2-b]pyridin-7-yloxy)-3-fluorophenyl)-N³-(2-methoxyphenyl)malonamide (28b)

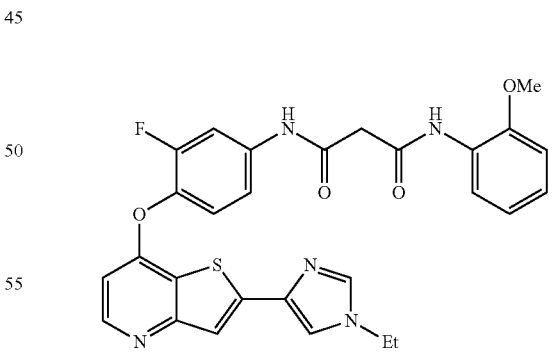

Following the procedure described above for the compound 28a (example 8, step 2) but replacing amine 9 for amine 15, title compound 28b was obtained in 69% yield. $^1$H NMR (DMSO-d$_6$) δ (ppm): 10.78 (s, 1H), 9.62 (s, 1H), 8.66 (d, 1H), 8.37 (broad, s, 1H), 8.33 (s, 1H), 8.05 (dd, 1H), 7.94 (s, 1H), 7.92 (dd, 1H), 7.55 (t, 1H), 7.47 (dd, 1H), 7.07 (m, 2H), 6.96 (d, 1H), 6.89 (m, 1H), 4.13 (q, 2H), 3.84 (s, 2H), 1.42 (t, 3H). MS (m/z): 546.0 (M+H).

Example 10

N[1]-(3-Fluoro-4-(2-(1-methyl-1H-imidazol-5-yl)thieno[3,2-b]pyridin-7-yloxy)phenyl)-N[3]-(2-methoxyphenyl)malonamide (28c)

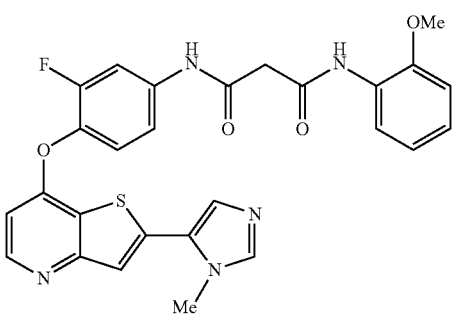

Following the procedure described above for the compound 28a (example 8, step 2) but replacing amine 9 for amine 18, title compound 28c was obtained in 24% yield. $^1$H NMR (DMSO-$d_6$) δ (ppm): 10.58 (s, 1H), 9.62 (s, 1H), 8.49 (d, 1H), 8.05 (dd, 1H), 7.85 (m, 2H), 7.77 (s, 1H), 7.48 (t, 1H), 7.41 (m, 2H), 7.05 (m, 2H), 6.90 (m, 2H) 6.63 (dd, 1H), 3.88 (s, 3H), 3.84 (s, 3H), 3.63 (s, 2H). MS (m/z): 531.8 (M+H).

Scheme 9

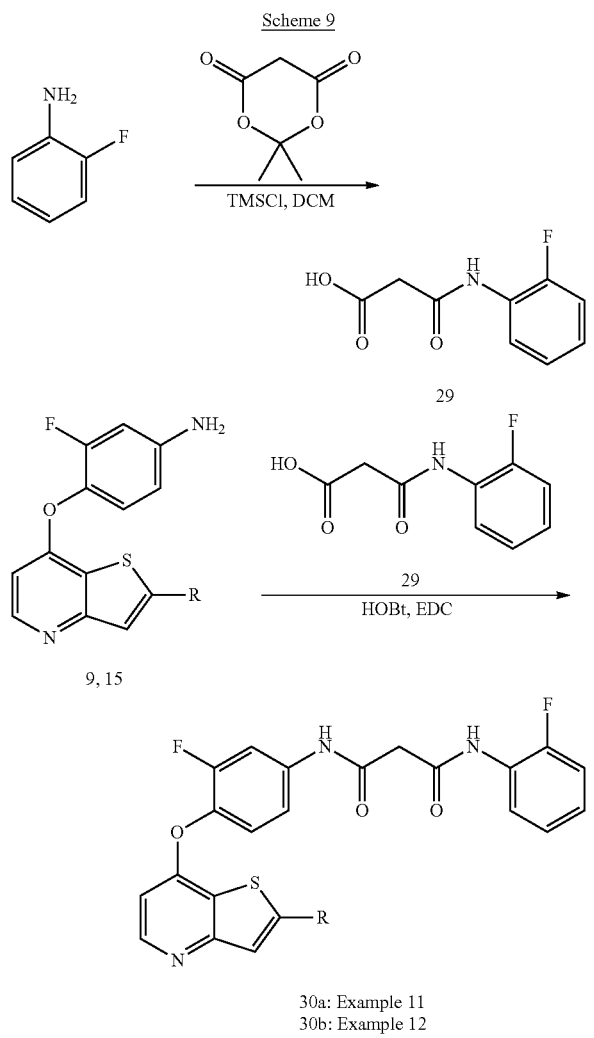

30a: Example 11
30b: Example 12

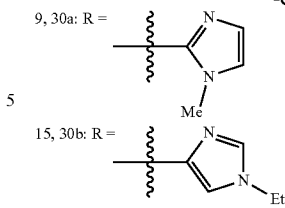

Example 11

N[1]-(3-Fluoro-4-(2-(1-methyl-1H-imidazol-2-yl)thieno[3,2-b]pyridin-7-yloxy)phenyl)-N[3]-(2-fluorophenyl)malonamide (30a)

Step 1: 3-(2-Fluorophenylamino)-3-oxopropanoic acid (29)

To a suspension of 2-fluorobenzeneamine (1 mL, 7.80 mmol) in DCM (78 mL) was added TMSCl (0.99 mL, 7.80 mmol) at RT [Rigo, B.; Fasseur, D.; Cauliez, P. and Couturier, D. *Tetrahedron Lett.;* 30; 23; 1989; 3073-3076.]. The reaction mixture was stirred for 30 min then 2,2-dimethyl-1,3-dioxane-4,6-dione (1.12 g, 7.80 mmol) was added and the combined mixture was stirred overnight. The solvent was removed under reduced pressure and the residue was dissolved in NaHCO$_3$ solution, which was washed with EtOAc. The organic phase was discarded and the aqueous phase was acidified with conc. HCl to pH~3, extracted with EtOAc; extract was dried (anhydrous Na$_2$SO$_4$) and concentrated. The residue was purified by flash chromatography (eluent CHCl$_3$/MeOH/AcOH 8:1:0.1) to afford the acid 29 (0.4 g, 26% yield) as a white solid. $^1$H NMR (DMSO-$d_6$) δ (ppm): 12.67 (s, broad, 1H), 9.95 (s, 1H), 7.95 (m, 1H), 7.25 (m, 1H), 7.12 (m, 1H), 3.43 (s, 2H). MS (m/z): 198.0 (M+H).

Step 2: N[1]-(3-Fluoro-4-(2-(1-methyl-1H-imidazol-2-yl)thieno[3,2-b]pyridin-7-yloxy)phenyl)-N[3]-(2-fluoroxyphenyl)malonamide (30a)

Starting from the amine 9 and following the procedure described above for the compound 28a (example 8, step 2) but substituting acid 27 for the acid 29, title compound 30a was obtained as a white solid in 5% yield. $^1$H NMR (DMSO-$d_6$) δ (ppm): 10.56 (s, 1H), 10.04 (s, 1H), 8.50 (d, 1H), 7099-7.95 (m, 1H), 7.88 (s, 1H), 7.86 (dd, 1H), 7.50 (t, 2H) 7.42 (dd, 1H), 7.40 (s, 1H), 7.29-7.24 (m, 1H), 7.17-7.14 (m, 1H), 7.03 (s, 1H), 6.69 (d, 1H), 4.00 (s, 3H), 3.64 (s, 2H). MS (m/z): 520.1 (M+H).

Example 12

N[1]-(4-(2-(1-Ethyl-1H-imidazol-4-yl)thieno[3,2-b]pyridin-7-yloxy)-3-fluorophenyl)-N[3]-(2-fluorophenyl)malonamide (30b)

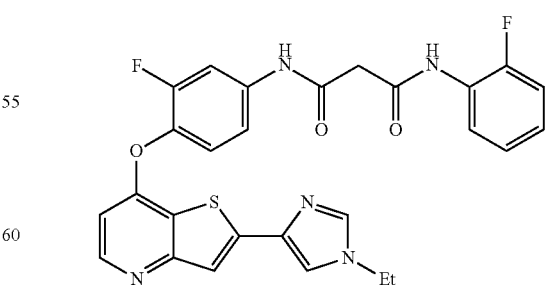

Following the procedure described above for the compound 30a (example 12, step 2) but substituting amine 9 for the amine 15, title compound 30b was obtained in 42% yield. $^1$H NMR (DMSO-$d_6$) δ (ppm): 10.55 (s, 1H), 10.05 (s, 1H), 8.41 (d, 1H), 7.97 (m, 1H), 7.95 (s, 1H), 7.85 (dd, 1H), 7.77 (d, 1H), 7.65 (s, 1H), 7.45 (dd, 1H), 7.41 (dd, 1H), 7.26 (m, 1H), 7.16 (m, 1H), 6.57 (d, 1H), 4.03 (q, 2H), 3.60 (s, 2H), 1.38 (t, 3H). MS (m/z): 534.0 (M+H).

Scheme 10

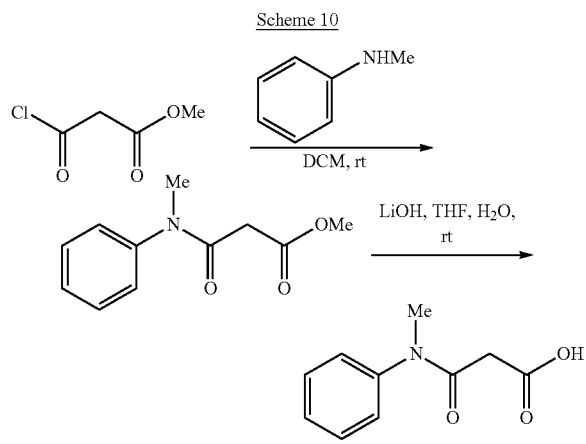

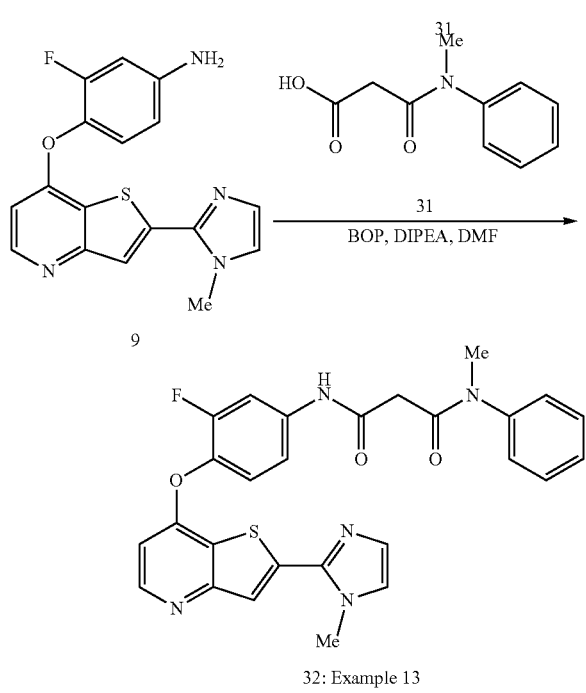

32: Example 13

Example 13

N$^1$-(3-Fluoro-4-(2-(1-methyl-1H-imidazol-2-yl)thieno[3,2-b]pyridin-7-yloxy)phenyl)-N$^3$-methyl-N$^3$-phenylmalonamide (32)

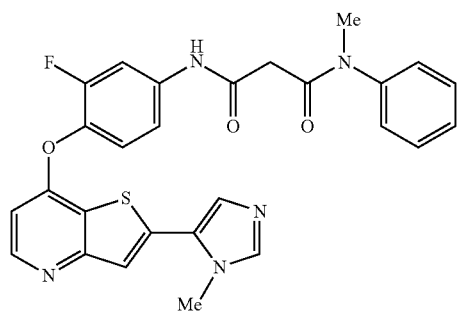

Step 1: 3-(Methyl(phenyl)amino)-3-oxopropanoic acid (31)

A solution of methyl 3-chloro-3-oxopropanoate (1 mL, 9.32 mmol) and N-methyl aniline (1.01 mL, 9.32 mmol) in DCM (18.6 mL) was stirred overnight at room temperature. The solvent was removed under reduced pressure and the residue (N-methyl-N-phenyl-malonamic acid methyl ester, 2.55 g) was dissolved in THF (9 mL). A solution of LiOH× H$_2$O (0.7 g, 18.64 mmol) in water (9 mL) was added and the mixture stirred for 1 h at room temperature. The THF was removed under reduced pressure and the remaining aqueous solution was acidified with 1N HCl (until pH~3) then extracted with EtOAc. The organic phase was concentrated under reduced pressure to afford the acid 31 (1.67 g, 93% yield) as a brown foam. MS (m/z): 194.0 (M+H).

Step 2: N$^1$-(3-Fluoro-4-(2-(1-methyl-1H-imidazol-2-yl)thieno[3,2-b]pyridin-7-yloxy)phenyl)-N$^3$-methyl-N$^3$-phenylmalonamide (32)

To a solution of the amine 9 (80 mg, 0.235 mmol), acid 31 (47 mg, 0.235 mmol), and BOP (114.6 mg, 0.254 mmol) in DMF (2.4 mL), DIPEA (0.164 mL, 0.941 mmol) was added and the mixture was stirred for 2 h at room temperature. The reaction mixture was diluted with EtOAc (100 mL), water (50 mL) was added and the mixture filtered through paper filter. The organic phase was separated, washed with water (50 mL), brine (20 mL), dried (anhydrous Na$_2$SO$_4$) and concentrated under reduced pressure. The residue was purified by flash chromatography (eluent EtOAc/MeOH 10:1) to afford the title compound 32 (36.2 mg, 30% yield) as a creamy solid. $^1$H NMR (DMSO-d$_6$) δ (ppm): 10.29 (s, 1H), 8.49 (d, J=5.5 Hz, 1H), 7.87 (s, 1H), 7.77 (d, J=12.7 Hz, 1H), 7.46-7.30 (m, 8H), 7.03 (s, 1H), 6.66 (d, J=5.5 Hz, 1H), 3.98 (s, 3H), 3.22 (s, 2H), 2.52 (3H, s). MS (m/z): 516.3 (M+H).

Scheme 11

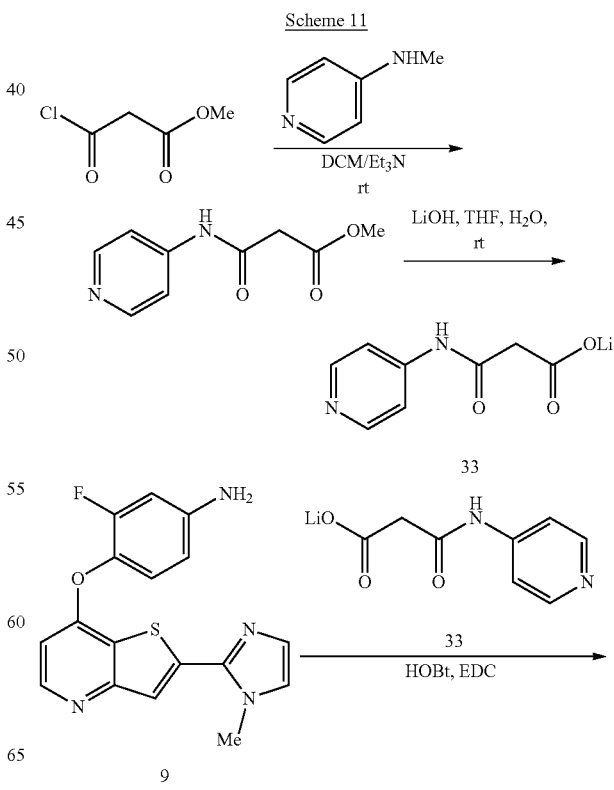

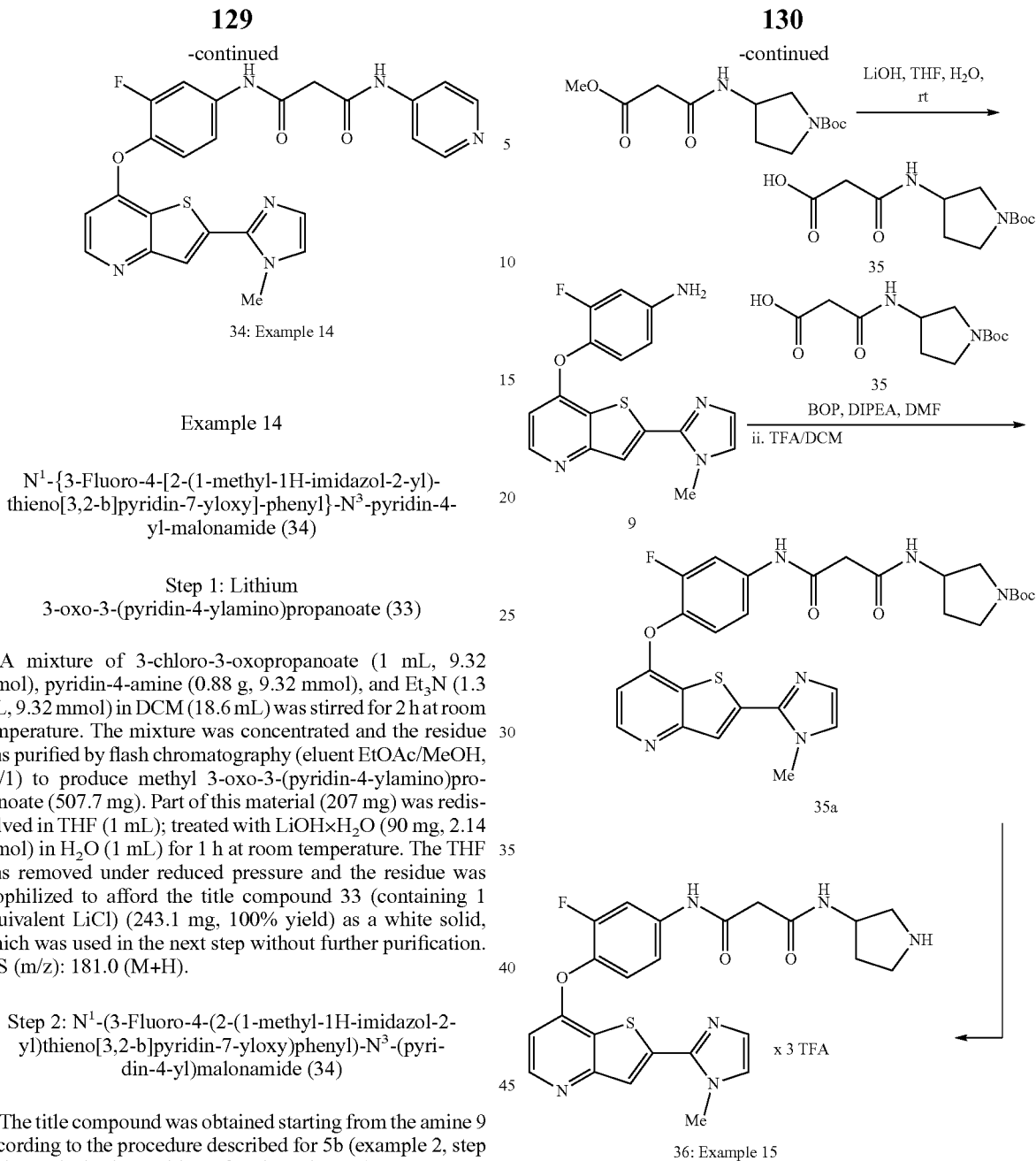

Example 14

N¹-{3-Fluoro-4-[2-(1-methyl-1H-imidazol-2-yl)-thieno[3,2-b]pyridin-7-yloxy]-phenyl}-N³-pyridin-4-yl-malonamide (34)

Step 1: Lithium 3-oxo-3-(pyridin-4-ylamino)propanoate (33)

A mixture of 3-chloro-3-oxopropanoate (1 mL, 9.32 mmol), pyridin-4-amine (0.88 g, 9.32 mmol), and Et₃N (1.3 mL, 9.32 mmol) in DCM (18.6 mL) was stirred for 2 h at room temperature. The mixture was concentrated and the residue was purified by flash chromatography (eluent EtOAc/MeOH, 19/1) to produce methyl 3-oxo-3-(pyridin-4-ylamino)propanoate (507.7 mg). Part of this material (207 mg) was redissolved in THF (1 mL); treated with LiOH×H₂O (90 mg, 2.14 mmol) in H₂O (1 mL) for 1 h at room temperature. The THF was removed under reduced pressure and the residue was lyophilized to afford the title compound 33 (containing 1 equivalent LiCl) (243.1 mg, 100% yield) as a white solid, which was used in the next step without further purification. MS (m/z): 181.0 (M+H).

Step 2: N¹-(3-Fluoro-4-(2-(1-methyl-1H-imidazol-2-yl)thieno[3,2-b]pyridin-7-yloxy)phenyl)-N³-(pyridin-4-yl)malonamide (34)

The title compound was obtained starting from the amine 9 according to the procedure described for 5b (example 2, step 6) but substituting acid 27 for the salt 33 (57 mg, 0.251 mmol). After purification (preparative HPLC, C-18 column, MeOH 60% to MeOH 95% in water) title compound 34 was obtained as a white fluffy solid in 23% yield. ¹H NMR (DMSO-d₆) δ (ppm): 10.68 (s, 2H), 8.45 (d, J=5.5 Hz, 1H), 8.42 (d, J=5.9 Hz, 1H), 8.31 (bs, 1H), 7.86 (m, 2H), 7.56 (m, 2H), 7.49 (t, J=8.8 Hz, 1H), 7.42 (m, 2H), 7.03 (d, J=1 Hz, 1H), 6.69 (d, J=5.5 Hz, 1H), 3.99 (s, 3H), 3.57 (s, 2H), 2.52 (2H, s). MS (m/z): 503.3 (M+H).

Example 15

N¹-(3-Fluoro-4-(2-(1-methyl-1H-imidazol-2-yl)thieno[3,2-b]pyridin-7-yloxy)phenyl)-N³-(pyrrolidin-3-yl)malonamide (36)

Step 1: tert-Butyl 3-(3-chloro-3-oxopropanamido)pyrrolidine-1-carboxylate (35)

A mixture of 3-chloro-3-oxopropanoate (0.235 mL, 2.2 mmol), tert-butyl 3-aminopyrrolidine-1-carboxylate (410 mg, 2.2 mmol), DCM (4.4 mL) and DIPEA (0.766 mL, 4.4 mmol) was stirred for 2 h at room temperature. The reaction mixture was concentrated under reduced pressure and the residue was re-dissolved in THF (2.2 mL), treated with LiOH×H₂O (0.185 g, 4.4 mmol) in water (2.2 mL) for 2 h at room temperature and concentrated under reduced pressure to remove the THF. The remaining aqueous solution was extracted with EtOAc, acidified with 2N HCl (until pH~5), extracted again with EtOAc. The combined organic extracts were dried over anhydrous Na$_2$SO$_4$, filtered and concentrated under reduced pressure to afford the title compound 35 (286 mg, 48% yield) as a light brown foam which was used in the next step without further purification. MS (m/z): 273.1 (M+H).

Step 2: N$^1$-(3-Fluoro-4-(2-(1-methyl-1H-imidazol-2-yl)thieno[3,2-b]pyridin-7-yloxy)phenyl)-N$^3$-(pyrrolidin-3-yl)malonamide (36)

To a solution of the amine 9 (80 mg, 0.235 mmol), acid 35 (64 mg, 0.235 mmol) and BOP (114.6 mg, 0.254 mmol) in DMF (2.4 mL) was added DIPEA (0.164 mL, 0.941 mmol) and the mixture stirred 2 h at room temperature. EtOAc (100 mL) and water (50 mL) were added and the mixture was filtered through a paper filter. The organic phase was collected, washed with water (50 mL), brine (20 mL), dried over anhydrous Na$_2$SO$_4$, filtered and concentrated under reduced pressure. The residue was purified by flash chromatography (eluent EtOAc/MeOH 7:1) giving tert-butyl 3-(3-(3-fluoro-4-(2-(1-methyl-1H-imidazol-2-yl)thieno[3,2-b]pyridin-7-yloxy)phenylamino)-3-oxopropanamido)pyrrolidine-1-carboxylate (35a, 29.7 mg, 21% yield) as a glassy solid. MS (m/z): 595.1 (M+H). This material was dissolved in a solution of TFA (0.5 mL) and DCM (0.5 mL) and stirred for 1 h at room temperature. The reaction mixture was concentrated under reduced pressure, water was added to the residue and the mixture was lyophilized. The resultant solid was purified by preparative HPLC (Aquasil C-18 column, gradient: MeOH 60% to MeOH 95% in water) to afford the title compound 36 as tris-trifluoroacetate salt (13.9 mg, 35%), creamy fluffy solid. $^1$H NMR (DMSO-d$_6$) δ (ppm): 10.51 (s, 1H), 8.81 (bs, 1H), 8.72 (bs, 1H), 8.57 (d, J=5.4 Hz, 1H), 8.47 (d, J=6.3 Hz, 1H), 7.86 (m, 1H), 7.58 (s, 1H), 7.50 (t, J=9.0 Hz, 1H), 7.40 (m, 1H), 7.31 (s, 1H), 6.76 (d, J=5.4 Hz, 1H), 4.29 (m, 1H), 3.82 (s, 3H), 3.40 (m, 1H), 3.36-3.20 (m, 4H), 2.99 (m, 1H), 2.16 (m, 1H), 1.85 (m, 1H). MS (m/z): 495.2 (M+H).

Scheme 13

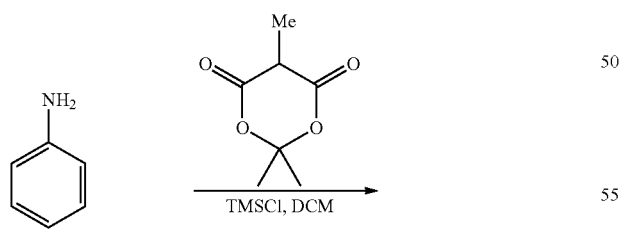

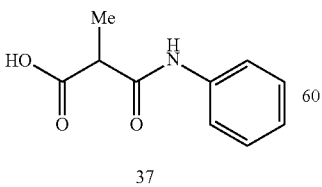

37

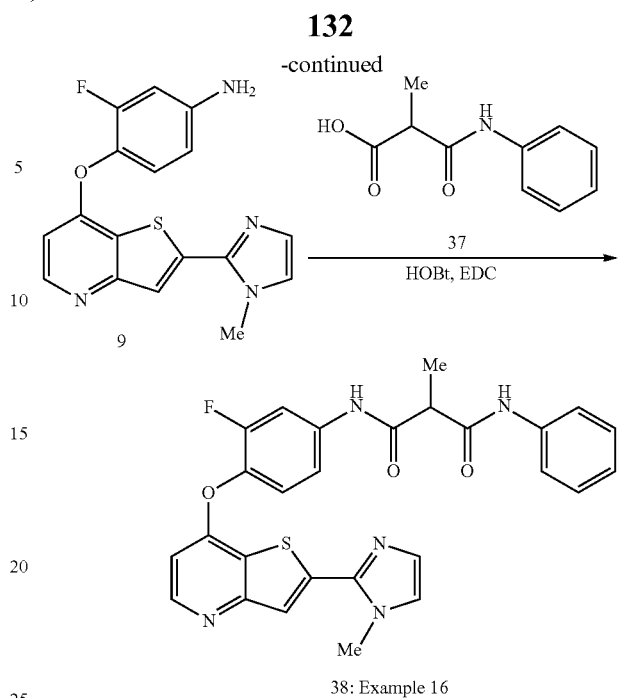

38: Example 16

Example 16

N$^1$-(3-Fluoro-4-(2-(1-methyl-1H-imidazol-2-yl)thieno[3,2-b]pyridin-7-yloxy)phenyl)-2-methyl-N$^3$-phenylmalonamide (38)

Step 1: 2-Methyl-3-oxo-3-(phenylamino)propanoic acid (37)

Following the procedure described above for compound 1 (example 2, step 1, scheme 2) title compound 37 was obtained as a white solid (58% yield). $^1$H NMR (DMSO-d$_6$) δ (ppm): 12.61 (s, 1H), 10.12 (s, 1H), 7.56 (m, 2H), 7.29 (m, 2H), 7.02 (m, 1H), 4.47 (q, 1H), 1.31 (d, 3H). MS (m/z): 194.1 (M+H).

Step 2: N$^1$-(3-Fluoro-4-(2-(1-methyl-1H-imidazol-2-yl)thieno[3,2-b]pyridin-7-yloxy)phenyl)-2-methyl-N$^3$-phenylmalonamide (38)

Starting from the amine 9 and following the procedure described above for compound 28a (example 8, step 2) but substituting acid 27 for the acid 37, title compound 38 was obtained as a white solid (20% yield). $^1$H NMR (d$_6$-DMSO) δ (ppm): 10.99 (s, 1H), 10.51 (s, 1H), 8.64 (d, 1H), 8.25 (s, 1H), 7.94 (s, 1H), 7.80 (s, 1H), 7.65 (d, 2H) 7.57-7.48 (m, 2H), 7.28 (t, 7.03 (t, 1H), 6.88 (d, 1H), 4.08 (s, 3H), 1.18 (s, 3H). MS (m/z): 516.1 (M+H).

Scheme 14

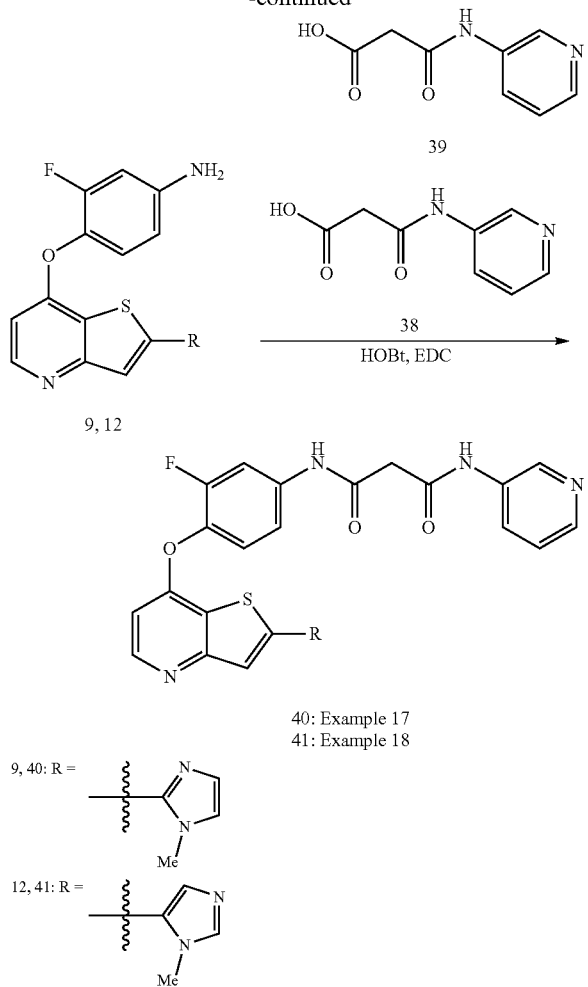

Example 17

N[1]-(3-Fluoro-4-(2-(1-methyl-1H-imidazol-2-yl)thieno[3,2-b]pyridin-7-yloxy)phenyl)-2-methyl-N[3]-(pyridin-3-yl)malonamide (40)

Step 1: 3-Oxo-3-(pyridine-3-ylamino)propanoic acid (39)

To a suspension of pyridine-3-amine (1 g, 10.6 mmol) in DCM (100 mL) was added TMSCl (1.3 mL, 10.6 mmol) at room temperature. The reaction mixture was stirred for 30 min. 2,2-Dimethyl-1,3-dioxane-4,6-dione (1.44 g, 10.6 mmol) was added and the combined mixture stirred overnight and concentrated under reduced pressure. The residue was dissolved in dilute NaHCO$_3$ solution and washed with EtOAc. The aqueous phase was collected and acidified with conc. HCl to pH~3 and extracted with EtOAc. The extract was dried over anhydrous Na$_2$SO$_4$, filtered and concentrated. The remaining solid was purified by flash chromatography (eluent CHCl$_3$/MeOH/AcOH 8:1:0.1) to afford the title compound 39 as a white solid (0.5 g, 26% yield). $^1$H NMR (DMSO-d$_6$) δ (ppm): 12.04 (bs, 1H), 9.67 (s, 1H), 8.18 (d, 1H), 8.01 (d, 1H), 7.29 (m, 1H), 2.97 (s, 2H). MS (m/z): 181.1 (M+H).

Step 2: N[1]-(3-Fluoro-4-(2-(1-methyl-1H-imidazol-2-yl)thieno[3,2-b]pyridin-7-yloxy)phenyl)-N[3]-(pyridine-3-yl)malonamide (40)

To a solution of the acid 39 (58 mg, 0.32 mmol) and HOBt (47 mg, 0.35 mmol) in DMF (5 mL), was added amine 9 (108 mg, 0.32 mmol). After stirring for 5 min, EDC (75 mg, 0.39 mmol) was added and the reaction mixture was stirred overnight at room temperature then poured into dilute NaHCO$_3$ solution and extracted with EtOAc. The extract was dried over anhydrous Na$_2$SO$_4$, filtered and concentrated. The residue was purified by preparative HPLC (Aquasil C-18, gradient: MeOH in water 60% to 95%) to afford the title compound 40 as a white solid. (20 mg, 12%) $^1$H NMR (DMSO-d$_6$) δ (ppm): 10.65 (s, 1H), 10.50 (s, 1H), 8.73 (d, 1H), 8.50 (d, 1H), 8.26 (dd, 1H), 8.05 (m, 1H), 7.88 (s, 1H), 7.87 (dd, 1H), 7.48 (t, 1H), 7.41 (m, 2H), 7.35 (m, 1H), 6.69 (d, 1H), 3.99 (s, 3H), 3.56 (s, 2H). MS (m/z): 503.1 (M+H).

Example 18

N-{3-Fluoro-4-[2-(3-methyl-3H-imidazol-4-yl)-thieno[3,2-b]pyridin-7-yloxy]-phenyl}-N'-pyridin-3-yl-malonamide (41)

Following the procedure described above for the compound 40 (example 17, step 2, scheme 14) but substituting the amine 9 for the amine 12, title compound 41 was obtained in 33% yield (scheme 14) $^1$H NMR (DMSO-d$_6$) δ (ppm): 10.58 (s, 1H), 10.44 (s, 1H), 8.74 (d, 1H), 8.49 (d, 1H), 8.27 (dd, 1H), 8.05 (m, 1H), 7.86 (m, 2H), 7.77 (s, 1H), 7.48 (t, 1H), 7.42 (m, 2H), 7.35 (q, 1H), 6.63 (d, 1H), 3.88 (s, 3H), 3.54 (s, 2H). MS (m/z): 502.7 (M+H).

Scheme 15

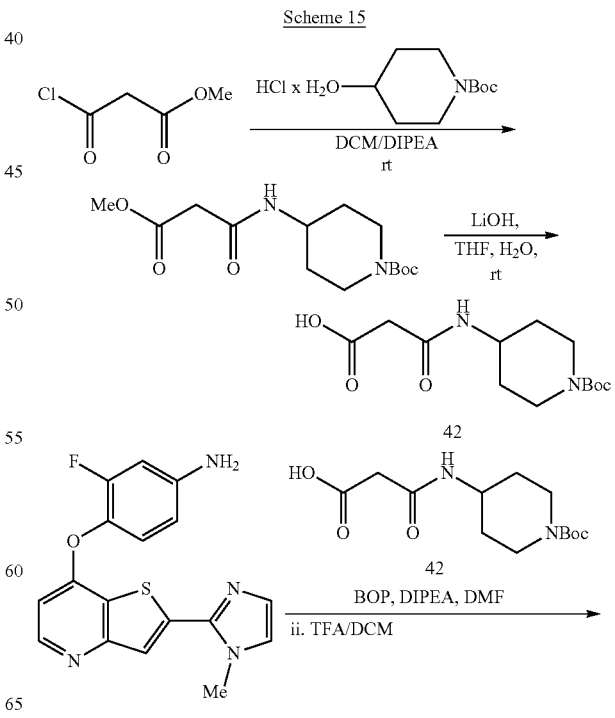

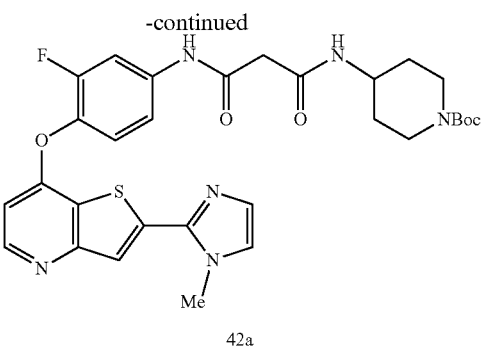

42a

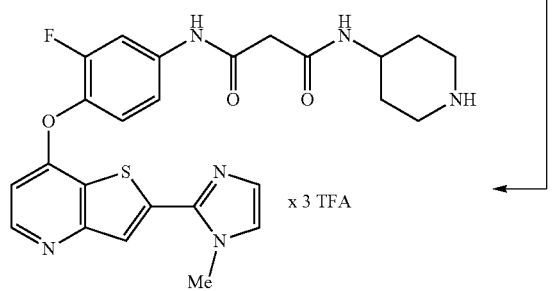

43: Example 19

Example 19

N¹-(3-Fluoro-4-(2-(1-methyl-1H-imidazol-2-yl)thieno[3,2-b]pyridin-7-yloxy)phenyl)-N³-(piperidin-4-yl)malonamide (43)

Step 1: 3-(1-(tert-Butoxycarbonyl)piperidin-4-ylamino)-3-oxopropanoic acid (42)

The mixture of tert-butyl-aminopiperidine-1-carboxylate hydrochloride (512 mg, 2.16 mmol), methyl 3-chloro-3-oxopropanoate (232 μL, 2.16 mmol), and DIPEA (828 μL, 4.75 mmol) in DCM (20 mL) was stirred at room temperature overnight. The solvent was removed under reduced pressure and the residue was purified by flash chromatography (eluent EtOAc) to afford tert-butyl 4-(3-methoxy-3-oxopropanamido) piperidine-1-carboxylate as a white solid (500 mg, 78%). MS (m/z): 301.1 (M+H). This material (500 mg, 1.67 mmol) was dissolved in MeOH/THF/H₂O (2 mL/2 mL/1 mL), and LiOH×H₂O (280 mg, 6.75 mmol) was added to the solution. The reaction mixture was stirred for 2 hrs, the solvent was removed under reduced pressure and the residue was purified by flash chromatography (eluent CH₃Cl/MeOH/AcOH) to afford the title compound 42 (300 mg, 63% yield) as yellowish syrup. MS (m/z): 287.1 (M+H).

Step 2: N¹-(3-Fluoro-4-(2-(1-methyl-1H-imidazol-2-yl)thieno[3,2-b]pyridin-7-yloxy)phenyl)-N³-(piperidin-4-yl)malonamide (43)

To a solution of acid 42 (76 mg, 0.266 mmol) and HOBt (40 mg, 0.30 mmol) was added amine 9 (100 mg, 0.29 mmol) and the mixture was stirred at room temperature for 5 min. EDC (62 mg, 0.32 mmol) was added and combined mixture was stirred for additional 48 hours. Additional 42 (38 mg, 0.133 mmol) and EDC (31 mg, 0.16 mmol) were added and the reaction mixture was stirred for a further 24 hours. Again additional 42 (38 mg, 0.133 mmol) and EDC (31 mg, 0.16 mmol) were added and the reaction mixture was stirred for 24 hours more then partitioned between EtOAc and NaHCO₃ solution. The organic phase was washed with brine, dried over anhydrous Na₂SO₄ then filtered and concentrated. The residue was purified by preparative HPLC to afford tert-butyl 4-(3-(3-fluoro-4-(2-(1-methyl-1H-imidazol-2-yl)thieno[3,2-b]pyridin-7-yloxy)phenylamino)-3-oxopropanamido)piperidine-1-carboxylate 42a (20 mg, 13% yield) as a white solid. This material was dissolved in a solution of TFA/DCM (1 mL/2 mL), stirred for 20 min and concentrated. The residue was purified by preparative HPLC (column Aquasil C-18, gradient, MeOH 60% to MeOH 95% in water) to afford the title compound 43 as a tris-trifluoroacetate salt (31 mg, 99%), white solid. NMR (DMSO-d₆) δ (ppm): 10.49 (s, 1H), 8.55 (d, 1H), 8.49 (bs, 1H), 8.27 (d, 1H), 8.00 (s, 1H), 7.86 (dd, 1H), 7.55 (s, 1H), 7.49 (t, 1H), 7.39 (dd, 2H), 7.26 (s, 1H), 6.74 (d, 2H), 4.00 (s, 2H), 3.83 (m, 1H), 3.24 (m, 2H), 3.00 (m, 2H), 1.92 (m, 2H), 1.56 (m, 2H). MS (m/z): 509.1 (M+H).

Scheme 16

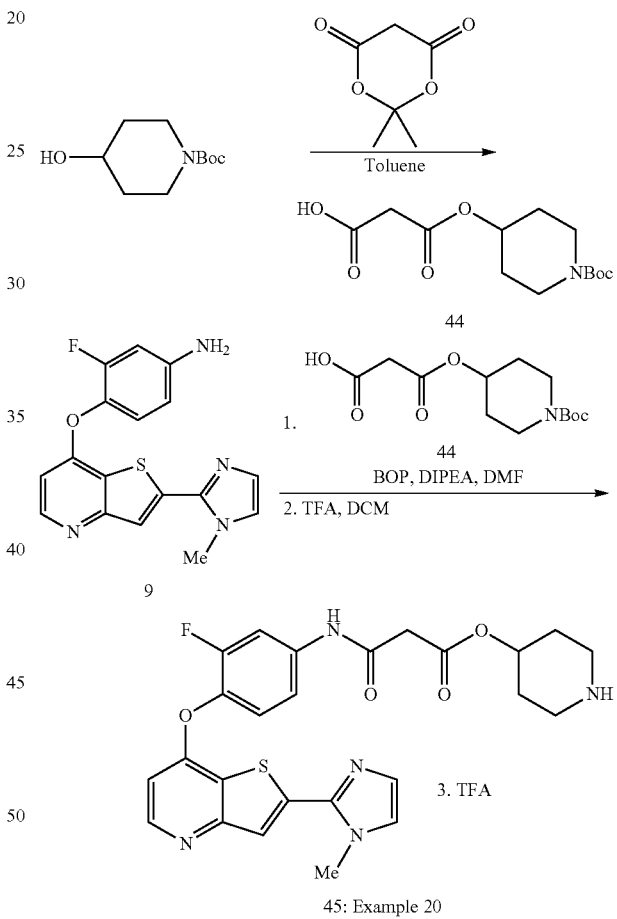

45: Example 20

Example 20

N-{3-Fluoro-4-[2-(1-methyl-1H-imidazol-2-yl)-thieno[3,2-b]pyridin-7-yloxy]-phenyl}-malonamic acid piperidin-4-yl ester (45)

Step 1: 3-(1-(tert-Butoxycarbony)piperidin-4-yloxy-3-oxopropanoic acid (44)

A mixture of tert-butyl 4-hydroxypiperidine-1-carboxylate (1 g, 4.97 mmol) and 2,2-dimethyl-1,3-dioxane-4,6-dione (0.72 g, 4.97 mmol) in toluene was refluxed overnight [Ryu, Y.; Scott, A. I.; *Tetrahedron Lett.;* 44; 40; 2003; 7494-7502]. The solvent was removed under reduced pressure and the residue was partitioned between EtOAc and NaHCO$_3$ solution. Aqueous phase was collected, acidified with 2N HCl and extracted with EtOAc. The extract was concentrated to afford the title compound 44 (0.816 g, 57% yield) as colorless syrup. MS (m/z): 288.1 (M+H).

Step 2: N-{3-Fluoro-4-[2-(1-methyl-1H-imidazol-2-yl)-thieno[3,2-b]pyridin-7-yloxy]-phenyl}-malonamic acid piperidin-4-yl ester (45)

To a solution of amine 9 (355 mg, 1.05 mmol), acid 44 (300 mg, 1.05 mmol) and BOP (464 mg, 1.05 mmol) in DMF (10 mL), DIPEA (0.22 mL, 1.26 mmol) was added and the mixture stirred at room temperature for 2 hours, partitioned between EtOAc and water. Organic phase was collected, washed with brine; dried over anhydrous anhydrous Na$_2$SO$_4$, filtered and concentrated. The residue was purified by flash chromatography (eluent EtOAc/MeOH) followed by crystallization from MeOH, to produce a solid material which was dissolved in DCM (1 mL) and TFA (1 mL), stirred for 30 min and concentrated to give the target compound 45 as a tris-trifluoroacetate salt (30 mg, 5% yield). $^1$H NMR (DMSO-d$_6$) δ (ppm): 10.61 (s, 1H), 8.57 (d, 1H), 8.47 (bs, 1H), 8.42 (bs, 1H), 8.02 (s, 1H), 8.02 (m, 3H), 7.83 (dd, 1H), 7.57 (s, 2H), 7.51 (t, 1H), 7.38 (dd, 2H), 7.29 (s, 1H), 6.75 (d, 1H), 5.0 (m, 4H), 4.02 (s, 1H), 3.56 (s, 2H), 3.15 (m, 3H), 1.98 (m, 2H), 1.80 (m, 2H). MS (m/z): 510.0 (M+H).

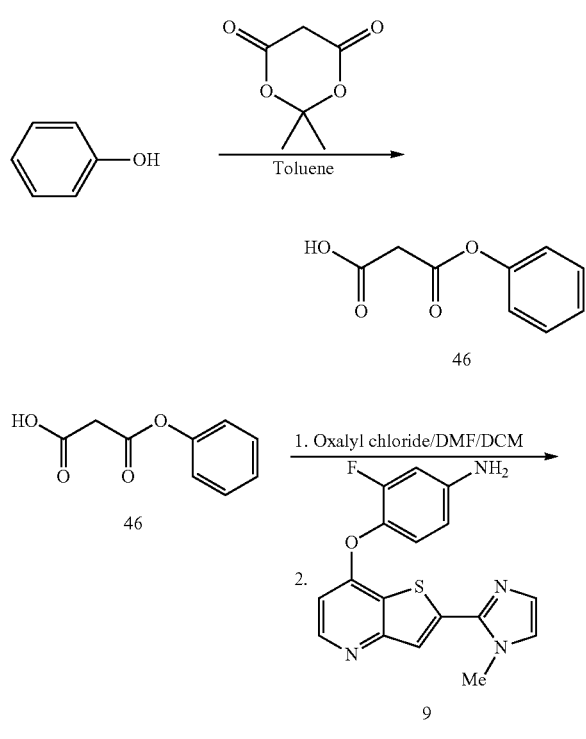

Scheme 17

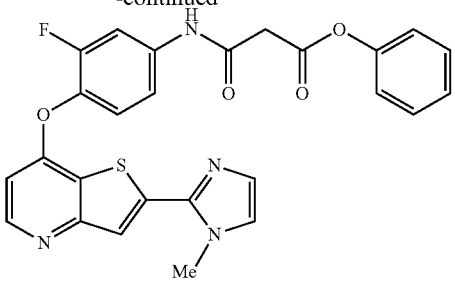

47: Example 21

Example 21

N-{3-Fluoro-4-[2-(1-methyl-1H-imidazol-2-yl)-thieno[3,2-b]pyridin-7-yloxy]-phenyl}-malonamic acid phenyl ester (47)

Step 1: 3-Oxo-3-(phenylamino)propanoic acid (46)

A solution of 2,2-dimethyl-1,3-dioxane-4,6-dione (5 g, 34.69 mmol) and phenol (3.26 g, 34.69 mmol) in toluene (69 mL) [Ryu. Y.; Scott, A. I.: *Tetrahedron Lett.;* 44: 40; 2003; 7494-7502], was refluxed for 5 hours, cooled to room temperature, and extracted with saturated NaHCO$_3$ solution, the aqueous extract was washed with toluene and acidified with conc. HCl (pH~3). The acidic solution was extracted with DCM and the organic phase was collected, dried over anhydrous Na$_2$SO$_4$, filtered and concentrated under reduced pressure to afford title compound 46 (3.88 g, 21.55 mmol, 62%) as a white solid. MS: 181.1 (M+H).

Step 2: N-[3-Fluoro-4-[2-(1-methyl-1H-imidazol-2-yl)-thieno[3,2-b]pyridin-7-yloxy]-phenyl]-malonamic acid phenyl ester (47)

To a solution of the acid 46 (63.5 mg, 0.353 mmol) in DCM (3.5 mL) containing a drop of DMF was added oxalyl chloride (0.032 mL, 0.37 mmol) at 0° C. The mixture was stirred 1 h at room temperature and concentrated. The residue was dissolved in DCM (0.7 mL) and added to a solution of the amine 9 (100 mg, 0.294 mmol) in a mixture of DMF (0.5 mL) and DCM (2.5 mL). The reaction mixture was stirred for 2 hours at room temperature and the DCM was removed under reduced pressure. The residue was diluted with EtOAc and washed with water. The organic phase was dried over anhydrous Na$_2$SO$_4$, filtered and concentrated under reduced pressure. The residue was purified by preparative HPLC (Aquasil C-18 column, gradient, MeOH 60% to MeOH 95% in water) to afford 47 (4.8 mg, 3.2% yield) as a white fluffy solid. $^1$H NMR (DMSO-d$_6$) δ (ppm): 10.70 (s, 2H), 8.5 (d, J=5.4 Hz, 1H), 7.86 (m, 2H), 7.5 (t, J=8.8 Hz, 1H), 7.46-7.41 (m, 4H), 7.28 (m, 2H), 7.16 (m, 2H), 7.04 (s, 1H), 6.69 (d, J=5.4 Hz, 1H), 3.99 (s, 3H), 3.81 (s, 2H). MS (m/z): 503.3 (M+H).

Scheme 18
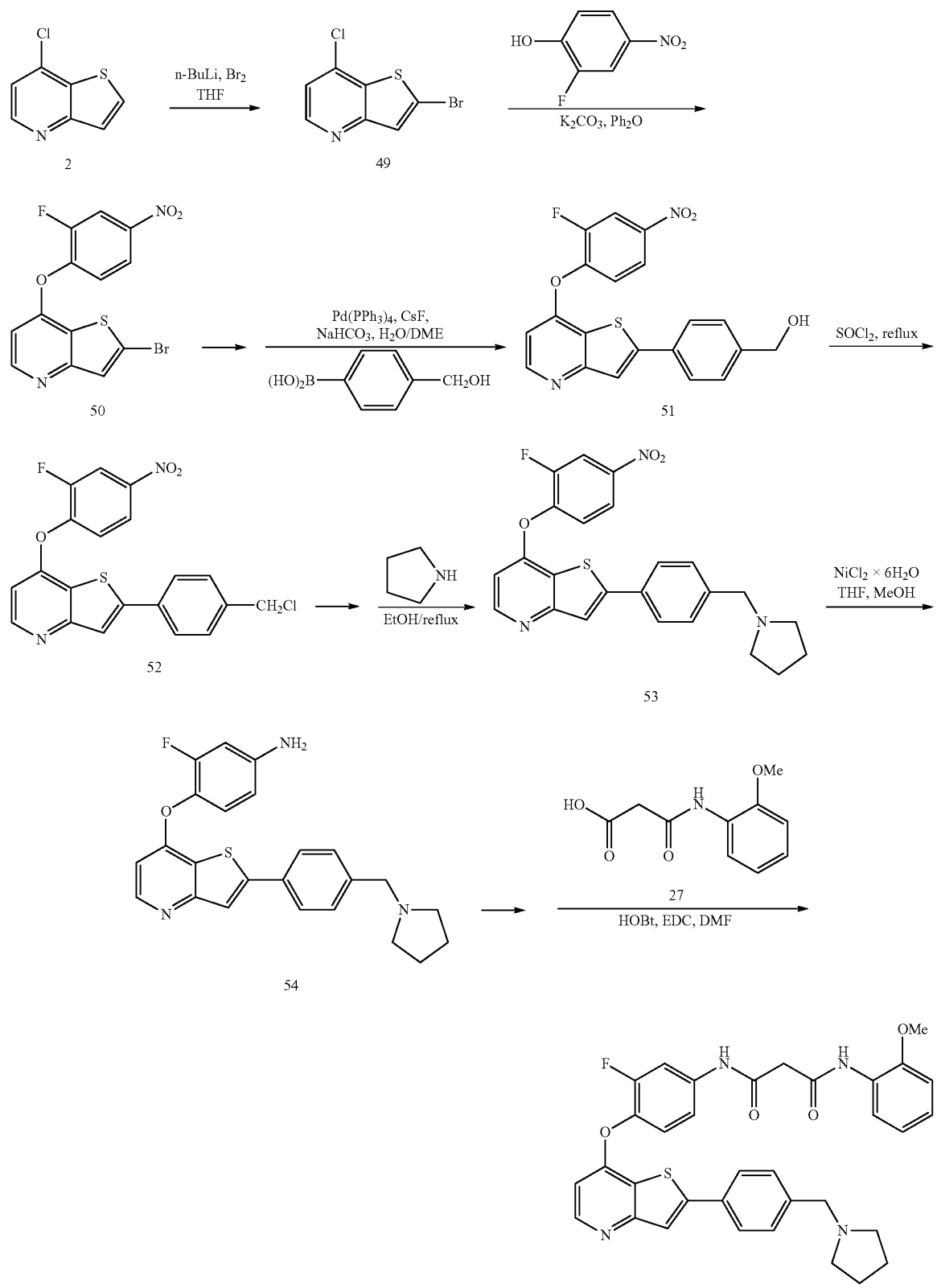
48: Example 22

Example 22

N[1]-(3-Fluoro-4-(2-(4-(pyrrolidin-1-ylmethyl)phenyl)-thieno[3,2-b]pyridin-7-yloxy)phenyl)-N[3]-(2-methoxyphenyl)malonamide (48)

Step 1. 2-Bromo-7-chloro-thieno[3,2-b]pyridine (49)

To a stirred solution of 2 (10.12 g, 5.59 mmol) in dry THF (200 ml) at −78° C. was added n-BuLi (24 ml, 76.7 mmol, 2.5 M solution in hexanes) and the resultant suspension was stirred for 15 minutes. Bromine (18.9 g, 120 mmol) was added slowly and the reaction mixture was stirred for additional 30 minutes, quenched with water and diluted with EtOAc. The organic phase was separated and dried over anhydrous sodium sulfate, filtered and concentrated under reduced pressure. Purification by column chromatography (eluent EtOAc/Hexane 9:1) afforded title compound 49 (10.5 g, 71% yield) as a yellow solid. $^1$H NMR (CDCl$_3$) δ (ppm): 8.62 (d, J=5.09 Hz, 1H), 7.92 (s, 1H), 7.59 (d, J=5.09 Hz, 1H).

Step 2. 2-Bromo-7-(2-fluoro-4-nitro-phenoxy)-thieno[3,2-h]pyridine (50)

A mixture of 49 (5.1 g, 20.5 mmol), potassium carbonate (5.65 g, 4 mmol) and 2-fluoro-4-nitrophenol (4.82 g, 30.7 mmol) was heated at 190° C. in Ph$_2$O (25 ml) for 3 hrs. After cooling to room temperature it was diluted with DCM and filtered. The filtrate was concentrated and the residue was purified by column chromatography (eluent ethyl acetate/hexane 3:1) to afford title compound 50 as a yellow solid (5.4 g, 71% yield). $^1$H NMR (DMSO-d$_6$) δ (ppm): 8.55 (d, J=5.28 Hz, 1H), 8.46 (dd, J=2.5 and 10.4 Hz, 1H), 8.19 (d, J=8.8 Hz, 1H), 7.87 (s, 1H), 7.72 (t, J=8.4 Hz), 6.99 (d, J=5.47 Hz, 1H).

Step 3. (4-(7-(2-Fluoro-4-nitrophenoxy)thieno[3,2-b]pyridin-2-yl)phenyl)methanol (51)

To a solution of 50 (1.0 g, 2.71 mmol) in dry DME (20 ml) was added 4-(hydroxymethyl)phenylboronic acid (823 mg, 5.4 mmol), NaHCO$_3$ (682 mg, 8.13 mmol), CsF (820 mg, 5.4 mmol) and water (10 ml), and the reaction mixture was refluxed under nitrogen for 2 hrs. After cooling to room temperature the solvent was removed under reduced pressure, the residue was dissolved in EtOAc and the resultant solution was washed with water, dried over anhydrous sodium sulfate and filtered. The filtrate was evaporated and the resultant solid was triturated with Et$_2$O to afford the title compound 51 as a white solid (880 mg, 82% yield). MS (m/z): 397.1 (M+H).

Step 4. 2-(4-(Chloromethyl)phenyl)-7-(2-fluoro-4-nitrophenoxy)thieno[3,2-b]pyridine (52)

The alcohol 51 (880 mg, 2.22 mmol) was suspended in SOCl$_2$ (10 ml) and the reaction mixture was refluxed for 1 hour, cooled and carefully poured onto ice/water mixture. A precipitate formed, which was collected by filtration and washed with additional cold water. The material was dried under reduced pressure and used directly in the next step (crude product, >100% yield). MS (m/z): 415.1 (M+H)

Step 5. 7-(2-Fluoro-4-nitrophenoxy)-2-(4-(pyrrolidin-1-ylmethyl)phenyl)thieno[3,2-b]pyridine (53)

To a suspension of 52 (444 mg, 0.98 mmol, crude material from the previous step) in iPrOH (10 ml) was added pyrrolidine (210 mg, 2.96 mmol) and the reaction mixture was refluxed for 4 hrs. The solvent was removed under reduced pressure and the residue was dissolved in EtOAc. The solution was washed with water and the organic layer was collected, dried over anhydrous sodium sulfate and filtered. The filtrate was evaporated and the resultant oil was purified by column chromatography (eluents EtOAc to 30% MeOH in EtOAc), to afford title compound 53 (200 mg, 45% yield) as an orange solid. MS (m/z): 450.2 (M+H).

Step 6. 3-Fluoro-4-[2-(4-pyrrolidin-1-ylmethyl-phenyl)-thieno[3,2-b]pyridin-7-yloxy]-phenylamine (54)

To a solution of the nitro compound 53 (256 mg, 0.57 mmol) in a mixture of MeOH (12 mL) and THF (4 mL) at 0° C. was added NiCl$_2$.6H$_2$O (279 mg, 1.14 mmol), followed by portion wise addition of NaBH$_4$ (87 mg, 2.27 mmol). The reaction mixture turned black after 15 min, and was filtered through a celite pad; the filtrate concentrated under reduced pressure. The residue was suspended in 2N HCl and the solids were removed by filteration. The filtrate was basified with NH$_4$OH to pH~10 then extracted with EtOAc. The organic phase was concentrated to afford the title compound 54 (260 mg, crude, >100% yield, HPLC pure) as yellowish foam. MS (m/z): 420.1 (M+H).

Step 7. N[1]-(3-Fluoro-4-(2-(4-(pyrrolidin-1-ylmethyl)phenyl)-thieno[3,2-b]pyridin-7-yloxy)phenyl)-N[3]-(2-methoxyphenyl)malonamide (48)

To a solution of amine 54 (260 mg, 0.57 mmol, crude) in DMF (6 mL), were added acid 27 (108 mg, 0.52 mmol) and HOBt (77 mg, 0.57 mmol). After stirring for 5 min, EDC (120 mg, 0.63 mmol) was added, and the reaction mixture was stirred at room temperature for additional 4 hours and concentrated under reduced pressure. The residue was purified by preparative HPLC (column Aquasil C-18, gradient, MeOH 60% to MeOH 95% in water) to afford title compound 48 (160 mg, 46% yield) as a white solid. $^1$H NMR (DMSO-d$_6$) δ (ppm): 10.87 (bs, 1H), 10.75 (s, 1H), 9.62 (s, 1H), 8.60 (d, 1H), 8.17 (s, 1H), 8.02 (m, 3H), 7.89 (d, 1H), 7.74 (d, 2H), 7.51 (m, 1H), 7.05 (m, 2H), 6.90 (t, 1H), 6.79 (d, 1H), 4.39 (d, 1H), 6.57 (d, 1H), 3.84 (s, 2H), 3.69 (s, 2H), 3.35 (m, 2H), 3.06 (m, 3H), 2.00 (m, 2H), 1.87 (m, 2H). MS (m/z): 610.0 (M+H).

Example 23

N[1]-(4-(2-(1-Ethyl-5-methyl-1H-imidazol-4-yl)thieno[3,2-b]pyridin-7-yloxy)-3-fluorophenyl)-N[3]-phenyl-malonamide (55)

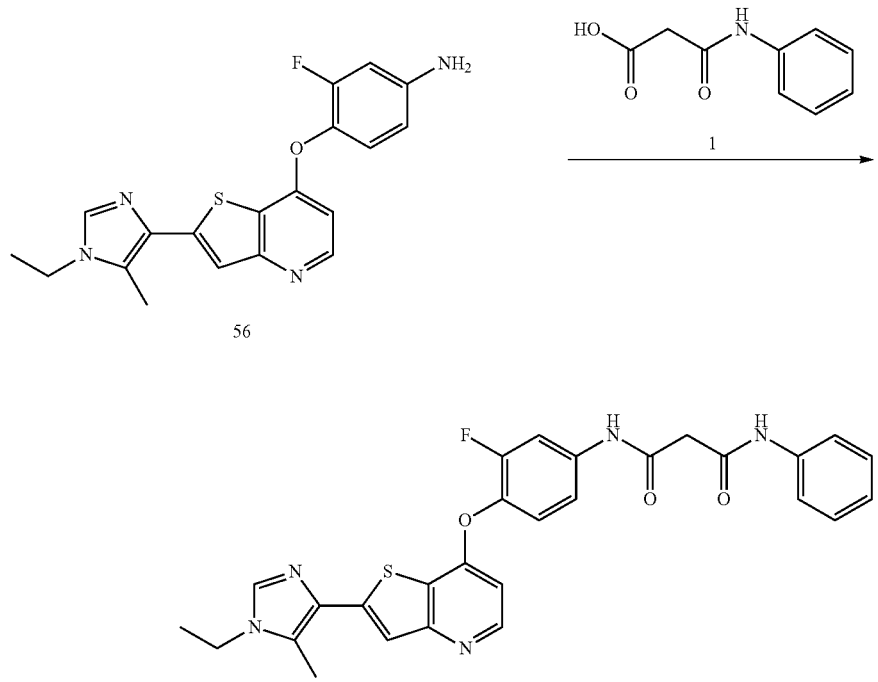

To a solution of the amine 56 (WO 2006010264) (189 mg, 0.513 mmol) in DMF (10 ml) was added the acid 1 (184 mg, 2 eq, 1.03 mmol), HOBT (139 mg, 2 eq, 1.03 mmol) and EDC (197 mg, 2 eq, 1.03 mmol). The reaction mixture was stirred at room temperature overnight, concentrated to dryness and partitioned between EtOAc/MeOH and water. The organic phase was collected, dried over sodium sulfate and filtered. The solvent was removed under reduced pressure and the crude product was purified by column chromatography (10% MeOH in Et$_2$O to 20% MeOH in Et$_2$O) to afford title compound 55 (80 mg, 29% yield) as a yellow fluffy solid. $^1$H NMR (400 MHz, d$_6$ DMSO) δ (ppm) 10.55 (s, 1H), 10.20 (s, 1H), 8.41 (d, J=5.48 Hz, 1H), 7.85 (dd, J=2.44 and 13.11 Hz, 1H), 7.72 (s, 1H), 7.59 (d, J=8.61 Hz, 2H), 7.51 (s, 1H), 7.42 (m, 4H), 7.30 (dt, J=2.15 and 6.65 Hz, 1H), 7.07 (dt, J=1.17 and 2.35 Hz, 1H), 6.57 (dd, J=0.78 and 5.52 Hz, 1H), 4.02 (q, J=7.24 Hz, 2H), 3.50 (s, 2H), 3.31 (s, 3H), 1.31 (t, J=7.24 Hz, 3H). MS (m/z): 530.0 (M+H).

Example 24

N[1]-Cyclohexyl-N[3]-(4-(2-(1-ethyl-1H-imidazol-4-yl)thieno[3,2-b]pyridin-7-yloxy)-3-fluorophenyl)malonamide (57)

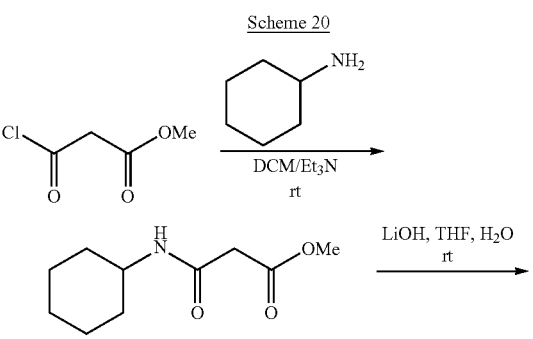

-continued

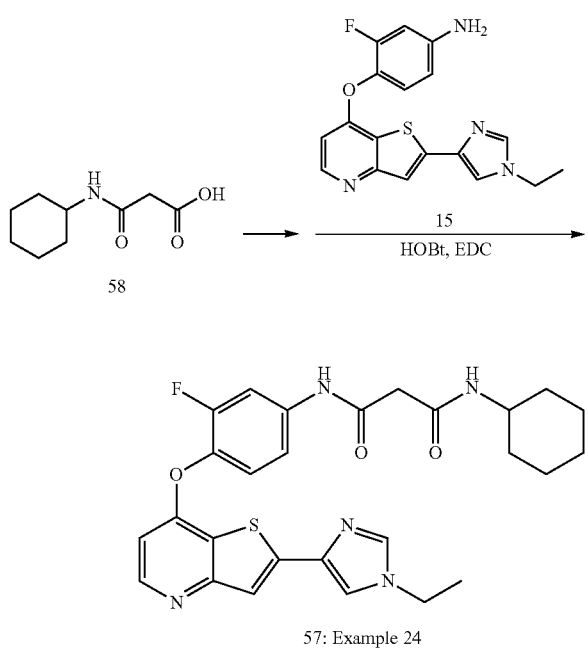

57: Example 24

Step 1: 3-(Cyclohexylamino)-3-oxopropanoic acid (58)

To a solution of methyl 3-chloro-3-oxopropanoate (2.2 g, 16.1 mmol) in dry DCM (30 ml) at 0° C. was added cyclohexylamine (4.0 g, 40.3 mmol). The reaction mixture was stirred for 1 hr at room temperature. The reaction mixture was washed with diluted HCl, saturated NaHCO$_3$ then brine well. The organic phase was collected, dried over anhydrous sodium sulfate then filtered and concentrated. The resultant crude amide was used directly in the next step with no additional purification (3.2 g, 100%). To a solution of this material (500 mg, 2.51 mmol) in THF/water (1:1, 20 ml) was added NaOH (200 mg, 5.02 mmol) and the mixture was stirred for 3 hrs at room temperature. The mixture was extracted with Et$_2$O then the aqueous phase was acidified to pH 1 and extracted with EtOAc. The organic phase was collected, dried over anhydrous sodium sulfate then filtered and concentrated to afford the title compound 58 as a beige solid (450 mg, 97% yield). MS (m/z): 186.2 (M+H).

Step 2: N$^1$-Cyclohexyl-N$^3$-(4-(2-(1-ethyl-1H-imidazol-4-yl)thieno[3,2-b]pyridin-7-yloxy)-3-fluorophenyl)malonamide (57)

The title compound was obtained starting from the amine 15 (117 mg, 0.33 mmol) according to the procedure described for 55 but substituting acid 1 for the acid 58 (122 mg, 0.66 mmol). After purification by column chromatography (EtOAc to 10% MeOH in EtOAc) the title compound 57 was obtained as a pink solid (7 mg, 5% yield). $^1$H NMR (DMSO-d$_6$) δ (ppm): 10.45 (s, 1H), 8.40 (d, J=5.48 Hz, 1H), 8.00 (d, J=7.63 Hz, 1H), 7.94 (s, 1H), 7.84 (dd, J=2.35 and 13.11 Hz, 1H), 7.71 (s, 1H), 7.65 (s, 1H), 7.39 (m, 2H), 6.54 (dd, J=0.78 and 5.48 Hz, 1H), 4.01 (q, J=7.24 Hz, 2H), 3.52 (m, 1H), 3.23 (s, 2H), 1.65 (m, 4H), 1.51 (m, 1H), 1.39 (t, J=7.24 Hz, 3H), 1.16 (m, 4H). MS (m/z): 522.1 (M+H).

Scheme 21

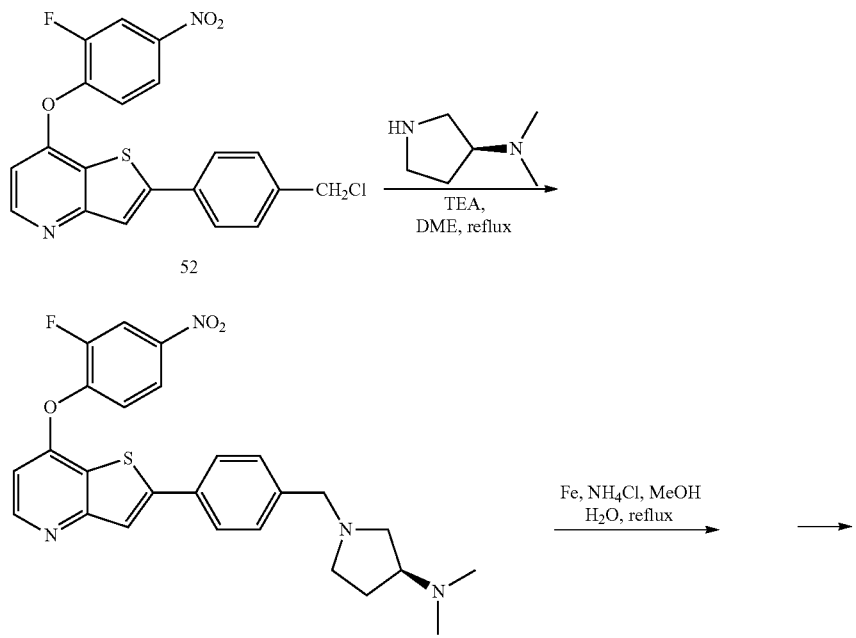

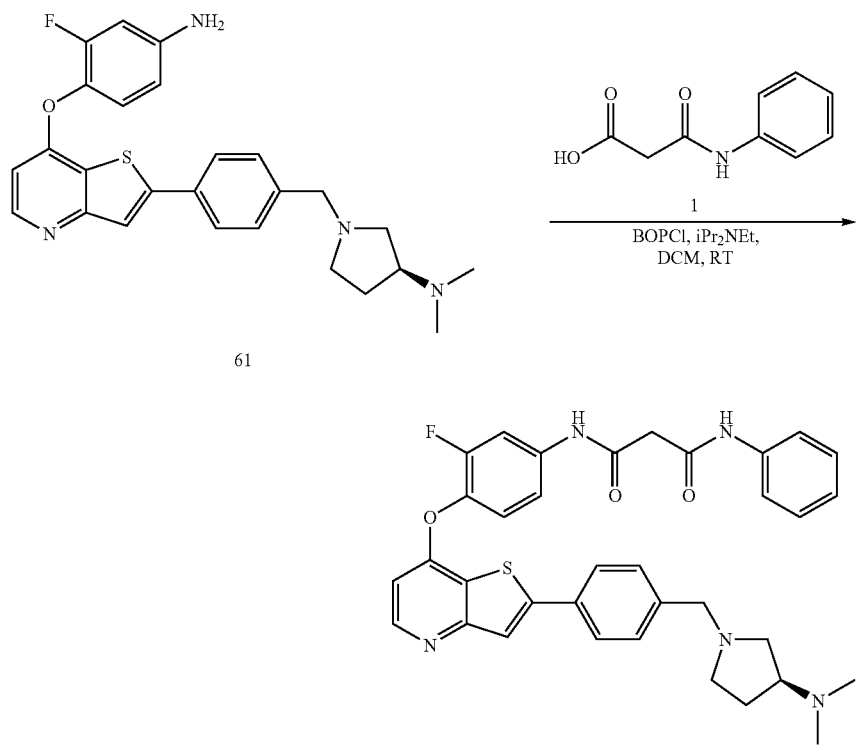

59: Example 25

Example 25

(S)—N[1]-(4-(2-(4-((3-(Dimethylamino)pyrrolidin-1-yl)methyl)phenyl)thieno[3,2-b]pyridin-7-yloxy)-3-fluorophenyl)-N[3]-phenylmalonamide (59)

Step 1: (S)-1-(4-(7-(2-Fluoro-4-nitrophenoxy)thieno[3,2-b]pyridin-2-yl)benzyl)-N,N-dimethylpyrrolidin-3-amine (60)

To a suspension of 52 (1.0 g, 2.41 mmol) in DME (~20 ml) was added (S)—N,N-dimethylpyrrolidin-3-amine (413 mg, 3.62 mmol) and TEA (486 mg, 2 eq, 4.82 mmol) and the reaction mixture was heated to reflux for an hour. The reaction mixture was cooled to RT, filtered then concentrated. The mixture was partitioned between EtOAc/H$_2$O and the biphasic system was filtered and the resultant yellow solid was collected was collected by filtration to afford title compound 60 (450 mg, 38% yield). The organic phase was separated from the biphasic system; it was then dried over Na$_2$SO$_4$, filtered and concentrated. The residue was purified by column chromatography (9:1 EtOAc:MeOH+1% conc NH4OH solution) to afford an additional amount of 60 (82 mg, 7% yield). MS (m/z): 493 (M+H).

Step 2: (S)—N[1]-(4-(2-(4-((3-(Dimethylamino)pyrrolidin-1-yl)methyl)phenyl)thieno[3,2-b]pyridin-7-yloxy)-3-fluorophenyl)-N[3]-phenylmalonamide (59)

To a suspension of the 60 (200 mg, 0.41 mmol) in MeOH (~5 ml) and water (~2 ml) was added ammonium chloride (18 mg, 0.84 eq, 0.34 mmol) and Fe (207 mg, 9 eq, 3.69 mmol) and the reaction mixture was heated to reflux for 2 hours. The reaction mixture was cooled to RT, filtered through celite then concentrated. The mixture was partitioned between DCM/H$_2$O and the DCM was collected, dried over Na$_2$SO$_4$, filtered and concentrated to afford the amine 61, which was used directly in the next step (189 mg, 100%).

To a solution of the acid 1 (148 mg, 2 eq, 0.826 mmol) in dry DCM (7 ml), at 0° C., was added, BOPCl (210 mg, 2 eq, 0.826 mmol) and the reaction mixture was stirred for 10 minutes. A solution of the amine 61 (189 mg, 0.409 mmol) and iPr$_2$NEt (316 mg, 6 eq, 2.45 mmol) in dry DCM (~7 ml) was then added and the reaction mixture was stirred at RT for 2 hrs. The reaction mixture was concentrated to dryness and partitioned between EtOAc and satd NaHCO$_3$ soln, the organic phase was washed twice with satd NaHCO$_3$ soln then collected, dried over sodium sulfate and filtered. The solvent was removed under reduced pressure and the crude was purified by column chromatography (2:8 MeOH/EtOAc+1% NH$_4$OH soln) to afford the desired product 59 as an off white solid (54 mg, 21% yield). $^1$H NMR (DMSO-d$_6$) δ (ppm): 10.73 (s, 1H), (s, 1H), 10.33 (s, 1H), 8.48 (d, J=5.48 Hz, 1H), 8.20 (s, 1H), 8.02 (s, 1H), 7.87 (dd, J=2.15 and 13.1 Hz, 1H), 7.82 (d, J=8.21 Hz, 2H), 7.50 (m, 4H), 7.30 (t, J=8.41 Hz, 2H), 7.03 (t, J=7.43 Hz, 1H), 6.61 (dd, J=0.78 and 5.48 Hz, 1H), 3.60 (m, 10H), 2.64 (m, 2H), 2.51 (m, 2H), 2.42 (m, 2H), 2.32 (m, 1H), 1.87 (m, 1H), 1.61 (m, 1H). MS (m/z): 624.0 (M+H). (formate)

Scheme 22

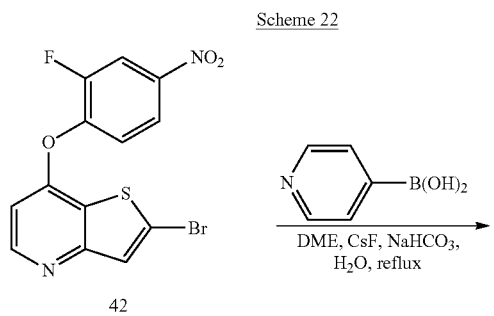

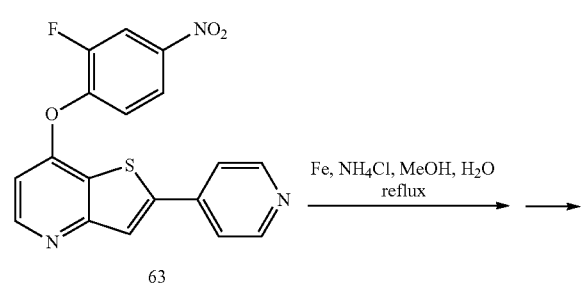

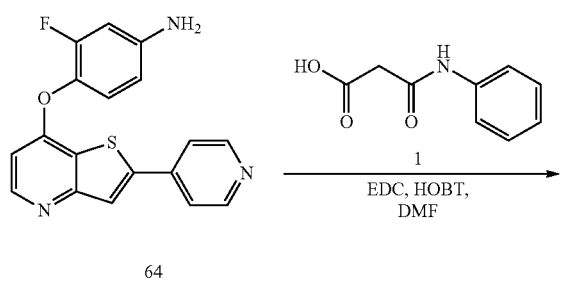

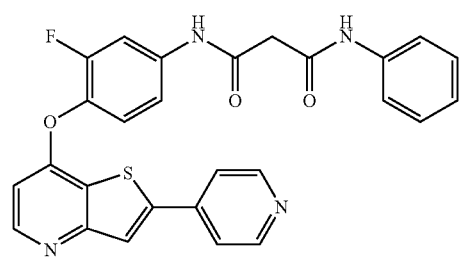

Example 26

N$^1$-(3-fluoro-4-(2-(pyridin-4-yl)thieno[3,2-b]pyridin-7-yloxy)phenyl)-N$^3$-phenylmalonamide (62)

Step 1: 7-(2-Fluoro-4-nitrophenoxy)-2-(pyridin-4-yl)thieno[3,2-b]pyridine (63)

A mixture of the nitro compound 50 (890 mg, 2.41 mmol), pyridin-4-ylboronic acid (593 mg, 2 eq, 4.82 mmol), CsF (1.1 g, 3 eq, 7.23 mmol) and Pd(PPh$_3$)$_4$ (278 mg, 0.1 eq, 0.241 mmol) were suspended in DME (30 ml) and NaHCO$_3$ (607 mg, 3 eq, 7.23 mmol), dissolved in the minimum amount of water, was added. The mixture was de-aerated by bubbling N$_2$ through the solution for 10 min, heated to reflux for 4 hrs and concentrated to dryness. The formed residue was dissolved in DCM and washed with water. The DCM was collected, dried over sodium sulfate, filtered and the DCM was removed by evaporation. The resultant solid was triturated with Et$_2$O to afford the title compound 63 (660 mg, 75% yield), which was used without further purification. MS (m/z): 368.0 (M+H).

Step 2: N$^1$-(3-Fluoro-4-(2-(pyridin-4-yl)thieno[3,2-b]pyridin-7-yloxy)phenyl)-N$^3$-phenylmalonamide (64)

To a suspension of the 63 (660 mg, 1.80 mmol) in MeOH (15 ml) and water (3 ml) was added ammonium chloride (81 mg, 0.84 eq, 1.51 mmol) and Fe (907 mg, 9 eq, 16.2 mmol) and the reaction mixture was heated to reflux for 2 hours. The reaction mixture was cooled to RT, filtered through celite then concentrated. The mixture was partitioned between DCM/H$_2$O and the DCM was collected, dried over Na$_2$SO$_4$, filtered and concentrated to produce the amine 64 which was used directly in the next step (607 mg, 100%). To a solution of the amine 64 (607 mg, 1.80 mmol) in dry DMF (~7 ml) was added the acid 1 (644 mg, 2 eq, 3.6 mmol), HOBT (365 mg, 1.5 eq, 2.7 mmol) and EDC (690 mg, 2 eq, 3.6 mmol) and the reaction mixture was stirred at RT overnight. The reaction mixture was concentrated to dryness and partitioned between EtOAc and water, the organic phase was collected, dried over sodium sulfate and filtered. The solvent was removed under reduced pressure and the crude was purified by column chromatography (EtOAc) to afford title compound 62 as a white solid (150 mg, 17% yield). $^1$H NMR (DMSO-d$_6$) δ (ppm): 10.57 (s, 1H), 10.20 (s, 1H), 8.70 (m, 2H), 8.55 (d, J=5.28 Hz, 1H), 8.37 (s, 1H), 7.89 (m, 3H), 7.60 (m, 2H), 7.58 (m, 2H), 7.30 (dt, J=1.96 and 7.43 Hz, 2H), 7.07 (m, 1H), 6.70 (dd, J=0.78 and 5.28 Hz, 1H), 3.51 (s, 2H). MS (m/z): 499.1 (M+H).

Scheme 23

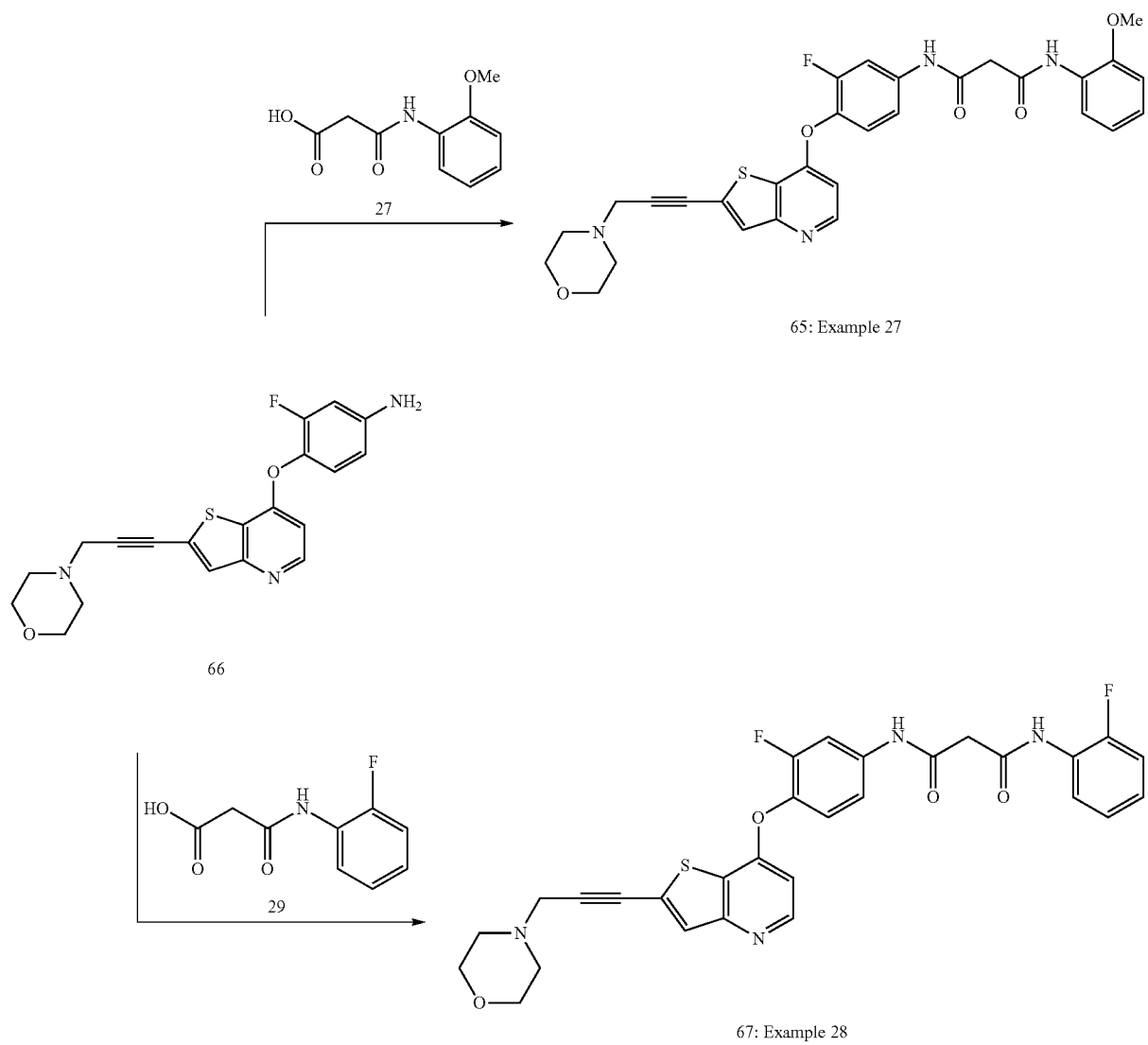

Example 27

N$^1$-(3-Fluoro-4-(2-(3-morpholinoprop-1-ynyl)thieno[3,2-b]pyridin-7-yloxy)phenyl)-N$^3$-(2-methoxyphenyl)malonamide (65)

To a solution of the amine 66 (WO 2006010264) (1.39 g, 3.62 mmol) in DMF (15 ml) was added the acid 27 (1.52 g, 2 eq, 7.25 mmol), HOBT (587 mg, 1.2 eq, 4.34 mmol) and EDC (691 mg, 2 eq, 7.25 mmol). The reaction mixture was stirred at RT overnight. The reaction mixture was concentrated to dryness and partitioned between EtOAc and water, the organic phase was collected, dried over sodium sulfate and filtered. The solvent was removed under reduced pressure and the crude was purified by column chromatography (EtOAc to 10% MeOH in EtOAc) to afford 65 (700 mg, 34% yield) as a white solid. $^1$H NMR (DMSO-d$_6$) δ (ppm): 10.58 (s, 1H), 9.62 (s, 1H), 8.53 (d, J=5.48 Hz, 1H), 8.04 (dd, J=1.17 and 8.80 Hz, 1H), 7.85 (dd, J=2.35 and 12.91 Hz, 1H), 7.78 (s, 1H), 7.42 (m, 2H), 7.06 (m, 2H), 6.89 (m, 1H), 6.72 (d, J=5.28 Hz, 1H), 3.83 (s, 3H), 2.60 (m, 8H), 2.48 (m, 4H). MS (m/z): 575.1 (M+H).

Example 28

N$^1$-(3-Fluoro-4-(2-(3-morpholinoprop-1-ynyl)thieno[3,2-b]pyridin-7-yloxy)phenyl)-N$^3$-(2-fluorophenyl)malonamide (67)

To a solution of the amine 66 (WO 2006010264) (928 mg, 2.42 mmol) in DMF (10 ml) was added the acid 29 (953 mg, 2 eq, 4.84 mmol), HOBT (360 mg, 1.1 eq, 2.66 mmol) and EDC (924 mg, 2 eq, 4.84 mmol). The reaction mixture was stirred for 72 hrs. The reaction mixture was concentrated to dryness and partitioned between EtOAc and water; the organic phase was collected, dried over sodium sulfate and filtered. The solvent was removed under reduced pressure and the crude was purified by column chromatography (EtOAc to 10% MeOH in EtOAc) to afford 67 (600 mg, 44% yield) as a yellow solid. $^1$H NMR (DMSO-d$_6$) δ (ppm): 10.58 (s, 1H), 9.62 (s, 1H), 8.53 (d, J=5.48 Hz, 1H), 8.04 (dd, =1.17 and 8.80 Hz, 1H), 7.85 (dd, J=2.35 and 12.91 Hz, 1H), 7.78 (s, 1H), 7.42 (m, 2H), 7.06 (m, 2H), 6.89 (m, 1H), 6.72 (d, J=5.28 Hz, 1H), 3.83 (s, 3H), 2.60 (m, 8H), 2.48 (m, 4H). MS (m/z): 575.1 (M+H).

2734], triethylamine (2.05 g, 2.5 eq, 20.3 mmol), CuI (154 mg, 0.1 eq, 0.813 mmol) and Pd(PPh$_3$)$_2$Cl$_2$ (319 mg, 0.056 eq, 0.046 mmol). The reaction mixture was degassed with nitrogen and refluxed for 2 hrs, cooled to room temperature and adsorbed onto silica. Purification by column chromatography (eluent EtOAc to 20% MeOH in EtOAc) afforded 69 as

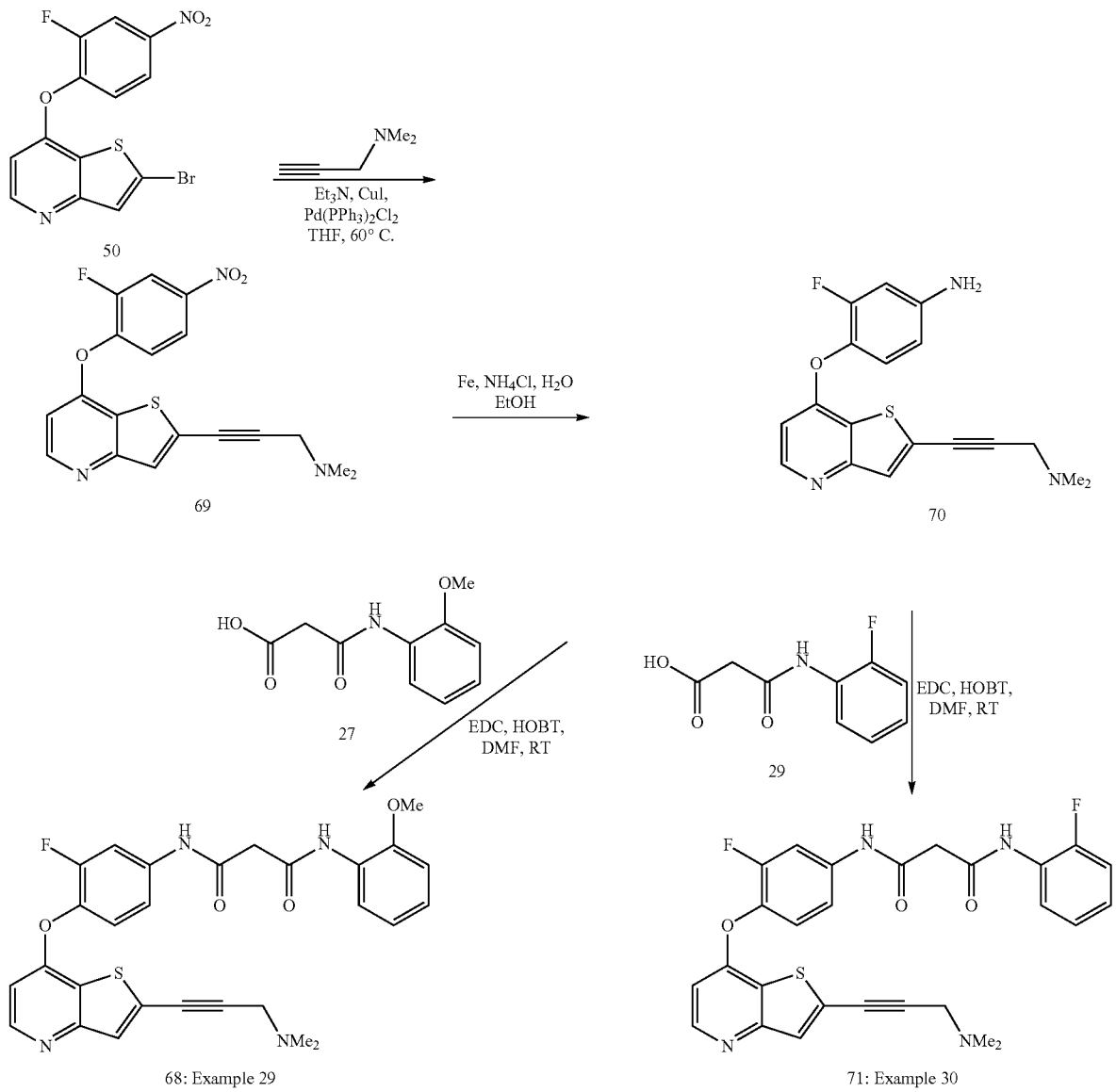

Scheme 24

Example 29

N$^1$-(4-(2-(3-(dimethylamino)prop-1-ynyl)thieno[3,2-b]pyridin-7-yloxy)-3-fluorophenyl)-N$^3$-(2-methoxyphenyl)malonamide (68)

Step 1: 3-(7-(2-fluoro-4-nitrophenoxy)thieno[3,2-b]pyridin-2-yl)-N,N-dimethylprop-2-yn-1-amine (69)

To a solution of bromide 50 (3.0 g, 8.13 mmol) in THF (40 ml) was added 4-(prop-2-ynyl) dimethylamine (2.70 g, 32.5 mmol) [H-W. Tsou, et. al. *J. Med. Chem.*, 2001, 44, 2719- a yellow solid (2.5 g, 83% yield). $^1$H NMR (DMSO-d$_6$) δ (ppm): 8.65 (m, 1H), 8.48 (dd, J=2.74 and 10.56 Hz, 1H), 8.22 (m, 1H), 7.85 (s, 1H), 7.75 (m, 1H), 6.98 (d, J=5.28 Hz, 1H), 3.59 (s, 2H), 2.26 (s, 6H).

Step 2: N$^1$-(4-(2-(3-(dimethylamino)prop-1-ynyl)thieno[3,2-b]pyridin-7-yloxy)-3-fluorophenyl)-N$^3$-(2-fluorophenyl)malonamide (68)

To a suspension of 69 (1.0 g, 2.93 mmol) in EtOH (15 ml) and water (3 ml) was added ammonium chloride (132 mg, 0.84 eq, 2.46 mmol) and Fe (1.48 g, 9 eq, 26.4 mmol) and the reaction mixture was heated to reflux for 2 hours. The reaction mixture was cooled to RT, filtered through celite then concentrated. The mixture was partitioned between DCM/H$_2$O and the DCM was collected, dried over Na$_2$SO$_4$, filtered and concentrated to afford amine 70 which was used directly in the next step (900 mg, 90% yield). To a solution of the amine 70 (900 mg, 2.63 mmol) was added the acid 27 (1.10 g, 2 eq, 5.27 mmol), HOBT (533 mg, 1.5 eq, 3.95 mmol) and EDC (1.01 g, 2 eq, 5.27 mmol). The reaction mixture was stirred at RT overnight. The DMF was removed by evaporation and the mixture was partitioned between water and EtOAc. The organic phase was collected, dried over anhydrous sodium sulfate and concentrated. Purification by column chromatography (EtOAc to 20% MeOH in EtOAc) afforded the desired product 68 as a white solid (734 mg, 52% yield). $^1$H NMR (DMSO-d$_6$) δ (ppm): 10.58 (s, 1H), 9.62 (s, 1H), 8.53 (d, J=5.48 Hz, 1H), 8.04 (dd, J=1.37 and 8.90 Hz, 1H), 7.85 (dd, J=2.35 and 12.91 Hz, 1H), 7.77 (m, 1H), 7.42 (m, 2H), 7.05 (m, 2H), 6.91 (m, 1H), 6.70 (d, J=5.48 Hz, 1H), 3.84 (s, 3H), 3.62 (s, 2H), 3.57 (s, 2H), 2.24 (s, 6H). MS (m/z): 521.1 (M+H).

Example 30

N$^1$-(4-(2-(3-(dimethylamino)prop-1-ynyl)thieno[3,2-b]pyridin-7-yloxy)-3-fluorophenyl)-N$^3$-(2-fluorophenyl)malonamide (71)

The title compound was obtained starting from the amine 70 (1.19 g, 3.49 mmol) according to the procedure described for 68 but substituting acid 27 for the acid 29 (1.37 g, 2 eq, 6.97 mmol). After purification by column chromatography (EtOAc to 20% MeOH in EtOAc) the title compound 71 (760 mg, 42% yield) was obtained as a white solid. $^1$H NMR (DMSO-d$_6$) δ (ppm) 10.57 (s, 1H), 10.04 (s, 1H), 8.53 (d, J=5.28 Hz, 1H), 7.97 (m, 1H), 7.85 (dd, J=2.35 and 12.91 Hz, 1H), 7.78 (m, 1H), 7.25 (m, 1H), 7.15 (m, 2H), 6.70 (d, J=5.28 Hz, 1H), 3.60 (s, 2H), 3.57 (s, 2H), 2.48 (s, 6H). MS (m/z): 521.1 (M+H).

Scheme 25

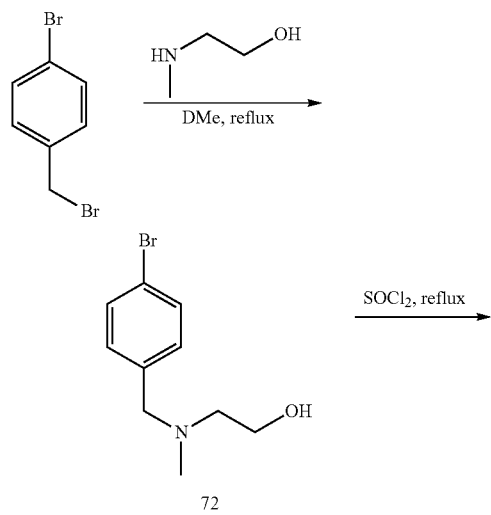

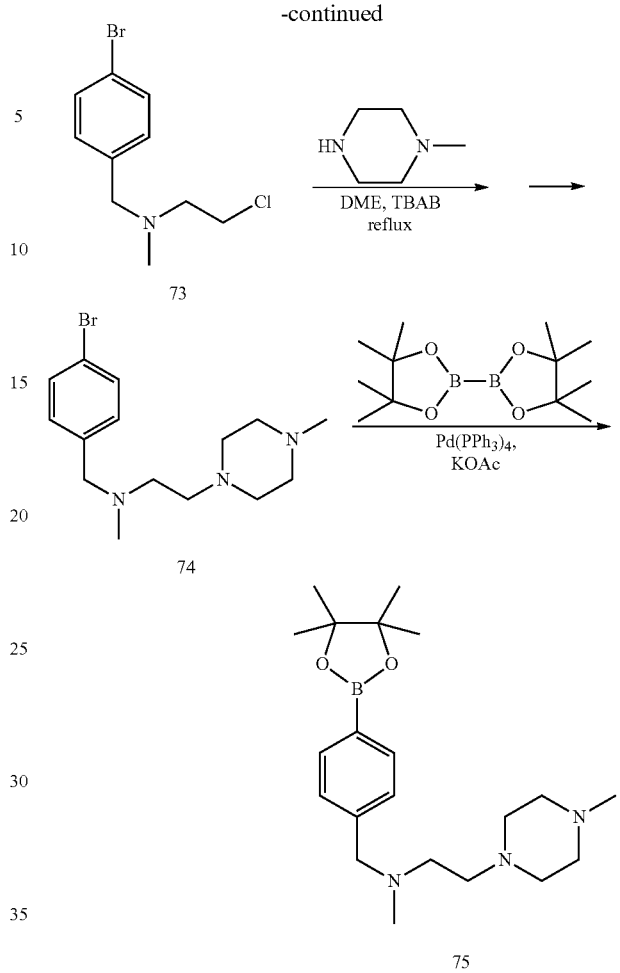

N-Methyl-2-(4-methylpiperazin-1-yl)-N-(4-(4,4,5,5-tetramethyl-1,3,2-dioxaborolan-2-yl)benzyl)ethanamine (75)

Step 1: 2-((4-Bromobenzyl)(methyl)amino)ethanol (72)

To a solution of 1-bromo-4-(bromomethyl)benzene (5.0 g, 20.0 mmol) in DME (30 ml) was added the alcohol (3.76 g, 2.5 eq, 50.0 mmol) and the reaction mixture was heated to 40° C. for an hour. The reaction mixture was cooled to RT and concentrated. The crude was dissolved in EtOAc, washed with water and the organic phase was collected, dried over Na2SO4, filtered and concentrated. Purification by column chromatography (EtOAc) afforded 72 as a yellow oil (4.88 g, 100% yield). MS (m/z): 245/247 (M+H).

Step 2:
N-(4-Bromobenzyl)-2-chloro-N-methylethanamine (73)

To a solution of 72 (2.9 g, 11.9 mmol) in toluene (20 ml) at RT was added SOCl$_2$ (2.83 g, 2 eq, 23.8 mmol) and the mixture was heated to 60° C. for 3 hrs. The solvent was removed and the crude was dissolved in EtOAc then partitioned between water and satd NaHCO₃ soln. The organic phase was collected, dried over Na₂SO₄, filtered and concentrated. The crude was purified by column chromatography (20% EtOAc in hexane) to afford 73 as a brown oil (2.9 g, 93% yield). ¹H NMR (DMSO-d₆) δ (ppm): 7.45 (m, 2H), 7.21 (m, 2H), 3.57 (t, J=6.85 Hz, 2H), 3.52 (s, 2H), 2.74 (t, J=6.85 Hz, 2H), 2.26 (s, 3H).

Step 3: N-(4-Bromobenzyl)-N-methyl-2-(4-methylpiperazin-1-yl)ethanamine (74)

To a solution of 73 (3.5 g, 13.3 mmol) in DME (20 ml) was added N-methylpiperazine (3.33 g, 2.5 eq, 33.3 mmol) and tetrabutylammonium bromide (cat). The reaction mixture was heated to reflux for 3 hrs, then cooled to RT and concentrated. The crude was dissolved in EtOAc, washed well with water and the organic phase was collected, dried over Na₂SO₄ and filtered then concentrated. Purification by column chromatography (20% MeOH in EtOAc+1% TEA) afforded 74 as colorless oil (3.0 g, 69% yield). MS (m/z): 326.0/328.0 (M+H).

Step 4: N-Methyl-2-(4-methylpiperazin-1-yl)-N-(4-(4,4,5,5-tetramethyl-1,3,2-dioxaborolan-2-yl)benzyl)ethanamine (75)

To a solution of 74 (600 mg, 1.84 mmol) in toluene (20 ml) was added boron reagent (700 mg, 1.5 eq, 2.76 mmol), Pd(PPh₃)₄ (214 mg, 0.1 eq, 0.184 mmol) and KOAc (541 mg, 3 eq, 5.52 mmol). The reaction mixture was degassed with N₂ and heated to reflux for 3 hrs under N₂. The mixture was cooled to RT, diluted with EtOAc and water then the organic phase was collected, dried over Na₂SO₄, filtered and concentrated to afford the title compound 75 as black oil which was used crude in the next step (686 mg, 100% yield). MS (m/z): 374.2 (M+H).

TABLE 2

Aryl boronates 76-77 prepared according to the scheme 25

| Cpd | Aryl boronate | Chemical name | Characterization MS (m/z) | Bromide reagents used to obtain the aryl boronates |
|---|---|---|---|---|
| 76 | | N¹,N¹,N²-trimethyl-N²-(4-(4,4,5,5-tetramethyl-1,3,2-dioxaborolan-2-yl)benzyl)ethane-1,2-diamine | 319.2 (M + H) | |
| 77 | | N-Methyl-2-(4-methylpiperazin-1-yl)-N-(3-(4,4,5,5-tetramethyl-1,3,2-dioxaborolan-2-yl)benzyl)ethanamine | 374.2 (M + H) | |

Scheme 26

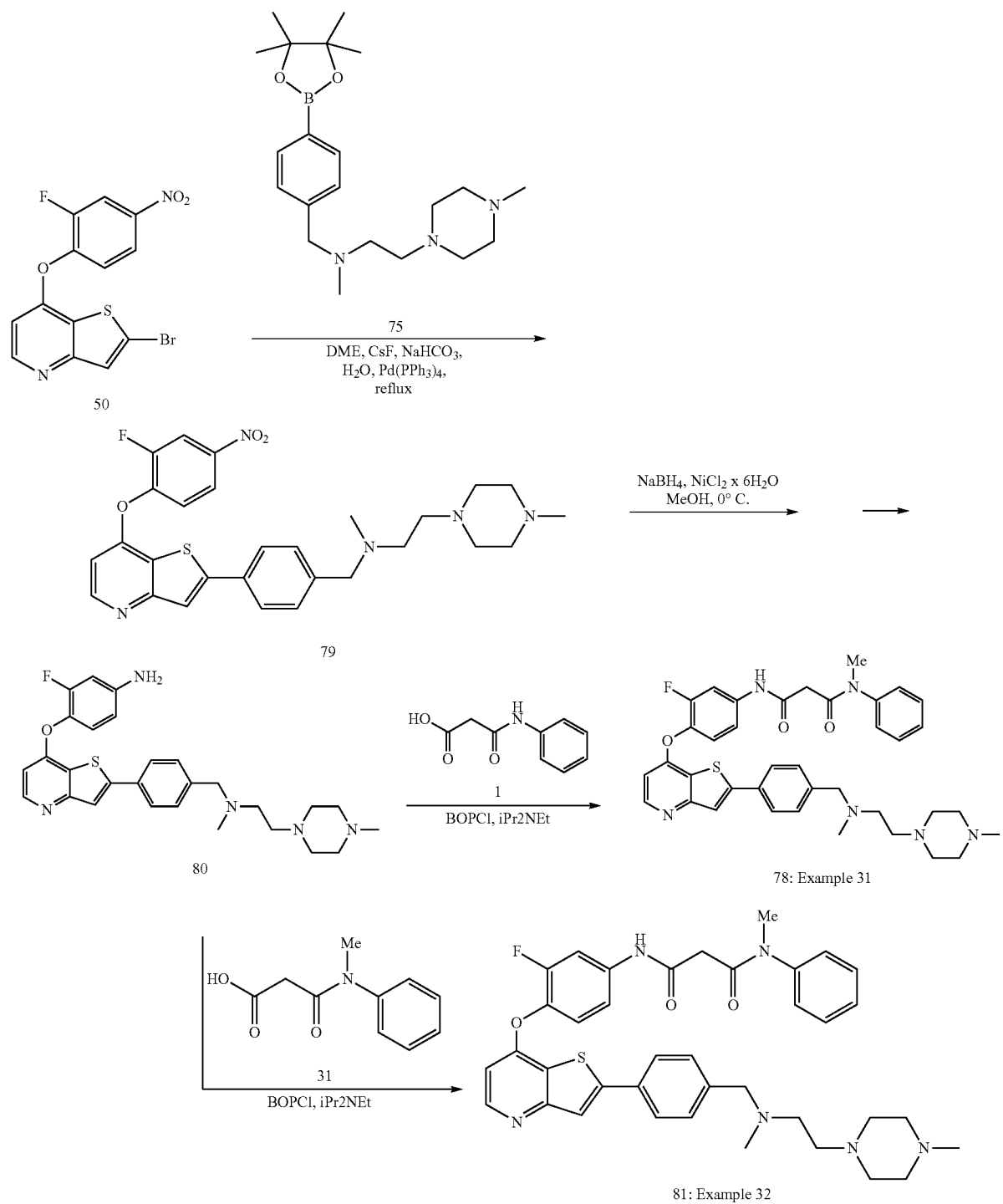

Example 31

N[1]-(3-Fluoro-4-(2-(4-((methyl(2-(4-methylpiper-azin-1-yl)ethyl)amino)methyl)phenyl)thieno[3,2-b]pyridin-7-yloxy)phenyl)-N[3]-phenylmalonamide (78)

Step 1. N-(4-(7-(2-fluoro-4-nitrophenoxy)thieno[3,2-b]pyridin-2-yl)benzyl)-N-methyl-2-(4-methylpiper-azin-1-yl)ethanamine (79)

To a mixture of the nitro compound 50 (440 mg, 1.19 mmol) in DME (20 ml) was added the boronate 75 (667 mg, 1.5 eq, 1.79 mmol), CsF (542 mg, 3 eq, 3.57 mmol) and Pd(PPh$_3$)$_4$ (139 mg, 0.1 eq, 0.19 mmol) were suspended in DME (30 ml) and NaHCO$_3$ (100 mg, 3 eq, 3.57 mmol), dissolved in the minimum amount of water, was added. The mixture was de-aerated by bubbling N$_2$ through the solution for 10 min, heated to reflux for 4 hrs. The mixture was cooled to room temperature, diluted with EtOAc and water then the organic phase was collected, dried over sodium sulfate and filtered. The solvent was removed and the residue was purified by column chromatography (20% MeOH in EtOAc+1%

TEA) to afford title compound 79 as brown oil (248 mg, 39% yield). MS (m/z): 536.1 (M+H).

Steps 2-3. $N^1$-(3-Fluoro-4-(2-(4-((methyl(2-(4-methylpiperazin-1-yl)ethyl)amino)methyl)phenyl)thieno[3,2-b]pyridin-7-yloxy)phenyl)-$N^3$-phenylmalonamide (78)

To a solution of 79 (200 mg, 0.37 mmol) in MeOH (10 mL) at 0° C. was added $NiCl_2 \times 6H_2O$ (176 mg, 2 eq, 0.74 mmol) and $NaBH_4$ (55 mg, 4 eq, 1.48 mmol). The reaction mixture was allowed to stir for 1 hr, concentrated to dryness and the resultant solid was dissolved in 2 M HCl. This solution was then made basic with concentrated aqueous ammonium hydroxide and extracted with DCM. The DCM extract was dried over anhydrous sodium sulfate, filtered and evaporated to give the amine 80 (188 mg, 100% yield), which was used without characterization and further purification.

To a solution of the acid 1 (165 mg, 2 eq, 0.92 mmol) in dry DCM (~5 ml), at 0° C., was added, BOPCl (234 mg, 2 eq, 0.92 mmol) and the reaction mixture was stirred for 10 minutes. A solution of 80 (232 mg, 0.46 mmol) and $iPr_2NEt$ (356 mg, 6 eq, 2.76 mmol) in dry DCM (~7 ml) was then added and the reaction mixture was stirred at RT for 2 hrs. The reaction mixture was concentrated to dryness and partitioned between EtOAc and satd $NaHCO_3$ soln, the organic phase was washed twice with saturated $NaHCO_3$ then collected, dried over sodium sulfate and filtered. The solvent was removed under reduced pressure and the crude was purified by column chromatography (1:1 MeOH/EtOAc+1% TEA) to afford title compound 78 as beige solid (36 mg, 12% yield). $^1$H NMR (DMSO-$d_6$) δ(ppm): 10.59 (s, 1H), 10.23 (s, 1H), 8.50 (d, J=5.5 Hz, 1H), 8.04 (s, 1H), 7.89 (dd, J=2.4 and 13.0 Hz, 1H), 7.85 (d, J=8.4 Hz, 2H), 7.61 (dd, J=1.1 and 8.7 Hz, 2H), 7.51 (t, J=8.9 Hz, 1H), 7.47-7.43 (m, 3H), 7.35-7.31 (m, 2H), 7.07 (tt, J=1.2 and 7.3 Hz, 1H), 6.64 (dd, J=1.0 and 5.5 Hz, 1H), 3.53 (s, 2H), 3.52 (s, 2H), 2.46-2.29 (m, 12H), 2.16 (s, 3H), 2.13 (s, 3H).

Example 32

$N^1$-(3-Fluoro-4-(2-(4-((methyl(2-(4-methylpiperazin-1-yl)ethyl)amino)methyl)phenyl)thieno[3,2-b]pyridin-7-yloxy)phenyl)-$N^3$-methyl-$N^3$-phenylmalonamide (81)

The title compound was obtained starting from the amine 80 (232 mg, 0.46 mmol) according to the procedure described for 78 (example 31) but substituting acid 1 for the acid 31 (178 mg, 2 eq, 0.92 mmol). After purification by column chromatography (40% MeOH in EtOAc+1% $NH_4OH$ soln) the title compound 81 (26 mg, 8% yield) was obtained as a white solid Compounds 82 (example 33) and 83 (example 34) were synthesized similarly to the compound 78 according to the scheme 26, starting from boronates 76 and 77, respectively).

TABLE 3

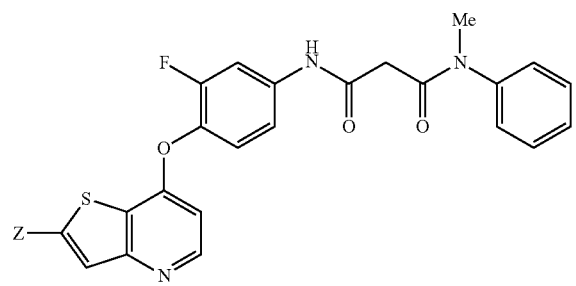

82: Example 33
83: Example 34

| Ex. | Cpd | Z | Chemical name | Characterization |
|---|---|---|---|---|
| 33 | 82 | | $N^1$-(4-(2-(4-(((3-(dimethylamino)propyl)(methyl)amino)methyl)phenyl)thieno[3,2-b]pyridin-7-yloxy)-3-fluorophenyl)-$N^3$-methyl-$N^3$-phenylmalonamide | $^1$H NMR (DMSO-$d_6$) δ (ppm): 10.33 (s, 1H), 8.47 (d, J = 5.48 Hz, 1H), 8.23 (s, 1H), 8.02 (s, 1H), 7.78 (m, 4H), 7.30 (m, 11H), 6.60 (d, J = 5.48 Hz, 1H), 3.49 (s, 3H), 3.19 (m, 5H), 2.21 (m, 5H), 2.10 (s, 3H), 1.63 (m, 2H). MS (m/z): 640.2 (M + H). (formate) |

TABLE 3-continued
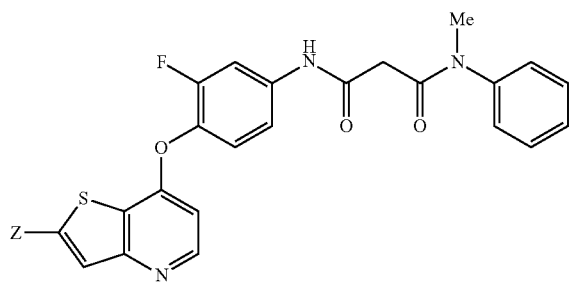
82: Example 33
83: Example 34
| Ex. | Cpd | Z | Chemical name | Characterization |
|---|---|---|---|---|
| 34 | 83 | (3-((4-methylpiperazin-1-yl)ethyl)(methyl)amino)methyl)phenyl group | N$^1$-(3-fluoro-4-(2-(3-((methyl(2-(4-methylpiperazin-1-yl)ethyl)amino)methyl)phenyl)thieno[3,2-b]pyridin-7-yloxy)phenyl)-N$^3$-methyl-N$^3$-phenylmalonamide | $^1$H NMR (DMSO-d$_6$) δ (ppm): 10.32 (s, 1H), 8.48 (d, J = 5.48 Hz, 1H), 8.20 (s, 1H), 8.02 (s, 1H), 7.76 (m, 3H), 7.35 (m, 11H), 6.60 (d, J = 5.48 Hz, 1H), 3.55 (s, 2H), 2.47 (s, 3H), 2.37 (m, 11H), 2.17 (s, 3H), 2.09 (s, 3H). MS (m/z): 681.1 (M + H). (formate) |
Scheme 27
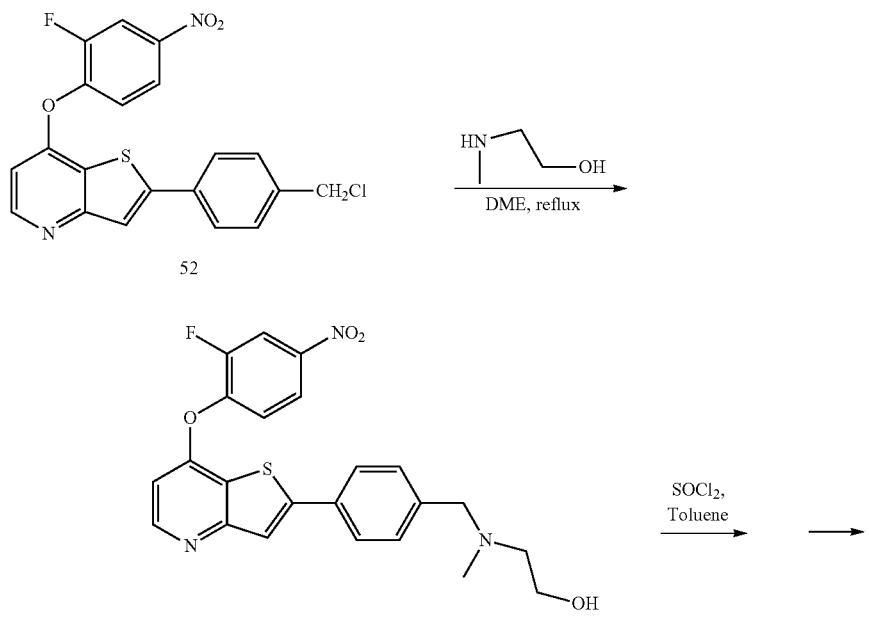

-continued
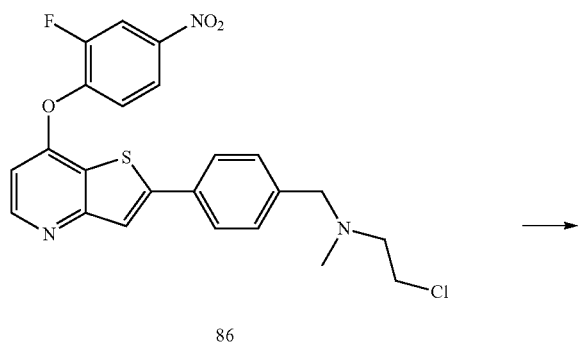
86
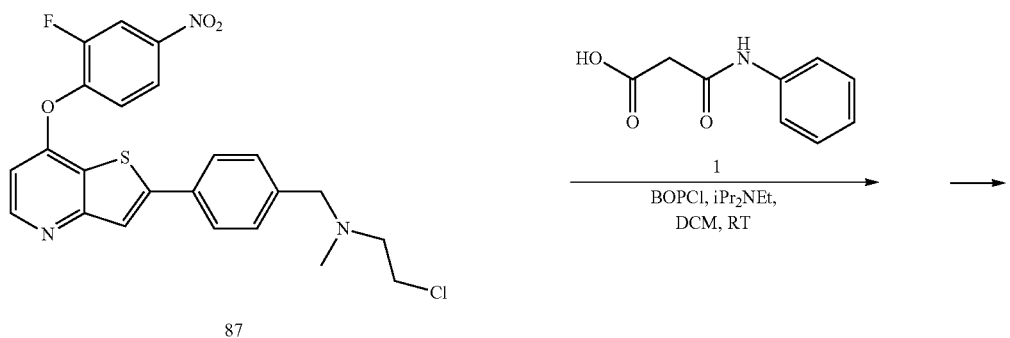
87
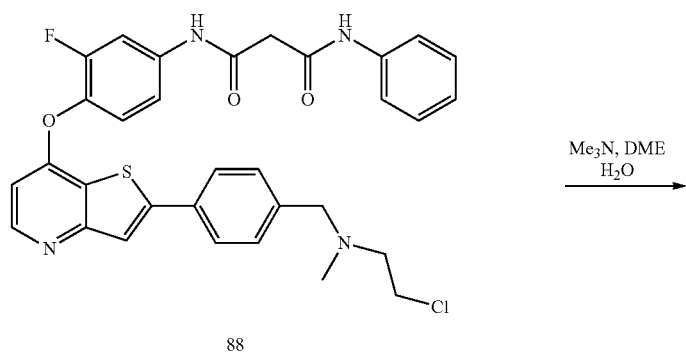
88
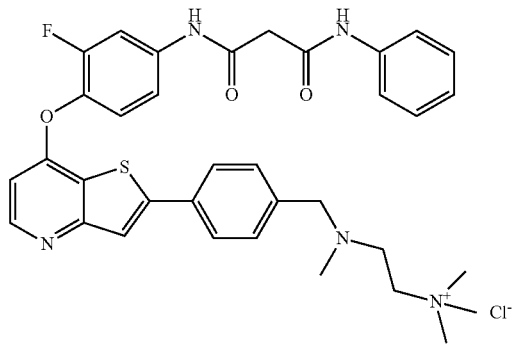
84: Example 35

Example 35

2-((4-(7-(2-Fluoro-4-(3-oxo-3-(phenylamino)propanamido)phenoxy)thieno[3,2-b]pyridin-2-yl)benzyl)(methyl)amino)-N,N,N-trimethylethanaminium chloride (84)

Step 1: 2-((4-(7-(2-Fluoro-4-nitrophenoxy)thieno[3,2-b]pyridin-2-yl)benzyl)(methyl)amino)ethanol (85)

To a suspension of 52 (1.2 g, 2.89 mmol) in DME (30 ml) was added 2-(methylamino)ethanol (2.17 g, 10 eq, 28.9 mmol) and the reaction mixture was stirred at RT for 2 hrs. The reaction mixture was concentrated then partitioned between EtOAc/H$_2$O and the EtOAc was collected, dried over Na$_2$SO$_4$, filtered and concentrated. The crude mixture was purified by column chromatography (8:2 EtOAc:MeOH) to afford title compound 85 (813 mg, 45% yield). $^1$H NMR (DMSO-d$_6$) δ (ppm): 8.57 (d, J=5.48 Hz, 1H), 8.48 (m, 1H), 8.21 (m, 1H), 8.08 (s, 1H), 7.83 (d, J=8.02 Hz, 1H), 7.71 (t, J=8.61 Hz, 2H), 7.43 (d, J=8.22 Hz, 2H), 6.91 (d, J=5.48 Hz, 1H), 4.41 (t, J=5.48 Hz, 1H), 3.53 (m, 4H), 2.42 (t, J=6.46 Hz, 2H), 2.15 (s, 3H).

Step 2: 2-Chloro-N-(4-(7-(2-fluoro-4-nitrophenoxy)thieno[3,2-b]pyridin-2-yl)benzyl)-N-methylethanamine (86)

To a solution of 89 (500 mg, 1.1 mmol) in toluene/dichloromethane (1:1, 30 ml) was added SOCl$_2$ (262 mg, 2 eq, 2.29 mmol). The reaction mixture was heated to 70° C. for 2 hrs then concentrated to dryness and the title compound 86 was used directly in the next step with no additional purification (519 mg, 100% yield). $^1$H NMR (DMSO-d$_6$) δ (ppm): 8.57 (d, J=5.48 Hz, 1H), 8.47 (m, 1H), 8.21 (m, 1H), 8.06 (s, 1H), 7.84 (d, J=8.22 Hz, 1H), 7.71 (m, 1H), 7.43 (d, J=8.02 Hz, 2H), 6.91 (d, J=5.48 Hz, 1H), 3.70 (t, J=6.65 Hz, 2H), 3.58 (s, 1H), 2.69 (m, 2H), 2.19 (s, 3H).

Steps 3-4: N$^1$-(4-(2-(4-(((2-Chloroethyl)(methyl)amino)methyl)phenyl)thieno[3,2-b]pyridin-7-yloxy)-3-fluorophenyl)-N$^3$-phenylmalonamide (88)

To a solution of 86 (375 mg, 0.79 mmol) in MeOH (15 ml) was added SnCl$_2$×2H$_2$O (891 mg, 5, eq, 3.95 mmol) and the reaction mixture was heated to reflux for 3 hours. The mixture was cooled to RT and poured onto ice/water then basified to pH 9. The mixture was filtered and the aqueous solution was extracted with EtOAc and the EtOAc was washed with brine solution. The organic phase was collected, dried over Na$_2$SO$_4$, filtered and concentrated and the 4-(2-(4-(((2-chloroethyl)(methyl)amino)methyl)phenyl)thieno[3,2-b]pyridin-7-yloxy)-3-fluorobenzenamine (87) (348 mg, 100% yield) was used immediately in the next step with no additional purification.

To a solution of the acid 1 (142 mg, 2 eq, 1.58 mmol) in dry DCM (10 ml), at 0° C., was added, BOPCl (502 mg, 2 eq, 0.826 mmol) and the reaction mixture was stirred for 10 minutes. A solution of the amine 87 (348 mg, 0.79 mmol) and iPr$_2$NEt (610 mg, 6 eq, 4.72 mmol) in dry DCM (7 ml) was then added and the reaction mixture was stirred at RT overnight. The reaction mixture was concentrated to dryness and partitioned between EtOAc and satd NaHCO$_3$ soln, the organic phase was washed twice with saturated NaHCO$_3$ then collected, dried over sodium sulfate and filtered. The solvent was removed under reduced pressure and the crude was purified by column chromatography (EtOAc) to afford the desired product 88 as an off-white solid (102 mg, 21% yield). $^1$H NMR (DMSO-d$_6$) δ (ppm): 10.58 (s, 1H), 10.22 (s, 1H), 8.48 (d, J=5.28 Hz, 1H), 8.03 (s, 1H), 7.85 (m, 3H), 7.59 (m, 2H), 7.43 (m, 4H), 7.32 (m, 2H), 7.05 (t, J=7.43 Hz, 1H), 6.61 (m, 1H), 3.70 (t, J=6.65 Hz, 2H), 3.59 (s, 2H), 3.50 (s, 2H), 2.69 (m, 2H), 2.20 (s, 3H).

Step 5: 2-((4-(7-(2-Fluoro-4-(3-oxo-3-(phenylamino)propanamido)phenoxy)thieno[3,2-b]pyridin-2-yl)benzyl)(methyl)amino)-N,N,N-trimethylethanaminium chloride (84)

To a solution of 88 (80 mg, 0.133 mmol) in DME (1 mL) was added NMe$_3$ (15.7 mg, 2 eq, 0.27 mmol) and the reaction mixture was heated to 100° C. in a sealed tube for an hour. The mixture was cooled to RT and concentrated. Purification (Gilson, 45 mins, 40% MeOH in water to 80% MeOH in water) afforded title compound 84 (20 mg, 9% yield). $^1$H NMR (DMSO-d$_6$) δ (ppm): 10.85 (s, 1H), 10.41 (s, 1H), 8.47 (m, 2H), 8.05 (s, 1H), 7.85 (m, 3H), 7.59 (m, 2H), 7.42 (m, 5H), 7.32 (m, 2H), 7.05 (t, J=7.43 Hz, 1H), 6.63 (d, J=5.67 Hz, 1H), 3.60 (s, 2H), 3.51 (m, 2H), 3.1 (s, 9H), 2.81 (m, 2H), 2.20 (s, 3H). MS (m/z) 626.1 (M+H).

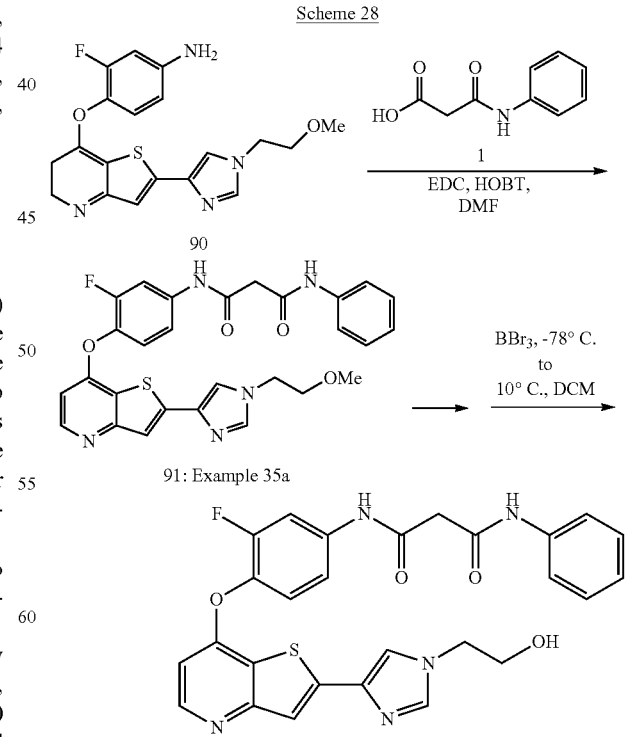

Scheme 28

Example 35a

N$^1$-(3-Fluoro-4-(2-(1-(2-methoxyethyl)-1H-imidazol-4-yl)thieno[3,2-b]pyridin-7-yloxy)phenyl)-N$^3$-phenylmalonamide (91) and

Example 36

N$^1$-(3-Fluoro-4-(2-(1-(2-hydroxyethyl)-1H-imidazol-4-yl)thieno[3,2-b]pyridin-7-yloxy)phenyl)-N$^3$-phenylmalonamide (89)

Step 1: N$^1$-(3-Fluoro-4-(2-(1-(2-methoxyethyl)-1H-imidazol-4-yl)thieno[3,2-b]pyridin-7-yloxy)phenyl)-N$^3$-phenylmalonamide (91)

To a solution of 3-fluoro-4-(2-(1-(2-methoxyethyl)-1H-imidazol-4-yl)thieno[3,2-b]pyridin-7-yloxy)benzenamine (90) (WO 2006010264) (135 mg, 0.35 mmol) in dry DMF (7 ml) was added the acid (192 mg, 4.5 eq, 1.56 mmol), HOBT (72 mg, 1.5 eq, 0.63 mmol) and EDC (306 mg, 4.5 eq, 1.56 mmol) and the reaction mixture was stirred at RT overnight. The reaction mixture was concentrated to dryness and partitioned between EtOAc and sat NaHCO$_3$ soln, the organic phase was collected, dried over anhydrous sodium sulfate and filtered. The solvent was removed under reduced pressure and the crude was purified by column chromatography (EtOAc to 15% MeOH in EtOAc) to afford title compound 91 (150 mg, 58% yield). MS (m/z): 546.1 (M+H).

Step 2: N$^1$-(3-Fluoro-4-(2-(1-(2-hydroxyethyl)-1H-imidazol-4-yl)thieno[3,2-b]pyridin-7-yloxy)phenyl)-N$^3$-phenylmalonamide (89)

To a solution of 91 (85 mg, 0.156 mmol) in dry DCM (2 mL) was added, at −78° C., BBr$_3$ (0.6 mL, 4 eq, 0.62 mmol, 1M soln in DCM) and the reaction mixture was slowly warmed to 0° C. and allowed to stir at 0° C. for 30 mins. The reaction mixture was quenched with MeOH and the solvents were removed under reduced pressure. Purification by column chromatography (Gilson, 25% MeOH in water to 75% MeOH in water) afforded title compound 89 (26 mg, 27% yield). MS (m/z): 532.1 (M+H).

Scheme 29

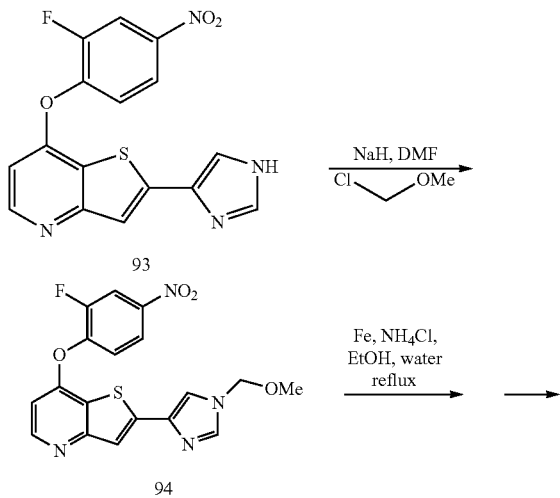

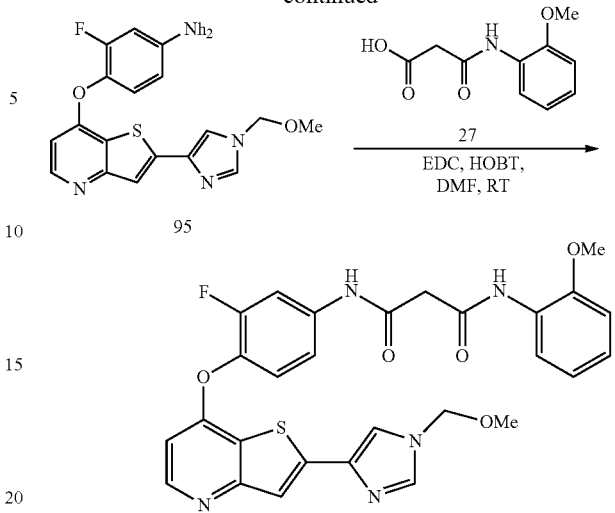

92: Example 37

Example 37

N$^1$-(3-Fluoro-4-(2-(1-(methoxymethyl)-1H-imidazol-4-yl)thieno[3,2-b]pyridin-7-yloxy)phenyl)-N$^3$-(2-methoxyphenyl)malonamide (92)

Step 1: 7-(2-Fluoro-4-nitrophenoxy)-2-(1-(methoxymethyl)-1H-imidazol-4-yl)thieno[3,2-b]pyridine (94)

To a solution of 7-(2-fluoro-4-nitrophenoxy)-2-(1H-imidazol-4-yl)thieno[3,2b]pyridine (93) (WO 2006010264) (300 mg, 0.84 mmol) in dry DMF (3 ml) at 0° C. was added NaH (40 mg, 60% dispersion in oil, 1.0 mmol). The mixture was allowed to warm to room temperature over 0.5 h then re-cooled to 0° C. MOMCl (74 mg, 1.1 eq, 0.92 mmol) was added and mixture was allowed to warm to room temperature over 20 hours, concentrated and partitioned between EtOAc and water. The EtOAc phase was dried over anhydrous sodium sulfate, filtered, concentrated and purified by column chromatography (100% hexane to 100% acetone) to afford the title compound 94 (126 mg, 36% yield). MS (m/z): 401.0 (M+H).

Step 2: 3-fluoro-4-(2-(1-(methoxymethyl)-1H-imidazol-4-yl)thieno[3,2-b]pyridin-7-yloxy)aniline (95)

To a suspension of 94 (132 mg, 0.33 mmol) in EtOH (7 ml) and water (3 ml) was added ammonium chloride (16 mg, 0.9 eq, 0.3 mmol) and Fe (157 mg, 8.5 eq, 0.28 mmol) and the reaction mixture was heated to reflux for 2 hours. The reaction mixture was cooled to RT, filtered through celite then concentrated. The mixture was partitioned between DCM/water and the DCM was collected, dried over anhydrous sodium sulfate, filtered and concentrated. Crude 95 was used directly in the next step (122 mg, 100% yield). MS (m/z): 371.1 (M+H).

Step 3: N$^1$-(3-Fluoro-4-(2-(1-(methoxymethyl)-1H-imidazol-4-yl)thieno[3,2-b]pyridin-7-yloxy)phenyl)-N$^3$-(2-methoxyphenyl)malonamide (92)

To a solution of 95 (136 mg, 0.37 mmol) in dry DMF (7 ml) was added the acid 27 (300 mg, 3.0 eq, 1.1 mmol), HOBT (74 mg, 1.5 eq, 0.55 mmol) and EDC (210 mg, 3.0 eq, 1.1 mmol) and the reaction mixture was stirred at RT overnight. The reaction mixture was concentrated to dryness and partitioned between EtOAc and sat NaHCO$_3$ soln, the organic phase was collected, dried over anhydrous sodium sulfate and filtered.

171

The solvent was removed under reduced pressure and the crude was triturated with Et$_2$O to afford title compound 92 (150 mg, 72% yield). $^1$H NMR (DMSO-d$_6$) δ (ppm): 10.57 (s, 1H), 9.62 (s, 1H), 8.43 (d, J=5.48 Hz, 1H), 8.06 (m, 2H), 7.93 (m, 1H), 7.85 (m, 1H), 7.76 (s, 1H), 7.45 (m, 2H), 7.05 (m, 2H), 6.90 (m, 1H), 6.58 (m, 1H), 5.35 (s, 2H), 3.84 (m, 3H), 3.63 (s, 2H), 3.25 (s, 3H). MS (m/z): 562.1 (M+H).

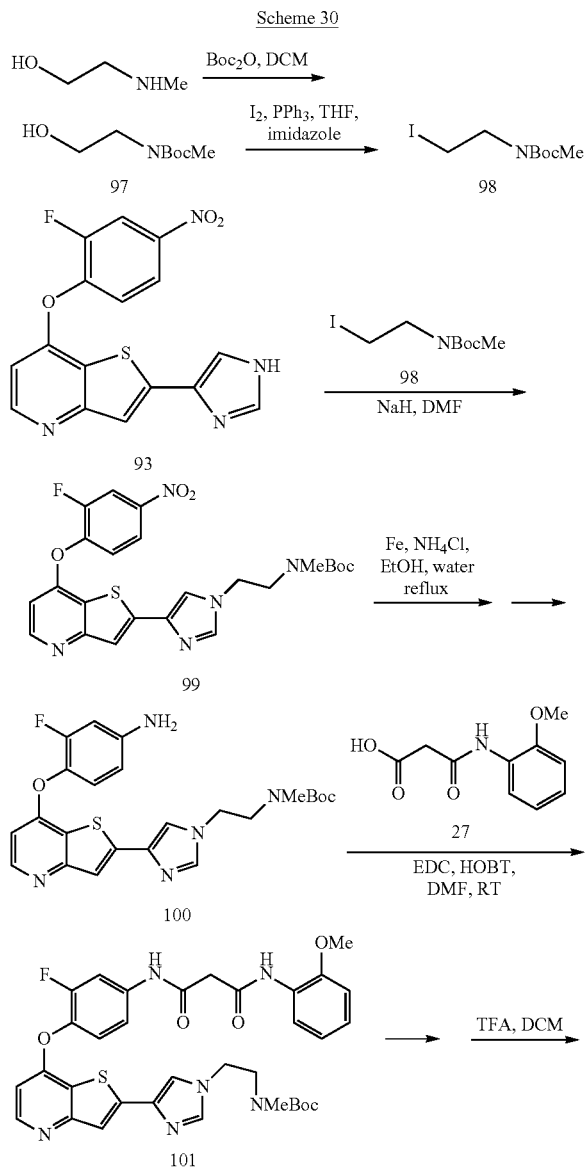

172

Example 38

N$^1$-(3-Fluoro-4-(2-(1-(2-(methylamino)ethyl)-1H-imidazol-4-yl)thieno[3,2-b]pyridin-7-yloxy)phenyl)-N$^3$-(2-methoxyphenyl)malonamide (96)

Step 1: tert-Butyl 2-hydroxyethyl(methyl)carbamate (97) (*J. Med. Chem.*, 1999, 42, 11, 2008)

To a solution of 2-(methylamino)ethanol (5.0 g, 67 mmol) in THF (50 ml) at RT was added Boc$_2$O (15.7 g, 72 mmol) and the reaction mixture was stirred at RT for 4 hours. The reaction mixture was concentrated to dryness and the title compound 97 was used directly in the next step with no additional purification (11.74 g, 100% yield). MS (m/z): 176.2 (M+H).

Step 2: tert-Butyl 2-iodoethyl(methyl)carbamate (98) (*J. Med. Chem.*, 1999, 42, 11, 2008)

To a solution of 97 (520 mg, 3.0 mmol) in THF (50 mL) was added PPh$_3$ (1.25 g, 1.6 eq, 4.75 mmol), imidazole (306 mg, 1.5 eq, 4.5 mmol) and iodine (571 mg, 1.5 eq, 4.5 mmol). The reaction mixture was stirred at RT for an hour and the solvent was removed. The crude was dissolved in EtOAc, washed with satd NaHCO$_3$ soln and the organic phase was collected, dried over anhydrous sodium sulfate and filtered. Purification by column chromatography (hexane to 20% EtOAc in hexane) afforded title compound 98 (500 mg, 39% yield). MS (m/z): 308.1 (M+Na).

Step 3: tert-Butyl 2-(4-(7-(2-fluoro-4-nitrophenoxy) thieno[3,2-b]pyridin-2-yl)-1H-imidazol-1-yl)ethyl (methyl)carbamate (99)

To a solution of 7-(2-fluoro-4-nitrophenoxy)-2-(1H-imidazol-4-yl)thieno[3,2-b]pyridine (93) (WO 2006010264) (150 mg, 0.42 mmol) in dry DMF (2 ml) at 0° C. was added NaH (34 mg, 60% dispersion in oil, 2 eq, 0.84 mmol). The mixture was allowed to warm to room temperature over 0.5 h then re-cooled to 0° C. Compound 98 (132 mg, 1.1 eq, 0.46 mmol) was added and mixture was allowed to stir at RT overnight, then concentrated and partitioned between EtOAc and water. The EtOAc phase was dried over anhydrous sodium sulfate, filtered, concentrated and purified by column chromatography (100% hexane to 100% acetone) to afford the title compound 99 (30 mg, 14% yield). MS (m/z): 514.0 (M+H).

Step 4: tert-Butyl 2-(4-(7-(4-amino-2-fluorophenoxy)thieno[3,2-b]pyridin-2-yl)-1H-imidazol-1-yl) ethyl(methyl)carbamate (100)

To a suspension of 99 (30 mg, 0.058 mmol) in EtOH (1.6 ml) and water (0.6 ml) was added ammonium chloride (3 mg, 0.9 eq, 0.053 mmol) and Fe (28 mg, 8.5 eq, 0.49 mmol) and the reaction mixture was heated to reflux for 45 min. The reaction mixture was cooled to RT, filtered through celite then concentrated to afford title compound 100 (30 mg, 100% yield). MS (m/z): 484.1 (M+H).

Step 5: tert-Butyl 2-(4-(7-(2-fluoro-4-(3-(2-methoxyphenylamino)-3-oxopropanamido)phenoxy)thieno [3,2-h]pyridin-2-yl)-1H-imidazol-1-yl)ethyl(methyl) carbamate (101)

To a solution of 100 (145 mg, 0.30 mmol) in dry DMF (7 ml) was added the acid (125 mg, 2.0 eq, 0.6 mmol), HOBT (45 mg, 1.5 eq, 0.33 mmol) and EDC (115 mg, 2.0 eq, 0.6 mmol) and the reaction mixture was stirred at RT overnight. The reaction mixture was concentrated to dryness and partitioned between EtOAc and sat NaHCO$_3$ soln, the organic phase was collected, dried over sodium sulfate and filtered. The solvent was removed under reduced pressure and the crude was purified by column chromatography (70% acetone in hexane) afforded title compound 101 (48 mg, 24% yield). MS (m/z): 675.1 (M+H).

Step 6: $N^1$-(3-Fluoro-4-(2-(1-(2-(methylamino) ethyl)-1H-imidazol-4-yl)thieno[3,2-b]pyridin-7-yloxy)phenyl)-$N^3$-(2-methoxyphenyl)malonamide (96)

To a solution of 101 (31 mg, 0.046 mmol) in toluene (1 ml) was added TFA (excess) and the reaction mixture was stirred at RT for an hour. The solvents were removed and the title compound 96 (47 mg, 100% yield) was obtained after trituration of the resultant solid. MS (m/z): 575.1 (M+H).

Example 39

$N^1$-(4-(2-(1H-Imidazol-4-yl)thieno[3,2-b]pyridin-7-yloxy)-3-fluorophenyl)-$N^3$-(2-methoxyphenyl)malonamide (102)

Steps 1-2: $N^1$-(3-Fluoro-4-(2-(1-((2-(trimethylsilyl)ethoxy)methyl)-1H-imidazol-4-yl)thieno[3,2-b]pyridin-7-yloxy)phenyl)-$N^3$-(2-methoxyphenyl)malonamide (105)

To a solution of 7-(2-fluoro-4-nitrophenoxy)-2-(1-((2-(trimethylsilyl)ethoxy)methyl)-1H-imidazol-4-yl)thieno[3,2-b]pyridine (103) (WO 2006010264) (400 mg, 0.82 mmol) in MeOH (10 mL) at 0° C. was added NiCl$_2$×6H$_2$O (650 mg, 2.5

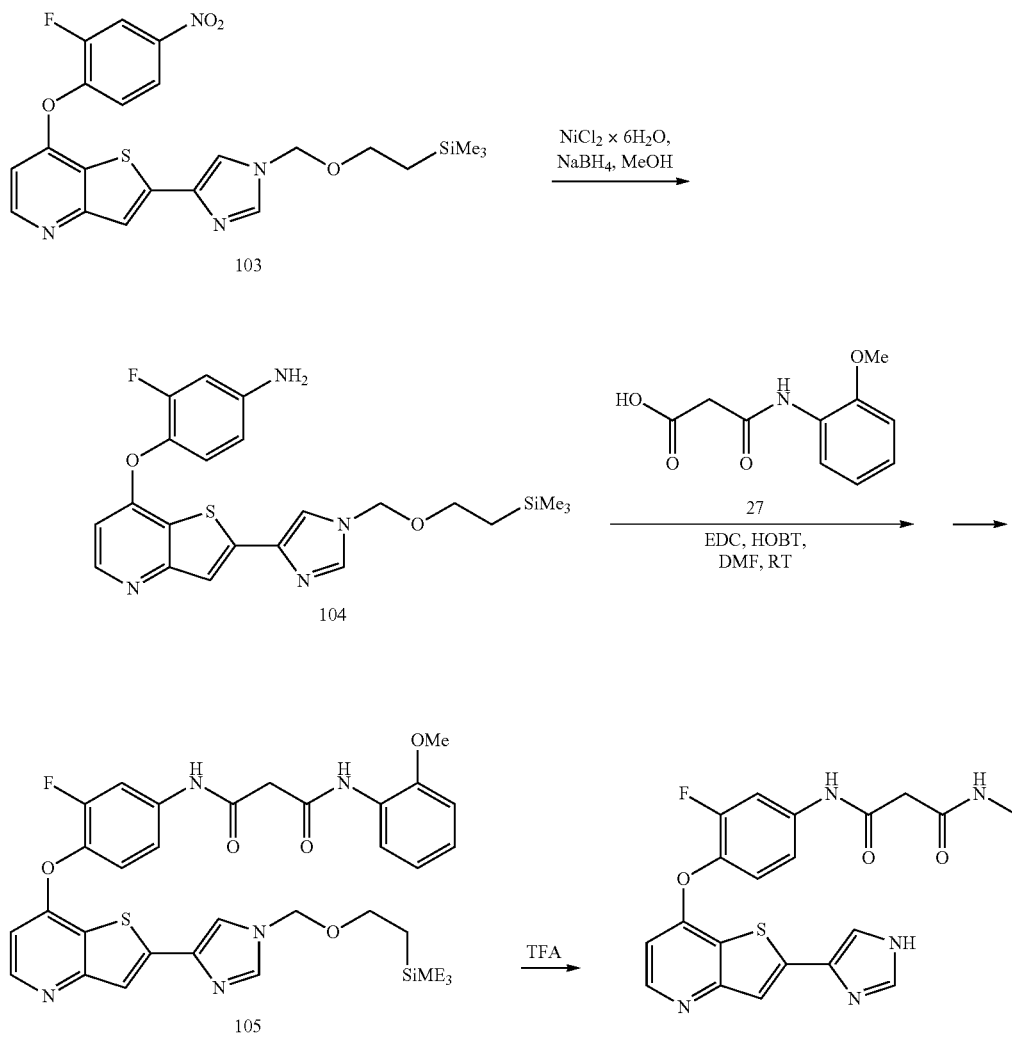

Scheme 31 eq, 2.73 mmol) and NaBH$_4$ (165 mg, 4 eq, 4.4 mmol). The reaction mixture was allowed to stir for 1 hr, concentrated to dryness and the resultant solid was dissolved in 2 M HCl. This solution was then made basic with concentrated aqueous ammonium hydroxide and extracted with DCM. The DCM extract was dried over anhydrous sodium sulfate, filtered and evaporated to give 3-fluoro-4-(2-(1-((2-(trimethylsilyl)ethoxy)methyl)-1H-imidazol-4-yl)thieno[3,2-b]pyridin-7-yloxy)benzenamine (104) (350 mg, 100% yield).

To a solution of the acid 27 (59 mg, 2 eq, 0.28 mmol) and HOBT (19 mg, 1 eq, 0.14 mmol) in DMF (3 ml) was added amine 104 (64 mg, 0.14 mmol) and the reaction mixture was stirred for 10 mins. EDC (54 mg, 2 eq, 0.28 mmol) was added and the reaction mixture was stirred at RT overnight. The solvents were removed and the residue was partitioned between EtOAc and water. The organic phase was collected, dried over anhydrous sodium sulfate, filtered and concentrated. Purification by column chromatography (20% acetone in hexane to 100% acetone) afforded title compound 105 (53 mg, 58% yield). MS (m/z): 648.2 (M+H).

Step 3: N$^1$-(4-(2-(1H-Imidazol-4-yl)thieno[3,2-b]pyridin-7-yloxy)-3-fluorophenyl)-N$^3$-(2-methoxyphenyl)malonamide (102)

A solution of 105 (42 mg, 0.0648 mmol) in TFA (1 ml) was stirred at RT for 30 mins. The TFA was removed by evaporation and then 4N HCl in dioxane (0.5 ml) was added and the mixture was concentrated to dryness. The residual solid was triturated with diethyl ether to afford title compound 102 (38 mg, 100% yield). MS (m/z): 518.1 (M+H).

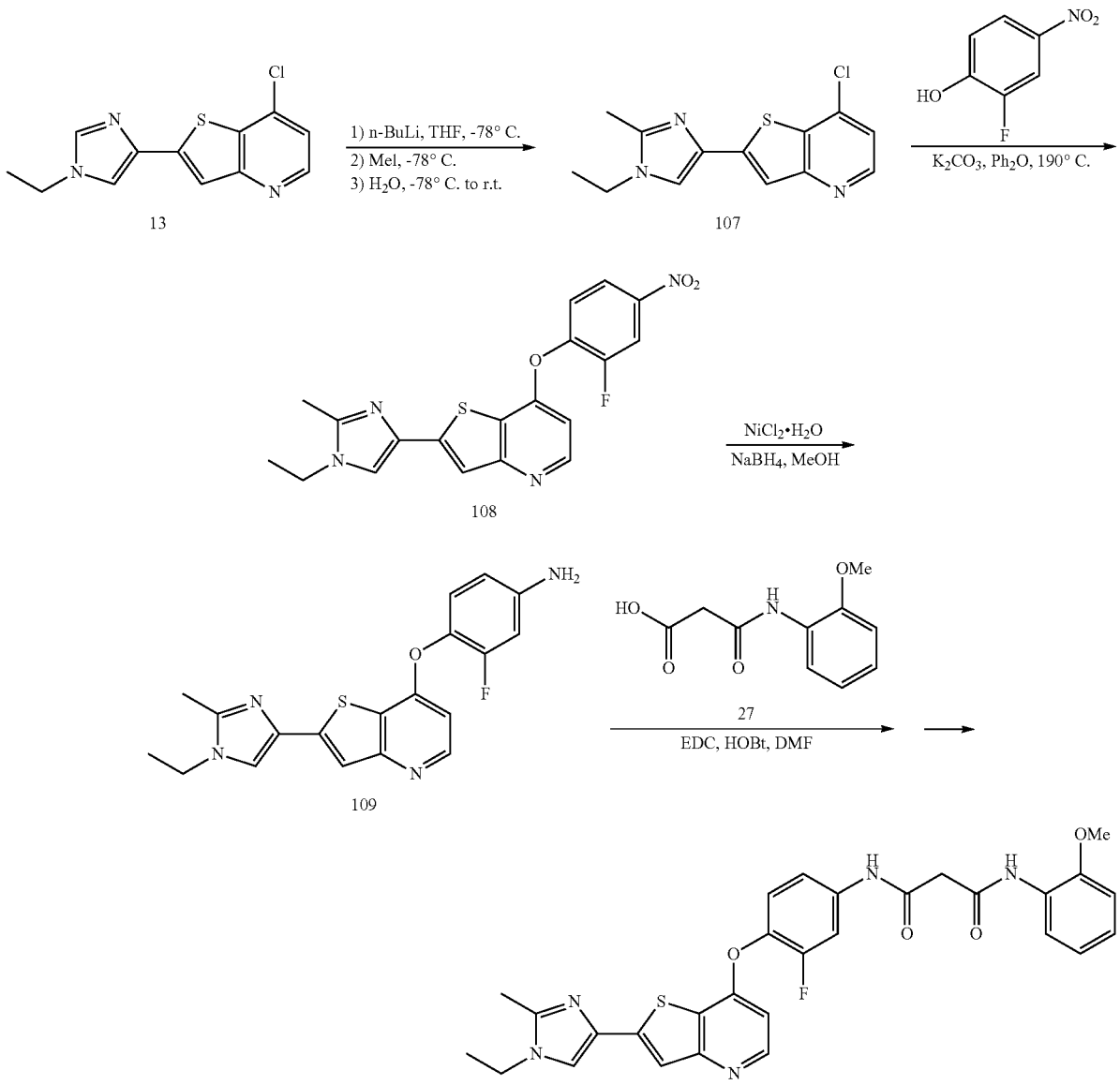

Example 40

N$^1$-(4-(2-(1-Ethyl-2-methyl-1H-imidazol-4-yl)thieno[3,2-b]pyridin-7-yloxy)-3-fluorophenyl)-N$^3$-(2-methoxyphenyl)malonamide (106)

Step 1: 7-Chloro-2-(1-ethyl-2-methyl-1H-imidazol-4-yl)thieno[3,2-b]pyridine (107)

n-Butyllithium was added to a solution at −78° C. of 7-chloro-2-(1-ethyl-1H-imidazol-4-yl)thieno[3,2-b]pyridine (13, scheme 4) in tetrahydrofuran and stirred for about 15 minutes. Methyl iodide was added slowly and the reaction mixture was stirred at −78° C. until completion of the reaction. The mixture was quenched with water then allowed to warm to room temperature. The aqueous solution was extracted three times with ethyl acetate. The combined organic extracts were washed with water and brine, then dried over anhydrous MgSO$_4$, filtered and evaporated. The crude product was purified by flash chromatography (eluent: 100% DCM to 2% MeOH/98% DCM) to afford the title compound 107 (as a mixture with about 15% of the starting material 13) as a yellow solid (190 mg, 80% yield). MS (m/z): 278.0 (M+H).

Step 2: 2-(1-Ethyl-2-methyl-1H-imidazol-4-yl)-7-(2-fluoro-4-nitrophenoxy)thieno[3,2-b]pyridine (108)

Starting from the chloride 107 and 2-fluoro-4-nitrophenol and following the same procedure as described above for the synthesis of compound 14 (scheme 4) title compound 108 was obtained in 31% yield. MS (m/z): 399.0 (M+H).

Step 3: 4-(2-(1-Ethyl-2-methyl-1H-imidazol-4-yl)thieno[3,2-b]pyridin-7-yloxy)-3-fluoroaniline (109)

Starting from the nitro compound 108 and following the same procedure as described above for the synthesis of compound 23 (scheme 6), title compound 109 was obtained in 16% yield MS (m/z): 369.0 (M+H).

Step 4: N$^1$-(4-(2-(1-Ethyl-2-methyl-1H-imidazol-4-yl)thieno[3,2-b]pyridin-7-yloxy)-3-fluorophenyl)-N$^3$-(2-methoxyphenyl)malonamide (106)

Starting from the amine 109 and the acid 27 and following the same procedure as described for the synthesis of compound 5d (scheme 4) title compound 106 was obtained in 9% yield. $^1$H NMR (DMSO-d$_6$). δ (ppm): 10.60 (s, 1H), 9.64 (s, 1H), 8.42 (d, J=5.5 Hz, 1H), 8.07 (dd, J=1.2 and 8.0 Hz, 1H), 7.87 (dd, J=2.3 and 13.1 Hz, 1H), 7.84 (s, 1H), 7.62 (s, 1H), 7.50-7.41 (m, 2H), 7.09-7.05 (m, 2H), 6.94-6.90 (m, 1H), 6.57 (d, J=5.1 Hz, 1H), 3.96 (q, J=7.2 Hz, 2H), 3.86 (s, 3H), 3.64 (s, 2H), 2.35 (s, 3H), 1.34 (t, J=7.2 Hz, 3H). MS (m/z): 560.0 (M+H).

Scheme 33

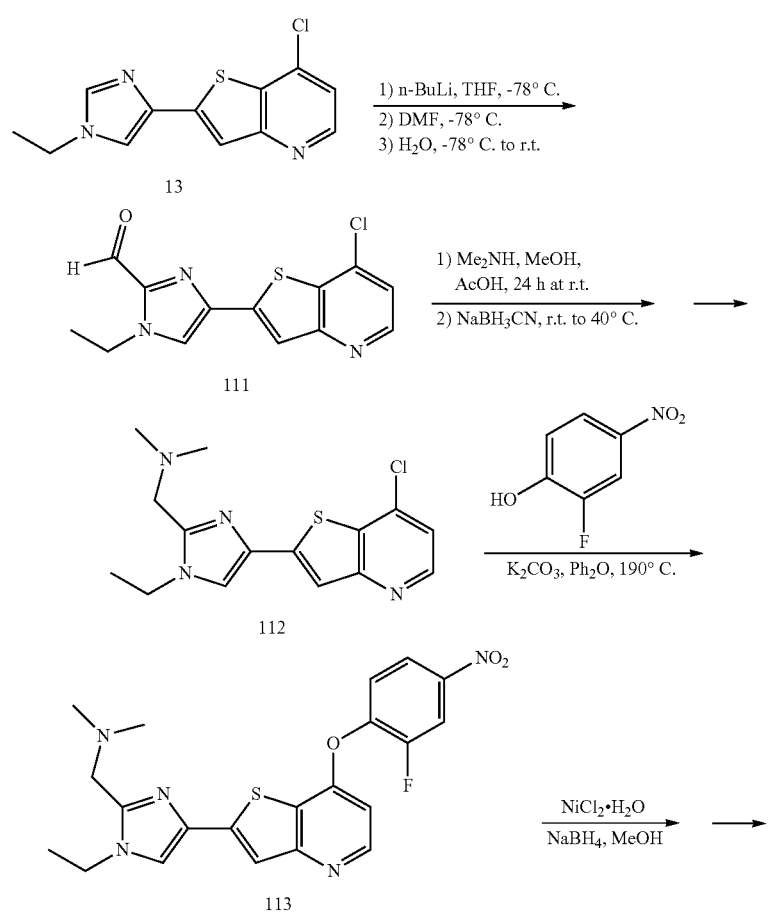

-continued

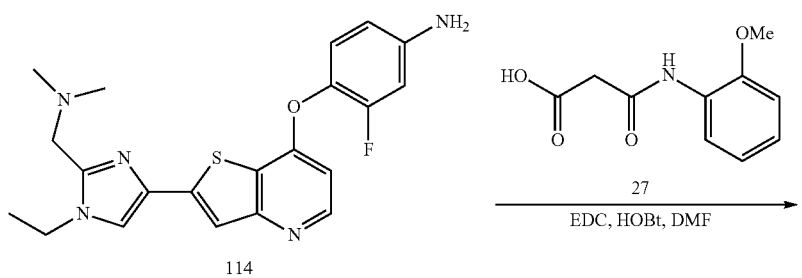

114

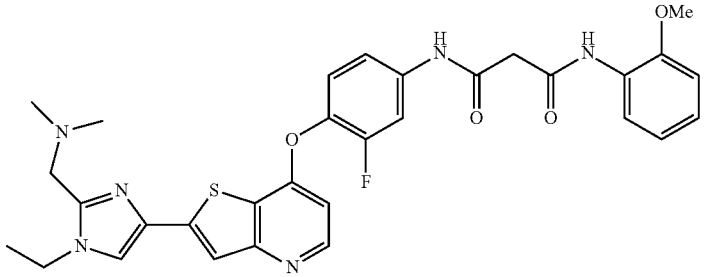

110: Example 41

Example 41

N¹-(4-(2-(2-((Dimethylamino)methyl)-1-ethyl-1H-imidazol-4-yl)thieno[3,2-b]pyridin-7-yloxy)-3-fluorophenyl)-N³-(2-methoxyphenyl)malonamide (110)

Step 1: 4-(7-Chlorothieno[3,2-b]pyridin-2-yl)-1-ethyl-1H-imidazole-2-carbaldehyde (111)

To a solution of 7-chloro-2-(1-ethyl-1H-imidazol-4-yl)thieno[3,2-b]pyridine (13, scheme 4) (1.50 g, 5.69 mmol) in tetrahydrofuran at −78° C. (1.3 mL) was added n-Butyllithium (3.4 mL, 8.53 mmol) and the reaction mixture was stirred for about 15 minutes. Dimethylformamide (0.66 mL, 8.53 mmol) was added slowly and the reaction mixture was stirred at −78° C. until completion of the reaction. The mixture was warmed to room temperature and quenched with water. The precipitate was removed by filteration, washed with water and dried well. The crude product was purified by trituration with dichloromethane, filtered, washed with additional dichloromethane and dried to afford the title compound III as a yellow solid (682 mg, 41% yield). MS (m/z): 291.9 (M+H).

Step 2: 1-(4-(7-Chlorothieno[3,2-b]pyridin-2-yl)-1-ethyl-1H-imidazol-2-yl)-N,N-dimethylmethanamine (112)

A mixture of the aldehyde 111 (344 mg, 1.18 mmol) and dimethylamine (0.7 mL, 1.41 mmol) in methanol (24 mL) and acetic acid (few drops) were stirred at RT overnight. Sodium cyanoborohydride (237 mg, 3.77 mmol) was added and the reaction mixture was allowed to stir at room temperature until completion of the reaction. The solvents were evaporated and water was added to the residue and the mixture was extracted with ethyl acetate. The combined organic layers were washed with brine, dried over anhydrous MgSO₄, filtered and evaporated. The crude product was purified by flash chromatography (eluent: 2.5% MeOH/97.5% DCM to 10% MeOH/90% DCM) to afford title compound 112 as a yellow solid (129 mg, 34% yield). MS (m/z): 321.1 (M+H).

Step 3: 1-(1-Ethyl-4-(7-(2-fluoro-4-nitrophenoxy)thieno[3,2-b]pyridin-2-yl)-1H-imidazol-2-yl)-N,N-dimethylmethanamine (113)

Starting from the chloride 112 and 2-fluoro-4-nitrophenol and following the same procedure as described above for the synthesis of compound 14 (scheme 4), title compound 113 was obtained as yellow solid in 48% yield. MS (m/z): 442.1 (M+H).

Step 4: 4-(2-(2-((Dimethylamino)methyl)-1-ethyl-1H-imidazol-4-yl)thieno[3,2-b]pyridin-7-yloxy)-3-fluoroaniline (114)

Starting from the nitro compound 113 and following the same procedure as described above for the synthesis of compound 23 (scheme 6) title compound 114 was obtained as a dark-yellow solid in 78% yield. MS (m/z): 412.2 (M+H).

Step 5: N¹-(4-(2-(2-((Dimethylamino)methyl)-1-ethyl-1H-imidazol-4-yl)thieno[3,2-b]pyridin-7-yloxy)-3-fluorophenyl)-N³-(2-methoxyphenyl)malonamide (110)

Starting from the amine 114 and the acid 27 and following the same procedure as described for the synthesis of compound 5d (scheme 4) title compound 110 was obtained as a white solid in 22% yield. ¹H NMR (DMSO-d₆). δ (ppm): 10.59 (s, 1H), 9.64 (s, 1H), 8.43 (d, J=5.5 Hz, 1H), 8.07 (dd, J=1.4 and 7.4 Hz, 1H), 7.95 (s, 1H), 7.87 (dd, J=2.2 and 12.9 Hz, 1H), 7.65 (s, 1H), 7.50-7.41 (m, 2H), 7.11-7.05 (m, 2H), 6.94-6.90 (m 1H), 6.57 (d, J=4.7 Hz, 1H), 4.08 (q, J=7.2 Hz, 2H), 3.86 (s, 3H), 3.64 (s, 2H), 3.50 (s, 2H), 2.17 (s, 6H), 1.38 (t, 3H). MS (m/z): 603.2 (M+H).

Scheme 34

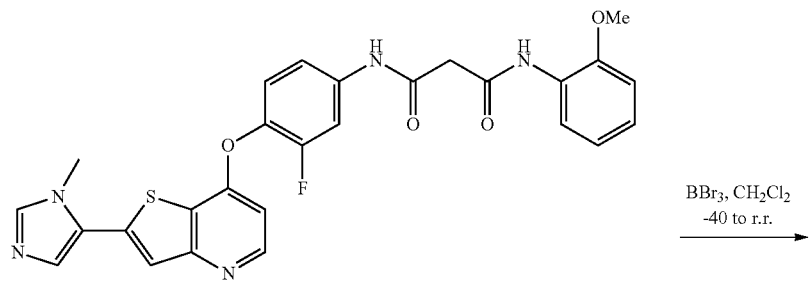

28c: Example 10

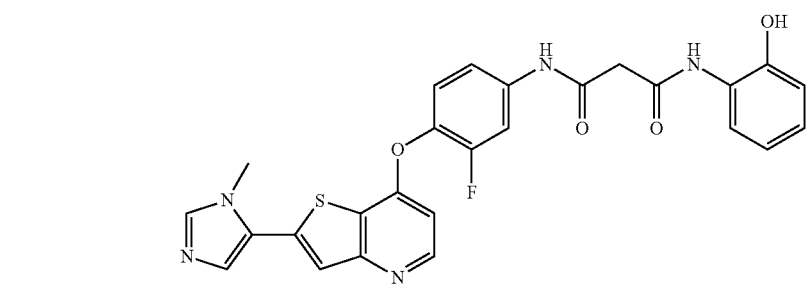

115: Example 42

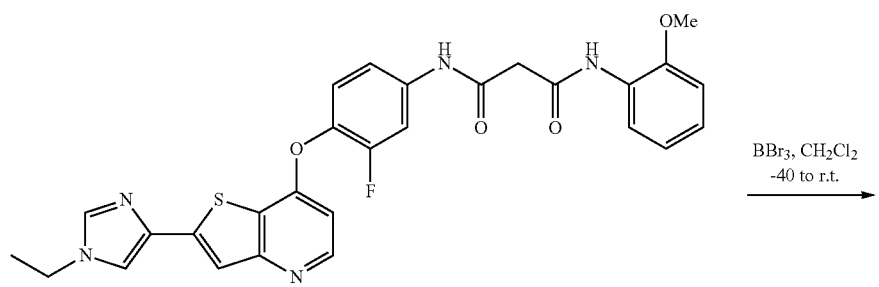

28b: Example 9

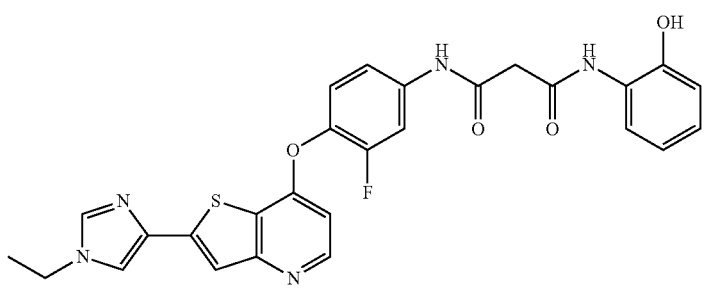

116: Example 43

Example 42

N¹-(3-Fluoro-4-(2-(1-methyl-1H-imidazol-5-yl) thieno[3,2-b]pyridin-7-yloxy)phenyl)-N³-(2-hydroxyphenyl)malonamide (115)

To a solution of compound 28c (example 10, scheme 8) (115 mg, 0.21 mmol) in DCM (10 mL) at −40° C. was added BBr$_3$ (1.0M, 0.86 mL, 0.86 mmol). The reaction mixture was allowed to stir for 1 hr then diluted with MeOH (2 mL) and water (1 mL) and concentrated. The residue was purified by preparative HPLC (Thermo C-18 column, gradient MeOH/water from 95:5 to 60:40) to afford title compound 115 (30 mg, 27% yield) as a white solid. $^1$H NMR (DMSO-d$_6$). δ (ppm): 10.57 (s, 1H), 9.88 (s, 1H), 9.59 (s, 1H), 8.49 (d, J=5.4 Hz, 1H), 7.92 (dd, J=8.0 Hz, J=1.5 Hz, 1H), 7.86 (dd, J=12.7 Hz, J=2.1 Hz, 1H), 7.85 (s, 1H), 7.76 (s, 1H), 7.48 (t, J=8.8 Hz, 1H), 7.42 (dd, J=9.0 Hz, J=1.7 Hz, 1H), 7.40 (s, 1H), 6.93-6.84 (m, 2H), 6.75 (t, J=8.0 Hz, 1H), 6.63 (d, J=5.5 Hz, 1H), 3.88 (s, 3H), 3.61 (s, 2H). MS (m/z): 518.1 (M+H).

Example 43

N[1]-(4-(2-(1-Ethyl-1H-imidazol-4-yl)thieno[3,2-b]pyridin-7-yloxy)-3-fluorophenyl)-N[3]-(2-hydroxyphenyl)malonamide (116)

Starting from the compound 28c (example 10, scheme 8) and following the same procedure as described above for the synthesis of compound 115, title compound 116 was obtained as light-beige solid in 23% yield. $^1$H NMR (DMSO-$d_6$). δ (ppm): 10.59 (s, 1H), 9.90 (s, 1H), 9.62 (s, 1H), 8.43 (d, J=5.6 Hz, 1H), 7.96 (d, J=1.2 Hz, 1H), 7.94 (dd, J=1.6 and 8.0 Hz, 1H), 7.87 (dd, J=2.0 and 12.8 Hz, 1H), 7.79 (d, J=1.2 Hz, 1H), 7.67 (s, 1H), 7.49 (t, J=8.8 Hz, 1H), 7.45-7.40 (m, 1H), 7.96-7.90 (m, 1H), 6.87 (dd, J=1.2 and 8.0 Hz, 1H), 6.80-6.75 (m, 1H), 6.58 (d, J=5.6 Hz, 1H), 4.06 (q, J=7.2 Hz, 2H), 3.63 (s, 2H), 1.40 (t. J=7.2 Hz, 3H). MS (m/z): 532.1 (M+H).

Example 44

N[1]-(4-(2-(1-Ethyl-1H-imidazol-5-yl)thieno[3,2-b]pyridin-7-yloxy)-3-fluorophenyl)-N[3]-(2-fluorophenyl)malonamide (117)

Step 1: 7-Chloro-2-(1-ethyl-1H-imidazol-5-yl)thieno[3,2-b]pyridine (118)

To a solution of chloride 2 (scheme 1) (4.77 g, 28.12 mmol) in THF (120 mL) at −78° C. was slowly added n-BuLi (2.5M in hexane, 14.06 mL, 35.15 mmol). The reaction mixture was stirred for one hour at −78° C. followed by the slow addition of ZnCl$_2$ (0.5M in THF, 70.3 mL, 35.15 mmol). After a few minutes, the reaction mixture was allowed to warm to room temperature and stirred for one hour.

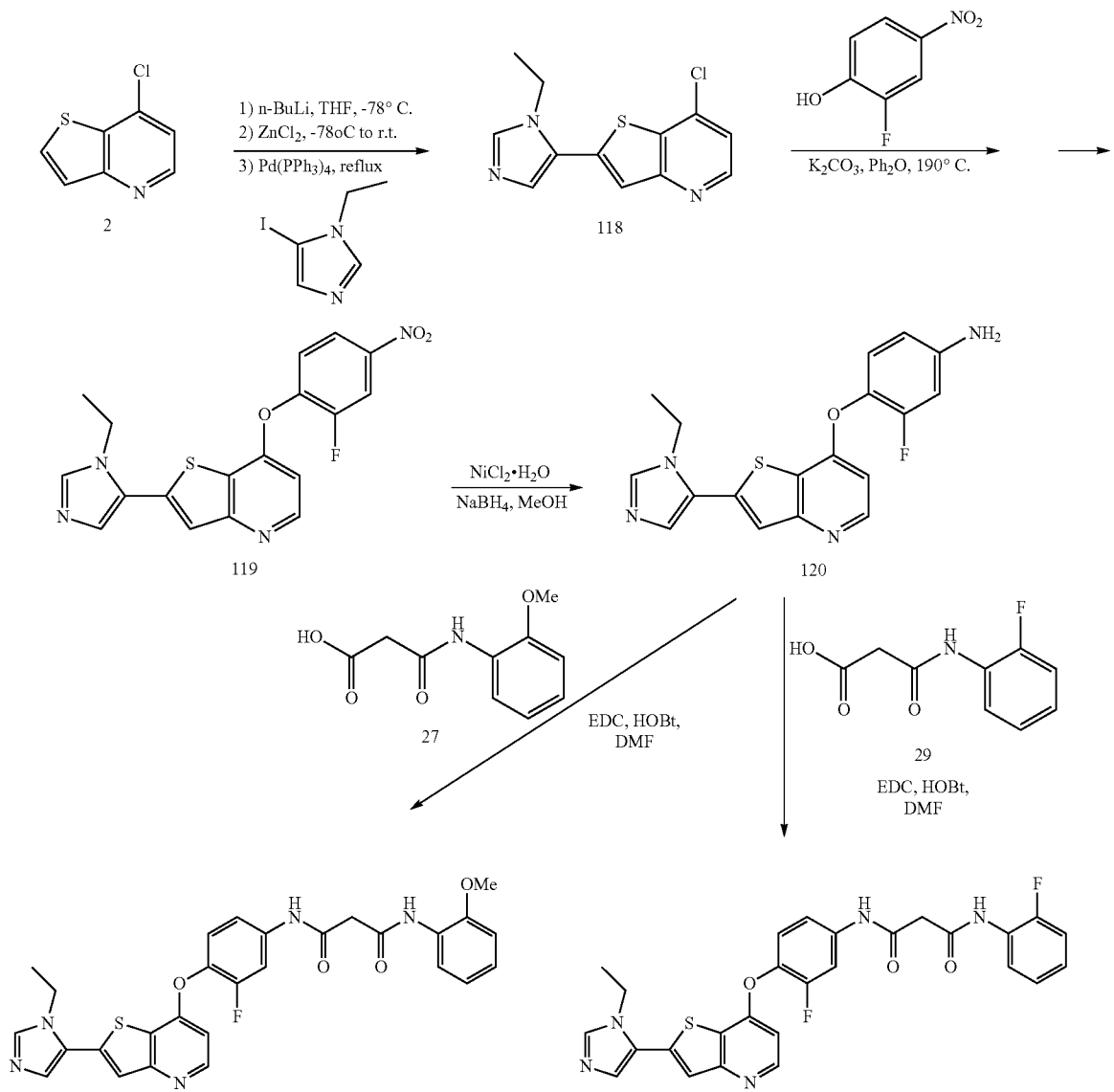

Scheme 35

To a solution of 1-ethyl-5-iodo-1H-imidazole (2.04 g, 8.65 mmol) (*Tet. Lett.* 2004, 45, 5529) in THF (5 mL) was added Pd(PPh$_3$)$_4$ (0.81 g, 0.70 mmol) and the reaction mixture was heated to reflux for 1.5 hours, cooled to room temperature then diluted with aqueous ammonium hydroxide. The solution was extracted with EtOAc and the extract was washed with water and brine then dried over anhydrous magnesium sulfate, filtered and evaporated under reduced pressure. The residue was purified by flash chromatography (eluents DCM, then DCM-MeOH, 97:3, 95:5, 9:1) to afford title compound 118 (4 g, 54% yield) as a yellow solid. MS (m/z): 264.1 (M+H).

Step 2. 2-(1-Ethyl-1H-imidazol-5-yl)-7-(2-fluoro-4-nitrophenoxy)thieno[3,2-b]pyridine (119)

To a solution of 118 (4 g, 15.16 mmol) in Ph$_2$O (60 ml) was added 2-fluoro-4-nitrophenol (4.76 g, 30.33 mmol) and potassium carbonate (8.38 g, 60.66 mmol). The reaction mixture was heated to 195° C. for 18 hrs the cooled to room temperature. The residue was purified by column chromatography (eluents EtOAc/Hex (9/1 to 5/5) then MeOH/CH$_2$Cl$_2$ (98/2)), to afford title compound 119 (3.05 g, 52% yield) as a yellow solid. MS (m/z): 385.0 (M+H).

Step 3. 4-(2-(1-Ethyl-1H-imidazol-5-yl)thieno[3,2-b]pyridin-7-yloxy)-3-fluoroaniline (120)

To a solution of the nitro compound 119 (3.05 g, 7.93 mmol) in MeOH/THF (50 ml/50 mL) was added NiCl$_2$×6H$_2$O (3.77 g, 15.86 mmol) and NaBH$_4$ (1.18 g, 31.73 mmol). The reaction mixture was allowed to stir for 1 hr, concentrated to dryness and the resultant solid was dissolved in 2 M HCl. The acidic solution was then made basic with aqueous ammonium hydroxide solution and extracted with EtOAc. The organic extract was dried over anhydrous sodium sulfate, filtered and evaporated. The residue was purified by flash chromatography (eluents DCM-MeOH, 98:2, 95:5, 9:1) to afford title compound 120 (2.00 g, 71% yield) as a yellow solid. MS (m/z): 355.1 (M+H).

Step 4. N$^1$-(4-(2-(1-Ethyl-1H-imidazol-5-yl)thieno[3,2-b]pyridin-7-yloxy)-3-fluorophenyl)-N$^3$-(2-fluorophenyl)malonamide (117)

To a solution of the amino compound 120 (400 mg, 1.08 mmol) in DMF (10 mL), 3-(2-fluorophenylamino)-3-oxopropanoic acid (444 mg, 2.25 mmol), EDC (519 mg, 2.70 mmol) was added HOBT (364 mg, 2.70 mmol). The reaction mixture was allowed to stir for 1 hr. The solution was extracted with EtOAc and the extract was washed with water, aqueous ammonium chloride and brine then dried over anhydrous magnesium sulfate, filtered and evaporated under reduced pressure. The residue was purified by flash chromatography (eluents DCM-MeOH, 98:2, 95:5) to afford title compound 117 (348 mg, 58% yield) as a white solid. $^1$H NMR (DMSO-d$_6$). δ ppm: 10.58 (s, 1H), 10.06 (s, 1H), 8.52 (d, J=5.6 Hz, 1H), 8.10-7.76 (m, 1H), 7.94 (d, J=1.2 Hz, 1H), 7.88 (dd, J=2.4 and 13.2 Hz, 1H), 7.74 (s, 1H)), 7.51 (t, J=8.8 Hz, 1H), 7.43 (dd, J=1.6 and 8.8 Hz, 1H), 7.39 (d, J=1.2 Hz, 1H), 7.32-7.25 (m, 1H), 7.21-7.14 (m, 2H), 6.66 (d, J=5.6 Hz, 1H), 4.29 (q, J=7.2 Hz, 2H), 3.62 (s, 2H), 1.34 (t, J=7.2 Hz, 3H). MS (m/z): 534.1 (M+H).

Example 45

N$^1$-(4-(2-(1-Ethyl-1H-imidazol-5-yl)thieno[3,2-b]pyridin-7-yloxy)-3-fluorophenyl)-N$^3$-(2-methoxyphenyl)malonamide (121)

Title compound 121 (scheme 35) was obtained similarly to the compound 117 (example 44, scheme 35) starting from the amine 120 and replacing the acid 29 with the acid 27. $^1$H NMR (DMSO-d$_6$). δ (ppm): 10.59 (s, 1H), 9.63 (s, 1H), 8.52 (d, J=5.6 Hz, 1H), 8.07 (d, J=7.6 Hz, 1H), 7.94 (d, J=1.2 Hz, 1H), 7.88 (dd, J=2.4 and 13.2 Hz, 1H), 7.74 (s, 1H), 7.51 (t, J=8.8 Hz, 1H), 7.43 (dd, J=1.6 and 8.8 Hz, 1H), 7.40 (d, J=1.2 Hz, 1H), 7.12-7.4 (m, 2H), 6.96-6.88 (m, 1H), 6.66 (d, J=5.6 Hz, 1H), 4.29 (q, J=7.2 Hz, 2H), 3.86 (s, 3H), 3.64 (s, 2H), 1.34 (t, J=7.2 Hz, 3H).

Scheme 36

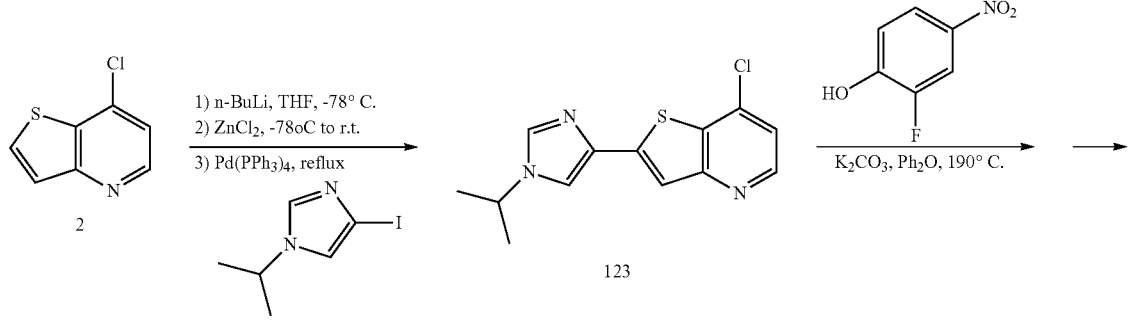

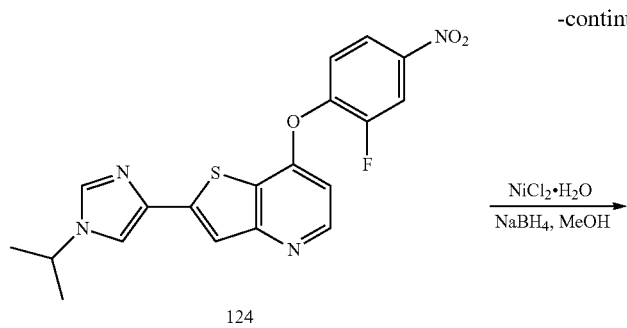
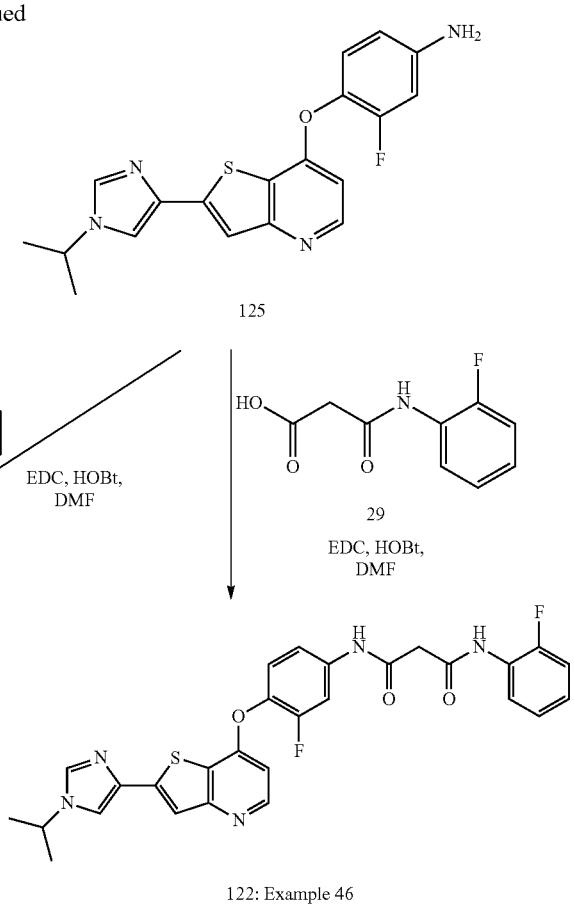

Example 46

N¹-(3-Fluoro-4-(2-(1-isopropyl-1H-imidazol-4-yl)thieno[3,2-b]pyridin-7-yloxy)phenyl)-N³-2-fluorophenyl)malonamide (122)

Step 1: 7-Chloro-2-(1-isopropyl-1H-imidazol-4-yl)thieno[3,2-b]pyridine (123)

To a solution of chloride 2 (scheme 1) (2.93 g, 17.31 mmol) in THF (120 mL) at −78° C. was slowly added n-BuLi (2.5M in hexane, 8.66 mL, 21.64 mmol). The reaction mixture was stirred for one hour at −78° C. followed by the slow addition of ZnCl$_2$ (1M in THF, 21.6 mL, 21.64 mmol). After a few minutes the reaction mixture was allowed to warm to room temperature and stirred for one hour.

To a solution of 4-iodo-1-isopropyl-1H-imidazole (2.04 g, 8.65 mmol) [*Tet. Lett.* 2004, 45, 5529] in THF (5 mL) was added Pd(PP$_3$)$_4$ (0.500 g, 0.43 mmol) and the reaction mixture which was heated to reflux for 5 hour then cooled to room temperature, diluted with aqueous ammonium hydroxide. The solution was extracted with EtOAc and the extract was washed with water and brine, dried over anhydrous magnesium sulfate, filtered and evaporated under reduced pressure. The residue was purified by flash chromatography (eluents DCM, then DCM-MeOH, 97:3, 95:5, 9:1) to afford title compound 123 (1.16 g, 24% yield) as a yellow solid. MS (m/z): 278.0 (M+H).

Step 2: 7-(2-Fluoro-4-nitrophenoxy)-2-(1-isopropyl-1H-imidazol-4-yl)thieno[3,2-b]pyridine (124)

To a solution of 123 (1.16 g, 4.18 mmol) in Ph$_2$O (20 ml) was added 2-fluoro-4-nitrophenol (1.31 g, 8.37 mmol) and potassium carbonate (2.31 g, 16.72 mmol). The reaction mixture was heated to 195° C. for 18 hrs then cooled to room temperature. The residue was purified by column chromatography, eluents EtOAc/Hex (9/1 to 5/5), then MeOH/CH$_2$Cl$_2$ (98/2), to afford title compound 124 (1.47 g, 88% yield) as a yellow solid. MS (m/z): 399.0 (M+H).

Step 3: 3-Fluoro-4-(2-(1-isopropyl-1H-imidazol-4-yl)thieno[3,2-b]pyridin-7-yloxy)aniline (125)

To a solution of the nitro compound 124 (1.47 g, 3.68 mmol) in MeOH/THF (50 ml/50 mL) was added NiCl$_2$× 6H$_2$O (1.75 g, 7.37 mmol) and NaBH$_4$ (550 mg, 14.75 mmol). The reaction mixture was allowed to stir for 1 hr then concentrated to dryness and the resultant solid was dissolved in 2 M HCl. The acidic solution was then made basic with aqueous ammonium hydroxide solution and extracted with EtOAc. The organic extract was dried over anhydrous sodium sulfate, filtered and evaporated The residue was purified by flash chromatography (eluents DCM-MeOH, 98:2, 95:5, 9:1) to afford title compound 125 (3.31 g, 88% yield) as a pink solid. MS (m/z): 368.1 (M+H).

Step 4: N¹-(3-Fluoro-4-(2-(1-isopropyl-1H-imidazol-4-yl)thieno[3,2-b]pyridin-7-yloxy)phenyl)-N³-2-fluorophenyl)malonamide (122)

To a solution of the amino compound 125 (400 mg, 1.08 mmol) in DMF (20 mL), 3-(2-fluorophenylamino)-3-oxopropanoic acid (427 mg, 2.17 mmol), EDC (352 mg, 2.60 mmol) was added HOBT (499 mg, 2.60 mmol). The reaction mixture was allowed to stir for 1 hr. The solution was extracted with EtOAc and the extract was washed with water, aqueous ammonium chloride and brine then dried over anhydrous magnesium sulfate, filtered and evaporated under reduced pressure. The residue was purified by flash chromatography (eluents DCM-MeOH, 98:2, 95:5) to afford title compound 122 (384 mg, 65% yield) as a yellow solid. ¹H NMR (DMSO-$d_6$). δ ppm: 10.57 (s, 1H), 10.06 (s, 1H), 8.43 (d, J=5.6 Hz, 1H), 8.04 (dd, J=1.6 and 7.2 Hz, 1H), 8.04-7.96 (m, 1H), 7.87 (dd, J=2.4 and 12.8 Hz, 1H), 7.84 (d, J=1.2 Hz, 1H), 7.67 (s, 1H), 7.49 (t, J=8.8 Hz, 1H), 7.42 (dd, J=1.6 and 8.8 Hz, 1H), 7.32-7.25 (m, 1H), 7.22-7.13 (m, 2H), 6.58 (d, J=5.6 Hz, 1H), 4.48 (quin, J=6.4 Hz, 1H), 3.63 (s, 2H), 1.46 (d, J=6.8 Hz, 6H), 3.62 (s, 2H), 1.34 (t, J=7.2 Hz, 3H). MS (m/z): 548.1 (M+1).

Example 47

N¹-(3-Fluoro-4-(2-(1-isopropyl-1H-imidazol-4-yl)thieno[3,2-b]pyridin-7-yloxy)phenyl)-N³-(2-methoxyphenyl)malonamide (126)

Title compound 126 (scheme 36) was obtained similarly to the compound 122 (example 45, scheme 36) starting from the amine 125 and replacing the acid 29 with the acid 27. ¹H NMR (DMSO-$d_6$). δ (ppm): 10.58 (s, 1H), 9.64 (s, 1H), 8.43 (d, J=5.6 Hz, 1H), 8.07 (dd, J=1.6 and 7.2 Hz, 1H), 8.05 (d, J=1.2 Hz, 1H), 7.87 (dd, J=2.4 and 12.8 Hz, 1H), 7.84 (d, J=1.2 Hz, 1H), 7.67 (s, 1H), 7.49 (t, J=8.8 Hz, 1H), 7.43 (dd, J=1.6 and 8.8 Hz, 1H), 7.12-7.04 (m, 2H), 6.92 (ddd, J=2.4, 7.2 and 8.8 Hz, 1H), 6.58 (d, J=5.6 Hz, 1H), 4.48 (quin, J=6.4 Hz, 1H), 3.86 (s, 3H), 3.64 (s, 2H), 1.46 (d, J=6.8 Hz, 6H). MS (m/z): 559.2 (M+H).

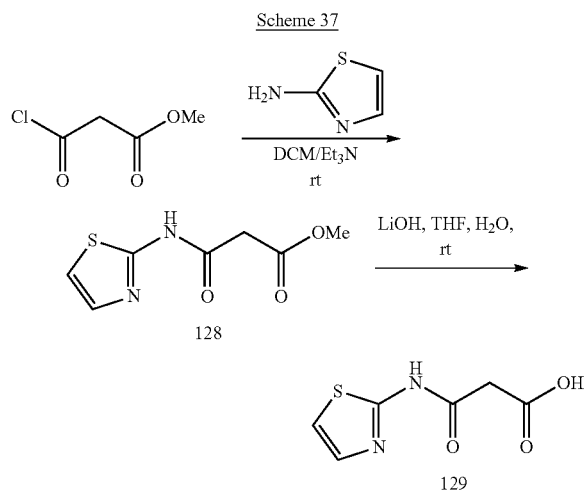

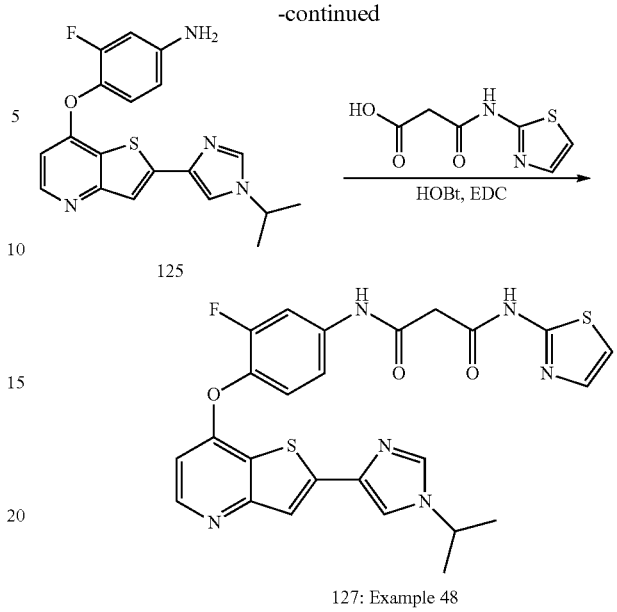

127: Example 48

Example 48

N¹-(3-Fluoro-4-(2-(1-isopropyl-1H-imidazol-4-yl)thieno[3,2-b]pyridin-7-yloxy)phenyl)-N³-(thiazol-2-yl)malonamide (127)

Step 1: 3-Oxo-3-(thiazol-2-ylamino)propanoic acid (129)

To a solution of 2-aminothiazole (2.0 g, 19.97 mmol) in dry DCM (30 ml) at 0° C. was added TEA (4.03 g, 2 eq, 39.94 mmol) and methyl 3-chloro-3-oxopropanoate (3.0 g, 1.1 eq, 21.97 mmol). The reaction mixture was stirred for 1 hr at room temperature. The reaction mixture was concentrated to dryness, dissolved in EtOAc and washed well with water. The organic phase was collected, dried over anhydrous sodium sulfate then filtered and concentrated. The resultant solid was triturated with Et₂O and used directly in the next step with no additional purification (1.1 g, 30% yield). To a solution of the ester 128 (500 mg, 2.49 mmol) in THF/water (1:1, 20 ml) was added LiOH×H₂O (209 mg, 2 eq, 4.98 mmol) and the mixture stirred for 2 hrs at room temperature. The mixture was neutralized with 1 M HCl solution and adsorbed onto silica gel. Purification by column chromatography (60% EtOAc in hexanes) afforded the acid 129 as a white solid (320 mg, 69% yield). MS (m/z): 187.2 (M+H).

Step 2: N¹-(3-Fluoro-4-(2-(1-isopropyl-1H-imidazol-4-yl)thieno[3,2-b]pyridin-7-yloxy)phenyl)-N³-(thiazol-2-yl)malonamide (127)

The title compound was obtained starting from the amine 125 (100 mg, 0.27 mmol) (scheme 36) according to the procedure described for 55 (example 23, scheme 19) but substituting acid 1 for the acid 129 (101 mg, 2 eq, 0.53 mmol). After purification by column chromatography (10% MeOH/EtOAc) the title compound 127 was obtained as a white solid (7 mg, 5% yield). ¹H NMR (DMSO-$d_6$) δ (ppm): 12.32 (s, 1H), 10.60 (s, 1H), 8.41 (d, J=5.48 Hz, 1H), 8.03 (s, 1H), 7.82 (m, 2H), 7.65 (s, 1H), 7.44 (m, 3H), 7.22 (d, J=3.52 Hz, 1H), 6.55 (d, J=5.48 Hz, 1H), 4.46 (m, 1H), 3.63 (s, 2H), 1.45 (d, J=6.65 Hz, 6H). MS (m/z): 536.9 (M+H).

Scheme 38

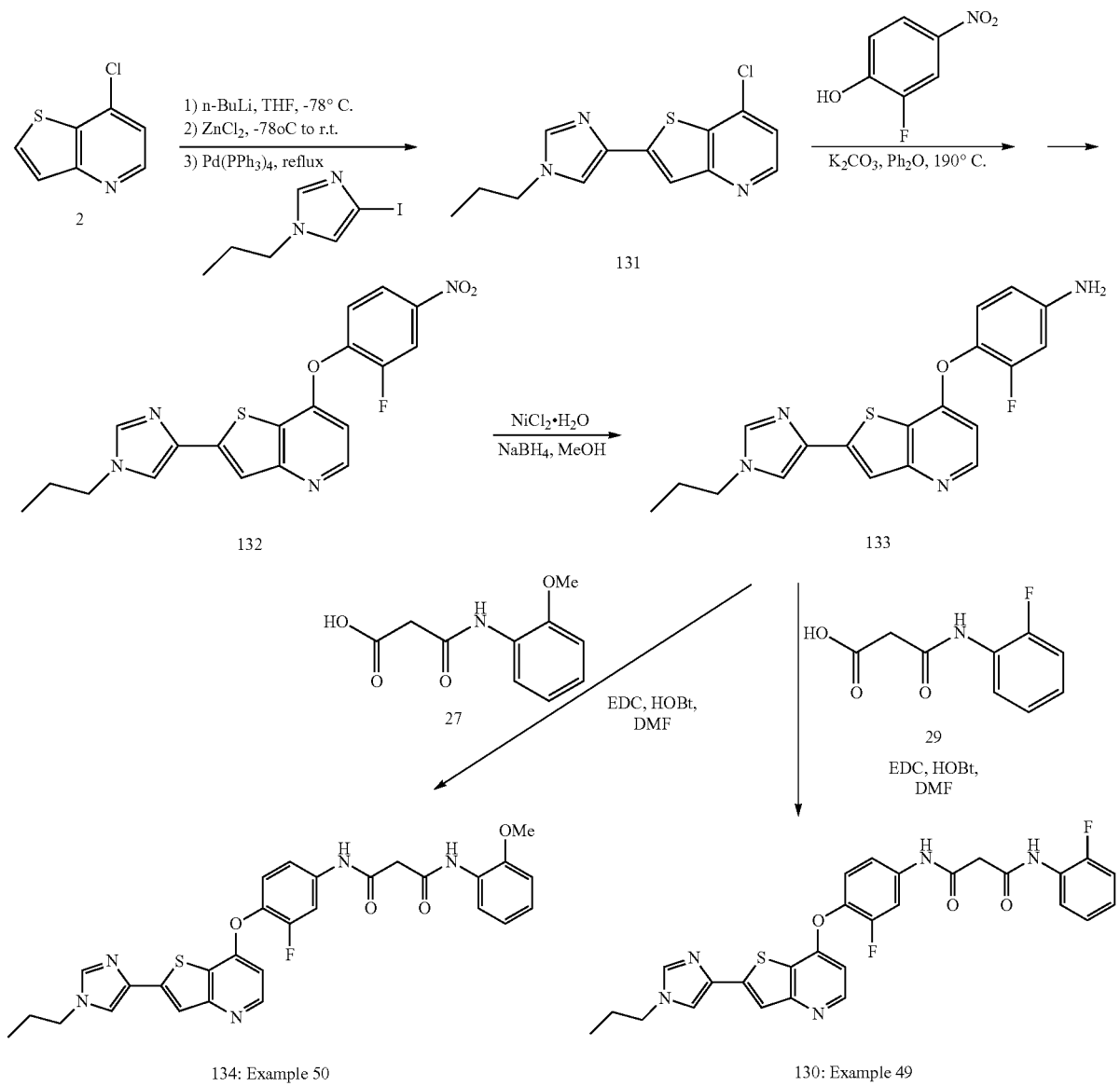

134: Example 50

130: Example 49

Example 49

N¹-(3-Fluoro-4-(2-(1-propyl-1H-imidazol-4-yl) thieno[3,2-b]pyridin-7-yloxy)phenyl)-N³-(2-fluorophenyl)malonamide (130)

Step 1. 7-Chloro-2-(1-propyl-1H-imidazol-4-yl) thieno[3,2-b]pyridine (131)

To a solution of chloride 2 (scheme 1) (4.38 g, 25.84 mmol) in THF (120 mL) at −78° C. was slowly added n-BuLi (2.5M in hexane, 12.9 mL, 32.31 mmol). The reaction mixture was stirred for one hour at −78° C. followed by the slow addition of ZnCl₂ (0.5M in THF, 64.6 mL, 32.31 mmol). After a few minutes the reaction mixture was allowed to warm to room temperature and stirred for one hour.

To a solution of 4-iodo-1-propyl-1H-imidazole (3.05 g, 12.92 mmol) [*Tet. Lett.* 2004, 45, 5529] in THF (5 mL) was added Pd(PPh₃)₄ (0.74 g, 0.64 mmol) and the reaction mixture which was heated to reflux for 2.5 hours, cooled to room temperature then diluted with aqueous ammonium hydroxide. The solution was extracted with EtOAc, the extract was washed with water and brine then dried over anhydrous magnesium sulfate, filtered and evaporated under reduced pressure. The residue was purified by flash chromatography (eluents DCM, then DCM-MeOH, 97:3, 95:5) to afford title compound 131 (3.37 g, 47% yield) as a yellow solid. MS (m/z): 278.0 (M+H).

Step 2. 7-(2-Fluoro-4-nitrophenoxy)-2-(1-propyl-1H-imidazol-4-yl)thieno[3,2-b]pyridine (132)

To a solution of 131 (3.37 g, 12.13 mmol) in Ph₂O (40 ml) was added 2-fluoro-4-nitrophenol (3.81 g, 24.26 mmol) and potassium carbonate (6.70 g, 48.52 mmol). The reaction mixture was heated to 195° C. for 20 hrs then cooled to room temperature. The residue was purified by column chromatography, eluents EtOAc/Hex (9/1 to 5/5), then MeOH/DCM (98/2), to afford title compound 132 (4.13 g, 85% yield) as a yellow solid. MS (m/z): 399.0 (M+H).

Step 3. 3-Fluoro-4-(2-(1-propyl-1H-imidazol-4-yl)thieno[3,2-b]pyridin-7-yloxy)aniline (133)

To a solution of the nitro compound 132 (4.13 g, 10.36 mmol) in MeOH/THF (100 ml/100 mL) was added NiCl$_2$× 6H$_2$O (4.92 g, 20.73 mmol) and NaBH$_4$ (1.54 mg, 41.44 mmol). The reaction mixture was allowed to stir for 1 hr, concentrated to dryness and the resultant solid was dissolved in 2 M HCl. The acidic solution was then made basic with aqueous ammonium hydroxide solution and extracted with EtOAc. The organic extract was dried over anhydrous sodium sulfate, filtered and evaporated The residue was purified by flash chromatography (eluents DCM-MeOH, 98:2, 95:5) to afford title compound 133 (3.31 g, 86% yield) as a pink solid. MS (m/z): 368.1 (M+H).

Step 4. N$^1$-(3-Fluoro-4-(2-(1-propyl-1H-imidazol-4-yl)thieno[3,2-b]pyridin-7-yloxy)phenyl)-N$^3$-(2-fluorophenyl)malonamide (130)

To a solution of the amino compound 133 (400 mg, 1.08 mmol) in DMF (20 mL), 3-(2-fluorophenylamino)-3-oxopropanoic acid (29) (427 mg, 2.17 mmol), EDC (352 mg, 2.60 mmol) was added HOBT (499 mg, 2.60 mmol). The reaction mixture was allowed to stir for 1 hr. The solution was extracted with EtOAc and the extract was washed with water, aqueous ammonium chloride and brine then dried over anhydrous magnesium sulfate, filtered and evaporated under reduced pressure. The residue was purified by flash chromatography (eluents DCM-MeOH, 98:2, 95:5) to afford title compound 130 (215 mg, 36% yield) as a yellow solid. $^1$H NMR (DMSO-d$_6$). δ (ppm): 10.56 (s, 1H), 10.06 (s, 1H), 8.43 (d, J=5.6 Hz, 1H), 8.10-7.96 (m, 1H), 7.94 (d, J=1.2 Hz, 1H), 7.87 (dd, J=1.6 and 12.8 Hz, 1H), 7.77 (d, J=1.2 Hz, 1H), 7.68 (s, 1H), 7.49 (t, J=8.8 Hz, 1H), 7.42 (dd, J=2.0 and 8.8 Hz, 1H), 7.32-7.25 (m, 1H), 7.22-7.14 (m, 2H), 6.58 (d, J=5.6 Hz, 1H), 3.98 (t, J=7.2 Hz, 2H), 3.62 (s, 2H), 1.78 (sex, J=7.2 Hz, 2H), 0.87 (t, J=7.2 Hz, 3H). MS (m/z): 548.1 (M+H).

Example 50

N$^1$-(3-fluoro-4-(2-(1-propyl-1H-imidazol-4-yl)thieno[3,2-b]pyridin-7-yloxy)phenyl)-N$^3$-(2-methoxyphenyl)malonamide (134)

Title compound 134 (scheme 38) was obtained similarly to the compound 130 (example 49, scheme 38) starting from the amine 133 and replacing the acid 29 with the acid 27. $^1$H NMR (DMSO-d$_6$). δ (ppm): 10.58 (s, 1H), 9.64 (s, 1H), 8.43 (d, J=5.6 Hz, 1H), 8.07 (dd, J=1.2 and 8.8 Hz, 1H), 7.94 (d, J=1.2 Hz, 1H), 7.87 (dd, J=1.6 and 12.8 Hz, 1H), 7.77 (d, J=1.2 Hz, 1H), 7.68 (s, 1H), 7.49 (t, J=8.8 Hz, 1H), 7.43 (dd, J=2.0 and 8.8 Hz, 1H), 7.11-7.04 (m, 2H), 6.92 (ddd, J=2.4, 6.4 and 8.0 Hz, 1H), 6.58 (d, J=5.6 Hz, 1H), 3.98 (t, J=7.2 Hz, 2H), 3.86 (s, 3H), 3.64 (s, 2H), 1.78 (sex, J=7.2 Hz, 2H), 0.87 (t, J=7.2 Hz, 3H). MS (m/z): 559.2 (M+H).

Scheme 39

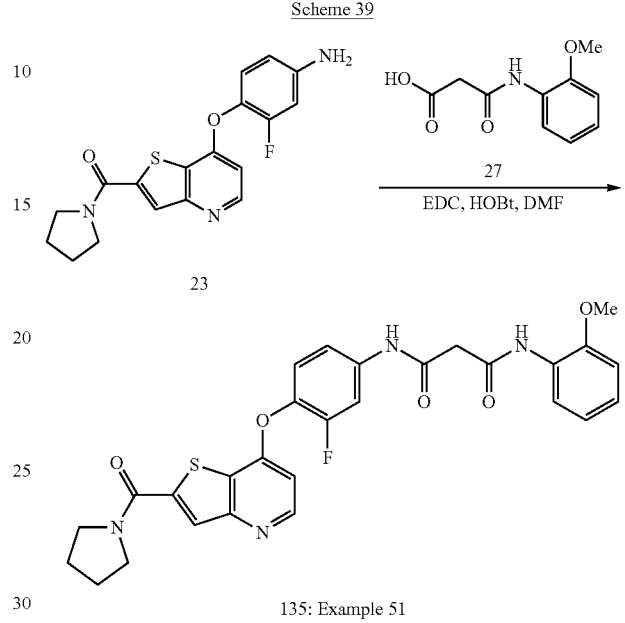

135: Example 51

Example 51

N$^1$-(3-Fluoro-4-(2-(pyrrolidine-1-carbonyl)thieno[3,2-b]pyridin-7-yloxy)phenyl)-N$^3$-(2-methoxyphenyl)malonamide (135)

Starting from (7-(4-amino-2-fluorophenoxy)thieno[3,2-b]pyridin-2-yl)(pyrrolidin-1-yl)methanone (23, scheme 6) and the acid 27, and following the same procedure as described above for the synthesis of compound 130 (scheme 38, example 49) title compound 135 was obtained as white solid in 51% yield. $^1$H NMR (DMSO-d$_6$). δ (ppm): 10.65 (s, 1H), 10.25 (s, 1H), 8.61 (d, J=5.6 Hz, 1H), 8.03 (s, 1H), 7.92-7.86 (m, J=13.2 Hz, 1H), 7.60 (d, J=8.4 Hz, 2H), 7.50 (t, J=8.4 Hz, 1H), 7.47-7.20 (m, 1H), 7.30 (t, J=8.0 Hz, 2H), 7.04 (t, J=7.2 Hz, 1H), 6.83 (d, J=5.6 Hz, 1H), 3.54 (t, J=6.4 Hz, 2H), 3.53 (s, 2H), 1.97 (quin, J=6.4 Hz, 2H), 1.89 (quin, J=6.4 Hz, 2H). MS (m/z): 549.2 (M+H).

Scheme 40

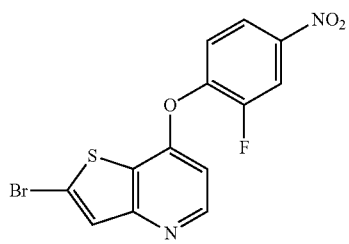 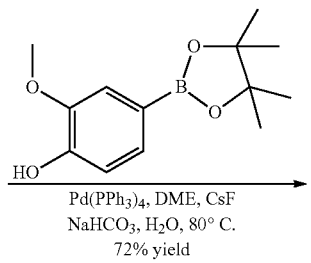

Pd(PPh$_3$)$_4$, DME, CsF
NaHCO$_3$, H$_2$O, 80° C.
72% yield

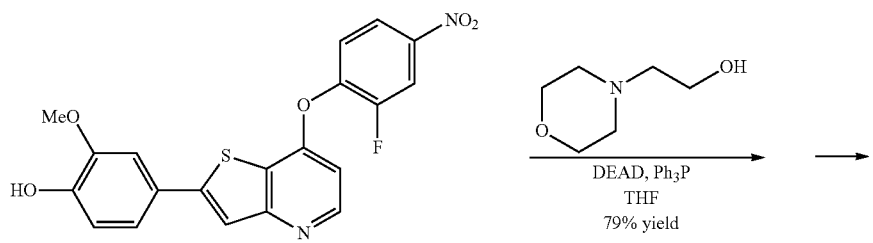
137
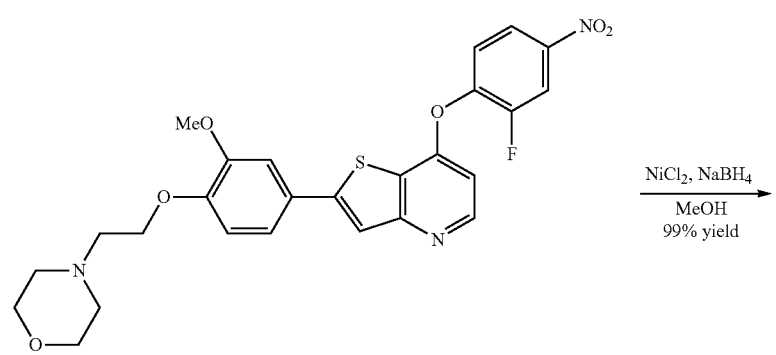
138
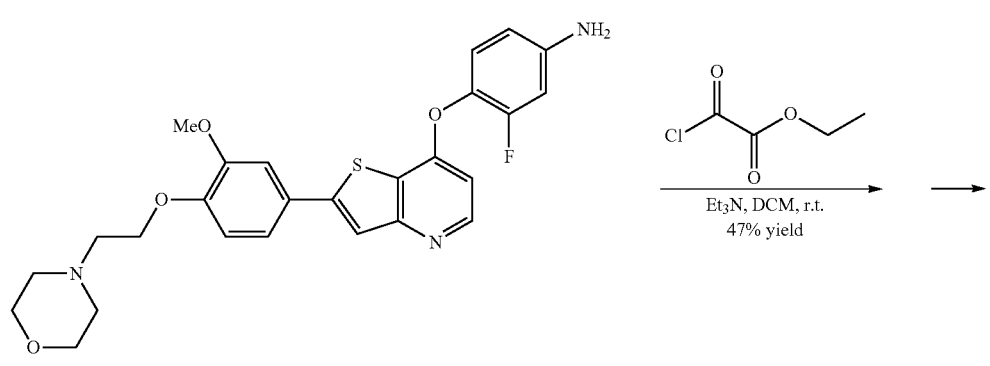
139
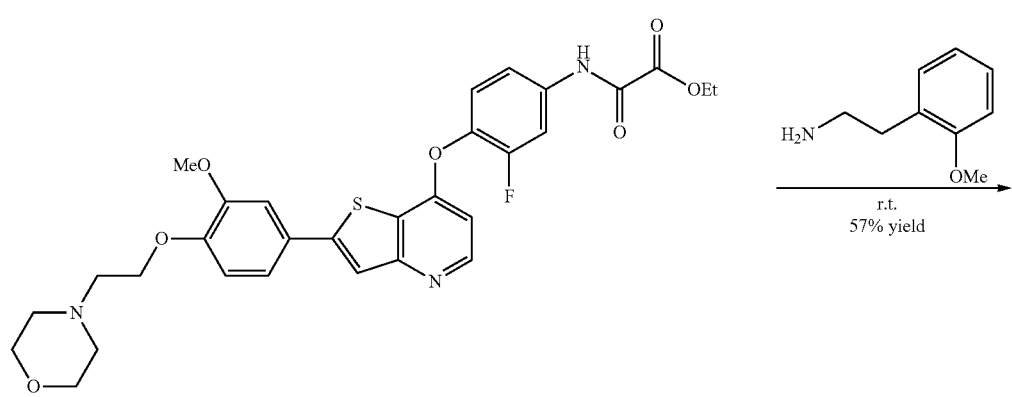
140

-continued

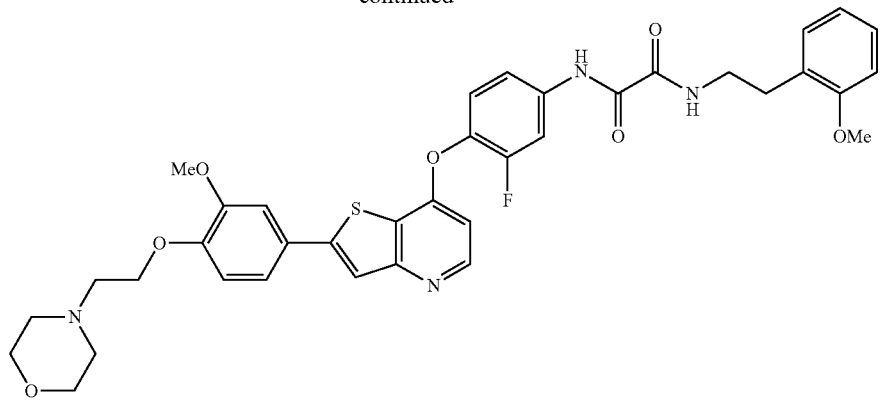

136: Example 52

Example 52

N$^1$-(3-Fluoro-4-(2-(3-methoxy-4-(2-morpholinoethoxy)phenyl)thieno[3,2-b]pyridin-7-yloxy)phenyl)-N$^2$-(2-methoxyphenethyl)oxalamide (136)

Step 1: 4-(7-(2-Fluoro-4-nitrophenoxy)thieno[3,2-b]pyridin-2-yl)-2-methoxyphenol (137)

Starting from the nitro compound 50 and 2-methoxy-4-(4,4,5,5-tetramethyl-1,3,2-dioxaborolan-2-yl)phenol, and following the same procedure as described for the synthesis of compound 63 (scheme 22) title compound 137 was obtained as light-brown solid in 72% yield. MS (m/z): 413.1 (M+H).

Step 2: 4-(2-(4-(7-(2-Fluoro-4-nitrophenoxy)thieno[3,2-b]pyridin-2-yl)-2-methoxyphenoxy)ethyl) morpholine (138)

DEAD (0.96 mL, 6.07 mmol) was added to a solution of the compound 137 (1.78 g, 4.33 mmol), 2-morpholinoethanol (0.74 mL, 6.07 mmol) and triphenylphosphine (1.59 g, 6.07 mmol) in THF (43 mL). The reaction mixture was stirred at room temperature until completion of the reaction. The mixture was quenched with a saturated aqueous solution of ammonium chloride then extracted three times with ethyl acetate and 3 times with dichloromethane (with a bit of methanol inside). The combined organic layers were washed with water and brine, dried over anhydrous MgSO$_4$, filtered and evaporated. The residue was triturated with diethyl ether, filtered and dried on a vacuum pump to afford title compound 138 as a yellow-brown solid (1.80 g, 79% yield). MS (m/z): 526.2 (M+H).

Step 3: 3-Fluoro-4-(2-(3-methoxy-4-(2-morpholinoethoxy)phenyl)thieno[3,2-h]pyridin-7-yloxy)aniline (139)

Starting from the nitro compound 138 and following the same procedure as described for the synthesis of the amine 23 (scheme 6) title compound 139 was obtained as yellow solid, in 99% yield (crude product). MS (m/z): 496.3 (M+H).

Step 4: Ethyl 2-(3-Fluoro-4-(2-(3-methoxy-4-(2-morpholinoethoxy)phenyl)thieno[3,2-b]pyridin-7-yloxy)phenylamino)-2-oxoacetate (140)

Ethyl chlorooxoacetate (0.11 mL, 0.95 mmol) was added to a solution of the amine 139 (313 mg, 0.63 mmol) and triethylamine (0.18 mL, 1.26 mmol) in dichloromethane (16 mL). The reaction mixture was stirred at room temperature until completion of the reaction. The mixture was quenched with a saturated aqueous solution of ammonium chloride and extracted three times with ethyl acetate. The combined organic layers were washed with brine, dried over anhydrous MgSO$_4$, filtered and evaporated. The crude product was purified by flash chromatography (eluent: 5% MeOH/95% DCM to 7% MeOH/93% DCM) to afford title compound 140 as a yellow solid (178 mg, 47% yield). MS (m/z): 596.1 (M+H).

Step 5: N$^1$-(3-Fluoro-4-(2-(3-methoxy-4-(2-morpholinoethoxy)phenyl)thieno[3,2-b]pyridin-7-yloxy)phenyl)-N$^2$-(2-methoxyphenethyl)oxalamide (136)

Amino ester 140 (80 mg, 0.13 mmol) and 2-(2-methoxyphenyl)ethanamine (0.2 mL, 1.34 mmol) were mixed together and stirred at room temperature until completion of the reaction. The mixture was quenched with a saturated aqueous solution of ammonium chloride and extracted three times with dichloromethane. The combined organic layers were washed with brine, dried over anhydrous MgSO$_4$, filtered and evaporated. The crude product was purified by flash chromatography (eluent: 3% MeOH/97% DCM to 5% MeOH/95% DCM). This solid product was then triturated with ethyl acetate to afford pure title compound 136 as a white solid (52 mg, 57% yield). $^1$H NMR (DMSO-d$_6$) δ (ppm): 11.03 (s, 1H), 9.04 (t, J=5.9 Hz, 1H), 8.48 (d, J=5.5 Hz, 1H), 8.05-8.01 (m, 2H), 7.82 (d, J=9.0 Hz, 1H), 7.53 (t, J=9.1 Hz, 1H), 7.47 (d, J=2.2 Hz, 1H), 7.38 (dd, J=2.2 and 8.2 Hz, 1H), 7.21 (td, J=1.8 and 7.8 Hz, 1H), 7.14 (dd, J=1.8 and 7.4 Hz, 1H), 7.11 (d, J=8.6 Hz, 1H), 6.97 (d, J=7.4 Hz, 1H), 6.88 (td, J=1.0 and 7.3 Hz, 1H), 6.60 (d, J=5.5 Hz, 1H), 4.14 (t, J=6.0 Hz, 2H), 3.89 (s, 3H), 3.80 (s, 3H), 3.59-3.57 (m, 4H), 3.46-3.41 (m, 2H), 2.83 (t, J=7.0 Hz, 2H), 2.73-2.70 (m, 2H), one peak (4H) did not show, it was probably under H$_2$O or DMSO. MS (m/z): 701.1 (M+H).

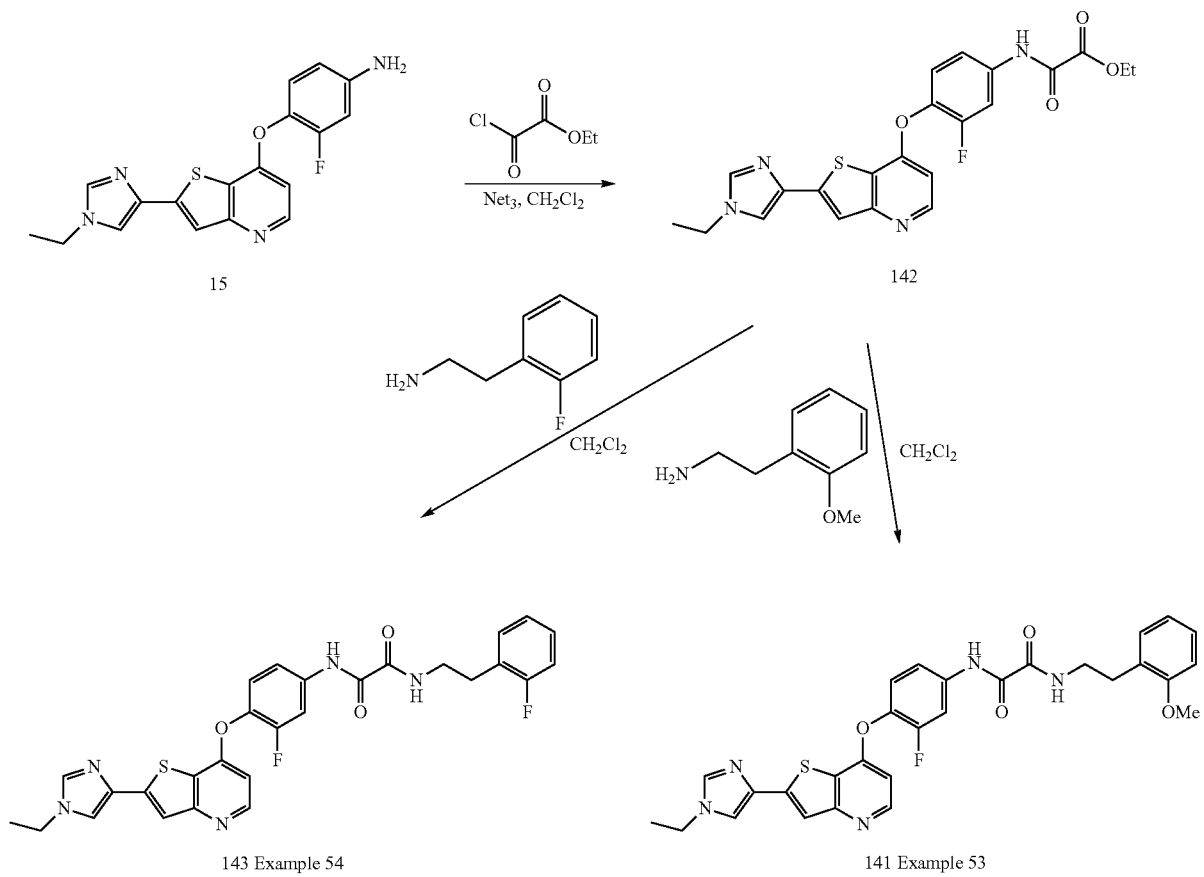

Scheme 41

Example 53

N[1]-(4-(2-(1-Ethyl-1H-imidazol-4-yl)thieno[3,2-b]pyridin-7-yloxy)-3-fluorophenyl)-N[2]-(2-methoxyphenethyl)oxalamide (141)

Step 1. Ethyl 2-(3-fluoro-4-(2-(1-ethyl-1H-imidazol-4-yl)thieno[3,2-b]pyridin-7-yloxy)phenylamino)-2-oxoacetate (142)

Starting from the amine 15 (scheme 4) and following the same procedure as described for the synthesis of compound 140 (scheme 40), title compound 142 was obtained as white solid in 14% yield. MS (m/z): 455.1 (M+H).

Step 2: N[1]-(4-(2-(1-Ethyl-1H-imidazol-4-yl)thieno[3,2-b]pyridin-7-yloxy)-3-fluorophenyl)-N[2]-(2-methoxyphenethyl)oxalamide (141)

Starting from the amino ester 142 and following the same procedure as described for the synthesis of compound 136 (example 52, scheme 40), title compound 141 was obtained as white solid in 90% yield. $^1$H NMR (DMSO-$d_6$) δ (ppm): 11.04 (s, 1H), 9.06 (t, J=6.4 Hz, 1H), 8.43 (d, J=5.6 Hz, 1H), 8.02 (dd, J=2.4 and 12.8 Hz, 1H), 7.97 (d, J=1.2 Hz, 1H), 7.84-7.78 (m, 1H), 7.79 (d, J=1.2 Hz, 1H), 7.67 (s, 1H), 7.52 (t, J=5.2 Hz, 1H), 7.20 (td, J=1.6 and 8.0 Hz, 1H), 7.14 (dd, J=1.6 and 7.2 Hz, 1H), 6.96 (d, J=8.0 Hz, 1H), 6.87 (t, J=7.2 Hz, 1H), 6.58 (d, J=5.6 Hz, 1H), 4.06 (q, J=7.2 Hz, 2H), 3.79 (s, 3H), 3.42 (q, J=7.2 Hz, 2H), 2.82 (t, J=7.2 Hz, 2H), 1.40 (7.2 Hz, 3H). MS (m/z): 560.2 (M+H).

Example 54

N[1]-(4-(2-(1-Ethyl-1H-imidazol-4-yl)thieno[3,2-b]pyridin-7-yloxy)-3-fluorophenyl)-N[3]-(2-fluorophenethyl)oxalamide (143)

Title compound 143 was obtained similarly to the compound 141 (example 53) according to the scheme 41. $^1$H NMR (DMSO-$d_6$) δ (ppm): 11.04 (s, 1H), 9.16 (t, J=6.0 Hz, 1H), 8.43 (d, J=5.6 Hz, 1H), 8.02 (dd, J=2.4 and 12.8 Hz, 1H), 7.96 (d. J=1.2 Hz, 1H), 7.84-7.79 (m, 1H), 7.79 (d, J=1.2 Hz, 1H), 7.68 (s, 1H), 7.52 (t, J=8.8 Hz, 1H), 7.34-7.24 (m, 2H), 7.19-7.11 (m, 2H), 6.58 (d, J=5.6 Hz, 1H), 4.06 (q, J=7.2 Hz, 2H), 3.46 (q, J=7.2 Hz, 2H), 2.88 (t, J=7.2 Hz, 2H), 1.40 (t. J=7.2 Hz, 3H).

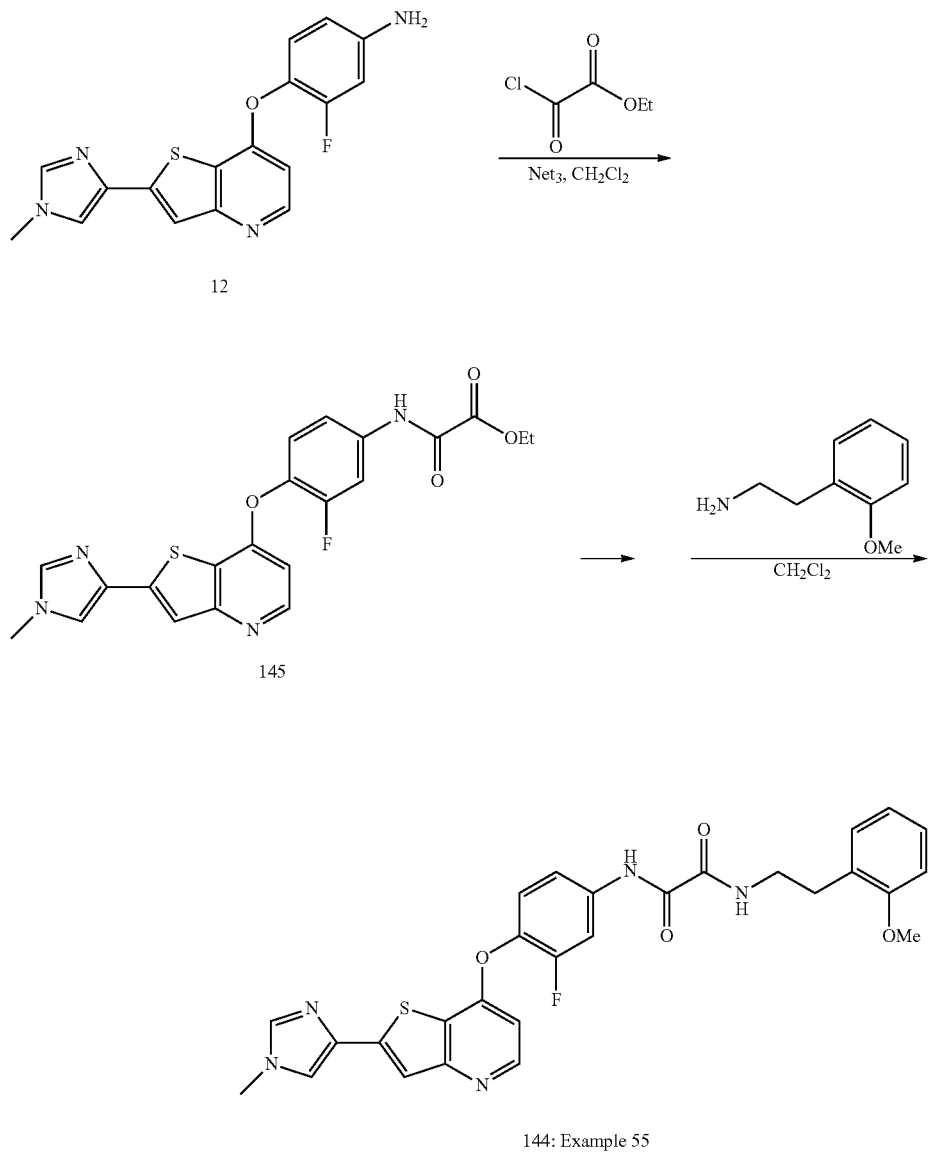

Example 55

N[1]-(3-Fluoro-4-(2-(1-methyl-1H-imidazol-4-yl)thieno[3,2-b]pyridin-7-yloxy)phenyl)-N[2]-(2-methoxyphenethyl)oxalamide (144)

Step 1. Ethyl 2-(3-fluoro-4-(2-(1-methyl-1H-imidazol-4-yl)thieno[3,2-b]pyridin-7-yloxy)phenylamino)-2-oxoacetate (145)

Starting from the amine 12 (scheme 3) and following the same procedure as described for the synthesis of compound 140 (scheme 40), title compound 145 was obtained as a white solid in 14% yield. MS (m/z): 441.1 (M+H).

Step 2. N[1]-(3-Fluoro-4-(2-(3-methoxy-4-(2-morpholinoethoxy)phenyl)thieno[3,2-b]pyridin-7-yloxy)phenyl)-N[2]-(2-methoxyphenethyl)oxalamide (144)

Starting from the amino ester 145 and following the same procedure as described for the synthesis of compound 136 (example 52, scheme 40), title compound 144 was obtained as white solid in 33% yield. $^1$H NMR (DMSO-$d_6$) δ (ppm): 11.03 (s, 1H), 9.04 (t, J=5.6 Hz, 1H), 8.43 (d, J=5.6 Hz, 1H), 8.02 (dd, J=2.4 and 12.8 Hz, 1H), 7.86 (s, 1H), 7.84-7.78 (m, 1H), 7.72 (s, 1H), 7.68 (s, 1H), 7.51 (t, J=8.8 Hz, 1H), 7.20 (td, J=1.6 and 7.6 Hz, 1H), 7.14 (dd, J=1.6 and 7.6 Hz, 1H), 6.96 (d, J=7.6 Hz, 1H), 6.87 (t, J=7.6 Hz, 1H), 6.58 (d, J=5.6 Hz, 1H), 3.799s, 3H), 3.72 (s, 3H), 3.43 (q, J=6.8 Hz, 2H), 2.82 (t. J=6.8 Hz, 2H). MS (m/z): 546.2 (M+H).

Scheme 43
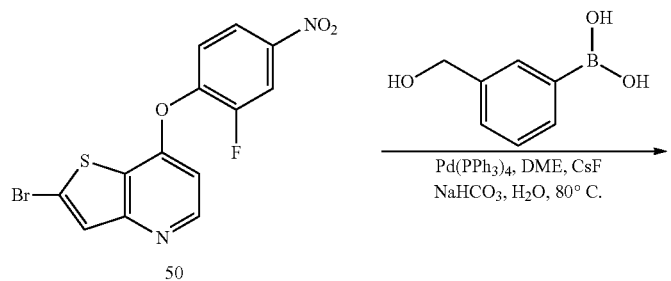
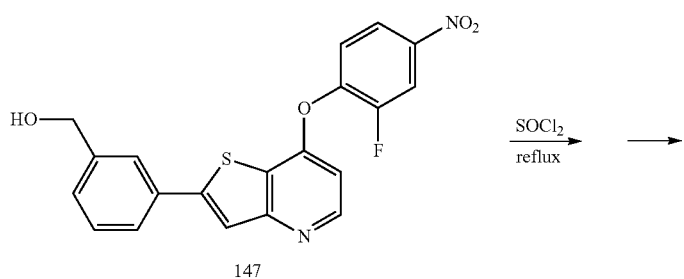
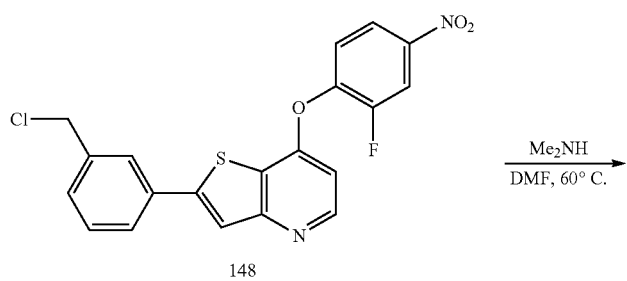
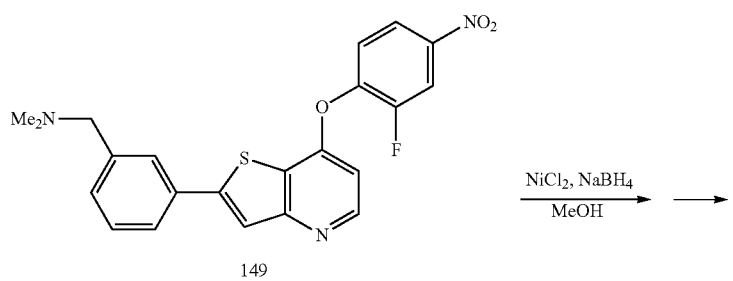
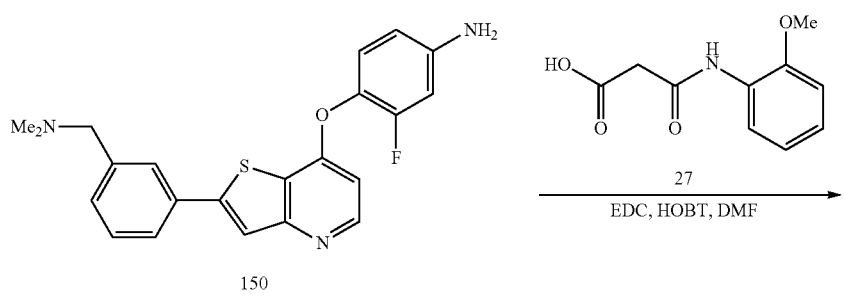

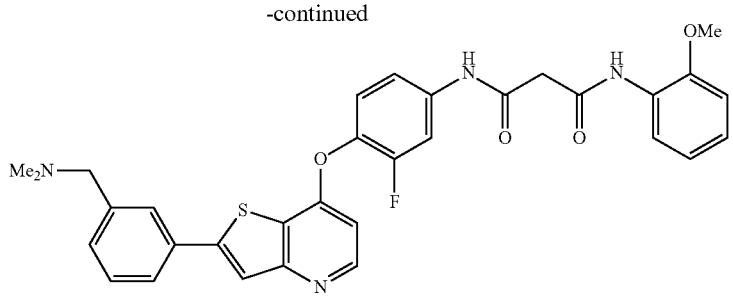

146: Example 56

Example 56

N¹-(4-(2-(3-((Dimethylamino)methyl)phenyl)thieno[3,2-b]pyridin-7-yloxy)-3-fluorophenyl)-N³-(2-methoxyphenyl)malonamide (146)

Step 1: (3-(7-(2-Fluoro-4-nitrophenoxy)thieno[3,2-b]pyridin-2-yl)phenyl)methanol (147)

Starting from the nitro compound 50 and 3-(hydroxymethyl)phenylboronic acid, and following the same procedure as described for the synthesis of compound 63 (scheme 22) title compound 147 was obtained as beige-brown solid in 71% yield. MS (m/z): 397.0 (M+H).

Step 2: 2-(3-(Chloromethyl)phenyl)-7-(2-fluoro-4-nitrophenoxy)thieno[3,2-b]pyridine (148)

The hydroxy-compound 147 (685 mg, 1.73 mmol) was suspended in thionyl chloride (8.6 mL) and the reaction mixture was refluxed for about one hour. The mixture was cooled to RT then poured into an ice/water mixture. The resultant solid was collected by filtration, washed with water and well dried to afford title compound 148 as a yellow solid (730 mg, 93% yield). MS (m/z): 415.0 (M+H).

Step 3: 1-(3-(7-(2-Fluoro-4-nitrophenoxy)thieno[3,2-b]pyridin-2-yl)phenyl)-N,N-dimethylmethanamine (149)

To a suspension of the chloride 148 (3.8 g, 8.42 mmol) in dimethylformamide (42 mL) was added dimethylamine (8.4 mL, 16.84 mmol) and the reaction mixture was heated to 60° C. After few hours the reaction was complete and the dimethylformamide was evaporated. The residue was triturated with ethyl acetate, collected by filtration, washed with ethyl acetate and dried to afford title compound 149 as a yellow solid (1.71 g, 48% yield). MS (m/z): 424.0 (M+H).

Step 4: 4-(2-(3-((Dimethylamino)methyl)phenyl)thieno[3,2-b]pyridin-7-yloxy)-3-fluoroaniline (150)

Starting from the compound 149 and following the same procedure as described above for the synthesis of compound 23 (scheme 6), title compound 150 was obtained in 44% yield MS (m/z): 394.0 (M+H).

Step 5: N¹-(4-(2-(3-((Dimethylamino)methyl)phenyl)thieno[3,2-b]pyridin-7-yloxy)-3-fluorophenyl)-N³-(2-methoxyphenyl)malonamide (146)

To a solution of the amine 150 (334 mg, 0.85 mmol), 3-(2-methoxyphenylamino)-3-oxopropanoic acid (27) (355 mg, 1.70 mmol), 1-hydroxybenzotriazole (275 mg, 2.04 mmol) in dimethylformamide (8.5 mL) was added N-(3-dimethylaminopropyl)-N-ethylcarbodiimide hydrochloride (391 mg, 2.04 mmol) and the reaction mixture was stirred at room temperature until completion of the reaction. The dimethylformamide was evaporated and the residue was quenched with a saturated solution of sodium bicarbonate. The aqueous layer was extracted three times with ethyl acetate. The combined organic layers were washed with water and brine, dried over anhydrous MgSO₄, filtered and evaporated to afford title compound 146 as a white solid (180 mg, 36% yield). ¹H NMR (DMSO-d₆) δ (ppm): 10.59 (s, 1H), 9.64 (s, 1H), 8.52-8.50 (m, 1H), 8.08-8.06 (m, 2H), 7.88 (d, J=12.9 Hz, 1H), 7.78 (m, 2H), 7.51-7.38 (m, 4H), 7.07 (s, 2H), 6.92 (m, 1H), 6.65 (m, 1H), 3.86 (s, 3H), 3.65 (s, 2H), 3.48 (s, 2H), 2.18 (s, 6H). MS (m/z): 585.2 (M+H).

Compounds 151 (example 57), 152 (example 58), 153 (example 59), 154 (example 60) and 155 (example 61), prepared according to the scheme 43.

TABLE 4

| Compd | Example | Structure | Characterization |
|---|---|---|---|
| 151 | 57 | 151: Example 57<br>N¹-3-fluoro-4-(2-(3-(morpholinomethyl)phenyl)thieno[3,2-b]pyridin-7-yloxy)phenyl)-N³-(2-methoxyphenyl)malonamide | ¹H NMR (DMSO-d₆) δ (ppm): 10.61 (s, 1H), 9.64 (s, 1H), 8.51 (d, J = 5.1 Hz, 1H), 8.08-8.06 (m, 2H), 7.89 (d, J = 13.1 Hz, 1H), 7.81 (s, 2H), 7.54-7.40 (m, 4H), 7.07 (s, 2H), 6.92 (m, 1H), 6.66 (m, 1H), 3.86 (s, 3H), 3.65-3.56 (m 8H), 2.40 (s, 4H). |

TABLE 4-continued

| Compd | Example | Structure | Characterization |
|---|---|---|---|
| 152 | 58 | 152: Example 58<br>N$^1$-(3-fluoro-4-(2-(3-(morpholinomethyl)phenyl)thieno[3,2-b]pyridin-7-yloxy)phenyl)- N$^3$-(2-fluorophenyl)malonamide | $^1$H NMR (DMSO-d$_6$) δ (ppm): 10.58 (s, 1H), 10.06 (s, 1H), 8.51 (d, J = 5.5 Hz, 1H), 8.06 (s, 1H), 8.01-7.90 (m, 1H), 7.87 (d, J = 2.2 Hz, 1H), 7.81-7.79 (m, 2H), 7.53-7.40 (m, 4H), 7.31-7.26 (m, 1H), 7.02-7.15 (m, 2H), 6.65 (d, J = 5.3 Hz, 1H), 3.63-3.56 (m, 8H), 2.40 (s, 4H). |
| 153 | 59 | 153: Example 59<br>N$^1$-(4-(2-(3-((dimethylamino)methyl)phenyl)thieno[3,2-b]pyridin-7-yloxy)-3-fluorophenyl)-N$^3$-(2-fluorophenyl)malonamide | $^1$H NMR (DMSO-d$_6$) δ (ppm): 10.59 (s, 1H), 10.07 (s, 1H), 8.51 (d, J = 5.5 Hz, 1H), 8.06 (s, 1H), 8.01-7.97 (m, 1H), 7.89 (dd, J = 12.9/2.3 Hz, 1H), 7.81-7.79 (m, 2H), 7.53-7.38 (m, 4H), 7.31-7.20 (m, 1H), 7.19-7.15 (m, 2H), 6.65 (d, J = 5.5 Hz, 1H), 3.63 (s, 2H), 3.49 (s, 2H), 2.19 (s, 6H). |
| 154 | 60 | 154: Example 60<br>N$^1$-(3-fluoro-4-(2-(4-((4-methylpiperazin-1-yl)methyl)phenyl)thieno[3,2-b]pyridin-7-yloxy)phenyl)-N$^3$-phenylmalonamide | $^1$H NMR (DMSO-d$_6$) δ (ppm): 10.63 (s, 1H), 10.26 (s, 1H) 8.50 (d, J = 5.5 Hz, 1H) 8.04 (s, 1H), 7.90 (dd, J = 13.0/2.3 Hz, 1H), 7.85 (d, J = 9.1 Hz, 2H), 7.62 (d, J = 7.4 Hz, 2H), 7.53-7.42 (m, 3H), 7.33 (t, J = 8.0 Hz, 2H), 7.09-7.05 (m, 2H), 6.64 (d, J = 4.9 Hz, 1H), 3.53 (s, 2H), 3.51 (s, 2H), 2.38-2.17 (m, 8H), 2.15 (s, 3H). |
| 155 | 61 | 155: Example 61<br>N$^1$-(3-fluoro-4-(2-(4-((4-methylpiperazin-1-yl)methyl)phenyl)thieno[3,2-b]pyridin-7-yloxy)phenyl)-N$^3$-methyl-N$^3$-phenylmalonamide | $^1$H NMR (DMSO-d$_6$) δ (ppm): 10.32 (s, 1H), 8.50 (d, J = 5.5 Hz, 1H), 8.04 (s, 1H), 7.86-7.79 (m, 3H), 7.50-7.13 (m, 9H), 6.62 (d, J = 5.5 Hz, 1H), 3.51 (s, 2H), 3.23-3.21 (m, 5H), 2.49-2.20 (m, 8H), 2.15 (s, 3H). |

Scheme 44

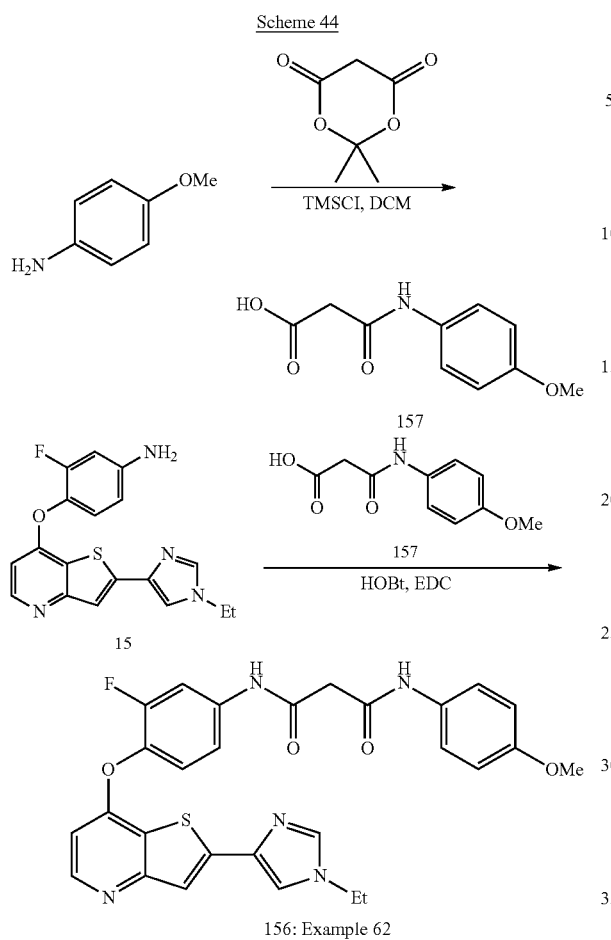

156: Example 62

Scheme 45

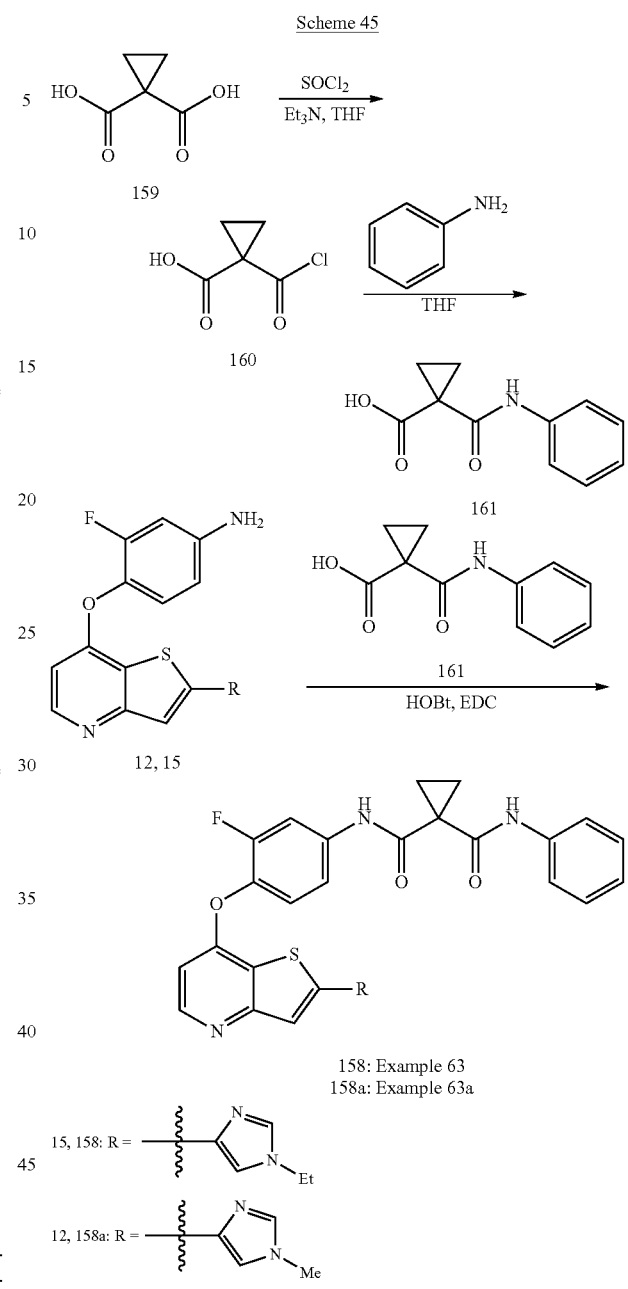

15, 158: R = imidazole-Et 12, 158a: R = imidazole-Me

Example 62

N$^1$-(4-(2-(1-ethyl-1H-imidazol-4-yl)thieno[3,2-b]pyridin-7-yloxy)-3-fluorophenyl)-N$^3$-(4-methoxyphenyl)malonamide (156)

Step 1: 3-(4-Methoxyphenylamino)-3-oxopropanoic acid (157)

Starting from 4-methoxyaniline and following the procedure described above for the synthesis of compound 27 (example 8, scheme 8), title compound 157 was obtained in 56% yield. MS (m/z): 210.0 (M+H).

Step 2: N$^1$-(4-(2-(1-Ethyl-1H-imidazol-4-yl)thieno[3,2-b]pyridin-7-yloxy)-3-fluoro phenyl)-N$^3$-(4-methoxyphenyl)malonamide (156)

Starting from the amine 15 (scheme 4) and following the procedure described above for the synthesis of compound 28a (example 8, step 2, scheme 8) title compound 156 was obtained in 42% yield. $^1$H NMR (DMSO-d$_6$) δ (ppm): 10.54 (s, 1H), 10.07 (s, 1H), 8.40 (d. J=5.3 Hz, 1H), 7.94 (d, J=1.2 Hz, 1H), 7.64 (dd. J=2.4 and 13.1 Hz, 1H), 7.77 (d, J=1.2 Hz, 1H), 7.65 (s, 1H), 7.51-7.49 (m, 2H), 7.46 (d, J=8.8 Hz, 1H), 7.41 (dd, J=1.0 and 9.0 Hz, 1H), 6.89-6.87 (m, 2H), 6.56 (d, J=5.5 Hz, 1H), 4.05 (q, 2H), 3.70 (s, 3H), 3.45 (s, 2H), 1.42 (t, 3H). MS (m/z): 546.0 (M+H).

Example 63

N-(4-(2-(1-Ethyl-1H-imidazol-4-yl)thieno[3,2-b]pyridin-7-yloxy)-3-fluorophenyl)-N-phenylcyclopropane-1,1-dicarboxamide (158)

Step 1: 1-(Phenylcarbamoyl)cyclopropanecarboxylic acid (161)

To a solution of di-acid 159 (2.5 g, 19.2 mmol) in THF (500 mL), was added Et$_3$N (1.40 mL, 19.2 mmol) dropwise under nitrogen and the mixture was stirred for 30 min at 0° C. before the addition of thionyl chloride (2.68 mL, 19.2 mmol). The reaction mixture was stirred for an additional 30 mins at 0° C. [to generate in situ the acyl chloride 160], followed by the addition of a solution of aniline (2.22 mL, 21.2 mmol) in THF (25 mL). The reaction mixture was stirred for 4 hrs at 0° C. then diluted with EtOAc and extracted three times with 2N NaOH solution. The aqueous phase was titrated with 2N HCl solution to PH~1-2, and then extracted with EtOAc. The organic phase was dried with Na₂SO₄ and concentrated under vacuum to give the title compound (161) (2.86 g, 72% yield) as a white solid. MS (m/z): 206.0 (M+H).

Step 2: N-(4-(2-(1-Ethyl-1H-imidazol-4-yl)thieno[3,2-b]pyridin-7-yloxy)-3-fluorophenyl)-N-phenyl cyclopropane-1,1-dicarboxamide (158)

Starting from the amine 15 and the acid 161, and following the procedure described above for the synthesis of the compound 28a (example 8, step 2, scheme 8) title compound 158 was obtained in 65% yield. $^1$H NMR (DMSO-$d_6$) δ (ppm): 10.35 (s, 1H), 9.99 (s, 1H), 8.42 (d, J=5.5 Hz, 1H), 7.94 (d, J=1.2 Hz, 1H), 7.88 (dd, J=2.1 and 14.1 Hz, 1H), 7.77 (d, J=1.2 Hz, 1H), 7.66 (s, 1H), 7.61 (dd, J=2.2 and 8.8 Hz, 2H), 7.49 (dd, J=1.9 and 8.8 Hz, 2H), 7.45 (t, 1H, J=8.8 Hz), 7.31-7.26 (m, 2H), 7.05 (t, 1H, J=6.1 Hz), 6.52 (d, J=5.4 Hz, 1H), 4.04 (q, 2H), 1.40 (s, 4H), 1.38 (t, 3H). MS (m/z): 542.1 (M+H).

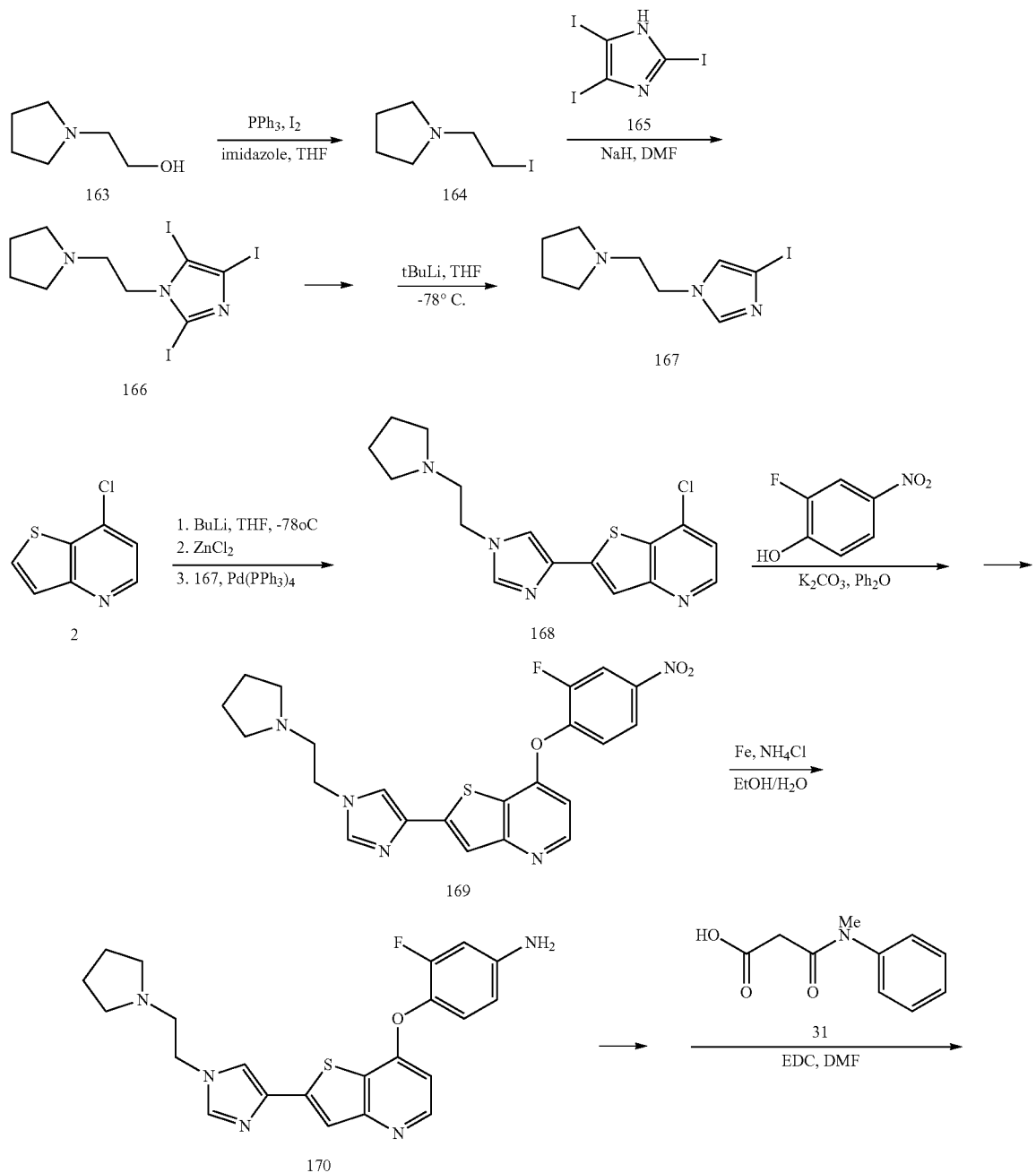

Scheme 46

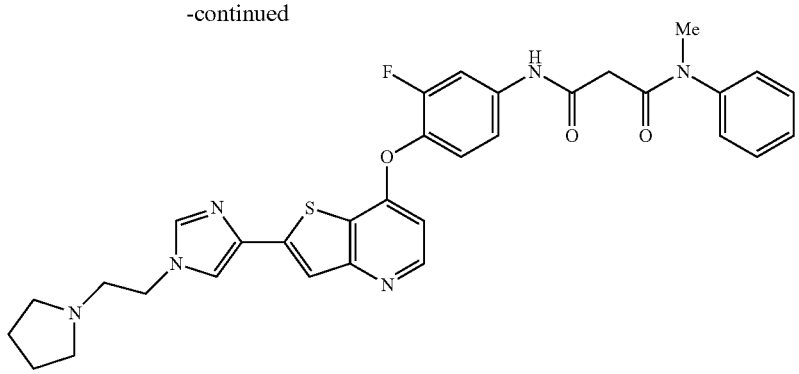

162: Example 64

Example 64

N[1]-(3-Fluoro-4-(2-(1-(2-(pyrrolidin-1-yl)ethyl)-1H-imidazol-4-yl)thieno[3,2-b]pyridin-7-yloxy)phenyl)-N-3-methyl-N-3-phenylmalonamide (162)

Step 1: 1-(2-Iodoethyl)pyrrolidine×HI (164)

A suspension of triphenylphosphine (4.46 g, 17.7 mmol), imidazole (1.2 g, 17.7 mmol) and iodine (4.50 g, 17.7 mmol) in THF (90 mL) was stirred for 5 min before 2-(pyrrolidin-1-yl)ethanol (163) (2 mL, 17.7 mmol) was added dropwise. The resultant precipitate was stirred for 4 hr. The resultant precipitate was collected by filtration, washed several time with EtOAc, and dried overnight to produce the title compound 164 (4.85 g, 76%) as a white solid. MS (m/z): 226.0 (M+H).

Step 2: 2,4,5-Triiodo-1-(2-(pyrrolidin-1-yl)ethyl)-1H-imidazole (166)

To a solution of 2,4,5-triiodo-1H-imidazole (165) (4.08 g, 9.1 mmol) in DMF (28 mL) at 0° C., was added NaH (1.46 g, 36.4 mmol) portionwise over 30 mins. Then 1-(2-iodoethyl)pyrrolidine×HI 164 (4.85 g, 13.65 mmol) was added at 0° C., and the reaction mixture was allowed to warm to room temperature over a period of 4 hrs. EtOAc (50 mL) was added and the mixture was washed with NaHCO$_3$ aqueous solution. The organic phase was separated and extracted with citric acid solution (3%), the acidic aqueous extract was basified with 2N NaOH solution to pH~10, the resultant solid was collected by filtration to give the title compound 166 (1.75 g, 35%) as a light brown solid. MS (m/z): 543.5 (M+H).

Step 3: 4-Iodo-1-(2-(pyrrolidin-1-yl)ethyl)-1H-imidazole (167)

To a solution of 2,4,5-triiodo-1-(2-(pyrrolidin-1-yl)ethyl)-1H-imidazole (166) (1.75 g, 3.22 mmol) in THF (32 mL) at −78° C. was added tBuLi (7.57 mL, 12.88 mmol) dropwise over a period of an hour. The reaction mixture was poured into water, extracted with EtOAc, and the organic extract was separated, dried over Na$_2$SO$_4$, and concentrated in vacuo to give the title compound 167 (0.9 g, 96% yield) as a dark yellow syrup. $^1$H NMR (DMSO-d$_6$) δ (ppm): 7.59 (s, 1H), 7.36 (s, 1H), 4.02 (m, 2H), 2.78 (m, 2H), 2.42 (m, 4H), 1.63 (m, 4H). MS (m/z): 292.1 (M+H).

Step 4: 7-Chloro-2-(1-(2-(pyrrolidin-1-yl)ethyl)-1H-imidazol-4-yl)thieno[3,2-b]pyridine (168)

Following the procedure described above for the synthesis of compound 123 (scheme 36) but replacing 4-iodo-1-isopropyl-1H-imidazole with the compound 167 title compound 168 was obtained in 47% yield as a yellow solid. MS (m/z): 333.0 (M+H).

Step 5: 7-(2-Fluoro-4-nitrophenoxy)-2-(1-(2-(pyrrolidin-1-yl)ethyl)-1H-imidazol-4-yl)thieno[3,2-b]pyridine (169)

Starting from the compound 168 and following the procedure described above for the synthesis of compound 124 (scheme 36), title compound 169 was obtained in 61% yield as a yellow solid. MS (m/z): 454.0 (M+H).

Step 6: 3-Fluoro-4-(2-(1-(2-(pyrrolidin-1-yl)ethyl)-1H-imidazol-4-yl)thieno[3,2-b]pyridin-7-yloxy)aniline (170)

To a solution of nitro compound 169 (400 mg, 0.88 mmol) in EtOH/H$_2$O (8 mL/4 mL) at 100° C. (bath) was added iron powder (420 mg, 7.48 mmol) and NH$_4$Cl (41 mg, 0.76 mmol) and the reaction mixture was stirred vigorously at reflux temperature for an hour. The mixture was cooled to room temperature and filtered through a Celite pad. The filtrate was collected and concentrated to give the title compound 170 (4.20 mg, 88% purity) as a yellow solid. MS (m/z): 424.0 (M+H).

Step 7: N[1]-(3-fluoro-4-(2-(1-(2-(pyrrolidin-1-yl)ethyl)-1H-imidazol-4-yl)thieno[3,2-b]pyridin-7-yloxy)phenyl)-N[3]-methyl-N[3]-phenylmalonamide (162)

Following the procedure described above for the compound 28a (example 8, step 2), but replacing amine 9 for amine 170, title compound 162 was obtained in 47% yield. $^1$H NMR (DMSO-d$_6$) δ (ppm): 10.29 (s, 1H), 8.42 (d, J=5.5 Hz, 1H), 7.94 (s, 1H), 7.77 (m, 2H), 7.66 (s, 1H), 7.46 (m, 3H), 7.39 (m, 3H), 7.30 (m, 1H), 6.56 (d, J=5.5 Hz, 1H), 4.11 (t, 2H), 3.19 (m, 4H), 3.14 (s, 3H), 2.77 (t, 2H), 1.65 (s, 4H). MS (m/z): 599.0 (M+H).

Scheme 47

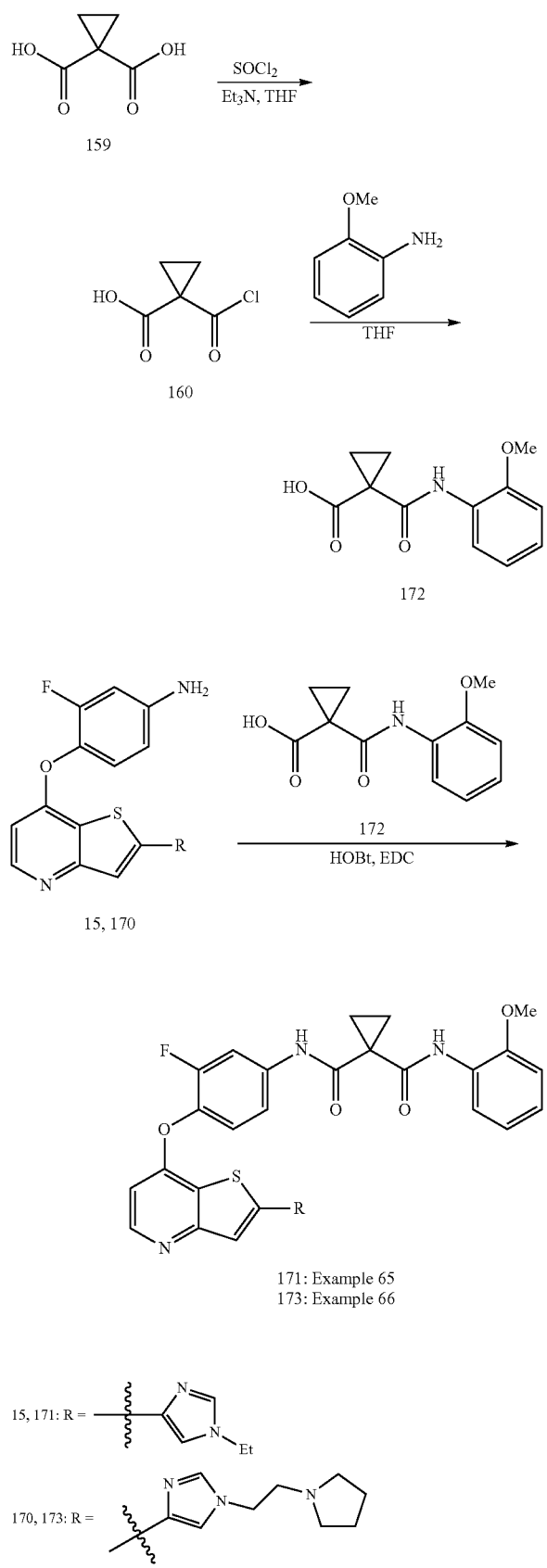

171: Example 65
173: Example 66

15, 171: R = (imidazole with Et)

170, 173: R = (imidazole with ethyl-pyrrolidine)

Example 65

N-(4-(2-(1-Ethyl-1H-imidazol-4-yl)thieno[3,2-b]pyridin-7-yloxy)-3-fluorophenyl)-N-(2-methoxyphenyl)cyclopropane-1,1-dicarboxamide (171)

Step 1: 1-(2-Methoxyphenylcarbamoyl)cyclopropanecarboxylic acid (172)

Following the procedure described above for the synthesis of compound 161 (Scheme 45), but replacing aniline for 2-methoxyaniline, title compound 172 was obtained in 44% yield. M/S (m/z): 236.0 (M+H).

Step 2: N-(4-(2-(1-ethyl-1H-imidazol-4-yl)thieno[3,2-b]pyridin-7-yloxy)-3-fluorophenyl)-N-(2-methoxyphenyl)cyclopropane-1,1-dicarboxamide (171)

Starting from the amine 15 and following the procedure described above for the synthesis of compound 28a (example 8, step 2, scheme 8), but replacing acid 27 for the acid 172, title compound 171 was obtained in 33% yield. $^1$H NMR (DMSO-$d_6$) δ (ppm): 10.29 (s, 1H), 10.11 (s, 1H), 8.42 (d, J=5.5 Hz, 1H), 8.04 (d, 1H, J=7.2 Hz), 7.94 (s, 1H), 7.82 (d, J=12.5 Hz, 1H), 7.77 (s, 1H), 7.66 (s, 1H), 7.50 (m, 2H), 7.05 (m, 2H), 6.90 (t, 1H), 6.56 (d, J=5.5 Hz, 1H), 4.04 (q, 2H), 3.81 (s, 3H), 1.59 (s, 2H), 1.55 (s, 2H), 1.38 (t, 3H). MS (m/z): 572.0 (M+H).

Example 66

N-(3-Fluoro-4-(2-(1-(2-(pyrrolidin-1-yl)ethyl)-1H-imidazol-4-yl)thieno[3,2-b]pyridin-7-yl oxy)phenyl)-N-(2-methoxyphenyl)cyclopropane-1,1-dicarboxamide (173)

Following the procedure described above for the compound 28a (example 8, step 2, scheme 8), but replacing amine 9 for amine 65 and acid 27 for the acid 172, title compound 173 was obtained in 11% yield. $^1$H NMR (DMSO-$d_6$) δ (ppm): 10.29 (s, 1H), 10.12 (s, 1H), 8.42 (d, J=5.5 Hz, 1H), 8.12 (s, 1H), 8.02 (d, J=7.6 Hz, 1H), 7.92 (s, 1H), 7.82 (d, J=13.7 Hz, 1H), 7.77 (s, 1H), 7.66 (s, 1H), 7.50 (m, 2H), 7.05 (m, 2H), 6.90 (m, 1H), 6.56 (d, J=5.5 Hz, 1H), 4.13 (t, 2H), 3.81 (s, 3H), 2.84 (s, 2H), 2.53 (s, 2H), 2.47 (s, 2H), 1.67 (m, 4H), 1.59 (m, 2H), 1.55 (m, 2H). MS (m/z): 641.0 (M+H).

Scheme 48

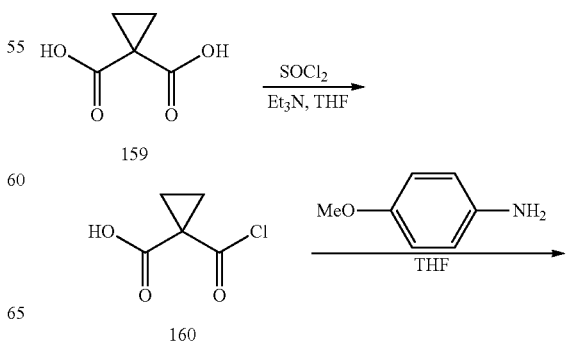

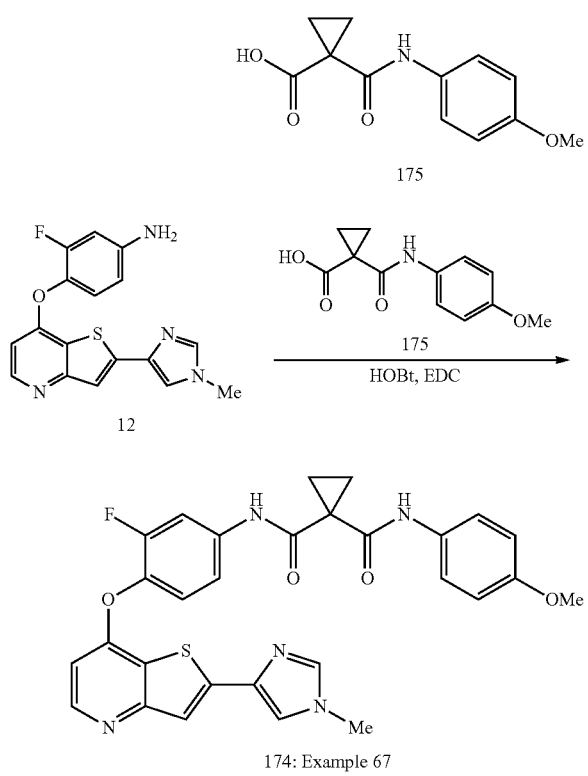
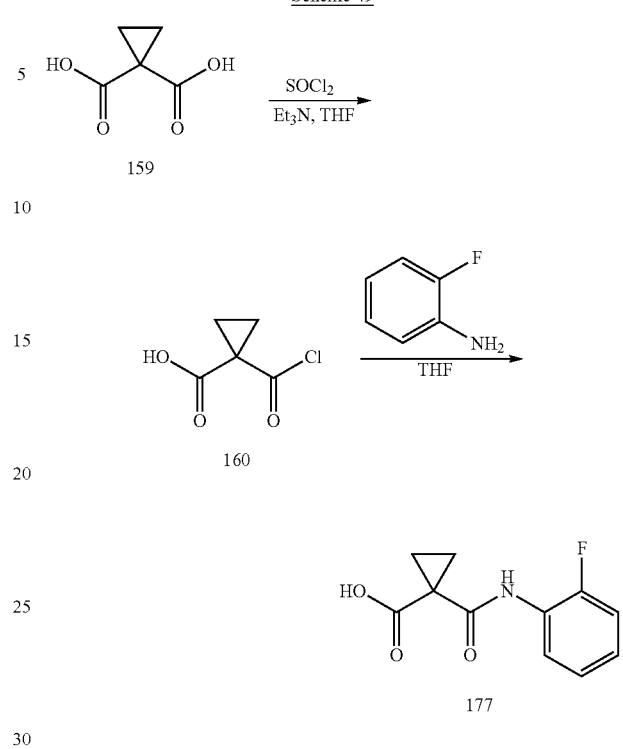

Example 67

N-(3-Fluoro-4-(2-(1-methyl-1H-imidazol-4-yl)thieno[3,2-b]pyridin-7-yloxy)phenyl)-N-(4-methoxyphenyl)cyclopropane-1,1-dicarboxamide (174)

Step 1:
1-(2-Methoxyphenylcarbamoyl)cyclopropanecarboxylic acid (175)

Following the procedure described above for compound 161 (scheme 45), but replacing aniline for 4-methoxyaniline, title compound 175 was obtained in 68% yield. M/S (m/z): 236.0 (M+H).

Step 2: N-(3-Fluoro-4-(2-(1-methyl-1H-imidazol-4-yl)thieno[3,2-b]pyridin-7-yloxy)phenyl)-N-(4-methoxyphenyl)cyclopropane-1,1-dicarboxamide (174)

Following the procedure described above for the compound 5c (scheme 3), but replacing amine acid 1 for the acid 175, title compound 174 was obtained in 44% yield. $^1$H NMR (DMSO-$d_6$) δ(ppm): 10.44 (s, 1H), 9.78 (s, 1H), 8.42 (d, J=5.5 Hz, 1H), 7.87 (dd, J=1.2 and 7.4 Hz, 1H), 7.84 (s, 1H), 7.70 (s, 1H), 7.66 (s, 1H), 7.49 (m, 3H), 7.42 (t, J=9.0 Hz, 1H), 6.87 (m, 2H), 6.53 (d, J=5.5 Hz, 1H), 3.71 (s, 3H), 1.44 (t, 3H). MS (m/z): 558.0 (M+H).

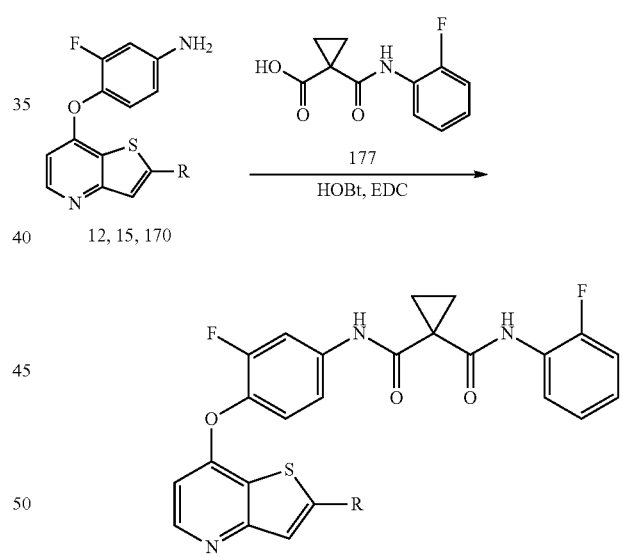
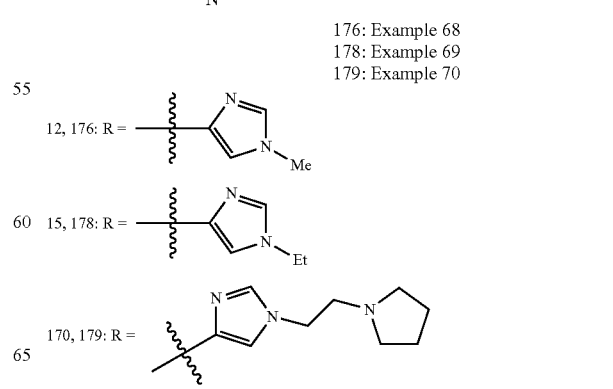

Example 68

N-(3-Fluoro-4-(2-(1-methyl-1H-imidazol-4-yl)thieno[3,2-b]pyridin-7-yloxy)phenyl)-N-(2-fluorophenyl)cyclopropane-1,1-dicarboxamide (176)

Step 1: 1-(2-Fluorophenylcarbamoyl)cyclopropanecarboxylic acid (68)

Following the procedure described above for compound 161 (scheme 45), but replacing aniline for 2-fluoroaniline, title compound 177 was obtained in 57% yield. M/S (m/z): 224.0 (M+H).

Step 2: N-(3-Fluoro-4-(2-(1-methyl-1H-imidazol-4-yl)thieno[3,2-b]pyridin-7-yloxy)phenyl)-N-(4-methoxyphenyl)cyclopropane-1,1-dicarboxamide (176)

Starting from the amine 12, following the procedure described above for the synthesis of compound 5c (scheme 3), but replacing acid 1 for the acid 177, title compound 176 was obtained in 30% yield. $^1$H NMR (DMSO-$d_6$) δ(ppm): 10.34 (s, 1H), 10.26 (s, 1H), 8.42 (d, J=5.5 Hz, 1H), 7.86-7.82 (m, 3H), 7.70 (s, 1H), 7.66 (s, 1H), 7.51-7.43 (m, 2H), 7.28-7.23 (m, 1H), 7.18-7.15 (m, 2H), 6.55 (d, J=5.5 Hz, 1H), 3.71 (s, 3H), 1.60-1.53 (m, 4H). MS (m/z): 546.1 (M+H).

Example 69

N-(4-(2-(1-ethyl-1H-imidazol-4-yl)thieno[3,2-b]pyridin-7-yloxy)-3-fluorophenyl)-N-(2-fluorophenyl)cyclopropane-1,1-dicarboxamide (178)

Starting from the amine 15, following the procedure described above for the synthesis of compound 5d (scheme 4) but replacing acid 1 for the acid 177, title compound 178 was obtained in 13% yield. $^1$H NMR (DMSO-$d_6$) δ (ppm): 10.34 (s, 1H), 10.26 (s, 1H), 8.42 (d, J=5.5 Hz, 1H), 7.95 (s, 1H), 7.86-7.83 (m, 2H), 7.77 (d, 1H, J=1.2 Hz), 7.66 (s, 1H), 7.51-7.43 (m, 2H), 7.28-7.23 (m, 1H), 7.17-7.15 (m, 2H), 6.54 (d, J=5.5 Hz, 1H), 4.04 (q, 2H), 1.60-1.53 (m, 4H), 1.38 (t, 3H). MS (m/z): 560.2 (M+H).

Example 70

N-(3-Fluoro-4-(2-(1-(2-(pyrrolidin-1-yl)ethyl)-1H-imidazol-4-yl)thieno[3,2-b]pyridin-7-yloxy)phenyl)-N-(2-fluorophenyl)cyclopropane-1,1-dicarboxamide (179)

Starting from the amine 170 (scheme 46), following the procedure described above for the compound 28a (example 8, step 2), but replacing acid 27 for the acid 177, title compound 179 was obtained in 11% yield. $^1$H NMR (DMSO-$d_6$) δ (ppm): 10.28 (s, 1H), 10.26 (s, 1H), 8.42 (d, J=5.5 Hz, 1H), 7.92 (d, J=1.1 Hz, 1H), 7.86 (d, J=1.9 Hz, 1H), 7.83-7.79 (m, 1H), 7.76 (d, 1H, J=1.4 Hz), 7.66 (s, 1H), 7.49 (dd, J=2.1 and 9.0 Hz, 1H), 7.45 (t, J=8.6 Hz, 1H), 7.28-7.23 (m, 1H), 7.17-7.14 (m, 2H), 6.54 (d, 1H, J=5.5 Hz), 4.12 (q, 2H), 2.76 (t, 2H), 2.45 (m, 2H), 1.67-1.64 (m, 4H), 1.60-1.53 (m, 4H). MS (m/z): 629.1 (M+H).

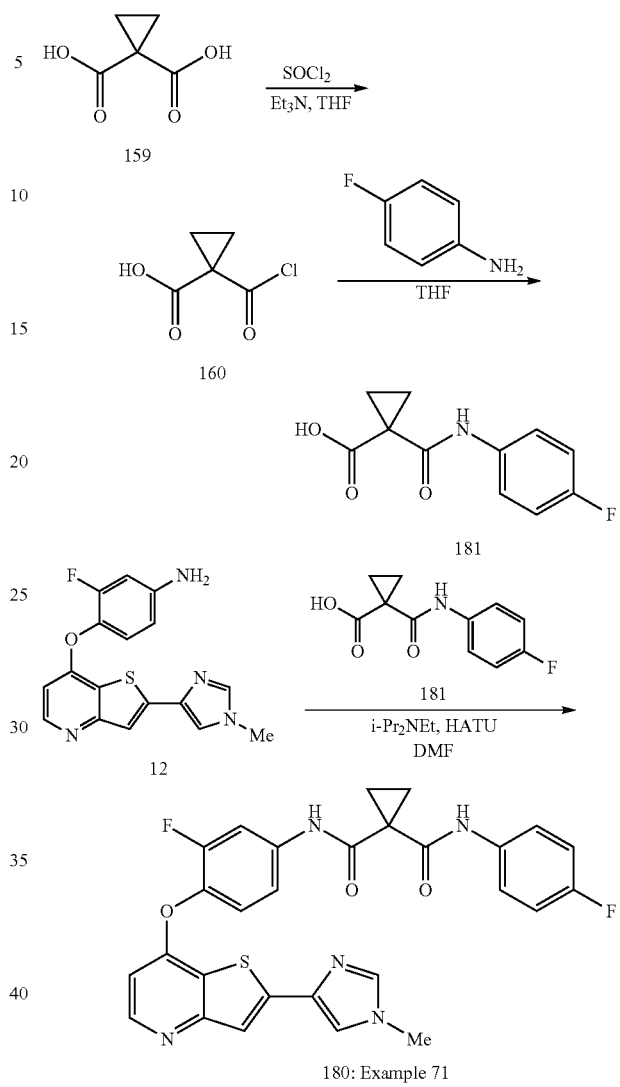

Scheme 50

180: Example 71

Example 71

N-(3-Fluoro-4-(2-(1-methyl-1H-imidazol-4-yl)thieno[3,2-b]pyridin-7-yloxy)phenyl)-N-(4-fluorophenyl)cyclopropane-1,1-dicarboxamide (180)

Step 1: 1-(4-Fluorophenylcarbamoyl)cyclopropanecarboxylic acid (181)

Following the procedure described above for the compound 161 (scheme 45), but replacing aniline for 4-fluoroaniline, title compound 181 was obtained in 57% yield. MS (m/z): 224.0 (M+H).

Step 2: N-(3-Fluoro-4-(2-(1-methyl-1H-imidazol-4-yl)thieno[3,2-b]pyridin-7-yloxy)phenyl)-N-(4-fluorophenyl)cyclopropane-1,1-dicarboxamide (180)

Starting from the amine 12 (scheme 3) and following the procedure described above for the compound 5c (example 3, scheme 3), but replacing acid 1 for the acid 181, title compound 180 was obtained in 24% yield. ¹H NMR (DMSO-d₆) δ (ppm): 10.39 (s, 1H), 10.01 (s, 1H), 8.42 (d, J=5.5 Hz, 1H), 7.87 (dd, J=14.2 and 2.4 Hz, 1H), 7.85 (d, 1H, J=1.2 Hz), 7.70 (d, 1H, J=1.1 Hz), 7.66 (s, 1H), 7.64-7.61 (m, 2H), 7.50 (dd, J=2.0 and 8.8 Hz, 1H), 7.43 (t, 1H, J=8.8 Hz), 7.16-7.11 (m, 2H), 6.55 (d, 1H, J=5.5 Hz), 3.71 (s, 3H), 1.44 (m, 4H). MS (m/z): 546.0 (M+H).

(125 mg, 1.5 eq, 5.61 mmol), iPr₂NEt (16 mg, 3.5 eq, 1.31 mmol) and HATU (426 mg, 3 eq, 1.12 mmol). The reaction mixture was stirred at RT for 24 hrs. The reaction mixture was concentrated to dryness and partitioned between satd NaHCO₃ solution and EtOAc. The EtOAc was washed twice with satd NaHCO₃ solution before being dried over anhydrous Na₂SO₄ and filtered. The solvent was removed under reduced pressure and the crude mixture was purified initially Scheme 51

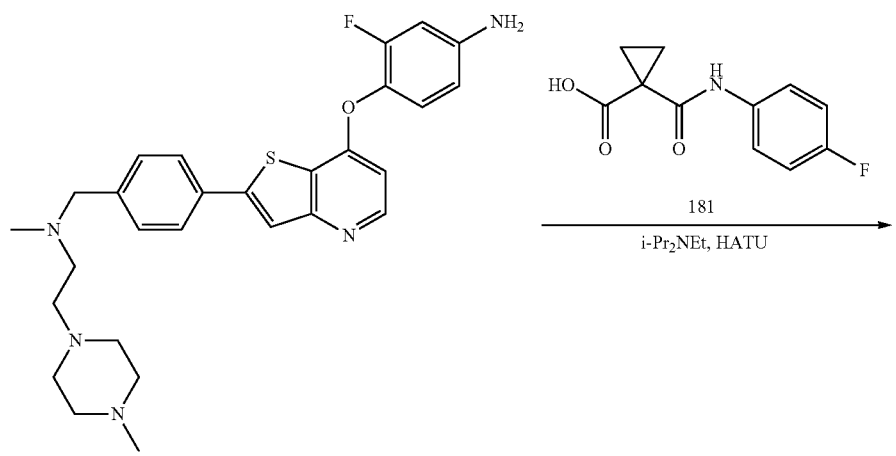

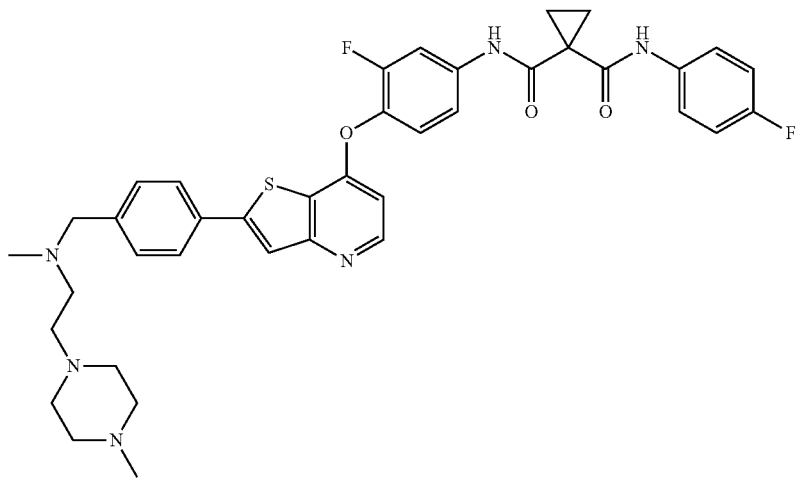

182: Example 72

Example 72

N-(3-Fluoro-4-(2-(4-((methyl(2-(4-methylpiperazin-1-yl)ethyl)amino)methyl)phenyl)thieno[3,2-b]pyridin-7-yloxy)phenyl)-N-(4-fluorophenyl)cyclopropane-1,1-dicarboxamide (182)

To a solution of the amine compound 80 (189 mg, 0.374 mmol) (scheme 26) in DMF (~7 ml) was added the acid 181 by column chromatography (25% MeOH/EtOAc+1% NH₄OH solution) and then using the Gilson (30% MeOH/H₂O to 80% MeOH/H₂O over 45 mins) to afford title compound 182 as a white solid (64 mg, 24% yield). ¹H NMR (DMSO-d₆) δ (ppm): 8.48 (d, J=5.48 Hz, 1H), 8.02 (s, 1H), 7.90 (dd, J=1.77 and 12.91 Hz, 1H), 7.82 (d, J=8.22 Hz, 2H), 7.62 (m, 2H), 7.42 (m, 4H), 7.13 (t, J=8.99 Hz, 2H), 6.58 (d, J=5.48 Hz, 1H), 3.51 (s, 1H), 2.40 (m, 12H), 2.14 (s, 3H), 2.10 (s, 3H), 1.44 (m, 4H). MS (m/z): 711.1 (M+H). (formate salt)

Scheme 52
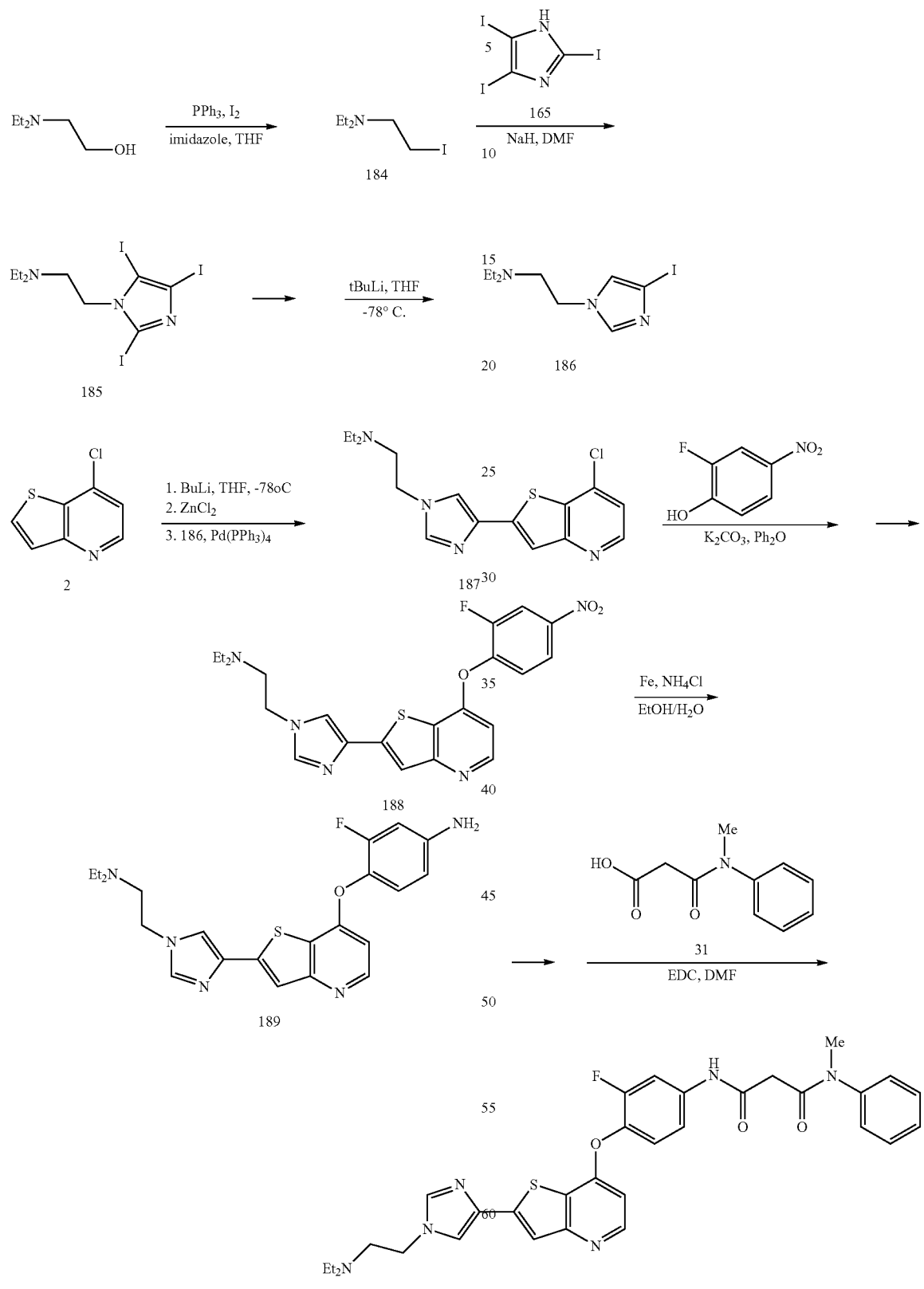
183: Example 73

Example 73

N¹-(4-(2-(1-(2-(Diethylamino)ethyl)-1H-imidazol-4-yl)thieno[3,2-b]pyridin-7-yloxy)-3-fluorophenyl)-N³-methyl-N³-phenylmalonamid (183)

Step 1: N,N-Diethyl-2-iodoethanamine (184)

Following the procedure described above for the synthesis of compound 164 (scheme 46), title compound 184 was obtained in 42% yield. MS (m/z): 228.0 (M+H).

Step 2: N,N-Diethyl-2-(2,4,5-triiodo-1H-imidazol-1-yl)ethanamine (185)

Following the procedure described above for the synthesis of compound 166 (scheme 46), title compound 185 was obtained in 62% yield. MS (m/z): 546.0 (M+H).

Step 3: N,N-Diethyl-2-(4-iodo-1H-imidazol-1-yl)ethanamine (186)

Following the procedure described above for the synthesis of compound 167 (scheme 46), title compound 186 was obtained in 97% yield. MS (m/z): 294.0 (M+H).

Step 4: 2-(4-(7-Chlorothieno[3,2-b]pyridin-2-yl)-1H-imidazol-1-yl)-N,N-diethylethanamine (187)

Following the procedure described above for the synthesis of compound 168 (scheme 46), title compound 187 was obtained in 78% yield. MS (m/z): 335.0 (M+H).

Step 5: NA-Diethyl-2-(4-(7-(2-fluoro-4-nitrophenoxy)thieno[3,2-b]pyridin-2-yl)-1H-imidazol-1-yl)ethanamine (188)

Following the procedure described above for the synthesis of compound 169 (scheme 46), title compound 188 was obtained in 10% yield. MS (m/z): 456.0 (M+H).

Step 6: 4-(2-(1-(2-(Diethylamino)ethyl)-1H-imidazol-4-yl)thieno[3,2-b]pyridin-7-yloxy)-3-fluoroaniline (189)

Following the procedure described above for the synthesis of compound 170 (scheme 46), title compound 189 was obtained in 83% yield. MS (m/z): 426.0 (M+H).

Step 7: N¹-(4-(2-(1-(2-(diethylamino)ethyl)-1H-imidazol-4-yl)thieno[3,2-b]pyridin-7-yloxy)-3-fluorophenyl)-N³-methyl-N³-phenylmalonamid (183)

Following the procedure described above for the synthesis of compound 163 (scheme 46), title compound 183 was obtained in 38% yield. ¹H NMR (DMSO-d₆) δ (ppm): 10.34 (s, 1H), 8.40 (d, J=5.3 Hz, 2H), 7.91 (s, 1H), 7.79 (m, 2H), 7.63 (s, 1H), 7.46-7.28 (m, 7H), 6.54 (d, J=5.5 Hz, 1H), 4.03 (t, 2H), 3.20-3.19 (m, 5H), 2.70 (t, 2H), 2.44 (q, 4H), 0.89 (t, 6H). MS (m/z): 601.0 (M+H).

Scheme 53

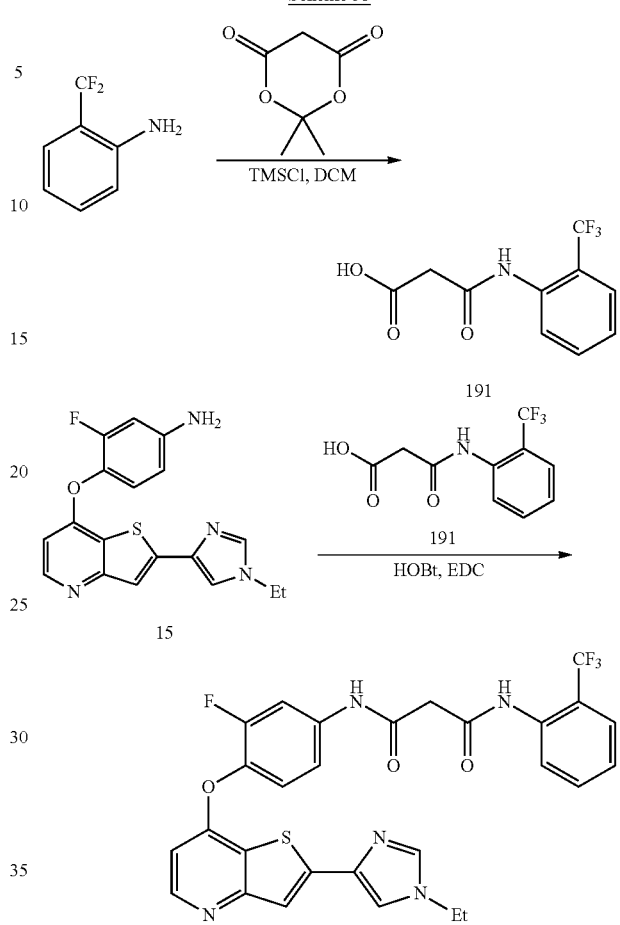

190: Example 74

Example 74

N¹-(4-(2-(1-Ethyl-1H-imidazol-4-yl)thieno[3,2-b]pyridin-7-yloxy)-3-fluorophenyl)-N³-(2-(trifluoromethyl)phenyl)malonamide (190)

Step 1: 3-Oxo-3(2-(trifluoromethyl)phenylamino)propanoic acid (191)

Following the procedure described above for the synthesis of compound 27 (scheme 8) but replacing 2-methoxybenzenamine with 2-(trifluoromethyl)benzenamine title compound 191 was obtained in 6% yield. MS (m/z): 248.0 (M+H).

Step 2: N′44-(2-(1-Ethyl-1H-imidazol-4-yl)thieno[3,2-b]pyridin-7-yloxy)-3-fluoro phenyl)-N³-(2-(trifluoromethyl)phenyl)malonamide (190)

Starting from the amine 15 and following the procedure described above for the synthesis of compound 28a (example 8, step 2, scheme 8) but replacing acid 27 with the acid 191 title compound 190 was obtained in 27% yield. ¹H NMR (DMSO-d₆) δ (ppm): 10.57 (s, 1H), 10.56 (s, 1H), 8.40 (d, J=5.3 Hz, 1H), 8.10 (s, 1H), 7.94 (d, J=1.2 Hz, 1H), 7.85 (dd, J=2.2 and 13.0 Hz, 1H), 7.77 (s, 1H), 7.76 (d, J=8.6 Hz, 1H), 7.65 (s, 1H), 7.56 (t, J=7.8 Hz, 1H), 7.44 (t, 1H, J=8.6 Hz), 7.41-7.40 (m, 2H), 6.56 (d, 1H), 4.03 (q, 2H), 3.54 (s, 1H), 1.33 (t, 3H). MS (m/z): 583.1.0 (M+H).

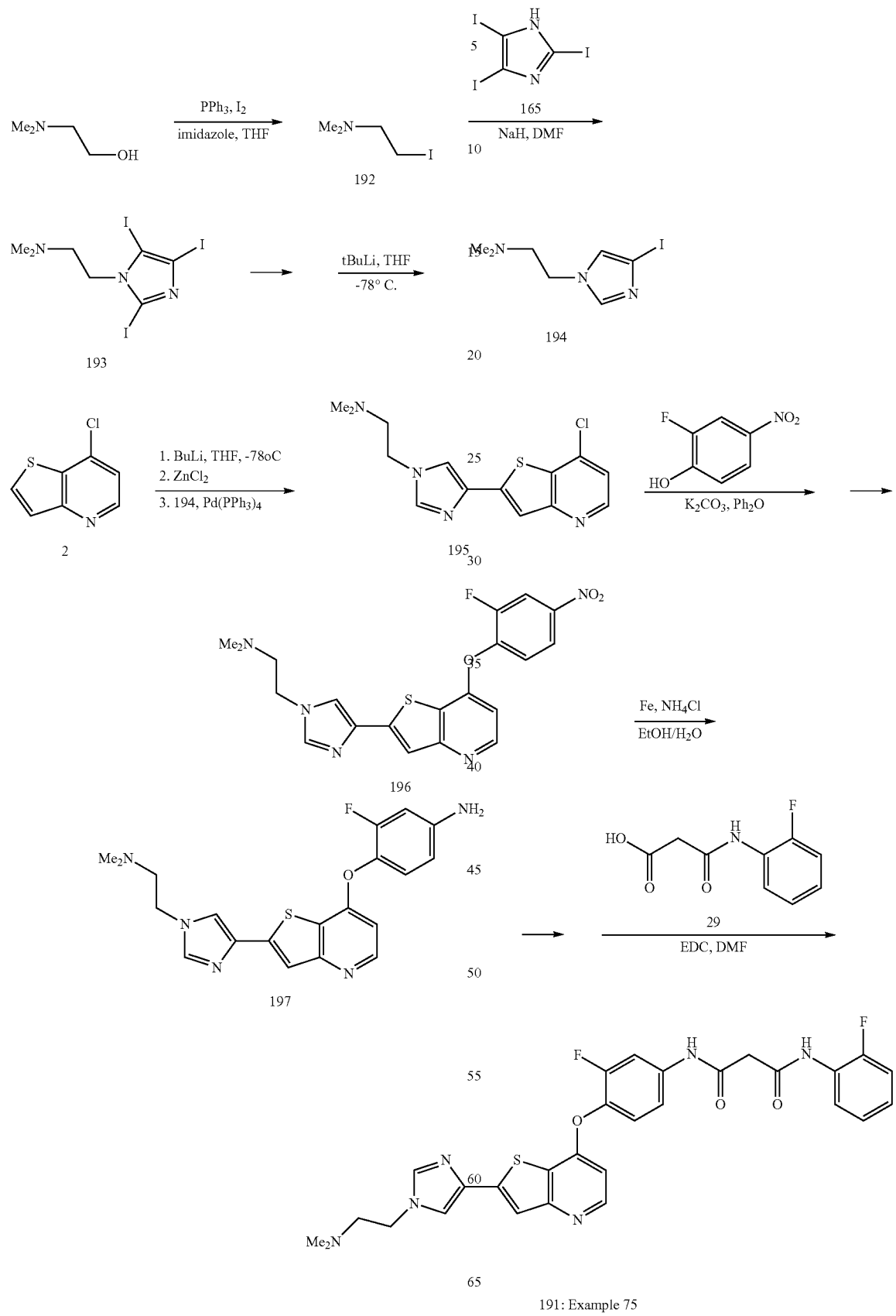

Example 75

N¹-(4-(2-(1-(2-(Dimethylamino)ethyl)-1H-imidazol-4-yl)thieno[3,2-b]pyridin-7-yloxy)-3-fluorophenyl)-N³-(2-fluorophenyl)malonamide (191)

Step 1: 2-Iodo-N,N-dimethylethanamine (192)

Following the procedure described above for the synthesis of compound 164 (scheme 46), title compound 192 was obtained in 61% yield. MS (m/z): 200.0 (M+H).

Step 2: N,N-Dimethyl-2-(2,4,5-triiodo-1H-imidazol-1-yl)ethanamine (193)

Following the procedure described above for the synthesis of compound 166 (scheme 46), title compound 193 was obtained in 27% yield. MS (m/z): 518.0 (M+H).

Step 3: 2-(4-iodo-1H-imidazol-1-yl)-N,N-dimethylethanamine (194)

Following the procedure described above for the compound 167 (scheme 46), title compound 194 was obtained in 97% yield. MS (m/z): 266.0 (M+H).

Step 4: 2-(4-(7-Chlorothieno[3,2-b]pyridin-2-yl)-1H-imidazol-1-yl)-N,N-dimethylethanamine 95)

Following the procedure described above for the compound 168 (scheme 46), title compound 195 was obtained in 41% yield. MS (m/z): 307.0 (M+H).

Step 5: 2-(4-(7-(2-Fluoro-4-nitrophenoxy)thieno[3,2-b]pyridin-2-yl)-1H-imidazol-1-yl)-N,N-dimethylethanamine (196)

Following the procedure described above for the compound 168 (scheme 46), title compound 196 was obtained in 36% yield. MS (m/z): 428.0 (M+H).

Step 6: 4-(2-(1-(2-(Dimethylamino)ethyl)-1H-imidazol-4-yl)thieno[3,2-b]pyridin-7-yloxy)-3-fluoroaniline (197)

Following the procedure described above for the compound 170 (scheme 46), title compound 197 was obtained in 93% yield. MS (m/z): 398.0 (M+H).

Step 7: N¹-(4-(2-(1-(2-(Dimethylamino)ethyl)-1H-imidazol-4-yl)thieno[3,2-b]pyridin-7-yloxy)-3-fluorophenyl)-N³-(2-fluorophenyl)malonamide (191)

Following the procedure described above for the compound 163 (scheme 46), title compound 191 was obtained in 55% yield. ¹H NMR (DMSO-d₆) δ (ppm): 10.61 (s, 1H), 10.07 (s, 1H), 8.40 (d, J=5.5 Hz, 1H), 8.38 (s, 1H), 7.99-7.93 (m, 1H), 7.90 (d, J=1.0 Hz, 1H), 7.85 (dd, J=2.1 and 13.1 Hz, 1H), 7.75 (d, J=1.0 Hz, 1H), 7.64 (s, 1H), 7.47 (t, 1H, J=8.8 Hz), 7.40 (dd, J=2.1 and 8.8 Hz, 1H), 7.29-7.23 (m, 1H), 7.18-7.12 (m, 2H), 6.55 (d, J=5.5 Hz, 1H), 4.09 (t, J=6.2 Hz, 2H), 3.61 (s, 2H), 2.59 (t, J=6.2 Hz, 2H), 2.17 (s, 6H). MS (m/z): 577.1 (M+H).

Scheme 55

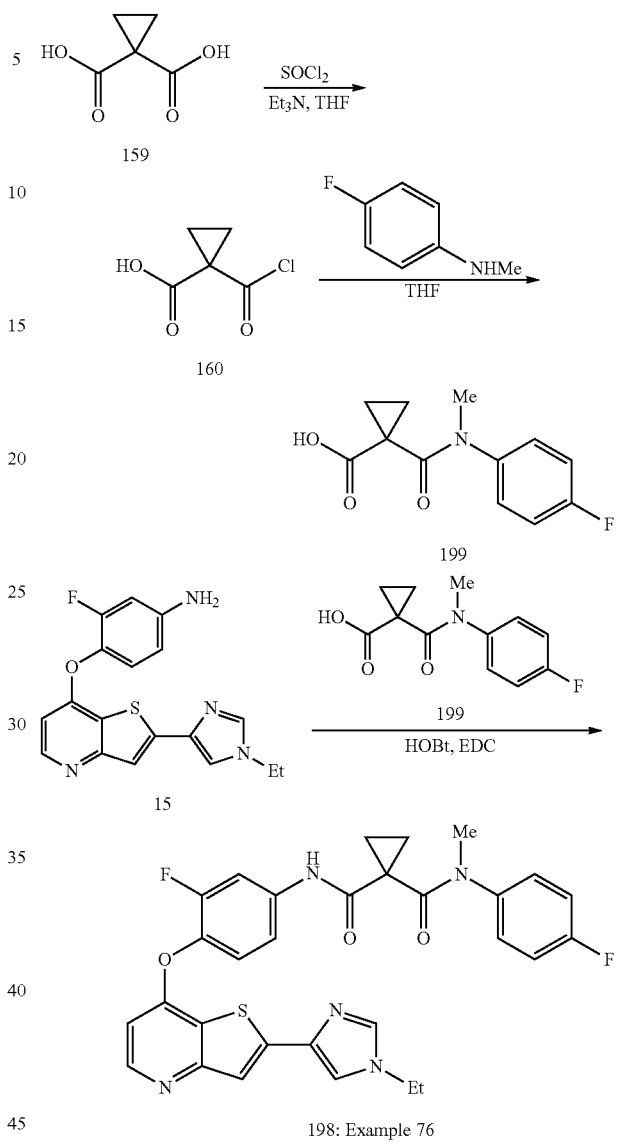

198: Example 76

Example 76

N-(4-(2-(1-Ethyl-1H-imidazol-4-yl)thieno[3,2-b]pyridin-7-yloxy)-3-fluorophenyl)-N-(2-fluorophenyl)-N-methylcyclopropane-1,1-dicarboxamide (198)

Step 1: 1-((4-Fluorophenyl)(methyl)carbamoyl)cyclopropanecarboxylic acid (199)

Following the procedure described above for the synthesis of compound 161 (scheme 45), but replacing aniline for 4-fluoro-N-methylaniline, title compound 199 was obtained in 66% yield. M/S (m/z): 238.0 (M+H).

Step 2: N-(4-(2-(1-ethyl-1H-imidazol-4-yl)thieno[3,2-b]pyridin-7-yloxy)-3-fluorophenyl)-N-(2-fluorophenyl)-N-methylcyclopropane-1,1-dicarboxamide (198)

Following the procedure described above for the synthesis of compound 5d (example 4, scheme 4) title compound 198 was obtained in 15% yield. $^1$H NMR (CD$_3$OD) δ (ppm): 8.40 (d, J=8.6 Hz, 1H), 7.79 (dd, 2H), 7.65 (s, 1H), 7.46-7.38 (m, 1H), 7.31-7.27 (m, 3H), 7.20-7.16 (m, 1H), 7.06 (t, J=8.6 Hz, 1H), 6.55 (d, J=5.7 Hz, 1H), 4.12 (q, 2H), 3.32 (s, 3H, N-Me), 1.50 (m, 5H), 1.33 (s, 2H). MS (m/z): 574.1 (M+H).

Example 77

N$^1$-Ethyl-N$^3$-(4-(2-(1-ethyl-1H-imidazol-4-yl)thieno[3,2-b]pyridin-7-yloxy)-3-fluorophenyl)-N$^1$-phenylmalonamide (200)

Step 1: 3-(Ethyl(phenyl)amino)-3-oxopropanoic acid (201)

Following the procedure described above for the compound 31 (scheme 10), title compound 201 was obtained in 81% yield. MS (m/z): 208.0 (M+H).

Step 2: N$^1$-Ethyl-N$^3$-(4-(2-(1-ethyl-1H-imidazol-4-yl)thieno[3,2-b]pyridin-7-yloxy)-3-fluorophenyl)-N$^1$-phenylmalonamide (200)

Following the procedure described above for the compound 5d (example 4, scheme 4), title compound 200 was obtained in 49% yield. $^1$H NMR (DMSO-d$_6$) δ (ppm): 10.24 (s, 1H), 8.40 (d, J=5.5 Hz, 1H), 7.94 (d, J=1.2 Hz, 1H), 7.77 (d, J=1.2 Hz, 1H), 7.76 (dd, J=2.3 and 2.9 Hz, 1H), 7.65 (s, 1H), 7.49-7.27 (m, 8H), 6.54 (d, J=5.3 Hz, 1H), 4.04 (q, 2H), 3.67 (q, 2H), 3.14 (s, 2H), 1.38 (t, 3H), 1.01 (t, 3H) MS (m/z): 544.1 (M+H).

Scheme 56

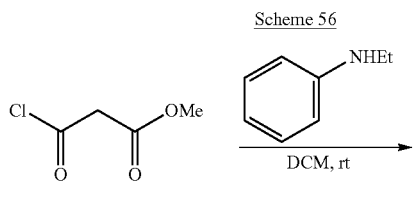

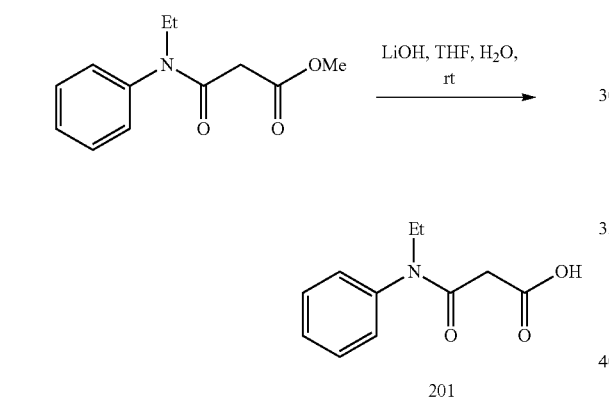

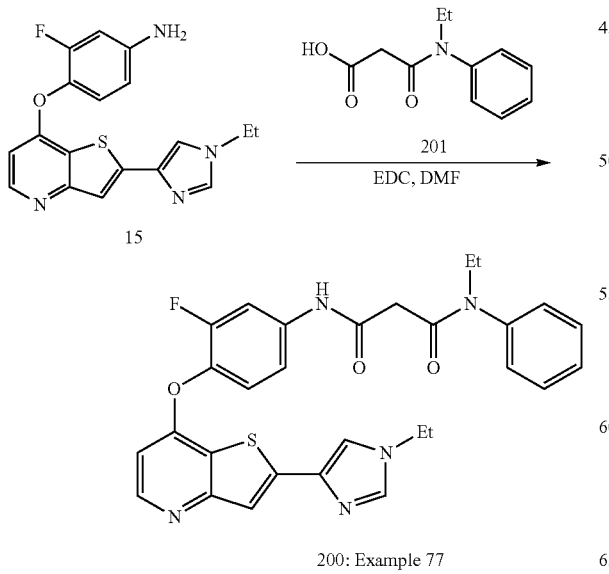

200: Example 77

Scheme 57

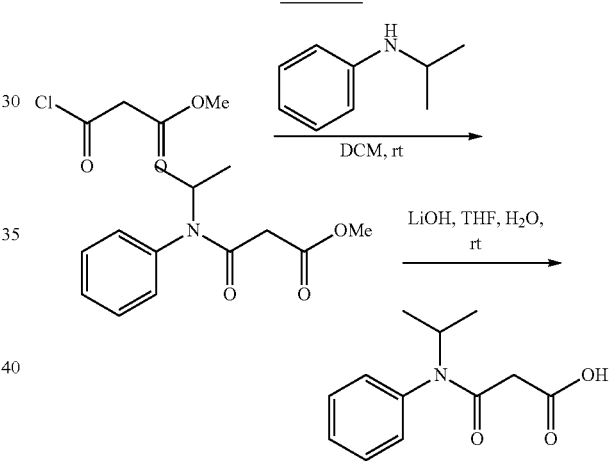

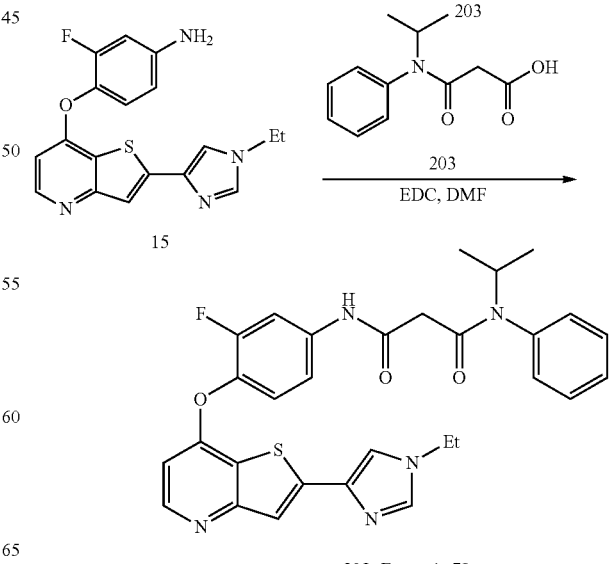

202: Example 78

Example 78

N¹-(4-(2-(1-Ethyl-1H-imidazol-4-yl)thieno[3,2-b]pyridin-7-yloxy)-3-fluorophenyl)-N³-isopropyl-N³-phenylmalonamide (202)

Step 1: 3-(Isopropyl(phenyl)amino)-3-oxopropanoic acid (203)

Following the procedure described above for the compound 31 (scheme 10), title compound 203 was obtained in 49% yield. MS (m/z): 222.0 (M+H).

Step 2: N¹-(4-(2-(1-Ethyl-1H-imidazol-4-yl)thieno[3,2-b]pyridin-7-yloxy)-3-fluorophenyl)-N³-isopropyl-N³-phenylmalonamide (202)

Following the procedure described above for the compound 5d (example 4, scheme 4), title compound 202 was obtained in 28% yield. ¹H NMR (DMSO-$d_6$) δ (ppm): 10.19 (s, 1H), 8.40 (d, J=5.5 Hz, 1H), 7.94 (d, J=1.3 Hz, 1H), 7.77-7.73 (m, 2H), 7.65 (s, 1H), 7.49-7.39 (m, 4H), 7.28-7.24 (m, 3H), 6.54 (dd, J=0.6 and 5.3 Hz, 1H), 4.82 (m, 1H), 4.04 (q, 1H), 3.02 (s, 2H), 1.38 (t, 3H), 0.99 (s, 3H), 0.98 (s, 3H). MS (m/z): 558.0 (M+H).

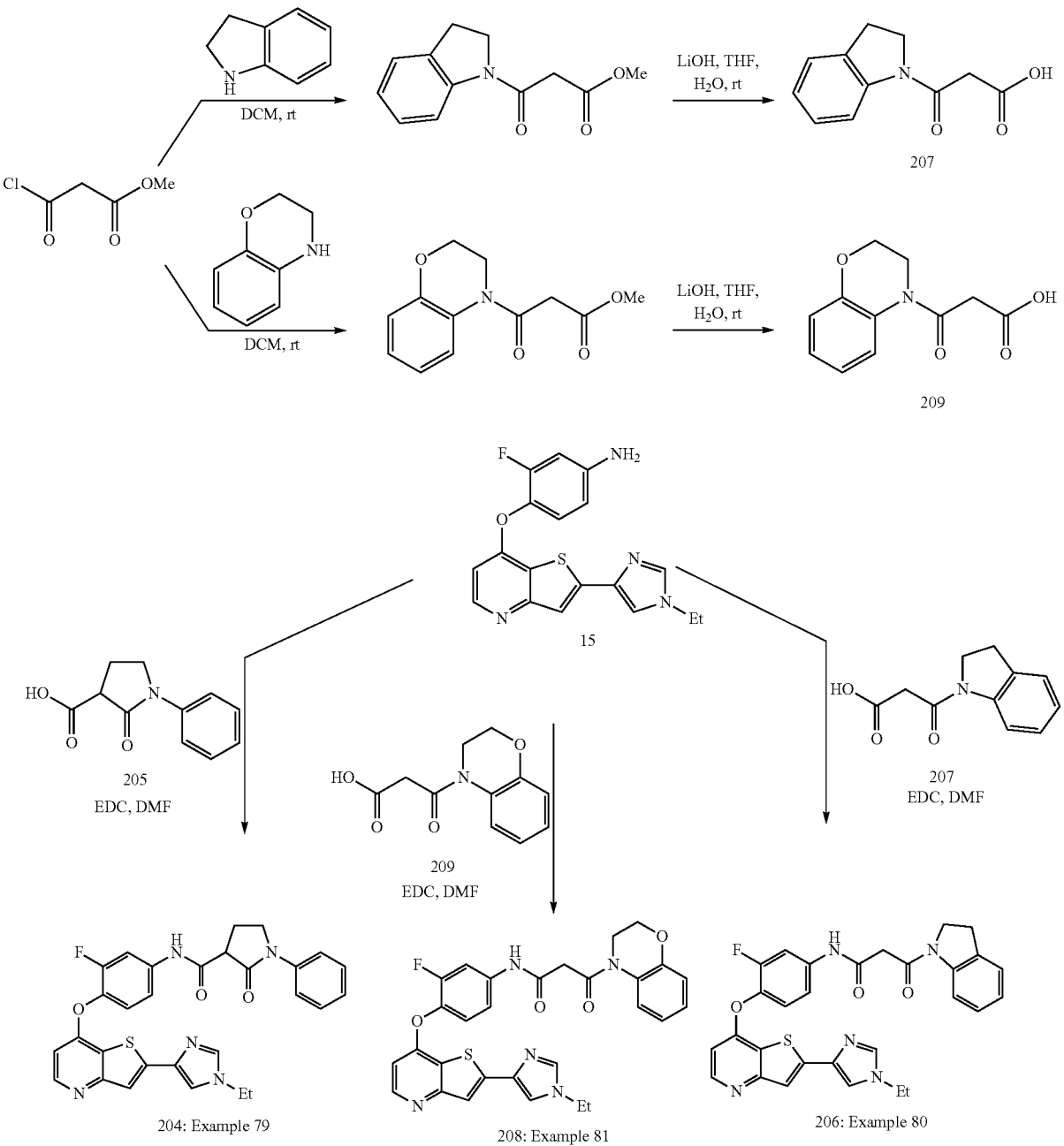

Scheme 58

Example 79

N-(4-(2-(1-Ethyl-1H-imidazol-4-yl)thieno[3,2-b]pyridin-7-yloxy)-3-fluorophenyl)-2-oxo-1-phenylpyrrolidine-3-carboxamide (204)

Following the procedure described above for the synthesis of compound 5d (scheme 4), but replacing acid 1 with the acid 205, title compound 204 was obtained in 40% yield. $^1$H NMR (DMSO-d$_6$) δ (ppm): 10.72 (s, 1H), 8.49 (d, J=5.7 Hz, 1H), 8.06 (d, J=1.0 Hz, 1H), 7.96-7.90 (m, 2H), 7.72 (s, 1H), 7.67-7.65 (m, 2H), 7.53-7.49 (m, 2H), 7.41-7.37 (m, 2H), 7.16 (t, J=7.2 Hz, 1H), 6.70 (d, J=5.5 Hz, 1H), 4.06 (q, 2H), 3.93 (m, 2H), 3.77 (t, J=8.2 Hz, 1H), 4.42 (m, 2H), 1.40 (t, 3H). MS (m/z): 542.0 (M+H).

Example 80

N-(4-(2-(1-Ethyl-1H-imidazol-4-yl)thieno[3,2-b]pyridin-7-yloxy)-3-fluorophenyl)-3-(indolin-1-yl)-3-oxopropanamide (206)

Step 1: 3-(Indolin-1-yl)-3-oxopropanoic acid (207)

Following the procedure described above for the compound 31 (scheme 10), title compound 207 was obtained in 75% yield. MS (m/z): 206.0 (M+H).

Step 2: N-(4-(2-(1-Ethyl-1H-imidazol-4-yl)thieno[3,2-b]pyridin-7-yloxy)-3-fluorophenyl)-3-(indolin-1-yl)-3-oxopropanamide (206)

Following the procedure described above for the compound 5d (scheme 4), title compound 206 was obtained in 40% yield. $^1$H NMR (DMSO-d$_6$) δ (ppm): 10.56 (s, 1H), 8.42 (d, J=5.5 Hz, 1H), 8.06 (d, J=8.0 Hz, 1H), 7.95 (s, J=1.2 Hz, 1H), 7.87 (dd, J=2.2 and 13.1 Hz, 1H), 7.78 (d, J=1.2 Hz, 1H), 7.67 (s, 1H), 7.47 (t, J=8.8 Hz, 1H), 7.40 (dd, J=1.5 and 8.0 Hz, 1H), 7.25 (d, J=7.7 Hz, 1H), 7.16 (t, J=7.5 Hz, 1H), 7.02 (t, J=7.3 Hz, 1H), 6.57 (d, J=5.3 Hz, 1H), 4.16 (s, 2H), 4.06 (q, 2H), 3.69 (s, 2H), 3.32-3.15 (m, 2H), 1.39 (t, 3H). MS (m/z): 542.1 (M+H).

Example 81

3-(2H-Benzo[b][1,4]oxazin-4(3H)-yl)-N-(4-(2-(1-ethyl-1H-imidazol-4-yl)thieno[3,2-b]pyridin-7-yloxy)-3-fluorophenyl)-3-oxopropanamide (208)

Step 1: 3-(2H-Benzo[b][1,4]oxazin-4(3H)-yl)-3-oxopropanoic acid (209)

Following the procedure described above for the compound 31 (scheme 10), title compound 209 was obtained in 75% yield. MS (m/z): 222.0 (M+H).

Step 2: 3-(2H-Benzo[b][1.4]oxazin-4(3H)-yl)-N-(4-(2-(1-ethyl-1H-imidazol-4-yl)thieno[3,2-b]pyridin-7-yloxy)-3-fluorophenyl)-3-oxopropanamide (208)

Following the procedure described above for the compound 5d (scheme 4), title compound 208 was obtained in 40% yield. $^1$H NMR (DMSO-d$_6$) δ (ppm): 10.55 (s, 1H), 8.44 (d. J=5.5 Hz, 1H), 7.98 (s, 1H), 7.83 (s, 1H), 7.82 (bs, 1H), 7.68 (s, 1H), 7.46 (t, 1H), 7.38 (bs, 1H), 7.06 (bs, 1H), 6.89 (m, 2H), 6.60 (d, J=5.5 Hz, 1H), 4.32 (t, 2H), 4.05 (q, 2H), 3.91 (t, 2H), 3.81 (s, 2H), 1.39 (t, 3H). MS (m/z): 558.1 (M+H).

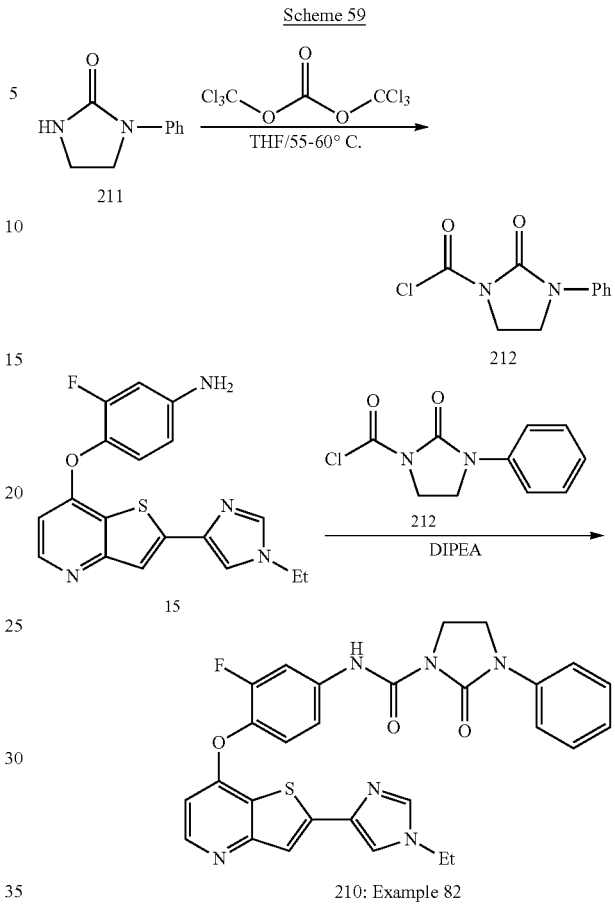

Scheme 59

Example 82

N-(4-(2-(1-Ethyl-1H-imidazol-4-yl)thieno[3,2-b]pyridin-7-yloxy)-3-fluorophenyl)-2-oxo-3-phenylimidazolidine-1-carboxamide (210)

To a solution of 1-phenylimidazolidin-2-one (211) (100 mg, 0.62 mmol) [P. Mayer, P. Brunel, C. Chaplain, C. Piedecoq, F. Calmel, P. Schambel, P. Chopin, T. Wurch, P. J. Pauwels, M. Marien, J.-L. Vidaluc, T. Imbert *J. Med. Chem.* 2000, 43, 3653-3664; W. Su, Y. Zhang *J. Chem. Res. Synop.* 2000, 9, 440-441] in THF (6 mL) was added triphosgene (189 mg, 0.62 mmol) and the solution was stirred for 3 hrs at 60° C. The reaction mixture was cooled to RT before the addition of aniline 15 (229 mg, 0.65 mmol) and DIPEA (648 µL, 3.72 mmol) and stirring was continued for an hour. The reaction mixture was concentrated and partitioned between EtOAc and water. A precipitate was formed which was collected by filtration. The organic layer was separated, dried and concentrated. The residue was combined with the collected precipitate, dry loaded to a column and eluted with EtOAc/MeOH (9:1), to produce title compound 210 (150 mg, 43% yield) as an off-white solid. $^1$H NMR (DMSO-d$_6$) δ (ppm): 10.57 (s, 1H), 8.42 (d, J=5.5 Hz, 1H), 7.95 (d, J=1.1 Hz, 1H), 7.83 (dd, J=2.5 and 13.3 Hz, 2H), 7.77 (d, J=1.2 Hz, 1H), 7.66 (s, 1H), 7.61 (dd, J=1.0 and 8.8 Hz, 1H), 7.49-7.41 (m, 4H), 7.16 (t, J=7.2 Hz, 1H), 6.57 (d, J=5.5 Hz, 1H), 4.03 (q, 2H), 4.04-3.92 (m, 4H), 1.38 (t, 3H). MS (m/z): 543.0 (M+H).

TABLE 5

Compounds 211-219 (examples 83-91) prepared according to the scheme 59

| Compd | Example | Structure | Characterization |
|---|---|---|---|
| 211 | 83 | 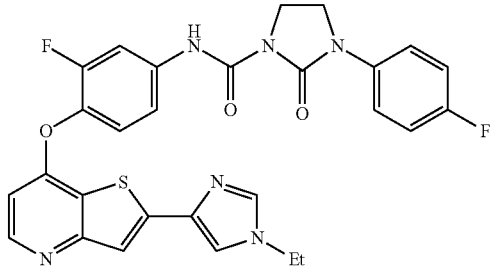

N-(4-(2-(1-Ethyl-1H-imidazol-4-yl)thieno[3,2-b]pyridin-7-yloxy)-3-fluorophenyl)-3-(4-fluorophenyl)-2-oxoimidazolidine-1-carboxamide | $^1$H NMR (DMSO-d$_6$) δ (ppm): 10.55 (s, 1H), 8.43 (d, J = 5.3 Hz, 1H), 7.95 (d, J = 1.2 Hz, 1H), 7.83 (dd, J = 2.3 and 12.9 Hz, 1H), 7.77 (d, J = 1.2 Hz, 1H), 7.67 (s, 1H), 7.65-7.62 (m, 2H), 7.47 (t, J = 8.8 Hz, 1H), 7.42 (dd, J = 2.2 and 9.0 Hz, 1H), 7.29-7.25 (m, 2H), 6.57 (d, J = 5.5 Hz, 1H), 4.05 (q, 2H), 3.95 (m, 4H), 1.39 (t, 3H). MS (m/z): 561.2 (M + H) |
| 212 | 84 | 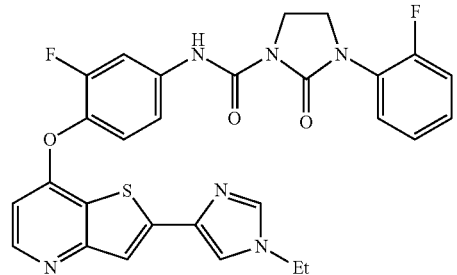

N-(4-(2-(1-Ethyl-1H-imidazol-4-yl)thieno[3,2-b]pyridin-7-yloxy)-3-fluorophenyl)-3-(2-fluorophenyl)-2-oxoimidazolidine-1-carboxamide | $^1$H NMR (DMSO-d$_6$) δ (ppm): 10.51 (s, 1H), 8.44 (d, J = 5.1 Hz, 1H), 7.97 (s, 1H), 7.85 (d, J = 12.5 Hz, 1H), 7.79 (s, 1H), 7.68 (s, 1H), 7.61 (d, J = 11.7 Hz, 1H), 7.47-7.41 (m, 4H), 7.02 (t, J = 7.7 Hz, 1H), 6.59 (d, J = 5.1 Hz, 1H), 4.06 (q, J = 7.0 Hz, 2H), 3.97 (s, 4H), 1.40 (t, J = 7.1 Hz, 3H). MS (m/z): 561.2 (M + H). |
| 213 | 85 | 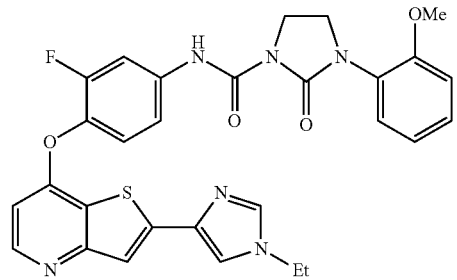

N-(4-(2-(1-Ethyl-1H-imidazol-4-yl)thieno[3,2-b]pyridin-7-yloxy)-3-fluorophenyl)-3-(2-methoxyphenyl)-2-oxoimidazolidine-1-carboxamide | $^1$H NMR (DMSO-d$_6$) δ (ppm): 10.58 (s, 1H), 8.44 (d, J = 5.6 Hz, 1H), 7.96 (s, 1H), 7.85-7.77 (m, 1H), 7.79 (s, 1H), 7.67 (s, 1H), 7.46 (t, J = 9.2 Hz, 1H), 7.42-7.36 (m, 3H), 7.16 (d, J = 8.4 Hz, 1H), 7.02 (t, J = 8.0 Hz, 1H), 6.58 (d, J = 5.6 Hz, 1H), 4.08 (q, J = 4.8 Hz, 2H), 3.98 (t, J = 8.8 Hz, 2H), 3.84 (s, 3H), 3.81 (t, J = 8.8 Hz, 2H), 1.40 (t, J = 4.8 Hz, 3H). |
| 214 | 86 | 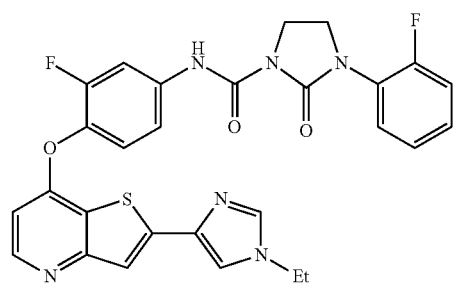

N-(4-(2-(1-Ethyl-1H-imidazol-4-yl)thieno[3,2-b]pyridin-7-yloxy)-3-fluorophenyl)-3-(2-fluorophenyl)-2-oxoimidazolidine-1-carboxamide | $^1$H NMR (DMSO-d$_6$) δ (ppm): 10.51 (s, 1H), 8.44 (d, J = 5.1 Hz, 1H), 7.97 (s, 1H), 7.85 (d, J = 12.5 Hz, 1H), 7.79 (s, 1H), 7.68 (s, 1H), 7.61 (d, J = 11.7 Hz, 1H), 7.47-7.41 (m, 4H), 7.02 (t, J = 7.7 Hz, 1H), 6.59 (d, J = 5.1 Hz, 1H), 4.06 (q, J = 7.0 Hz, 2H), 3.97 (s, 4H), 1.40 (t, J = 7.1 Hz, 3H). MS (m/z): 561.2 (M + H). |

TABLE 5-continued

Compounds 211-219 (examples 83-91) prepared according to the scheme 59

| Compd | Example | Structure | Characterization |
|---|---|---|---|
| 215 | 87 | 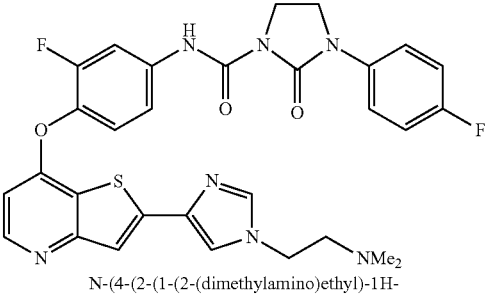

N-(4-(2-(1-(2-(dimethylamino)ethyl)-1H-imidazol-4-yl)thieno[3,2-b]pyridin-7-yloxy)-3-fluorophenyl)-3-(4-fluorophenyl)-2-oxoimidazolidine-1-carboxamide | $^1$H NMR (DMSO-$d_6$) δ (ppm): 10.55 (s, 1H), 8.43 (d, J = 5.3 Hz, 1H), 7.91 (d, J = 1.2 Hz, 1H), 7.83 (dd, J = 2.3 and 12.9 Hz, 1H), 7.77 (d, J = 1.2 Hz, 1H), 7.67 (s, 1H), 7.65-7.62 (m, 2H), 7.47 (t, J = 8.6 Hz, 1H), 7.42 (dd, J = 2.2 and 9.0 Hz, 1H), ), 7.30-7.25 (m, 2H), 6.57 (d, J = 5.5 Hz, 1H), 4.12 (t, 2H), 3.95 (m, 4H), 2.62 (m, 2H), 2.19 (s, 6H). MS (m/z): 604.2 (M + H) |
| 216 | 88 | 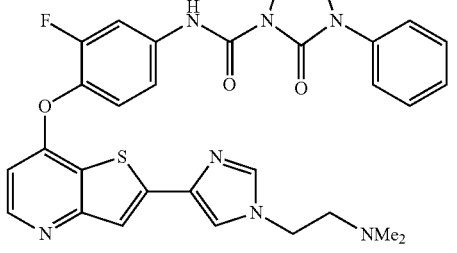

N-(4-(2-(1-(2-(Dimethylamino)ethyl)-1H-imidazol-4-yl)thieno[3,2-b]pyridin-7-yloxy)-3-fluorophenyl)-2-oxo-3-phenylimidazolidine-1-carboxamide | $^1$H NMR (DMSO-$d_6$) δ (ppm): 10.52 (s, 1H), 8.37 (d, J = 5.5 Hz, 1H), 7.86 (d, J = 1.2 Hz, 1H), 7.79 (dd, J = 2.4 and 12.9 Hz, 1H), 7.60-7.56 (m, 3H), 7.44-7.34 (m, 4H), 7.11 (t, J = 8.4 Hz, 1H), 6.52 (dd, J = 0.6 and 5,5 Hz, 1H), 4.05 (t, 1H), 3.91-3.88 (m, 4H), 2.54 (t, 2H), 2.12 (s, 3H). MS (m/z): 586.1 (M + H) |
| 217 | 89 | 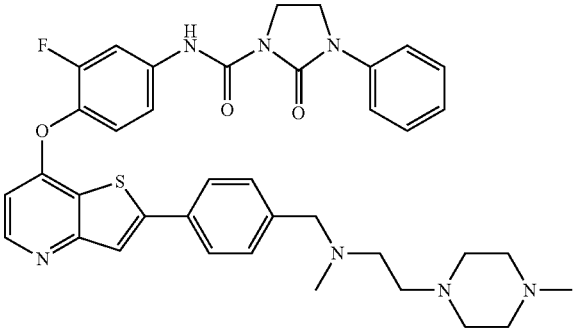

N-(3-Fluoro-4-(2-(4-((methyl(2-(4-methylpiperazin-1-yl)ethyl)amino)methyl)phenyl)thieno[3,2-b]pyridin-7-yloxy)phenyl)-2-oxo-3-phenylimidazolidine-1-carboxamide | $^1$H NMR (DMSO-$d_6$) δ (ppm): 10.57 (s, 1H), 8.51 (d, J = 5.3 Hz, 1H), 8.12 (s, 1H), 8.04 (s, 1H), 7.86-7.82 (m, 3H), 7.63-7.60 (m, 2H), 7.51-7.39 (m, 6H), 7.16 (tt, J = 1.4 and 7.3 Hz, 1H), 6.62 (dd, J = 0.8 and 5.3 Hz, 1H), 3.96-3.92 (m, 4H), 3.61 (s, 2H), 2.69 (bs, 4H), 2.60 (m, 4H), 2.57 (m, 4H), 2.39 (s, 3H), 2.20 (s, 3H). MS (m/z): 694.1 (M + H) |
| 218 | 90 | 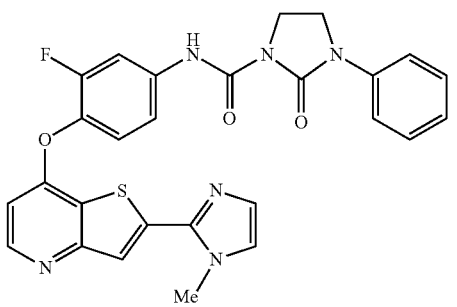

N-(3-fluoro-4-(2-(1-methyl-1H-imidazol-2-yl)thieno[3,2-b]pyridin-7-yloxy)phenyl)-2-oxo-3-phenylimidazolidine-1-carboxamide | $^1$H NMR (DMSO-$d_6$) δ (ppm): 10.52 (s, 1H), 8.51 (d, J = 5.48 Hz, 1H), 7.88 (s, 1H), 7.80 (d, J = 13.1 Hz, 1H), 7.62 (d, J = 5.8 Hz, 1H), 7.43 (m, 5H), 7.16 (t, J = 5.28 Hz, 1H), 7.03 (s, 1H), 6.71 (d, J = 5.48 Hz, 1H), 3.95 (m, 7H). MS (m/z): 529.1 (M + H). |

TABLE 5-continued

Compounds 211-219 (examples 83-91) prepared according to the scheme 59

| Compd | Example | Structure | Characterization |
|---|---|---|---|
| 219 | 91 | 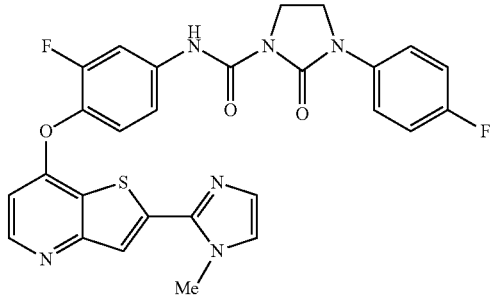<br>N-(3-fluoro-4-(2-(1-methyl-1H-imidazol-2-yl)thieno[3,2-b]pyridin-7-yloxy)phenyl)-3-(4-fluorophenyl)-2-oxoimidazolidine-1-carboxamide | $^1$H (DMSO-$d_6$) δ (ppm): 10.56 (s, 1H). 8.52 (d, J = 5.48 Hz, 1H) 7.89 (dd, J = 2.3 and 13.1 Hz, 1 H), 7.64 (m, 3H), 7.50 (m, 2H), 7.30 (m, 2H), 7.04 (s, 1H), 6.70 (d, J = 5.28 Hz, 1H), 3.99 (s, 3H), 3.95 (m, 4H). MS (m/z): 547.2 (M + H). |

Compounds 211-214 were synthesized starting from the amine 15 (scheme 4), compounds 215-216 were prepared starting from the amine 197 (scheme 54), compound 217 was obtained starting from the amine 80 (scheme 26), while compounds 218-219 were derived starting from the amine 9 (scheme 2).

Scheme 60

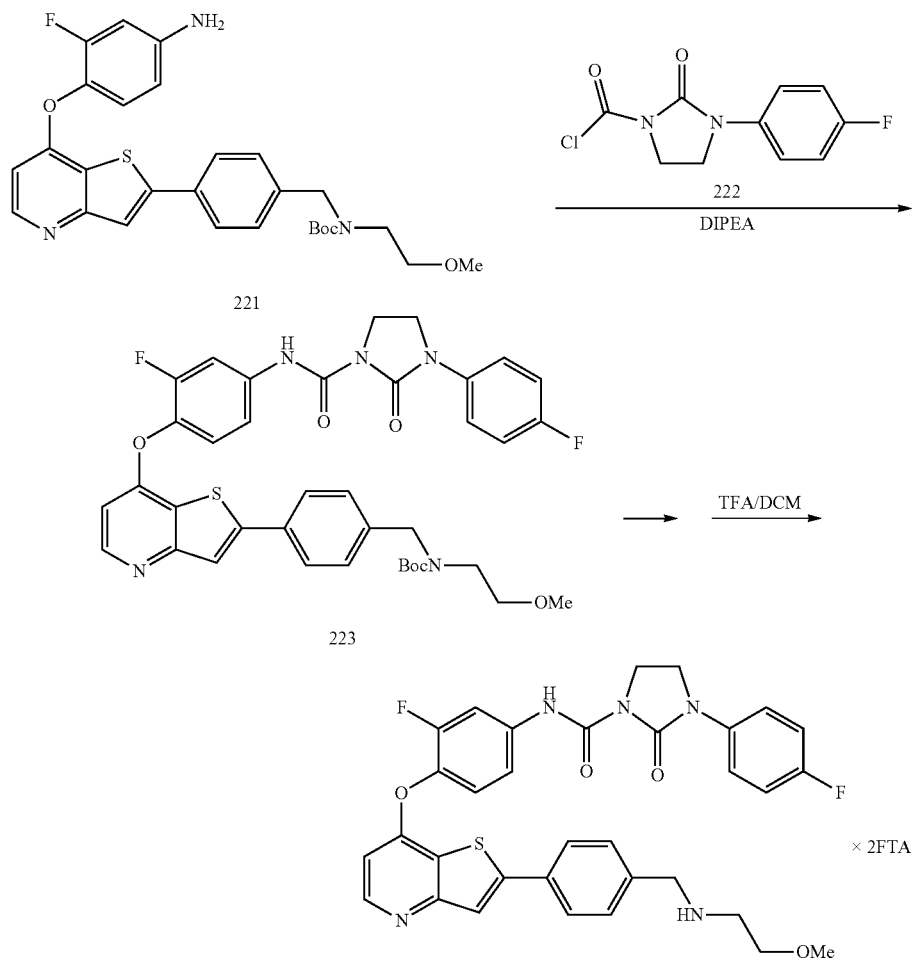

Example 92

N-(3-Fluoro-4-(2-(4-((2-methoxyethylamino)methyl)phenyl)thieno[3,2-b]pyridin-7-yloxy)phenyl)-3-(4-fluorophenyl)-2-oxoimidazolidine-1-carboxamide (220)

Step 1: tert-Butyl 4-(7-(2-fluoro-4-(3-(4-fluorophenyl)-2-oxoimidazolidine-1-carboxamido)phenoxy)thieno[3,2-b]pyridin-2-yl)benzyl(2-methoxyethyl)carbamate (223)

Starting from the amine 221 [prepared according to the scheme 26, using arylboronate 76 as an intermediate (Table 2)] and 3-(4-fluorophenyl)-2-oxoimidazolidine-1-carbonyl chloride (222), and following the procedure described above for the synthesis of compound 210 (example 82, scheme 59), title compound 223 was obtained in 40% yield. MS (m/z): 730.3 (M+H).

Step 2: N-(3-Fluoro-4-(2-(4-((2-methoxyethylamino)methyl)phenyl)thieno[3,2-b]pyridin-7-yloxy)phenyl)-3-(4-fluorophenyl)-2-oxoimidazolidine-1-carboxamide (220)

A solution of 223 (60 mg, 0.082 mmol) and TFA (1 mL) in toluene (2 mL) was stirred 30 min at room temperature. The reaction mixture was concentrated under reduced pressure. The residue was triturated with diethyl ether, the solid was collected and dried to give the title compound 220 (70 mg, 99.5%) as an off-white solid. $^1$H NMR (DMSO-$d_6$) δ (ppm): 10.55 (s, 1H), 8.95 (s, broad, 2H), 8.52 (d, J=5.5 Hz, 1H), 8.13 (s, 1H), 7.97 (d, J=8.4 Hz, 2H), 7.84 (dd, J=2.5 and 13.1 Hz, 1H), 7.65-7.61 (m, 4H), 7.49 (t, J=8.8 Hz, 1H), 7.44 (dd, J=2.4 and 8.8 Hz, 1H), 7.30-7.25 (m, 2H), 6.65 (d, J=5.5 Hz, 1H), 4.21 (t, 1H), 3.93 (m, 4H), 3.57 (t, 2H), 3.30 (s, 3H), 3.11 (m, 2H). MS (m/z): 630.3 (M+H).

Scheme 61

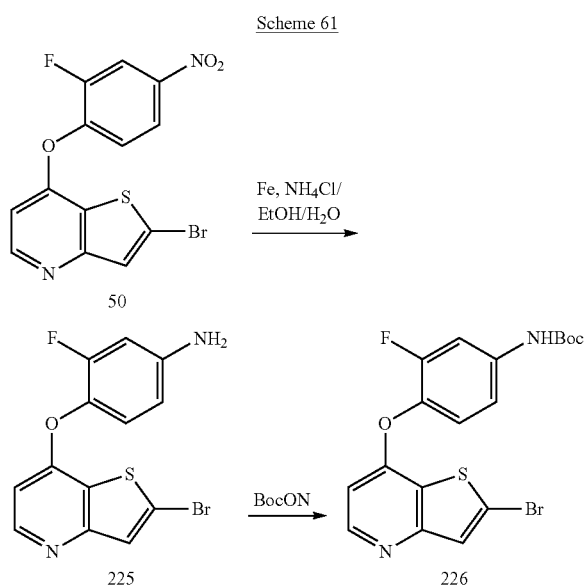

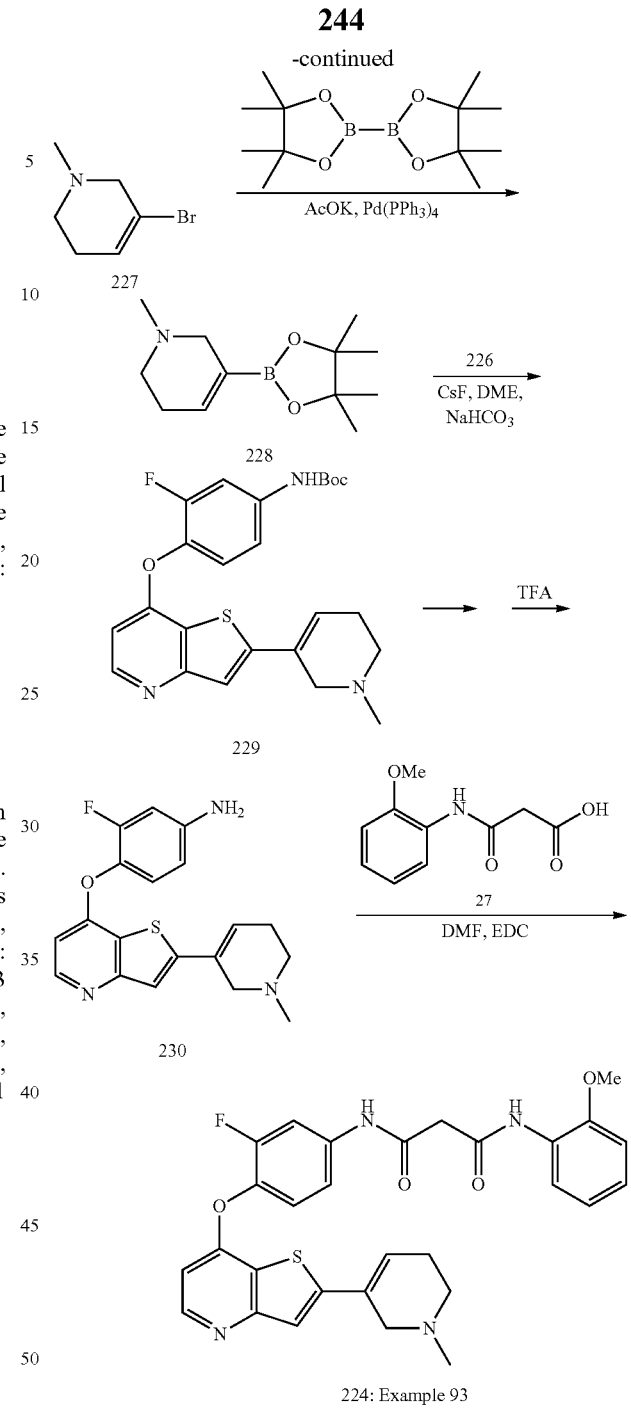

224: Example 93

Example 93

$N^1$-(3-Fluoro-4-(2-(1-methyl-1,2,5,6-tetrahydropyridin-3-yl)thieno[3,2-b]pyridin-7-yloxy)phenyl)-$N^3$-(2-methoxyphenyl)malonamide (224)

Step 1: 4-(2-Bromothieno[3,2-b]pyridin-7-yloxy)-3-fluorobenzenamine (225)

To a mixture of compound 50 (1.0 g, 2.96 mmol) and NH$_4$Cl (46 mg, 0.86 mmol) in EtOH (29 mL)/water (15 mL) at 100° C., Fe (1.4 g, 25.15 mmol) was added in one portion and the mixture was refluxed with vigorous stirring for 40 min. The mixture was filtered through Celite®, the Celite® washed with EtOH and the combined filtrate concentrated under reduced pressure. The residue was suspended in EtOAc, washed with water; the organic phase was dried over anhydrous Na₂SO₄ and evaporated affording title compound 225 (916.15 mg, 91% yield). MS (m/z): 338.9 (96%), 340.9 (100%).

Step 2: tert-Butyl 4-(2-bromothieno[3,2-b]pyridin-7-yloxy)-3-fluorophenylcarbamate (226)

A solution of the aniline 225 (300 mg, 0.887 mmol) and BocON (194 mg, 0.887 mmol) in MeCN (1.8 mL) was stirred overnight at room temperature. The crude mixture was concentrated under reduced pressure affording title compound 226 (380 mg, 98% yield) that was used in the next step without further purification. MS (m/z): 439.1 (96%), 441.1 (100%).

Step 3: tert-Butyl 3-fluoro-4-(2-(1-methyl-1,2,5,6-tetrahydropyridin-3-yl)thieno[3,2-b]pyridin-7-yloxy)phenylcarbamate (229) (two-step procedure)

To a mixture of 5-bromo-1-methyl-1,2,3,6-tetrahydropyridine 227 (Drinkuth, S; Gruetsch, 5; Peter. K; Christl, M. *Eur. J. Org. Chem.*; 14; 2001: 2665-2670) (1.0 g, 5.71 mmol), bis(pinacolato)diboron (8.66 mmol, 2.18 g) and AcOK (1.7 g, 17.3 mmol) in toluene (11.4 mL), Pd(PPh₃)₄ (0.171 mmol, 198 mg) was added in one portion and the mixture was heated to reflux under N₂ for 2 h. The suspension was concentrated under reduced pressure, giving crude 228 that was re-dissolved in DME (29 mL) and kept under nitrogen. tert-Butyl 4-(2-bromothieno[3,2-b]pyridin-7-yloxy)-3-fluorophenylcarbamate 226 (380 mg, 0.87 mmol), CsF (2.64 mmol, 401 mg), NaHCO₃ (2.64 mmol, 222 mg), and water (1 mL) were added to an aliquot of the DME solution of 228 (4 mL, 1.22 mmol) and the mixture refluxed overnight under nitrogen. The crude was diluted with EtOAc and extracted with 1N HCl. The aqueous phase was extracted with DCM, basified to pH~11 by addition of 1N NaOH solution, extracted with EtOAc. The extract was dried over anhydrous Na₂SO₄ and concentrated under reduced pressure giving crude 229 (105 mg, 26% yield) that was used in the next step without further purification. MS (m/z): 456.1 (100%).

Step 4: 3-Fluoro-4-(2-(1-methyl-1,2,3,6-tetrahydropyridin-4-yl)thieno[3,2-b]pyridin-7-yloxy)aniline (230)

TFA (1 mL) was added to tert-butyl 3-fluoro-4-(2-(1-methyl-1,2,5,6-tetrahydropyridin-3-yl)thieno[3,2-b]pyridin-7-yloxy)phenylcarbamate (229) (105 mg, 0.23 mmol) and the mixture was stirred for 1 h at room temperature. The solution was concentrated under reduced pressure, the residue co-distilled with MeCN, redissolved in MeOH and purified by preparative HPLC (gradient 40% to 95% MeOH in water, 45 min) giving 230 (50 mg, 0.1 mmol, 48% yield) as a white solid. MS (m/z): (M+1) 356.1 (100%).

Step 5: N¹-(3-Fluoro-4-(2-(1-methyl-1,2,3,6-tetrahydropyridin-4-yl)thieno[3,2-b]pyridin-7-yloxy)phenyl)-N³-(2-methoxyphenyl)malonamide (224)

A solution of 3-fluoro-4-(2-(1-methyl-1,2,3,6-tetrahydropyridin-4-yl)thieno[3,2-b]pyridin-7-yloxy)aniline (230) (50 mg, 0.110 mmol), 3-(2-methoxyphenylamino)-3-oxopropanoic acid 27 (34 mg, 0.165 mmol) (scheme 8), EDC (25 mg, 0.165 mmol) and HOBt (22 mg, 0.165 mmol) in DMF (1.1 mL) was stirred overnight at room temperature. More 27 (34 mg, 0.165 mmol) and EDC (25 mg, 0.165 mmol) were added and the mixture stirred for a further 6 h. The mixture was diluted with EtOAc, extracted with water, dried over anhydrous Na₂SO₄, and concentrated under reduced pressure. The residue was re-dissolved in MeOH and purified by preparative HPLC (gradient 40% to 95% MeOH in water, 45 min) followed by flash chromatography (MeOH/CHCl₃/NH₄Cl 1:9:0.1) giving title compound 224 (19 mg, 0,056 mmol, 51% yield) as a white solid. ¹H NMR (400 MHz, DMSO-d₆) δ (ppm): 10.61 (s, 1H), 9.64 (s, 1H), 8.45 (d, J=5.5 Hz, 1H), 8.07 (dd, J=8.8 Hz, J=1.4 Hz, 1H), 7.86 (dd, J=2.3 Hz, J=13.1 Hz, 1H), 7.49-7.41 (m, 3H), 7.11-7.05 (m, 2H), 6.92 (m, 1H), 6.61 (dd, J=0.8 Hz, J=5.5 Hz, 1H), 6.43 (m, 1H), 3.86 (s, 3H), 3.64 (s, 2H), 3.33 (m, 2H), 2.52-2.50 (m, 2H), 2.49 (m, 2H), 2.36-2.33 (m, 5H). MS (m/z): 547.42 (100% yield).

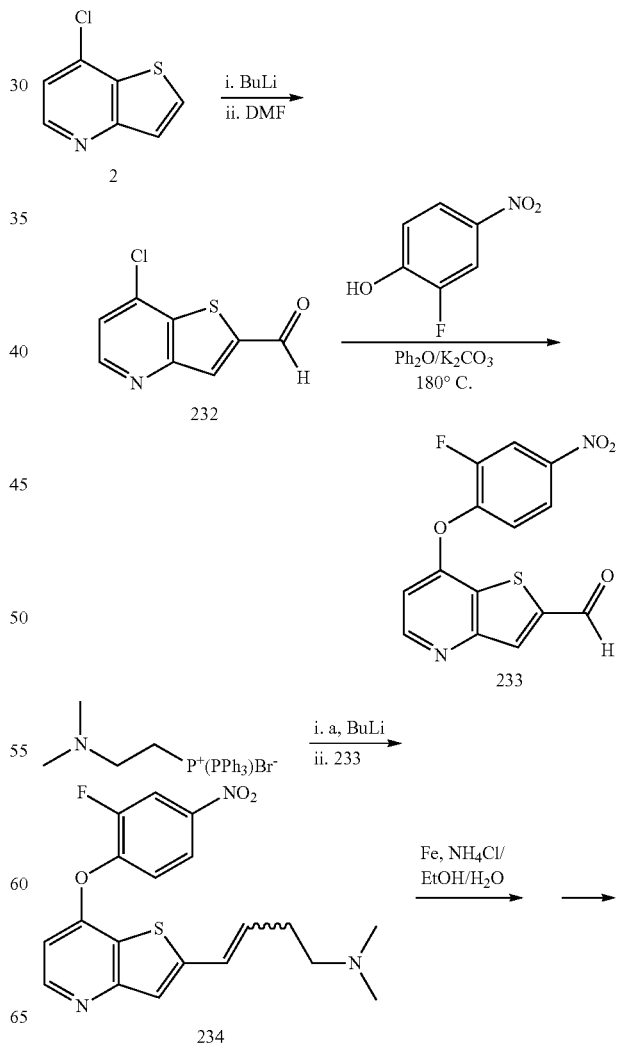

Scheme 62

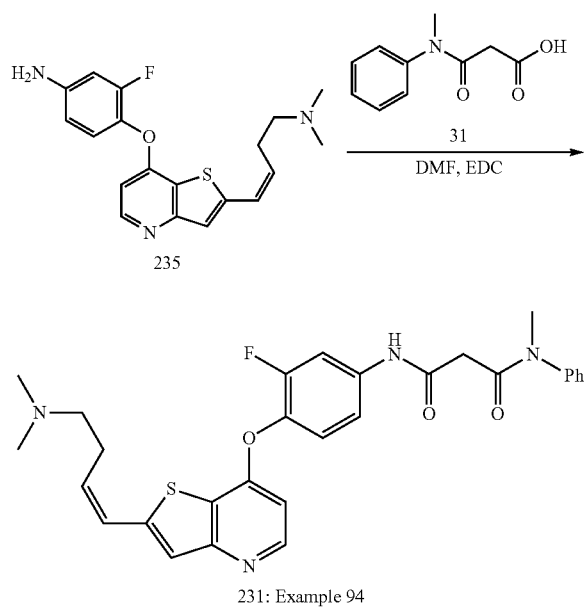

Example 94

(Z)—N$^1$-(4-(2-(4-(Dimethylamino)but-1-enyl)thieno[3,2-b]pyridin-7-yloxy)-3-fluorophenyl)-N$^3$-methyl-N$^3$-phenylmalonamide (231)

Step 1: 7-Chlorothieno[3,2-b]pyridine-2-carbaldehyde (232)

To a solution of 7-chlorothieno[3,2-b]pyridine (2) (2 g, 11.83 mmol) in THF (40 mL) n-BuLi (2.5M in hexanes, 5.7 mL, 14.2 mmol) was added dropwise at −78° C. and the reaction mixture stirred 1 h. DMF (2.7 mL, 35.5 mmol) was added and stirring continued 1 h more. The reaction mixture was poured into water, extracted with EtOAc, the combined organics dried over anhydrous Na$_2$SO$_4$, and concentrated under reduced pressure. The residue was triturated with ether and filtered affording title compound 232 (2 g, 10.12 mmol, 86% yield). MS (m/z): 197.9 (36%), (M+MeOH+1) 230.0 (100%).

Step 2: 7-(2-Fluoro-4-nitrophenoxy)thieno[3,2-b]pyridine-2-carbaldehyde (233)

A mixture of aldehyde 232 (500 mg, 2.53 mmol), 2-fluoro-4-nitrophenol (595 mg, 3.79 mmol), K$_2$CO$_3$ (700 mg, 5.06 mmol) and Ph$_2$O (3.4 mL) was stirred in a sealed tube for 12 h at 170° C. The mixture was suspended in a water/EtOAc mixture, sonicated a few minutes and filtered, the solid residue was washed successively with water, EtOAc and ether, giving crude 233 (500 mg, 1.17 mmol, 46% yield) that was used in the next step without further purification. MS (m/z): (M+1) 319.0 (14%), (M+MeOH+1) 351.0 (100%).

Step 3: 4-(7-(2-Fluoro-4-nitrophenoxy)thieno[3,2-b]pyridin-2-yl)-N,N-dimethylbut-3-en-1-amine (234)

To a solution of (2-(dimethylamino)ethyl)triphenylphosphonium bromide (680 mg, 1.54 mmol) in THF (7.7 mL) was added n-BuLi (2.5M in hexanes, 0.65 mL, 1.62 mmol) dropwise at 0° C., the resulting mixture was warmed to room temperature and stirred for 30 min. 7-(2-fluoro-4-nitrophenoxy)thieno[3,2-b]pyridine-2-carbaldehyde 233 (500 mg, 1.17 mmol) was added in one portion and the mixture was stirred for 2 h. The mixture was poured into water, extracted with EtOAc; the organic phase was extracted with 3% citric acid, the combined aqueous phase was basified to pH~11 by the addition of 1N NaOH. It was then extracted with EtOAc, dried over anhydrous Na$_2$SO$_4$ and concentrated under reduced pressure affording title compound 234 (360 mg, 0.929 mmol, 78% yield) as a crude mixture that was used in the next step without further purification. MS (m/z): (M+1) 388.1 (100%).

Step 4: (Z)-4-(2-(4-(Dimethylamino)but-1-enyl)thieno[3,2-b]pyridin-7-yloxy)-3-fluoroaniline (235)

To a mixture of 4-(7-(2-fluoro-4-nitrophenoxy)thieno[3,2-b]pyridin-2-yl)-N,N-dimethylbut-3-en-1-amine (234) (171 mg, 0.44 mmol) and NH$_4$Cl (20 mg, 0.37 mmol) in EtOH (4.4 mL)/water (2.2 mL) at 100° C., Fe (209 mg, 3.75 mmol) was added in one portion and the mixture was heated to reflux with vigorous stirring for 40 min. The mixture was filtered through Celite®, the Celite® washed with EtOH and the combined organic solutions concentrated under reduced pressure. The residue was dissolved in MeOH and purified by preparative HPLC (gradient 40% to 95% MeOH in water, 45 min) giving title compound 235 as a yellow solid (122.8 mg, 0.3 mmol, 69% yield). MS (m/z): (M+1) 358.1 (100%).

Step 5: (Z)—N$^1$-(4-(2-(4-(Dimethylamino)but-1-enyl)thieno[3,2-b]pyridin-7-yloxy)-3-fluorophenyl)-N$^3$-methyl-N$^3$-phenylmalonamide (231)

A solution of (Z)-4-(2-(4-(dimethylamino)but-1-enyl)thieno[3,2-b]pyridin-7-yloxy)-3-fluoroaniline (235) (69.1 mg, 0.193 mmol), 3-(methyl(phenyl)amino)-3-oxopropanoic acid 31 (46 mg, 0.26 mmol) (scheme 10), and EDC (45 mg, 0.24 mmol) in DMF (2.8 mL) was stirred overnight at room temperature. More 31 (45 mg, 0.26 mmol) and EDC (45 mg, 0.24 mmol) were added and the mixture stirred 6 h more. The mixture was diluted with EtOAc, washed with water, dried over anhydrous Na$_2$SO$_4$, and concentrated under reduced pressure. The residue was redissolved in MeOH and purified twice by preparative HPLC (gradient 40% to 95% MeOH in water, 45 min) giving title compound 231 (35 mg, 0.066 mmol, 34% yield) as a white solid. $^1$H NMR (400 MHz, DMSO-d$_6$) δ (ppm): 10.32 (s, 1H), 8.48 (d, J=5.5 Hz, 1H), 7.80 (d, J=12.7 Hz, 1H), 7.54 (s, 1H), 7.5-7.3 (m, 7H), 6.78 (d, J=12.2 Hz, 1H), 6.62 (d, J=5.5 Hz, 1H), 5.92 (tt, J=7.2 Hz, J=4.5 Hz, 11.7 Hz, 1H), 3.21 (s, 5H), 2.59 (m, 2H), 2.42 (dd, 6.8 Hz, 7.4 Hz, 2H), 2.16 (s, 6H). MS (m/z): (M+1) 533.1 (100 N.

Scheme 63

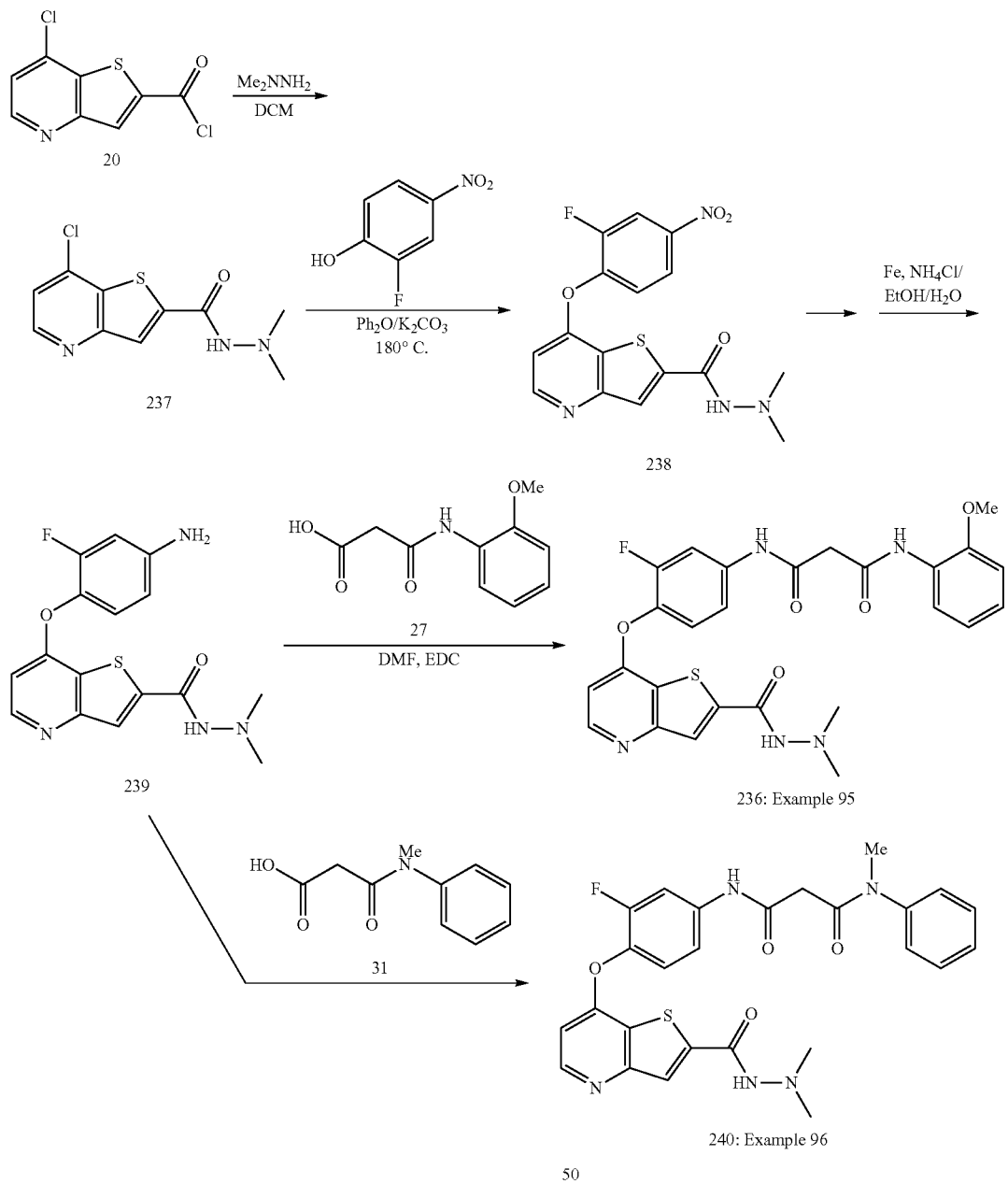

Example 95

N[1]-(4-(2-(2,2-Dimethylhydrazinecarbonyl)thieno[3,2-b]pyridin-7-yloxy)-3-fluorophenyl)-N[3]-(2-methoxyphenyl)malonamide (236)

Step 1: 7-Chloro-N',N[1]-dimethylthieno[3,2-b]pyridine-2-carbohydrazide (237)

To a suspension of 7-chlorothieno[3,2-b]pyridine-2-carbonyl chloride 20 (1 g, 4.33 mmol) (scheme 6) in DCM (22 mL), 1,1-dimethylhydrazine (0.33 mL, 4.33 mmol) was added in one portion and the mixture was stirred for 5 h. More 1,1-dimethylhydrazine (0.33 mL, 4.33 mmol) was added and the mixture was stirred overnight at room temperature. The crude was diluted with EtOAc, extracted with 1N HCl, the aqueous solution basified to pH~11 by addition of 1N NaOH, extracted with EtOAc, the organic phase dried over anhydrous $Na_2SO_4$ and concentrated under reduced pressure affording 237 (798 mg, 3.13 mmol, 72%) as a crude mixture that was used in the next step without further purification. MS (m/z): (M+1) 255.9 (100%), 257.9 (39%).

Step 2: 7-(2-Fluoro-4-nitrophenoxy)-N',N[1]-dimethylthieno[3,2-b]pyridine-2-carbohydrazide (238)

A mixture of 7-chloro-N',N[1]-dimethylthieno[3,2-b]pyridine-2-carbohydrazide (237) (798 mg, 3.13 mmol), 2-fluoro-4-nitrophenol (740 mg, 4.70 mmol), $K_2CO_3$ (830 mg, 6.26 mmol) and $Ph_2O$ (4.2 mL) was stirred in a sealed tube for 12 h at 170° C. The mixture was diluted with DCM, extracted with water, the organic phase dried with anhydrous $Na_2SO_4$ and concentrated. The residue was purified by flash chromatography (EtOAc/hexanes 1:1) giving 238 (772.5 mg, 2.05 mmol, 66% yield) as a brown foam. MS (m/z): (M+1) 377.0 (100%).

Step 3: 7-(4-Amino-2-fluorophenoxy)-N,N$^1$-dimethylthieno[3,2-b]pyridine-2-carbohydrazide (239)

To a mixture of 7-(2-fluoro-4-nitrophenoxy)-N,N-dimethylthieno[3,2-b]pyridine-2-carbohydrazide 238 (772 mg, 2.05 mmol) and NH$_4$Cl (93 mg, 1.74 mmol) in EtOH (20.5 mL)/water (10.3 mL) at 100° C., Fe (973 mg, 17.73 mmol) was added in one portion and the mixture was heated to reflux with vigorous stirring 40 min. The mixture was filtered through Celite®, the Celite® washed with EtOH and the combined organic solutions concentrated under reduced pressure. The residue was purified by flash chromatography (MeOH/DCM 1:9) giving 239 (605 mg, 1.75 mmol, 85%). MS (m/z): (M+1) 347.0 (100%).

Step 4: N$^1$-(4-(2-(2,2-Dimethylhydrazinecarbonyl)thieno[3,2-b]pyridin-7-yloxy)-3-fluorophenyl)-N$^3$-(2-methoxyphenyl)malonamide (236)

A solution of 7-(4-amino-2-fluorophenoxy)-N',N$^1$-dimethylthieno[3,2-b]pyridine-2-carbohydrazide 239 (200 mg, 0.578 mmol), 3-(2-methoxyphenylamino)-3-oxopropanoic acid 27 (195 mg, 0.693 mmol), and EDC (230 mg, 0.693 mmol) in DMF (8.3 mL) was stirred overnight at room temperature. More 27 (195 mg, 0.693 mmol) and EDC (230 mg, 0.693 mmol) were added and the mixture stirred 6 h more. The crude was diluted with EtOAc, extracted with water, over with anhydrous Na$_2$SO$_4$, and concentrated under reduced pressure. The residue was re dissolved in MeOH and purified twice by flash chromatography (DCM/MeOH 9:1) affording 236 (207 mg, 0.385 mmol, 67% yield) as a white solid. $^1$H NMR (400 MHz, DMSO-d$_6$) δ (ppm): 10.60 (s, 1H), 9.94 (s, 0.51-1), 9.63 (s, 1H), 9.49 (s, 0.5H), 8.57 (dd, J=5.5 Hz, J=7.2 Hz, 1H), 8.26 (m, 1H), 8.07 (d, J=7.4 Hz, 1H), 7.88 (d, J=12.9 Hz, 1H), 7.54-7.43 (m, 2H), 7.07 (m, 2H), 6.91 (m, 1H), 6.73 (m, 1H), 3.86 (s, 3H), 3.65 (s, 2H), 2.63 (s, 3H), 2.61 (s, 3H). MS (m/z): (M+1) 538.0 (100%).

Example 96

N$^1$-(4-(2-(2,2-Dimethylhydrazinecarbonyl)thieno[3,2-b]pyridin-7-yloxy)-3-fluorophenyl)-N$^3$-methyl-N$^3$-phenylmalonamide (240)

Following the procedure described above for compound 236 (example 95, scheme 63) but replacing acid 27 with 3-(methyl(phenyl)amino)-3-oxopropanoic acid (31), title compound 240 was obtained in 44% yield. $^1$H NMR (400 MHz, DMSO-d$_6$) δ (ppm): 10.36 (s, 1H), 10.08 (br, 0.3H), 9.52 (s, 0.7H), 8.58 (dd, J=5.5 Hz, 3=8.4 Hz, 1H), 8.20 (m, 1H), 7.79 (m, 1H), 7.49-7.30 (m, 7H), 6.75 (d, J=5.5 Hz, 1H), 3.21 (s, 2H), 3.2 (s, 3H), 2.64 (s, 3H) 2.59 (s, 3H). MS (m/z): (M+1) 522.1 (100%).

Scheme 64

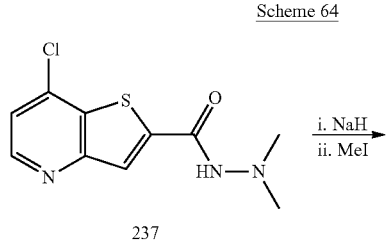

237

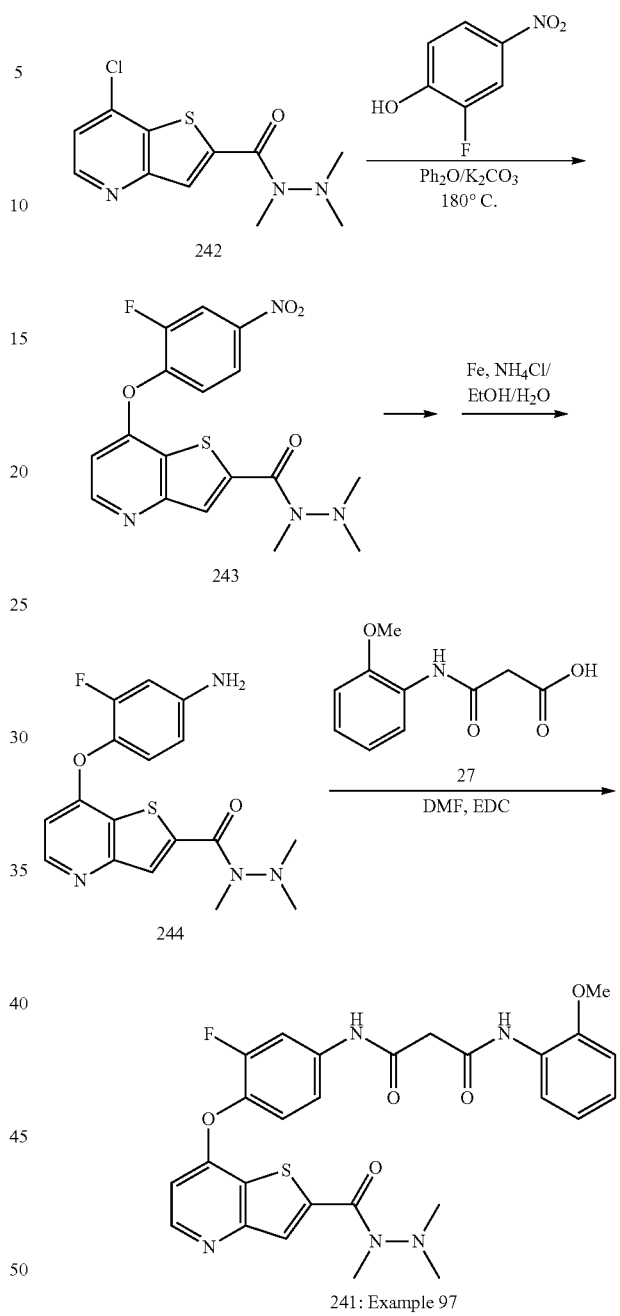

242

243

244

241: Example 97

Example 97

N$^1$-(3-Fluoro-4-(2-(1,2,2-trimethylhydrazinecarbonyl)thieno[3,2-b]pyridin-7-yloxy)phenyl)-N$^3$-(2-methoxyphenyl)malonamide (241)

Step 1: 7-Chloro-N,N',N$^1$-trimethylthieno[3,2-b]pyridine-2-carbohydrazide (242)

To a solution of 7-chloro-N',N$^1$-dimethylthieno[3,2-b]pyridine-2-carbohydrazide 237 (scheme 63) (357.9 mg, 1.4 mmol) in THF (14 mL)/DMF (9 mL), at 0° C., NaH (60% in mineral oil, 112 mg, 2.8 mmol) was added in one portion and the mixture was stirred for 1 h. MeI (0.118 mL, 2.8 mmol) was added and the mixture was warmed to room temperature and stirred for 1 h. The suspension was poured into water and extracted with EtOAc. The organic phase was extracted with 0.1N HCl, the aqueous phase basified to pH~11 by addition of 1 N NaOH and extracted with EtOAc. The organic phase was dried over anhydrous $Na_2SO_4$ and concentrated under reduced pressure affording 242 (111.2 mg, 0.41 mmol, 29%) as a yellow solid. MS (m/z): (M+1) 269.9 (100%), 271.0 (38%).

Step 2: 7-(2-Fluoro-4-nitrophenoxy)-N,N',N$^1$-trimethylthieno[3,2-b]pyridine-2-carbohydrazide (243)

Following the procedure described above for compound 238 (step 2, example 95, scheme 63) but replacing chloride 237 with compound 242, title compound 243 was obtained in 66% yield. MS (m/z): (M+1) 391.1 (100%).

Step 3: 7-(4-Amino-2-fluorophenoxy)-N,N',N$^1$-trimethylthieno[3,2-b]pyridine-2-carbohydrazide (244)

Following the procedure described above for compound 239 (step 3, example 95, scheme 63) but replacing 238 with compound 243, title compound 244 was obtained in 33% yield. MS (m/z): (M+1) 361.1 (100%).

Step 4: N$^1$-(3-fluoro-4-(2-(1,2,2-trimethylhydrazinecarbonyl)thieno[3,2-b]pyridin-7-yloxy)phenyl)-N$^3$-(2-methoxyphenyl)malonamide (241)

Following the procedure described above for compound 236 (step 4, example 95, scheme 63) but replacing amine 239 with 7-(4-amino-2-fluorophenoxy)-N,N',N'-trimethylthieno[3,2-b]pyridine-2-carbohydrazide (244), title compound 241 was obtained in 43% yield. $^1$H NMR (400 MHz, DMSO-d$_6$) δ (ppm): 10.45 (s, 1H), 8.45 (d, J=5.4 Hz, 1H), 7.79 (d, J=13.3 Hz, 1H), 7.67 (s, 1H), 7.62-7.31 (m, 7H), 6.62 (d, J=5.4 Hz, 1H), 3.40 (s, 9H), 3.23 (s, 2H), 3.21 (s, 3H). MS (m/z): (M+1) 536.2 (100%).

Scheme 65

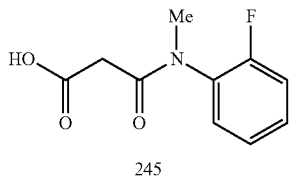

3-((2-Fluorophenyl)(methyl)amino)-3-oxopropanoic acid (245)

To a solution of methyl 3-chloro-3-oxopropanoate (1.75 mL, 15.99 mmol) in dry DCM (32 ml) was added 2-fluoro-N-methylaniline (2 g, 15.99 mmol) and the reaction mixture was stirred at 0° C. for 1 h, evaporated then redissolved in EtOAc, washed with dilute NaHCO$_3$, and brine. The organic phase was dried over sodium sulfate, and concentrated under reduced pressure to afford methyl 3((2-fluorophenyl)(methyl)amino)-3-oxopropanoate as yellow oil which was used without further purification (3.3 g, 16 mmol, 97%, crude). To a solution of this material (3.3 g, 16 mmol) in THF (16 ml) and water (16 ml) was added LiOH H$_2$O (1.35 g, 31.5 mmol) and the reaction mixture was stirred overnight, evaporated (to remove the THF) and then extracted with EtOAc. The aqueous phase was acidified to pH~1 by addition of 1N HCl and extracted with EtOAc. The solution was dried over Na$_2$SO$_4$, filtered and concentrated under reduced pressure to afford the title compound 245 as a brown solid, which was used without further purification (2.75 g, 13.03 mmol, 81% yield). MS (m/z): (M+1) 218.0 (88%), (2M+Li) 429.0 (100%).

1-(Methyl(phenyl)carbamoyl)cyclopropanecarboxylic acid (246)

To a solution of cyclopropane-1,1-dicarboxylic acid (1.5 g, 11.53 mmol) in THF (24 mL) TEA (1.6 mL, 11.53 mmol) was added dropwise and under stirring thionyl chloride (0.83 mL, 11.53 mmol) and the mixture stirred 30 min at room temperature. A solution of N-methylaniline (1.3 mL, 11.53 mmol) in THF (14 mL) was added dropwise at 0° C. and the mixture was stirred for 2 h. The mixture was diluted with EtOAc, extracted with 2N NaOH, acidified to pH~2 by addition of 2N HCl and extracted with EtOAc, dried over anhydrous Na$_2$SO$_4$ and concentrated under reduced pressure affording 246 (1.24 g, 5.66 mmol, 49%) as a white solid. MS (m/z): (M+1) 220.0 (100%).

TABLE 6

Compounds 247-252 (examples 98-103) prepared starting from the amine 12 and acids 27, 29, 161, 31, 245 and 246, according to the scheme 3

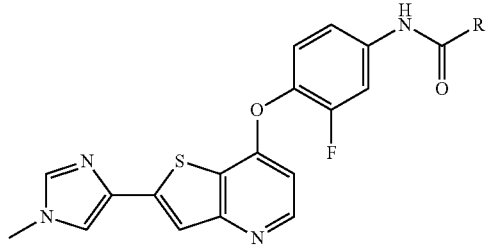

| Cpd | Ex. | R | Name | Characterization |
|---|---|---|---|---|
| 247 | 98 | | N¹-(3-fluoro-4-(2-(1-methyl-1H-imidazol-4-yl) thieno[3,2-b]pyridin-7-yloxy)phenyl)-N³-(2-methoxyphenyl)malonamide | ¹H NMR (400 MHz, DMSO-d₆) δ (ppm): 10.57 (s, 1H), 9.63 (s, 1H), 8.40 (d, J = 5.5 Hz, 1H), 8.08 (dd, J = 8.9 Hz, J = 1.4 Hz, 1H), 7.96 (d, J = 1.2 Hz, 1H), 7.85 (dd, J = 12.9 Hz, J = 2.4 Hz, 1H), 7.68 (s, 1H), 7.51-7.41 (m, 2H), 7.09-7.05 (m, 2H), 6.94-6.90 (m, 2H), 6.59 (d, J = 5.5 Hz, 1H), 3.86 (s, 3H), 3.73 (s, 3H), 3.65 (s, 2H). MS (m/z): (M + 1) 532.0 (100%) |
| 248 | 99 | | N¹-(3-fluoro-4-(2-(1-methyl-1H-imidazol-4-yl)thieno[3,2-b]pyridin-7-yloxy)phenyl)-N³-(2-fluorophenyl)malonamide | ¹H NMR (400 MHz, DMSO-d₆) δ (ppm): 10.57 (s, 1H), 10.06 (s, 1H), 8.43 (d, J = 5.5 Hz, 1H), 7.99 (m, 1H). 7.87 (dd, J = 12.9 Hz, J = 2.3 Hz, 1H), 7.86 (d, J = 1.2 Hz, 1H), 7.70 (d, J = 0.9 Hz, 1H), 7.68 (s, 1H), 7.51-7.41 (m, 2H), 7.28 (m, 1H), 7.20-7.15 (m, 2H), 6.59 (dd, J = 5.3 Hz, J = 0.6 Hz, 1H), 3.72 (s, 3H), 3.63 (s, 2H). MS (m/z): (M + 1) 520.1 (100%) |
| 249 | 100 | | N-(3-fluoro-4-(2-(1-methyl-1H-imidazol-4-yl)thieno[3,2-b]pyridin-7-yloxy)phenyl)-N-phenylcyclopropane-1,1-dicarboxamide | ¹H NMR (400 MHz, DMSO-d₆) δ (ppm): 10.39 (s, 1H), 10.02 (s, 1H), 8.44 (d, J = 5.4 Hz, 1H), 8.24 (s, 1H), 7.92-7.87 (m, 2H), 7.7 (d, J = 7.8 Hz, 2H), 7.63 (d, J = 7.8 Hz, 2H), 7.53-7.43 (m, 2H), 7.31 (dd, J = 7.6 Hz, J = 8.2 Hz, 2H), 7.07 (t, J = 7.3 Hz, 1H), 6.56 (d, J = 5.4 Hz, 1H), 3.72 (s, 3H), 1.48 (s, 4H). MS (m/z): (M + 1) 528.0 (100%) |
| 250 | 101 | | N¹-(3-fluoro-4-(2-(1-methyl-1H-imidazol-4-yl)thieno[3,2-b]pyridin-7-yloxy)phenyl)-N³-methyl-N³-phenylmalonamide | ¹H NMR (400 MHz, DMSO-d₆) δ (ppm): 10.29 (s, 1H), 8.43 (d, J = 5.5 Hz, 1H), 7.87 (d, J = 1.2 Hz, 1H), 7.79 (d, J = 13.1, 1H), 7.72 (d, J = 0.7 Hz, 1H), 7.68 (s, 1H), 7.50-7.30 (m, 7H), 6.57 (d, J = 5.5 Hz, 1H), 3.72 (s, 3H), 3.22 (s, 2H), 3.21 (s, 3H). MS (m/z): (M + 1) 516.1 (100%) |
| 251 | 102 | | N¹-(3-fluoro-4-(2-(1-methyl-1H-imidazol-4-yl)thieno[3,2-b]pyridin-7-yloxy)phenyl)-N³-(2-fluorophenyl)-N³-methylmalonamide | ¹H NMR (400 MHz, DMSO-d₆) δ (ppm): 10.31 (s, 1H), 8.52 (d, J = 5.2 Hz, 1H), 7.9 (s, 1H), 7.77 (d, J = 14.4 Hz, 1H), 7.75-7.30 (m, 7H), 7.05 (s, 1H), 6.68 (d, 5.2 Hz, 1H), 3.99 (s, 3H), 3.2 (m, 5H). MS (m/z): (M + 1) 534.0 (100%) |
| 252 | 103 | | N-(3-fluoro-4-(2-(1-methyl-1H-imidazol-4-yl)thieno[3,2-b]pyridin-7-yloxy)phenyl)-N-methyl-N-phenylcyclopropane-1,1-dicarboxamide | ¹H NMR (400 MHz, DMSO-d₆) δ (ppm): 9.92 (s, 1H), 8,45 (d, J = 5.5 Hz, 1H), 7.87 (s, 1H), 7.76-7.68 (m, 2H), 7.38-7.14 (m, 8H), 6.55 (d, J = 5.5 Hz, 1H), 3.72 (s, 3H), 3.26 (s, 3H), 1.44 (m, 2H), 1.24 (m, 1H). MS (m/z): (M + 1) 542.0 (100%) |

TABLE 7

Compounds 253-255 (examples 104-106) prepared starting from the amines 15 and 197 (scheme 54) and acids 31 and 27 according to the schemes 4 and 54

| Cpd | Ex. | Structure | Characterization |
|---|---|---|---|
| 253 | 104 | 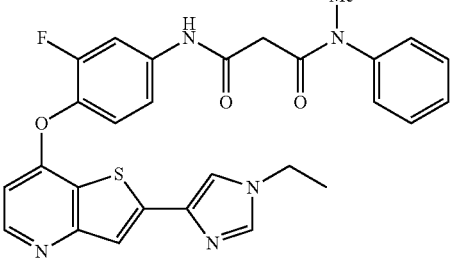<br>N$^1$-(4-(2-(1-Ethyl-1H-imidazol-4-yl)thieno[3,2-b]pyridin-7-yloxy)-3-fluorophenyl)-N$^3$-methyl-N$^3$-phenylmalonamide | $^1$H NMR (400 MHz, DMSO-d$_6$) δ (ppm): 10.30 (s, 1H), 8.42 (d, J = 5.5 Hz, 1H), 7.96 (d, J = 1 Hz, 1H), 7.79 (d, J = 1 Hz, 1H), 7.77 (s, 1H), 7.67 (s, 1H), 7.50-7.30 (m, 7H), 6.57 (d, J = 5.5 Hz, 1H), 4.06 (q, J = 7.3 Hz, 2H), 3.22 (s, 2H), 3.21 (s, 3H), 1.40 (t, J = 7.3 Hz, 3H). MS (m/z): (M + 1) 530.0 (100%) |
| 254 | 105 | 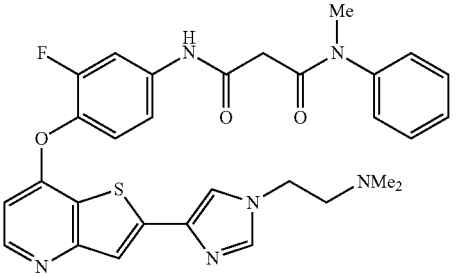<br>N$^1$-(4-(2-(1-(2-(dimethylamino)ethyl)-1H-imidazol-4-yl)thieno[3,2-b]pyridin-7-yloxy)-3-fluorophenyl)-N$^3$-methyl-N$^3$-phenylmalonamide | $^1$H NMR (400 MHz, DMSO-d$_6$) δ (ppm): 10.30 (s, 1H), 8.42 (d, J = 5.5 Hz, 1H), 7.92 (d, J = 1.2 Hz, 1H), 7.87 (d, J = 1.2 Hz, 1H), 7.80 (s, 1H), 7.77 (d, J = 1.2 Hz, 1H), 7.50-7.30 (m, 7H), 6.57 (d, J = 5.5 Hz, 1H), 4.11 (t, J = 6.3 Hz, 2H), 3.22 (s, 2H), 3.21 (s, 3H), 2.61 (t, J = 6.3 Hz, 2H), 2.18 (s, 6H). MS (m/z): (M + 1) 573.2 (100%) |
| 255 | 106 | 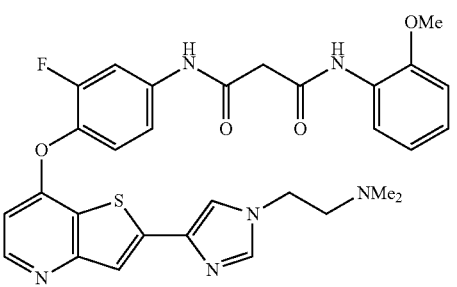<br>N$^1$-(4-(2-(1-(2-(dimethylamino)ethyl)-1H-imidazol-4-yl)thieno[3,2-b]pyridin-7-yloxy)-3-fluorophenyl)-N$^3$-(2-methoxyphenyl)malonamide | $^1$H NMR (400 MHz, DMSO-d$_6$) δ (ppm): 10.61 (s, 1H), 9.65 (s, 1H), 8.43 (d, J = 5.5 Hz, 1H), 8.07 (dd, J = 1.4 Hz, J = 9 Hz, 1H), 7.92 (d, J = 1.2 Hz, 1H), 7.86 (dd, J = 12.9 Hz, J = 2.3 Hz, 1H), 7.77 (d, J = 1.1 Hz, 1H), 7.67 (s, 1H), 7.51-7.41 (m, 2H), 7.09-7.01 (m, 2H), 6.94-6.89 (m, 1H), 6.58 (dd, J = 5.5 Hz, 0.6 Hz, 1H), 4.11 (t, J = 6.3 Hz, 2H), 3.86 (s, 3H), 3.65 (s, 2H), 2.61 (t, J = 6.3 Hz, 2H), 2.19 (s, 6H). MS (m/z): (M + 1) 598.1 (100%) |

Scheme 66

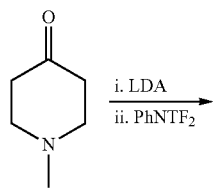

i. LDA
ii. PhNTf$_2$

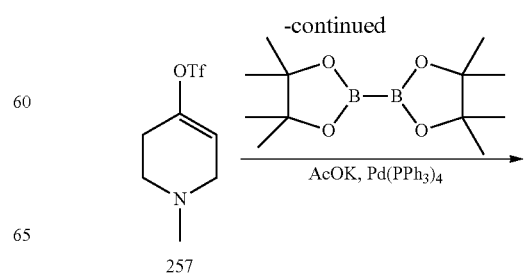

AcOK, Pd(PPh$_3$)$_4$

257

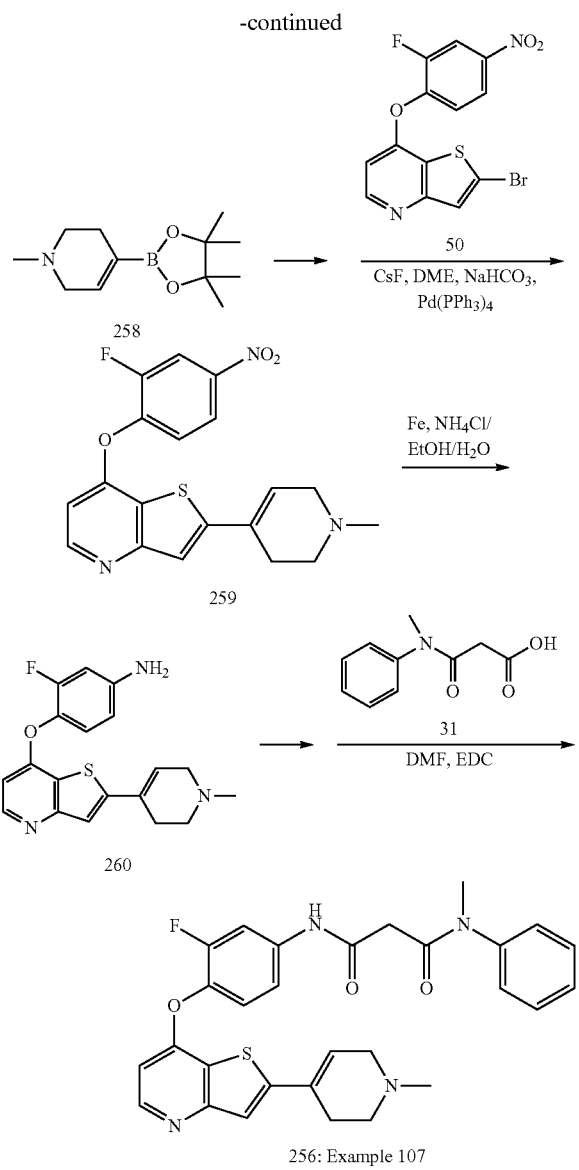

Example 107

N[1]-(3-Fluoro-4-(2-(1-methyl-1,2,3,6-tetrahydropyridin-4-yl)thieno[3,2-b]pyridin-7-yloxy)phenyl)-N[3]-methyl-N[3]-phenylmalonamide (256)

Step 1: 1-Methyl-1,2,3,6-tetrahydropyridin-4-yl trifluoromethanesulfonate (257)

LDA (1.5 N in THF, 8.1 mL, 12.17 mmol) was added to a solution of 1-methylpiperidin-4-one (1.4 mL, 12.17 mmol) in THF (16 mL) at −78° C., the mixture was allowed to warm to room temperature and stirred for 30 min. The solution was cooled once more to −78° C. and PhNTf$_2$ (5 g, 18.12 mmol) was added in one portion, the solution warmed to room temperature and stirred for 3 h. The reaction mixture was poured into water, extracted with ether, the organic phase dried over anhydrous Na$_2$SO$_4$ and concentrated under reduced pressure. The residue was purified by flash chromatography (EtOAc/Hexanes 1:5) affording 257 (2.38 g, 9.7 mmol, 80%) as orange oil. MS (m/z): (M+1) 245.9 (100% yield).

Step 2: 7-(2-Fluoro-4-nitrophenoxy)-2-(1-methyl-1,2,3,6-tetrahydropyridin-4-yl)thieno[3,2-b]pyridine (259)

To a mixture of 1-methyl-1,2,3,6-tetrahydropyridin-4-yl trifluoromethanesulfonate 257 (450 mg, 1.84 mmol), bis(pinacolato)diboron (477 mg, 2.02 mmol) and K$_2$CO$_3$ (541 mg, 5.52 mmol) in DME (3.7 mg), Pd(PPh$_3$)$_4$ (106 mg, 0.092 mmol) was added in one portion and the system was heated to reflux for 2 h under N$_2$. The reaction mixture was cooled down and filtered. To the filtrate containing the intermediate 258 were added bromide 50 (435 mg, 1.84 mmol), CsF (838 mg, 5.52 mmol), NaHCO$_3$ (463 mg, 5.52 mmol) and water (0.8 mL), and the mixture was heated to reflux for 2 h more. The reaction mixture was diluted with water and extracted with DCM; the organic phase was extracted with 1N HCl, the aqueous phase basified to pH~11 by addition of 2N aqueous NaOH, extracted with DCM, dried over anhydrous Na$_2$SO$_4$ and concentrated under reduced pressure affording 259 (279 mg, 0.72 mmol, 39% yield) as a brown solid. MS (m/z): (M+1) 385.9 (100%).

Step 3: 3-Fluoro-4-(2-(1-methyl-1,2,3,6-tetrahydropyridin-4-yl)thieno[3,2-b]pyridin-7-yloxy)aniline (260)

To a mixture of 4-(7-(2-fluoro-4-nitrophenoxy)thieno[3,2-b]pyridin-2-yl)-1-methyl-1,2,3,6-tetrahydropyridine 259 (279 mg, 0.72 mmol) and NH$_4$Cl (33 mg, 0.612 mmol) in EtOH (7.2 mL)/water (3.6 mL) at 100° C. Fe (342 mg, 6.2 mmol) was added in one portion and the mixture heated to reflux with vigorous stirring for 40 min. The mixture was filtered through Celite®, the Celite® washed with EtOH and the combined organic solutions concentrated under reduced pressure. The residue was dissolved in MeOH and purified by flash chromatography (DCM/MeOH 5:1) giving 260 (171.3 mg, 0.48 mmol, 67% yield) as a yellow solid. MS (m/z): (M+1) 356.0 (100%).

Step 4: N[1]-(3-Fluoro-4-(2-(1-methyl-1,2,3,6-tetrahydropyridin-4-yl)thieno[3,2-b]pyridin-7-yloxy)phenyl)-N[3]-methyl-N[3]-phenylmalonamide (256)

Following the procedure described above for the compound 5c (scheme 3) but replacing acid 1 with the acid 31 and amine 12 with amine 260; the title compound 256 was obtained in 44% yield. $^1$H NMR (400 MHz, DMSO-d$_6$) δ (ppm): 10.31 (s, 1H), 8.44 (d, J=5.48 Hz, 1H), 7.79 (d, 12.72 Hz, 1H), 7.5-7.3 (m, 8H), 6.59 (d, J=5.48 Hz, 1H), 6.38 (t, J=3.52 Hz, 1H), 3.22 (s, 2H), 3.21 (s, 3H), 3.08 (m, 2H), 2.61 (m, 4H), 2.30 (s, 3H). MS (m/z): (M+1) 531.0 (100%).

TABLE 8

Compounds 261-263 (examples 108-110) prepared starting from the amine 260 (scheme 66) and acids 161, 203 and 212 according to the schemes 45, 57 and 59

| Compd | Example | Structure | Characterization |
|---|---|---|---|
| 261 | 108 | N-(3-Fluoro-4-(2-(1-methyl-1,2,3,6-tetrahydropyridin-4-yl)thieno[3,2-b]pyridin-7-yloxy)phenyl)-N-phenylcyclopropane-1,1-dicarboxamide | $^1$H NMR (400 MHz, DMSO-d$_6$) δ (ppm): 10.19 (s, 1H), 8.41 (d, 1H, J = 5.5 Hz), 7.74 (dd, 1H, J1 = 2.2 Hz, J2 = 13.1 Hz), 7.46-7.37 (m, 5H), 7.28-7.24 (m, 3H), 6.56 (d, 1H, J = 5.5 Hz), 6.35 (s, br, 1H), 4.82 (m, 1H), 3.03 (s, 2H), 3.01 (s, 2H), 2,58 (s, 4H), 2.27 (s, 3H), 0.99 (s, 3H), 0.98 (s, 3H). MS (m/z): 543.0 (M + H) |
| 262 | 109 | N$^1$-(3-Fluoro-4-(2-(1-methyl-1,2,3,6-tetrahydropyridin-4-yl)thieno[3,2-b]pyridin-7-yloxy)phenyl)-N$^3$-isopropyl-N$^3$-phenylmalonamide | $^1$H NMR (400 MHz, DMSO-d$_6$) δ (ppm): 10.19 (s, 1H), 8.41 (d, 1H, J = 5.5 Hz), 7.74 (dd, 1H, J$_1$ = 2.2 Hz, J$_2$ = 13.1 Hz), 7.46-7.37 (m, 5H), 7.28-7.24 (m, 3H), 6.56 (d, 1H, J = 5.5 Hz), 6.35 (s, br, 1H), 4.82 (m, 1H), 3.03 (s, 2H), 3.01 (s, 2H), 2,58 (s, 4H), 2.27 (s, 3H), 0.99 (s, 3H), 0.98 (s, 3H) MS (m/z): 559.1 (M + H). |
| 263 | 110 | N-(3-Fluoro-4-(2-(1-methyl-1,2,3,6-tetrahydropyridin-4-yl)thieno[3,2-b]pyridin-7-yloxy)phenyl)-2-oxo-3-phenylimidazolidine-1-carboxamide | $^1$H NMR (400 MHz, DMSO-d$_6$) δ (ppm): 10.57 (s, 1H), 8.44 (d, 1H, J = 5.5 Hz), 7.84 (dd, 1H, J$_1$ = 2.2 Hz, J$_2$ = 13.3 Hz), 7.62 (d, 1H, J = 7.8 Hz), 7.49 (s, 1H), 7.46-7.40 (m, 4H), 7.17 (t, 1H, J = 7.2 Hz), 6.60 (d, 1H, J = 5.3 Hz), 6.37 (t, 1H, J = 3.8 Hz), 3.95 (m, 4H), 3.05 (m, 2H), 2.59 (s, 4H), 2.28 (s, 3H). MS (m/z): 544.1 (M + H) |

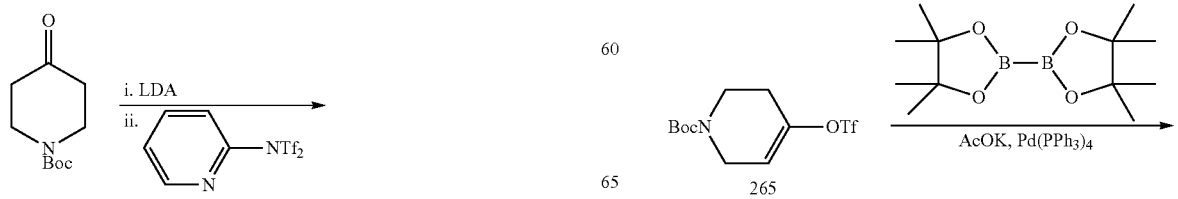

Scheme 67

263
-continued

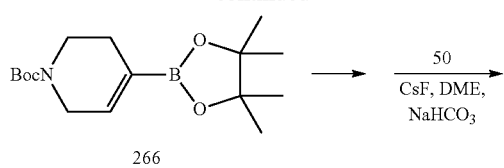
266

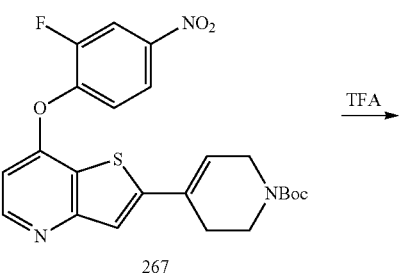
267

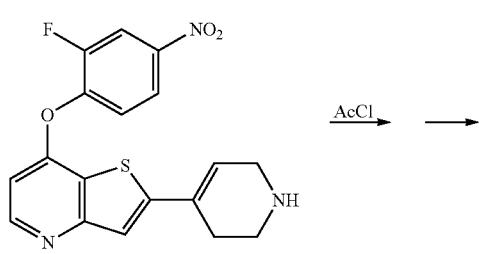
268

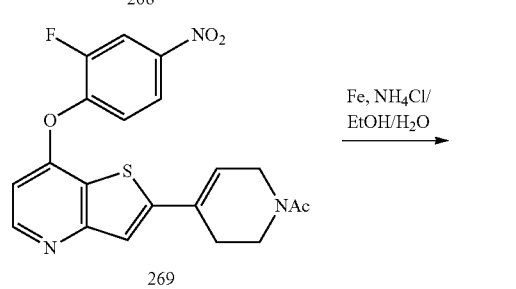
269

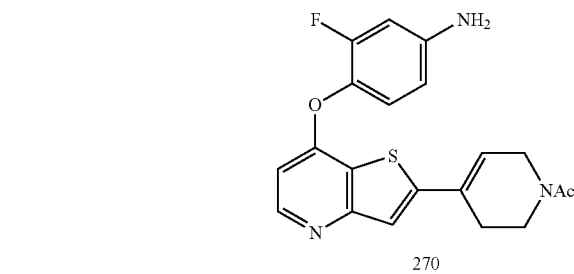
270

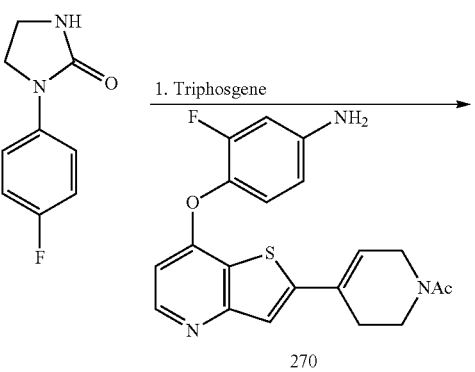
270

264
-continued

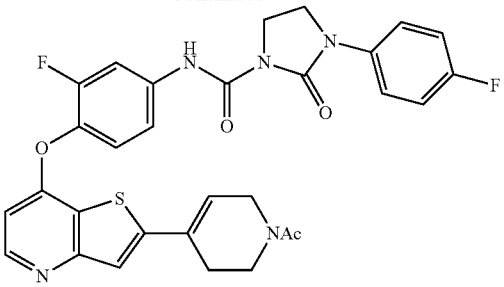
264: Example 111

Example 111

N-(3-Fluoro-4-(2-(1-methyl-1,2,3,6-tetrahydropyridin-4-yl)thieno[3,2-b]pyridin-7-yloxy)phenyl)-3-(4-fluorophenyl)-2-oxoimidazolidine-1-carboxamide (264)

Step 1: tert-Butyl 4-(trifluoromethylsulfonyloxy)-5,6-dihydropyridine-1(2H)-carboxylate (265)

LDA (1.5 N in THF, 7.2 mL, 10.68 mmol) was added to a solution of tert-butyl 4-oxopiperidine-1-carboxylate (1.94 mL, 9.74 mmol) in THF (13 mL) at −78° C., the mixture was warmed to room temperature and stirred for 30 min. The solution was cooled to −78° C. and 1,1,1-trifluoro-N-(pyridin-2-yl)-N-(trifluoromethylsulfonyl)methanesulfonamide (4.0 g, 11.2 mmol) was added in one portion, the solution was warmed to room temperature and stirred for 1 h. The mixture was diluted with EtOAc, washed with 1N HCl, water, brine and concentrated under reduced pressure to a minimum volume, and filtered. The filtrate was collected, further concentrated and the residue was distilled under reduced pressure affording 265 (2.80 g, 8.17 mmol, 86% yield) as brown liquid. MS (m/z): (M−Boc+1) 232.1 (26%).

Step 2: tert-Butyl 4-(7-(2-fluoro-4-nitrophenoxy)thieno[3,2-b]pyridin-2-yl)-5,6-dihydropyridine-1(2H)-carboxylate (267)

Following the procedure described above for compound 259 (scheme 66) but replacing compound 257 with tert-butyl 4-(trifluoromethylsulfonyloxy)-5,6-dihydropyridine-1(2H)-carboxylate (265); the title compound 267 was obtained in 56% yield. MS (m/z): (M+1) 472.5 (25%).

Step 3: 7-(2-Fluoro-4-nitrophenoxy)-2-(1,2,3,6-tetrahydropyridin-4-yl)thieno[3,2-b]pyridine (268)

To a solution of tert-butyl 4-(7-(2-fluoro-4-nitrophenoxy)thieno[3,2-b]pyridin-2-yl)-5,6-dihydropyridine-1(2H)-carboxylate 267 (1 g, 2.13 mmol) in DCM (4.3 mL) TFA (4.3 mL) was added and the reaction mixture was stirred for 2 h at room temperature. The solvent was removed under reduced pressure, the residue was suspended in aqueous sodium bicarbonate, the mixture extracted with DCM, EtOAc and DCM;

the combined organic phases were filtered and the recovered solids dried. The organic phase was dried over anhydrous Na₂SO₄, concentrated under reduced pressure and the residue was combined with the solid material obtained earlier to provide 268 (806 mg, 2.12 mmol, 100% yield) as a yellow solid. MS (m/z): (M+1) 372.1 (100%).

Step 4: 1-(4-(7-(2-Fluoro-4-nitrophenoxy)thieno[3,2-b]pyridin-2-yl)-5,6-dihydropyridin-1(2H)-yl)ethanone (269)

To a suspension of 4-(7-(2-fluoro-4-nitrophenoxy)thieno[3,2-b]pyridin-2-yl)-1,2,3,6-tetrahydropyridine 268 (400 mg, 1.08 mmol) and DIPEA (0.207 mL, 1.19 mmol) in DCM was added acetyl chloride (0.15 mL, 2.16 mmol) at room temperature and the mixture (that turned homogeneous soon after) was stirred for 1 h. The crude mixture was concentrated under reduced pressure and the residue purified by flash chromatography (5% MeOH to 10% MeOH in DCM) affording 269 (358.2 mg, 0.87 mmol, 80% yield) as a white solid. MS (m/z): (M+1) 414.4 (100%).

Step 5: 1-(4-(7-(4-Amino-2-fluorophenoxy)thieno[3,2-b]pyridin-2-yl)-5,6-dihydropyridin-1(2H)-yl)ethanone (270)

To a mixture of 1-(4-(7-(2-fluoro-4-nitrophenoxy)thieno[3,2-b]pyridin-2-yl)-5,6-dihydropyridin-1(2H)-yl)ethanone (269) (358.2 mg, 0.87 mmol) and NH₄Cl (39.4 mg, 0.74 mmol) in EtOH (8.7 mL)/water (4.3 mL) at 100° C. was added Fe (411.3 mg, 7.36 mmol) in one portion and the mixture heated to reflux with vigorous stirring for 40 min. The mixture was filtered through Celite®, the Celite® washed with EtOH and the combined organic solutions concentrated under reduced pressure. The residue was dissolved in DCM, extracted with water, dried aver anhydrous Na₂SO₄ and concentrated under reduced pressure affording 270 (256.5 mg, 0.67 mmol, 77% yield) as a white solid. MS (m/z): (M+1) 384.2 (100%).

Step 6: N-(3-Fluoro-4-(2-(1-methyl-1,2,3,6-tetrahydropyridin-4-yl)thieno[3,2-b]pyridin-7-yloxy)phenyl)-3-(4-fluorophenyl)-2-oxoimidazolidine-1-carboxamide (264)

Triphosgene (209.2, 0.47 mmol) was added to a solution of 1-(4-fluorophenyl)imidazolidin-2-one (209.2 mg, 0.71 mmol) in THF (4.7 mL) and the mixture was heated to reflux for 6 h. 1-(4-(7-(4-Amino-2-fluorophenoxy)thieno[3,2-b]pyridin-2-yl)-5,6-dihydropyridin-1(2H)-yl)ethanone 270 (120.0 mg, 0.31 mmol) and DIPEA (0.1 mL, 0.5 mmol) were added and the mixture was stirred for 1 h at room temperature. The reaction mixture was transferred to a silica gel flash chromatography column and eluted with 3% MeOH in DCM affording 264 (97.6 mg, 0.16 mmol, 52% yield) as a white solid. ¹H NMR (400 MHz, DMSO-d₆) δ (ppm): 10.55 (s, 1H), 8.47 (d, 5.5 Hz, 1H), 7.84 (dd, J=2.4 Hz, 13.1 Hz, 1H), 7.71-7.63 (m, 2H), 7.54 (m, 1H), 7.48-7.42 (m, 2H), 7.31-7.27 (m, 2H), 6.63 (m, 1H), 6.42 (m, 1H), 4.21 (br, 1H), 4.15 (br, 1H), 3.96-3.93 (m, 4H), 3.71-3.65 (m, 2H), 2.70 (br, 1H), 2.59 (br, 1H), 2.09 (s, 1.5H), 2.05 (s, 1.5H). MS (m/z): (M+1) 590.2 (100%).

Scheme 68

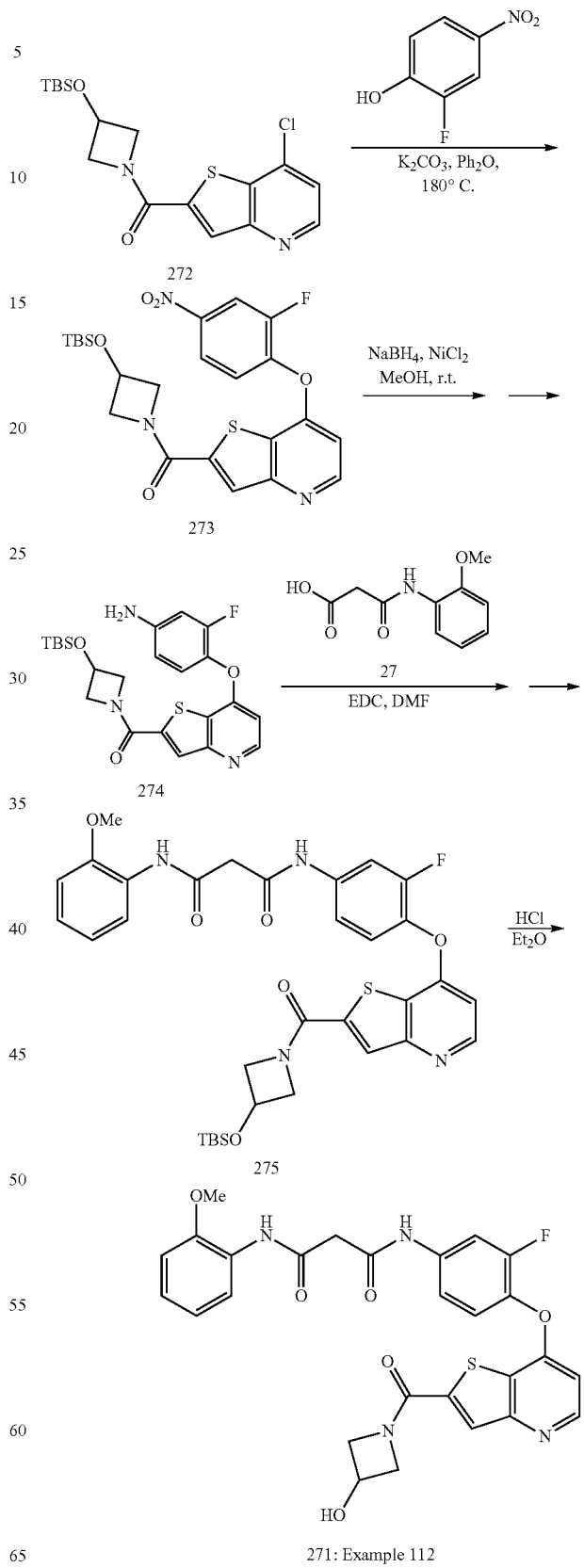

271: Example 112

Example 112

N[1]-(3-Fluoro-4-(2-(3-hydroxyazetidine-1-carbonyl) thieno[3,2-b]pyridin-7-yloxy)phenyl)-N[3]-(2-methoxyphenyl)malonamide (271)

Step 1: (3-(tert-Butyldimethylsilyloxy)azetidin-1-yl) (7-(2-fluoro-4-nitrophenoxy)thieno[3,2-b]pyridin-2-yl)methanone (273)

A mixture of (3-(tert-butyldimethylsilyloxy)azetidin-1-yl) (7-chlorothieno[3,2-b]pyridin-2-yl)methanone 272 (749.7 mg, 1.96 mmol) (WO 2006/010264), 2-fluoro-4-nitrophenol (461 mg, 2.94 mmol), $K_2CO_3$ (518 mg, 3.92 mmol) and $Ph_2O$ (2.6 mL) was stirred in a sealed tube for 1.5 h at 170° C. The mixture was diluted with DCM, extracted with water, the organic phase dried over anhydrous $Na_2SO_4$ and concentrated. The residue was purified by flash chromatography (eluted successively with: EtOAc/hexanes 1:1, EtOAc, EtOAc/MeOH 4:1) affording 273 (336 mg, 0.67 mmol, 34% yield). MS (m/z): (M+1) 504.1 (100%).

Step 2: (7-(4-amino-2-fluorophenoxy)thieno[3,2-b]pyridin-2-yl)(3-(tert-butyldimethylsilyloxy)azetidin-1-yl)methanone (274)

To a solution of (3-(tert-butyldimethylsilyloxy)azetidin-1-yl)(7-(2-fluoro-4-nitrophenoxy)thieno[3,2-b]pyridin-2-yl) methanone 273 (336 mg, 0.67 mmol) and $NiCl_2.6H_2O$ (318 g, 1.34 mmol) in MeOH/THF (4.7 mL/4.7 mL) was added $NaBH_4$ (101 g, 2.68 mmol) at 0° C. and the mixture stirred for 1 hr. The reaction mixture was added to an EDTA.4Na (1.1 g/100 mL) solution and extracted with EtOAc. The aqueous layer was filtered and extracted again with EtOAc. The combined organic phase was dried over anhydrous $Na_2SO_4$ and concentrated under reduced pressure. The residue was purified by flash chromatography (pure EtOAc) giving 274 as creamy foam (145.2 mg, 46% yield). MS (m/z): (M+1) 474.1 (100%).

Step 3: N[1]-(4-(2-(3-(tert-Butyldimethylsilyloxy)azetidine-1-carbonyl)thieno[3,2-b]pyridin-7-yloxy)-3-fluorophenyl)-N[3]-(2-methoxyphenyl)malonamide (275)

A mixture of (7-(4-amino-2-fluorophenoxy)thieno[3,2-b]pyridin-2-yl)(3-(tert-butyldimethylsilyloxy)azetidin-1-yl) methanone 274 (145.2 mg, 0.31 mmol), 27 (77 mg, 0.367 mmol), and EDC (70.3 mg, 0.367 mmol) in DMF (4.4 mL) was stirred overnight at room temperature. The crude mixture was diluted with EtOAc, extracted with water, dried over anhydrous $Na_2SO_4$ and concentrated under reduced pressure affording crude 275 (178.4 mg, 0.269 mmol, 87% yield) that was used in the next step without further purification. MS (m/z): (M+1) 665.1 (100%).

Step 4: N[1]-(3-Fluoro-4-(2-(3-hydroxyazetidine-1-carbonyl)thieno[3,2-b]pyridin-7-yloxy)phenyl)-N[3]-(2-methoxyphenyl)malonamidexHCl (271)

To a suspension of N[1]-(4-(2-(3-(tert-butyldimethylsilyloxy)azetidine-1-carbonyl)thieno[3,2-b]pyridin-7-yloxy)-3-fluorophenyl)-N[3]-(2-methoxyphenyl) malonamide 275 (179 mg, 0.268 mmol) in MeOH (18 mL) HCl (1N in dioxane, 0.54 mL, 0.54 mmol) was added dropwise and the mixture was stirred for 15 min at room temperature. The solvent was removed under reduced pressure, MeOH was added to the residue and concentrated, the residue was suspended in water and lyophilized affording 271 (104.6 mg, 0.18 mmol, 67% yield) as a white solid. $^1$H NMR (400 MHz, DMSO-$d_6$) δ (ppm): 10.68 (s, 1H), 9.64 (s, 1H), 8.64 (d. J=5.5 Hz, 1H), 8.06 (dd, J=1.9 Hz, J=9 Hz, 1H), 7.94 (s, 1H), 7.89 (dd, J=12.9 Hz, J=2.4 Hz, 1H), 7.51 (t, J=8.8 Hz, 1H), 7.46 (dd, J=1.6 Hz, J=8.8 Hz, 1H), 7.11-7.04 (m, 2H), 6.92 (m, 1H), 6.84 (dd, J=5.5 Hz, J=1 HZ, 1H), 6.90 (m, 1H), 4.59 (m, 1H), 4.36-4.31 (m, 2H), 3.88-3.84 (m, 4H), 3.67 (s, 2H). MS (m/z): (M+1) 551.0 (100%).

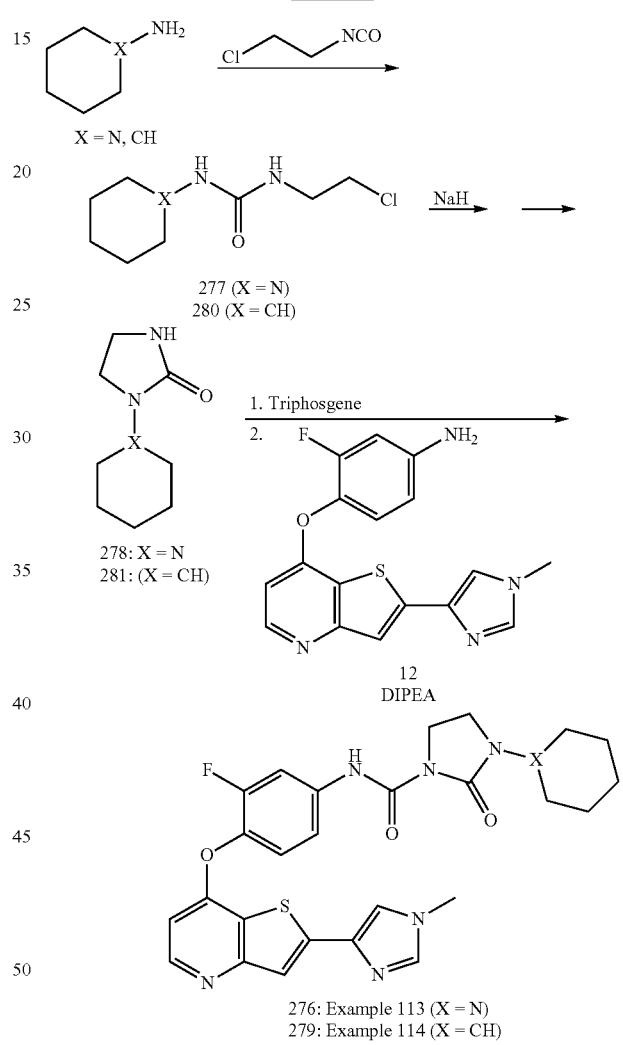

Scheme 69

Example 113

N-(3-Fluoro-4-(2-(1-methyl-1H-imidazol-4-yl)thieno [3,2-b]pyridin-7-yloxy)phenyl)-2-oxo-3-(piperidin-1-yl)imidazolidine-1-carboxamide (276)

Step 1: 1-(Piperidin-1-yl)imidazolidin-2-one (278)

To a solution of piperidin-1-amine (5 mL, 46.32 mmol) in THF (46 mL) 1-chloro-2-isocyanatoethane (4.35 mL, 50.95 mmol) was added dropwise at 0° C.; after the addition was completed the mixture was stirred for 1 h at 0° C. The reaction was quenched with water, the mixture was extracted with DCM and the organic phase was concentrated under reduced pressure to produce the chloride 277 (not isolated). This material was dissolved in THF (93 mL), NaH (60% in mineral oil, 3.7 g, 93 mmol) was added at 0° C. and the mixture stirred overnight. The solution quenched with water, extracted with DCM, dried over anhydrous $Na_2SO_4$ and concentrated under reduced pressure. The residue was triturated with hexanes and filtered affording 278 (7.2 g, 43 mmol, 92% yield) as a white solid. MS (m/z): (M+1) 191.9 (100%).

Step 2: N-(3-Fluoro-4-(2-(1-methyl-1H-imidazol-4-yl)thieno[3,2-b]pyridin-7-yloxy)phenyl)-2-oxo-3-(piperidin-1-yl)imidazolidine-1-carboxamide (276)

Triphosgene (107 mg, 0.36 mmol) was added to a solution of 1-(piperidin-1-yl)imidazolidin-2-one (278) (120 mg, 0.71 mmol) in THF (7.1 mL) and the mixture was refluxed 6 h the solution was cooled down. 3-Fluoro-4-(2-(1-methyl-1H-imidazol-4-yl)thieno[3,2-b]pyridin-7-yloxy)aniline (12) (150.0 mg, 0.44 mmol) and DIPEA (0.186 mL, 1.07 mmol) were added and the mixture stirred 1 h at room temperature. The reaction mixture was filtered, the solution transferred to a flash chromatography column and eluted with 2% to 5% MeOH in DCM affording title compound 276 (176.4 mg, 0.33 mmol, 75% yield) as a creamy solid. $^1$H NMR (400 MHz, DMSO-$d_6$) δ (ppm): 10.57 (s, 1H), 8.4 (d, J=5.4 Hz, 1H), 7.86 (s, 1H), 7.79 (dd, J=2 Hz, J=12.9 Hz, 1H), 7.72 (s, 1H), 7.68 (s, 1H), 7.46 (t, J=8.9 Hz, 1H), 7.36 (m, 1H), 6.58 (d, 5.4 Hz, 1H), 3.76 (dd, J=7.7 Hz, J=8.2 Hz, 2H), 3.73 (s, 3H), 3.54 (dd, J=8.2 Hz, J=7.7 Hz, 2H), 2.9-2.87 (m, 4H), 1.59 (m, 4H), 1.35 (m, 2H). MS (m/z): (M+1) 536.2 (100%)

Example 114

3-Cyclohexyl-N-(3-fluoro-4-(2-(1-methyl-1H-imidazol-4-yl)thieno[3,2-b]pyridin-7-yloxy)phenyl)-2-oxoimidazolidine-1-carboxamide (279)

Step 1: 1-(Piperidin-1-yl)imidazolidin-2-one (281)

Following the procedure described above for compound 278 (scheme 69) but replacing piperidin-1-amine with cyclohexylamine, the title compound 281 was obtained in 23% yield (via the intermediate 280). MS (m/z): (M+1) 169.2 (56%), (2M+23) 359.3 (100%).

Step 2: 3-Cyclohexyl-N-(3-fluoro-4-(2-(1-methyl-1H-imidazol-4-yl)thieno[3,2-b]pyridin-7-yloxy)phenyl)-2-oxoimidazolidine-1-carboxamide (279)

Following the procedure described above for the compound 276 (example 113) but replacing 1-(piperidin-1-yl) imidazolidin-2-one (278) by 1-cyclohexylimidazolidin-2-one (281), the title compound 279 was obtained in 68% yield. $^1$H NMR (400 MHz, DMSO-$d_6$) δ (ppm): 10.69 (s, 1H), 8.44 (dd, J=5.5 Hz, 1H), 7.86 (s, 1H), 7.79 (dd, J=2.5 Hz, J=13 Hz, 1H), 7.72 (s, 1H), 7.68 (s, 1H), 7.46 (t, J=8.9 Hz, 1H), 7.35 (d, J=5.5 Hz, 1H), 6.58 (d, J=5.5 Hz, 1H), 3.8 (dd, J=7.6 Hz, J=8.0 Hz, 2H), 3.73 (s, 3H), 3.7-3.6 (m, 1H), 3.44 (dd, J=7.2 Hz, J=8.0 Hz, 2H), 1.79-1.60 (m, 5H), 1.47-1.41 (m, 2H), 1.36-1.29 (m, 2H), 1.7 (m, 1H). MS (m/z): (M+1) 535.2.

Scheme 70

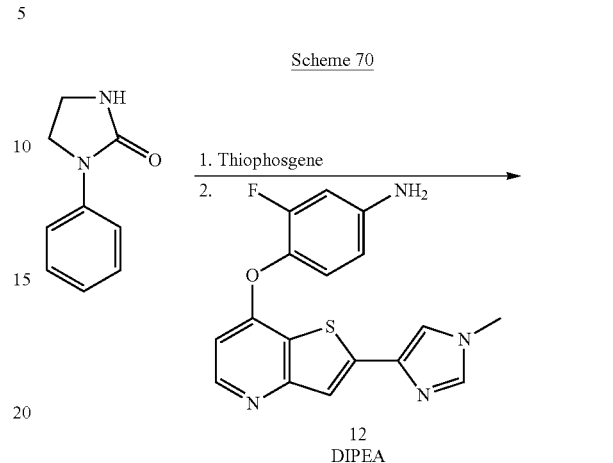

12
DIPEA

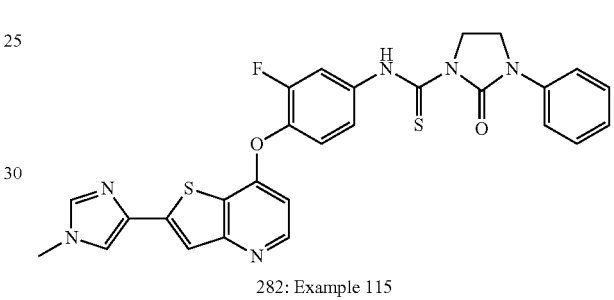

282: Example 115

Example 115

N-(3-Fluoro-4-(2-(1-methyl-1H-imidazol-4-yl)thieno[3,2-b]pyridin-7-yloxy)phenyl)-2-oxo-3-phenylimidazolidine-1-carbothioamide (282)

Thiophosgene (0.052 mL, 0.68 mmol) was added to a solution of 1-phenylimidazolidin-2-one (100 mg, 0.62 mmol) in THF (6.2 mL) and the mixture was heated at 50° C. over night. The amine 12 (150.0 mg, 0.44 mmol) and DIPEA (0.115 mL, 0.66 mmol) were added and the mixture was stirred for 1 h at room temperature. The mixture was diluted with DCM, the solution was extracted with 3% citric acid solution, dried ($Na_2SO_4$) and concentrated under reduced pressure. The residue was purified by flash chromatography (MeOH/DCM) 1:9 affording 282 (143 mg, 0.269 mmol, 61% yield) as a brown solid. $^1$H NMR (400 MHz, DMSO-do) δ (ppm): 12.37 (s, 1H), 8.47 (d, J=5.4 Hz, 1H), 8.06 (dd, J=2 Hz, J=11.3 Hz, 1H), 7.87 (d, J=1 Hz, 1H), 7.71 (m, 2H), 7.63 (m, 2H), 7.54 (m, 2H), 7.45 (m, 2H), 7.21 (dd, J=7.2 Hz, J=7.4 Hz, 1H), 6.61 (d, 5.4 Hz, 1H), 4.24 (dd, J=7.9 Hz, J=6.5 Hz, 2H) 3.98 (dd, J=7.9 Hz, J=6.5 Hz, 2H), 3.72 (s, 3H). MS (m/z): (M+1) 545.1 (100%).

Example 116

N-(3-Fluoro-4-(2-(1-methyl-1H-imidazol-2-yl)thieno[3,2-b]pyridin-7-yloxy)phenyl)-3-(4-fluorophenyl)-2-oxoimidazolidine-1-carboxamide (283)

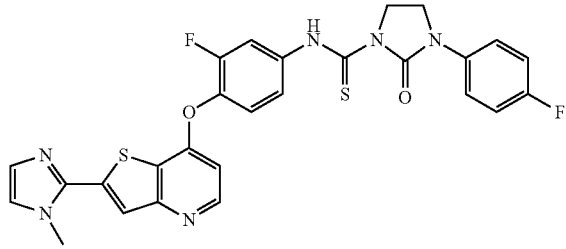

283: Example 116

Title compound 283 was obtained similarly to the compound 282 (example 115) according to the Scheme 69, starting from 1-(4-fluorophenyl)imidazolidin-2-one and amine 9 (Scheme 2). $^1$H NMR (400 MHz, DMSO-d$_6$) δ (ppm) 12.34 (s, 1H), 8.55 (d, J=5.48 Hz, 1H), 8.05 (d, J=13.1 Hz, 1H), 7.91 (s, 1H), 7.64 (m, 2H), 7.54 (m, 2H), 7.42 (s, 1H), 7.30 (t, J=8.80 Hz, 2H), 7.05 (s, 1H), 6.71 (d, J=5.28 Hz, 1H), 4.23 (t, J=7.43 Hz, 2H), 3.98 (m, 5H). MS (m/z): 563.2 (M+H).

Scheme 71

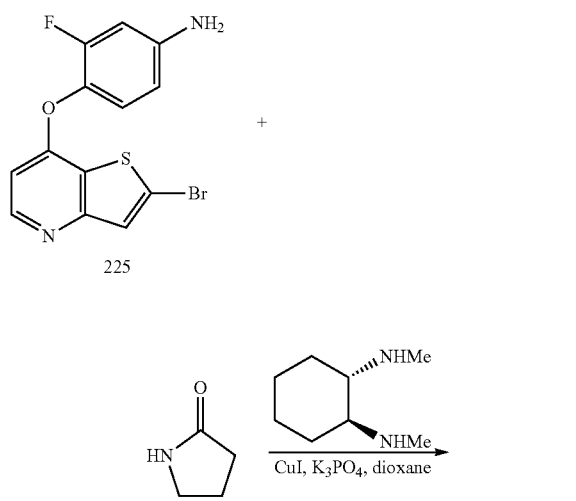

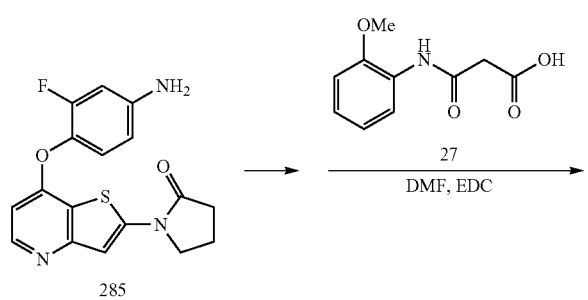

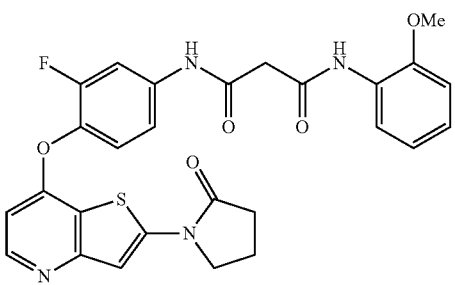

284: Example 117

Example 117

N$^1$-(3-Fluoro-4-(2-(2-oxopyrrolidin-1-yl)thieno[3,2-b]pyridin-7-yloxy)phenyl)-N-(2-methoxyphenyl)malonamide (284)

Step 1: 1-(7-(4-Amino-2-fluorophenoxy)thieno[3,2-b]pyridin-2-yl)pyrrolidin-2-one (285)

A mixture of the amine 225 (200 mg, 0.59 mmol) (scheme 61), trans-N$^1$,N$^2$-dimethylcyclohexane-1,2-diamine (17 mg, 0.118 mmol), pyrrolidin-2-one (0.054 mL, 0.71 mmol), CuI (22 mg, 0.118 mmol) and K$_3$PO$_4$ (250 mg, 1.18 mmol) in dioxane (0.6 mL) was stifled under nitrogen at 70° C. overnight. The crude mixture was purified by flash chromatography (MeOH/DCM 1:19) affording title compound 285 (83.7 mg, 0.243 mmol, 41% yield) as an orange solid. MS (m/z): (M+1) 344.0 (100%).

Step 2: N$^1$-(3-Fluoro-4-(2-(2-oxopyrrolidin-1-yl)thieno[3,2-b]pyridin-7-yloxy)phenyl)-N$^3$-(2-methoxyphenyl)malonamide (284)

A solution of the amino lactam 285 (80.7 mg, 0.243 mmol), 3-(2-methoxyphenylamino)-3-oxopropanoic acid 27 (76.1 mg, 0.365 mmol), EDC (70 mg, 0.365 mmol) and HOBt (56 mg, 0.365 mmol) in DMF (2.4 mL) was stirred overnight at room temperature. More 27 (76.1 mg, 0.365 mmol) and EDC (70 mg, 0.365 mmol) were added and the mixture was stirred 6 h more. The mixture was diluted with EtOAc, extracted with water, dried over anhydrous Na$_2$SO$_4$, and concentrated under reduced pressure. The residue was crystallized from MeCN affording title compound 284 (24 mg, 0.044 mmol, 18% yield). $^1$H NMR (400 MHz, DMSO-d$_6$) δ (ppm): 10.73 (s, 1H), 9.63 (s, 1H), 8.64 (d, J=6.5 Hz, 1H), 8.06 (dd, J=10 Hz, J=1.5 Hz, 1H), 7.92 (dd. J=13.1 Hz, J=2.3 Hz, 1H), 7.59-7.48 (m, 2H), 7.12-7.05 (m, 3H), 6.94-6.90 (m, 2H), 4.07 (dd, J=7.0 Hz, J=7.4 Hz, 2H), 3.86 (s, 3H), 3.67 (s, 2H), 2.69 (dd, J=7.8 Hz, J=8.2 Hz, 2H), 2.24 (m, 2H). MS (m/z): (M+1) 535.1 (100%).

Example 118

N-(3-Fluoro-4-(2-(1-methyl-1H-imidazol-4-yl)thieno[3,2-b]pyridin-7-yloxy)phenyl)-3-phenyl-2-thioxoimidazolidine-1-carboxamide (286)

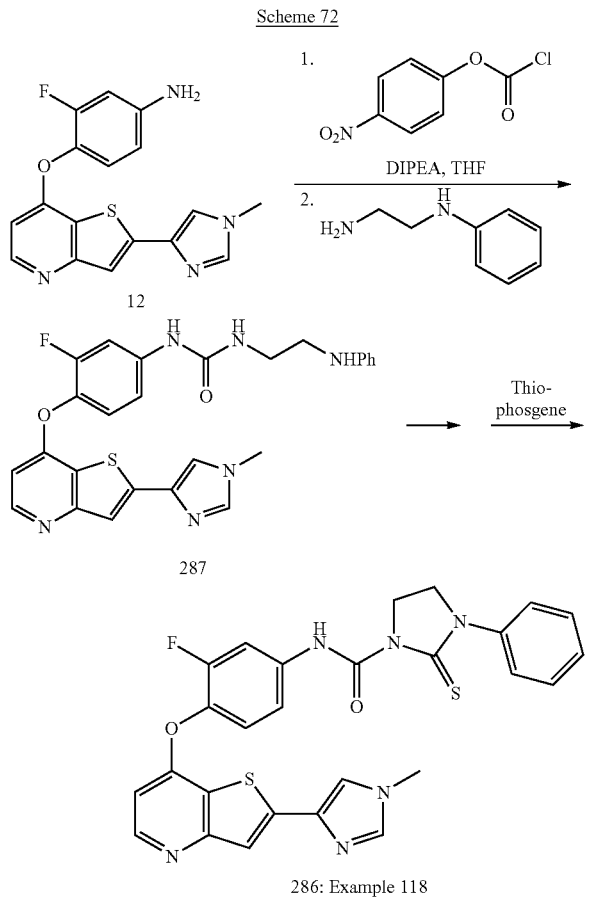

Scheme 72

To a mixture of 12 (150 mg, 0.44 mmol) and DIPEA (0.084 mL, 0.48 mmol) in THF (4.5 mL) 4-nitrophenyl carbamate (97 mg, 0.48 mmol) was added and the mixture stirred 30 min at room temperature. Thereafter $N^1$-phenylethane-1,2-diamine (0.086 mL, 0.66 mmol) was added and the mixture was stirred for 1 h more, to form the intermediate 287 (not isolated). Thiophosgene (0.05 mL, 0.66 mmol) and DIPEA (0.232 mL, 1.38 mmol) were added and the mixture was stirred overnight at room temperature. More thiophosgene (0.05 mL, 0.66 mmol) was added and the mixture was heated to reflux for 3 h more. The mixture was diluted with DCM, extracted with water, dried over anhydrous $Na_2SO_4$ and concentrated under reduced pressure. The residue was purified by flash chromatography (5% MeOH in DCM) followed by trituration of the resulting solid with MeOH affording title compound 286 (61 mg, 0.11 mmol, 25%) as a cream solid. $^1$H NMR (400 MHz, DMSO-$d_6$) δ (ppm): 12.56 (s, 1H), 8.45 (d, J=5.5 Hz, 1H), 7.87 (d, J=1.2 Hz, 1H), 7.82 (dd, J=2.5 Hz, J=12.7 Hz, 1H), 7.73 (d, J=0.8 Hz, 1H), 7.67 (s, 1H), 7.52-7.48 (m, 5H), 7.42-7.35 (m, 2H), 6.31 (dd, J=5.5 Hz, J=0.8 Hz, 1H), 4.27-4.22 (m, 2H), 4.13-4.09 (m, 2H), 3.73 (s, 3H). MS (m/z): (M+1) 545.2 (100%).

TABLE 9

Compounds 288-290 (examples 119-121) prepared starting from the amine 197 (scheme 54) and acids 1, 161 and 177

| Cpd | Ex | Structure | Characterization |
|---|---|---|---|
| 288 | 119 | $N^1$-(4-(2-(1-(2-(Dimethylamino)ethyl)-1H-imidazol-4-yl)thieno[3,2-b]pyridin-7-yloxy)-3-fluorophenyl)-$N^3$-phenylmalonamide | $^1$H NMR (400 MHz, DMSO-$d_6$) δ (ppm): 10.57 (s, 1H), 10.22 (s, 1H), 8.43 (d, J = 5.6 Hz, 1H), 7.92 (d, J = 1.2 Hz, 1H), 7.88 (dd, J = 12.4, 2.4 Hz, 1H), 7.77 (d, J = 1.2 Hz, 1H), 7.66 (s, 1H), 7.61 (dd, J = 8.8, 1.2 Hz, 2H), 7.49 (t, J = 8.8 Hz, 1H), 7.43 (dd, J = 8.8, 2.4 Hz, 1H), 7.33 (t, J = 8.0 Hz, 2H), 7.07 (t, J = 7.6 Hz, 1H), 6.58 (d, J = 5.6 Hz, 1H), 4.11 (t, J = 6.4 Hz, 2H), 3.52 (s, 2H), 2.61 (t, J = 6.4 Hz, 2H), 2.19 (s, 6H). |

TABLE 9-continued

Compounds 288-290 (examples 119-121) prepared starting from the amine 197 (scheme 54) and acids 1, 161 and 177

| Cpd | Ex | Structure | Characterization |
|---|---|---|---|
| 289 | 120 | N-(4-(2-(1-(2-(dimethylamino)ethyl)-1H-imidazol-4-yl)thieno[3,2-b]pyridin-7-yloxy)-3-fluorophenyl)-N-phenylcyclopropane-1,1-dicarboxamide | $^1$H NMR (400 MHz, DMSO-$d_6$) δ (ppm): 10.37 (s, 1H), 10.00 (s, 1H), 8.43 (d, J = 5.2 Hz, 1H), 7.94-7.87 (d, 2H), 7.77 (d, J = 1.2 Hz, 1H), 7.66 (s, 1H), 7.63 (d, J = 8.4 Hz, 2H), 7.51 (dd, J = 9.2, 2.0 Hz, 1H), 7.45 (t, J = 8.8 Hz, 1H), 7.31 (t, J = 8.0 Hz, 2H), 7.07 (t, J = 7.6 Hz, 1H), 6.55 (d, J = 5.6 Hz, 1H), 4.11 (t, J = 6.4 Hz, 2H), 2.61 (t, J = 6.4 Hz, 2H), 2.19 (s, 6H), 1.48 (s, 4H). |
| 290 | 121 | N-(4-(2-(1-(2-(Dimethylamino)ethyl)-1H-imidazol-4-yl)thieno[3,2-b]pyridin-7-yloxy)-3-fluorophenyl)-N-(2-fluorophenyl)cyclopropane-1,1-dicarboxamide | $^1$H NMR (400 MHz, DMSO-$d_6$) δ (ppm): 10.37 (bs, 1H), 10.30 (bs, 1H), 8.44 (d, J = 5.6 Hz, 1H), 7.92 (d, J = 1.0 Hz, 1H), 7.90-7.80 (m, 2H), 7.77 (d, J = 1.0 Hz, 1H), 7.67 (s, 1H), 7.52 (dd, J = 8.8, 2.0 Hz, 1H), 7.47 (t, J = 8.8 Hz, 1H), 7.31-7.23 (m, 1H), 7.23-7.15 (m, 2H), 6.56 (d, J = 5.6 Hz, 1H), 4.11 (t, J = 6.4 Hz, 2H), 2.61 (t, J = 6.4 Hz, 2H), 2.19 (s, 6H), 1.63-1.52 (m 4H). |

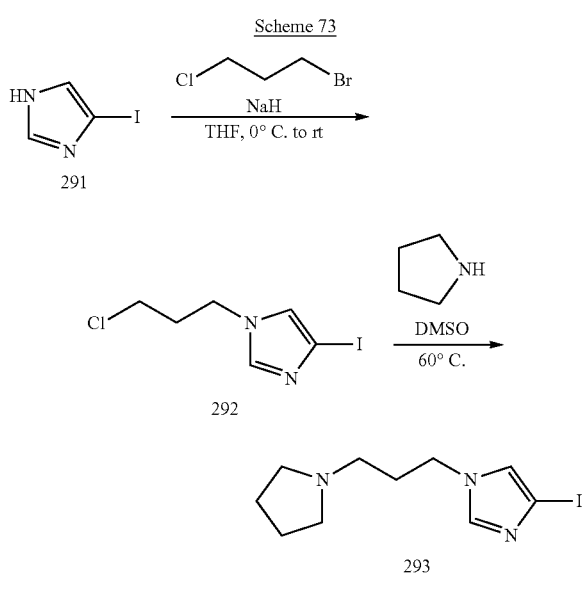

Scheme 73

4-Iodo-1-(3-(pyrrolidin-1-yl)propyl)-1H-imidazole (293)

Step 1. 1-(3-Chloropropyl)-4-iodo-1H-imidazole (292)

To a stirred solution of 4-iodo-1H-imidazole (291, 2 g, 10.3 mmol) [a) Y. He et al., *Tet. Lett.* 45, 2004, 5529-5532, b) Panosyan, F. B., Still, I. W. J., *Can. J. Chem.* 79, 2001, 1110-1114.] in dry tetrahydrofuran (40 mL) at 0° C. under nitrogen was added sodium hydride (60% in oil, 0.91 g, 22.7 mmol). The mixture was stirred for 20 min. at 0° C., 1-bromo-3-chloropropane (1.2 mL, 12.4 mmol) was added and stirring was continued for 24 h at room temperature. Water was added and the aqueous solution was extracted twice with ethyl acetate. The combined organic layers were dried over anhydrous sodium sulfate and the solvent was removed under reduced pressure. The residue was purified by column chromatography on silica gel (eluent ethyl acetate-dichloromethane, 4:96) to afford 292 (1.35 g, 5.0 mmol, 49% yield) as a light yellow oil. $^1$H NMR (400 MHz, DMSO-$d_6$) δ ppm: 7.63 (d, J=1.2 Hz, 1H), 7.42 (d, J=1.2 Hz, 1H), 4.08 (t, J=6.8

Hz, 2H), 3.55 (d, J=6.8 Hz, 2H), 2.16 (q, J=6.8 Hz, 2H). MS (m/z): 271.0 (M+H, 100%), 273.0 (M+H, 32%).

Step 2. 4-Iodo-1-(3-(pyrrolidin-1-yl)propyl)-1H-imidazole (293)

A solution of the chloride 292 (1.2 g, 4.44 mmol) and pyrrolidine (1.1 mL, 13.3 mmol) in dry DMSO (2 mL) was heated at 60° C. under nitrogen for 3 h. The reaction mixture was cooled, diluted with water and the aqueous phase was extracted twice with ethyl acetate. The combined organic layers were dried over anhydrous sodium sulfate and the solvent was removed under reduced pressure. The residue was purified by column chromatography on silica gel (eluent methanol-dichloromethane, 5:95 to 20:80) to afford 293 (1.06 g, 3.47 mmol, 78% yield) as a colorless oil. $^1$H NMR (400 MHz, DMSO-$d_6$) δ ppm: 7.59 (d, J=1.2 Hz, 1H), 7.39 (d, J=1.2 Hz, 1H), 3.98 (t, J=7.2 Hz, 2H), 2.45-2.33 (m, 4H), 2.29 (t, J=7.2 Hz, 2H), 1.84 (q, J=7.2 Hz, 2H), 1.72-1.62 (m, 4H). MS (m/z): 305.9 (M+H).

Imidazole 293 was used for the synthesis of compounds 294-299 (examples 122-127), Table 10.

TABLE 10

Compounds 294-299 (examples 122-127) prepared according to the schemes 46, 58 and 59

| Compd | Example | Structure | Characterization |
|---|---|---|---|
| 294 | 122 | 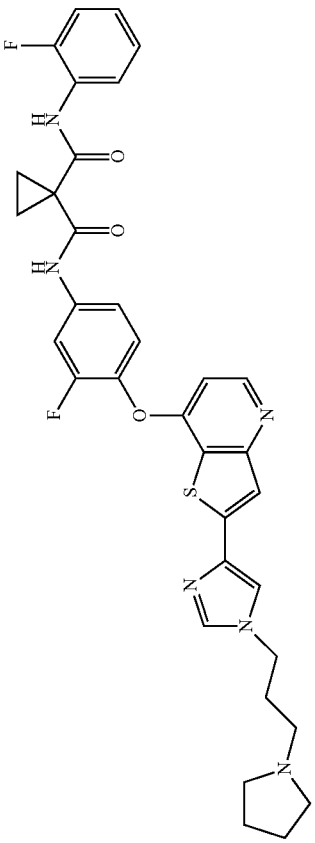<br>N-(3-fluoro-4-(2-(1-(3-(pyrrolidin-1-yl)propyl)-1H-imidazol-4-yl)thieno[3,2-b]pyridin-7-yloxy)phenyl)-N-(2-fluorophenyl)cyclopropane-1,1-dicarboxamide | $^1$H NMR (400 MHz, DMSO-$d_6$) δ (ppm): 10.37 (bs, 1H), 10.28 (bs, 1H), 8.44 (d, J = 5.2 Hz, 1H), 7.95 (d, J = 1.2 Hz, 1H), 7.89-7.80 (m, 2H), 7.76 (d, J = 1.2 Hz, 1H), 7.68 (s, 1H), 7.52 (dd, J = 8.8, 2.0 Hz, 1H), 7.48 (t, J = 8.8 Hz, 1H), 7.31-7.24 (m, 1H), 7.22-7.16 (m, 2H), 6.57 (d, J = 5.2 Hz, 1H), 4.06 (t, J = 6.6 Hz, 2H), 2.46-2.39 (m, 4H), 2.37 (t, J = 6.6 Hz, 2H), 1.93 (q, J = 6.6 Hz, 2H), 1.69 (q, J = 4.0 Hz, 4H), 1.63-1.54 (m, 4H). MS (m/z): 643.0 (M + H). |
| 295 | 123 | 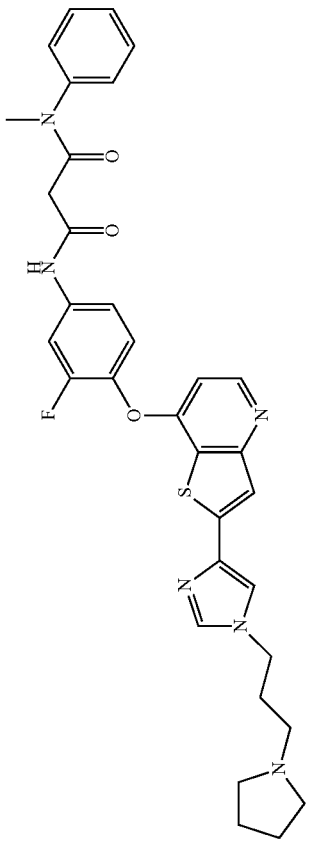<br>N$^1$-(3-fluoro-4-(2-(1-(3-(pyrrolidin-1-yl)propyl)-1H-imidazol-4-yl)thieno[3,2-b]pyridin-7-yloxy)phenyl)-N$^3$-methyl-N$^3$-phenylmalonamide | $^1$H NMR (400 MHz, DMSO-$d_6$) δ (ppm): 10.30 (s, 1H), 8.43 (d, J = 5.4 Hz, 1H), 8.16 (s, 1H), 7.95 (d, J = 1.2 Hz, 1H), 7.83-7.76 (m, 1H), 7.78 (d, J = 1.2 Hz, 1H), 7.68 (s, 1H), 7.52-7.29 (m, 6H), 6.57 (d, J = 5.4 Hz, 1H), 4.08 (t, J = 7.0 Hz, 2H), 3.23 (s, 2H), 3.21 (s, 3H), 2.64-2.58 (m, 4H), 2.53 (t, J = 7.0 Hz, 2H), 1.98 (q, J = 7.0 Hz, 2H), 1.74 (q, J = 3.2 Hz, 4H). |

TABLE 10-continued

Compounds 294-299 (examples 122-127) prepared according to the schemes 46, 58 and 59

| Compd | Example | Structure | Characterization |
|---|---|---|---|
| 296 | 124 | N-(3-Fluoro-4-(2-(1-(3-(pyrrolidin-1-yl)propyl)-1H-imidazol-4-yl)thieno[3,2-b]pyridin-7-yloxy)phenyl)-2-oxo-1-phenylpyrrolidine-3-carboxamide | 1H NMR (400 MHz, DMSO-d$_6$) δ (ppm): 10.72 (s, 1H), 8.43 (d, J = 5.6 Hz, 1H), 8.19 (s, 1H), 7.95 (d, J = 1.2 Hz, 1H), 7.94-7.89 (m, 1H), 7.77 (d, J = 1.2 Hz, 1H), 7.70-7.67 (m, 3H), 7.52-7.46 (m, 2H), 7.41 (t, J = 8.0 Hz, 2H), 7.18 (t, J = 8.0 Hz, 1H), 6.60 (d = J = 5.6 Hz, 1H), 4.07 (t, J = 6.8 Hz, 2H), 4.0-3.89 (m, 2H), 3.79 (t, J = 8.4 Hz, 1H), 2.54-2.35 (m, 8H), 1.94 (q, J = 6.8 Hz, 2H), 1.70 (q, J = 3.2 Hz, 4H). MS (m/z): 625.1 (M + H). |
| 297 | 125 | N-(3-Fluoro-4-(2-(1-(3-(pyrrolidin-1-yl)propyl)-1H-imidazol-4-yl)thieno[3,2-b]pyridin-7-yloxy)phenyl)-2-oxo-3-phenylimidazolidine-1-carboxamide | 1H NMR (400 MHz, DMSO-d6) δppm: 10.58 (s, 1H), 8.45 (d, J = 5.6 Hz, 1H), 7.95 (d, J = 1.2 Hz, 1H), 7.85 (dd, J = 2.0 and 13.2 Hz, 1H), 7.77 (d, J = 1.2 Hz, 1H), 7.68 (s, 1H), 7.63 (d, J = 8.0 Hz, 2H), 7.54-7.40 (m, 4H), 7.18 (t, J = 8.0 Hz, 2H), 6.60 (d, J = 5.6 Hz, 1H), 4.08 (t, J = 6.8 Hz, 2H), 4.04-3.90 (m, 4H), 2.06-1.92 (m, 2H), 1.84-1.66 (m, 4H). |

TABLE 10-continued

Compounds 294-299 (examples 122-127) prepared according to the schemes 46, 58 and 59

| Compd | Example | Structure | Characterization |
|---|---|---|---|
| 298 | 126 | 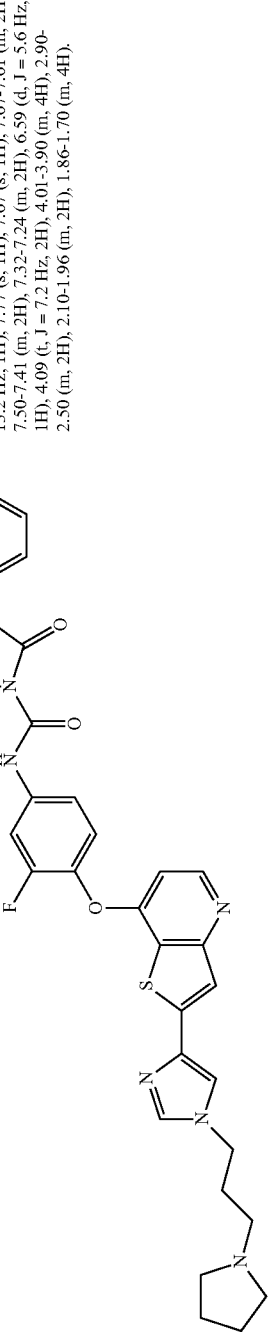<br>N-(3-Fluoro-4-(2-(1-(3-(pyrrolidin-1-yl)propyl)-1H-imidazol-4-yl)thieno[3,2-b]pyridin-7-yloxy)phenyl)-3-(4-fluorophenyl)-2-oxoimidazolidine-1-carboxamide | 1H NMR (400 MHz, DMSO-d6) δppm: 10.54 (s, 1H), 8.44 (d, J = 5.6 Hz, 1H), 7.94 (s, 1H), 7.84 (dd, J = 2.0 and 13.2 Hz, 1H), 7.77 (s, 1H), 7.67-7.61 (m, 2H), 7.50-7.41 (m, 2H), 7.32-7.24 (m, 2H), 6.59 (d, J = 5.6 Hz, 1H), 4.09 (t, J = 7.2 Hz, 2H), 4.01-3.90 (m, 4H), 2.90-2.50 (m, 2H), 2.10-1.96 (m, 2H), 1.86-1.70 (m, 4H). |
| 299 | 127 | 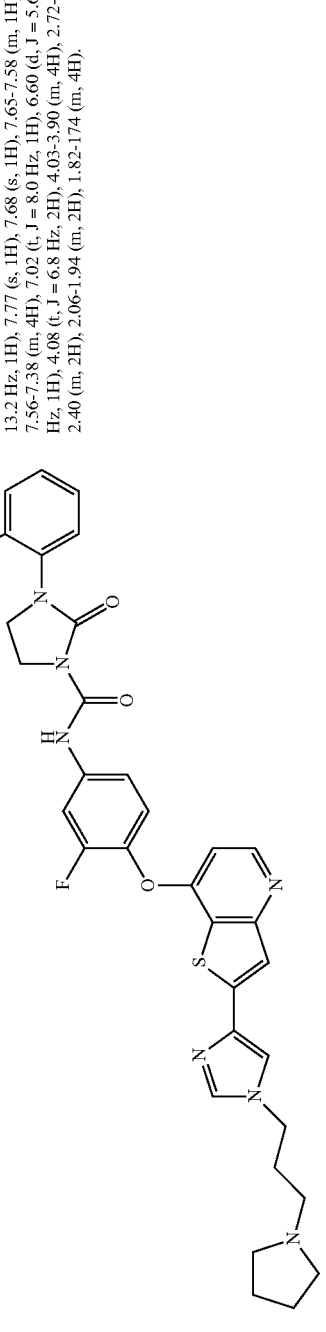<br>N-(3-Fluoro-4-(2-(1-(3-(pyrrolidin-1-yl)propyl)-1H-imidazol-4-yl)thieno[3,2-b]pyridin-7-yloxy)phenyl)-3-(2-fluorophenyl)-2-oxoimidazolidine-1-carboxamide | 1H NMR (400 MHz, DMSO-d6) δppm: 10.10 (s, 1H), 8.45 (d, J = 5.6 Hz, 1H), 7.95 (s, 1H), 7.86 (d, J = 2.0 and 13.2 Hz, 1H), 7.77 (s, 1H), 7.68 (s, 1H), 7.65-7.58 (m, 1H), 7.56-7.38 (m, 4H), 7.02 (t, J = 8.0 Hz, 1H), 6.60 (d, J = 5.6 Hz, 1H), 4.08 (t, J = 6.8 Hz, 2H), 4.03-3.90 (m, 4H), 2.72-2.40 (m, 2H), 2.06-1.94 (m, 2H), 1.82-174 (m, 4H). |

TABLE 11

Compounds 300-309 (examples 128-137) prepared according to the schemes 46, 58 and 59

| Compd | Example | Structure | Characterization |
|---|---|---|---|
| 300 | 128 | 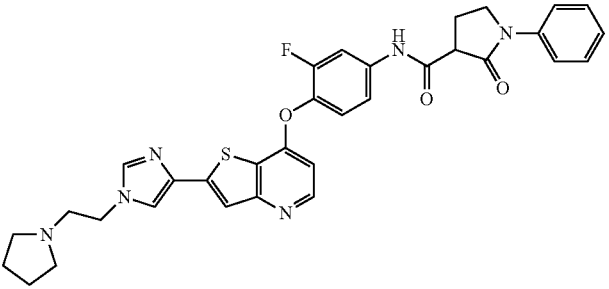<br>N-(3-Fluoro-4-(2-(1-(2-(pyrrolidin-1-yl)ethyl)-1H-imidazol-4-yl)thieno[3,2-b]pyridin-7-yloxy)phenyl)-2-oxo-1-phenylpyrrolidine-3-carboxamide | $^1$H NMR (400 MHz, DMSO-$d_6$) δ (ppm): 10.71 (s, 1H), 8.43 (d, J = 5.6 Hz, 1H), 7.95-7.89 (m, 2H), 7.79 (d, J = 1.2 Hz, 1H), 7.71-7.66 (m, 3H), 7.53-7.46 (m, 2H), 7.41 (t, J = 8.0 Hz, 2H), 7.18 (t, J = 7.6 Hz, 1H), 6.59 (d, J = 5.6 Hz, 1H), 4.14 (t, J = 6.0 Hz, 2H), 3.99-3.88 (m, 2H), 3.79 (t, J = 8.4 Hz, 1H), 2.85-2.75 (m, 2H), 2.56-2.33 (m, 6H), 1.73-1.65 (m, 4H). |
| 301 | 129 | 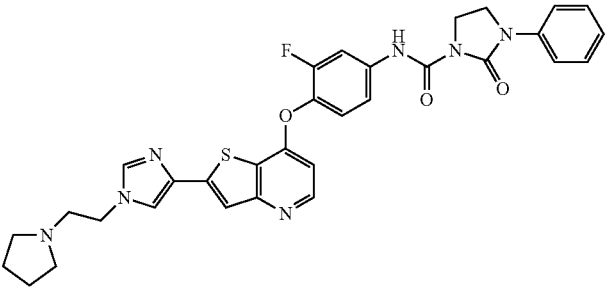<br>N-(3-Fluoro-4-(2-(1-(2-(pyrrolidin-1-yl)ethyl)-1H-imidazol-4-yl)thieno[3,2-b]pyridin-7-yloxy)phenyl)-2-oxo-3-phenylimidazolidine-1-carboxamide | $^1$H NMR (400 MHz, DMSO-$d_6$) δ (ppm): 10.59 (s, 1H), 8.44 (d, J = 5.6 Hz, 1H), 7.94 (d, J = 1.2 Hz, 1H), 7.85 (dd, J = 12.8, 2.4 Hz, 1H), 7.78 (d, J = 1.2 Hz, 1H), 7.67 (s, 1H), 7.64 (dd, J = 8.4, 0.6 Hz, 2H), 7.52-7.40 (m, 4H), 7.18 (t, J = 7.2 Hz, 1H), 6.59 (d, J = 5.6 Hz, 1H), 4.13 (t, J = 6.0 Hz, 2H), 4.02-3.91 (m, 4H), 2.79 (t, J = 6.0 Hz, 2H), 2.55-2.44 (m, 4H, hidden under DMSO), 1.73-1.63 (m, 4H). MS (m/z): 612.1 (M + H). |
| 302 | 130 | 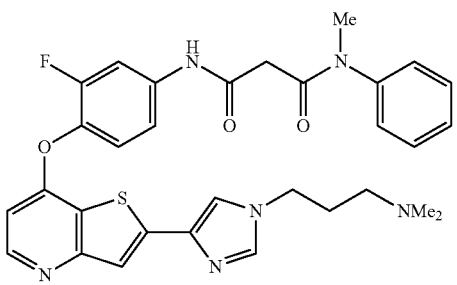<br>N$^1$-(4-(2-(1-(3-(Dimethylamino)propyl)-1H-imidazol-4-yl)thieno[3,2-b]pyridin-7-yloxy)-3-fluorophenyl)-N$^3$-methyl-N$^3$-phenylmalonamide | $^1$H NMR (400 MHz, $d_6$ DMSO) δ (ppm): 10.33 (s, 1H), 8.43 (d, J = 5.4 Hz, 1H), 8.23 (s, 1H), 7.95 (br, J = 1 Hz, 1H), 7.81 (br, 1H), 7.77 (d, J = 1 Hz, 1H), 7.68 (s, 1H), 7.50-7.31 (m, 8H), 6.57 (d, J = 5.4 Hz, 1H), 4.05 (t, J = 7 Hz, 2H), 3.23 (s, 2H), 3.21 (s, 3H), 2.26 (dd, J = 7 Hz, J = 6.9 Hz, 2H), 2.19 (s, 6H), 1.92 (m, 2H). MS (m/z): (M + H) 587.2 (100%) |
| 303 | 131 | 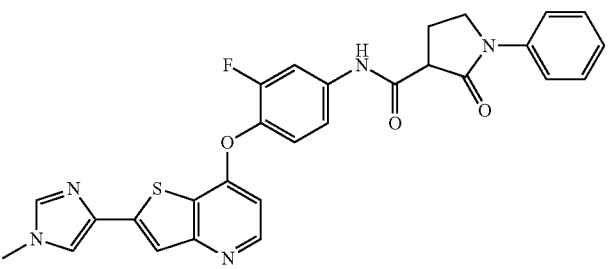<br>N-(3-Fluoro-4-(2-(1-methyl-1H-imidazol-4-yl)thieno[3,2-b]pyridin-7-yloxy)phenyl)-2-oxo-1-phenylpyrrolidine-3-carboxamide | $^1$H NMR (400 MHz, DMSO-$d_6$) δ (ppm): 10.72 (s, 1H), 8.43 (d, J = 5.6 Hz, 1H), 7.94-7.92 (m, 1H), 7.87 (d, J = 0.8 Hz, 1H), 7.73 (d, J = 1.2 Hz, 1H), 7.70-7.66 (m, 3H), 7.53-7.46 (m, 2H), 7.41 (t, J = 8.4 Hz, 2H), 7.18 (t, J = 7.6 Hz, 1H), 6.59 (d, J = 5.6 Hz, 1H), 4.0-3.88 (m, 2H), 3.79 (t, J = 8.8 Hz, 1H), 3.73 (s, 3H), 2.55-2.34 (m, 2H). |

TABLE 11-continued

Compounds 300-309 (examples 128-137) prepared according to the schemes 46, 58 and 59

| Compd | Example | Structure | Characterization |
|---|---|---|---|
| 304 | 132 | 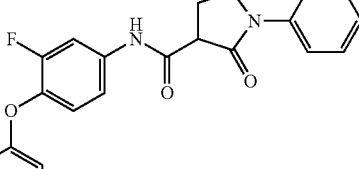<br>N-(3-fluoro-4-(2-(1-methyl-1H-imidazol-4-yl)thieno[3,2-b]pyridin-7-yloxy)phenyl)-1-(4-fluorophenyl)-2-oxopyrrolidine-3-carboxamide | $^1$H NMR (400 MHz, DMSO-d$_6$) δ (ppm): 10.72 (s, 1H), 8.44 (d, J = 5.6 Hz, 1H), 7.94-7.87 (m, 2H), 7.74 (s, 1H), 7.73-7.68 (m, 3H), 7.53-7.46 (m, 2H), 7.29-7.22 (m, 2H), 6.60 (d, J = 5.6 Hz, 1H), 3.98-3.87 (m, 2H), 3.79 (t, J = 8.8 Hz, 1H), 3.73 (s, 3H), 2.52-2.34 (m, 2H). |
| 305 | 133 | 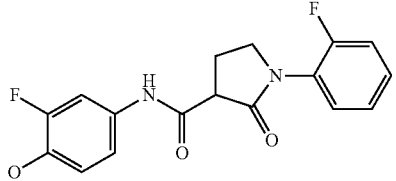<br>N-(3-Fluoro-4-(2-(1-methyl-1H-imidazol-4-yl)thieno[3,2-b]pyridin-7-yloxy)phenyl)-1-(2-fluorophenyl)-2-oxopyrrolidine-3-carboxamide | $^1$H NMR (400 MHz, DMSO-d$_6$) δ (ppm): 10.72 (s, 1H), 8.43 (d, J = 5.6 Hz, 1H), 7.95-7.89 (m, 1H), 7.87 (d, J = 1.2 Hz, 1H), 7.72 (d, J = 0.8 Hz, 1H), 7.68 (s, 1H), 7.52-7.46 (m, 3H), 7.42-7.24 (m, 3H), 6.59 (d, J = 5.6 Hz, 1H), 3.88-3.81 (m, 2H), 3.75 (t, J = 8.8 Hz, 1H), 3.73 (s, 3H), 2.61-2.38 (m, 2H). MS (m/z): 546.0 (M + H). |
| 306 | 134 | 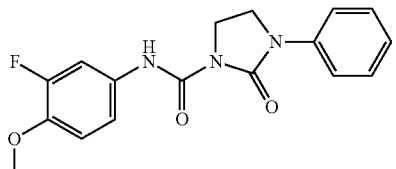<br>N-(3-Fluoro-4-(2-(1-methyl-1H-imidazol-4-yl)thieno[3,2-b]pyridin-7-yloxy)phenyl)-2-oxo-3-phenylimidazolidine-1-carboxamide | $^1$H NMR (400 MHz, DMSO-d$_6$) δ (ppm): 10.59 (s, 1H), 8.44 (d, J = 5.6 Hz, 1H), 7.88-7.83 (m, 2H), 7.72 (s, 1H), 7.69 (s, 1H), 7.64 (d, J = 8.0 Hz, 2H), 7.51-7.41 (m, 4H), 7.18 (t, J = 7.2 Hz, 1H), 6.59 (d, J = 5.6 Hz, 1H), 4.02-3.91 (m, 4H), 3.73 (s, 3H). MS (m/z): 529.0 (M + H). |
| 307 | 135 | 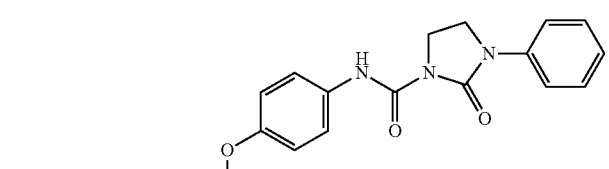<br>N-(4-(2-(1-methyl-1H-imidazol-4-yl)thieno[3,2-b]pyridin-7-yloxy)phenyl)-2-oxo-3-phenylimidazolidine-1-carboxamide | $^1$H NMR (400 MHz, DMSO-d$_6$) δ (ppm): 10.47 (s, 1H), 8.44 (d, J = 5.6 Hz, 1H), 7.86 (d, J = 1.2 Hz, 1H), 7.72 (d, J = 0.8 Hz, 1H), 7.70-7.62 (m, 5H), 7.46-7.40 (m, 2H), 7.31-7.26 (m, 2H), 7.20-7.15 (m, 1H), 6.59 (d, J = 5.6 Hz, 1H), 3.99-3.94 (m, 4H), 3.72 (s, 3H). MS (m/z): 511.2 (M + H). |

| Compd | Example | Structure | Characterization |
|---|---|---|---|
| 308 | 136 | N-(3-Fluoro-4-(2-(1-isopropyl-1H-imidazol-4-yl)thieno[3,2-b]pyridin-7-yloxy)phenyl)-2-oxo-1-phenylpyrrolidine-3-carboxamide | $^1$H NMR (400 MHz, DMSO-d$_6$) δ (ppm): 10.72 (s, 1H), 8.43 (d, J = 5.6 Hz, 1H), 8.05 (s, 1H), 7.92 (dd, J = 12.8, 2.0 Hz, 1H), 7.85 (s, 1H), 7.70-7.66 (m, 3H), 7.33-7.45 (m, 2H), 7.41 (t, J = 7.6 Hz, 1H), 7.18 (t, J = 7.6 Hz, 1H), 6.59 (d, J = 5.6 Hz, 1H), 4.48 (q, J = 7.0 Hz, 1H), 4.12 (td, J = 5.2, 5.2 Hz, 1H), 3.98-3.88 (m, 1H), 3.79 (t, J = 8.6 Hz, 1H), 2.55-2.30 (m, 7H), 1.46 (d, J = 7.0 Hz, 6H). MS (m/z): 556.0 (M + H). |
| 309 | 137 | N-(3-Fluoro-4-(2-(1-isopropyl-1H-imidazol-4-yl)thieno[3,2-b]pyridin-7-yloxy)phenyl)-5-oxo-1-phenylpyrrolidine-3-carboxamide | $^1$H NMR (400 MHz, DMSO-d$_6$) δ (ppm): 10.58 (s, 1H), 8.43 (d, J = 5.2 Hz, 1H), 8.05 (s, 1H), 7.89 (dd, J = 12.8, 2.0 Hz, 1H), 7.84 (s, 1H), 7.69 (s, 1H), 7.67 (s, 2H), 7.52-7.36 (m, 4H), 7.15 (t, J = 7.2 Hz, 1H), 6.57 (d, J = 5.2 Hz, 1H), 4.48 (q, J = 6.8 Hz, 1H), 4.13 (t, J = 9.6 Hz, 1H), 4.04 (dd, J = 10.0, 5.6 Hz, 1H), 3.54-3.44 (m, 1H), 2.87 (dd, J = 16.8, 9.2 Hz, 1H), 2.78 (dd, J = 16.8, 6.8 Hz, 1H), 1.46 (d, J = 6.8 Hz, 6H). MS (m/z): 556.0 (M + H). |

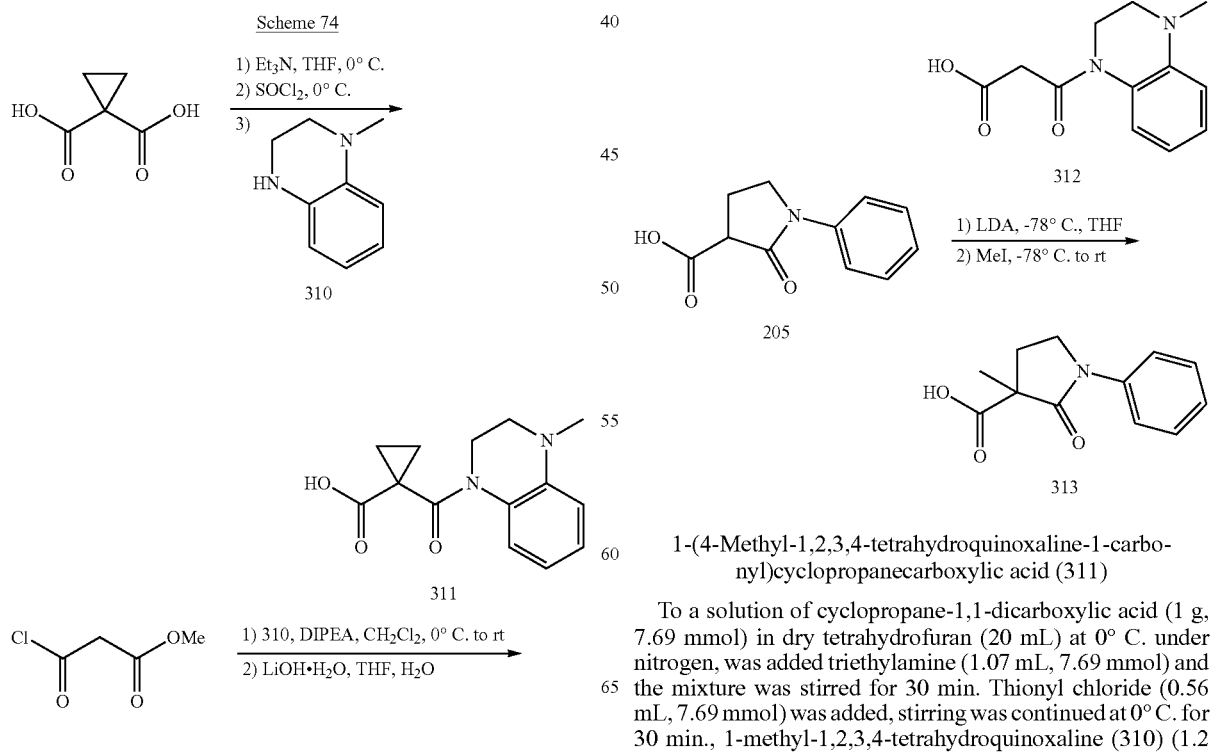

1-(4-Methyl-1,2,3,4-tetrahydroquinoxaline-1-carbonyl)cyclopropanecarboxylic acid (311)

To a solution of cyclopropane-1,1-dicarboxylic acid (1 g, 7.69 mmol) in dry tetrahydrofuran (20 mL) at 0° C. under nitrogen, was added triethylamine (1.07 mL, 7.69 mmol) and the mixture was stirred for 30 min. Thionyl chloride (0.56 mL, 7.69 mmol) was added, stirring was continued at 0° C. for 30 min., 1-methyl-1,2,3,4-tetrahydroquinoxaline (310) (1.2 g, 8.46 mmol)[Smith R. F. et al., *J. Org. Chem.*, 24, 1959, 205] was added and the reaction mixture was allowed to warm to room temperature. After stirring for 1 h, ethyl acetate was added and the resulting mixture was extracted twice with a 1N NaOH solution. The combined aqueous layers were acidified to pH 4-5 by addition of a 3N HCl solution and extracted 4 times with ethyl acetate. The combined organic layers were dried over anhydrous sodium sulfate and the solvent was removed under reduced pressure. The residue was purified by Biotage (Si 12M, gradient: MeOH in dichloromethane 0% to 10%) to afford title compound 311 (638 mg, 32% yield). MS (m/z): 259.0 (M−H).

3-(4-Methyl-3,4-dihydroquinoxalin-1(2H)-yl)-3-oxopropanoic acid (312)

To a solution of methyl 3-chloro-3-oxopropanoate (1 g, 7.32 mmol) and 1-methyl-1,2,3,4-tetrahydroquinoxaline (310) (1.09 g g, 7.32 mmol) [Smith R. F. et al., *J. Org. Chem.*, 24, 1959, 205] in dry dichloromethane (40 mL) at 0° C. under nitrogen was slowly added N,N-diisopropylethylamine (2.55 mL, 14.6 mmol). The reaction mixture was slowly warmed to room temperature (over 45 min). A saturated aqueous solution of sodium bicarbonate was added and the aqueous solution was extracted with dichloromethane. The organic layer was dried over anhydrous sodium sulfate and the solvent was removed under reduced pressure. The residue was purified by column chromatography on silica gel (eluent ethyl acetate-hexane 1:1) to afford an off-white solid (1.82 g). This solid was dissolved in tetrahydrofuran (40 mL) and water (20 mL), lithium hydroxide monohydrate (615 mg, 14.7 mmol) and the reaction mixture was stirred 16 h at room temperature. The solution was acidified to pH 4 with a 1H HCl solution and extracted 4 times with ethyl acetate. The combined organic layers were dried over anhydrous sodium sulfate and the solvent was removed under reduced pressure. The residue was purified by Biotage (Si 25M, gradient: MeOH in dichloromethane 0% to 10%) and trituration in a mixture of ethyl ether-hexane to afford title compound 312 (1.27 g, 74%) as a white solid. MS (m/z): 235.1 (M+H).

3-Methyl-2-oxo-1-phenylpyrrolidine-3-carboxylic acid (313)

To a stirred solution of 1-phenyl-2-oxo-3-pyrrolidinecarboxylic acid (205) (200 mg, 0.975 mmol) in dry tetrahydrofuran (5 mL) at −78° C. was added LDA (1.5M solution in cyclohexane, 1.63 mL, 2.44 mmol) and the mixture was stirred for 40 min. Iodomethane (152 µL, 2.44 mmol) was added and the reaction mixture was allowed to warm to room temperature and stirring was continued for 16 h. Water and ethyl acetate were added. The aqueous layer was collected, acidified to pH 4 with a 1N HCl solution and extracted twice with ethyl acetate. The combined organic layers were dried over anhydrous sodium sulfate and the solvent was removed under reduced pressure. The residue was purified by column chromatography on silica gel (eluent methanol-dichloromethane 2:98) to afford title compound 313 (170 mg, 80% yield) as a yellow solid. $^1$H NMR (400 MHz, DMSO-$d_6$) δ (ppm): 7.67 (dd, J=8.8, 1.2 Hz, 2H), 7.39 (dd, J=8.8, 7.2 Hz, 2H), 7.16 (tt, J=7.2, 1.2 Hz, 1H), 3.92-3.80 (m, 2H), 2.54-2.46 (m, 1H), 2.08-1.98 (m, 1H), 1.34 (s, 3H).

TABLE 12

Compounds 314-316 (examples 138-140) prepared according to the scheme 3 starting from the amine 12 and acids 311-313

| Cpd | Ex | Structure | Characterization |
|---|---|---|---|
| 314 | 138 | N-(3-Fluoro-4-(2-(1-methyl-1H-imidazol-4-yl)thieno[3,2-b]pyridin-7-yloxy)phenyl)-1-(4-methyl-1,2,3,4-tetrahydroquinoxaline-1-carbonyl)cyclopropanecarboxamide | $^1$H NMR (400 MHz, DMSO-$d_6$) δ (ppm): 9.94 (s, 1H), 8.43 (d, J = 5.6 Hz, 1H), 7.85 (d, J = 1.2 Hz, 1H), 7.70 (d, J = 0.8 Hz, 1H), 7.66 (s, 1H), 7.29 (t, J = 8.8 Hz, 1H), 7.28-6.86 (m, 3H), 6.87 (td, J = 8.0, 1.6 Hz, 1H), 6.48 (t, J = 7.2 Hz, 1H), 6.43 (d, J = 5.6 Hz, 1H), 6.46-6.37 (m, 1H), 3.83-3.75 (m, 2H), 3.70 (s, 3H), 3.46 (t, J = 5.2 Hz, 2H), 2.57 (bs, 3H), 1.56-1.50 (m, 2H), 1.43-1.37 (m, 2H). |
| 315 | 139 | N-(3-fluoro-4-(2-(1-methyl-1H-imidazol-4-yl)thieno[3,2-b]pyridin-7-yloxy)phenyl)-3-(4-methyl-3,4-dihydroquinoxalin-1(2H)-yl)-3-oxopropanamide | $^1$H NMR (400 MHz, DMSO-$d_6$) δ (ppm): 10.47 (bs, 1H), 8.43 (d, J = 5.6 Hz, 1H), 7.87 (d, J = 1.2 Hz, 1H), 7.86-7.77 (m, 1H), 7.72 (s, 1H), 7.68 (s, 1H), 7.46 (t, J = 8.8 Hz, 1H), 7.42-7.20 (m, 2H), 7.12-6.96 (m, 1H), 6.73 (d, J = 7.6 Hz, 1H), 6.65-6.56 (m, 1H), 6.57 (d, J = 5.6 Hz, 1H), 3.81 (t, J = 4.8 Hz, 2H), 3.73 (s, 3H), 3.43-3.33 (m, 2H), 2.92 (s, 3H). MS (m/z): 557.0 (M + H). |

TABLE 12-continued
Compounds 314-316 (examples 138-140) prepared according to the scheme 3 starting from the amine 12 and acids 311-313
| Cpd | Ex | Structure | Characterization |
|---|---|---|---|
| 316 | 140 | 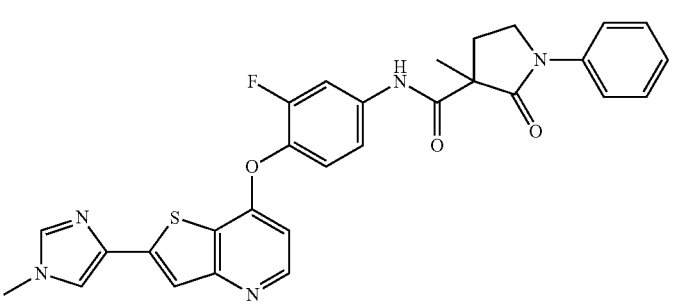 N-(3-fluoro-4-(2-(1-methyl-1H-imidazol-4-yl)thieno[3,2-b]pyridin-7-yloxy)phenyl)-3-methyl-2-oxo-1-phenylpyrrolidine-3-carboxamide | $^1$H NMR (400 MHz, DMSO-$d_6$) δ (ppm): 9.95 (s, 1H), 8.43 (d, J = 5.6 Hz, 1H), 7.93 (dd, J = 13.2, 2.0 Hz, 1H), 7.87 (d, J = 0.8 Hz, 1H), 7.74-7.70 (m, 3H), 7.69 (s, 1H), 7.61-7.57 (m, 1H), 7.47 (t, J = 8.8 Hz, 1H), 7.42 (t, J = 8.0 Hz, 2H), 7.19 (t, J = 8.0 Hz, 1H), 6.58 (d, J = 5.6 Hz, 1H), 3.95-3.83 (m, 2H), 3.72 (s, 3H), 2.78-2.70 (m, 1H), 2.12-2.04 (m, 1H), 1.59 (s, 3H). |
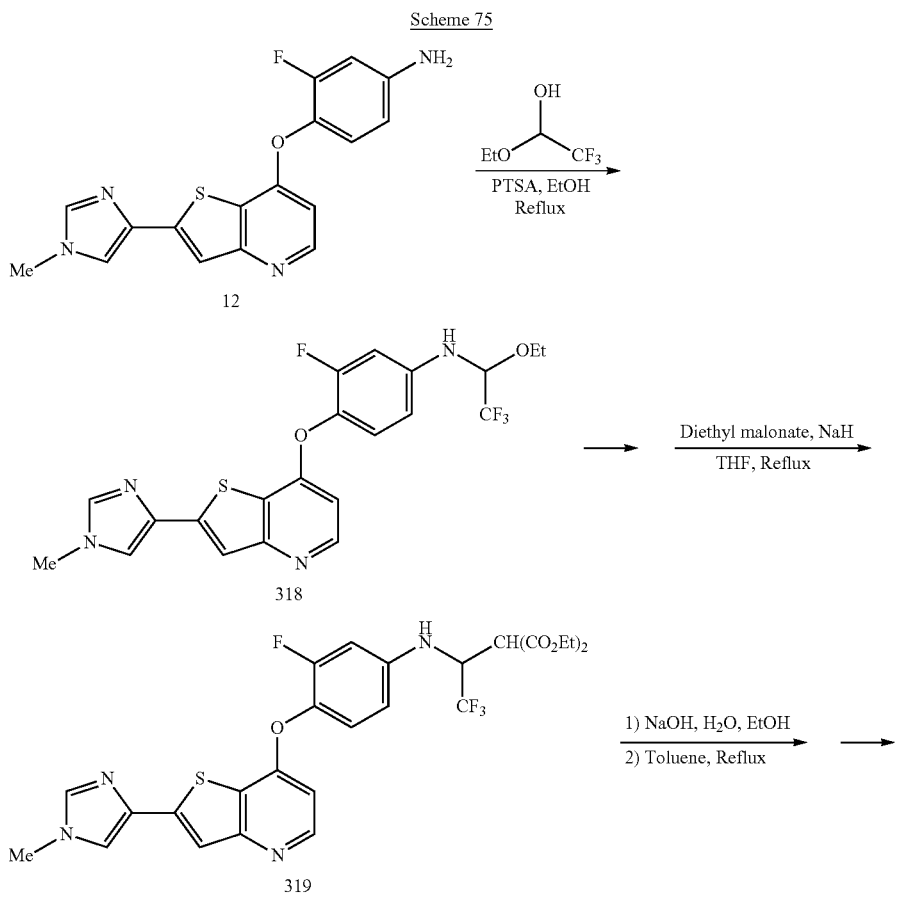
Scheme 75

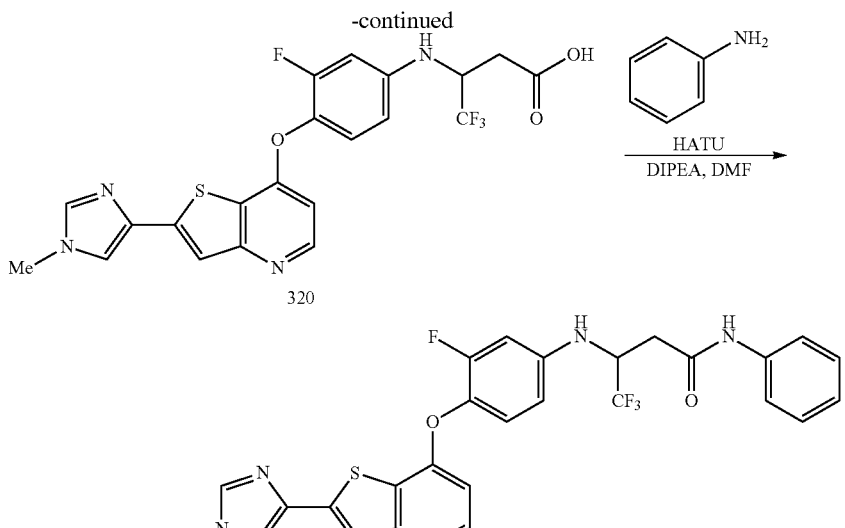

317: Example 141

Example 141

4,4,4-Trifluoro-3-(3-fluoro-4-(2-(1-methyl-1H-imidazol-4-yl)thieno[3,2-b]pyridin-7-yloxy)phenylamino)-N-phenylbutanamide (317)

Step 1. N-(1-Ethoxy-2,2,2-trifluoroethyl)-3-fluoro-4-(2-(1-methyl-1H-imidazol-4-yl)thieno[3,2-b]pyridin-7-yloxy)benzenamine (318)

A mixture of 12 (Scheme 3) (500 mg, 1.47 mmol), trifluoroacetaldehyde ethyl hemiacetal (0.35 mL, 2.94 mmol) and 4-toluenesulfonic acid monohydrate (280 mg, 1.47 mmol) in ethanol (25 mL) was heated to reflux for 48 h. The reaction mixture was concentrated and the residue was purified by column chromatography on silica gel (eluent methanol-dichloromethane 5:95 to 8:92) to afford title compound 318 (470 mg, 1.01 mmol, 68% yield). NMR (400 MHz, DMSO-$d_6$) δ ppm: 8.42 (d, J=5.5 Hz, 1H), 7.85 (d, J=1.2 Hz, 1H), 7.72 (d, J=0.8 Hz, 1H), 7.67 (s, 1H), 7.29 (t, J=9.2 Hz, 1H), 7.08-7.02 (m, 2H), 3.86 (dd, J=9.2, 2.0 Hz, 1H), 6.52 (d, J=5.5 Hz, 1H), 5.68 (qd, J=10.4, 5.2 Hz, 1H), 3.72 (s, 3H), 3.76-3.59 (m, 2H), 1.15 (t, J=7.0 Hz, 3H). LRMS (M+1) 467.0 (100%).

Step 2. Diethyl 2-(2,2,2-trifluoro-1-(3-fluoro-4-(2-(1-methyl-1H-imidazol-4-yl)thieno[3,2-b]pyridin-7-yloxy)phenylamino)ethyl)malonate (319)

To a solution of 318 (470 mg, 1.01 mmol) and diethyl malonate (0.17 mL, 1.11 mmol) in anhydrous tetrahydrofuran (10 mL) under nitrogen was added sodium hydride (60% in oil, 89 mg, 2.22 mmol). The mixture was heated to reflux for 2 h, cooled, diluted with EtOAc and water and acidified to pH 3 using a 1N HCl solution. The organic layer was separated and the aqueous layer extracted twice with EtOAc. The extracts were combined, dried over sodium sulfate and the solvents were removed under reduced pressure. The residue was purified by column chromatography on silica gel (eluent MeOH-dichloromethane, gradient 0:100 to 20:80) to afford 319 (490 mg, 0.84 mmol, 84% yield). $^1$H NMR (400 MHz, DMSO-$d_6$) δ ppm: 8.42 (d, J=5.2 Hz, 1H), 7.85 (s, 1H), 7.72 (s, 1H), 7.67 (s, 1H), 7.24 (t, J=9.2 Hz, 1H), 6.98 (dd, J=13.6, 2.8 Hz, 1H), 6.72 (dd, J=9.2, 2.8 Hz, 1H), 6.62 (d, J=10.0 Hz, 1H), 6.46 (d, J=5.2 Hz, 1H), 5.05-4.95 (m, 1H), 4.23-4.07 (m, 4H), 3.91 (d, J=9.2 Hz, 1H), 3.72 (s, 3H), 1.18 (t, J=7.0 Hz, 3H), 1.11 (t, J=7.0 Hz, 3H). LRMS (M+1) 581.0 (100%).

Step 3. 4,4,4-Trifluoro-3-(3-fluoro-4-(2-(1-methyl-1H-imidazol-4-yl)thieno[3,2-b]pyridin-7-yloxy)phenylamino)butanoic acid (320)

A solution of 319 (490 mg, 0.84 mmol) and sodium hydroxide (338 mg, 8.44 mmol) in water (0.7 mL) and ethanol (3.4 mL) was stirred at room temperature for 48 h. The solvents were removed under reduced pressure and the residue was dissolved in water (20 mL). The solution was neutralized to pH 4 with a 3N HCl solution and the solid thus formed was filtered off, rinsed with water and dried. The solid was suspended in dry toluene (20 mL), heated to reflux for 1 h under continuous stirring, and the solvent was removed under reduced pressure. The residue was purified by column chromatography on silica gel (eluent MeOH-dichloromethane, gradient 10:90 to 50:50) and the resulting solid was triturated in a mixture of dichloromethane, ethyl acetate and hexane, isolated by filtration, and dried under high vacuum to afford title compound 320 (150 mg, 0.31 mmol, 37% yield). LRMS (M+1) 480.9 (100%).

Step 4. 4,4,4-Trifluoro-3-(3-fluoro-4-(2-(1-methyl-1H-imidazol-4-yl)thieno[3,2-b]pyridin-7-yloxy)phenylamino)-N-phenylbutanamide (317)

To a stirred solution of 320 (150 mg, 0.31 mmol), aniline (43 μL, 0.47 mmol) and N,N-diisopropylethylamine (0.19 mL, 1.09 mmol) in dry N,N-dimethylformamide (4 mL) at room temperature was added HATU reagent (356 mg, 0.94 mmol). The mixture was stirred at room temperature for 16 h. A saturated aqueous solution of sodium bicarbonate was added and the aqueous solution was extracted twice with EtOAc, dried over anhydrous sodium sulfate and the solvent was removed under reduced pressure. The residue was purified by column chromatography on silica gel (eluent MeOH-dichloromethane, gradient 3:97 to 8:92) to afford the title compound 317 (111 mg, 0.20 mmol, 64% yield) as a white solid. $^1$H NMR (400 MHz, DMSO-d$_6$) δ ppm: 10.11 (s, 1H), 8.39 (d, J=5.6 Hz, 1H), 7.85 (d, J=1.2 Hz, 1H), 7.72 (d, J=0.8 Hz, 1H), 7.66 (s, 1H), 7.56 (d, J=7.2 Hz, 2H), 7.30 (t, J=8.0 Hz, 2H), 7.21 (t, J=8.8 Hz, 1H), 7.05 (t, J=7.2 Hz, 1H), 6.86 (dd, J=13.6, 2.4 Hz, 1H), 6.67 (dd, J=8.8, 2.0 Hz, 1H), 6.57 (d, J=8.8 Hz, 1H), 6.44 (d, J=5.6 Hz, 1H), 4.86-4.53 (m, 1H), 3.72 (s, 3H), 2.92 (dd, J=15.6, 3.2 Hz, 1H), 2.76 (dd, J=15.6, 9.6 Hz, 1H). LRMS (M+1) 556.0 (100%).

TABLE 13

Compounds 321-323 (examples 142-144) prepared according to the scheme 75

| Cpd | Ex. | Structure | Characterization |
|---|---|---|---|
| 321 | 142 | 4,4,4-Trifluoro-3-(3-fluoro-4-(2-(1-methyl-1H-imidazol-4-yl)thieno[3,2-b]pyridin-7-yloxy)phenylamino)-N-(4-fluorophenyl)butanamde | $^1$H NMR (400 MHz, DMSO-d$_6$) δ ppm: 10.18 (s, 1H), 8.39 (d, J = 5.2 Hz, 1H), 7.85 (d, J = 1.2 Hz, 1H), 7.72 (d, J = 1.2 Hz, 1H), 7.66 (s, 1H), 7.61-7.55 (m, 2H), 7.21 (t, J = 8.8 Hz, 1H), 7.18-7.11 (m, 2H), 6.85 (dd, J = 13.2, 2.4 Hz, 1H), 6.67 (dd, J = 8.8, 2.4 Hz, 1H), 6.57 (d, J = 9.2 Hz, 1H), 6.44 (d, J = 5.2 Hz, 1H), 4.85-4.73 (m, 1H), 3.72 (s, 3H), 2.91 (dd, J = 15.6, 4.0 Hz, 1H), 2.74 (dd, J = 15.6, 9.6 Hz, 1H). MS (m/z): 574.2 (M + H). |
| 322 | 143 | 4,4,4-trifluoro-3-(3-fluoro-4-(2-(1-methyl-1H-imidazol-4-yl)thieno[3,2-b]pyridin-7-yloxy)phenylamino)-N-(2-methoxypheny)butanamide | $^1$H NMR (400 MHz, DMSO-d$_6$) δ ppm: 9.38 (s, 1H), 8.39 (d, J = 5.6 Hz, 1H), 7.90 (dd, J = 8.4, 1.6 Hz, 1H), 7.85 (d, J = 1.2 Hz, 1H), 7.72 (d, J = 0.8 Hz, 1H), 7.66 (s, 1H), 7.21 (t, J = 9.2 Hz, 1H), 7.11-7.01 (m, 2H), 6.91-6.82 (m, 2H), 6.67 (dd, J = 8.6, 2.6 Hz, 1H), 6.56 (d, J = 8.8 Hz, 1H), 6.42 (d, J = 5.6 Hz, 1H), 4.85-4.74 (m, 1H), 3.82 (s, 3H), 3.72 (s, 3H), 2.89 (d, J = 6.8 Hz, 2H). MS (m/z): 586.3 (M + H). |
| 323 | 144 | 4,4,4-Trifluoro-N-(4-fluorophenyl)-3-(4-(2-(1-methyl-1H-imidazol-4-yl)thieno[3,2-b]pyridin-7-yloxy)phenylamino)butanamide | $^1$H NMR (400 MHz, DMSO-d$_6$) δ ppm: 10.17 (s, 1H), 8.48 (d, J = 6.0 Hz, 1H), 7.97 (s, 1H), 7.83 (s, 1H), 7.70 (s, 1H), 7.58 (dd, J = 9.2, 4.8 Hz, 2H), 7.14 (t, J = 9.2 Hz, 2H), 7.09 (d, J = 9.2 Hz, 2H), 6.88 (d, J = 9.2 Hz, 2H), 6.59 (d, J = 6.0 Hz, 1H), 6.32 (d, J = 9.2 Hz, 1H), 4.80-4.67 (m, 1H), 3.74 (s, 3H), 2.91 (dd, J = 15.6, 4.0 Hz, 1H), 2.75 (dd, J = 15.6, 9.2 Hz, 1H). MS (m/z): 556.2 (M + H). |

Scheme 76

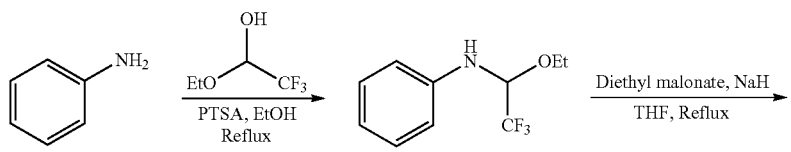

325

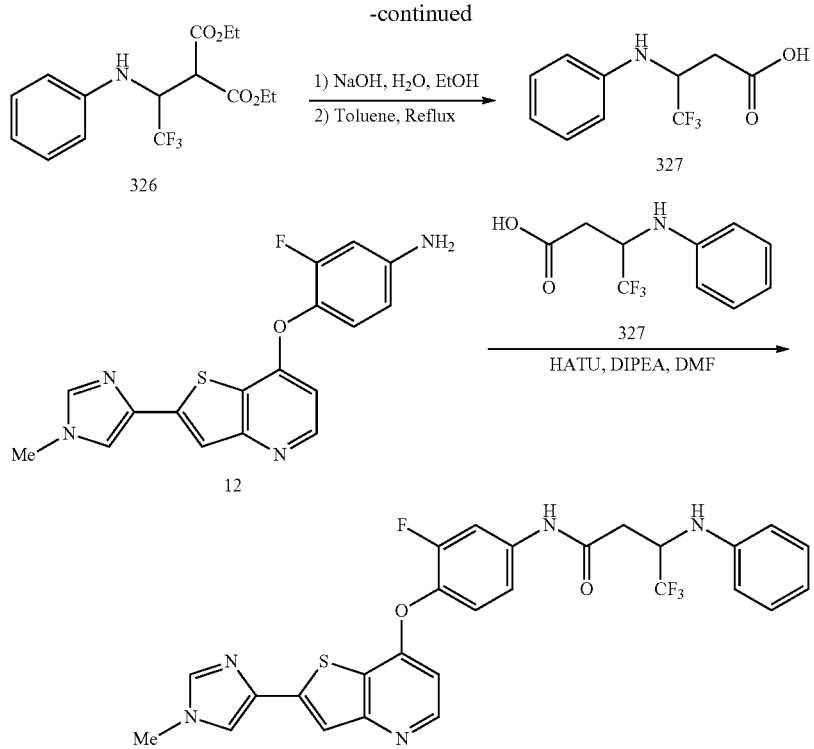

Example 145

4,4,4-Trifluoro-N-(3-fluoro-4-(2-(1-methyl-1H-imidazol-4-yl)thieno[3,2-b]pyridin-7-yloxy)phenyl)-3-(phenylamino)butanamide (324)

Step 1. N-(1-Ethoxy-2,2,2-trifluoroethyl)benzenamine (325)

A solution of aniline (2 mL, 21.9 mmol), trifluoroacetaldehyde ethyl hemiacetal (2.6 mL, 21.9 mmol) and p-toluenesulfonic acid monohydrate (220 mg, 1.16 mmol) in ethanol (25 mL) was heated to reflux for 3 h under continuous stirring. The reaction mixture was cooled, the solvent was removed under reduced pressure and the residue was dissolved in EtOAc. The organic layer was washed with a saturated aqueous solution of sodium bicarbonate, dried over anhydrous sodium sulfate and the solvent was removed under reduced pressure to afford title compound 325 (4.16 g, crude) as a yellow oil which was used directly for the next step.

Step 2. Diethyl 2-(2,2,2-trifluoro-1-(phenylamino)ethyl)malonate (326)

A solution of diethyl malonate (1.98 mL, 13.0 mmol) in anhydrous tetrahydrofuran (10 mL) was added dropwise, over 20 min, into a dispersion of sodium hydride (60% in oil, 0.52 g, 13.0 mmol) in dry tetrahydrofuran (30 mL) at 0° C., after which compound 325 (2.6 g, 11.9 mmol) was added and the mixture was stirred vigorously at reflux for 16 h. The reaction mixture was cooled, acidified to pH 3 using a 1N HCl solution. The aqueous layer was extracted twice with EtOAc. The extracts were combined, dried over sodium sulfate and the solvents were removed under reduced pressure. The residue was purified by column chromatography on silica gel (eluent dichloromethane-hexane, 0:100 to 60:40) to afford title compound 326 (2.16 g, 6.48 mmol, 54% yield) as a colorless oil. $^1$H NMR (400 MHz, CDCl$_3$) δ ppm: 7.21-7.16 (m, 2H), 6.81-6.76 (m, 1H), 6.75-6.71 (m, 2H), 5.06 (d, J=10.4 Hz, 1H), 4.83-4.73 (m, 1H), 4.25 (q, J=7.2 Hz, 2H), 4.18-4.05 (m, 2H), 3.85 (d, J=4.4 Hz, 1H), 1.28 (t, J=7.2 Hz, 3H), 1.13 (t, J=7.2 Hz, 3H). LRMS (M+1) 334.1 (100%).

Step 3. 4,4,4-Trifluoro-3-(phenylamino)butanoic acid (327)

A solution of compound 326 (2.16 g, 6.48 mmol) and sodium hydroxide (2.60 g, 64.8 mmol) in water (5.2 mL) and ethanol (26 mL) was stirred at room temperature for 24 h. The solvents were removed under reduced pressure leaving a white solid which was triturated in ether, isolated by filtration, rinsed with ether and dried under high vacuum. The white solid was dissolved in water (12 mL), and the solution was neutralized to pH 4 with a 3N HCl solution, extracted twice with EtOAc, the combined organic layers were dried over sodium sulfate and the solvent removed under reduced pressure. The solid was dissolved in dry toluene (20 mL), heated to reflux for 1 h with continuous stirring, and the solvent was removed under reduced pressure. The residue was purified by column chromatography on silica gel (eluent EtOAc-hexane, gradient 0:100 to 40:60) to afford title compound 327 (204 mg, 0.87 mmol, 13% yield) as a beige solid. $^1$H NMR (400 MHz, CDCl$_3$) δ ppm: 7.24-7.18 (m, 2H), 6.82 (tt, J=7.2, 1.0 Hz, 1H), 6.75-6.71 (m, 2H), 4.55-4.45 (m, 1H), 2.89 (dd, J=16.0, 4.4 Hz, 1H), 2.67 (dd, J=16.0, 8.8 Hz, 1H). LRMS (M−1) 231.9 (100%).

Step 4. 4,4,4-Trifluoro-N-(3-fluoro-4-(2-(1-methyl-1H-imidazol-4-yl)thieno[3,2-b]pyridin-7-yloxy)phenyl)-3-(phenylamino)butanamide (324)

To a stirred solution of compound 12 (scheme 3) (100 mg, 0.29 mmol), compound 327 (103 mg, 0.44 mmol) and N,N-diisopropylethylamine (0.18 mL, 1.03 mmol) in dry N,N-dimethylformamide (3 mL) at 0° C. was added HATU reagent (335 mg, 0.88 mmol). The mixture was stirred at room temperature for 16 h. A saturated aqueous solution of sodium bicarbonate was added and the aqueous solution was extracted twice with EtOAc, dried over anhydrous sodium sulfate and the solvent was removed under reduced pressure. The residue was purified by column chromatography on silica gel (eluent MeOH-dichloromethane, gradient 0:100 to 15:85). The resulting solid was triturated in methanol, filtered off and dried under reduced pressure to afford title compound 324 (81 mg, 0.15 mmol, 50% yield) as a white solid. $^1$H NMR (400 MHz, DMSO-$d_6$) δ ppm: 10.50 (s, 1H), 8.41 (d, J=5.6 Hz, 1H), 7.86 (d, J=1.2 Hz, 1H), 7.81 (dd, J=13.2, 2.0 Hz, 1H), 7.72 (s, 1H), 7.67 (s, 1H), 7.45 (t, J=8.8 Hz, 1H), 7.37 (dd, J=8.8, 1.6 Hz, 1H), 7.10 (dd, J=8.4, 7.2 Hz, 2H), 6.75 (d, J=8.0 Hz, 2H), 6.61 (t, J=7.2 Hz, 1H), 6.55 (d, J=5.6 Hz, 1H), 6.13 (d, J=9.2 Hz, 1H), 4.75-4.65 (m, 1H), 3.72 (s, 3H), 2.94 (dd, J=15.6, 3.6 Hz, 1H), 2.78 (dd, J=15.9, 9.6 Hz, 1H). LRMS (M+1) 556.0 (100%).

TABLE 14

Compounds 328-329 (examples 146-147) prepared according to the scheme 76

| Cpd | Ex. | Structure | Characterization |
|---|---|---|---|
| 328 | 146 | 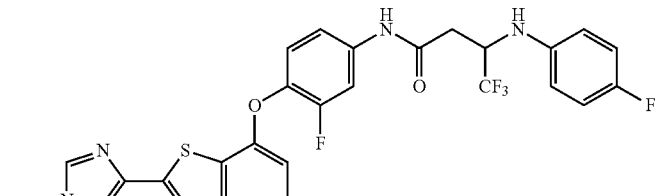<br>N-(4-(2-(1-Ethyl-1H-imidazol-4-yl)thieno[3,2-b]pyridin-7-yloxy)-3-fluorophenyl)-4,4,4-trifluoro-3-(4-fluorophenylamino)butanamide | $^1$H NMR (400 MHz, DMSO-$d_6$) δppm: 10.47 (s, 1H), 8.41 (d, J = 5.5 bHz, 1H), 7.96 (s, 1H), 7.82-7.78 (m, 2H), 7.67 (d, J = 0.4 Hz, 1H), 7.45 (t, J = 8.9 Hz, 1H), 7.37 (dd, J = 9.9/2.2 Hz, 1H), 6.95 (t, J = 8.8 Hz, 2H), 6.77-6.74 (m, 2H), 6.55 (d, J = 5.3 Hz, 1H), 6.06 (d, J = 8.8 Hz, 1H), 4.64 (m, 1H), 4.06 (q, J = 7.2 Hz, 2H), 2.93 (dd, J = 15.7/3.8 Hz, 1H), 2.76 (dd, J = 15.8/9.4 Hz, 1H), 1.40 (t, J = 7.2 Hz, 3H) LRMS 588.2 (M + H). |
| 329 | 147 | 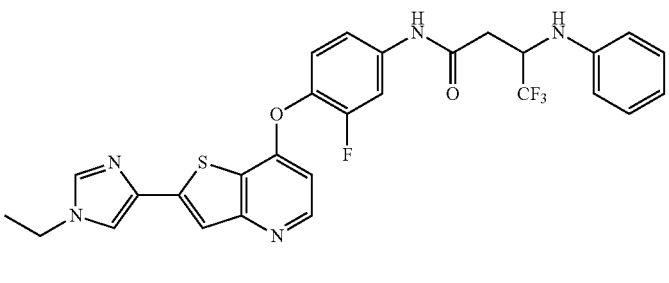<br>N-(4-(2-(1-Ethyl-1H-imidazol-4-yl)thieno[3,2-b]pyridin-7-yloxy)-3-fluorophenyl)-4,4,4-trifluoro-3-(phenylamino)butanamide | $^1$H NMR (400 MHz, DMSO-$d_6$) δppm: 10.50 (s, 1H), 8.41 (d, J = 5.5 Hz, 1H), 7.96 (d, J = 1.2 Hz, 1H), 7.82-7.78 (m, 2H), 7.66 (s, 1H), 7.45 (t, J = 8.8 Hz, 1H), 7.37 (dd, J = 9.0/1.4 Hz, 1H), 7.11 (dd, J = 8.4/7.4 Hz, 2H), 6.75 (d, J = 7.8 Hz, 2H) 6.61 (t, J = 7.3 Hz, 1H), 6.55 (d, J = 5.5 Hz, 1H), 6.12 (d, J = 9.2 Hz, 1H), 4.70 (m, 1H), 4.06 (quad., J = 7.2 Hz, 214), 2.94 (dd, J = 15.6/3.9 Hz, 1H), 2.78 (dd, J = 15.9/9.3 Hz, 1H) 1.40 (t, J = 7.3 Hz, 3H). |

Scheme 77

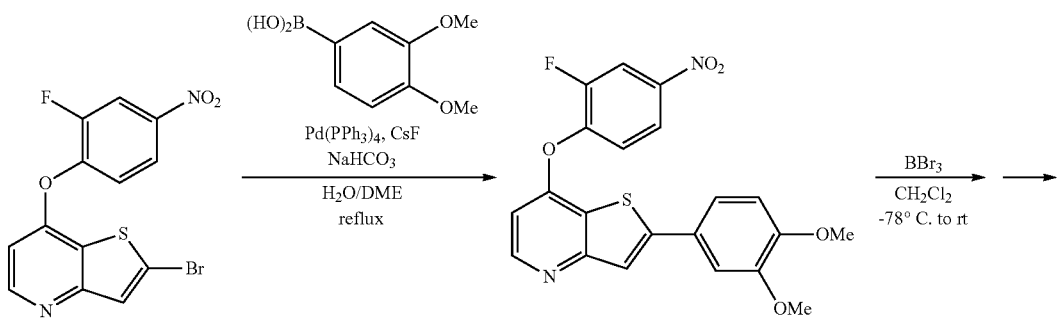

-continued
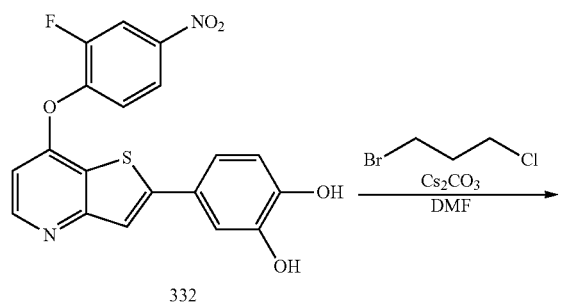
332
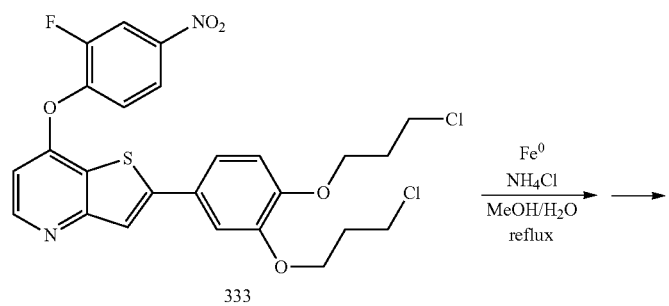
333
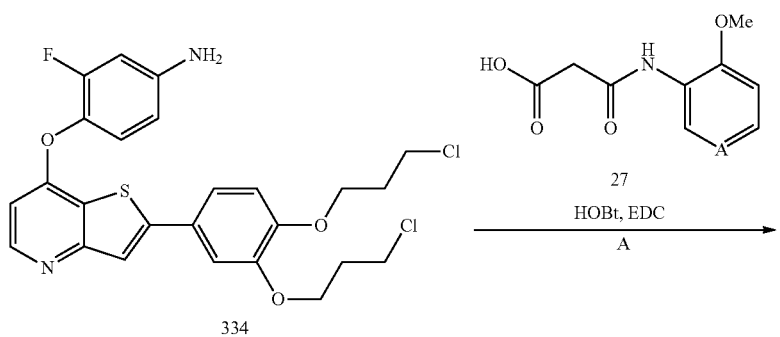
334
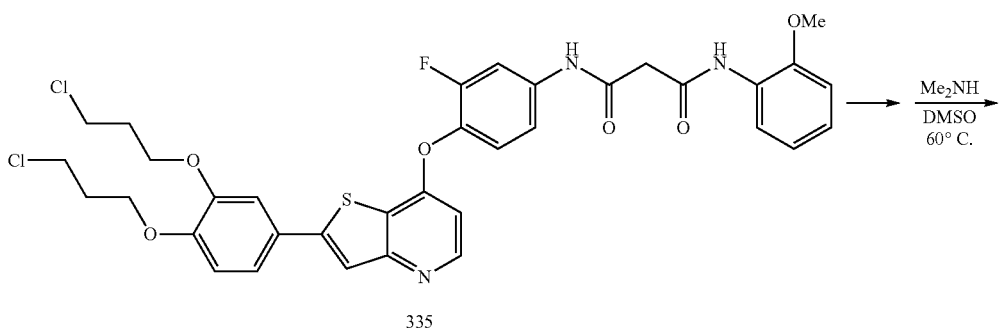
335
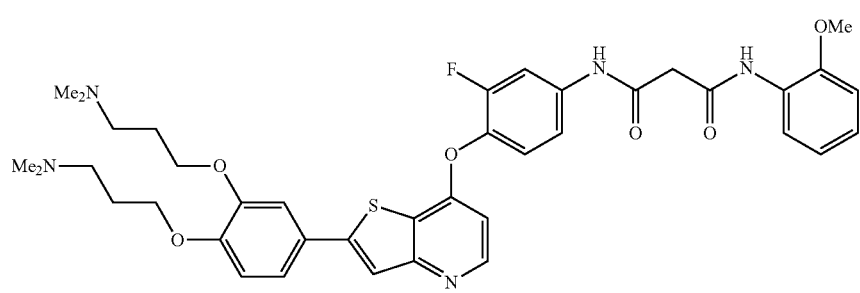
330: Example 148

Example 148

N[1]-(4-(2-(3,4-Bis(3-(dimethylamino)propoxy)phenyl)thieno[3,2-b]pyridin-7-yloxy)-3-fluorophenyl)-N[3]-(2-methoxyphenyl)malonamide (330)

Step 1. 2-(3,4-Dimethoxyphenyl)-7-(2-fluoro-4-nitrophenoxy)thieno[3,2-b]pyridine (331)

To a stirred solution of 50 (400 mg, 1.08 mmol) in DME (20 ml) was added 3,4-dimethoxyphenylboronic acid (394 mg, 2.17 mmol), NaHCO$_3$ (273 mg, 3.25 mmol), CsF (494 mg, 3.25 mmol), Pd(PPh$_3$)$_4$ (125 mg, 0.11 mmol) and water (10 ml). The reaction mixture was degassed for 15 min with a nitrogen stream, and was heated to reflux for 2.5 hrs under nitrogen. After cooling to room temperature the reaction mixture was diluted with AcOEt and successively washed with water, sat. NH$_4$Cl, brine, dried over anhydrous MgSO$_4$, filtered, and concentrated. The crude product was purified by flash column chromatography (eluents AcOEt/CH$_2$Cl$_2$: 5/95 to 30/70) and triturated in AcOEt/hexanes to afford title compound 331 (273 mg, 59% yield) as a yellow solid. MS (m/z): 427.1 (M+H)$^+$.

Step 2. 4-(7-(2-Fluoro-4-nitrophenoxy)thieno[3,2-b]pyridin-2-yl)benzene-1,2-diol (332)

To a stirred solution of 331 (172 mg, 0.40 mmol) in anhydrous dichloromethane (20 ml) at −78° C. was slowly added BBr$_3$ (~4 mL, 1.0 M in CH$_2$Cl$_2$). The temperature was allowed to warm to room temperature over 1.5 hrs, and the reaction mixture was stirred overnight. After cooling to 0° C., MeOH and 1 N NaOH (few mL) were added, respectively. The reaction mixture was stirred for 1 h, concentrated, diluted with MeOH and water, shaken for 30 min, isolated by filtration, and rinsed with MeOH. The mother liquid was concentrated, dissolved in a minimum of MeOH, and diluted with a small amount of water. The pH of the solution was adjusted to 4 with 1N NaOH in order to get a pale brown suspension. After shaking for 15 min, the suspension was filtered off, rinsed with water, air-dried, and dried under high vacuum to afford the title compound 332 (154 mg, 96% yield) as a yellow-green solid. MS (m/z): 399.0 (M+H)$^+$.

Step 3. 2-(3,4-Bis(3-chloropropoxy)phenyl)-7-(2-fluoro-4-nitrophenoxy)thieno[3,2-b]pyridine (333)

To a stirred solution of 332 (140 mg, 0.35 mmol) in anhydrous DMF (5 ml) were added 1-bromo-3-chloropropane (553 mg, 3.51 mmol) and cesium carbonate (573 mg, 1.76 mmol), respectively. The reaction mixture was stirred for 2 hrs at room temperature, diluted with AcOEt, and successively washed with water, sat. ammonium chloride, water, and concentrated. The crude material was adsorbed on silica gel and purified by flash column chromatography (eluents AcOEt/CH$_2$Cl$_2$: 10/90 to 20/80) to afford title compound 333 (120 mg, 62% yield) as a yellow solid. MS (m/z): 551.0 and 553.0 (M+H)$^+$.

Step 4. 4-(2-(3,4-Bis(3-chloropropoxy)phenyl)thieno[3,2-b]pyridin-7-yloxy)-3-fluoroaniline (334)

To a stirred suspension of nitro compound 333 (32 mg, 0.57 mmol) in a mixture of MeOH (2 mL) and water (1 mL) were added iron powder (16 mg, 0.29 mmol) and NH$_4$Cl (2.8 mg, 0.05 mmol). The reaction mixture was heated to reflux for 2.5 hrs, cooled to room temperature, diluted with ethyl acetate, filtered, and rinsed with AcOEt. The filtrate was successively washed with sat. ammonium chloride, sat. NaHCO$_3$, water, dried over anhydrous MgSO$_4$, filtered, and concentrated to afford title compound 334 (25 mg, 83% yield) as a pale yellow solid. MS (m/z): 521.0 and 523.0 (M+H)$^+$.

Step 5. N[1]-(4-(2-(3,4-Bis(3-chloropropoxy)phenyl)thieno[3,2-b]pyridin-7-yloxy)-3-fluorophenyl)-N[3]-(2-methoxyphenyl)malonamide (335)

The title compound 335 was obtained from 334 as an off-white solid following the same procedure as in example 22, step 7 (scheme 18).

Step 6. N[1]-(4-(2-(3,4-Bis(3-(dimethylamino)propoxy)phenyl)thieno[3,2-b]pyridin-7-yloxy)-3-fluorophenyl)-N[3]-(2-methoxyphenyl)malonamide (330)

A stirred solution of 335 (crude material) and a large excess of dimethylamine (2.3 mL, 2M in THF) in anhydrous DMSO (2 mL) was stirred at 60° C. for 5 hrs. The mixture was cooled to room temperature, and then concentrated and directly purified twice by preparative HPLC (Thermo, Aquasil C$_{18}$, 250× 21.2 mm, 5 μm; eluent MeOH/H$_2$O [both containing 0.05% HCO$_2$H], linear gradient 40/60→80/20 over 30 min), to afford title compound 330 (14.4 mg, 41% yield over 2 steps) as a pale yellow sticky film. $^1$H NMR (400 MHz, MeOH-d$_4$) δ (ppm): 9.00-8.20 (m, 2H), 8.11 (dd, J=8.0, 1.6 Hz, 1H), 7.87 (dd, J=12.5, 2.3 Hz, 1H), 7.70 (bs, 1H), 7.45-7.38 (m, 3H), 7.35 (t, J=8.7 Hz, 1H), 7.15-7.06 (m, 2H), 7.03 (dd, J=8.2, 1.2 Hz, 1H), 6.93 (td, J=7.7, 1.2 Hz, 1H), 6.61 (bd, J=4.5 Hz, 1H), 4.23 (t, J=5.9 Hz, 2H), 4.18 (t, J=5.8 Hz, 2H), 3.91 (s, 3H), 3.32-3.20 (m, 4H), 2.86 and 2.85 (2 s, 2×6H), 2.31-2.20 (m, 4H), one CH$_2$ is missing. MS (m/z): 730.4 (M+H)$^+$.

Scheme 78

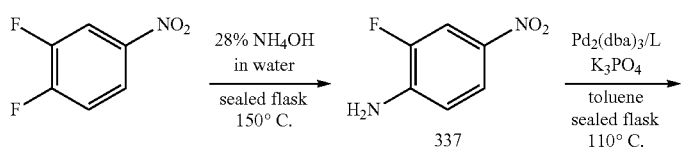

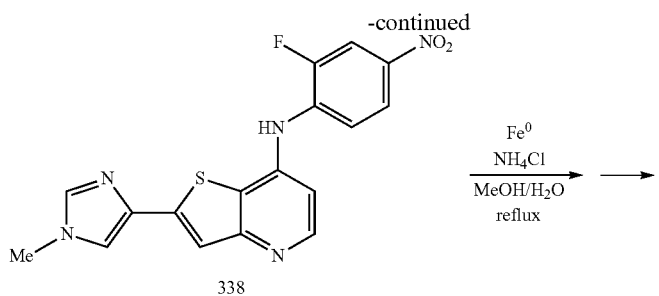

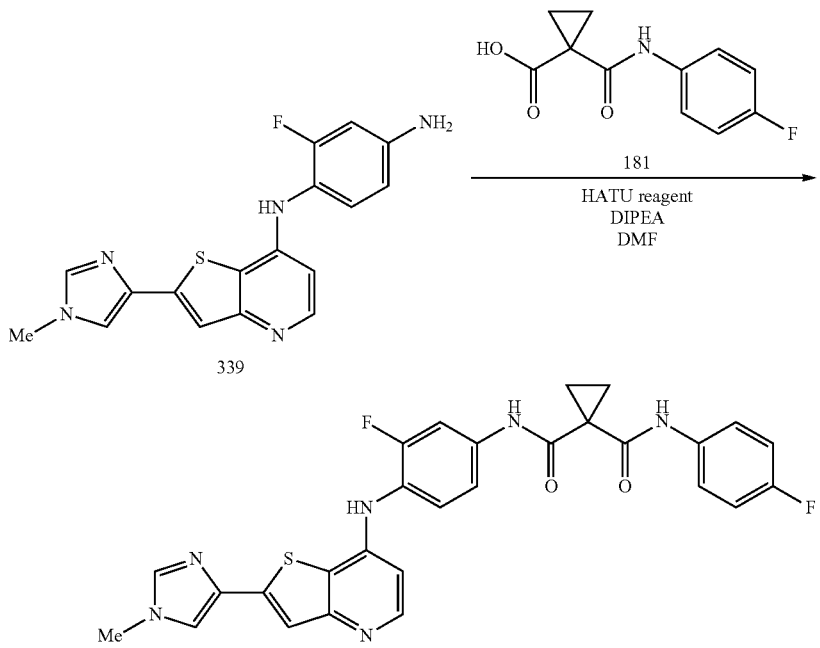

336: Example 149

Example 149

N-(3-Fluoro-4-(2-(1-methyl-1H-imidazol-4-yl)thieno[3,2-b]pyridin-7-ylamino)phenyl)-N-(4-fluorophenyl)cyclopropane-1,1-dicarboxamide (336)

Step 1. 2-Fluoro-4-nitroaniline (337)

A stirred solution of 3,4-difluoronitrobenzene (2.00 g, 12.57 mmol) in ammonium hydroxide (20 ml, 28% in water) was heated at 150° C. in a sealed flask for 3.5 hrs. The mixture was cooled to room temperature, and the resulting suspension was diluted in water, shaken for 15 min, the solid was isolated by filtration, rinsed with water, air-dried, and dried under high vacuum to afford title compound 337 (1.76 g, 90% yield) as a yellow crystalline solid. MS (m/z): 157.0 (M+H)$^{+\cdot}$ and 179.0 (M+Na)$^{+\cdot}$.

Step 2. N-(2-Fluoro-4-nitrophenyl)-2-(1-methyl-1H-imidazol-4-yl)thieno[3,2-b]pyridin-7-amine (338)

A stirred suspension of 10 (500 mg, 2.00 mmol), 337 (406 mg, 2.60 mmol), Pd$_2$(dba)$_3$ (73 mg, 0.08 mmol), (2-biphenyl)dicyclohexylphosphine (56 mg, 0.16 mmol), and K$_3$PO$_4$ (638 mg, 3.00 mmol) in toluene (20 ml) was degased for 15 min with nitrogen at room temperature, and then heated in a sealed flask at 110° C. for 22 hrs (J. P. Wolfe, H. Tomori, J. P. Sadighi. J. Yin. S. L. Buchwald *J. Org. Chem.* 2000, 65, 1158-1174). After cooling to room temperature the reaction mixture was filtered, rinsed with toluene, concentrated and adsorbed on silica gel. The crude product was purified by flash column chromatography (eluents MeOH/CH$_2$Cl$_2$: 2/98 to 10/90) and precipitated in AcOEt/hexanes to afford title compound 338 (370 mg, 50% yield) as a yellow-orange solid. $^1$H NMR (400 MHz, DMSO-d$_6$) δ (ppm): 9.57 (bs, 1H), 8.45 (d, 5.1 Hz, 1H), 8.22 (dd, J=11.3, 2.5 Hz, 1H), 8.06 (dd. J=8.9, 2.3 Hz, 1H), 7.83 (d, I=1.2 Hz, 1H), 7.70 (d, J=1.2 Hz, 1H), 7.63 (s, 1H), 7.24 (t, J=8.7 Hz, 1H), 6.94 (bd, J=4.7 Hz, 1H), 3.71 (s, 3H). MS (m/z): 370.0 (M+H)$^+$.

Step 3. 2-Fluoro-N-1-(2-(1-methyl-1H-imidazol-4-yl)thieno[3,2-b]pyridin-7-yl)benzene-1,4-diamine (339)

To a stirred suspension of nitro compound 338 (370 mg, 1.00 mmol) in a mixture of MeOH (20 mL) and water (10 mL) were added iron powder (280 mg, 5.01 mmol) and NH$_4$Cl (107 mg, 2.00 mmol). The reaction mixture heated to reflux for 2 hrs, cooled down to room temperature, filtered through Celite, and rinsed with methanol. The filtrate was concentrated, diluted a bit with methanol, precipitated with AcOEt/hexanes to afford title compound 339 (463 mg, quantitative yield, ammonium salt) as a yellow solid. MS (m/z): 340.0 (M+H)$^{+\cdot}$.

Step 4. N-(3-Fluoro-4-(2-(1-methyl-1H-imidazol-4-yl)thieno[3,2-b]pyridin-7-ylamino) phenyl)-N-(4-fluorophenyl)cyclopropane-1,1-dicarboxamide (336)

To a stirred solution of 339 (80 mg, 0.24 mmol) and 1-(4-fluorophenylcarbamoyl)cyclopropanecarboxylic acid (181, 111 mg, 0.50 mmol) in anhydrous DMF were added DIPEA (123 μL, 0.71 mmol) and HATU reagent (256 mg, 0.67 mmol). The reaction mixture was stirred at room temperature overnight under nitrogen, diluted with AcOEt, and successively washed with sat. NaHCO₃, water, sat. NH₄Cl, water and brine, and concentrated. The crude material was first purified by flash column chromatography (eluents 2% of NH₄OH in methanol/CH₂Cl₂: 10/90) and precipitated in AcOEt (with traces of acetone)/hexanes to afford title compound 336 (75 mg, 58% yield) as a white solid. $^1$H NMR (400 MHz, DMSO-d$_6$) δ (ppm): 10.32 (s, 1H), 10.04 (s, 1H), 8.65 (bs, 1H), 8.18 (d, J=5.5 Hz, 1H), 7.78 (dd, J=12.9, 2.2 Hz, 1H), 7.77 (d, J=1.8 Hz, 1H), 7.68 (d, J=1.2 Hz, 1H), 7.68-7.60 (m, 2H), 7.50 (s, 1H), 7.44 (dd, J=8.4, 1.8 Hz, 1H), 7.30 (t, J=8.9 Hz, 1H), 7.15 (t, J=9.0 Hz, 2H), 6.36 (dd, J=5.5, 1.6 Hz, 1H), 3.70 (s, 3H), 1.47 (s, 4H). MS (m/z): 545.0 (M+H)$^+$.

TABLE 15

Compounds 340-342 (examples 150-152) prepared according to the scheme 78

| Cpd | Ex. | Structure | Characterization |
|---|---|---|---|
| 340 | 150 | N-(3-Fluoro-4-(2-(1-methyl-1H-imidazol-4-yl)thieno[3,2-b]pyridin-7-ylamino)phenyl)-N-phenylcyclopropane-1,1-dicarboxamide | $^1$H NMR (400 MHz, DMSO-d$_6$) δ (ppm): 10.28 (s, 1H), 10.02 (s, 1H), 8.58 (s, 1H), 8.23 (bs, 1H), 8.17 (d, J = 5.5 Hz, 1H), 7.77 (dd, J = 13.0, 2.2 Hz, 1H), 7.76 (d, J = 1.2 Hz, 1H), 7.67 (d, J = 1.2 Hz, 1H), 7.63 (d, J = 7.4, 2H), 7.49 (s, 1H), 7.43 (dd, J = 8.4, 1.8 Hz, 1H), 7.35-7.26 (m, 3H), 7.07 (t, J = 7.2 Hz, 1H), 6.35 (dd, J = 5.5, 1.6 Hz, 1H), 3.70 (s, 3H), 1.48 (s, 4H). MS (m/z): 527.0 (M + H)$^+$. |
| 341 | 151 | N-(3-Fluoro-4-(2-(1-methyl-1H-imidazol-4-yl)thieno[3,2-b]pyridin-7-ylamino)phenyl)-2-oxo-1-phenylpyrrolidine-3-carboxamide | $^1$H NMR (400 MHz, DMSO-d$_6$) δ (ppm): 10.63 (s, 1H), 8.62 (s, 1H), 8.18 (bs, 1H), 7.79 (dd, J = 12.9, 2.2 Hz, 1H), 7.77 (s, 1H), 7.72-7.65 (m, 3H), 7.50 (bs, 1H), 7.41 (t, J = 7.9 Hz, 3H), 7.35 (t, J = 8.7 Hz, 1H), 7.18 (t, J = 7.3 Hz, 1H), 6.37 (d, J = 4.7 Hz, 1H), 4.00-3.88 (m, 2H), 3.79 (t, J = 8.6 Hz, 1H), 3.71 (s, 3H), 2.50-2.32 (m, 2H), MS (m/z): 527.0 (M + H)$^+$. |
| 342 | 152 | N-(3-Fluoro-4-(2-(1-(2-(pyrrolidin-1-yl)ethyl)-1H-imidazol-4-yl)thieno[3,2-b]pyridin-7-ylamino)phenyl)-2-oxo-3-phenylimidazolidine-1-carboxamide | $^1$H NMR (400 MHz, DMSO-d$_6$) δ (ppm): 10.55 (s, 1H), 8.67 (bs, 1H), 8.19 (d, J = 5.2 Hz, 1H), 7.86 (s, 1H), 7.79-7.69 (m, 2H), 7.64 (d, J = 8.0 Hz, 2H), 7.50 (s, 1H), 7.44 (t, J = 8.0 Hz, 2H), 7.38-7.30 (m, 2H), 7.18 (t, J = 7.6 Hz, 1H), 6.38 (d, J = 5.2 Hz, 1H), 4.30-4.06 (bs, 2H), 4.04-3.90 (m, 4H), 3.40-2.30 (m, 6H), 1.88-1.62 (m, 4H). MS (m/z): 611.3 (M + H). |

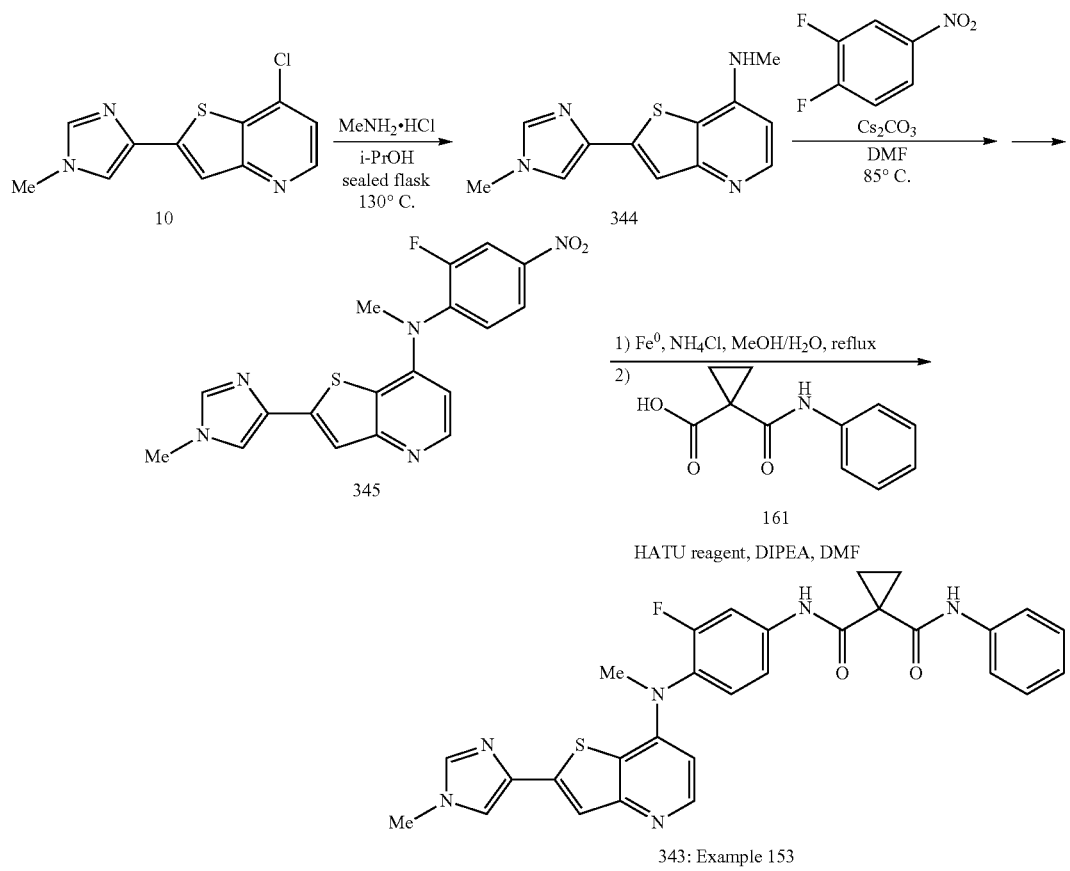

Scheme 79

Example 153

N-(3-Fluoro-4-(methyl(2-(1-methyl-1H-imidazol-4-yl)thieno[3,2-b]pyridin-7-yl)amino)phenyl)-N-phenylcyclopropane-1,1-dicarboxamide (343)

Step 1. N-Methyl-2-(1-methyl-1H-imidazol-4-yl)thieno[3,2-b]pyridin-7-amine (344)

A stirred suspension of 10 (500 mg, 2 mmol) and methylamine hydrochloride (15 g, 222 mmol) in isopropanol (50 ml) was heated at 130° C. in a sealed flask for four days, then cooled to room temperature. The reaction mixture was poured in water, and the pH was adjusted to ~10 with 1N NaOH. After extraction of the aqueous phase with AcOEt, the combined organic layer was concentrated and directly purified by flash column chromatography (eluents 2% of $NH_4OH$ in methanol/$CH_2Cl_2$: 10/90 to 40/60) to afford title compound 344 (487 mg, 99% yield, hydrate form) as a beige solid. MS (m/z): 245.0 $(M+H)^+$.

Step 2. N-(2-Fluoro-4-nitrophenyl)-N-methyl-2-(1-methyl-1H-imidazol-4-yl)thieno[3,2-b]pyridin-7-amine (345)

A stirred suspension of 344 (500 mg, ~2 mmol), 3,4-difluoronitrobenzene (795 mg, 5 mmol) and cesium carbonate (1.63 g, 5 mmol) in anhydrous DMF (50 ml) was heated at 85° C. under nitrogen for 7 h. The temperature was allowed to cool down to room temperature. The reaction mixture was poured into water, and extracted with dichloromethane. The combined organic phase was concentrated and directly purified twice by flash column chromatography (eluents 2% of $NH_4OH$ in methanol/$CH_2Cl_2$: 5/95 to 10/90) to afford title compound 345 (144 mg, 19% yield) as a sticky yellow solid. MS (m/z): 384.0 $(M+H)^+$.

Step 3. N-(3-Fluoro-4-(methyl(2-(1-methyl-1H-imidazol-4-yl)thieno[3,2-b]pyridin-7-yl)amino)phenyl)-N-phenylcyclopropane-1,1-dicarboxamide (343)

The title compound 343 (formate salt) was obtained in two steps from 345 as an off-white solid following the same procedure as in example 336, step 3 and 4 (scheme 78), but using in the last step acid 161 instead of 181. $^1$H NMR (400 MHz, DMSO-$d_6$) δ (ppm): 10.36 (s, 1H), 10.02 (s, 1H), 8.44-8.14 (m, 2H), 7.78 (dd, J=13.2, 2.1 Hz, 1H), 7.66 (d, J=1.2 Hz, 1H), 7.63 (d, J=7.6 Hz, 2H), 7.58 (d, J=0.8, 1H), 7.47 (dd, J=8.7, 2.1 Hz, 1H), 7.43 (s, 1H), 7.35 (t, J=8.9 Hz, 1H), 7.31 (t, J=8.0 Hz, 2H), 7.07 (t, J=7.3 Hz, 1H), 6.77 (bd, J=5.3 Hz, 1H), 3.65 (s, 3H), 3.33 (s, 3H), 1.54-1.44 (m, 4H). MS (m/z): 541.0 $(M+H)^+$.

TABLE 16

Compounds 344-347 (examples 154-155 prepared according to the scheme 79

| Cpd | Ex. | Structure | Characterization |
|---|---|---|---|
| 346 | 154 | 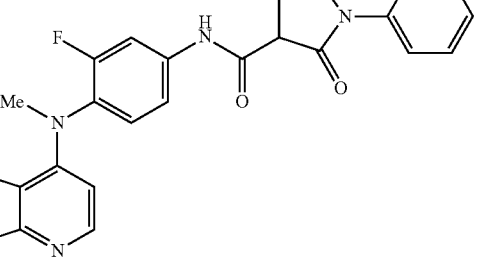<br>N-(3-Fluoro-4-(methyl(2-(1-methyl-1H-imidazol-4-yl)thieno[3,2-b]pyridin-7-yl)amino)phenyl)-2-oxo-1-phenylpyrrolidine-3-carboxamide | $^1$H NMR (400 MHz, DMSO-$d_6$) δ (ppm): 10.71 (s, 1H), 8.35 (d, J = 5.5 Hz, 1H), 7.79 (dd, J = 12.9, 2.0 Hz, 1H), 7.71-7.65 (m, 3H), 7.59 (bd, J = 1.2 Hz, 1H), 7.46-7.37 (m, 5H), 7.18 (t, J = 7.3 Hz, 1H), 6.78 (d, J = 5.7 Hz, 1H), 4.00-3.88 (m, 2H), 3.81 (t, J = 8.6 Hz, 1H), 3.65 (s, 3H), 3.35 (s, 3H), 2.50-2.30 (m, 2H). MS (m/z): 541.0 (M + H)$^+$, (solvate with methanol). |
| 347 | 155 | 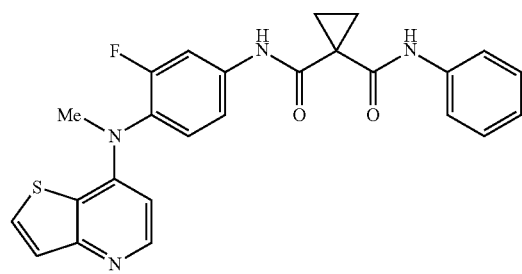<br>N-(3-Fluoro-4-(methyl(thieno[3,2-b]pyridin-7-yl)amino)phenyl)-N-phenylcyclopropane-1,1-dicarboxamide | ). $^1$H NMR (400 MHz, DMSO-$d_6$) δ (ppm): 10.38 (s, 1H), 9.98 (s, 1H), 8.41 (d, J = 5.5 Hz, 1H), 7.76 (dd, J = 13.1, 2.3 Hz, 1H), 7.75 (d, J = 5.7 Hz, 1H), 7.62 (bd, J = 7.6 Hz, 2H), 7.45 (dd, J = 8.8, 2.2 Hz, 1H), 7.38 (t, J = 8.9 Hz, 1H), 7.35-7.27 (m, 3H), 7.07 (t, J = 7.3 Hz, 1H), 6.81 (d, J = 5.5 Hz, 1H), 3.35 (s, 3H), 1.48 (bs, 4H). MS (m/z): 461 (M + H)$^+$. |

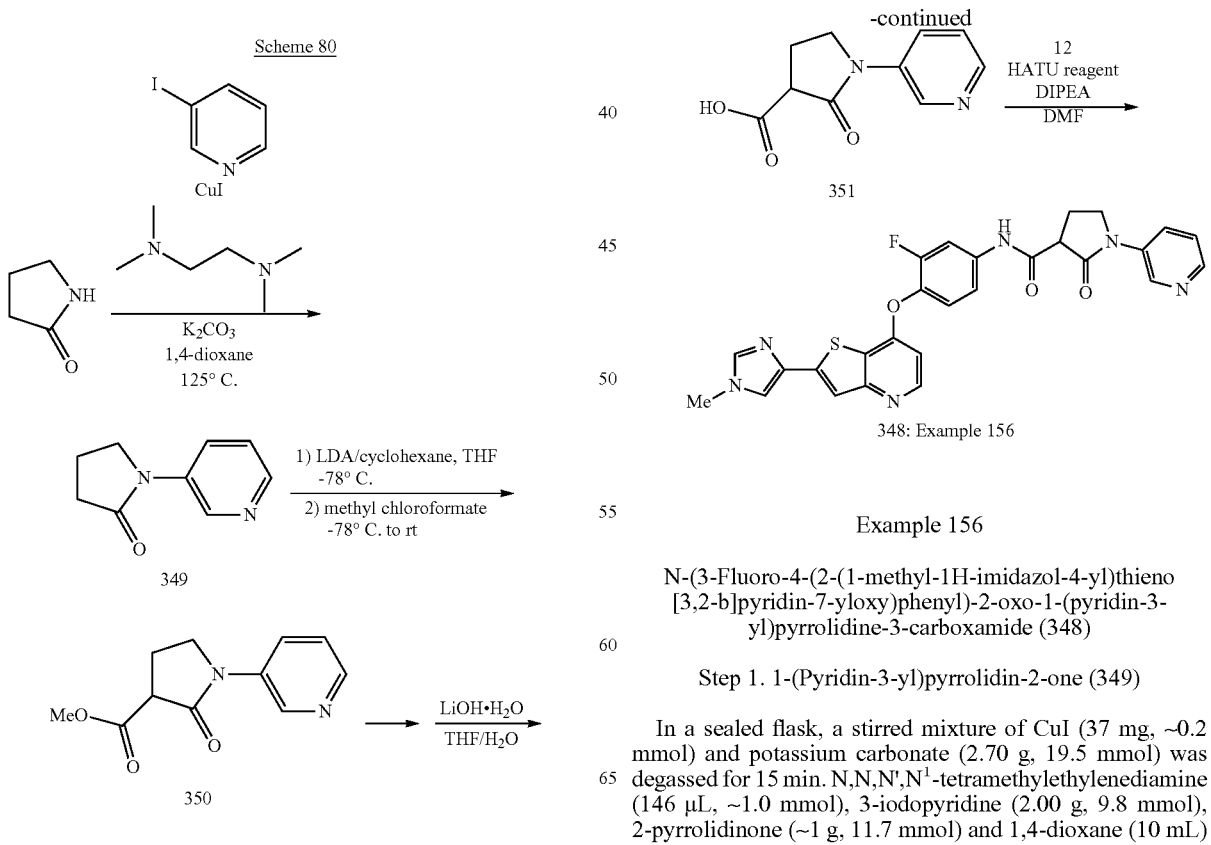

Example 156

N-(3-Fluoro-4-(2-(1-methyl-1H-imidazol-4-yl)thieno[3,2-b]pyridin-7-yloxy)phenyl)-2-oxo-1-(pyridin-3-yl)pyrrolidine-3-carboxamide (348)

Step 1. 1-(Pyridin-3-yl)pyrrolidin-2-one (349)

In a sealed flask, a stirred mixture of CuI (37 mg, ~0.2 mmol) and potassium carbonate (2.70 g, 19.5 mmol) was degassed for 15 min. N,N,N',N$^1$-tetramethylethylenediamine (146 µL, ~1.0 mmol), 3-iodopyridine (2.00 g, 9.8 mmol), 2-pyrrolidinone (~1 g, 11.7 mmol) and 1,4-dioxane (10 mL)

were added, respectively (A. Klapars. J. C. Antilla. X. Huang. S. L. Buchwald *J. Am. Chem. Soc.* 2001, 123, 7727-7729). The flow of nitrogen was removed, and the reaction mixture was then heated at 125° C. for 18 h. After cooling to room temperature the reaction mixture was filtered, rinsed with ethyl acetate, and concentrated. The crude product was purified by flash column chromatography (eluents MeOH/CH$_2$Cl$_2$: 2/98 to 5/95) to afford title compound 349 (1.49 g, 94% yield) as a yellow oily liquid. MS (m/z): 163.1 (M+H)$^{+\cdot}$.

Step 2. Methyl 2-oxo-1-(pyridin-3-yl)pyrrolidine-3-carboxylate (350)

To a stirred solution of 349 (1.48 g, 9.1 mmol) in anhydrous THF (25 ml) at −78° C. under nitrogen was slowly added a solution of LDA (mono THF, 13.4 mL, 20.1 mmol, 1.5 M in cyclohexane). After 45 min, methyl chloroformate (776 μL, 10.0 mmol) was added. The mixture was warmed to room temperature over 2 h, and then stirred overnight. Then, the reaction mixture was quenched by addition of sat. ammonium chloride and extracted with AcOEt. After separation, the organic layer was successively washed with sat. NH$_4$Cl, water, and brine. The aqueous phase was extracted twice with AcOEt. The combined organic layers were dried over anhydrous magnesium sulfate, filtered, and concentrated. The crude product was purified by flash column chromatography (eluents MeOH/CH$_2$Cl$_2$: 2/98 to 5/95) to afford title compound 350 (520 mg, 26% yield) as a pale yellow sticky solid. $^1$H NMR (400 MHz, DMSO-d$_6$) δ (ppm): 8.86 (d, J=2.5 Hz, 1H), 8.38 (dd, J=4.7, 1.4 Hz, 1H), 8.12-8.06 (m, 1H), 7.44 (dd, J=8.4, 4.7 Hz, 1H), 3.99-3.84 (m, 2H), 3.81 (t, J=8.8 Hz, 1H), 3.70 (s, 3H), 2.48-2.29 (m, 2H). MS (m/z): 221.0 (M+H)$^{+\cdot}$.

Step 3. 2-Oxo-1-(pyridin-3-yl)pyrrolidine-3-carboxylic acid (351)

To a stirred solution of 350 (514 mg, 2.33 mmol) in THF (20 ml) under nitrogen was added a solution of LiOH.H$_2$O (147 mg, 3.50 mmol) in water (5 mL). The reaction mixture was stirred overnight, concentrated, diluted with a small amount of water, filtered, neutralized with 1N HCl (pH~5-6), and extracted twice with dichloromethane. The aqueous phase was concentrated, and the residue was triturated in methanol (with traces of acetone). After filtration, the mother liquid was concentrated and dried under high vacuum to afford title compound 351 (493 mg, quantitative yield, contaminated with salts) as a pale yellow sticky solid. MS (m/z): 207.1 (M+H)$^{+\cdot}$.

Step 4. N-(3-Fluoro-4-(2-(1-methyl-1H-imidazol-4-yl)thieno[3,2-b]pyridin-7-yloxy)phenyl)-2-oxo-1-(pyridin-3-yl)pyrrolidine-3-carboxamide (348)

The title compound 348 (example 31) was obtained via coupling reaction of the acid 351 and the amine 12 as a beige solid, following the same procedure as described above for the synthesis of compound 336 (example 149, scheme 78); purified using Biotage System (Si 12M, gradient MeOH/dichloromethane: 0/100 to 20/80) followed by trituration with dichloromethane. $^1$H NMR (400 MHz, DMSO-d$_6$) δ (ppm): 10.73 (s, 1H), 8.91 (d, J=2.8 Hz, 1H), 8.43 (d, J=5.6 Hz, 1H), 8.39 (dd, J=4.4, 1.6 Hz, 1H), 8.13 (qd, J=8.4, 1.6 Hz, 1H), 7.94-7.88 (m, 1H), 7.87 (d, J=1.0 Hz, 1H), 7.72 (d, J=1.0 Hz, 1H), 7.69 (s, 1H), 7.53-7.43 (m, 3H), 6.60 (d, J=5.6 Hz, 1H), 4.04-3.92 (m, 2H), 3.82 (t, J=8.8 Hz, 1H), 3.73 (s, 3H), 2.55-2.36 (m, 2H). MS (m/z): 529.0 (M+H)$^{+\cdot}$.

TABLE 17

Compounds 352-360 (examples 157-165)

| Cpd | Ex. | Structure | Characterization |
|---|---|---|---|
| 352 | 157 | 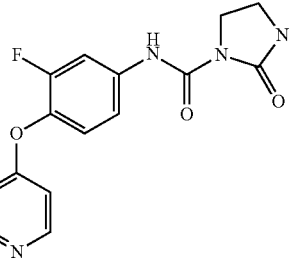 N-(3-Fluoro-4-(2-(1-methyl-1H-imidazol-4-yl)thieno[3,2-b]pyridin-7-yloxy)phenyl)-3-(4-fluorophenyl)-2-oxoimidazolidine-1-carboxamide | $^1$H NMR (400 MHz, DMSO-d$_6$) δ (ppm): 10.56 (s, 1H), 8.44 (d, J = 5.5 Hz, 1H), 7.90-7.80 (m, 2H), 7.76-7.60 (m, 4H), 7.53-7.40 (m, 2H), 7.29 (t, J = 8.8 Hz, 2H), 6.59 (d, J = 5.3 Hz, 1H), 4.00-3.92 (m, 4H), 3.73 (s, 3H). MS (m/z): 547.0 (M + H)$^+$. |
| 353 | 158 | 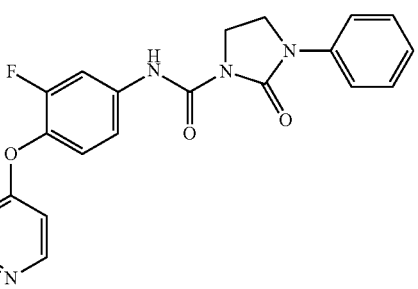 N-(4-(2-(3-acetylphenyl)thieno[3,2-b]pyridin-7-yloxy)-3-fluorophenyl)-2-oxo-3-phenylimidazolidine-1-carboxamide | $^1$H NMR (400 MHz, DMSO-d$_6$) δ (ppm): 10.59 (s, 1H), 8.55 (d, J = 5.5 Hz, 1H), 8.39 (t, J = 1.7 Hz, 1H), 8.24 (s, 1H), 8.19-8.14 (m, 1H), 8.05-8.00 (m, 1H), 7.87 (dd, J = 12.9, 2.3 Hz, 1H), 7.69 (t, J = 7.8 Hz, 1H), 7.66-7.61 (m, 2H), 7.52 (t, J = 8.6 Hz, 1H), 7.49-7.40 (m, 3H), 7.18 (t, J = 7.4 Hz, 1H), 6.68 (dd, J = 5.5, 0.8 Hz, 1H), 4.02-3.91 (m, 4H), 2.69 (s, 3H). MS (m/z): 567.2 (M + H)$^+$. |

TABLE 17-continued

Compounds 352-360 (examples 157-165)

| Cpd | Ex. | Structure | Characterization |
|---|---|---|---|
| 354 | 159 | N¹-(3-Fluoro-4-(2-(2-morpholinopyrimidin-5-yl)thieno[3,2-b]pyridin-7-yloxy)phenyl)-N³-(2-methoxyphenyl)malonamide | $^1$H NMR (400 MHz, DMSO-d$_6$) δ ppm: 10.58 (s, 1H), 9.63 (s, 1H), 8.92 (s, 2H), 8.48 (d, J = 5.6 Hz, 1H), 8.09-8.05 (m, 1H), 8.00 (s, 1H), 7.87 (dd, J = 2.0 and 12.8 Hz, 1H), 7.49 (t, J = 8.8 Hz, 1H), 7.46-7.41 (m, 1H), 7.11-7.04 (m, 2H), 6.92 (td, J = 2.0, 5.6 and 8.0 Hz, 1H), 6.60 (d, J = 5.6 Hz, 1H), 3.86 (s, 3H), 3.83-3.78 (m, 4H), 3.72-3.66 (m, 4H), 3.64 (s, 2H). LRMS 615.1 (M + H). |
| 355 | 160 | N¹-(3-Fluoro-4-(2-(4-(2-morpholinoethoxy)phenyl)thieno[3,2-b]pyridin-7-yloxy)phenyl)-N³-(2-methoxyphenyl)malonamide | $^1$H NMR (400 MHz, DMSO-d$_6$) δppm: 10.59 (s, 1H), 9.64 (s, 1H), 8.47 (d, J = 5.6 Hz, 1H), 8.10-8.05 (m, 1H), 7.93 (s, 1H), 7.90-7.79 (m, 3H), 7.54-7.37 (m, 2H), 7.13-7.06 (m, 4H), 6.96-6.88 (m, 1H), 6.61 (d, J = 5.6 Hz, 1H), 4.17 (t, J = 5.6 Hz, 2H), 3.86 (s, 3H), 3.64 (s, 2H), 3.59 (t, J = 4.8 Hz, 4H), 2.73 (t, J = 5.6 Hz, 2H), 2.54-2.47 (m, 4H). LRMS 516.2 (M + H). |
| 356 | 161 | N1-(4-(2-(1-Ethyl-1H-imidazol-4-yl)thieno[3,2-b]pyridin-7-yloxy)-3-fluorophenyl)-N3-(3-fluorophenyl)malonamide | $^1$H NMR (400 MHz, DMSO-d$_6$) δppm: 11.58 (s, 1H), 10.45 (s, 1H), 8.43 (d, J = 5.6 Hz, 1H), 7.96 (d, J = 1.2 Hz, 1H), 7.87 (dd, J = 2.4 and 12.8 Hz, 1H), 7.79 (d, J = 1.2 Hz, 1H), 7.67 (s, 1H), 7.62 (td, J = 2.4 and 11.6 Hz, 1H), 7.48 (t, J = 8.8 Hz, 1H), 7.45-7.28 (m, 3H), 6.94-6.87 (m, 1H), 6.58 (d, J = 5.6 Hz, 1H), 4.05 (q, J = 7.2 Hz, 2H), 3.53 (s, H), 1.40 (t, J = 7.2 Hz, 3H). |
| 357 | 162 | N1-(4-(2-(1-Ethyl-1H-imidazol-4-yl)thieno[3,2-b]pyridin-7-yloxy)-3-fluorophenyl)-N3-(3-methoxyphenyl)malonamide | $^1$H NMR (400 MHz DMSO-d$_6$) δppm: 10.57 (s, 1H), 10.21 (s, 1H), 8.43 (d, J = 5.6 Hz, 1H), 7.96 (d, J = 1.2 Hz, 1H), 7.88 (dd, J = 2.4 and 13.2 Hz, 1H), 7.79 (d, J = 1.2 Hz, 1H), 7.67 (s, 1H), 7.48 (t, J = 8.8 Hz, 1H), 7.43 (dd, J = 1.6 and 8.8 Hz 1H), 7.324, J = 2.4 hz, 1H), 7.224, J = 8.0 Hz, 1H), 7.16-7.12 (m, 1H), 6.65 (ddd, J = 1.6, 2.4 and 8.4 Hz, 1H), 6.58 (d, J = 5.6 Hz, 1H), 4.06 (q, J = 7.2 Hz, 2H), 3.73 (s, 3H), 3.51 (s, 2H), 1.40 t, J = 7.2 Hz, 3H). |

TABLE 17-continued

Compounds 352-360 (examples 157-165)

| Cpd | Ex. | Structure | Characterization |
|---|---|---|---|
| 358 | 163 | N1-(4-(2-(1-Ethyl-1H-imdazol-4-yl)thieno[3,2-b]pyridin-7-yloxy)-3-fluorophenyl)-N3-(4-fluorophenyl)malonamide | ¹H NMR (400 MHz, DMSO-d₆) δppm: 10.57 (s, 1H), 10.29 (s, 1H), 8.43 (d, J = 5.6 Hz, 1H), 7.96 (d, J = 1.2 Hz, 1H), 7.87 (dd, J = 1.6 and 12.8 Hz, 1H), 7.79 (d, J = 1.2 Hz, 1H), 7.67 (s, 1H), 7.68-7.60 (m, 3H), 7.48 (t, J = 8.8 Hz, 1H), 7.43 (dd, J = 2.0 and 9.2 Hz, 1H), 7.20-7.14 (m, H), 6.58 (d, J = 5.6 Hz, 1H), 4.06 (q, J = 7.2 Hz, 2H), 3.50 (s, 2H), 1.40 (t, J = 7.2 Hz, 3H). |
| 359 | 164 | N1-(3-Fluoro-4-(2-(1-propyl-1H-imidazol-4-yl)thieno[3,2-b]pyridin-7-yloxy)phenyl)-N3-(4-fluorophenyl)malonamide | 1H NMR (400 MHz, DMSO-d6) δppm: 10.55 (s, 1H), 10.26 (s, 1H), 8.41 (d, J = 5.5 Hz, 1H), 7.92 (d, J = 1.1 Hz, 1H), 7.87 (dd J = 11.9 Hz, J = 2.4 Hz, 1H), 7.75 (d, J = 1.3 Hz, 1H), 7.66 (s, 1H); 7.63-7.60 (m, 2H), 7.46 (t, J = 8.6 Hz, 1H), 7.41 (dd, J = 9.2 Hz, J = 2.2 Hz, 1H), 7.15 (t, J = 9.0 Hz, 2H), 6.56 (dd, J = 5.3 Hz, J = 0.8 Hz, 1H); 3.97 (t, J = 7.1 Hz, 2H), 3.49 (s, 2H), 1.76 (q, J = 7.0 Hz, 2H), 0.85 (t, J = 7.4 Hz, 3H). |
| 360 | 165 | N1-(3-Fluoro-4-(2-(1-propyl-1H-imidazol-4-yl)thieno[3,2-b]pyridin-7-yloxy)phenyl)-N3-(3-fluorophenyl)malonamide | 1H NMR (400 MHz, DMSO-d6) δppm: 10.56 (s, 1H), 10.43 (s, 1H), 8.41 (d, J = 5.5 Hz, 1H), 7.92 (d, J = 1.2 Hz, 1H), 7.85 (dd, J = 13.1 Hz, J = 2.5 Hz, 1H), 7.75 (d, J = 1.2 Hz, 1H), 7.66 (s, 1H), 7.60 (dt, J = 9.6 Hz, J = 2.2 Hz, 1H), 7.49-7.27 (m, 4H), 6.89 (td, J = 7.6 Hz, J = 2.5 Hz, 1H), 6.57 (d, J = 5.5 Hz, 1H), 3.97 (t, J = 7.1 Hz, 2H), 3.51 (s, 2H), 1.76 (m, J = 7.3 Hz, 2H), 0.85 (t, J = 7.3 Hz, 3H). |

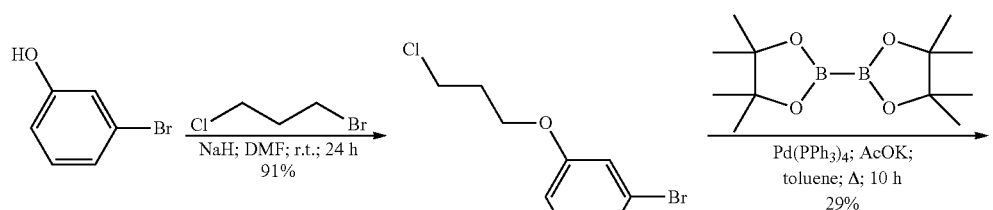

Scheme 81

-continued
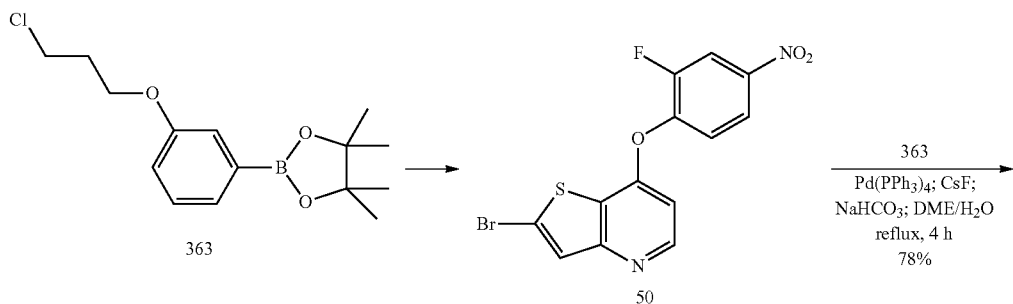
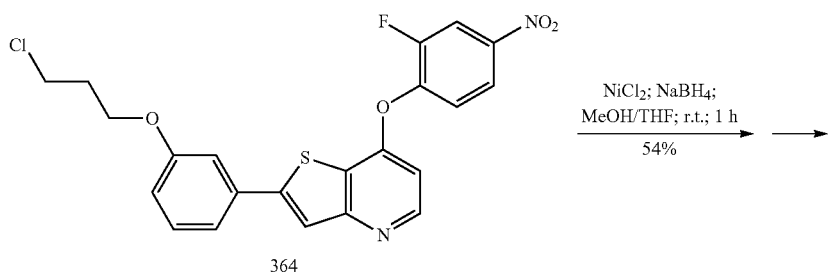
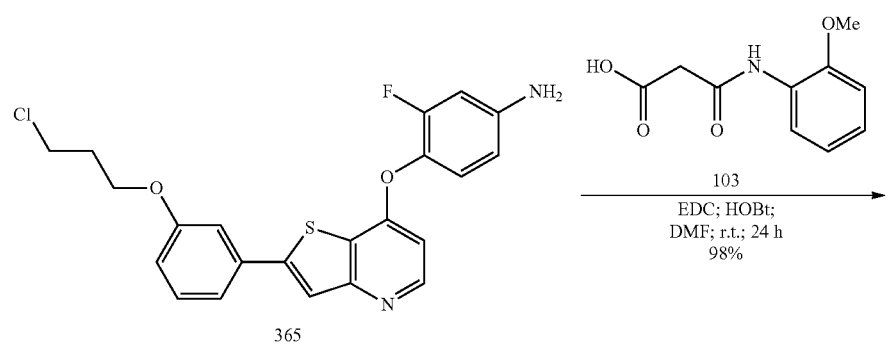
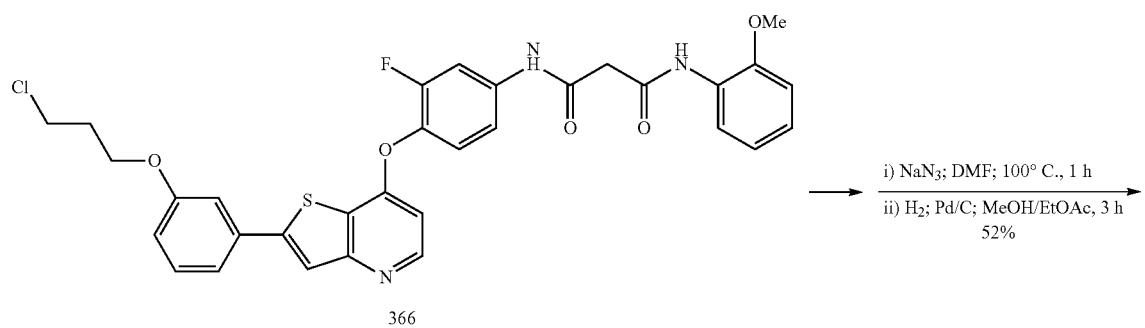
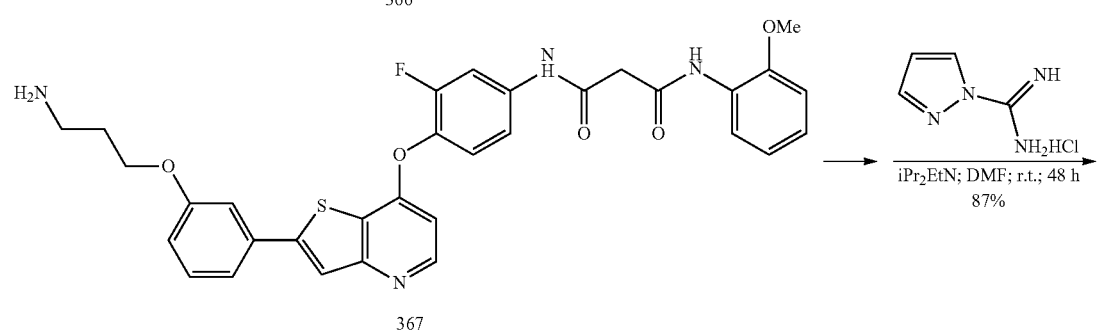

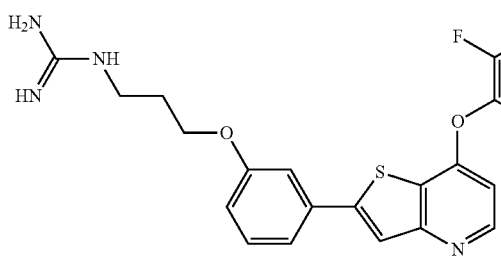
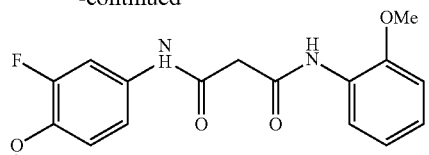

361: Example 166

Example 166

N¹-(3-Fluoro-4-(2-(3-(3-guanidinopropoxy)phenyl)thieno[3,2-b]pyridin-7-yloxy)phenyl)-N-3-(2-methoxyphenyl)malonamide (361)

Step 1: 2-(3-(3-Chloropropoxy)phenyl)-4,4,5,5-tetramethyl-1,3,2-dioxaborolane (363)

To 3-bromophenol (2.23 g, 12.9 mmol) in DMF (100 mL) was added, in small portions, sodium hydride (60% dispersion, 0.54 g, 13 mmol) over 30 min. 1-Bromo-3-chloropropane (2.1 g, 13 mmol) was then added dropwise and the mixture was stirred at r.t. for 24 h. It was then partitioned between ether and water, the organic phase was washed with water and brine, dried (anhydrous MgSO$_4$) and concentrated to afford 1-bromo-3-(3-chloropropoxy)benzene (362, 2.95 g, 91% yield) (used as is with no additional purification).

Ether 362 (2.95 g, 11.8 mmol), bis(pinacolato)diboron (4.00 g, 15.8 mmol), potassium acetate (1.20 g, 12.2 mmol) and tetrakis(triphenylphosphine)palladium (0.37 g, 0.32 mmol) were suspended in toluene (100 mL) and heated under reflux for 10 h. The mixture was then cooled and the toluene was removed under reduced pressure. The residue was partitioned between water and dichloromethane, the organic phase was dried (Na$_2$SO$_4$), filtered, concentrated and purified by flash chromatography (eluent 25% dichloromethane/hexanes) to afford title compound 363 (1.00 g, 29% yield). $^1$H NMR (400 MHz, DMSO-d$_6$) δ (ppm): 7.29 (t, J=7.8, 1H); 7.23 (dt, J=7.2, 1.0, 1H); 7.15 (d, J=2.5, 1H); 7.06 (ddd, J=8.0, 2.7, 1.4, 1H); 4.06 (t, J=6.1, 2H); 3.78 (t, J=6.7, 2H), 2.14 (quint, J=6.3, 2H); 1.27 (s, 12H). LRMS (M+H): 297.1.

Step 2: 2-(3-(3-Chloropropoxy)phenyl)-7-(2-fluoro-4-nitrophenoxy)thieno[3,2-b]pyridine (364)

Bromothienopyridine 50 (0.88 g, 2.38 mmol), boronate 363 (1.00 g, 3.40 mmol), and tetrakis(triphenylphosphine)palladium (0.10 g, 0.086 mmol) were dissolved in dry DME (100 mL). Cesium fluoride (1.26 g, 8.3 mmol) and sodium bicarbonate (0.70 g, 8.3 mmol) were dissolved in water (5 ml each) and added to the reaction mixture, which was then heated to reflux for 4 h, cooled, and concentrated. The residue was partitioned between ethyl acetate and water, washed with brine, dried (anhydrous MgSO$_4$), filtered, and concentrated. The residue was purified by flash chromatography (eluent 75% dichloromethane/hexanes) to afford 364 (0.85 g, 78% yield). $^1$H NMR (400 MHz, CDCl$_3$) δ (ppm): 8.60 (d, J=6.3, 1H); 8.27-8.24 (m, 2H); 8.18 (s, 1H); 7.58-7.54 (m, 1H); 7.45-7.36 (m, 2H); 7.31 (t, J=2.0, 1H); 7.07-7.04 (m, 1H); 6.78 (d, J=6.1, 1H); 4.21 (t, J=5.9, 2H); 3.79 (t, J=6.3, 2H); 2.29 (quint, J=6.1, 2H). LRMS (M+H): 459.1.

Step 3: 4-(2-(3-(3-Chloropropoxy)phenyl)thieno[3,2-b]pyridin-7-yloxy)-3-fluorobenzenamine (365)

To the nitro compound 364 (0.84 g, 1.8 mmol) and nickel chloride hexahydrate (0.87 g, 3.7 mmol) in 9:1 MeOH/THF was added sodium borohydride (0.30 g, 7.9 mmol) in small portions. The resulting mixture was stirred at r.t. for 1 h, then filtered through celite and concentrated. The residue was partitioned between water and dichloromethane, the organic phase was collected, washed with brine, dried (anhydrous MgSO$_4$), filtered, and concentrated. The residue was purified by flash chromatography (eluent 90% ethyl acetate/hexanes) to afford 365 (0.43 g, 54% yield). LRMS (M+H): 429.1.

Step 4: N¹-(4-(2-(3-(3-Chloropropoxy)phenyl)thieno[3,2-b]pyridin-7-yloxy)-3-fluorophenyl)-N³-(2-methoxyphenyl)malonamide (366)

To a solution of aniline 365 (0.42 g, 0.98 mmol) in DMF (20 mL) was added acid 103 (0.42 g, 2.0 mmol), HOBt (0.050 g, 0.38 mmol), and EDC×HCl (0.54 g, 2.8 mmol) and the mixture was stirred at r.t. for 24 h. It was then partitioned between ethyl acetate and water. The organic phase was collected, washed with water, NaHCO$_3$ $_{(aq)}$, brine, dried (anhydrous MgSO$_4$), filtered, and concentrated. The residue was triturated with ether to yield 366 (0.60 g, 98% yield). $^1$H NMR (400 MHz, DMSO-d$_6$) δ (ppm): 10.58 (s, 1H); 9.62 (s, 1H); 8.50 (d, J=5.3, 1H); 8.11 (s, 1H); 8.06 (d, J=8.8, 1H); 7.86 (dd. J=12.9, 2.4, 1H); 7.49-7.39 (m, 5H), 7.09-7.03 (m, 3H); 6.92-6.88 (m, 1H); 6.63 (d, J=5.3, 1H); 4.20 (t, J=6.1, 2H); 3.85 (s, 3H); 3.82 (t, J=6.7, 2H); 2.20 (quint, J=6.3, 2H). LRMS (M+H): 620.1.

Step 5: N1-(4-(2-(3-(3-Aminopropoxy)phenyl)thieno[3,2-b]pyridin-7-yloxy)-3-fluorophenyl)-N3-(2-methoxyphenyl)malonamide (367)

To a solution of 366 (0.19 g, 0.31 mmol) in DMF (5 mL) was added sodium azide (0.050 g, 0.77 mmol) and the reaction mixture was heated to 100° C. for 1 h. The mixture was then cooled, partitioned between ethyl acetate and water, the organic phase was collected, washed with water, brine, dried (anhydrous MgSO$_4$), filtered, and concentrated. The residue was filtered through a short plug of silica, eluting with ethyl acetate, and the eluate was concentrated. The residue was dissolved in 1:1 ethyl acetate/methanol (30 mL) mixture; to this solution was added palladium (10% on carbon), and the suspension was stirred under an atmosphere of hydrogen for 3 h. It was then filtered through celite and concentrated. The residue was purified by flash chromatography (eluent 95:3:2 chloroform/methanol/NH$_4$OH) to afford 367 (0.097 g, 52% yield): LRMS (M+H): 601.2.

Step 6: N1-(3-Fluoro-4-(2-(3-(3-guanidinopropoxy) phenyl)thieno[3,2-b]pyridin-7-yloxy)phenyl)-N3-(2-methoxyphenyl)malonamide (361)

Amine 367 (0.095 g, 0.16 mmol), pyrazole-1-carboxamidine (60 mg, 0.41 mmol), and Hunigs base (0.07 g, 0.5 mmol) were stirred in dry DMF (10 mL) for 48 h at r.t. The mixture was then partitioned between ethyl acetate and water. The aqueous phase was collected and treated with brine; a precipitate was formed which was isolated by suction filtration. The resulting solid was re-dissolved in 1:1 dichloromethane/methanol, filtered, and the filtrate was concentrated to afford 361 as a solid (90 mg, 87% yield). $^1$H NMR (400 MHz, DMSO-d$_6$) δ (ppm): 10.71 (br s, 1H); 9.63 (br s, 1H); 8.49 (d, J=5.5, 1H); 8.10 (s, 1H); 8.05 (d, J=8.4, 1H); 7.93-7.70 (m, 2H); 7.51-7.40 (m, 5H); 7.08-7.02 (m, 3H); 6.92-6.88 (m, 1H); 6.63 (d, J=5.5, 1H); 4.13 (t, J=5.9, 2H); 3.84 (s, 3H); 3.64 (s, 2H); 1.95 (quint, J=6.3, 2H). [A triplet corresponding to 3H is hidden by the residial DMSO peak]. LRMS (M+H): 643.0.

Example 167

N$^1$-(4-(2-(3-(3-(Ethylsulfinyl)propoxy)phenyl)thieno[3,2-b]pyridin-7-yloxy)-3-fluorophenyl)-N$^3$-(2-methoxyphenyl)malonamide (368)

To chloride 366 (0.048 g, 0.077 mmol) in dry DMF (10 mL) was added sodium ethanethiolate (100 mg, 1.19 mmol) and the mixture was heated to 50° C., for 18 h. It was cooled, partitioned between ethyl acetate and water, washed with brine, dried (MgSO$_4$), filtered, run through a short plug of silica gel, and concentrated. The residue was suspended in 1:1 ethyl acetate/methanol (50 mL) and sodium periodate (0.060 g, 0.28 mmol) in water (5 mL) was added. The reaction mixture was stirred for 6 h, concentrated and the residue was partitioned between ethyl acetate and water. The organic phase was collected, washed with brine, dried (anhydrous MgSO$_4$), filtered, and concentrated. Reverse phase HPLC (Aquasil C-18 column, 60-95% MeOH/H$_2$O+HCO$_2$H, 30 min. linear gradient elution) of the residue followed by lyophilization afforded 368 (0.015 g, 29% yield). $^1$H NMR (400 MHz, DMSO-d$_6$) δ (ppm): 10.71 (s, 1H); 9.66 (s, 1H); 8.51 (d, J=5.5, 1H); 8.12 (s, 1H); 8.07 (d, J=8.8, 1H); 7.89 (dd, J=12.9, 2.2, 1H); 7.53-7.41 (m, 5H); 7.09-7.03 (m, 3H); 6.94-6.90 (m, 1H); 6.64 (dd, J=5.5, 0.5, 1H); 4.22 (t, J=6.3, 2H); 3.86 (s, 3H); 3.65 (s, 2H); 2.93-2.65 (m, 4H); 2.13 (quint, J=8.0, 2H); 1.29 (t, J=7.4, 3H). LCMS: (M+H) 662.0.

Scheme 82

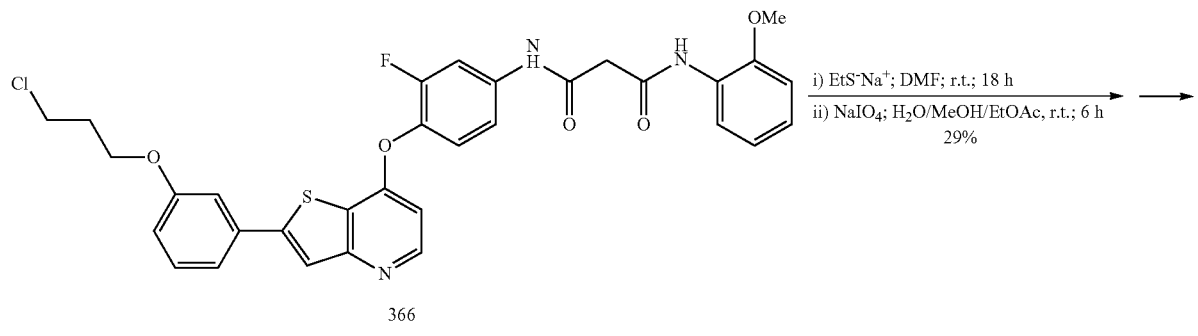

366

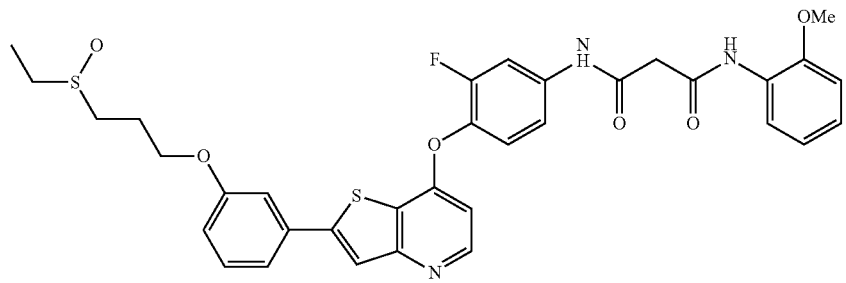

368: Example 167

Scheme 83

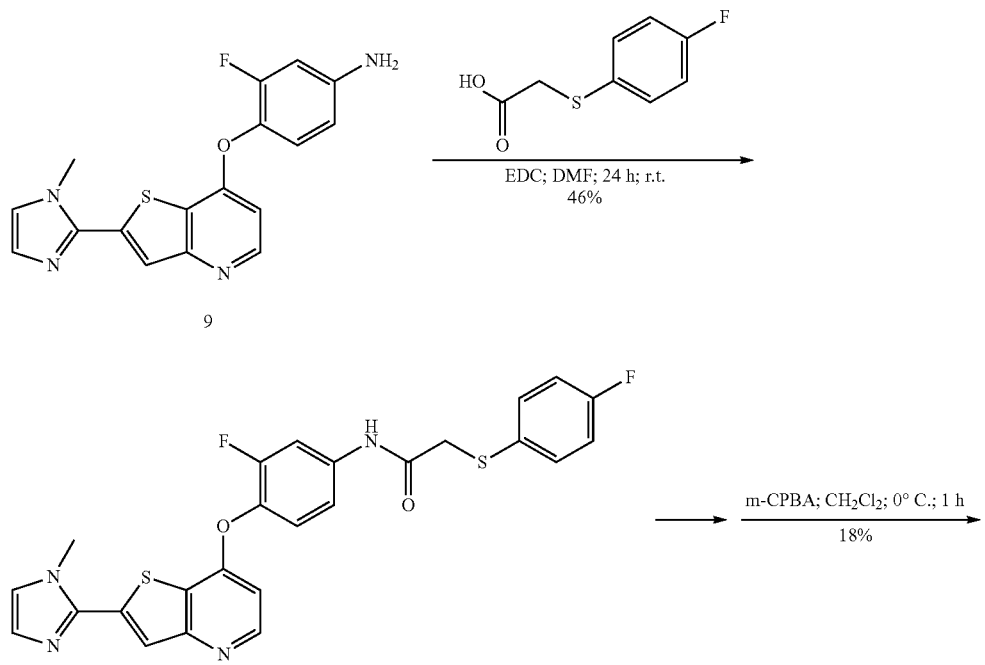

369: Example 168

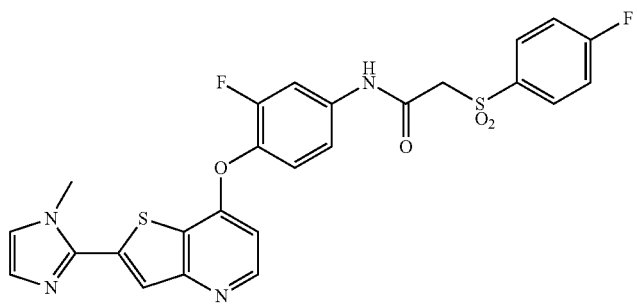

370: Example 169

Example 168

N-(3-Fluoro-4-(2-(1-methyl-1H-imidazol-2-yl)thieno[3,2-b]pyridin-7-yloxy)phenyl)-2-(4-fluorophenylthio)acetamide To aniline 9 (0.10 g, 0.30 mmol) in dry DMF (20 mL) was added (p-fluorophenylthio)acetic acid (0.11 g, 0.56 mmol), and EDC×HCl (0.13 g, 0.68 mmol) and the mixture was stirred at r.t. for 24 h. It was then partitioned between ethyl acetate and water. The organic phase was collected, washed with water, NaHCO$_3$ $_{(aq)}$, brine, dried (anhydrous MgSO$_4$), filtered and concentrated. Silica gel chromatography (eluent ethyl acetate->5% methanol/ethyl acetate) of the residue provided 369 (0.070 g, 46% yield). $^1$H NMR (400 MHz, DMSO-d$_6$) δ (ppm): 10.55 (s, 1H); 8.50 (d, J=5.5, 1H); 7.88 (s, 1H); 7.80 (dd, J=13.1, 2.5, 1H); 7.50-7.45 (m, 3H); 7.41-7.38 (m, 2H); 7.22-7.17 (m, 2H); 7.03 (d, J=1.2, 1H); 6.67 (d, J=4.7, 1H); 3.98 (s, 3H); 3.84 (s, 2H). LCMS: (M+H) 508.9.

Example 169

N-(3-Fluoro-4-(2-(1-methyl-1H-imidazol-2-yl)thieno[3,2-b]pyridin-7-yloxy)phenyl)-2-(4-fluorophenylsulfonyl)acetamide (370)

To a solution of amide 369 (0.067 g, 0.13 mmol) in dichloromethane (50 mL) at 0° C. was added m-CPBA (0.040 g, 0.24 mmol) and the mixture was left at −10° C. for 24 h. It was then washed with water, NaHCO$_3$ $_{(aq)}$, brine, dried (anhydrous MgSO$_4$), filtered, and concentrated. Silica gel chromatography (eluent 5% methanol/ethyl acetate) of the residue provided 370 (0.012 g, 18% yield). $^1$H NMR (400 MHz, CD$_3$OD) δ (ppm): 8.52 (d, J=5.7, 1H); 8.04-8.00 (m, 2H); 7.86 (s, 1H); 7.77 (dd, J=12.5, 2.4, 1H); 7.42-7.32 (m, 5H); 7.20 (d, J=1.4, 1H); 6.70 (dd, J=5.7, 1.2, 1H); 4.35 (s, 2H); 4.04 (s, 3H). LCMS: (M+H) 541.1.

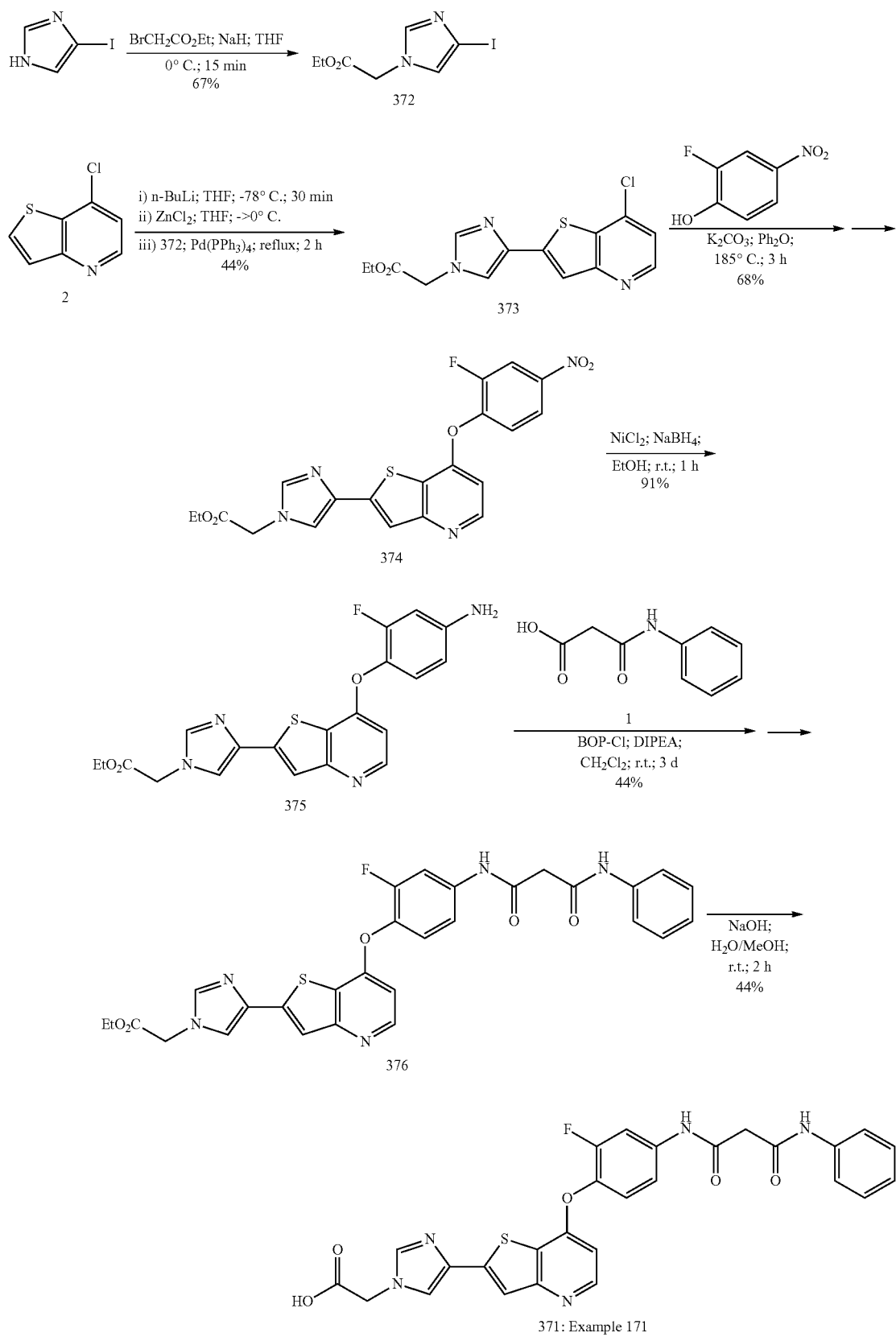

Example 171

2-(4-(7-(2-Fluoro-4-(3-oxo-3-(phenylamino)propanamido)phenoxy)thieno[3,2-b]pyridin-2-yl)-1H-imidazol-1-yl)acetic acid (371)

Step 1: Ethyl 2-(4-iodo-1H-imidazol-1-yl)acetate (372)

To a solution of 4-iodoimidazole (1.93 g, 9.95 mmol) in dry THF (50 mL) at 0° C. was added sodium hydride (60% dispersion, 0.43 g, 10.8 mmol) and the mixture was stirred for 20 min. Ethyl bromoacetate (1.1 mL, 1.7 g, 10 mmol) was added by syringe and the cloudy mixture was stirred for 15 min. It was then partitioned between ethyl acetate and water. The organic phase was collected, washed with brine, dried (anhydrous MgSO$_4$), filtered, and concentrated. Silica gel chromatography (50%->75% ethyl acetate/hexanes) of the residue provided 372 (1.88 g, 67% yield). $^1$H NMR (400 MHz, DMSO-d$_6$) δ (ppm): 7.57 (d, J=1.4, 1H); 7.32 (d, J=1.4, 1H); 4.93 (s, 2H); 4.13 (q, J=8.0, 2H); 1.20 (t, J=7.2, 3H). LRMS (M+H): 281.0.

Step 2: Ethyl 2-(4-(7-chlorothieno[3,2-b]pyridin-2-yl)-1H-imidazol-1-yl)acetate (373)

To a solution of 7-chlorothienopyridine (2.23 g, 13.1 mmol) in dry THF (50 mL) at −78° C. under N2 was added n-butyllithium (2.5 M in hexanes, 5.6 mL, 14 mmol), dropwise, with stirring. The resulting suspension was stirred for 30 min at −78° C., then ZnCl$_2$ (0.5M in THF, 30 mL, 15 mmol) was added and the mixture was allowed to warm to 0° C. Imidazole 372 (3.20 g, 11.4 mmol) and tetrakis(triphenylphosphine)palladium (0.40 g, 0.35 mmol) in THF (50 mL) were then added to the aryllithium suspension, and the mixture was heated under reflux for 2 h, then cooled and concentrated. The residue was partitioned between ethyl acetate and water. The organic phase was collected, filtered, dried (anhydrous MgSO$_4$), filtered again and concentrated.

The resulting solid was triturated (1:1 ethyl acetate/hexanes) to afford 373 (1.62 g, 44% yield). $^1$H NMR (400 MHz, DMSO-d$_6$) δ (ppm): 8.55 (d, J=5.1, 1H); 7.91 (d, J=1.2, 1H); 7.78 (d, J=1.2, 1H); 7.77 (s, 1H); 7.45 (d, J=5.2, 1H); 5.05 (s, 2H); 4.17 (q, J=7.2, 2H); 1.23 (t, J=7.0, 3H). LRMS (M+H): 322.0

Step 3: Ethyl 2-(4-(7-(2-fluoro-4-nitrophenoxy)thieno[3,2-b]pyridin-2-yl)-1H-imidazol-1-yl)acetate (374)

A suspension of 373 (1.05 g, 3.26 mmol), 2-fluoro-4-nitrophenol (1.10 g, 7.00 mmol), and K$_2$CO$_3$ (2.0 g, 15 mmol) in diphenyl ether (10 mL) was heated with stirring to 185° C. for 3 h. The mixture was cooled, diluted with dichloromethane, filtered, and the filtrate was concentrated. Silica gel chromatography (75% ethyl acetate/hexanes) of the residue provided 374 (0.98 g, 68% yield). $^1$H NMR (400 MHz, CD$_3$OD) δ (ppm): 8.52 (d, J=5.3, 1H); 8.46 (dd, J=10.4, 2.5, 1H); 8.20-8.17 (m, 1H); 7.89 (d, J=1.2, 1H), 7.77-7.74 (m, 1H); 7.75 (s, 1H); 7.69 (t, J=8.2, 1H); 6.86 (d, J=5.3, 1H); 5.04 (s, 2H); 4.17 (q, J=7.2, 2H); 1.22 (t, J=7.2, 3H). LRMS (M+H): 442.9.

Step 4: Ethyl 2-(4-(7-(4-amino-2-fluorophenoxy)thieno[3,2-b]pyridin-2-yl)-1H-imidazol-1-yl)acetate (375)

To a solution of thienopyridine 374 (0.25 g, 0.56 mmol) and nickel chloride hexahydrate (0.26 g, 1.1 mmol) in absolute EtOH (50 mL) was added sodium borohydride (0.085 g, 2.2 mmol) in small portions. The resulting mixture was stirred at r.t. for 1 h, then filtered through celite, run through a short plug of silica, eluting with 1:1 ethyl acetate/ethanol, and concentrated, affording title compound 375 (0.21 g, 91% yield). LRMS (M+H): 413.1.

Steps 5-6: 2-(4-(7-(2-Fluoro-4-(3-oxo-3-(phenylamino)propanamido)phenoxy)thieno[3,2-b]pyridin-2-yl)-1H-imidazol-1-yl)acetic acid (371)

To a solution of acid 1 (0.080 g, 0.44 mmol) in dichloromethane (10 mL) was added BOP—Cl (0.10 g, 0.39 g) in dichloromethane (10 mL) and the mixture was stirred at r.t. for 30 min. Then aniline 375 (0.11 g, 0.27 mmol) and DIPEA (0.20 mL, 0.15 g, 1.1 mmol) in dichloromethane (10 mL) were added, and the mixture was stirred at r.t. for 72 h. It was then washed with water, 1 M NaHCO$_{3\,(aq)}$, brine, dried (anhydrous MgSO$_4$), filtered, and concentrated. Silica gel chromatography (5% methanol/ethyl acetate) of the residue afforded title compound 376 (0.065 g, 43%), contaminated with some starting aniline 375. To impure amide 376 (0.050 g, 0.87 mmol) in 40% aqueous methanol (25 mL) was added NaOH (3M aqueous, 1 mL, 3 mmol) and the mixture was stirred at r.t. for 1 h. It was then partially concentrated, and the residue purified by reverse phase HPLC (Aquasil C-18 column, 40-95% MeOH/H$_2$O+HCO$_2$H, 30 min. linear gradient elution) and lyophilization. Trituration of the resulting solid (ethyl acetate) afforded acid 371 (0.021 g, 44% yield). $^1$H NMR (400 MHz, DMSO-d$_6$) δ (ppm): 11.00 (s, 1H); 10.61 (s, 1H); 8.33-8.31 (m, 3H); 7.87 (d, J=14.5, 1H); 7.78 (d, J=1.0, 1H); 7.63-7.60 (m, 4H); 7.32-7.27 (m, 4H); 7.04 (t, J=7.2, 1H); 6.40 (d, J=5.1, 1H); 4.38 (s, 2H); 3.51 (s, 2H, overlapping water peak). LRMS (M+H): 545.9.

Scheme 85

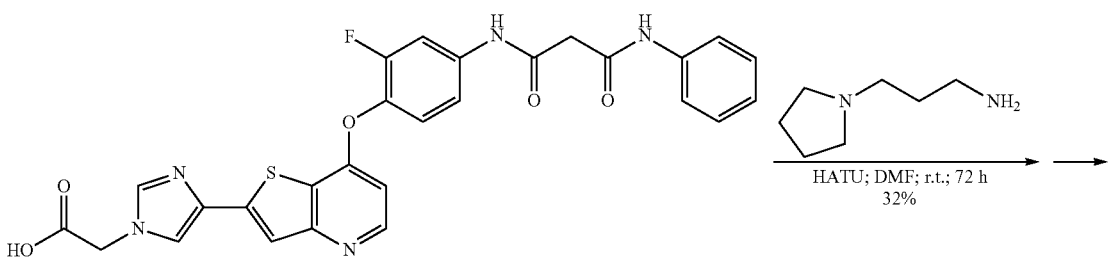

371: Example 171

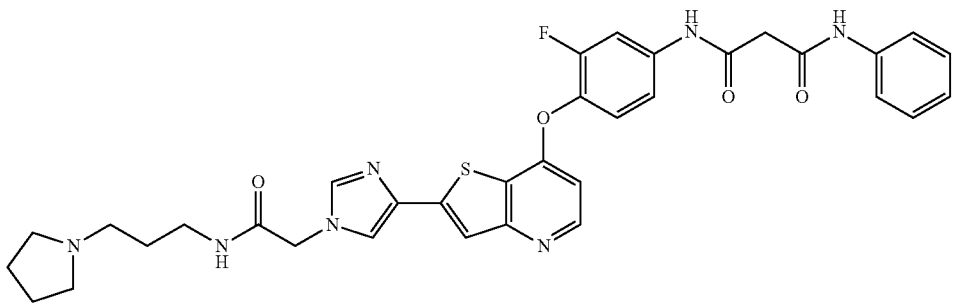

377: Example 172

Example 172

N¹-(3-Fluoro-4-(2-(1-(2-oxo-2-(3-(pyrrolidin-1-yl)propylamino)ethyl)-1H-imidazol-4-yl)thieno[3,2-b]pyridin-7-yloxy)phenyl)-N³-phenylmalonamide To a solution of acid 371 (0.016 g, 0.029 mmol) in dry DMF (5 mL) was added HATU (0.040 g, 0.11 mmol) and the mixture was stirred at r.t. for 10 min. 143-Aminopropyl)pyrrolidine (0.2 mL, 0.2 g, 2 mmol) was added and the resulting mixture was stirred at r.t. for 72 h and purified by reverse phase HPLC (Aquasil C-18 column, 45-90% MeOH/H$_2$O+HCO$_2$H, 30 min. linear gradient elution) and lyophilization. Trituration of the resulting solid with diethyl ether afforded title compound 372 (0.006 g, 32% yield). $^1$H NMR (400 MHz, CD$_3$OD) δ (ppm): 8.40 (d, J=5.7, 1H); 7.87 (dd, J=12.5, 2.4, 1H); 7.80 (s, 1H); 7.75 (s, 1H); 7.67 (s, 1H); 7.60-7.56 (m, 2H); 7.43-7.30 (m, 4H); 7.14-7.09 (m, 1H); 6.59 (d, J=5.5, 1H); 4.85 (s, 2H); 3.59 (s, 0.5H [exchanging with D?]), 3.35-3.30 (m, 2H); 3.08 (br s, 4H); 2.97 (t, J=8.0, 2H); 1.98 (br s, 4H); 1.89 (quint, J=7.8, 2H). LRMS: (M+H) 656.0.

Scheme 86

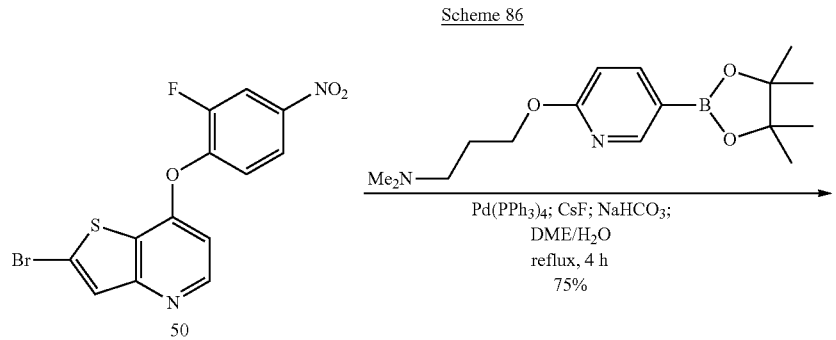

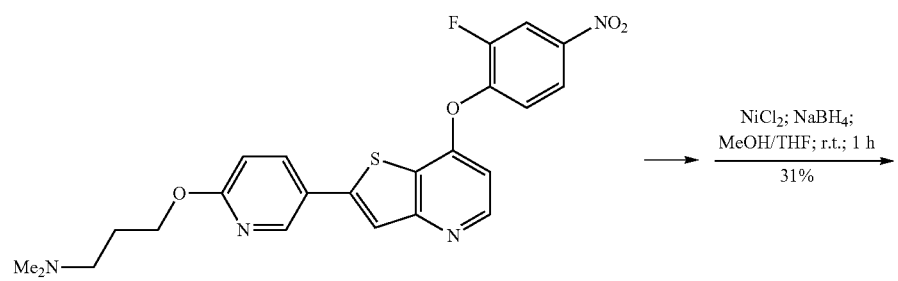

379

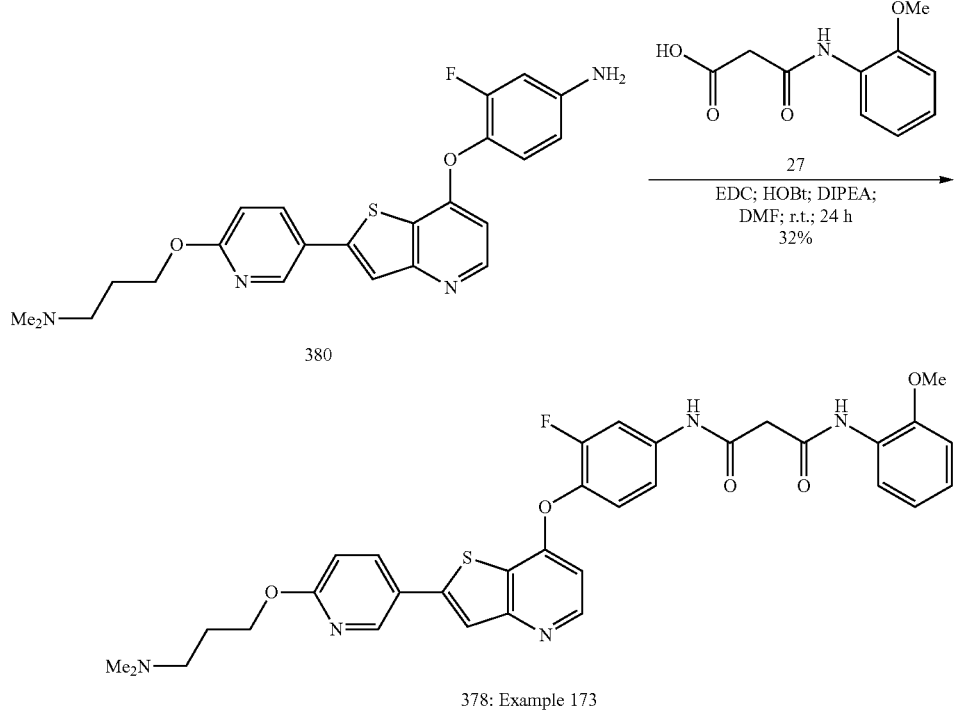

378: Example 173

Example 173

N$^1$-(4-(2-(6-(3-(Dimethylamino)propoxy)pyridin-3-yl)thieno[3,2-b]pyridin-7-yloxy)-3-fluorophenyl)-N-3-(2-methoxyphenyl)malonamide (378)

Step 1: 3-(5-(7-(2-Fluoro-4-nitrophenoxy)thieno[3,2-b]pyridin-2-yl)pyridin-2-yloxy)-N,N-dimethylpropan-1-amine (379)

Bromothienopyridine 50 (1.22 g, 3.30 mmol), N,N-dimethyl-3-(5-(4,4,5,5-tetramethyl-1,3,2-dioxaborolan-2-yl)pyridin-2-yloxy)propan-1-amine (1.15 g, 3.76 mmol), and tetrakis(triphenylphosphine)palladium (0.14 g, 0.12 mmol) were dissolved in dry DME (100 mL). Cesium fluoride (1.51 g, 10.0 mmol) and sodium bicarbonate (0.81 g, 9.6 mmol) were dissolved in water (5 ml each) and added to the reaction mixture, which was degassed with a stream of N$_2$, then heated to reflux for 4 h, cooled, and concentrated. The residue was partitioned between ethyl acetate and water. The organic phase was collected, washed with brine, dried (anhydrous MgSO$_4$), filtered, and concentrated. The resulting orange solid was triturated with ether to provide 379 (1.12 g, 75% yield). LRMS (M+H): 469.2.

Step 2: 4-(2-(6-(3-(Dimethylamino)propoxy)pyridin-3-yl)thieno[3,2-b]pyridin-7-yloxy)-3-fluorobenzenamine (380)

To thienopyridine 379 (1.11 g, 2.37 mmol) and nickel chloride hexahydrate (1.11 g, 4.68 mmol) in 9:1 MeOH/THF (50 mL) was added sodium borohydride (0.45 g, 11.9 mmol) in small portions. The resulting mixture was stirred at r.t. for 1 h, then filtered through celite and concentrated. The residue was partitioned between water and dichloromethane, the organic phase was washed with brine, dried (anhydrous MgSO$_4$), filtered, and concentrated. Flash chromatography (90:9:1 chloroform/methanol/NH$_4$OH) afforded 380 (0.32 g, 31% yield). $^1$H NMR (400 MHz, CD$_3$OD) δ (ppm): 8.43 (d, J=2.5, 1H); 8.33 (d, J=5.7, 1H); 7.93 (dd, J=8.8, 2.5, 1H); 7.59 (s, 1H); 7.00 (t, J=8.8, 1H); 6.77 (d, J=8.6, 1H); 6.57 (dd, J=12.5, 2.6, 1H); 6.53-6.49 (m, 2H); 4.29 (t, J=6.3, 2H); 2.48-2.43 (m, 2H); 2.24 (s, 6H); 1.95-1.90 (m, 2H). LRMS (M+H): 439.1.

Step 3: N$^1$-(4-(2-(6-(3-(Dimethylamino)propoxy)pyridin-3-yl)thieno[3,2-b]pyridin-7-yloxy)-3-fluorophenyl)-N$^3$-(2-methoxyphenyl)malonamide (378)

To a solution of aniline 380 (0.31 g, 0.71 mmol) and DIPEA (0.7 ml, 0.4 g, 3 mmol) in dry DMF (5 mL) was added acid 27 (0.30 g, 1.4 mmol), HOBt (0.040 g, 0.30 mmol), and EDC×HCl (0.40 g, 2.1 mmol) and the mixture was stirred at r.t. for 18 h. Additional EDC×HCl (0.050 g, 0.26 mmol) was added, and the mixture was stirred for a further 6 h. It was then partitioned between ethyl acetate and water. The organic phase was collected, washed with water, dried (anhydrous MgSO$_4$), filtered, and concentrated. Flash chromatography (chloroform/NH$_4$OH) of the residue followed by re-crystallization (90% ethyl acetate/methanol) provided 378 (0.15 g, 32% yield) as a colorless solid. $^1$H NMR (400 MHz. DMSO-d$_6$) δ (ppm): 10.58 (br s, 1H); 9.63 (br s, 1H); 8.68 (dd, J=2.7, 0.8, 1H); 8.48 (d, J=5.5, 1H); 8.20 (dd, J=8.6, 2.7, 1H); 8.05 (d, J=7.6, 1H); 8.03 (s, 1H); 7.86 (dd, J=13.1, 2.3, 1H); 7.49 (t, J=8.8, 1H); 7.42 (dd, J=8.8, 1.4, 1H); 7.09-7.03 (m, 2H); 6.94 (dd, J=8.8, 0.7, 1H); 6.92-6.88 (m, 1H); 6.61 (dd, J=5.5, 1.0, 1H); 4.33 (t, J=6.7, 2H); 3.85 (s, 3H); 3.63 (s, 2H); 2.33 (t, J=7.2, 2H); 2.13 (s, 6H); 1.84 (quint, J=7.2, 2H). LRMS (M+H): 630.2.

TABLE 18

Compounds 381-395 (examples 174-188)

| Cpd | Ex | Structure | Characterization |
|---|---|---|---|
| 381 | 174 | 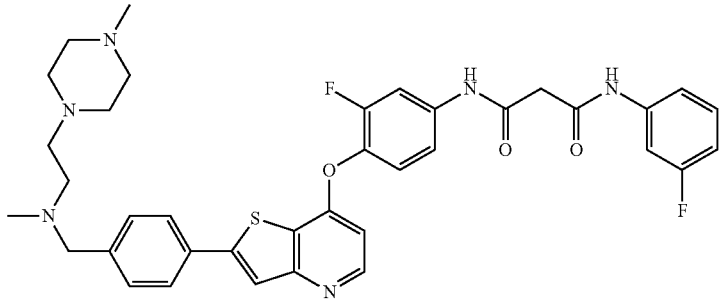<br>N1-(3-Fluoro-4-(2-(4-((methyl(2-(4-methylpiperazin-1-yl)ethyl)amino)methyl)phenyl)thieno[3,2-b]pyridin-7-yloxy)phenyl)-N3-(3-fluorophenyl)malonamide | $^1$H NMR (400 MHz, d$_6$ DMSO) δ (ppm) 10.69 (s, 1H), 10.54 (s, 1H), 8.48 (d, J = 5.48 Hz, 1H), 8.24 (s, 1H), 8.02 (s, 1H), 7.85 (m, 3H), 7.59 (m, 1H), 7.34 (m, 6H), 6.86 (m, 1H), 6.61 (d, J = 4.89 Hz, 1H), 3.52 (s, 2H), 2.43 (m, 13H), 2.14 (s, 3H), 2.12 (s, 3H). MS (m/z): 685.1 (M + H). (formate) |
| 382 | 175 | 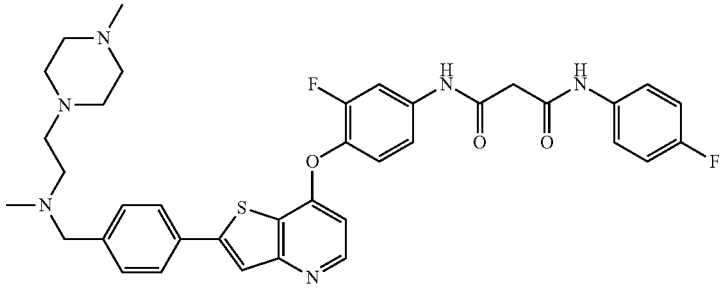<br>N1-(3-Fluoro-4-(2-(4-((methyl(2-(4-methylpiperazin-1-yl)ethyl)amino)methyl)phenyl)thieno[3,2-b]pyridin-7-yloxy)phenyl)-N3-(4-fluorophenyl)malonamide | $^1$H NMR (400 MHz, DMSO-d$_6$) δ (ppm): 10.59 (s, 1H); 10.29 (s, 2H); 8.48 (s, J = 5.5, 1H); 8.15 (s, 1H); 8.03 (s, 1H); 7.87 (dd, J = 13.1, 2.4, 1H); 7.83 (d, J = 8.4, 2H); 7.64-7.59 (m, 2H); 7.49 (t, J = 8.8, 1H); 7.44-7.40 (m, 3H); 7.17-7.12 (m, 2H); 6.61 (dd, J = 5.5, 1.0, 1H); 3.53 (s, 2H); 3.49 (s, 2H); 2.45 (br s, 4H); ~2.5-2.25 (br s, 8 H); 2.15 (s, 6H). LRMS (M + H): 685.1. |
| 383 | 176 | 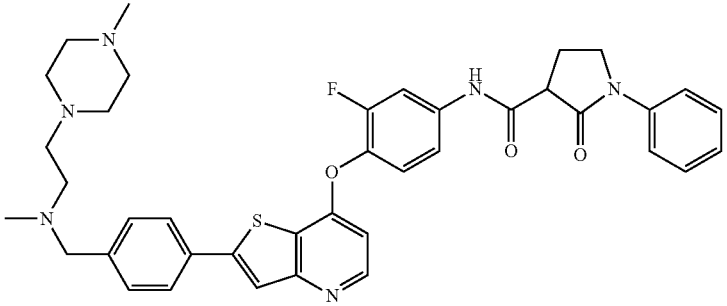<br>N-(3-Fluoro-4-(2-(4-((methyl(2-(4-methylpiperazin-1-yl)ethyl)amino)methyl)phenyl)thieno[3,2-b]pyridin-7-yloxy)phenyl)-2-oxo-1-phenylpyrrolidine-3-carboxamide | $^1$H NMR (400 MHz, DMSO-d$_6$) δ (ppm): 10.73 (s, 1H); 8.48 (d, J = 5.5, 1H); 8.20 (s, 1H); 8.02 (s, 1H); 7.93-7.89 (m, 1H); 7.83 (d, J = 8.2, 2H); 7.67-7.64 (m, 2H); 7.52-7.46 (m, 2H); 7.43-7.36 (m, 4H); 7.16 (t, J = 7.2, 1H); 6.63 (dd, J = 5.5, 0.8, 1H); 3.94-3.86 (m, 2H); 3.78 (t, J = 8.4, 1H); 3.52 (s, 2H); 2.48-2.25 (m, 14H); 2.14 (s, 3H); 2.12 (s, 3H). LCMS: (M + H) 693.1. |

TABLE 18-continued

Compounds 381-395 (examples 174-188)

| Cpd | Ex | Structure | Characterization |
|---|---|---|---|
| 384 | 177 | 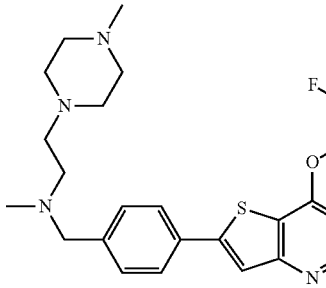<br>N1-(3-Fluoro-4-(2-(4-((methyl(2-(4-methylpiperazin-1-yl)ethyl)amino)methyl)phenyl)thieno[3,2-b]pyridin-7-yloxy)phenyl)-N3-(4-fluorophenyl)-N3-methylmalonamide | $^1$H NMR (400 MHz, DMSO-d$_6$) δ (ppm): 10.32 (s, 1H); 8.47 (d, J = 5.5, 1H); 8.22 (s, 1H); 8.02 (s, 1H); 7.83 (d, J = 8.2, 2H); 7.78 (dd, J = 13.1, 2.4, 1H); 7.46-7.40 (m, 5H); 7.30-7.25 (m, 3H); 6.60 (d, J = 5.1, 1H); 3.52 (s, 2H); 3.21 (s, 2H); 3.17 (s, 3H); 2.50-2.20 (m, 12H); 2.14 (s, 3H); 2.13 (s, 3H). LRMS (M + H): 699.2 |
| 385 | 178 | 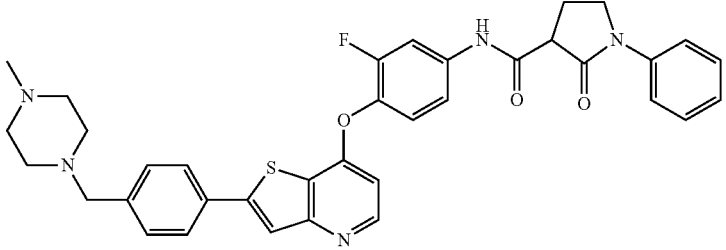<br>N-(3-Fluoro-4-(2-(4-((4-methylpiperazin-1-yl)methyl)phenyl)thieno[3,2-b]pyridin-7-yloxy)phenyl)-2-oxo-1-phenylpyrrolidine-3-carboxamide | $^1$H NMR (400 MHz, DMSO-d$_6$) δ (ppm): 10.70 (s, 1H); 8.49 (d, J = 5.3, 1H); 8.12 (s, 1H); 8.03 (s, 1H); 7.93-7.89 (m, 1H); 7.84 (d, J = 8.2, 2H); 7.68-7.65 (m, 2H); 7.52-7.48 (m, 2H); 7.43-7.37 (m, 4H); 7.18-7.14 (m, 1H); 6.63 (dd, J = 5.5, 1.0, 1H); 3.95-3.89 (m, 2H); 3.78 (t, J = 9.0, 1H); 3.52 (s, 2H); 2.52-2.34 (m, 10H?); 2.25 (s, 3H). LRMS: (M + H) 636.1. |
| 386 | 179 | 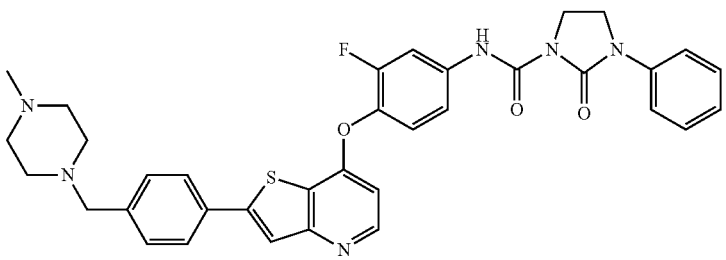<br>N-(3-Fluoro-4-(2-(4-((4-methylpiperazin-1-yl)methyl)phenyl)thieno[3,2-b]pyridin-7-yloxy)phenyl)-2-oxo-3-phenylimidazolidine-1-carboxamide | $^1$H NMR (400 MHz, DMSO-d$_6$) δ (ppm): 10.57 (s, 1H); 8.49 (d, J = 5.5, 1H); 8.02 (s, 1H); 7.87-7.82 (m, 3H); 7.62 (d, J = 7.6, 2H); 7.51-7.40 (m, 6H), 7.16 (t, J = 7.4, 1H); 6.62 (d, J = 5.5, 1H); 3.98-3.92 (m, 4H); 3.49 (s, 2H); 2.45-2.20 (m, 8H); 2.13 (s, 3H). LCMS: (M + H) 637.1. |
| 387 | 180 | 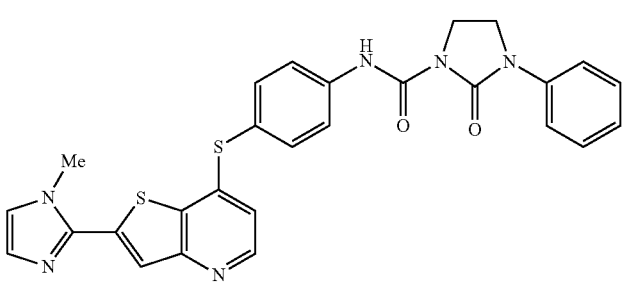<br>N-(4-(2-(1-Methyl-1H-imidazol-2-yl)thieno[3,2-b]pyridin-7-ylthio)phenyl)-2-oxo-3-phenylimidazolidine-1-carboxamide | $^1$H NMR (400 MHz, DMSO-d$_6$) δ (ppm): 10.60 (s, 1H); 8.48 (d, J = 5.1, 1H); 7.88 (s, 1H); 7.73 (d, J = 8.4, 2H); 7.63-7.60 (m, 4H); 7.44-7.40 (m, 3H); 7.17 (t, J = 6.9, 1H); 7.05 (s, 1H); 6.80 (d, J = 5.1, 1H); 3.98 (s, 3H); 3.97-3.93 (m, 4H). LRMS (M + H): 527.0. |

TABLE 18-continued

Compounds 381-395 (examples 174-188)

| Cpd | Ex | Structure | Characterization |
|---|---|---|---|
| 388 | 181 | 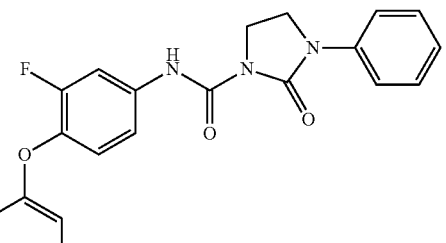<br>N-(4-(2-(1-Ethyl-1H-imidazol-2-yl)thieno[3,2-b]pyridin-7-yloxy)-3-fluorophenyl)-2-oxo-3-phenylimidazolidine-1-carboxamide | $^1$H NMR (400 MHz, DMSO-d$_6$) δ (ppm): 10.59 (s, 1H); 8.53 (d, J = 5.3, 1H); 7.85 (dd, J = 12.9, 2.1, 1H); 7.83 (s, 1H); 7.63 (d, J = 7.8, 2H); 7.52-7.40 (m, 5H); 7.17 (t, J = 7.4, 1H); 7.07 (s, 1H); 6.70 (d, J = 5.5, 1H); 4.37 (q, J = 7.2, 2H); 3.97-3.93 (m, 4H); 1.42 (t, J = 7.2, 3H). LRMS (M + H): 543.2. |
| 389 | 182 | 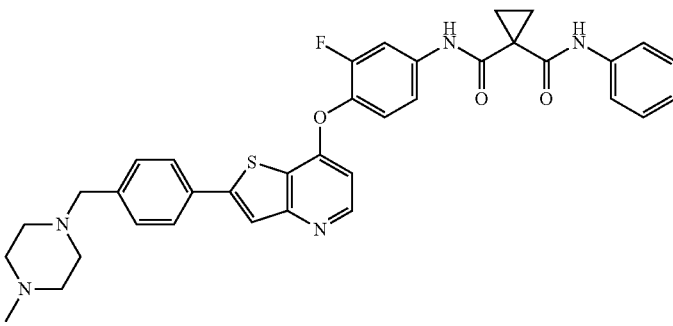<br>N-(3-Fluoro-4-(2-(4-((4-methylpiperazin-1-yl)methyl)phenyl)thieno[3,2-b]pyridin-7-yloxy)phenyl)-N-(4-fluorophenyl)cyclopropane-1,1-dicarboxamide | $^1$H NMR δ (400 MHz, CD$_3$OD): 8.42 (bs, 2H), 7.83 (dd, J = 2.3, 12.7 H, 1H), 7.79 (s, 1H), 7.76 (d, J = 3.5 Hz, 2H), 7.55 (m, 2H), 7.46 (d, J = 8.2 Hz, 2H), 7.41 (m, 1H), 7.32 (dd, J = 8.6, 8.8 Hz, 1H), 7.05 (m, 2H), 6.59 (d, J = 5.3 Hz, 1H), 3.65 (s, 2H), 3.14 (bs, 4H), 2.66-2.80 (bs, 7H), 1.63 (s, 4H) |
| 390 | 183 | 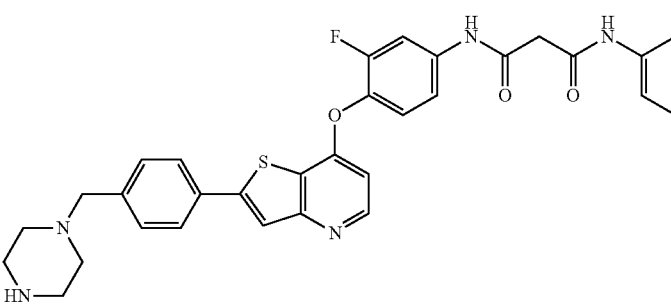<br>N1-(3-Fluoro-4-(2-(4-(piperazin-1-ylmethyl)phenyl)thieno[3,2-b]pyridin-7-yloxy)phenyl)-N3-phenylmalonamide | $^1$H NMR δ (ppm, CD$_3$OD): 10.57 (s,) H), 10.20 (s, 1 H), 8.48 (d, J = 5.5 Hz, 1H), 8.02 (s, 1H), 7.82-7.89 (m, 3H), 7.59 (dd, J = 8.6, 8.8 Hz, 2H), 7.49 (dd, J = 8.8, 9.0 Hz, 1H), 7.41-7.44 (m, 3H), 7.29-7.33 (m, 2H), 7.03-7.07 (m, 1H), 6.61-6.62 (m, 1H), 3.50 (s, 2H), 3.48 (s, 2H), 2.73 (m, 4H), 2.33 (m, 4H). |
| 391 | 184 | 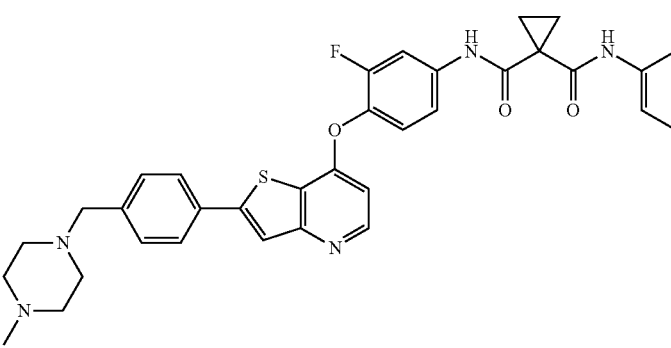<br>N-(3-Fluoro-4-(2-(4-((4-methylpiperazin-1-yl)methyl)phenyl)thieno[3,2-b]pyridin-7-yloxy)phenyl)-N-phenylcyclopropane-1,1-dicarboxamide | $^1$H NMR δ (400 MHz, CD$_3$OD): 10.37 (s, 1H), 9.98 (s, 1H), 8.49 (d, J = 5.5 Hz, 1H), 8.01 (s, 1H), 7.89 (dd, J = 2.2, 13.2 Hz, 1H), 7.82 (d, J = 8.2 Hz, 2H), 7.60-7.62 (m, 2H), 7.43-7.52 (m, 2H), 7.41 (d, J = 8.2 Hz, 2H), 7.21-7.32 (m, 2H), 7.03-7.07 (m, 1H), 6.58-6.60 (m, 1H), 3.48 (s, 2H), 2.22-2.42 (bs, 6H), 2.13 (s, 3H), 1.46 (2 s, 4H). |

TABLE 18-continued

Compounds 381-395 (examples 174-188)

| Cpd | Ex | Structure | Characterization |
|---|---|---|---|
| 392 | 185 | N1-(3-Fluoro-4-(6-(4-((4-methylpiperazin-1-yl)methyl)phenyl)thieno[3,2-d]pyrimidin-4-yloxy)phenyl)-N3-phenylmalonamide | $^1$H NMR δ (400 MHz, CD3OD): 8.59 (s, 1H), ), 8.45 (bs, 1H), ): 7.80-7.87 (m, 4H), 7.58-7.61 (m, 2H), 7.51 (bd, J = 8.2 Hz, 2H), 7.30-7.41 (m, 4H), 7.10-7.14 (m, 1H), 1.68 (s, 2H), 3.16 (bs, 4H), 2.66-2.80 (bs , 7H). |
| 393 | 186 | 4-(4-(7-(2-Fluoro-4-(2-oxo-3-phenylimidazolidine-1-carboxamido)phenoxy)thieno[3,2-b]pyridin-2-yl)benzyl)-N-methylpiperazine-1-carboxamide | $^1$H NMR δ (400 MHz, DMSO-d6): 10.53 (s, 1H), 8.43 (d, J = 5.5 Hz, 1H), 7.98 (s, 1H), 7.77-7.84 (m, 3H), 7.57 (d, J = 8.6 Hz, 2H), 7.34-7.48 (m, 6H), 7.12 (dd, J = 7.2, 7.4 Hz, 1 ), 6.58 (d, J = 5.3 Hz, 1H), 6.36 (m, 1H), 3.85-3.96 (m, 4H), 3.47 (s, 2H), 3.21 (bs, 4H), 2.48 (d, J = 4.3 Hz, 3H), 2.27 (bs, 4H). |
| 394 | 187 | N-(3-Fluoro-4-(2-(4-(piperazin-1-ylmethyl)phenyl)thieno[3,2-b]pyridin-7-yloxy)phenyl)-2-oxo-3-phenylimidazolidine-1-carboxamide | $^1$H NMR δ (400 MHz, DMSO-d6): 10.58 (s, 1H), 8.51 (d, J = 5.5 Hz, 1H), 8.03 (s, 1H), 7.83-7.88 (m, 3H), 7.13 (d, J = 8.2 Hz, 2H), 7.41-7.52 (m, 6H), 7.17 (dd, J = 7.2, 7.4 Hz, 1H), 6.64 (d, J = 5.5 Hz, 1H), 3.90-4.02 (m, 4H), 3.47 (s, 2H), 2.68 (m, 4H), 2.30 (bs, 4H). |

TABLE 18-continued

Compounds 381-395 (examples 174-188)

| Cpd | Ex | Structure | Characterization |
|---|---|---|---|
| 395 | 188 | (S)-N-(4-(2-(3-(Dimethylamino)pyrrolidine-1-carbonyl)thieno[3,2-b]pyridin-7-yloxy)-3-fluorophenyl)-2-oxo-3-phenylimidazolidine-1-carboxamide | $^1$H NMR δ (400 MHz, DMSO-d6): 10.60 (s, 1H), 8.58 (dd, J = 1.8, 5.5 Hz, 1H), 8.09. 8.03 (2 s, 1H), 7.85 (dd, J = 2.3, 13.0 Hz, 1H), 7.62 (m, 2H), 7.45 (m, 4H), 7.16 (m, 1H), 6.76 (d, J 5.5 Hz, 1H), 3.40-4.10 (m, 6H), 3.20-3.40 (a signal corresponding to 2H is hidden by a residual signal of water), 2.55 (m, 1H), 2.00-2.40 (m, 7H), 1.53-1.58 (m, 1H). |
| 395a | 188a | Ethyl 2-(2-(7-(2-fluoro-4-(3-oxo-3-(phenylamino)propanamido)phenoxy)thieno[3,2-b]pyridin-2-yl)oxazol-4-yl)acetate MG 89174 | $^1$H NMR (400 MHz, MeOH-d4) δ (ppm): 8.44 (d, 1H, J = 5.5 Hz), 7.79 (dd, 1H, J = 2.2 Hz, J = 12.2 Hz), 7.53 (d, 2H, J = 8.6 Hz), 7.45 (m, 1H), 7.2-7.4 (m, 4H), 7.14 (s, 1H), 7.09 (t, 1H, J = 7.4 Hz), 4.21 (q, 2H, J = 7.0 Hz), 3.86 (s, 2H), 3.49 (s, 2H), 1.28 (t, 3H, J = 7.0 Hz). MS (m/z): (M + 1) 575.0 (100%) |

Scheme 87

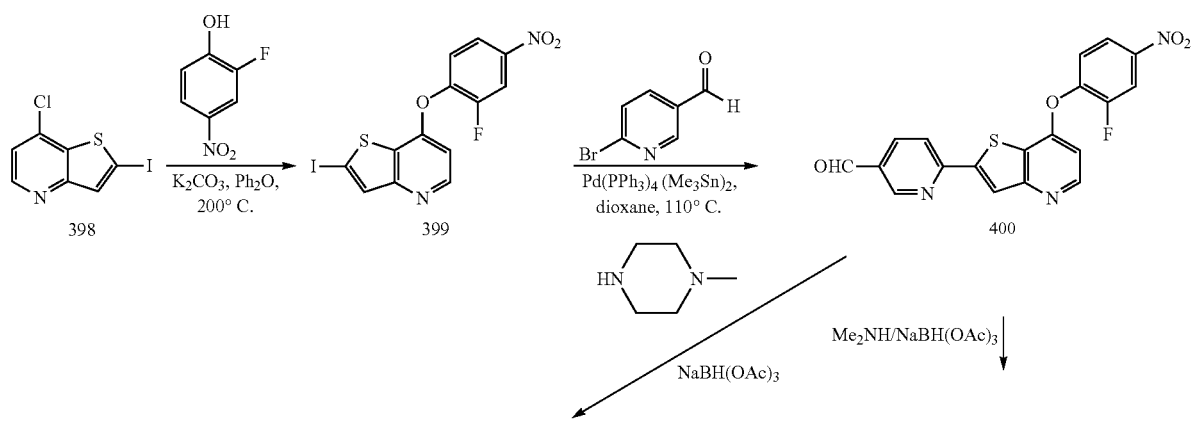

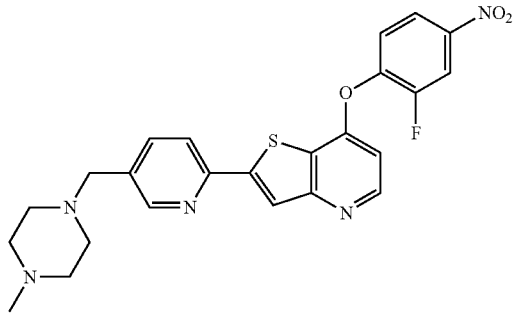

401

Fe, NH₃Cl ↓

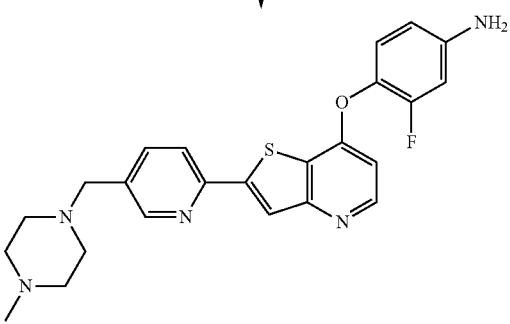

396

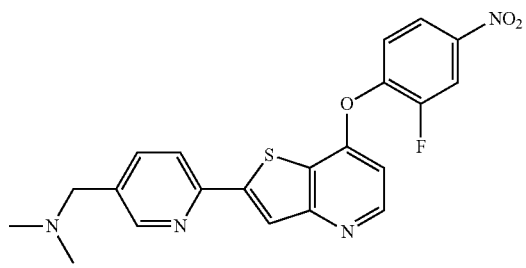

402

Fe, NH₄Cl ↓

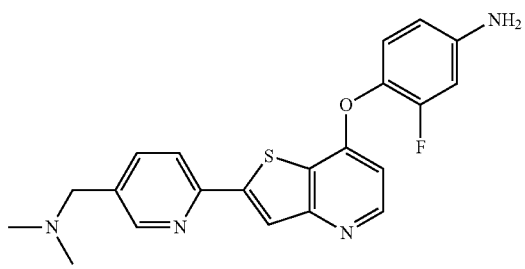

397

3-Fluoro-4-(2-(5-((4-methylpiperazin-1-yl)methyl)pyridin-2-yl)thieno[3,2-b]pyridin-7-yloxy)aniline (396) and 4-(2-(5-((Dimethylamino)methyl)pyridin-2-yl)thieno[3,2-b]pyridin-7-yloxy)-3-fluoroaniline (397)

Step 1: 7-(2-Fluoro-4-nitrophenoxy)-2-iodothieno[3,2-b]pyridine (399)

A mixture of the chloride 398 (Ragan J. A. et al, Organic Process Research and Development 2003, 7, 676-683) (7.0 g, 23.7 mmol), 2-fluoro-4-nitrophenol (11.15 g, 3 eq, 71.1 mmol), K₂CO₃ (13.08 g, 4 eq, 94.8 mmol) in Ph₂O (30 ml) was heated to 200° C. for 3 h. The reaction mixture was cooled to room temperature and diluted with DCM, filtered and concentrated. The resulting solid was triturated with diethyl ether, to afford 399 (7.3 g, 74% yield), which was used directly in the next step with no additional purification. MS (m/z): 417.0 (M+H).

Step 2: 6-(7-(2-Fluoro-4-nitrophenoxy)thieno[3,2-b]pyridin-2-yl)nicotinaldehyde (400)

A solution of 399 (1 g, 2.40 mmol) and 6-bromonicotinaldehyde (450 mg, 2.40 mmol) in 1,4-dioxane (10 mL) was treated sequentially with bis-trimethyl tin (500 µA, 787 mg, 2.40 mmol) and Pd(PPh₃)₄ (270 mg, 0.24 mmol). The reaction mixture was then heated to reflux under nitrogen overnight, cooled, and concentrated. The crude product was purified by flash chromatography using the gradient 5%-10% MeOH in DCM and subsequent trituration by MeOH, providing pure 400 (494 mg, 52% yield). ¹H NMR (400 MHz, DMSO-d₆) δ (ppm): 10.11 (s, 1H), 9.10 (m, 1H), 8.65 (d, 1H, J=5.2 Hz), 8.62 (s, 1H), 8.51 (d, 1H, J=8.8 Hz), 8.48 (dd, 1H, J=2.8 Hz, J=10.4 Hz), 8.38 (dd, 1H, J=2.1 Hz, J=8.2 Hz), 8.20 (m, 1H), 7.73 (t, 1H, J=9.0 Hz), 7.01 (d, 1H, J=5.5 Hz). MS (m/z): (M+1) 395.9.

Step 3: 7-(2-Fluoro-4-nitrophenoxy)-2-(5-((4-methylpiperazin-1-yl)methyl)pyridin-2-yl)thieno[3,2-b]pyridine (401)

A mixture of 400 (451 mg, 1.14 mmol) and 1-methylpiperazine (152 µL, 137 mg, 1.37 mmol) in DCM (7 mL) was stirred at room temperature for 10 min. It was then treated with NaBH(OAc)₃ (340 mg, 1.60 mmol) and stirred at room temperature overnight. The reaction mixture was diluted with DCM (20 mL) and washed with saturated NaHCO₃ solution (20 mL) The organic phase was collected, dried over anhydrous Na₂SO₄, filtered and concentrated. The residue was purified by flash chromatography using the gradient 30-50% MeOH (with 2% Et₃N) in EtOAc to afford 401 (308 mg, 52% yield). MS (m/z): (M+1) 480.0 (100%).

Step 3: 3-Fluoro-4-(2-(5-((4-methylpiperazin-1-yl)methyl)pyridin-2-yl)thieno[3,2-b]pyridin-7-yloxy)aniline (396)

To a solution of 401 (306 mg, 0.64 mmol) and NH₄Cl (30 mg, 0.54 mmol) in 2:1 EtOH/water (10.5 mL) was added iron powder (304 mg, 5.43 mmol) and the suspension was heated to reflux for 1 hour. The reaction mixture was filtered through celite and concentrated to provide title compound 396, that was used without further purification (343 mg, 100% yield). MS (m/z): (M+1) 450.0 (100%).

Step 4: 1-(6-(7-(2-Fluoro-4-nitrophenoxy)thieno[3,2-b]pyridin-2-yl)pyridin-3-yl)-N,N-dimethylmethanamine (402)

A mixture of 400 (360 mg, 0.91 mmol) and dimethylamine (2M THF solution, 550 µL, 1.09 mmol) in DCM (10 mL) was stirred at room temperature for 10 min. It was then treated with NaBH(OAc)₃ (270 mg, 1.27 mmol) and stirred at room temperature overnight. The reaction mixture was diluted with DCM (30 mL) and washed with saturated NaHCO₃ solution (30 mL), dried over anhydrous Na₂SO₄, filtered and concentrated. The residue was purified by flash chromatography using the gradient 10-30% MeOH in DCM as an eluent, to provide title compound 402 (321 mg, 83% yield). MS (m/z): (M+1) 425.1 (100%).

Step 5: 4-(2-(5-((Dimethylamino)methyl)pyridin-2-yl)thieno[3,2-b]pyridin-7-yloxy)-3-fluoroaniline (397)

To a solution of 402 (308 mg, 0.72 mmol) and NH₄Cl (33 mg, 061 mmol) in 2:1 EtOH/water (9 mL) was added iron powder (345 mg, 6.17 mmol) and the suspension was heated to reflux for 1 hour. The reaction mixture was filtered through celite and concentrated to provide title compound 397 (350 mg, quantitative yield), that was used without further purification. MS (m/z): (M+1) 395.1 (100%).

Scheme 88

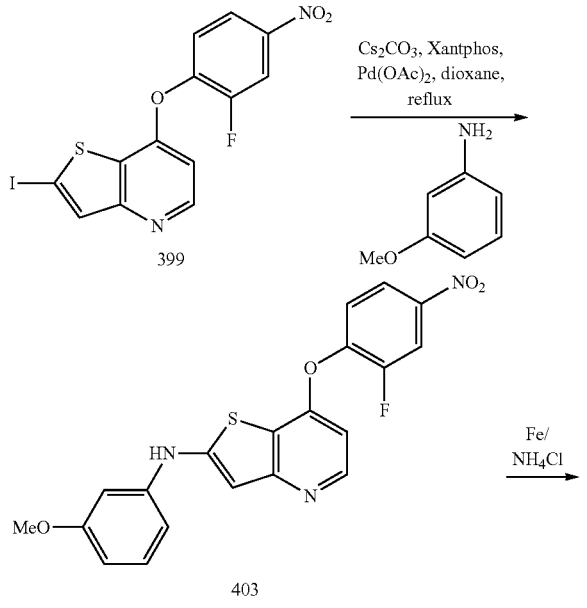

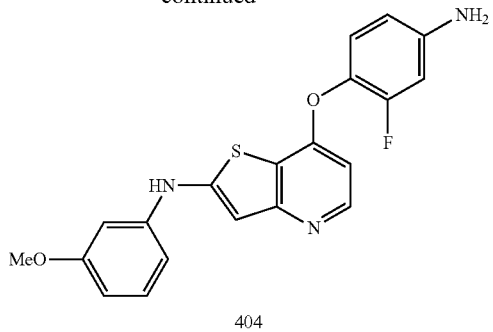

7-(4-Amino-2-fluorophenoxy)-N-(3-methoxyphenyl)thieno[3,2-b]pyridin-2-amine (404)

Step 1: 7-(2-Fluoro-4-nitrophenoxy)-N-(3-methoxyphenyl)thieno[3,2-b]pyridin-2-amine (403)

A solution of 399 (scheme 87) (700 mg, 1.68 mmol), Cs₂CO₃ (1.12 g, 3.43 mmol), 3-methoxyaniline (190 μL, 206 mg, 1.68 mmol), Pd(OAc)₂ (70 mg, 0.17 mmol) and Xantphos (1.43 g, 2.52 mmol) (*J. Org. Chem.*, 1999, 64, 6019-6022) in dioxane (15 mL) was heated to reflux for 5 hrs. The reaction mixture was cooled, concentrated and the residue was purified by flash chromatography using 80% EtOAc in hexanes as the eluent, to afford 403 (408 mg, 59% yield). MS (m/z): (M+1) 412.0 (100%).

Step 2: 7-(4-Amino-2-fluorophenoxy)-N-(3-methoxyphenyl)thieno[3,2-b]pyridin-2-amine (404)

To a solution of 403 (408 mg, 0.99 mmol) and NH₄Cl (45 mg, 084 mmol) in 2:1 EtOH/water (15 mL) was added iron powder (472 mg, 8.43 mmol) and the suspension was heated to reflux for 1 hour. The reaction mixture was filtered through celite and concentrated to provide 404 (278 mg, 74% yield), that was used without further purification. MS (m/z): (M+1) 382.0 (100%).

TABLE 19

Compounds 405-410 (examples 189-192) prepared from the amines 396, 397 and 404

| Cpd | Ex | Structure | Characterization |
|---|---|---|---|
| 405 | 189 | N-(3-Fluoro-4-(2-(5-((4-methylpiperazin-1-yl)methyl)pyridin-2-yl)thieno[3,2-b]pyridin-7-yloxy)phenyl)-2-oxo-1-phenylpyrrolidine-3-carboxamide | ¹H NMR δ (400 MHz, DMSO-d6): 10.72 (s, 1H), 8.52 (br.s., 1H), 8.50 (d, 1H, J = 5.5 Hz), 8.32 (s, 1H), 8.23 (d, 1H, J = 8.3 Hz), 7.92 (d, 1H, J = 11.6 Hz), 7.83 (dd, 1H, J = 2.0 Hz, J = 8.0 Hz), 7.65 (d, 1H, J = 7.6 Hz), 7.50 (m, 2H), 7.39 (t, 2H, J = 7.4 Hz), 7.16 (t, 1H, J = 7.4 Hz), 6.68 (d, 1H, J = 5.0 Hz), 3.91 (m, 2H), 3.77 (t, 1H, J = 8.4 Hz), 3.52 (s, 2H), 2.2-2.5 (m, 10H), 3.12 (s, 3H) MS (m/z): (M + 1) 637.1 (100%). |

TABLE 19-continued

Compounds 405-410 (examples 189-192) prepared from the amines 396, 397 and 404

| Cpd | Ex | Structure | Characterization |
|---|---|---|---|
| 406 | 190 | 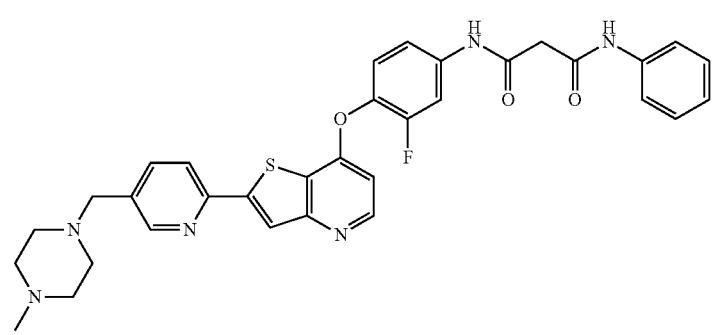<br>N1-(3-Fluoro-4-(2-(5-((4-methylpiperazin-1-yl)methyl)pyridin-2-yl)thieno[3,2-b]pyridin-7-yloxy)phenyl)-N3-phenylmalonamide | $^1$H NMR δ (400 MHz, CD3OD): 8.51 (d, 1H, J = 1.6 Hz), 8.39 (d, 1H, J = 5.5 Hz), 7.95 (s, 1H), 7.91 (d, 1H, J = 8.3 Hz), 7.8 (m, 2H), 7.55 (d, 2H, J = 8.6 Hz), 7.2-7.4 (m, 4H), 7.09 (t, 1H, J = 7.5 Hz), 6.51 (d, 1H, J = 5.5 Hz), 3.56 (s, 2H), 2.3-2.7 (m, 8H), 2.27 (s, 3H). MS (m/z): (M + 1) 611.1 (100%). |
| 407 | 191 | 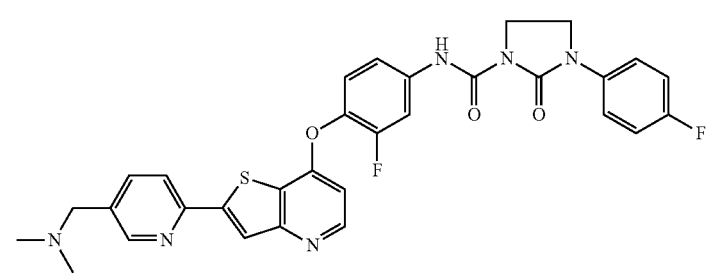<br>N-(4-(2-(5-((Dimethylamino)methyl)pyridin-2-yl)thieno[3,2-b]pyridin-7-yloxy)-3-fluorophenyl)-3-(4-fluorophenyl)-2-oxoimidazolidine-1-carboxamide | $^1$H NMR δ (400 MHz, DMSO-d6): 10.55 (s, 1H), 8.53 (m, 2H), 8.33 (s, 1H), 8.24 (d, 1H, J = 8.2 Hz), 7.84 (d, 2H, J = 8.5 Hz), 7.65 (m, 2H), 7.46 (m, 2H), 7.28 (t, 2H, J = 8.7 Hz), 6.69 (d, 1H. J = 5.5 Hz), 3.95 (s, 2H), [3.4 (4H)], 2.17 (s, 6H) MS (m/z): (M + 1) 601.3 (100%) |
| 408 | 192 | 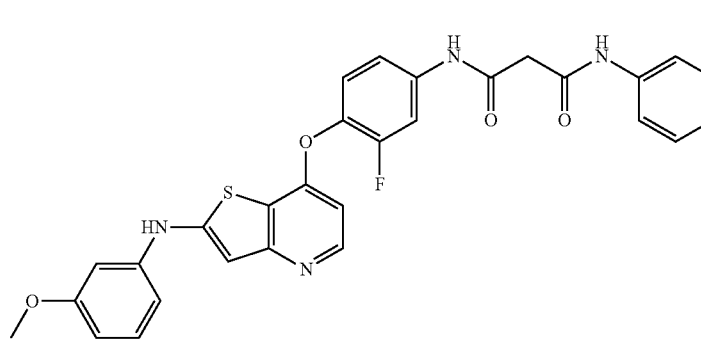<br>N1-(3-Fluoro-4-(2-(3-methoxyphenylamino)thieno[3,2-b]pyridin-7-yloxy)phenyl)-N3-phenylmalonamide | $^1$H NMR δ (400 MHz, MeOH-d4): 8.15 (br.s, 2H), 7.79 (dd, 1H, J = 2.4 Hz, J = 12.3 Hz), 7.55 (d, 2H, J = 8.8 Hz), 7.2-7.4 (m, 5H), 7.09 (t, 1H, J = 7.4 Hz), 6.85 (m, 2H), 6.74 (s, 1H), 6.58 (dd, 1H, J = 2.4 Hz, J = 8.3 Hz), 6.39 (d, 1H, J = 5.7 Hz), 3.79 (s, 3H), 3.53 (s, 2H). MS (m/z): (M + 1) 543.0 (100%). |

Scheme 89

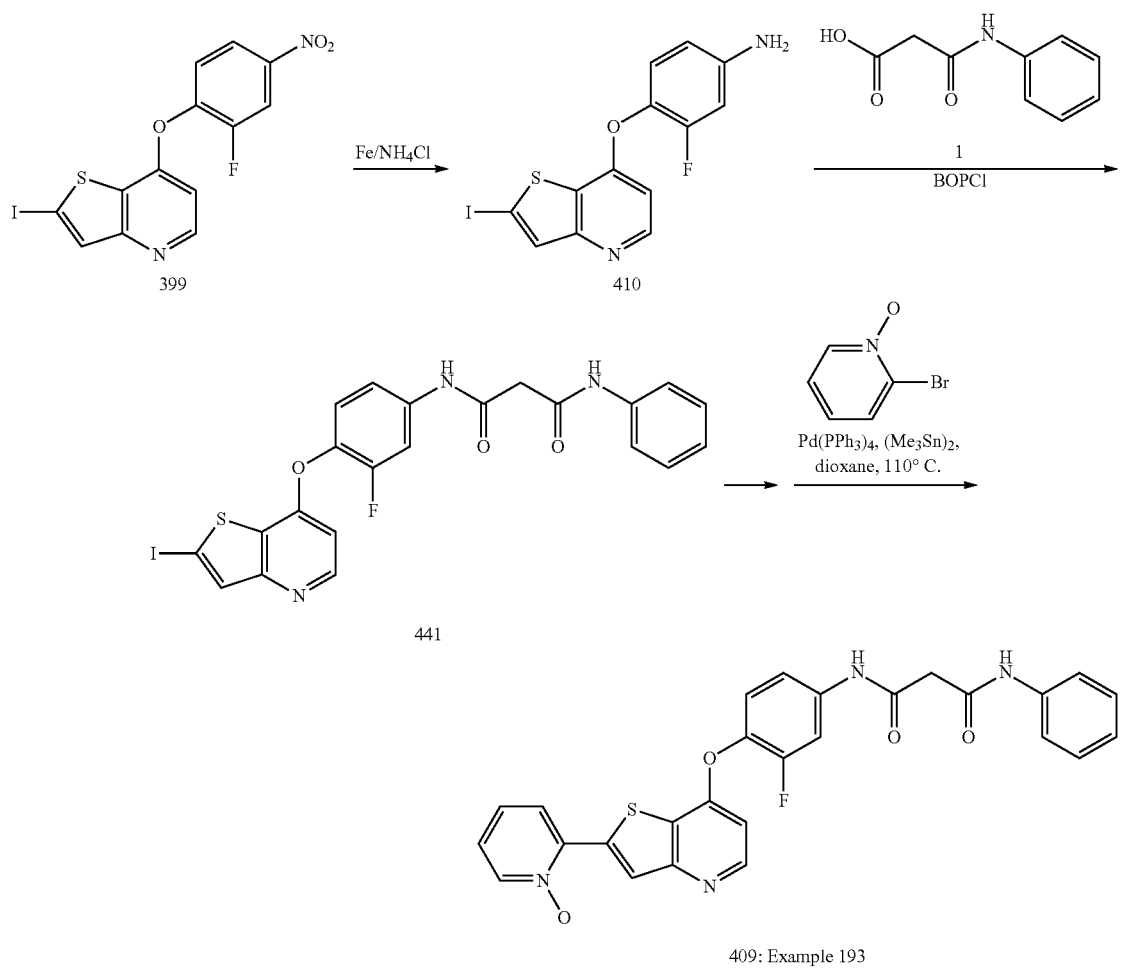

409: Example 193

Example 193

2-(7-(2-Fluoro-4-(3-oxo-3-(phenylamino)propana-mido)phenoxy)thieno[3,2-b]pyridin-2-yl)pyridine 1-oxide (409)

Steps 1: 3-Fluoro-4-(2-iodothieno[3,2-b]pyridin-7-yloxy)aniline (410)

To a solution of 399 (2 g, 4.81 mmol) and $NH_4Cl$ (220 mg, 4.08 mmol) in 2:1 EtOH/water (75 mL) was added iron powder (2.28 g, 40.8 mmol) and the suspension was heated to reflux for 1 hour. The reaction mixture was filtered through celite and concentrated to afford 410 (1.85 g, 100% yield), that was used without further purification MS. (m/z): (M+1) 386.8 (100%).

Steps 2: $N^1$-(3-Fluoro-4-(2-iodothieno[3,2-b]pyridin-7-yloxy)phenyl)-$N^3$-phenylmalonamide (411)

A solution of the acid 1 (465 mg, 2.59 mmol) and BOPCl (666 mg, 2.59 mmol) was mixed in DCM (5 mL) at 0° C. and stirred at the same temperature for 15 min. The reaction mixture was then treated with a solution of 410 (500 mg, 1.29 mmol) and $iPr_2NEt$ (1.3 mL, 1 g, 7.79 mmol) in DCM (5 mL) at 0° C. and allowed to stir at room temperature for overnight. The mixture was diluted in DCM (30 mL), washed with saturated $NaHCO_3$ solution (30 mL), dried over anhydrous $Na_2SO_4$, filtered and concentrated. The residue was purified by flash chromatography using the gradient 75-100% EtOAc in hexanes as an eluent, to provide 411 (382 mg, 54% yield). $^1H$ NMR δ (400 MHz, $CD_3OD$): 8.33 (d, 5.7 Hz), 7.79 (dd, 1H, J=2.4 Hz, J=12.3 Hz), 7.54 (m, 5H), 7.2-7.4 (m, 4H), 7.09 (t, 1H, J=7.2 Hz), 6.50 (d, 1H, J=5.5 Hz), 3.51 (s, 2H), 7.75 (s, 1H). MS (m/z): (M+1) 547.9 (100%).

Steps 3: 2-(7-(2-Fluoro-4-(3-oxo-3-(phenylamino) propanamido)phenoxy)thieno[3,2-b]pyridin-2-yl) pyridine 1-oxide (409)

A solution of 411 (45 mg, 0.08 mmol), 4-bromopyridine N-oxide (250 mg, 1.43 mmol), bistrimethyltin (26 μL, 40 mg, 0.12 mmol) and $Pd(PPh_3)_4$ (10 mg, 0.01 mmol) in dioxane (1 mL) was heated to reflux for 4 hrs. The reaction mixture was cooled, concentrated and the residue was purified by flash chromatography using the gradient 5-10% MeOH in DCM as an eluent, to afford 409 (11 mg, 27% yield). $^1H$ NMR δ (400 MHz, $CD_3OD$): 8.71 (d, 1H, J=5.4 Hz), 8.6 (m, 3H), 8.04 (dd, 1H, J=2.5 Hz, J=12.3 Hz), 7.85 (t, 1H, J=8.4 Hz), 7.78 (m, 2H), 7.65 (m, 1H), 7.62 (m, 1H), 7.53 (m, 3H), 7.32 (t, 1H, J=7.4 Hz), 6.81 (d, 1H, J=5.5 Hz), 3.75 (s, 2H). MS (m/z): (M+1) 515.0 (100%).

Scheme 90
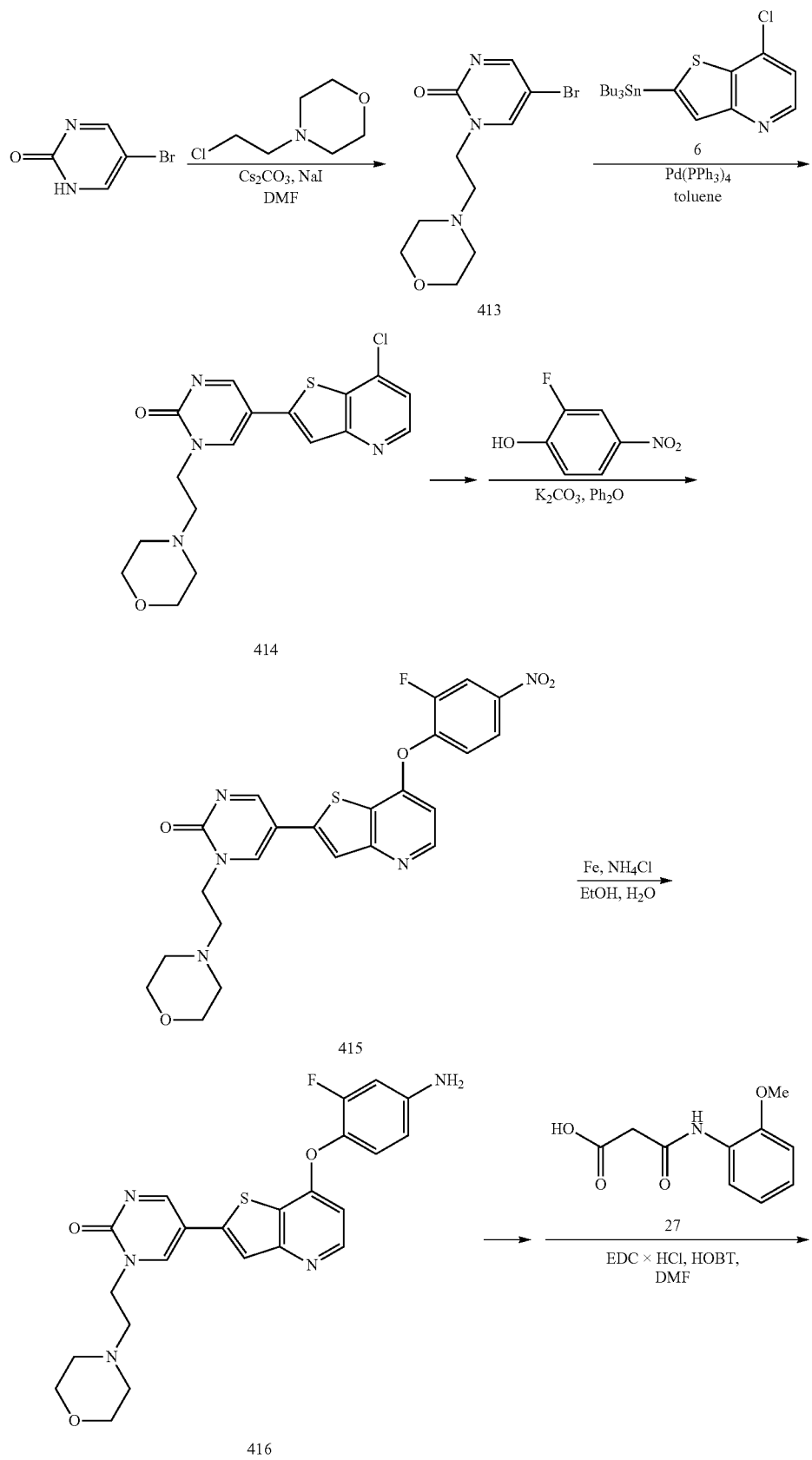

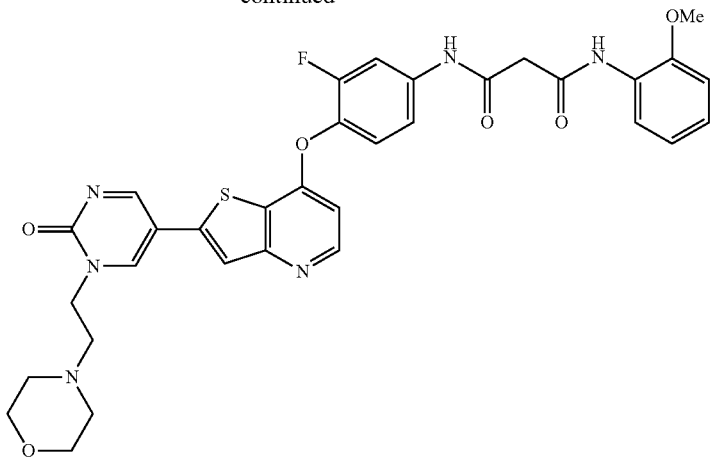

412: Example 194

Example 194

N$^1$-(3-Fluoro-4-(2-(1-(2-morpholinoethyl)-2-oxo-1, 2-dihydropyrimidin-5-yl)thieno[3,2-b]pyridin-7-yloxy)phenyl)-N$^3$-(2-methoxyphenyl)malonamide (412)

Step 1. 5-Bromo-1-(2-morpholinoethyl)pyrimidin-2 (1H)-one (413)

To a solution of 5-bromo-2-hydroxypyrimidine (1.00 g, 5.75 mmol) in DMF (19 mL) was added sodium iodide (1.29 g, 8.6 mmol), cesium carbonate (4.68 g, 14.4 mmol), 4-(2-chloroethyl)morpholine hydrochloride (1.18 g, 6.32 mmol) and the reaction mixture was stirred at 60° C. for 2.5 h. The solution was filtered, and the filtrate was concentrated. The residue was purified by flash chromatography, eluting with gradient of methanol (5-15%) in dichloromethane to give title compound 413 (1.29 g, 78% yield). MS (m/z): 288.1 (50%) (M+H), 290.0 (50%) (M+H). $^1$H NMR (DMSO-d$_6$) δ (ppm): 8.61 (d, J=3.3 Hz, 1H), 8.46 (d, J=3.3 Hz, 1H), 3.93 (t, J=5.9 Hz, 2H), 3.51 (t, J=4.5 Hz, 4H), 2.57 (t, J=6.1 Hz, 2H), 2.45-2.39 (m, 4H).

Step 2: 5-(7-Chlorothieno[3,2-b]pyridin-2-yl)-1-(2-morpholinoethyl)pyrimidin-2(1H)-one (414)

To a solution of the tributyltin derivative 6 (1.88 g, 4.1 mmol) (scheme 2) in toluene (39 mL) was added 5-bromo-1-(2-morpholinoethyl)pyrimidin-2(1H)-one (413, 1.29 g, 4.5 mmol) and Pd(PPh$_3$)$_4$ (474 mg, 0.41 mmol). The reaction mixture was stirred at 100° C. for 16 h. The mixture was filtered and the solvent was evaporated. The residue was triturated in hexanes, then triturated in EtOAc to produce title compound 414 (236 mg, 15% yield). MS (m/z): 377.0 (M+H). $^1$H NMR (DMSO-d$_6$) δ (ppm): 9.18 (d, J=3.5 Hz, 1H), 8.76 (d, J=3.3 Hz, 1H), 8.64 (d, J=5.1 Hz, 1H), 8.05 (s, 1H), 7.57 (d, J=5.1 Hz, 1H), 4.06 (t, J=5.9 Hz, 2H), 3.54 (t, J=4.5 Hz, 4H), 2.64 (t, J=5.9 Hz, 2H), 2.49-2.43 (m, 4H).

Step 3: 5-(7-(2-Fluoro-4-nitrophenoxy)thieno[3,2-b] pyridin-2-yl)-1-(2-morpholinoethyl)pyrimidin-2 (1H)-one (415)

To a solution of the pyridone 414 (236 mg, 0.63 mmol) in Ph$_2$O (1.3 mL) was added 2-fluoro-4-nitrophenol (197 mg, 1.26 mmol) and K$_2$CO$_3$ (173 mg, 1.26 mmol). The mixture was stirred at 100° C. for 1 h, then at 180° C. for 2 h, cooled and evaporated under reduced pressure. The residue was purified by flash chromatography with a gradient of methanol (2-10%) in dichloromethane to give title compound 415 (81 mg, 26% yield). MS (m/z): 498.0 (M+H). $^1$H NMR (DMSO-d$_6$) δ (ppm): 9.16 (d, J=3.3 Hz, 1H), 8.66 (d, J=3.3 Hz, 1H), 8.60 (d, J=5.3 Hz, 1H), 8.47 (dd, J=10, 2.5 Hz, 1H), 8.19 (d, J=8.8 Hz, 1H), 8.02 (s, 1H), 7.69 (t, J=8.6 Hz, 1H), 6.98 (d, J=5.3 Hz, 1H), 4.02 (t, J=5.5 Hz, 2H), 3.58-3.43 (m, 4H), 2.59 (t, J=5.5 Hz, 2H), 2.50-2.41 (m, 4H).

Step 4: 5-(7-(4-Amino-2-fluorophenoxy)thieno[3,2-b]pyridin-2-yl)-1-(2-morpholinoethyl)pyrimidin-2 (1H)-one (416)

To a solution the compound 415 (81 mg, 0.16 mmol) in ethanol (1 mL) and water (0.5 mL) was added NH$_4$Cl (9 mg, 0.16 mmol) and iron powder (73 mg, 1.30 mmol). The mixture was stirred at 80° C. for 45 min, filtered through celite, and the solvent was evaporated to give title compound (416). MS (m/z): 468.1 (M+H).

Step 5: N$^1$-(3-Fluoro-4-(2-(1-(2-morpholinoethyl)-2-oxo-1,2-dihydropyrimidin-5-yl)thieno[3,2-b]pyridin-7-yloxy)phenyl)-N$^3$-(2-methoxyphenyl)malonamide (412)

To a solution of the amine 416 (0.16 mmol) in DMF (1 mL) was added acid 27 (38 mg, 0.18 mmol), HOBT (24 mg, 0.18 mmol) and EDC×HCl (46 mg, 0.24 mmol). The mixture was stirred at room temperature for 16 h. The solvent was evaporated, then the residue was purified by flash chromatography with gradient of methanol (0-5%) in dichloromethane, followed by preparative HPLC purification with gradient of methanol (20-100%) in water to give title compound 412 (14 mg, 13% yield). MS (m/z): 659.1 (M+H). $^1$H NMR (DMSO-d$_6$) δ (ppm): 10.59 (s, 1H), 9.64 (s, 1H), 9.16 (d, J=3.3 Hz, 1H), 8.69 (d, J=3.3 Hz, 1H), 8.51 (d, J=5.5 Hz, 1H), 8.07 (d, J=7.4 Hz, 1H), 7.98 (s, 1H), 7.88 (dd, J=13.2.3 Hz, 1H), 7.51 (t, J=9.0 Hz, 1H), 7.43 (dd, J=8.8, 1.6 Hz, 1H), 7.11-7.05 (m, 2H), 6.94-6.90 (m, 1H), 6.67 (d, J=4.7 Hz, 1H), 4.05 (t, J=6.5 Hz, 2H), 3.86 (s, 3H), 3.64 (s, 2H), 3.55-3.50 (m, 4H), 2.63 (t, J=5.5 Hz, 2H), 2.46-2.42 (m, 4H).

Scheme 91
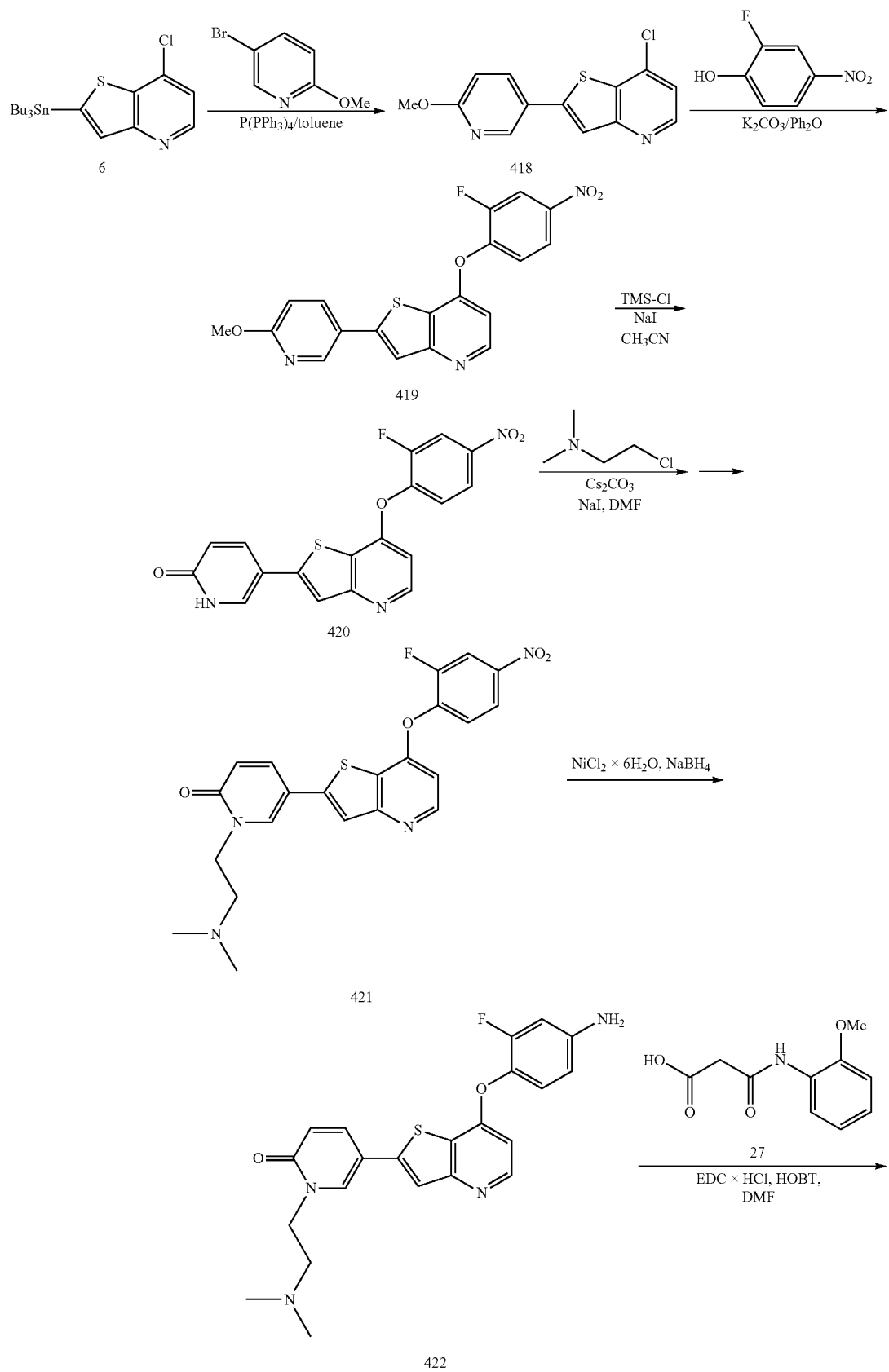

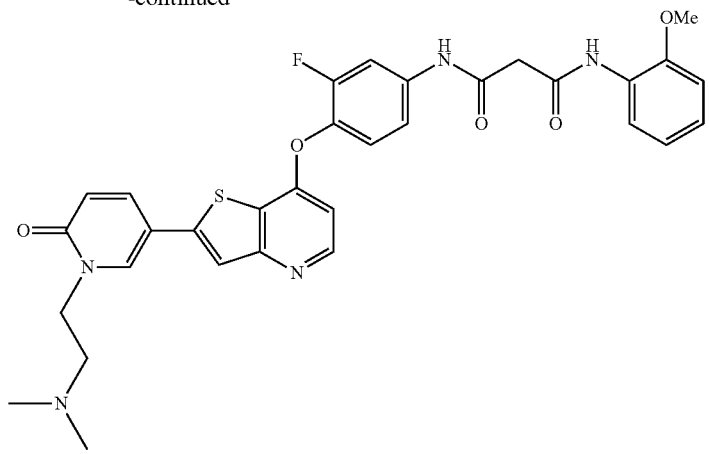

417: Example 195

Example 195

$N^1$-(4-(2-(1-(2-(Dimethylamino)ethyl)-6-oxo-1,6-dihydropyridin-3-yl)thieno[3,2-b]pyridin-7-yloxy)-3-fluorophenyl)-$N^3$-(2-methoxyphenyl)malonamide (417)

Step 1. 7-Chloro-2-(6-methoxypyridin-3-yl)thieno[3,2-b]pyridine (418)

To a solution of tributyltin derivative 6 (2.00 g, 4.36 mmol) (scheme 91) in toluene (10 mL) was added Ph(PPh$_3$)$_4$ (0.503 g, 0.436 mmol) followed by 5-bromo-2-methoxypyridine (0.62 mL, 4.8 mmol). Nitrogen gas was bubbled directly into the reaction mixture for 30 minutes before it was heated to reflux for 16 h. The reaction mixture was then cooled to room temperature and the yellow precipitate was collected by filtration and washed with hexanes. The material was then further purified by flash chromatography (eluent 20 to 50% ethyl acetate in hexanes) to afford the titled compound 418 as a fluffy white solid (0.752 g, 62% yield). MS (m/z): 277.0 (M+H).

Step 2. 7-(2-Fluoro-4-nitrophenoxy)-2-(6-methoxypyridin-3-yl)thieno[3,2-b]pyridine (419)

A suspension of 418 (0.638 g, 2.31 mmol), 2-fluoro-4-nitrophenol (0.725 g, 4.61 mmol) and potassium carbonate (0.638 g, 4.61 mmol) in diphenyl ether (6 mL) was heated to 170° C. for 8 h in a pressure tube. The resulting dark solution was cooled to room temperature, diluted with CH$_2$Cl$_2$ and then filtered. The filtrate was concentrated and the residue was purified by flash chromatography (eluent 100% hexanes to 50/50 ethyl acetate/hexanes) to produce title compound 419 as a yellow solid (0.395 g, 43% yield). MS (m/z): 398.0 (M+H).

Step 3. 5-(7-(2-Fluoro-4-nitrophenoxy)thieno[3,2-b]pyridin-2-yl)pyridin-2(1H)-one (420)

To a flask containing a suspension of 419 (0.299 g, 0.753 mmol) in acetonitrile (8 mL) was added chlorotrimethylsilane (0.095 mL, 0.748 mmol) followed by sodium iodide (0.112 g, 0.748 mmol). The mixture was then heated to between 70 to 100° C. over 24 hours. Over this time four additional portions of chlorotrimethylsilane (0.095 mL each portion) and sodium iodide (0.112 g each portion) were added. The reaction mixture was then cooled to room temperature and the formed precipitate was collected by filtration, washed with NH$_4$OH and water, and dried to provide title compound 420 as a brown solid (0.2832, 98%). MS (m/z): 384.0 (M+H), 406.0 (M+Na).

Step 4. 1-(2-(Dimethylamino)ethyl)-5-(7-(2-fluoro-4-nitrophenoxy)thieno[3,2-b]pyridin-2-yl)pyridin-2(1H)-one (421)

The pyridinone 420 (0.283 g, 0.739 mmol), 2-chloro-N,N-dimethylethanamine (0.128 g, 0.887 mmol), cesium carbonate (0.547 g, 1.68 mmol) and sodium iodide (0.132 g, 0.88 mmol) were heated in DMF (10 mL) at 70° C. for 3 days. An additional portion of 2-chloro-N,N-dimethylethanamine (64 mg, 0.44 mmol) and cesium carbonate (0.289 g, 0.887 mmol) were added. The reaction mixture was heated for additional 8 hours, cooled to room temperature and evaporated under reduced pressure. The residue was partitioned between water (50 mL) and 5% ethanol/dichloromethane. The organic phase was collected, dried over anhydrous Na$_2$SO$_4$, filtered and concentrated. The residue was then purified by silica gel chromatography using a 25M Biotage column and a gradient of 3 to 20% methanol in dichloromethane with 1% acetic acid, to provide title compound 421 as a solid material (0.108 g, 32% yield). MS (m/z): 228.0 ([M+2H]/2), 455.0 (M+H), 477.0 (M+Na).

Step 5. 5-(7-(4-Amino-2-fluorophenoxy)thieno[3,2-b]pyridin-2-yl)-1-(2-(dimethylamino)ethyl)pyridin-2(1H)-one (422)

To a solution of the nitro compound 421 (0.103 g, 0.227 mmol) in methanol (2 mL) and THF (2 ml) at 0° C. was added nickel chloride hexahydrate (0.162 g, 0.681 mmol) followed by sodium borohydride (28 mg, 0.749 mmol). After one hour of stirring at 0° C. another portion of nickel chloride hexahydrate (0.108 g, 0.458 mmol) and sodium borohydride (19 mg, 0.50 mmol) were added. The reaction mixture was then stirred at room temperature for 5 hours before it was concentrated and treated with 1N HCl(aq) and dichloromethane. The mixture was stirred for 10 minutes and then basified to pH 10 by the addition of NH$_4$OH. The basified solution was then extracted with dichloromethane. The extract was dried over anhydrous Na₂SO₄, filtered and concentrated. The residue was purified by flash chromatography (eluent a gradient of 10 to 100% methanol in ethyl acetate) to give the title compound 422 as yellow solid (26 mg, 27% yield). MS (m/z): 425.0 (M+H).

Step 6. $N^1$-(4-(2-(1-(2-(Dimethylamino)ethyl)-6-oxo-1,6-dihydropyridin-3-yl)thieno[3,2-b]pyridin-7-yloxy)-3-fluorophenyl)-$N^3$-(2-methoxyphenyl)malonamide (417)

To a solution of compound 422 (25 mg, 0.059 mmol) in DMF (0.5 mL) was added the acid 27 (25 mg, 0.12 mmol), hydroxybenzotriazole (11 mg, 0.071 mmol), then EDC (23 mg, 0.12 mmol). The reaction mixture was stirred at room temperature for 6 hours before the addition of saturated NaHCO₃ (8 mL). The mixture was then extracted with dichloromethane; the extract was dried over anhydrous Na₂SO₄, filtered and concentrated. The residue was then purified by flash chromatography (eluent a gradient of 0 to 20% methanol in dichloromethane) to give title compound 417 as a white solid (19 mg, 53% yield). ¹H NMR: (DMSO-d₆) δ(ppm): 10.58 (s, 1H), 9.62 (s, 1H), 8.45 (d, J=5.6 Hz, 1H), 8.28 (d, J=2.8 Hz, 1H), 8.05 (d, J=8.4 Hz, 1H), 7.95 (dd, J=2.8, 9.6 Hz, 1H), 7.88-7.84 (m, 2H), 7.45 (t, J=8.8 Hz, 1H), 7.43-7.40 (m, 1H), 7.07-7.03 (m, 2H), 6.92-6.88 (m, 1H), 6.60 (d, J=5.6 Hz, 1H), 6.51 (d, J=9.6 Hz, 1H), 4.05 (t, J=6.0 Hz, 2H), 3.84 (s, 3H), 3.62 (s, 2H), 2.53 (t, J=6.4 Hz, 2H), 2.47 (s, 6H). MS (m/z): 308.5 ([M+2H]/2), 616.1 (M+H).

The following compounds and other compounds described herein, and the compounds described in the assay examples below, are prepared essentially according to the procedures outlined in the schemes, charts, examples and preparations set forth herein.

TABLE 20

| Example | Compound No. | Compound Name |
|---|---|---|
| 1 | 5a | $N^1$-(3-Fluoro-4-(thieno[3,2-b]pyridin-7-yloxy)phenyl)-$N^3$-phenylmalonamide |
| 2 | 5b | $N^1$-(3-Fluoro-4-(2-(1-methyl-1H-imidazol-2-yl)thieno[3,2-b]pyridin-7-yloxy)phenyl)-$N^3$-phenylmalonamide |
| 3 | 5c | $N^1$-{3-Fluoro-4-[2-(1-methyl-1H-imidazol-4-yl)thieno[3,2-b]pyridin-7-yloxy]-phenyl}-$N^3$-phenylmalonamide |
| 4 | 5d | $N^1$-(4-(2-(1-ethyl-1H-imidazol-4-yl)thieno[3,2-b]pyridin-7-yloxy)-3-fluorophenyl)-$N^3$-phenylmalonamide |
| 5 | 5e | $N^1$-(3-fluoro-4-(2-(1-methyl-1H-imidazol-5-yl)thieno[3,2-b]pyridin-7-yloxy)phenyl)-$N^3$-phenylmalonamide |
| 6 | 5f | $N^1$-(3-Fluoro-4-(2-(pyrrolidine-1-carbonyl)thieno[3,2-b]pyridin-7-yloxy)phenyl)-$N^3$-phenylmalonamide |
| 7 | 5g | (R)-$N^1$-(4-(2-(3-(Dimethylamino)pyrrolidine-1-carbonyl)thieno[3,2-b]pyridin-7-yloxy)-3-fluorophenyl)-$N^3$-phenylmalonamide |
| 8 | 28a | $N^1$-(3-Fluoro-4-(2-(1-methyl-1H-imidazol-2-yl)thieno[3,2-b]pyridin-7-yloxy)phenyl)-$N^3$-(2-methoxyphenyl)malonamide |
| 9 | 28b | $N^1$-(4-(2-(1-ethyl-1H-imidazol-4-yl)thieno[3,2-b]pyridin-7-yloxy)-3-fluorophenyl)-$N^3$-(2-methoxyphenyl)malonamide |
| 10 | 28c | $N^1$-(3-fluoro-4-(2-(1-methyl-1H-imidazol-5-yl)thieno[3,2-b]pyridin-7-yloxy)phenyl)-$N^3$-(2-methoxyphenyl)malonamide |
| 11 | 30a | $N^1$-(3-fluoro-4-(2-(1-methyl-1H-imidazol-2-yl)thieno[3,2-b]pyridin-7-yloxy)phenyl)-$N^3$-(2-fluoroxyphenyl)malonamide |
| 12 | 30b | $N^1$-(4-(2-(1-ethyl-1H-imidazol-4-yl)thieno[3,2-b]pyridin-7-yloxy)-3-fluorophenyl)-$N^3$-(2-fluorophenyl)-$N^3$-(2-fluorophenyl)malonamide |
| 13 | 32 | $N^1$-(3-fluoro-4-(2-(1-methyl-1H-imidazol-2-yl)thieno[3,2-b]pyridin-7-yloxy)phenyl)-$N^3$-methyl-$N^3$-phenylmalonamide |
| 14 | 34 | N-{3-Fluoro-4-[2-(1-methyl-1H-imidazol-2-yl)-thieno[3,2-b]pyridin-7-yloxy]-phenyl}-N'-pyridin-4-yl-malonamide |
| 15 | 36 | $N^1$-(3-Fluoro-4-(2-(1-methyl-1H-imidazol-2-yl)thieno[3,2-b]pyridin-7-yloxy)phenyl)-$N^3$-(pyrrolidin-3-yl)malonamide |
| 16 | 38 | $N^1$-(3-fluoro-4-(2-(1-methyl-1H-imidazol-2-yl)thieno[3,2-b]pyridin-7-yloxy)phenyl)-2-methyl-$N^3$-phenylmalonamide |
| 17 | 40 | $N^1$-(3-fluoro-4-(2-(1-methyl-1H-imidazol-2-yl)thieno[3,2-b]pyridin-7-yloxy)phenyl)-2-methyl-$N^3$-phenylmalonamide |
| 18 | 41 | N-{3-Fluoro-4-[2-(3-methyl-3H-imidazol-4-yl)-thieno[3,2-b]pyridin-7-yloxy]-phenyl}-N'-pyridin-3-yl-malonamide |
| 19 | 43 | $N^1$-(3-Fluoro-4-(2-(1-methy-1H-imidazol-2-yl)thieno[3,2-b]pyridin-7-yloxy)phenyl)-$N^3$-(piperidin-4-yl)malonamide |
| 20 | 45 | N-{3-Fluoro-4-[2-(1-methyl-1H-imidazol-2-yl)-thieno[3,2-b]pyridin-7-yloxy]-phenyl}-malonamic acid piperidin-4-yl ester |
| 21 | 47 | N-{3-Fluoro-4-[2-(1-methyl-1H-imidazol-2-yl)-thieno[3,2-b]pyridin-7-yloxy]-phenyl}-malonamic acid phenyl ester |
| 22 | 48 | $N^1$-(3-Fluoro-4-(2-(4-(pyrrolidin-1-ylmethyl)phenyl)-thieno[3,2-b]pyridin-7-yloxy)phenyl)-$N^3$-(2-methoxyphenyl)malonamide |

Pharmaceutical Compositions

In a third aspect, the invention provides pharmaceutical compositions comprising an inhibitor of VEGF receptor signaling and HGF receptor signaling according to the invention and a pharmaceutically acceptable carrier, excipient, or diluent. Compositions of the invention may be formulated by any method well known in the art and may be prepared for administration by any route, including, without limitation, parenteral, oral, sublingual, transdermal, topical, intranasal, intratracheal, or intrarectal. In certain preferred embodiments, compositions of the invention are administered intravenously in a hospital setting. In certain other preferred embodiments, administration may preferably be by the oral route.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

As used herein, the term pharmaceutically acceptable salts refers to salts that retain the desired biological activity of the above-identified compounds and exhibit minimal or no undesired toxicological effects. Examples of such salts include, but are not limited to, salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, palmoic acid, alginic acid, polyglutamic acid, naphthalenesulfonic acid, naphthalenedisulfonic acid, methanesulfonic acid, p-toluenesulfonic acid and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The active compound is included in the pharmaceutically acceptable carrier or diluent in an amount sufficient to deliver to a patient a therapeutically effective amount without causing serious toxic effects in the patient treated. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

Inhibition of VEGF Receptor Signaling and HGF Receptor Signaling

In a fourth aspect, the invention provides a method of inhibiting VEGF receptor signaling and HGF receptor signaling in a cell, comprising contacting a cell in which inhibition of VEGF receptor signaling and HGF receptor signaling is desired with an inhibitor of VEGF receptor signaling and HGF receptor signaling according to the invention. Because compounds of the invention inhibit VEGF receptor signaling and HGF receptor signaling, they are useful research tools for in vitro study of the role of VEGF receptor signaling and HGF receptor signaling in biological processes.

Preferably, the method according to the fourth aspect of the invention causes an inhibition of cell proliferation of the contacted cells. The phrase "inhibiting cell proliferation" is used to denote an ability of an inhibitor of VEGF receptor signaling and HGF receptor signaling to retard the growth of cells contacted with the inhibitor as compared to cells not contacted. An assessment of cell proliferation can be made by counting contacted and non-contacted cells using a Coulter Cell Counter (Coulter, Miami, Fla.) or a hemacytometer. Where the cells are in a solid growth (e.g., a solid tumor or organ), such an assessment of cell proliferation can be made by measuring the growth with calipers and comparing the size of the growth of contacted cells with non-contacted cells.

Preferably, growth of cells contacted with the inhibitor is retarded by at least 50% as compared to growth of non-contacted cells. More preferably, cell proliferation is inhibited by 100% (i.e., the contacted cells do not increase in number). Most preferably, the phrase "inhibiting cell proliferation" includes a reduction in the number or size of contacted cells, as compared to non-contacted cells. Thus, an inhibitor of VEGF receptor signaling and HGF receptor signaling according to the invention that inhibits cell proliferation in a contacted cell may induce the contacted cell to undergo growth retardation, to undergo growth arrest, to undergo programmed cell death (i.e., to apoptose), or to undergo necrotic cell death.

In some preferred embodiments, the contacted cell is a neoplastic cell. The term "neoplastic cell" is used to denote a cell that shows aberrant cell growth. Preferably, the aberrant cell growth of a neoplastic cell is increased cell growth. A neoplastic cell may be a hyperplastic cell, a cell that shows a lack of contact inhibition of growth in vitro, a benign tumor cell that is incapable of metastasis in vivo, or a cancer cell that is capable of metastasis in vivo and that may recur after attempted removal. The term "tumorigenesis" is used to denote the induction of cell proliferation that leads to the development of a neoplastic growth.

In some preferred embodiments, the contacted cell is in an animal. Thus, the invention provides a method for treating a cell proliferative disease or condition in an animal, comprising administering to an animal in need of such treatment a therapeutically effective amount of a VEGF receptor signaling and HGF receptor signaling inhibitor of the invention. Preferably, the animal is a mammal, more preferably a domesticated mammal. Most preferably, the animal is a human.

The term "cell proliferative disease or condition" is meant to refer to any condition characterized by aberrant cell growth, preferably abnormally increased cellular proliferation. Examples of such cell proliferative diseases or conditions amenable to inhibition and treatment include, but are not limited to, cancer. Examples of particular types of cancer include, but are not limited to, breast cancer, lung cancer, colon cancer, rectal cancer, bladder cancer, leukemia and renal cancer. In particularly preferred embodiments, the invention provides a method for inhibiting neoplastic cell proliferation in an animal comprising administering to an animal having at least one neoplastic cell present in its body a therapeutically effective amount of a VEGF receptor signaling and HGF receptor signaling inhibitor of the invention.

ASSAY EXAMPLES

Assay Example 1

Inhibition of C-Met and VEGF Activity

The following protocols were used to assay the compounds of the invention.
In Vitro Receptor Tyrosine Kinase Assays (C-Met/HGF Receptor and VEGF Receptor KDR)

These tests measure the ability of compounds to inhibit the enzymatic activity of recombinant human c-Met/HGF receptor and VEGF receptor enzymatic activity.

A 1.3-kb cDNA corresponding to the intracellular domain of c-Met or c-Met IC (Genbank accession number NP000236-1 amino acid 1078 to 1337) was cloned into the BamHI/XhoI sites of the pBlueBacHis2A vector (Invitrogen) for the production of a histidine-tagged version of that enzyme. This constuct was used to generate recombinant baculovirus using the Bac-N-Blue™ system according to the manucfacturer's instructions (Invitrogen).

The c-Met IC protein was expressed in Hi-5 cells (*Trichoplusia Ni*) upon infection with recombinant baculovirus construct. Briefly, Hi-5 cells grown in suspension and maintained in serum-free medium (Sf900 II supplemented with gentamycin) at a cell density of about $2 \times 10^6$ cells/ml were infected with the above-mentioned viruses at a multiplicity of infection (MOI) of 0.2 during 72 hours at 27° C. with agitation at 120 rpm on a rotary shaker. Infected cells were harvested by centrifugation at 398 g for 15 min. Cell pellets were frozen at −80° C. until purification was performed.

All steps described in cell extraction and purification were performed at 4° C. Frozen Hi-5 cell pellets infected with the C-Met IC recombinant baculovirus were thawed and gently resuspended in Buffer A (20 mM Tris pH 8.0, 10% glycerol, 1 µg/ml pepstatin, 2 µg/ml Aprotinin and leupeptin, 50 µg/ml PMSF, 50 µg/ml TLCK and 10 µM E64, 0.5 mM DTT and 1 mM Levamisole) using 3 ml of buffer per gram of cells. The suspension was Dounce homogenized after which it was centrifuged at 22500 g, 30 min., 4° C. The supernatant (cell extract) was used as starting material for purification of c-Met IC.

The supernatant was loaded onto a QsepharoseFF column (Amersham Biosciences) equilibrated with Buffer B (20 mM Tris pH 8.0, 10% glycerol) supplemented with 0.05M NaCl. Following a ten column volume (CV) wash with equilibration buffer, bound proteins were eluted with a 5 CV salt linear gradient spanning from 0.05 to 1M NaCl in Buffer B. Typically, the conductivity of selected fractions ranked between 6.5 and 37 mS/cm. This Qsepharose eluate had an estimated NaCl concentration of 0.33M and was supplemented with a 5M NaCl solution in order to increase NaCl concentration at 0.5M and also with a 5M Imidazole (pH 8.0) solution to achieve a final imidazole concentration of 15 mM. This material was loaded onto a HisTrap affinity column (GE Healthcare) equilibrated with Buffer C (50 mM NaPO$_4$ pH 8.0, 0.5M NaCl, 10% glycerol) supplemented with 15 mM imidazole. After a 10 CV wash with equilibration buffer and an 8 CV wash with buffer C+40 mM imidazole, bound proteins were eluted with an 8 CV linear gradient (15 to 500 mM) of imidazole in buffer C. C-Met IC enriched fractions from this chromatography step were pooled based on SDS-PAGE analysis. This pool of enzyme underwent buffer exchange using PD-10 column (GE Healthcare) against buffer D (25 mM HEPES pH 7.5, 0.1M NaCl, 10% glycerol and 2 mM β-mercaptoethanol) Final C-Met IC protein preparations concentrations were about 0.5 mg/ml with purity approximating 80%. Purified c-Met IC protein stocks were supplemented with BSA at 1 mg/ml, aliquoted and frozen at −80° C. prior to use in enzymatic assay.

In the case of VEGF receptor KDR a 1.6-kb cDNA corresponding to the catalytic domain of VEGFR2 or KDR (Genbank accession number AF035121 amino acid 806 to 1356) was cloned into the Pst I site of the pDEST20 Gateway vector (Invitrogen) for the production of a GST-tagged version of that enzyme. This constuct was used to generate recombinant baculovirus using the Bac-to-Bac™ system according to the manucfacturer's instructions (Invitrogen).

The GST-VEGFR2$_{806-1356}$ protein was expressed in SP9 cells (*Spodoptera frugiperda*) upon infection with recombinant baculovirus construct. Briefly, Sf9 cells grown in suspension and maintained in serum-free medium (Sf900 II supplemented with gentamycin) at a cell density of about $2 \times 10^6$ cells/ml were infected with the above-mentioned viruses at a multiplicity of infection (MOI) of 0.1 during 72 hours at 27° C. with agitation at 120 rpm on a rotary shaker. Infected cells were harvested by centrifugation at 398 g for 15 min. Cell pellets were frozen at −80° C. until purification was performed.

All steps described in cell extraction and purification were performed at 4° C. Frozen Sf9 cell pellets infected with the GST-VEGFR2$_{806-1356}$ recombinant baculovirus were thawed and gently resuspended in Buffer A (PBS pH 7.3 supplemented with 1 µg/ml pepstatin, 2 µg/ml Aprotinin and leupeptin, 50 µg/ml PMSF, 50 µg/ml TLCK and 10 µM E64 and 0.5 mM DTT) using 3 ml of buffer per gram of cells. Suspension was Dounce homogenized and 1% Triton X-100 was added to the homogenate after which it was centrifuged at 22500 g, 30 min., 4° C. The supernatant (cell extract) was used as starting material for purification of GST-VEGFR2$_{806-1356}$.

The supernatant was loaded onto a GST-agarose column (Sigma) equilibrated with PBS pH 7.3. Following a four column volume (CV) wash with PBS pH 7.3+1% Triton X-100 and 4 CV wash with buffer B (50 mM Tris pH 8.0, 20% glycerol and 100 mM NaCl), bound proteins were step eluted with 5 CV of buffer B supplemented with 5 mM DTT and 15 mM glutathion. GST-VEGFR2$_{806-1356}$ enriched fractions from this chromatography step were pooled based on U.V. trace i.e. fractions with high O.D.$_{280}$. Final GST-VEGFR2$_{806-1356}$ protein preparations concentrations were about 0.7 mg/ml with purity approximating 70%. Purified GST-VEGFR2$_{806-1356}$ protein stocks were aliquoted and frozen at −80° C. prior to use in enzymatic assay.

Inhibition of c-Met/HGF receptor and VEGFR/KDR was measured in a DELFIA™ assay (Perkin Elmer). The substrate poly(Glu$_4$,Tyr) was immobilized onto black high-binding polystyrene 96-well plates. The coated plates were washed and stored at 4° C. During the assay, enzymes were pre-incubated with inhibitor and Mg-ATP on ice in polypropylene 96-well plates for 4 minutes, and then transferred to the coated plates. The subsequent kinase reaction took place at 30° C. for 10-30 minutes. ATP concentrations in the assay were 10 uM for C-Met (5× the $K_m$) and 0.6 uM for VEGFR/KDR (2× the $K_m$). Enzyme concentration was 25 nM (C-Met) or 5 nM (VEGFR/KDR). After incubation, the kinase reactions were quenched with EDTA and the plates were washed. Phosphorylated product was detected by incubation with Europium-labeled anti-phosphotyrosine MoAb. After washing the plates, bound MoAb was detected by time-resolved fluorescence in a Gemini SpectraMax reader (Molecular Devices). Compounds were evaluated over a range of concentrations and IC$_{50}$'s (concentration of compounds giving 50% inhibition of enzymatic activity) were determined.

C-Met Phosphorylation Cell-Based Assay

This test measures the ability of compounds to inhibit HGF stimulated auto-phosphorylation of the c-Met/HGF receptor itself in a whole cell system.

MNNGHOS cell line expressing TPR-MET fusion protein were purchased from ATCC. The TPR-MET is the product of a chromosomal translocation placing the TPR locus on chromosome 1 upstream of the MET gene on chromosome 7 encoding for its cytoplasmic region catalytic domain. Dimerization of the $M_r$ 65,000 TPR-Met oncoprotein through a leucine zipper motif encoded by the TPR portion leads to constitutive activation of the met kinase. Constitutive auto-phosphorylation occurs on residues Tyr361/365/366 of TPR-Met. These residues are homologous to Tyr1230/1234/1235 of MET which become phosphorylated upon dimerization of the receptor upon HGF binding.

Inhibitor of c-Met formulated as 30 mM stocks in DMSO. For MNNGHOS treatments, cells, compounds were added to tissue culture media at indicated doses for 3 hours prior to cell lysis. Cells were lysed in ice-cold lysis buffer containing 50 mM HEPES (pH 7.5), 150 mM NaCl, 1.5 mM MgCl2, 10% glycerol, 1% Triton X-100, 1 mM 4-(2-Aminoethyl)benzenesulfonyl fluoride hydrochloride, 200 µM sodium orthovanadate, 1 mM sodium fluoride, 10 µg/ml of leupeptin, 10 µg/ml of aprotinin/ml, 1 µg/ml of pepstatin and 50 µg/ml Na-p-Tosyl-L-lysine chloromethyl ketone hydrochloride.

Lysate were separated on 5-20% PAGE-SDS and immunoblots were performed using Immobilon P polyvinylidene difluoride membranes (Amersham) according to the manufacturer's instructions for handling. The blots were washed in Tris-buffered saline with 0.1% Tween 20 detergent (TBST). Tyr361/365/366 of TPR-Met were detected with polyclonal rabbit antibodies against tyrosine phosphorylated Met (Biosource International) and secondary antibodies anti-rabbit-horseradish peroxidase (Sigma) by chemiluminescence assays (Amersham, ECL) were performed according to the manufacturer's instructions and followed by film exposure. Signal was quantitated by densitometry on Alpha-Imager. $IC_{50}$ values were defined as the dose required to obtain 50% inhibition of the maximal HGF stimulated phosphorylated c-Met levels.

TABLE 21

Biological profile of selected compounds

| Example | Cpd | C-Met ($IC_{50}$, µM) | VEGFR ($IC_{50}$, µM) | Y1230-34-35 TPR-MET phosphorylation ($IC_{50}$, µM) |
|---|---|---|---|---|
| 1 | 5a | 0.27 | 0.199 | n/d |
| 2 | 5b | 0.052 | 0.004 | 0.04 |
| 3 | 5c | 0.019 | 0.003 | 0.008 |
| 4 | 5d | 0.019 | 0.005 | n/d |
| 5 | 5e | 0.016 | 0.005 | 0.155 |
| 6 | 5f | 0.04 | 0.004 | ~2 |
| 7 | 5g | 0.065 | 0.089 | n/d |
| 8 | 28a | 0.042 | 0.005 | ~0.2 |
| 9 | 28b | 0.025 | 0.003 | n/d |
| 10 | 28c | 0.040 | 0.013 | 0.59 |
| 11 | 30a | 0.031 | 0.005 | 0.028 |
| 12 | 30b | 0.024 | n/d | n/d |
| 13 | 32 | 0.109 | 0.005 | >5 |
| 14 | 34 | 0.365 | 0.019 | >5 |
| 16 | 38 | 0.077 | 0.005 | n/d |

TABLE 21-continued

Biological profile of selected compounds

| Example | Cpd | C-Met ($IC_{50}$, µM) | VEGFR ($IC_{50}$, µM) | Y1230-34-35 TPR-MET phosphorylation ($IC_{50}$, µM) |
|---|---|---|---|---|
| 17 | 40 | 0.268 | 0.013 | ~0.5 |
| 18 | 41 | 0.132 | 0.024 | n/d |
| 21 | 47 | 0.173 | 0.014 | n/d |
| 22 | 48 | 0.06 | 0.013 | n/d |

In Vivo Solid Tumor Disease Model

This test measures the capacity of compounds to inhibit solid tumor growth.

Tumor xenografts are established in the flank of female athymic CD1 mice (Charles River Inc.), by subcutaneous injection of $1 \times 10^6$ U87, A431 or SKLMS cells/mouse. Once established, tumors are then serially passaged s.c. in nude mice hosts. Tumor fragments from these host animals are used in subsequent compound evaluation experiments. For compound evaluation experiments female nude mice weighing approximately 20 g are implanted s.c. by surgical implantation with tumor fragments of ~30 mg from donor tumors. When the tumors are approximately 100 mm³ in size (~7-10 days following implantation), the animals are randomized and separated into treatment and control groups. Each group contains 6-8 tumor-bearing mice, each of which is ear-tagged and followed individually throughout the experiment.

Mice are weighed and tumor measurements are taken by calipers three times weekly, starting on Day 1. These tumor measurements are converted to tumor volume by the well-known formula $(L+W/4)^3 4/3\pi$. The experiment is terminated when the control tumors reach a size of approximately 1500 mm³. In this model, the change in mean tumor volume for a compound treated group/the change in mean tumor volume of the control group (non-treated or vehicle treated)×100 (ΔT/ΔC) is subtracted from 100 to give the percent tumor growth inhibition (% TGI) for each test compound. In addition to tumor volumes, body weight of animals is monitored twice weekly for up to 3 weeks.

The activities of a number of compounds according to the invention measured by various assays are displayed in Table 21 and Table 22. In these tables, "a" indicates inhibitory activity at a concentration of less than 50 nanomolar; "b" indicates inhibitory activity at a concentration ≧50 but <250 nanomolar, "c" indicates inhibitory activity at ≧250 but <500 and "d" indicates inhibitory activity at a concentration of ≧500 nanomolar; and "e" indicates no activity as measured by that assay.

HGF has well known activity in terms of inducing scattering and migration (wound healing) (Wells et al., Cell Motil Cytoskeleton. 2005 November 62(3):180-94; Miura et al., Urology 2001 December 58(6):1064-9; Nishimura et al., Int J Urol. 1998 May 5(3):276-81; Wang et al., Mol Cancer Ther. 2003 November; 2(11):1085-92; and Christensen et al., Cancer Res. 2003 Nov. 1; 63(21):7345-55). Assays to evaluate inhibitor ability to block these HGF dependent activities have been employed and follow the methods employed in Christensen et al. For Table 22, for columns directed to A549 wound healing inhibition and DU145 scattering inhibition, $IC_{50}$ values are in mM, with "A" indicating $IC_{50}$ of less than 1 mM, "B" indicating $IC_{50}$ of ≧1 mM but <5 mM, "C" indicating $IC_{50}$ of ≧5 mM but <10 mM, and "D" indicating $IC_{50}$ of ≧10 mM.

In Table 23 "a" indicates % TGI in the range of 75-100; "b" indicates % TGI in the range of 50-74; "c" indicates % TGI in the range of 25-49, and "d" indicates % TGI in the range of 0-24. Regiment of administration was once daily.

TABLE 22

| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| 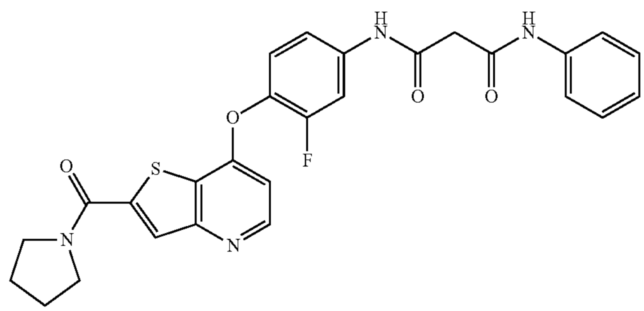 | a | a | | |
| | d | d | D | D |
| 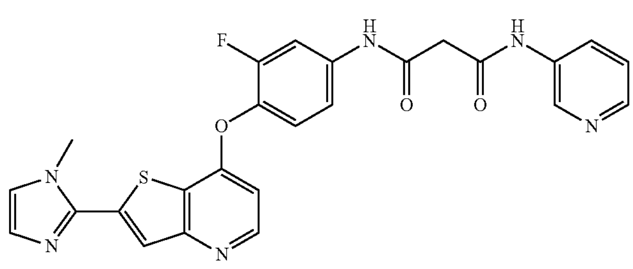 | c | a | A | B |
| | d | d | D | D |

TABLE 22-continued

| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| (structure) | a | a | A | B |
| (structure) | a | a | A | A |
| (structure) | b | a | B | B |
| (structure) | a | a | A | A |
| (structure) | a | a | A | A |

TABLE 22-continued
| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| 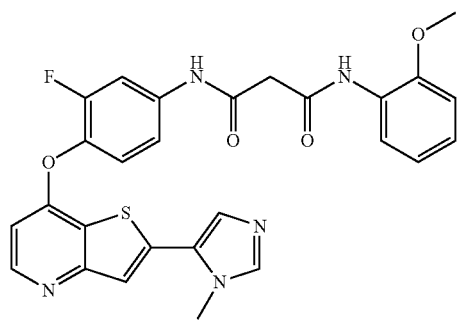 | a | a | B | B |
| 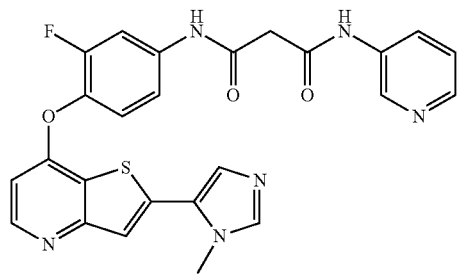 | b | a | B | B |
| 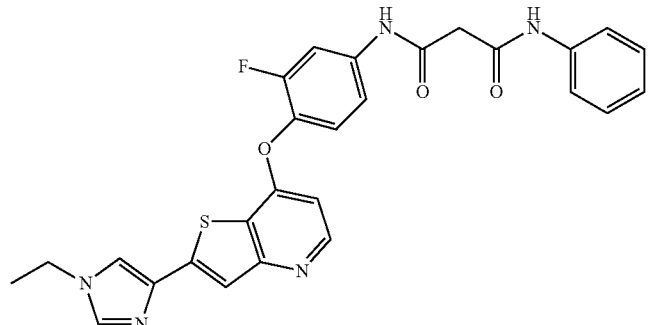 | a | b | A | A |
| 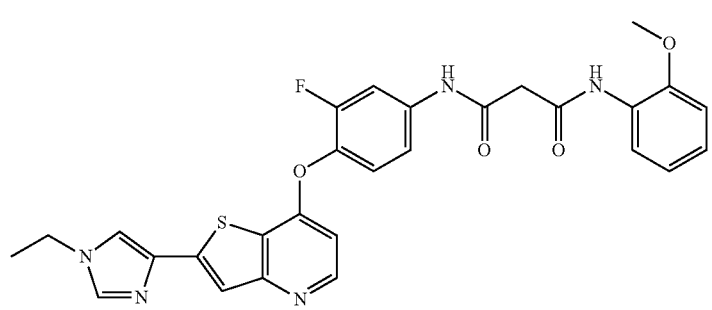 | a | a | B | A |

TABLE 22-continued

| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| (structure) | a | a | A | A |
| (structure) | b | b | A | B |
| (structure) | b | a | B | A |
| (structure) | b | a | B | B |

TABLE 22-continued
| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| 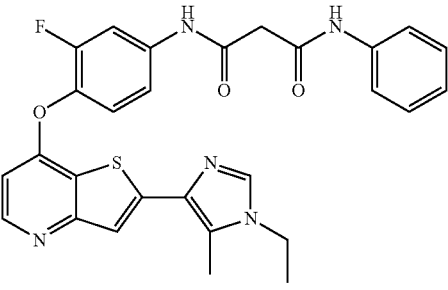 | a | a | A | A |
| 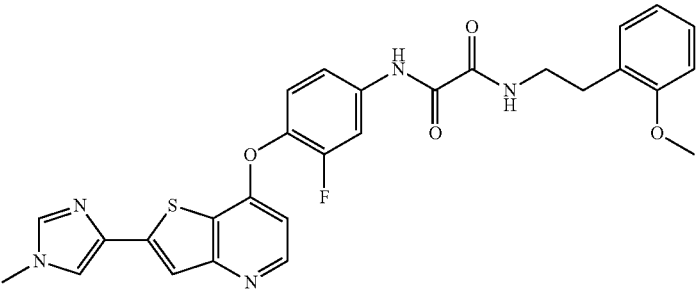 | c | a | C | D |
| 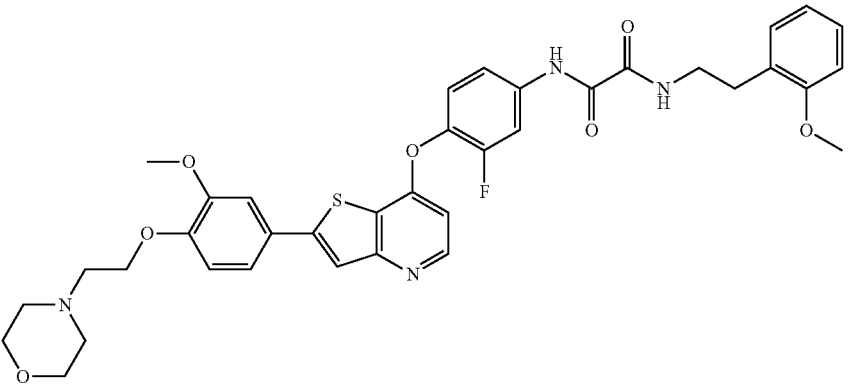 | c | d | B | D |
| 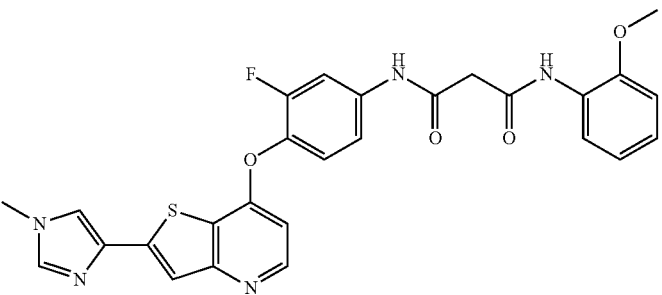 | b | a | A | A |

TABLE 22-continued

| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| (structure) | a | a | A | A |
| (structure) | b | a | A | B |
| (structure) | b | a | A | B |
| (structure) | b | a | B | B |
| (structure) | b | a | B | D |

TABLE 22-continued
| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| 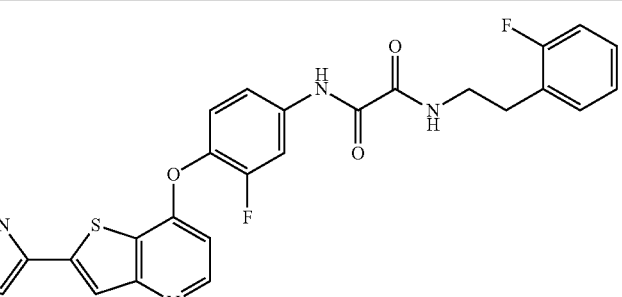 | b | b | B | D |
| 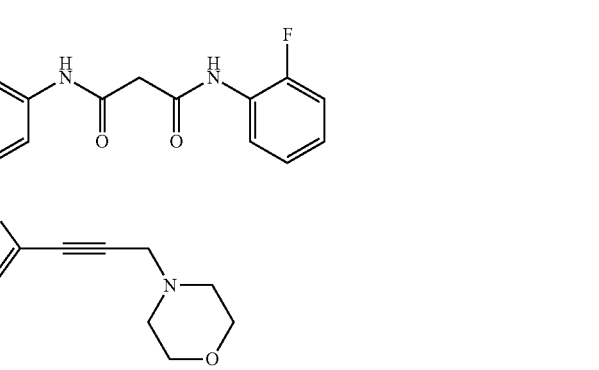 | b | c | B | D |
| 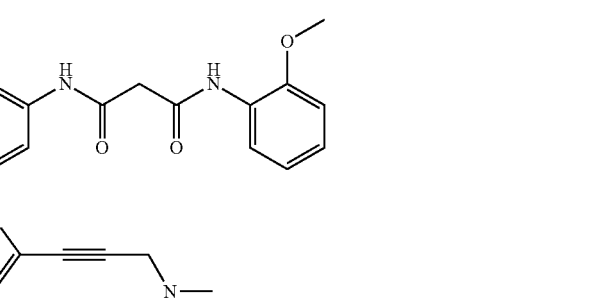 | b | b | D | D |
| 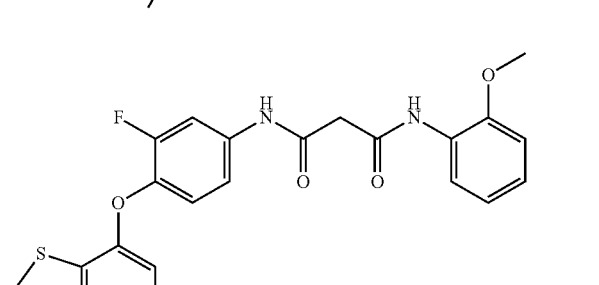 | b | a | B | B |

TABLE 22-continued

| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| | b | b | D | B |
| | b | b | B | B |
| | b | b | B | A |
| | b | b | D | B |

TABLE 22-continued

| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| | a | b | B | B |
| | a | b | A | A |
| | a | b | B | A |
| | a | a | A | A |

TABLE 22-continued

| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| (structure) | a | a | A | A |
| (structure) | a | a | B | A |
| (structure) | a | a | A | A |
| (structure) | a | a | B | A |

TABLE 22-continued

| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| *(structure)* | a | a | A | A |
| *(structure)* | a | a | A | A |
| *(structure)* | b | a | B | B |
| *(structure)* | b | a | D | B |

TABLE 22-continued
| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| 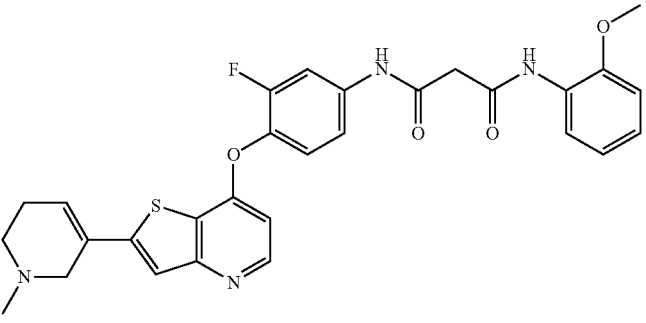 | b | c | B | B |
| 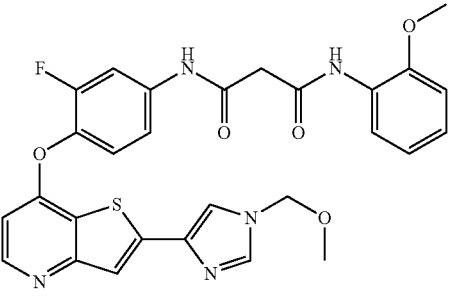 | b | a | B | A |
| 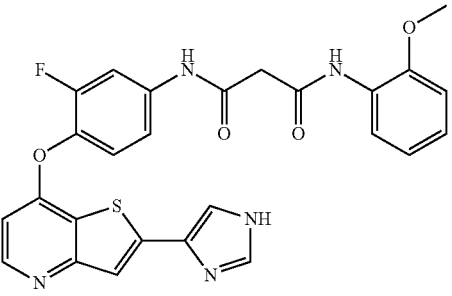 | b | b | A | A |
| 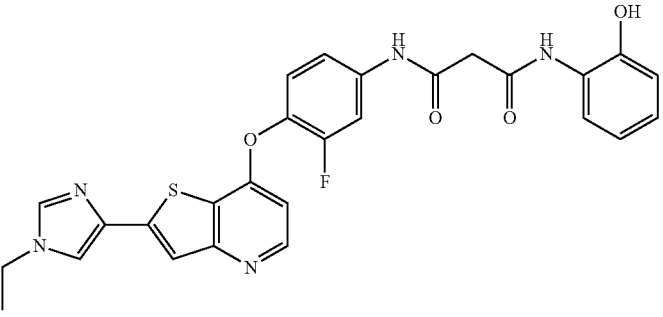 | a | a | B | B |

TABLE 22-continued
| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| 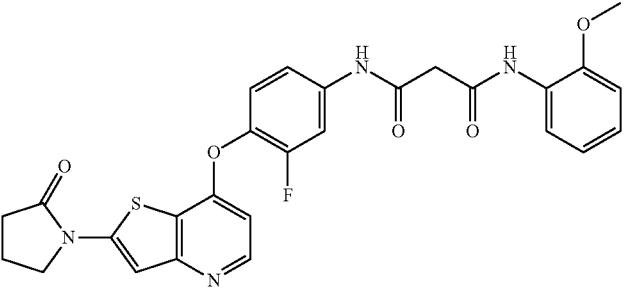 | b | b | A | A |
| 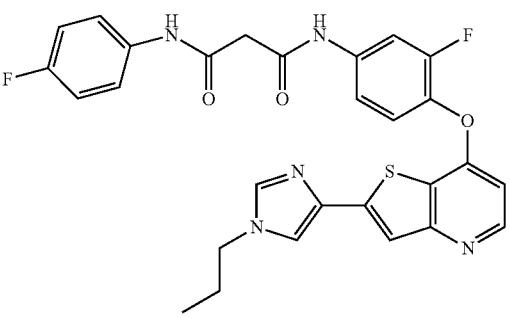 | a | a | A | A |
| 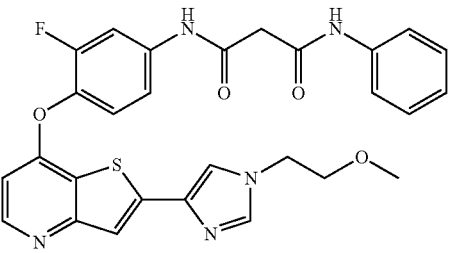 | a | a | A | A |
| 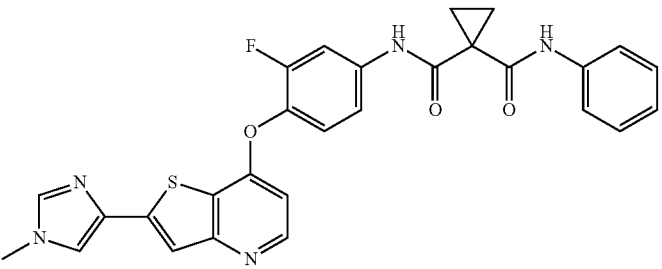 | a | a | A | A |
| 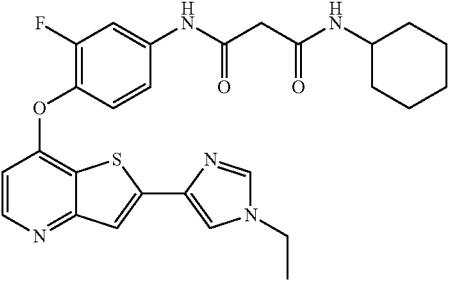 | b | a | A | A |

TABLE 22-continued

| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| [structure] | b | a | A | A |
| [structure] | b | a | B | A |
| [structure] | a | a | A | A |
| [structure] | c | d | B | B |

TABLE 22-continued

| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| (structure) | c | d | D | D |
| (structure) | b | a | A | A |
| (structure) | b | a | A | A |
| (structure) | a | a | A | A |
| (structure) | a | a | B | A |

TABLE 22-continued

| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| | b | a | B | B |
| | a | a | A | A |
| | b | c | B | B |
| | a | a | A | A |

TABLE 22-continued

| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| *structure* | a | a | A | A |
| *structure* | d | d | D | D |
| *structure* | c | d | D | D |
| *structure* | a | a | A | A |
| *structure* | a | a | A | A |

TABLE 22-continued

| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| (structure) | a | a | A | A |
| (structure) | a | b | D | D |
| (structure) | b | d | B | D |
| (structure) | b | b | C | D |
| (structure) | a | a | A | A |

TABLE 22-continued
| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| 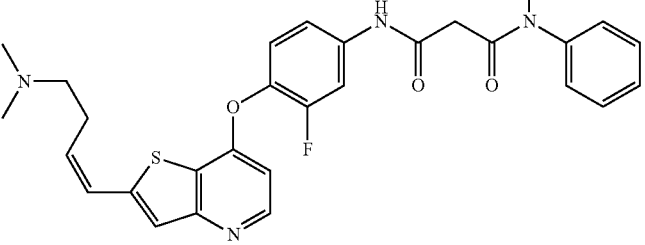 | b | b | B | B |
| 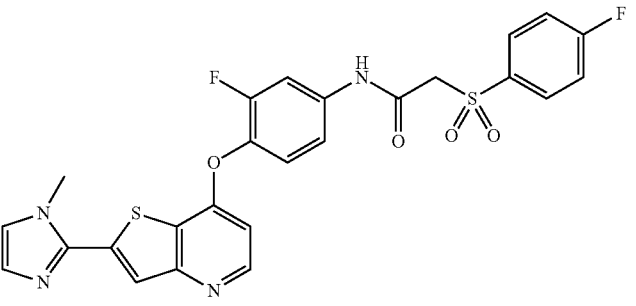 | c | b | B | B |
| 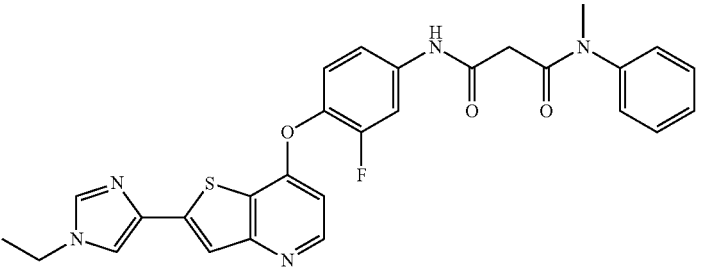 | a | a | A | A |
| 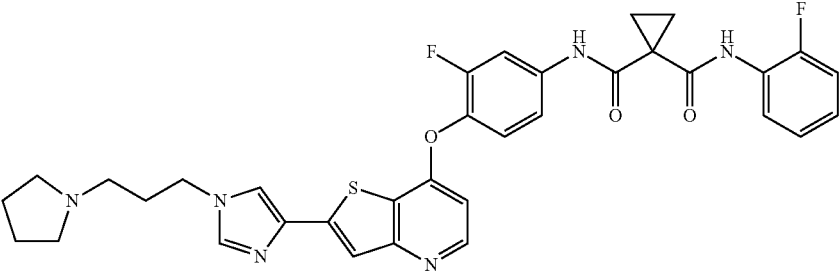 | a | a | A | A |
| 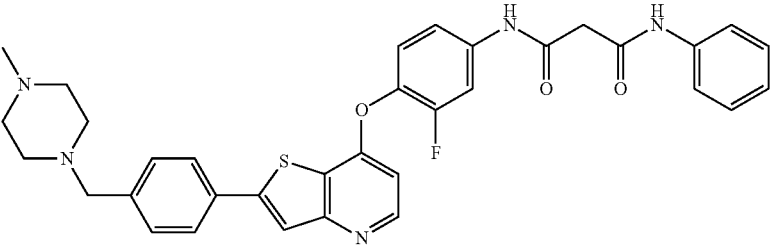 | a | a | B | A |

TABLE 22-continued

| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| *(structure)* | a | a | B | A |
| *(structure)* | a | a | B | A |
| *(structure)* | a | a | B | A |
| *(structure)* | a | a | A | A |
| *(structure)* | b | a | A | B |

TABLE 22-continued

| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| (structure) | b | a | B | A |
| (structure) | a | a | D | D |
| (structure) | a | a | B | B |
| (structure) | a | b | B | B |
| (structure) | a | a | A | A |

TABLE 22-continued

| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| (structure) | c | d | B | D |
| (structure) | b | a | B | A |
| (structure) | a | a | A | A |
| (structure) | c | d | B | B |
| (structure) | a | a | B | C |

TABLE 22-continued

| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| | b | a | A | A |
| | b | a | A | A |
| | a | a | A | A |
| | a | a | A | A |

TABLE 22-continued

| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| *structure* | a | a | A | A |
| *structure* | a | a | A | A |
| *structure* | b | a | B | B |
| *structure* | a | a | A | A |
| *structure* | a | a | A | A |

TABLE 22-continued
| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| 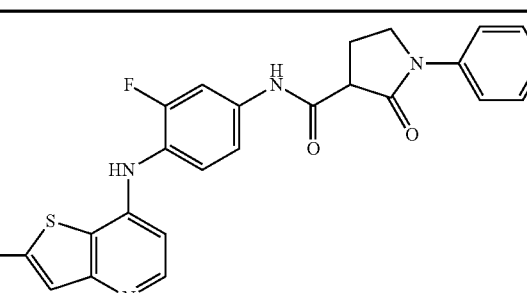 | b | c | A | B |
| 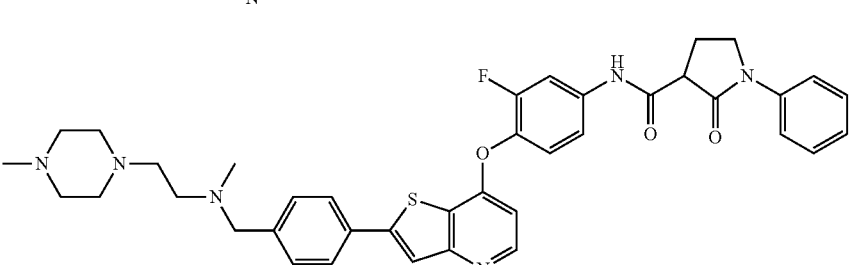 | a | a | B | A |
| 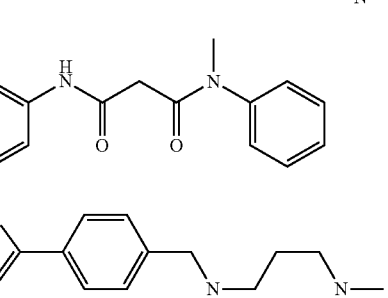 | a | a | A | A |
| 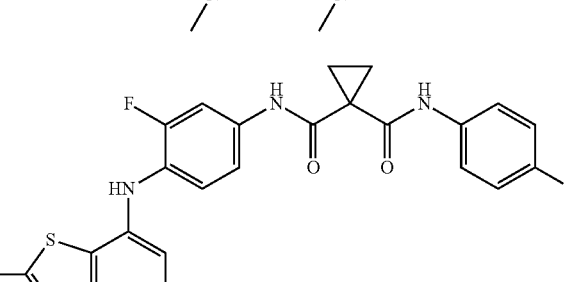 | a | a | A | A |
| 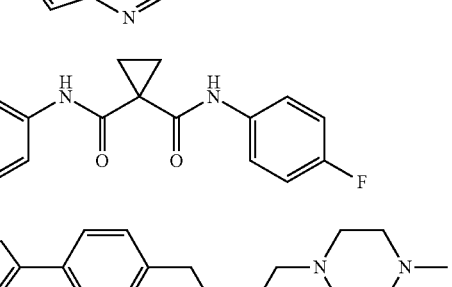 | a | a | B | A |

TABLE 22-continued
| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| 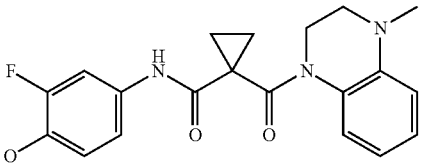 | d | a | B | B |
| 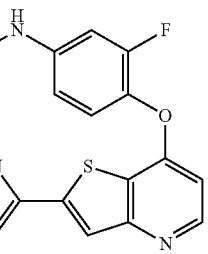 | d | b | A | B |
| 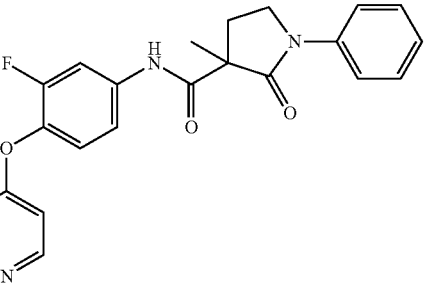 | b | c | B | B |
| 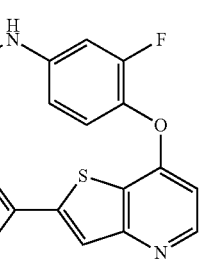 | a | a | A | A |
| 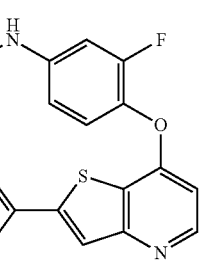 | a | a | A | A |

TABLE 22-continued

| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| | b | a | B | B |
| | a | a | B | A |
| | b | a | B | A |
| | a | a | D | B |

TABLE 22-continued

| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| (structure) | c | a | D | D |
| (structure) | b | a | D | B |
| (structure) | b | d | B | B |
| (structure) | b | a | B | B |

TABLE 22-continued

| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| (structure) | a | a | B | B |
| (structure) | a | a | B | A |
| (structure) | a | a | A | A |
| (structure) | a | a | A | A |

TABLE 22-continued

| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| 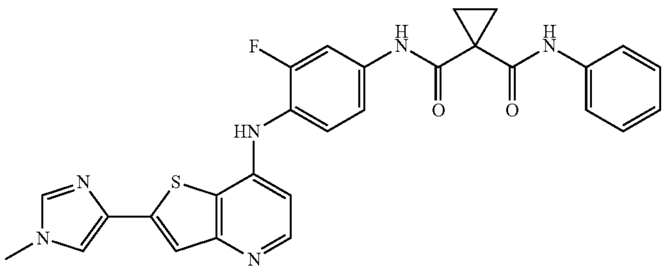 | a | b | A | A |
| | b | e | B | A |
| | b | c | A | B |
| 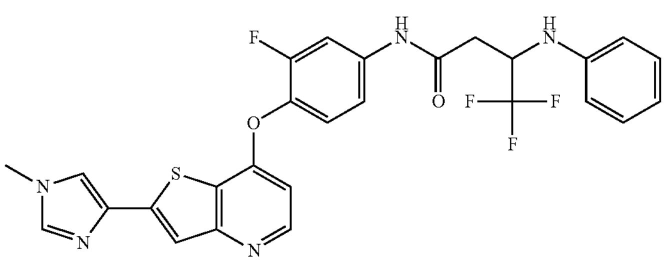 | d | b | B | B |
| | b | a | B | A |

TABLE 22-continued

| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| | a | a | A | A |
| | b | a | B | B |
| 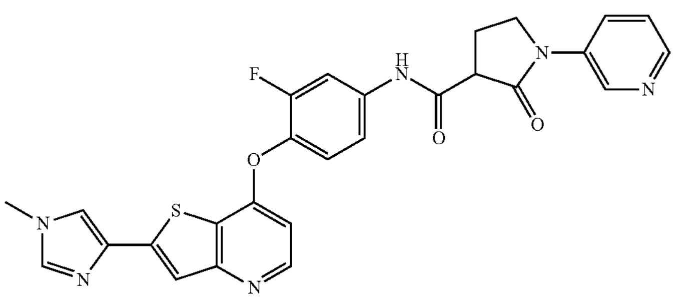 | c | c | B | B |
| | b | a | B | B |
| | a | a | B | A |

TABLE 22-continued

| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| | a | a | B | A |
| | a | a | A | A |
| 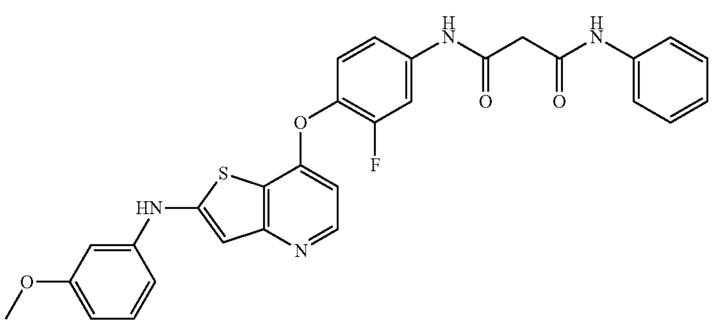 | b | d | B | B |
| | a | a | A | A |

TABLE 22-continued

| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| (structure 1) | a | a | A | A |
| (structure 2) | a | a | A | A |
| (structure 3) | c | d | D | D |
| (structure 4) | a | a | A | A |
| (structure 5) | a | b | A | A |

TABLE 22-continued
| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| 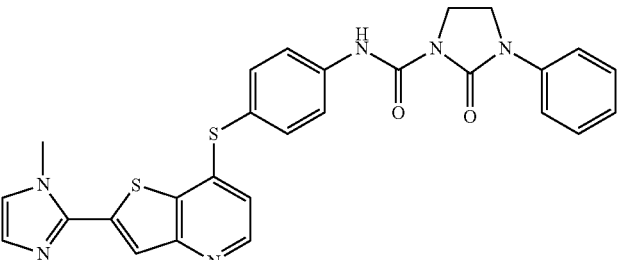 | a | b | A | A |
| 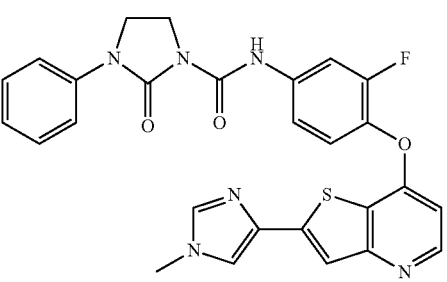 | a | a | A | A |
| 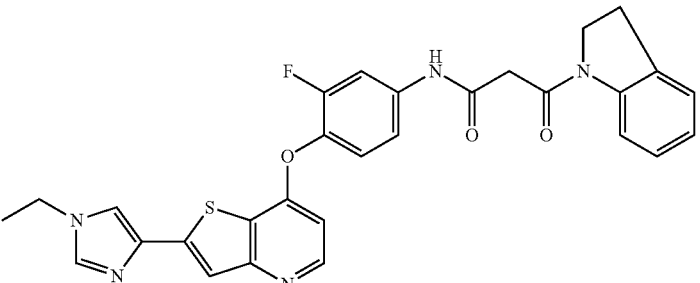 | a | a | A | A |
| 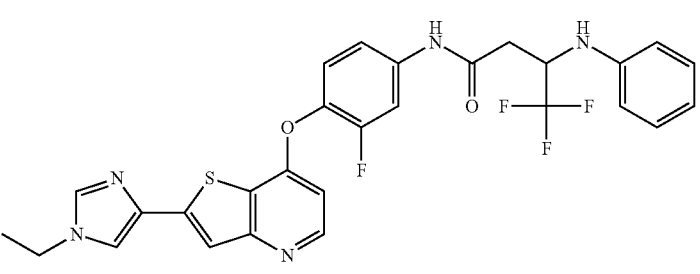 | b | b | B | B |
| 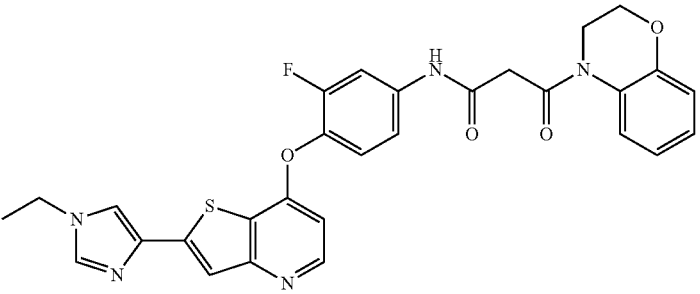 | a | a | A | A |

TABLE 22-continued

| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| (structure) | a | a | A | A |
| (structure) | a | a | A | A |
| (structure) | a | a | A | A |
| (structure) | b | a | A | A |

TABLE 22-continued

| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| | b | a | A | A |
| | b | a | A | A |
| | a | a | A | A |
| | a | a | A | A |
| | b | a | C | D |

TABLE 22-continued
| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| 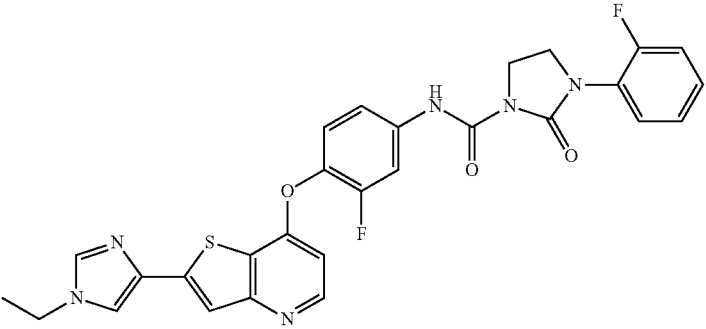 | a | a | A | A |
| 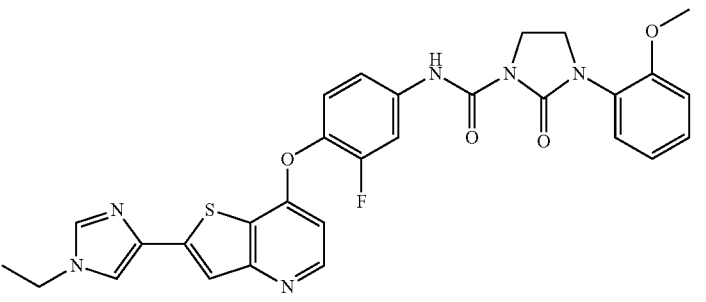 | a | a | B | A |
| 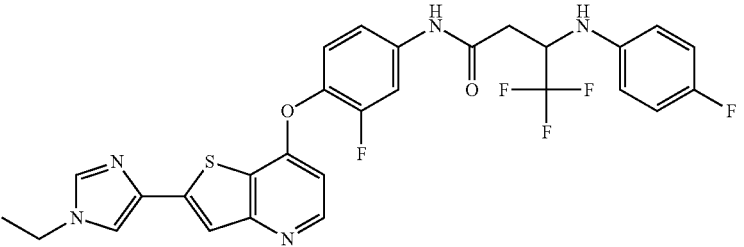 | c | b | D | B |
| 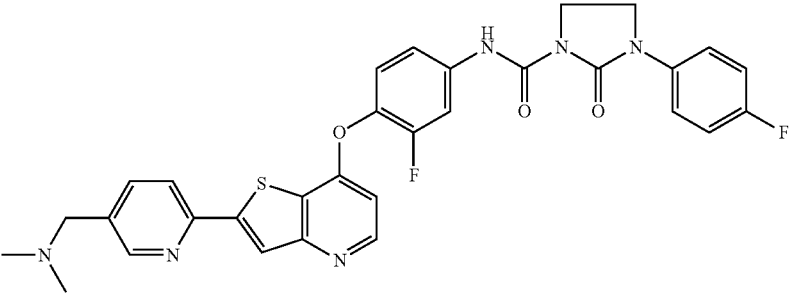 | a | a | A | A |
| 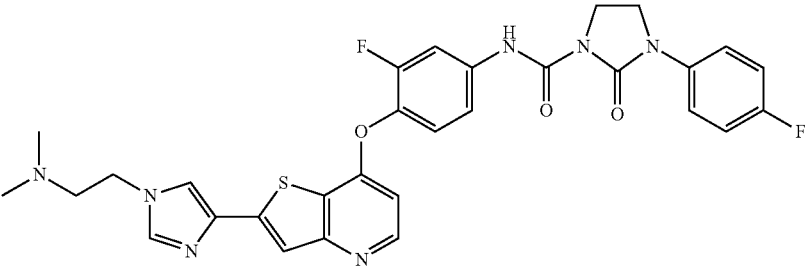 | a | a | A | A |

TABLE 22-continued

| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| | a | b | B | A |
| | a | c | D | D |
| | a | a | B | A |
| 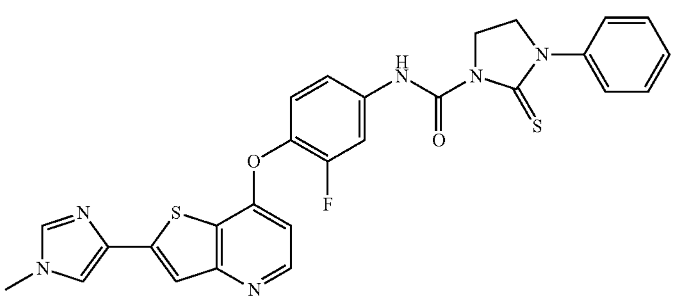 | d | d | D | D |
| | a | a | A | A |

TABLE 22-continued
| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| 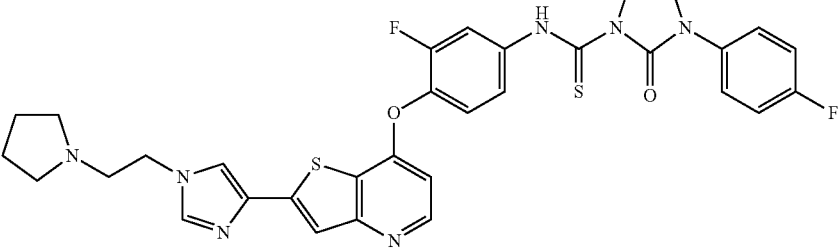 | a | a | A | A |
| 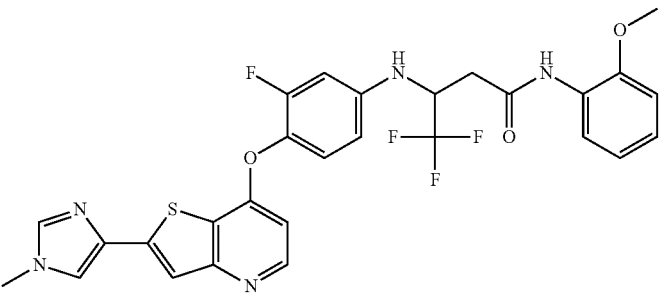 | d | a | B | D |
| 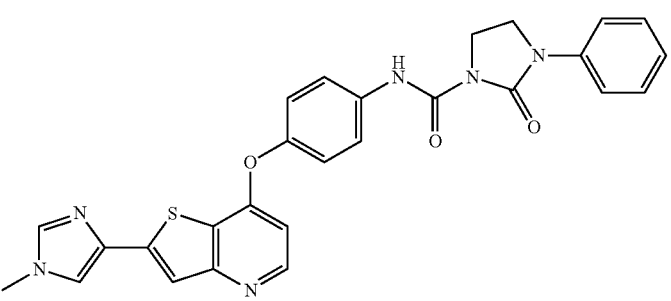 | a | b | A | A |
| 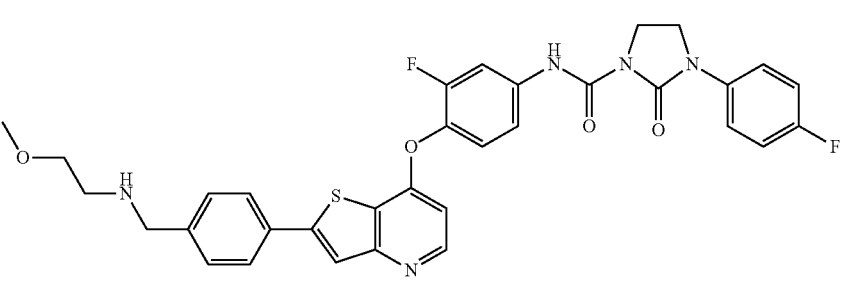 | a | a | A | A |

TABLE 22-continued
| STRUCTURE | CMET IC50 (mM) | VEGFR IC50 (mM) | A549 WOUND HEALING INHIB IC50 (mM) | DU145 SCATTERING INHIB IC50 (mM) |
|---|---|---|---|---|
| 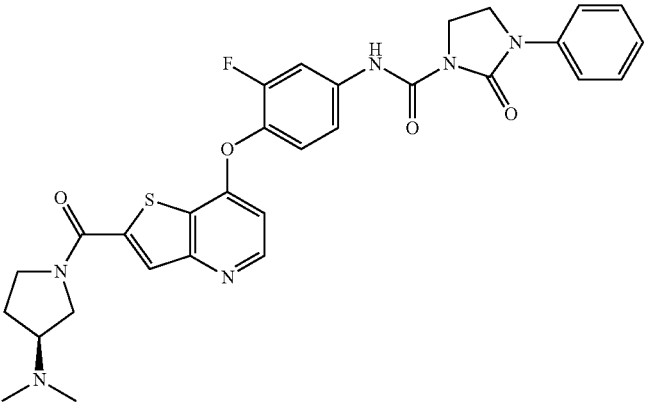 | a | a | A | A |
| 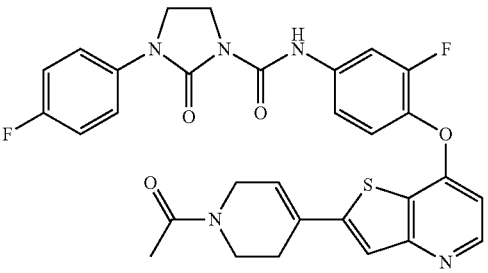 | a | a | A | A |
| 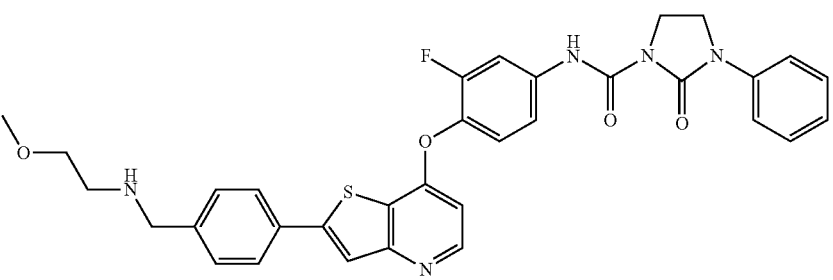 | a | a | A | A |
| 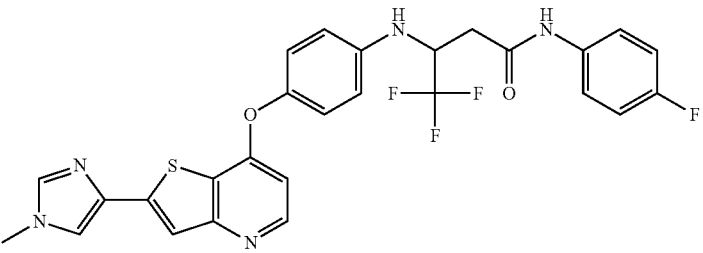 | b | a | B | B |

TABLE 23

Tumor Growth Inhibition by selected Compounds

| Structure | Dosage mg/kg (once daily) | Tumor type | Duration of experiment (days) | Tumor Growth Inhibition (%) |
| --- | --- | --- | --- | --- |
| (structure 1) | 75 (p.o.) | U87MG | 14 | b |
| (structure 2) | 75 (p.o.) | U87MG | 14 | b |
| (structure 3) | 20 (p.o.) | A549 | 14 | b |
| (structure 4) | 40 (p.o.) | A549 | 14 | b |
| (structure 5) | 20 (p.o.) | MV4-11 | 14 | b |

TABLE 23-continued

Tumor Growth Inhibition by selected Compounds

| Structure | Dosage mg/kg (once daily) | Tumor type | Duration of experiment (days) | Tumor Growth Inhibition (%) |
|---|---|---|---|---|
| 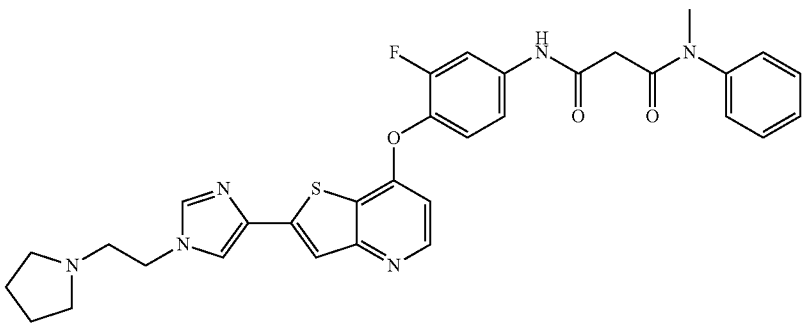 | 30 (i.p.) | Colo265 | 14 | b |

What is claimed is:

1. A method of inhibiting VEGF receptor signaling and HGF receptor signaling in a patient, the method comprising administering to said patient an inhibitory amount of a compound of formula A or a composition thereof

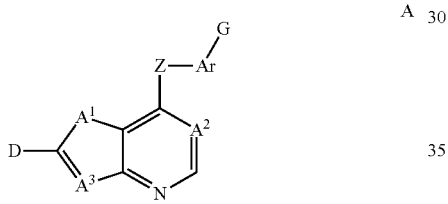

or a pharmaceutically acceptable salt, or hydrate thereof, wherein,

D is selected from the group consisting of $R^7$ and $R^{21}$, wherein $R^7$ is selected from the group consisting of —$NR^{42}R^{43}$, heteroaryl and 5-10 membered heterocyclyl, and the aforementioned $R^7$ groups are optionally substituted by 1 to 5 $R^{38}$, or $R^7$ is -heterocycle, optionally substituted with 1 to 3 independently selected $Y^2$ groups, wherein each $Z^3$ is selected from the group consisting of H, F and ($C_1$-$C_6$)alkyl, or two $Z^3$ groups on adjacent carbon atoms are selected together to optionally form a carbocycle;

each $Y^2$ is selected from the group consisting of halogen, cyano, nitro, tetrazolyl, guanidino, amidino, methylguanidino, azido, —C(O)$Z^7$, —OC(O)$NH_2$, —OC(O)$NHZ^7$, —OC(O)$NZ^7Z^8$, —NHC(O)$Z^7$, —NHC(O)$NH_2$, —NHC(O)$NHZ^7$, —NHC(O)$NZ^7Z^8$, —C(O)OH, —C(O)$OZ^7$, —C(O)$NH_2$, —C(O)$NHZ^7$, —C(O)$NZ^7Z^8$, —P(O)$_3H_2$, —P(O)$_3(Z^7)_2$, —S(O)$_3H$, —S(O)$Z^7$, —S(O)$_2Z^7$, —S(O)$_3Z^7$, -$Z^7$, —$OZ^7$, —OH, —$NH_2$, —$NHZ^7$, —$NZ^7Z^8$, —C(=NH)$NH_2$, —C(=NOH)$NH_2$, —N-morpholino, ($C_2$-$C_6$)alkenyl, ($C_2$-$C_6$)alkynyl, ($C_1$-$C_6$)haloalkyl, ($C_2$-$C_6$)haloalkenyl, ($C_2$-$C_6$)haloalkynyl, ($C_1$-$C_6$)haloalkoxy, —($CZ^9Z^{10}$)$_r$$NH_2$, —($CZ^9Z^{10}$)$_r$$NHZ^3$, —($CZ^9Z^{10}$)$_r$$NZ^7Z^8$, —$X^6$($CZ^9Z^{10}$)$_r$—($C_3$-$C_8$)cycloalkyl, —$X^6$($CZ^9Z^{10}$)$_r$—($C_5$-$C_8$)cycloalkenyl, —$X^6$($CZ^9Z^{10}$)$_r$-aryl and —$X^6$($CZ^9Z^{10}$)$_r$-heterocycle, wherein r is 1, 2, 3 or 4;

$X^6$ is selected from the group consisting of O, S, NH, —C(O)—, —C(O)NH—, —C(O)O—, —S(O)—, —S(O)$_2$— and —S(O)$_3$—;

$Z^7$ and $Z^8$ are independently selected from the group consisting of an alkyl of 1 to 12 carbon atoms, an alkenyl of 2 to 12 carbon atoms, an alkynyl of 2 to 12 carbon atoms, a cycloalkyl of 3 to 8 carbon atoms, a cycloalkenyl of 5 to 8 carbon atoms, an aryl of 6 to 14 carbon atoms, a heterocycle of 5 to 14 ring atoms, an aralkyl of 7 to 15 carbon atoms, and a heteroaralkyl of 5 to 14 ring atoms, or $Z^7$ and $Z^8$ together may optionally form a heterocycle;

$Z^9$ and $Z^{10}$ are independently selected from the group consisting of H, F, a ($C_1$-$C_{12}$)alkyl, a ($C_6$-$C_{14}$)aryl, a ($C_5$-$C_{14}$)heteroaryl, a ($C_7$-$C_{15}$)aralkyl and a ($C_5$-$C_{14}$)heteroaralkyl, or $Z^9$ and $Z^{10}$ are taken together form a carbocycle, or two $Z^9$ groups on adjacent carbon atoms are taken together to form a carbocycle; or any two $Y^2$ groups attached to adjacent carbon atoms may be taken together to be —O[C($Z^9$)($Z^{10}$)]$_r$O or —O[C($Z^9$)($Z^{10}$)]$_{r+1}$, or any two $Y^2$ groups attached to the same or adjacent carbon atoms may be selected together to form a carbocycle or heterocycle; and wherein, any of the above-mentioned substituents comprising a $CH_3$ (methyl), $CH_2$ (methylene), or CH (methine) group which is not attached to a halogen, SO or $SO_2$ group or to a N, O or S atom optionally bears on said group a substituent selected from hydroxy, halogen, ($C_1$-$C_4$)alkyl, ($C_1$-$C_4$)alkoxy and an —N[($C_1$-$C_4$)alkyl][($C_1$-$C_4$)alkyl];

$R^{21}$ is the group defined by -($Z^{11}$)-($Z^{12}$)$_m$-($Z^{13}$)$_{m1}$, wherein $Z^{11}$ is heterocyclyl, when m and m1 are 0, or heterocyclylene, when either m or m1 are 1;

$Z^{12}$ is selected from the group consisting of OC(O), OC(S) and C(O);

$Z^{13}$ is selected from the group consisting of heterocyclyl, aralkyl, N(H)$R^{52}$, ($C_1$-$C_3$)alkyl, —$OR^{52}$, halo, S(O)$_2$$R^{56}$, ($C_1$-$C_3$)hydroxyalkyl and ($C_1$-$C_3$)haloalkyl;

m is 0 or 1;

m1 is 0 or 1;

$R^{52}$ is selected from the group consisting of H, —($CH_2$)$_q$S(O)$_2$$R^{54}$, —($C_1$-$C_6$)alkyl-$NR^{53}R^{53}$, ($C_1$-$C_3$)alkyl, —($CH_2$)$_q$$OR^{53}$, —C(O)$R^{54}$ and —C(O)$OR^{53}$;

each $R^{53}$ is independently $(C_1-C_3)$alkyl;
$R^{54}$ is $(C_1-C_3)$alkyl or $N(H)R^{53}$;
$R^{56}$ is selected from the group consisting of $NH_2$, $(C_1-C_3)$ alkyl and $OR^{52}$;
$A^1$ is —S—;
$A^2$ is CR, wherein R is —H;
$A^3$ is CH;
Ar is a group of the formula C wherein,
$A^4$, $A^5$, $A^6$ and $A^7$ are —CH—;
$R^2$ at each occurrence is independently selected from the group consisting of —H, halogen, trihalomethyl, —CN, —$NO_2$, —$NH_2$, —$OR^3$, —$NR^3R^4$, —$S(O)_{0-2}R^3$, —$S(O)_2NR^3R^3$, —$C(O)OR^3$, —$C(O)NR^3R^3$, —$N(R^3)SO_2R^3$, —$N(R^3)C(O)R^3$, —$N(R^3)CO_2R^3$, —$C(O)R^3$, $C_1$-$C_4$ alkoxy, $C_1$-$C_4$ alkylthio, —$O(CH_2)_n$aryl, —$O(CH_2)_n$heteroaryl, —$(CH_2)_{0-5}$(aryl), —$(CH_2)_{0-5}$(heteroaryl), $C_1$-$C_6$ alkyl, $C_2$-$C_6$ alkenyl, $C_2$-$C_6$ alkynyl, —$CH_2(CH_2)_{0-4}$-$T^2$, wherein $T^2$ is selected from the group consisting of —OH, —OMe, —OEt, —$NH_2$, —NHMe, —$NMe_2$, —NHEt and —$NEt_2$, and wherein the aryl, heteroaryl, $C_1$-$C_6$ alkyl, $C_2$-$C_6$ alkenyl, and $C_2$-$C_6$ alkynyl are optionally substituted; and
q is an integer from 0 to 4;
G is selected from the group consisting of -continued wherein any methylene group is independently optionally substituted with $R^{25}$, wherein
$R^{25}$ is selected from the group consisting of halogen, trihalomethyl, —CN, —$NO_2$, —$NH_2$, —$OR^3$, —$NR^3R^4$, —$S(O)_{0-2}R^3$, —$SO_2NR^3R^3$, —$CO_2R^3$, —$C(O)NR^3R^3$, —N(R$^3$)SO$_2$R$^3$, —N(R$^3$)C(O)R$^3$, —N(R$^3$)CO$_2$R$^3$, —C(O)R$^3$, an optionally substituted aryl, an optionally substituted arylalkyl, an optionally substituted heteroarylalkyl, and an optionally substituted (C$_1$-C$_6$)alkyl, two R$^{25}$, together with the carbon or carbons to which they are attached, can combine to form a three- to seven-membered alicyclic or heteroalicyclic, and R$^9$ is selected from the group consisting of a C$_{1-6}$ alkyl on which one or more hydrogen atoms are optionally substituted by —R$^{24}$, -T$^1$—R$^{15}$, or —NR$^{16}$R$^{17}$, a —N(R$^{18}$)(R$^{19}$) moiety and a saturated or unsaturated three- to eight-membered carbocyclic or heterocyclic group which is optionally substituted by a C$_{1-6}$ alkyl, a C$_{1-6}$ alkoxy, a halogen atom, nitro, a trifluoromethyl, a C$_{1-6}$ alkoxy carbonyl, cyano, a cyano C$_{1-6}$ alkyl, a C$_{1-6}$ alkylthio, a phenoxy, an acetyl, or a saturated or unsaturated five- or six-membered heterocyclyl ring wherein, when the three- to eight-membered carbocyclic or heterocyclic group is substituted by two C$_{1-6}$ alkyl groups, the two alkyl groups may combine together to form an alkylene chain, or the three- to eight-membered carbocyclic or heterocyclic group may be a bicyclic group condensed with another saturated or unsaturated three- to eight-membered carbocyclic or heterocyclic group, wherein T$^1$ is selected from the group consisting of —O—, —S— and —NH—;

R$^{24}$ represents a saturated or unsaturated three- to eight-membered carbocyclic or heterocyclic group;

R$^{15}$, R$^{16}$, and R$^{17}$, which may be the same or different, represent a C$_{1-6}$ alkyl or a saturated or unsaturated three- to eight-membered carbocyclic or heterocyclic group; wherein the three- to eight-membered carbocyclic or heterocyclic group represented by R$^{24}$, R$^{15}$, R$^{16}$, and R$^{17}$ is optionally substituted by a C$_{1-6}$ alkyl, a C$_{1-6}$ alkoxy, a halogen atom, nitro, a trifluoromethyl, a C$_{1-6}$ alkoxy carbonyl, a cyano, a cyano C$_{1-6}$ alkyl, a C$_{1-6}$ alkylthio, a phenoxy, an acetyl, or a saturated or unsaturated five- or six-membered heterocyclyl ring; and wherein when the three- to eight-membered carbocyclic or heterocyclic group is substituted by two C$_{1-6}$ alkyl groups, the two alkyl groups may combine together to form an alkylene chain; and wherein the three- to eight-membered carbocyclic or heterocyclic group may be a bicyclic group condensed with another saturated or unsaturated three- to eight-membered carbocyclic or heterocyclic group; and R$^{18}$ and R$^{19}$, which may be the same or different, represent (1) a hydrogen atom, (2) a C$_{1-6}$ alkyl which is optionally substituted by a C$_{1-6}$ alkoxy, a C$_{1-6}$ alkylthio, or a saturated or unsaturated three- to eight-membered carbocyclic or heterocyclic group in which the three- to eight-membered carbocyclic or heterocyclic group is optionally substituted by a C$_{1-6}$ alkyl, a C$_{1-6}$ alkoxy, a halogen atom, nitro, a trifluoromethyl, a C$_{1-6}$ alkoxy carbonyl, cyano, a cyano C$_{1-6}$ alkyl, a C$_{1-6}$ alkylthio, a phenoxy, an acetyl, or a saturated or unsaturated five- or six-membered heterocyclyl ring and wherein when the three- to eight-membered carbocyclic or heterocyclic group is substituted by two C$_{1-6}$ alkyl groups, the two alkyl groups may combine together to form an alkylene chain, or the three- to eight-membered carbocyclic or heterocyclic group may be a bicyclic group condensed with another saturated or unsaturated three- to eight-membered carbocyclic or heterocyclic group, or (3) a saturated or unsaturated three- to eight-membered carbocyclic or heterocyclic group which is optionally substituted by a C$_{1-6}$ alkyl, a C$_{1-6}$ alkoxy, a halogen atom, nitro, a trifluoromethyl, a C$_{1-6}$ alkoxy carbonyl, cyano, a cyano C$_{1-6}$ alkyl, a C$_{1-6}$ alkylthio, a phenoxy, an acetyl, or a saturated or unsaturated five- or six-membered heterocyclyl ring and in which, when the three to eight-membered carbocyclic or heterocyclic group is substituted by two C$_{1-6}$ alkyl groups, the two alkyl groups may combine together to form an alkylene chain, or the three- to eight-membered carbocyclic or heterocyclic group may be a bicyclic group condensed with another saturated or unsaturated three- to eight-membered carbocyclic or heterocyclic group;

X and X$^1$ are each independently selected from the group consisting of —H, halogen, cyano, nitro, C$_1$-C$_6$ alkyl, or X and X$^1$ taken together with the atom to which they are attached, form a C$_3$-C$_7$ cycloalkyl;

M$^1$ represents —C(R$^{26}$)(R$^{27}$)—, wherein

R$^{26}$ and R$^{27}$ are independently selected from the group consisting of a hydrogen atom, a C$_{1-4}$ alkyl, a C$_{1-4}$ alkoxy and —N(R$^{12}$), wherein R$^{12}$ is a hydrogen atom or a C$_{1-4}$ alkyl;

R$^{13}$ is selected from the group consisting of —H, —CN, —NO$_2$, —NH$_2$, —OR$^3$, —NR$^3$R$^4$, —S(O)$_{0-2}$R$^3$, —S(O)$_2$NR$^3$R$^3$, —C(O)OR$^3$, —C(O)NR$^3$R$^3$, —N(R$^3$)SO$_2$R$^3$, —N(R$^3$)C(O)R$^3$, —N(R$^3$)CO$_2$R$^3$, —C(O)R$^3$, —C(O)SR$^3$, C$_1$-C$_4$ alkoxy, C$_1$-C$_4$ alkylthio, —O(CH$_2$)$_n$aryl, —O(CH$_2$)$_n$heteroaryl, —(CH$_2$)$_{0-5}$(aryl), —(CH$_2$)$_{0-5}$(heteroaryl), C$_1$-C$_6$ alkyl, C$_2$-C$_6$ alkenyl, C$_2$-C$_6$ alkynyl, —CH$_2$(CH$_2$)$_{0-4}$-T$^2$, an optionally substituted C$_{1-4}$ alkylcarbonyl, and a saturated or unsaturated three- to seven-membered carboxylic or heterocyclic group, wherein T$^2$ is selected from the group consisting of —OH, —OMe, —OEt, —NH$_2$, —NHMe, —NMe$_2$, —NHEt and —NEt$_2$, and wherein the aryl, heteroaryl, C$_1$-C$_6$ alkyl, C$_2$-C$_6$ alkenyl, and C$_2$-C$_6$ alkynyl are optionally substituted;

two R$^{13}$, together with the atom or atoms to which they are attached, can combine to form a heteroalicyclic optionally substituted with between one and four of R$^{60}$, wherein the heteroalicyclic can have up to four annular heteroatoms, and the heteroalicyclic can have an aryl or heteroaryl fused thereto, in which case the aryl or heteroaryl is optionally substituted with an additional one to four of R$^{60}$;

each R$^3$ is independently selected from the group consisting of —H and R$^4$;

R$^4$ is selected from the group consisting of a (C$_1$-C$_6$)alkyl, an aryl, a lower arylalkyl, a heterocyclyl and a lower heterocyclylalkyl, each of which is optionally substituted, or R$^3$ and R$^4$, taken together with a common nitrogen to which they are attached, form an optionally substituted five- to seven-membered heterocyclyl, the optionally substituted five- to seven-membered heterocyclyl optionally containing at least one additional annular heteroatom selected from the group consisting of N, O, S and P;

R$^{60}$ is selected from the group consisting of —H, halogen, trihalomethyl, —CN, —NO$_2$, —NH$_2$, —OR$^3$, —NR$^3$R$^4$, —S(O)$_{0-2}$R$^3$, —SO$_2$NR$^3$R$^3$, —CO$_2$R$^3$, —C(O)NR$^3$R$^3$, —N(R$^3$)SO$_2$R$^3$, —N(R$^3$)C(O)R$^3$, —N(R$^3$)CO$_2$R$^3$, —C(O)R$^3$, an optionally substituted (C$_1$-C$_6$)alkyl, an optionally substituted aryl, an optionally substituted heteroarylalkyl and an optionally substituted arylalkyl;

two R$^{60}$, when attached to a non-aromatic carbon, can be oxo;

Q is selected from the group consisting of phenyl, napthyl, 1,2,3,4-tetrahydronaphthyl, indanyl, benzodioxanyl, benzofuranyl, phenazinyl, phenothiazinyl, phenoxazinyl, tetrahydroisoquinolyl, pyrrolyl, pyrazolyl, pyrazolidinyl, imidazolyl, imidazolinyl, imidazolidinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, thiazolyl, thiazolinyl, thiazolidinyl, isothiazolyl, isothiazolidinyl, indolyl, isoindolyl, indolinyl, isoindolinyl, octahydroindolyl, octahydroisoindolyl, quinolyl, isoquinolyl, benzimidazolyl, thiadiazolyl, benzopyranyl, benzothiazolyl, benzoxazolyl, furyl, thienyl, benzothienyl, and oxadiazolyl, each optionally substituted with between one and four of $R^{20}$;

$R^{20}$ is selected from the group consisting of —H, halogen, trihalomethyl, —CN, —$NO_2$, —$NH_2$, —$OR^3$, —$OCF_3$, —$NR^3R^4$, —$S(O)_{0-2}R^3$, —$S(O)_2NR^3R^3$, —$C(O)OR^3$, —$C(O)NR^3R^3$, —$N(R^3)SO_2R^3$, —$N(R^3)C(O)R^3$, —$N(R^3)C(O)OR^3$, —$C(O)R^3$, —$C(O)SR^3$, $C_1$-$C_4$ alkoxy, $C_1$-$C_4$ alkylthio, —$O(CH_2)_n$aryl, —$O(CH_2)_n$heteroaryl, —$(CH_2)_{0-5}$(aryl), —$(CH_2)_{0-5}$(heteroaryl), $C_1$-$C_6$ alkyl, $C_2$-$C_6$ alkenyl, $C_2$-$C_6$ alkynyl, —$CH_2$($CH_2$)$_{0-4}$-$T^2$, an optionally substituted $C_{1-4}$ alkylcarbonyl, $C_{1-4}$ alkoxy, an amino optionally substituted by $C_{1-4}$ alkyl optionally substituted by $C_{1-4}$ alkoxy and a saturated or unsaturated three- to seven-membered carboxyclic or heterocyclic group, wherein $T^2$ is selected from the group consisting of —OH, —OMe, —OEt, —$NH_2$, —NHMe, —$NMe_2$, —NHEt and —$NEt_2$, and wherein the aryl; heteroaryl, $C_1$-$C_6$ alkyl, $C_2$-$C_6$ alkenyl, and $C_2$-$C_6$ alkynyl are optionally substituted;

each $R^{38}$ is independently selected from halo, cyano, nitro, trifluoromethoxy, trifluoromethyl, azido, —$C(O)R^{40}$, —$C(O)OR^{40}$, —$OC(O)R^{40}$, —$OC(O)OR^{40}$, —$NR^{36}C(O)R^{39}$, —$C(O)NR^{36}R^{39}$, —$NR^{36}R^{39}$, —$OR^{37}$, —$SO_2NR^{36}R^{39}$, $C_1$-$C_6$ alkyl, —$(CH_2)_jO(CH_2)_i$$NR^{36}R^{39}$, —$(CH_2)_nO(CH_2)_iOR^{37}$, —$(CH_2)_nOR^{37}$, —$S(O)_j(C_1$-$C_6$ alkyl), —$(CH_2)_n(C_6$-$C_{10}$ aryl), —$(CH_2)_n$(5-10 membered heterocyclyl); —$C(O)(CH_2)_n(C_6$-$C_{10}$ aryl), —$(CH_2)_nO(CH_2)_j(C_6$-$C_{10}$ aryl), —$(CH_2)_nO(CH_2)_i$ (5-10 membered heterocyclyl), —$C(O)(CH_2)_n$(5-10 membered heterocyclyl), —$(CH_2)_jNR^{39}(CH_2)_iNR^{36}R^{39}$, —$(CH_2)_jNR^{39}CH_2C(O)NR^{36}R^{39}$, —$(CH_2)_jNR^{39}(CH_2)_iNR^{37}C(O)R^{40}$, —$(CH_2)_jNR^{39}(CH_2)_nO(CH_2)_nOR^{37}$, —$(CH_2)_jNR^{39}(CH_2)_jS(O)_j(C_1$-$C_6$ alkyl), —$(CH_2)_jNR^{39}(CH_2)_nR^{36}$, —$SO_2(CH_2)_n(C_6$-$C_{10}$ aryl), —$SO_2(CH_2)_n$(5-10 membered heterocyclyl), —$(CH_2)_nNR^{36}R^{39}$, —$NR^{37}SO_2NR^{36}R^{39}$, $SO_2R^{36}$, $C_2$-$C_6$ alkenyl, $C_3$-$C_{10}$ cycloalkyl and $C_1$-$C_6$ alkylamino, wherein j is an integer ranging from 0 to 2, n is an integer ranging from 0 to 6, i is an integer ranging from 2 to 6, and the alkyl, aryl and heterocyclyl moieties of the foregoing $R^{38}$ groups are optionally substituted by one or more substituents independently selected from halo, cyano, nitro, trifluoromethyl, azido, —OH, —$C(O)R^{40}$, —$C(O)OR^{40}$, —$OC(O)R^{40}$, —$OC(O)OR^{40}$, —$NR^{36}C(O)R^{39}$, —$C(O)NR^{36}R^{39}$, —$(CH_2)_nNR^{36}R^{39}$, $C_1$-$C_6$ alkyl, $C_3$-$C_{10}$ cycloalkyl, —$(CH_2)_n(C_6$-$C_{10}$ aryl), —$(CH_2)_n$(5-10 membered heterocyclyl), —$(CH_2)_nO(CH_2)_nOR^{37}$, and —$(CH_2)_nOR^{37}$, wherein n is an integer ranging from 0 to 6 and i is an integer ranging from 2 to 6;

each $R^{36}$ and $R^{39}$ is independently selected from the group consisting of H, —OH, $C_1$-$C_6$ alkyl, $C_3$-$C_{10}$ cycloalkyl, —$(CH_2)_n(C_6$-$C_{10}$ aryl), —$(CH_2)_n$(5-10 membered heterocyclyl), —$(CH_2)_nO(CH_2)_iOR^{37}$, —$(CH_2)_nCN$($CH_2)_nOR^{37}$, —$(CH_2)_nCN(CH_2)_nR^{37}$, and —$(CH_2)_nOR^{37}$, wherein n is an integer ranging from 0 to 6 and i is an integer ranging from 2 to 6, and the alkyl, aryl and heterocyclyl moieties of the foregoing $R^{36}$ and $R^{39}$ groups are optionally substituted by one or more substituents independently selected from —OH, halo, cyano, nitro, trifluoromethyl, azido, —$C(O)R^{40}$, —$C(O)OR^{40}$, —$CO(O)R^{40}$, —$OC(O)OR^{40}$, —$NR^{37}C(O)R^{41}$, —$C(O)NR^{37}R^{41}$, —$NR^{37}R^{41}$, —$C_1$-$C_6$ alkyl, —$(CH_2)_n(C_6$-$C_{10}$ aryl), —$(CH_2)_n$(5 to 10 membered heterocyclyl), —$(CH_2)_nO(CH_2)_nOR^{37}$, and —$(CH_2)_nOR^{37}$, wherein n is an integer ranging from 0 to 6 and i is an integer ranging from 2 to 6, with the proviso that when $R^{36}$ and $R^{39}$ are both attached to the same nitrogen, then $R^{36}$ and $R^{39}$ are not both bonded to the nitrogen directly through an oxygen;

each $R^{40}$ is independently selected from H, $C_1$-$C_{10}$ alkyl, —$(CH_2)_n(C_6$-$C_{10}$ aryl), $C_3$-$C_{10}$ cycloalkyl, and —$(CH_2)_n$(5-10 membered heterocyclyl), wherein n is an integer ranging from 0 to 6;

each $R^{37}$ and $R^{41}$ is independently selected from H, $OR^{36}$, $C_1$-$C_6$ alkyl and $C_3$-$C_{10}$ cycloalkyl;

$R^{42}$ and $R^{43}$ taken together with the nitrogen to which they are attached form a $C_5$-$C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring, wherein said $C_5$-$C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring are optionally substituted by 1 to 5 $R^{44}$ substituents, with the proviso that $R^{42}$ and $R^{43}$ are not both bonded to the nitrogen directly through an oxygen;

each $R^{44}$ is independently selected from the group consisting of halo, cyano, nitro, trifluoromethoxy, trifluoromethyl, azido, —$C(O)R^{40}$, —$C(O)OR^{40}$, —$OC(O)R^{40}$, —$OC(O)OR^{40}$, —$NR^{36}C(O)R^{39}$, —$C(O)NR^{36}R^{39}$, —$NR^{36}R^{39}$, —$OR^{37}$, —$SO_2NR^{36}R^{39}$, —$SO_2R^{36}$, —$NR^{36}SO_2R^{39}$, —$NR^{36}SO_2NR^{37}R^{41}$, $C_1$-$C_6$ alkyl, $C_2$-$C_6$ alkenyl, $C_2$-$C_6$ alkynyl, $C_3$-$C_{10}$ cycloalkyl, —$C_1$-$C_6$ alkylamino, —$(CH_2)_jO(CH_2)_iNR^{36}R^{39}$, —$(CH_2)_nO(CH_2)_iOR^{37}$, —$(CH_2)_nOR^{37}$, —$S(O)_j(C_1$-$C_6$ alkyl), —$(CH_2)_n(C_6$-$C_{10}$ aryl), —$(CH_2)_n$(5-10 membered heterocyclyl), —$C(O)(CH_2)_n(C_6$-$C_{10}$ aryl), —$(CH_2)_nO(CH_2)_j(C_6$-$C_{10}$ aryl), —$(CH_2)_nO(CH_2)_i$ (5 to 10 membered heterocyclyl), —$C(O)(CH_2)_n$(5 to 10 membered heterocyclyl), —$(CH_2)_jNR^{39}(CH_2)_iNR^{36}R^{39}$, —$(CH_2)_jNR^{39}CH_2C(O)NR^{36}R^{39}$, —$(CH_2)_jNR^{39}(CH_2)_iNR^{37}C(O)R^{40}$, —$(CH_2)_jNR^{39}(CH_2)_nO(CH_2)_iOR^{37}$, —$(CH_2)_iNR^{39}(CH_2)_iS(O)_j(C_1$-$C_6$ alkyl), —$(CH_2)_jNR^{39}(CH_2)_nR^{36}$, —$SO_2(CH_2)_n(C_6$-$C_{10}$ aryl), and —$SO_2(CH_2)_n$(5 to 10 membered heterocyclyl) wherein, j is an integer from 0 to 2, n is an integer from 0 to 6 and i is an integer ranging from 2 to 6, and the alkyl, aryl and heterocyclyl moieties of the foregoing $R^{44}$ groups are optionally substituted by 1 or more substituents independently selected from the group consisting of halo, cyano, nitro, trifluoromethyl, azido, —OH, —$C(O)R^{40}$, —$C(O)OR^{40}$, —$OC(O)R^{40}$, —$OC(O)OR^{40}$, —$NR^{36}C(O)R^{39}$, —$C(O)NR^{36}R^{39}$, —$(CH_2)_nNR^{36}R^{39}$, —$SO_2R^{36}$, —$SO_2NR^{36}R^{39}$, $C_1$-$C_6$ alkyl, $C_3$-$C_{10}$ cycloalkyl, —$(CH_2)_n(C_6$-$C_{10}$ aryl), —$(CH_2)_n$(5 to 10 membered heterocyclyl), —$(CH_2)_nO(CH_2)_iOR^{37}$ and —$(CH_2)_nOR^{37}$, wherein n is an integer from 0 to 6 and i is an integer from 2 to 6; and Z is selected from the group consisting of —O— and —$S(O)_{0-2}$.

2. The method according to claim 1, wherein

D is selected from the group consisting of $R^7$, wherein $R^7$ is selected from the group consisting of $-NR^{42}R^{43}$, heteroaryl and 5-10 membered heterocyclyl, and the aforementioned $R^7$ groups are optionally substituted by 1 to 5 $R^{38}$;

$A^1$ is $-S-$;

$A^2$ is CR, wherein R is $-H$;

$A^3$ is CH;

Ar is a group of the formula C,

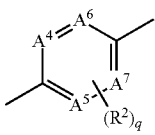

wherein, $A^4$, $A^5$, $A^6$ and $A^7$ are $-CH-$;

$R^2$ at each occurrence is independently selected from the group consisting of $-H$, halogen, trihalomethyl, $-CN$, $-NO_2$, $-NH_2$, $-OR^3$, $-NR^3R^4$, $-S(O)_{0-2}R^3$, $-S(O)_2NR^3R^3$, $-C(O)OR^3$, $-C(O)NR^3R^3$, $-N(R^3)SO_2R^3$, $-N(R^3)C(O)R^3$, $-N(R^3)CO_2R^3$, $-C(O)R^3$, $C_1$-$C_4$ alkoxy, $C_1$-$C_4$ alkylthio, $-O(CH_2)_n$aryl, $-O(CH_2)_n$heteroaryl, $-(CH_2)_{0-5}$(aryl), $-(CH_2)_{0-5}$(heteroaryl), $C_1$-$C_6$ alkyl, $C_2$-$C_6$ alkenyl, $C_2$-$C_6$ alkynyl, $-CH_2(CH_2)_{0-4}$-$T^2$, wherein $T^2$ is selected from the group consisting of $-OH$, $-OMe$, $-OEt$, $-NH_2$, $-NHMe$, $-NMe_2$, $-NHEt$ and $-NEt_2$, and wherein the aryl, heteroaryl, $C_1$-$C_6$ alkyl, $C_2$-$C_6$ alkenyl, and $C_2$-$C_6$ alkynyl are optionally substituted; and q is an integer from 0 to 4;

G is selected from the group consisting of

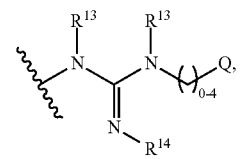 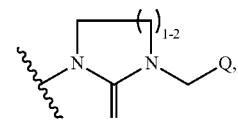

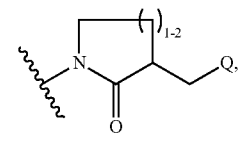 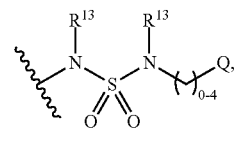

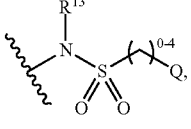 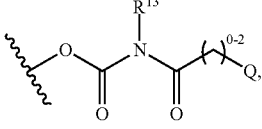

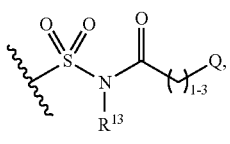 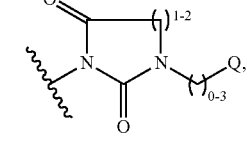

-continued

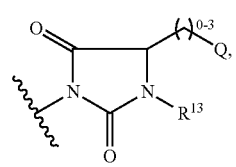 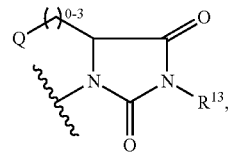

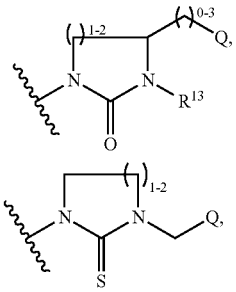 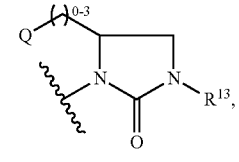

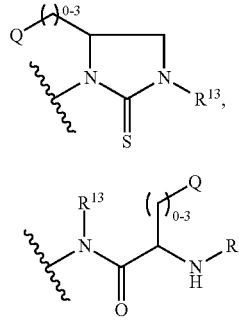 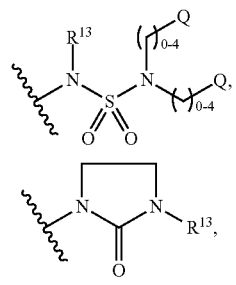

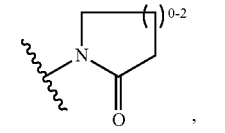 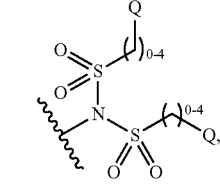

,

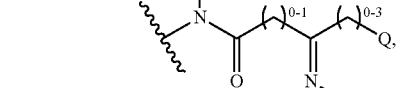

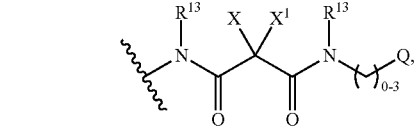

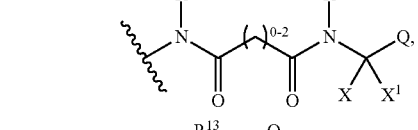

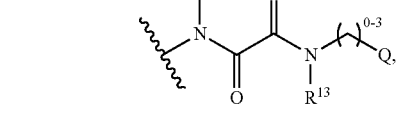

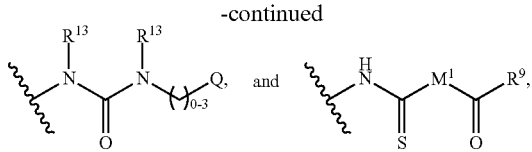

wherein any methylene group is independently optionally substituted with $R^{25}$, wherein $R^{25}$ is selected from the group consisting of halogen, trihalomethyl, —CN, —NO$_2$, —NH$_2$, —OR$^3$, —NR$^3$R$^4$, —S(O)$_{0-2}$R$^3$, —SO$_2$NR$^3$R$^3$, —CO$_2$R$^3$, —C(O)NR$^3$R$^3$, —N(R$^3$)SO$_2$R$^3$, —N(R$^3$)C(O)R$^3$, —N(R$^3$)CO$_2$R$^3$, —C(O)R$^3$, an optionally substituted aryl, an optionally substituted arylalkyl, an optionally substituted heteroarylalkyl, and an optionally substituted (C$_1$-C$_6$)alkyl, two $R^{25}$, together with the carbon or carbons to which they are attached, can combine to form a three- to seven-membered alicyclic or heteroalicyclic, and $R^9$ is selected from the group consisting of a $C_{1-6}$ alkyl on which one or more hydrogen atoms are optionally substituted by -R$^{24}$, -T$^1$-R$^{15}$, or —NR$^{16}$R$^{17}$, a —N(R$^{18}$)(R$^{19}$) moiety and a saturated or unsaturated three- to eight-membered carbocyclic or heterocyclic group which is optionally substituted by a $C_{1-6}$ alkyl, a $C_{1-6}$ alkoxy, a halogen atom, nitro, a trifluoromethyl, a $C_{1-6}$ alkoxy carbonyl, cyano; a cyano $C_{1-6}$ alkyl, a $C_{1-6}$ alkylthio, a phenoxy, an acetyl, or a saturated or unsaturated five- or six-membered heterocyclyl ring wherein, when the three- to eight-membered carbocyclic or heterocyclic group is substituted by two $C_{1-6}$ alkyl groups, the two alkyl groups may combine together to form an alkylene chain, or the three- to eight-membered carbocyclic or heterocyclic group may be a bicyclic group condensed with another saturated or unsaturated three- to eight-membered carbocyclic or heterocyclic group, wherein $T^1$ is selected from the group consisting of —O—, —S— and —NH—;

$R^{24}$ represents a saturated or unsaturated three- to eight-membered carbocyclic or heterocyclic group;

$R^{15}$, $R^{16}$, and $R^{17}$, which may be the same or different, represent a $C_{1-6}$ alkyl or a saturated or unsaturated three- to eight-membered carbocyclic or heterocyclic group; wherein the three- to eight-membered carbocyclic or heterocyclic group represented by $R^{24}$, $R^{15}$, $R^{16}$, and $R^{17}$ is optionally substituted by a $C_{1-6}$ alkyl, a $C_{1-6}$ alkoxy, a halogen atom, nitro, a trifluoromethyl, a $C_{1-6}$ alkoxy carbonyl, a cyano, a cyano $C_{1-6}$ alkyl, a $C_{1-6}$ alkylthio, a phenoxy, an acetyl, or a saturated or unsaturated five- or six-membered heterocyclyl ring; and wherein when the three- to eight-membered carbocyclic or heterocyclic group is substituted by two $C_{1-6}$ alkyl groups, the two alkyl groups may combine together to form an alkylene chain; and wherein the three- to eight-membered carbocyclic or heterocyclic group may be a bicyclic group condensed with another saturated or unsaturated three- to eight-membered carbocyclic or heterocyclic group; and $R^{18}$ and $R^{19}$, which may be the same or different, represent (1) a hydrogen atom, (2) a $C_{1-6}$ alkyl which is optionally substituted by a $C_{1-6}$ alkoxy, a $C_{1-6}$ alkylthio, or a saturated or unsaturated three- to eight-membered carbocyclic or heterocyclic group in which the three- to eight-membered carbocyclic or heterocyclic group is optionally substituted by a $C_{1-6}$ alkyl, a $C_{1-6}$ alkoxy, a halogen atom, nitro, a trifluoromethyl, a $C_{1-6}$ alkoxy carbonyl, cyano, a cyano $C_{1-6}$ alkyl, a $C_{1-6}$ alkylthio, a phenoxy, an acetyl, or a saturated or unsaturated five- or six-membered heterocyclyl ring and wherein when the three- to eight-membered carbocyclic or heterocyclic group is substituted by two $C_{1-6}$ alkyl groups, the two alkyl groups may combine together to form an alkylene chain, or the three- to eight-membered carbocyclic or heterocyclic group may be a bicyclic group condensed with another saturated or unsaturated three- to eight-membered carbocyclic or heterocyclic group, or (3) a saturated or unsaturated three- to eight-membered carbocyclic or heterocyclic group which is optionally substituted by a $C_{1-6}$ alkyl, a $C_{1-6}$ alkoxy, a halogen atom, nitro, a trifluoromethyl, a $C_{1-6}$ alkoxy carbonyl, cyano, a cyano $C_{1-6}$ alkyl, a $C_{1-6}$ alkylthio, a phenoxy, an acetyl, or a saturated or unsaturated five- or six-membered heterocyclyl ring and in which, when the three to eight-membered carbocyclic or heterocyclic group is substituted by two $C_{1-6}$ alkyl groups, the two alkyl groups may combine together to form an alkylene chain, or the three- to eight-membered carbocyclic or heterocyclic group may be a bicyclic group condensed with another saturated or unsaturated three- to eight-membered carbocyclic or heterocyclic group;

X and $X^1$ are each independently selected from the group consisting of —H, halogen, cyano, nitro, $C_1$-$C_6$ alkyl, or X and $X^1$ taken together with the atom to which they are attached, form a $C_3$-$C_7$ cycloalkyl;

$M^1$ represents —C(R$^{26}$)(R$^{27}$)—, wherein $R^{26}$ and $R^{27}$ are independently selected from the group consisting of a hydrogen atom, a $C_{1-4}$ alkyl, a $C_{1-4}$ alkoxy and —N(R$^{12}$), wherein $R^{12}$ is a hydrogen atom or a $C_{1-4}$ alkyl;

$R^{13}$ is selected from the group consisting of —H, —CN, —NO$_2$, —NH$_2$, —OR$^3$, —NR$^3$R$^4$, —S(O)$_{0-2}$R$^3$, —S(O)$_2$NR$^3$R$^3$, —C(O)OR$^3$, —C(O)NR$^3$R$^3$, —N(R$^3$)SO$_2$R$^3$, —N(R$^3$)C(O)R$^3$, —N(R$^3$)CO$_2$R$^3$, —C(O)R$^3$, —C(O)SR$^3$, $C_1$-$C_4$ alkoxy, $C_1$-$C_4$ alkylthio, —O(CH$_2$)$_n$ aryl, —O(CH$_2$)$_n$heteroaryl, —(CH$_2$)$_{0-5}$(aryl), —(CH$_2$)$_{0-5}$(heteroaryl), $C_1$-$C_6$ alkyl, $C_2$-$C_6$ alkenyl, $C_2$-$C_6$ alkynyl, —CH$_2$(CH$_2$)$_{0-4}$-T$^2$, an optionally substituted $C_{1-4}$ alkylcarbonyl, and a saturated or unsaturated three- to seven-membered carboxylic or heterocyclic group, wherein $T^2$ is selected from the group consisting of —OH, —OMe, —OEt, —NH$_2$, —NHMe, —NMe$_2$, —NHEt and —NEt$_2$, and wherein the aryl, heteroaryl, $C_1$-$C_6$ alkyl, $C_2$-$C_6$ alkenyl, and $C_2$-$C_6$ alkynyl are optionally substituted;

two $R^{13}$, together with the atom or atoms to which they are attached, can combine to form a heteroalicyclic optionally substituted with between one and four of $R^{60}$, wherein the heteroalicyclic can have up to four annular heteroatoms, and the heteroalicyclic can have an aryl or heteroaryl fused thereto, in which case the aryl or heteroaryl is optionally substituted with an additional one to four of $R^{60}$;

each $R^3$ is independently selected from the group consisting of —H and $R^4$;

$R^4$ is selected from the group consisting of a (C$_1$-C$_6$)alkyl, an aryl, a lower arylalkyl, a heterocyclyl and a lower heterocyclylalkyl, each of which is optionally substituted, or $R^3$ and $R^4$, taken together with a common nitrogen to which they are attached, form an optionally substituted five- to seven-membered heterocyclyl, the optionally substituted five- to seven-membered heterocyclyl optionally containing at least one additional annular heteroatom selected from the group consisting of N, O, S and P;

$R^{60}$ is selected from the group consisting of —H, halogen, trihalomethyl, —CN, —NO$_2$, —NH$_2$, —OR$^3$, —NR$^3$R$^4$, —S(O)$_{0-2}$R$^3$, —SO$_2$NR$^3$R$^3$, —CO$_2$R$^3$, —C(O)NR$^3$R$^3$, —N(R$^3$)SO$_2$R$^3$, —N(R$^3$)C(O)R$^3$, —N(R$^3$)CO$_2$R$^3$, —C(O)R$^3$, an optionally substituted (C$_1$-C$_6$)alkyl, an optionally substituted aryl, an optionally substituted heteroarylalkyl and an optionally substituted arylalkyl;

two $R^{60}$, when attached to a non-aromatic carbon, can be oxo;

Q is selected from the group consisting of phenyl, napthyl, 1,2,3,4-tetrahydronaphthyl, indanyl, benzodioxanyl, benzofuranyl, phenazinyl, phenothiazinyl, phenoxazinyl, tetrahydroisoquinolyl, pyrrolyl, pyrazolyl, pyrazolidinyl, imidazolyl, imidazolinyl, imidazolidinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, thiazolyl, thiazolinyl, thiazolidinyl, isothiazolyl, isothiazolidinyl, indolyl, isoindolyl, indolinyl, isoindolinyl, octahydroindolyl, octahydroisoindolyl, quinolyl, isoquinolyl, benzimidazolyl, thiadiazolyl, benzopyranyl, benzothiazolyl, benzoxazolyl, furyl, thienyl, benzothienyl, and oxadiazolyl, each optionally substituted with between one and four of $R^{20}$;

$R^{20}$ is selected from the group consisting of —H, halogen, trihalomethyl, —CN, —NO$_2$, —NH$_2$, —OR$^3$, —OCF$_3$, —NR$^3$R$^4$, —S(O)$_{0-2}$R$^3$, —S(O)$_2$NR$^3$R$^3$, —C(O)OR$^3$, —C(O)NR$^3$R$^3$, —N(R$^3$)SO$_2$R$^3$, —N(R$^3$)C(O)R$^3$, —N(R$^3$)C(O)OR$^3$, —C(O)R$^3$, —C(O)SR$^3$, C$_1$-C$_4$ alkoxy, C$_1$-C$_4$ alkylthio, —O(CH$_2$)$_n$aryl, —O(CH$_2$)$_n$heteroaryl, —(CH$_2$)$_{0-5}$(aryl), —(CH$_2$)$_{0-5}$(heteroaryl), C$_1$-C$_6$ alkyl, C$_2$-C$_6$ alkenyl, C$_2$-C$_6$ alkynyl, —CH$_2$(CH$_2$)$_{0-4}$-T$^2$, an optionally substituted C$_{1-4}$ alkylcarbonyl, C$_{1-4}$ alkoxy, an amino optionally substituted by C$_{1-4}$ alkyl optionally substituted by C$_{1-4}$ alkoxy and a saturated or unsaturated three- to seven-membered carboxyclic or heterocyclic group, wherein T$^2$ is selected from the group consisting of —OH, —OMe, —OEt, —NH$_2$, —NHMe, —NMe$_2$, —NHEt and —NEt$_2$, and wherein the aryl, heteroaryl, C$_1$-C$_6$ alkyl, C$_2$-C$_6$ alkenyl, and C$_2$-C$_6$ alkynyl are optionally substituted;

each $R^{38}$ is independently selected from halo, cyano, nitro, trifluoromethoxy, trifluoromethyl, azido, —C(O)R$^{40}$, —C(O)OR$^{40}$, —OC(O)R$^{40}$, —OC(O)OR$^{40}$, —NR$^{36}$C(O)R$^{39}$, —C(O)NR$^{36}$R$^{39}$, —NR$^{36}$R$^{39}$, —OR$^{37}$, —SO$_2$NR$^{36}$R$^{39}$, C$_1$-C$_6$ alkyl, —(CH$_2$)$_j$O(CH$_2$)$_i$NR$^{36}$R$^{39}$, —(CH$_2$)$_n$O(CH$_2$)$_i$OR$^{37}$, —(CH$_2$)$_n$OR$^{37}$, —S(O)$_j$(C$_1$-C$_6$ alkyl), —(CH$_2$)$_n$(C$_6$-C$_{10}$ aryl), —(CH$_2$)$_n$(5-10 membered heterocyclyl); —C(O)(CH$_2$)$_n$(C$_6$-C$_{10}$ aryl), —(CH$_2$)$_n$O(CH$_2$)$_j$(C$_6$-C$_{10}$ aryl), —(CH$_2$)$_n$O(CH$_2$)$_i$(5-10 membered heterocyclyl), —C(O)(CH$_2$)$_n$(5-10 membered heterocyclyl), —(CH$_2$)$_j$NR$^{39}$(CH$_2$)$_n$NR$^{36}$R$^{39}$, —(CH$_2$)$_j$NR$^{39}$CH$_2$C(O)NR$^{36}$R$^{39}$, —(CH$_2$)$_j$NR$^{39}$(CH$_2$)$_i$NR$^{37}$C(O)R$^{40}$, —(CH$_2$)$_j$NR$^{39}$(CH$_2$)$_n$O(CH$_2$)$_i$OR$^{37}$, —(CH$_2$)$_j$NR$^{39}$(CH$_2$)$_i$S(O)$_j$(C$_1$-C$_6$ alkyl), —(CH$_2$)$_j$NR$^{39}$(CH$_2$)$_n$R$^{36}$, —SO$_2$(CH$_2$)$_n$(C$_6$-C$_{10}$ aryl), —SO$_2$(CH$_2$)$_n$(5-10 membered heterocyclyl), —(CH$_2$)$_n$NR$^{36}$R$^{39}$, —NR$^{37}$SO$_2$NR$^{36}$R$^{39}$, SO$_2$R$^{36}$, C$_2$-C$_6$ alkenyl, C$_3$-C$_{10}$ cycloalkyl and C$_1$-C$_6$ alkylamino, wherein j is an integer ranging from 0 to 2, n is an integer ranging from 0 to 6, i is an integer ranging from 2 to 6, and the alkyl, aryl and heterocyclyl moieties of the foregoing $R^{38}$ groups are optionally substituted by one or more substituents independently selected from halo, cyano, nitro, trifluoromethyl, azido, —OH, —C(O)R$^{40}$, —C(O)OR$^{40}$, —OC(O)R$^{40}$, —OC(O)OR$^{40}$, —NR$^{36}$C(O)R$^{39}$, —C(O)NR$^{36}$R$^{39}$, —(CH$_2$)$_n$NR$^{36}$R$^{39}$, C$_1$-C$_6$ alkyl, C$_3$-C$_{10}$ cycloalkyl, —(CH$_2$)$_n$(C$_6$-C$_{10}$ aryl), —(CH$_2$)$_n$(5-10 membered heterocyclyl), —(CH$_2$)$_n$O(CH$_2$)$_i$OR$^{37}$, and —(CH$_2$)$_n$OR$^{37}$, wherein n is an integer ranging from 0 to 6 and i is an integer ranging from 2 to 6;

each $R^{36}$ and $R^{39}$ is independently selected from the group consisting of H, —OH, C$_1$-C$_6$ alkyl, C$_3$-C$_{10}$ cycloalkyl, —(CH$_2$)$_n$(C$_6$-C$_{10}$ aryl), —(CH$_2$)$_n$(5-10 membered heterocyclyl), —(CH$_2$)$_n$O(CH$_2$)$_i$OR$^{37}$, —(CH$_2$)$_n$CN(CH$_2$)$_n$OR$^{37}$, —(CH$_2$)$_n$CN(CH$_2$)$_n$R$^{37}$, and —(CH$_2$)$_n$OR$^{37}$, wherein n is an integer ranging from 0 to 6 and i is an integer ranging from 2 to 6, and the alkyl, aryl and heterocyclyl moieties of the foregoing $R^{36}$ and $R^{39}$ groups are optionally substituted by one or more substituents independently selected from —OH, halo, cyano, nitro, trifluoromethyl, azido, —C(O)R$^{40}$, —C(O)OR$^{40}$, —CO(O)R$^{40}$, —OC(O)OR$^{40}$, —NR$^{37}$C(O)R$^{41}$, —C(O)NR$^{37}$R$^{41}$, —NR$^{37}$R$^{41}$, —C$_1$-C$_6$ alkyl, —(CH$_2$)$_n$(C$_6$-C$_{10}$ aryl), —(CH$_2$)$_n$(5 to 10 membered heterocyclyl), —(CH$_2$)$_n$O(CH$_2$)$_i$OR$^{37}$, and —(CH$_2$)$_n$OR$^{37}$, wherein n is an integer ranging from 0 to 6 and i is an integer ranging from 2 to 6, with the proviso that when $R^{36}$ and $R^{39}$ are both attached to the same nitrogen, then $R^{36}$ and $R^{39}$ are not both bonded to the nitrogen directly through an oxygen;

each $R^{40}$ is independently selected from H, C$_1$-C$_{10}$ alkyl, —(CH$_2$)$_n$(C$_6$-C$_{10}$ aryl), C$_3$-C$_{10}$ cycloalkyl, and —(CH$_2$)$_n$(5-10 membered heterocyclyl), wherein n is an integer ranging from 0 to 6;

each $R^{37}$ and $R^{41}$ is independently selected from H, OR$^{36}$, C$_1$-C$_6$ alkyl and C$_3$-C$_{10}$ cycloalkyl;

$R^{42}$ and $R^{43}$ taken together with the nitrogen to which they are attached form a C$_5$-C$_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring, wherein said C$_5$-C$_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring are optionally substituted by 1 to 5 $R^{44}$ substituents, with the proviso that $R^{42}$ and $R^{43}$ are not both bonded to the nitrogen directly through an oxygen;

each $R^{44}$ is independently selected from the group consisting of halo, cyano, nitro, trifluoromethoxy, trifluoromethyl, azido, —C(O)R$^{40}$, —C(O)OR$^{40}$, —OC(O)R$^{40}$, —OC(O)OR$^{40}$, —NR$^{36}$C(O)R$^{39}$, —C(O)NR$^{36}$R$^{39}$, —NR$^{36}$R$^{39}$, —OR$^{37}$, —SO$_2$NR$^{36}$R$^{39}$, —SO$_2$R$^{36}$, —NR$^{36}$SO$_2$R$^{39}$, —NR$^{36}$SO$_2$NR$^{37}$R$^{41}$, C$_1$-C$_6$ alkyl, C$_2$-C$_6$ alkenyl, C$_2$-C$_6$ alkynyl, C$_3$-C$_{10}$ cycloalkyl, —C$_1$-C$_6$ alkylamino, —(CH$_2$)$_j$O(CH$_2$)$_i$NR$^{36}$R$^{39}$, —(CH$_2$)$_n$O(CH$_2$)$_i$OR$^{37}$, —(CH$_2$)$_n$OR$^{37}$, —S(O)$_j$(C$_1$-C$_6$ alkyl), —(CH$_2$)$_n$(C$_6$-C$_{10}$ aryl), —(CH$_2$)$_n$(5-10 membered heterocyclyl), —C(O)(CH$_2$)$_n$(C$_6$-C$_{10}$ aryl), —(CH$_2$)$_n$O(CH$_2$)$_j$(C$_6$-C$_{10}$ aryl), —(CH$_2$)$_n$O(CH$_2$)$_i$(5 to 10 membered heterocyclyl), —C(O)(CH$_2$)$_n$(5 to 10 membered heterocyclyl), —(CH$_2$)$_j$NR$^{39}$(CH$_2$)$_n$NR$^{36}$R$^{39}$, —(CH$_2$)$_j$NR$^{39}$CH$_2$C(O)NR$^{36}$R$^{39}$, —(CH$_2$)$_j$NR$^{39}$(CH$_2$)$_i$NR$^{37}$C(O)R$^{40}$, —(CH$_2$)$_j$NR$^{39}$(CH$_2$)$_n$O(CH$_2$)$_i$OR$^{37}$, —(CH$_2$)$_j$NR$^{39}$(CH$_2$)$_i$S(O)$_j$(C$_1$-C$_6$ alkyl), —(CH$_2$)$_j$NR$^{39}$(CH$_2$)$_n$R$^{36}$, —SO$_2$(CH$_2$)$_n$(C$_6$-C$_{10}$ aryl), and —SO$_2$(CH$_2$)$_j$(5 to 10 membered heterocyclyl) wherein, j is an integer from 0 to 2, n is an integer from 0 to 6 and i is an integer ranging from 2 to 6, and the alkyl, aryl and heterocyclyl moieties of the foregoing $R^{44}$ groups are optionally substituted by 1 or more substituents independently selected from the group consisting of halo, cyano, nitro, trifluoromethyl, azido, —OH, —C(O)R$^{40}$, —C(O)OR$^{40}$, —OC(O)R$^{40}$, —OC(O)OR$^{40}$, —NR$^{36}$C(O)R$^{39}$, —C(O)NR$^{36}$R$^{39}$, —(CH$_2$)$_n$NR$^{36}$R$^{39}$, —SO$_2$R$^{36}$, —SO$_2$NR$^{36}$R$^{39}$, C$_1$-C$_6$ alkyl, C$_3$-C$_{10}$ cycloalkyl, —(CH$_2$)$_n$(C$_6$-C$_{10}$ aryl), —(CH$_2$)$_n$(5 to 10 membered heterocyclyl), —(CH$_2$)$_n$O(CH$_2$)$_i$OR$^{37}$ and —(CH$_2$)$_n$ OR$^{37}$, wherein n is an integer from 0 to 6 and i is an integer from 2 to 6; and Z is selected from the group consisting of —O— and —S(O)$_{0-2}$.

3. The method according to claim 1, wherein,

D is selected from the group consisting of R$^7$, wherein R$^7$ is selected from the group consisting of —NR$^{42}$R$^{43}$, heteroaryl and 5-10 membered heterocyclyl, and the aforementioned R$^7$ groups are optionally substituted by 1 to 5 R$^{38}$;

A$^1$ is —S—;

A$^2$ is CR, wherein R is —H;

A$^3$ is CH;

Ar is a group of the formula C,

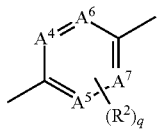

C wherein,

A$^4$, A$^5$, A$^6$ and A$^7$ are —CH—;

R$^2$ at each occurrence is independently selected from the group consisting of —H, halogen, trihalomethyl, —CN, —NO$_2$, —NH$_2$, —OR$^3$, —NR$^3$R$^4$, —S(O)$_{0-2}$R$^3$, —S(O)$_2$NR$^3$R$^3$, —C(O)OR$^3$, —C(O)NR$^3$R$^3$, —N(R$^3$)SO$_2$R$^3$, —N(R$^3$)C(O)R$^3$, —N(R$^3$)CO$_2$R$^3$, —C(O)R$^3$, C$_1$-C$_4$ alkoxy, C$_1$-C$_4$ alkylthio, —O(CH$_2$)$_n$aryl, —O(CH$_2$)$_n$heteroaryl, —(CH$_2$)$_{0-5}$(aryl), —(CH$_2$)$_{0-5}$(heteroaryl), C$_1$-C$_6$ alkyl, C$_2$-C$_6$ alkenyl, C$_2$-C$_6$ alkynyl, —CH$_2$(CH$_2$)$_{0-4}$-T$^2$, wherein T$^2$ is selected from the group consisting of —OH, —OMe, —OEt, —NH$_2$, —NHMe, —NMe$_2$, —NHEt and —NEt$_2$, and wherein the aryl, heteroaryl, C$_1$-C$_6$ alkyl, C$_2$-C$_6$ alkenyl, and C$_2$-C$_6$ alkynyl are optionally substituted; and q is an integer from 0 to 4;

G is selected from the group consisting of

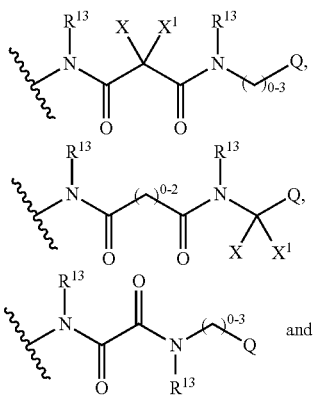

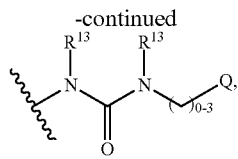

-continued wherein

X and X$^1$ are each independently selected from the group consisting of —H, halogen, cyano, nitro, C$_1$-C$_6$ alkyl, or X and X$^1$ taken together with the atom to which they are attached, form a C$_3$-C$_7$ cycloalkyl;

R$^{13}$ is selected from the group consisting of —H, —CN, —NO$_2$, —NH$_2$, —OR$^3$, —NR$^3$R$^4$, —S(O)$_{0-2}$R$^3$, —S(O)$_2$NR$^3$R$^3$, —C(O)OR$^3$, —C(O)NR$^3$R$^3$, —N(R$^3$) SO$_2$R$^3$, —N(R$^3$)C(O)R$^3$, —N(R$^3$)CO$_2$R$^3$, —C(O)R$^3$, —C(O)SR$^3$, C$_1$-C$_4$ alkoxy, C$_1$-C$_4$ alkylthio, —O(CH$_2$)$_n$ aryl, —O(CH$_2$)$_n$heteroaryl, —(CH$_2$)$_{0-5}$(aryl), —(CH$_2$)$_{0-5}$(heteroaryl), C$_1$-C$_6$ alkyl, C$_2$-C$_6$ alkenyl, C$_2$-C$_6$ alkynyl, —CH$_2$(CH$_2$)$_{0-4}$-T$^2$, an optionally substituted C$_{1-4}$alkylcarbonyl, and a saturated or unsaturated three- to seven-membered carboxyclic or heterocyclic group, wherein T$^2$ is selected from the group consisting of —OH, —OMe, —OEt, —NH$_2$, —NHMe, —NMe$_2$, —NHEt and —NEt$_2$, and wherein the aryl, heteroaryl, C$_1$-C$_6$ alkyl, C$_2$-C$_6$ alkenyl, and C$_2$-C$_6$ alkynyl are optionally substituted;

two R$^{13}$, together with the atom or atoms to which they are attached, can combine to form a heteroalicyclic optionally substituted with between one and four of R$^{60}$, wherein the heteroalicyclic can have up to four annular heteroatoms, and the heteroalicyclic can have an aryl or heteroaryl fused thereto, in which case the aryl or heteroaryl is optionally substituted with an additional one to four of R$^{60}$;

each R$^3$ is independently selected from the group consisting of —H and R$^4$;

R$^4$ is selected from the group consisting of a (C$_1$-C$_6$)alkyl, an aryl, a lower arylalkyl, a heterocyclyl and a lower heterocyclylalkyl, each of which is optionally substituted, or R$^3$ and R$^4$, taken together with a common nitrogen to which they are attached, form an optionally substituted five- to seven-membered heterocyclyl, the optionally substituted five- to seven-membered heterocyclyl optionally containing at least one additional annular heteroatom selected from the group consisting of N, O, S and P;

R$^{60}$ is selected from the group consisting of —H, halogen, trihalomethyl, —CN, —NO$_2$, —NH$_2$, —OR$^3$, —NR$^3$R$^4$, —S(O)$_{0-2}$R$^3$, —SO$_2$NR$^3$R$^3$, —CO$_2$R$^3$, —C(O)NR$^3$R$^3$, —N(R$^3$)SO$_2$R$^3$, —N(R$^3$)C(O)R$^3$, —N(R$^3$)CO$_2$R$^3$, —C(O)R$^3$, an optionally substituted (C$_1$-C$_6$)alkyl, an optionally substituted aryl, an optionally substituted heteroarylalkyl and an optionally substituted arylalkyl;

two R$^{60}$, when attached to a non-aromatic carbon, can be oxo;

Q is selected from the group consisting of phenyl, napthyl, 1,2,3,4-tetrahydronaphthyl, indanyl, benzodioxanyl, benzofuranyl, phenazinyl, phenothiazinyl, phenoxazinyl, tetrahydroisoquinolyl, pyrrolyl, pyrazolyl, pyrazolidinyl, imidazolyl, imidazolinyl, imidazolidinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, thiazolyl, thiazolinyl, thiazolidinyl, isothiazolyl, isothiazolidinyl, indolyl, isoindolyl, indolinyl, isoindolinyl, octahydroindolyl, octahydroisoindolyl, quinolyl, isoquinolyl, benzimidazolyl, thiadiazolyl, benzopyranyl, benzothiazolyl, benzoxazolyl, furyl, thienyl, benzothienyl, and oxadiazolyl, each optionally substituted with between one and four of $R^{20}$;

$R^{20}$ is selected from the group consisting of —H, halogen, trihalomethyl, —CN, —NO$_2$, —NH$_2$, —OR$^3$, —OCF$_3$, —NR$^3$R$^4$, —S(O)$_{0-2}$R$^3$, —S(O)$_2$NR$^3$R$^3$, —C(O)OR$^3$, —C(O)NR$^3$R$^3$, —N(R$^3$)SO$_2$R$^3$, —N(R$^3$)C(O)R$^3$, —N(R$^3$)C(O)OR$^3$, —C(O)R$^3$, —C(O)SR$^3$, C$_1$-C$_4$ alkoxy, C$_1$-C$_4$ alkylthio, —O(CH$_2$)$_n$aryl, —O(CH$_2$)$_n$heteroaryl, —(CH$_2$)$_{0-5}$(aryl), —(CH$_2$)$_{0-5}$(heteroaryl), C$_1$-C$_6$ alkyl, C$_2$-C$_6$ alkenyl, C$_2$-C$_6$ alkynyl, —CH$_2$(CH$_2$)$_{0-4}$-T$^2$, an optionally substituted C$_{1-4}$ alkylcarbonyl, C$_{1-4}$ alkoxy, an amino optionally substituted by C$_{1-4}$ alkyl optionally substituted by C$_{1-4}$ alkoxy and a saturated or unsaturated three- to seven-membered carboxyclic or heterocyclic group, wherein T$^2$ is selected from the group consisting of —OH, —OMe, —OEt, —NH$_2$, —NHMe, —NMe$_2$, —NHEt and —NEt$_2$, and wherein the aryl, heteroaryl, C$_1$-C$_6$ alkyl, C$_2$-C$_6$ alkenyl, and C$_2$-C$_6$ alkynyl are optionally substituted;

each $R^{38}$ is independently selected from halo, cyano, nitro, trifluoromethoxy, trifluoromethyl, azido, —C(O)R$^{40}$, —C(O)OR$^{40}$, —OC(O)R$^{40}$, —OC(O)OR$^{40}$, —NR$^{36}$C(O)R$^{39}$, —C(O)NR$^{36}$R$^{39}$, —NR$^{36}$R$^{39}$, —OR$^{37}$, —SO$_2$NR$^{36}$R$^{39}$, C$_1$-C$_6$ alkyl, —(CH$_2$)$_j$O(CH$_2$)$_i$NR$^{36}$R$^{39}$, —(CH$_2$)$_n$O(CH$_2$)$_i$OR$^{37}$, —(CH$_2$)$_n$OR$^{37}$, —S(O)$_j$(C$_1$-C$_6$ alkyl), —(CH$_2$)$_n$(C$_6$-C$_{10}$ aryl), —(CH$_2$)$_n$(5-10 membered heterocyclyl); —C(O)(CH$_2$)$_n$(C$_6$-C$_{10}$ aryl), —(CH$_2$)$_n$O(CH$_2$)$_i$(C$_6$-C$_{10}$ aryl), —(CH$_2$)$_n$O(CH$_2$)$_i$(5-10 membered heterocyclyl), —C(O)(CH$_2$)$_n$(5-10 membered heterocyclyl), —(CH$_2$)$_j$NR$^{39}$(CH$_2$)$_i$NR$^{36}$R$^{39}$, —(CH$_2$)$_j$NR$^{39}$CH$_2$C(O)NR$^{36}$R$^{39}$, —(CH$_2$)$_j$NR$^{39}$(CH$_2$)$_i$NR$^{37}$C(O)R$^{40}$, —(CH$_2$)$_j$NR$^{39}$(CH$_2$)$_n$O(CH$_2$)$_i$OR$^{37}$, —(CH$_2$)$_j$NR$^{39}$(CH$_2$)$_i$S(O)$_j$(C$_1$-C$_6$ alkyl), —(CH$_2$)$_j$NR$^{39}$(CH$_2$)$_n$R$^{36}$, —SO$_2$(CH$_2$)$_n$(C$_6$-C$_{10}$ aryl), —SO$_2$(CH$_2$)$_n$(5-10 membered heterocyclyl), —(CH$_2$)$_n$NR$^{36}$R$^{39}$, —NR$^{37}$SO$_2$NR$^{36}$R$^{39}$, SO$_2$R$^{36}$, C$_2$-C$_6$ alkenyl, C$_3$-C$_{10}$ cycloalkyl and C$_1$-C$_6$ alkylamino, wherein j is an integer ranging from 0 to 2, n is an integer ranging from 0 to 6, i is an integer ranging from 2 to 6, and the alkyl, aryl and heterocyclyl moieties of the foregoing $R^{38}$ groups are optionally substituted by one or more substituents independently selected from halo, cyano, nitro, trifluoromethyl, azido, —OH, —C(O)R$^{40}$, —C(O)OR$^{40}$, —OC(O)R$^{40}$, —OC(O)OR$^{40}$, —NR$^{36}$C(O)R$^{39}$, —C(O)NR$^{36}$R$^{39}$, —(CH$_2$)$_n$NR$^{36}$R$^{39}$, C$_1$-C$_6$ alkyl, C$_3$-C$_{10}$ cycloalkyl, —(CH$_2$)$_n$(C$_6$-C$_{10}$ aryl), —(CH$_2$)$_n$(5-10 membered heterocyclyl), —(CH$_2$)$_n$O(CH$_2$)$_i$OR$^{37}$, and —(CH$_2$)$_n$OR$^{37}$, wherein n is an integer ranging from 0 to 6 and i is an integer ranging from 2 to 6;

each $R^{36}$ and $R^{39}$ is independently selected from the group consisting of H, —OH, C$_1$-C$_6$ alkyl, C$_3$-C$_{10}$ cycloalkyl, —(CH$_2$)$_n$(C$_6$-C$_{10}$ aryl), —(CH$_2$)$_n$(5-10 membered heterocyclyl), —(CH$_2$)$_n$O(CH$_2$)$_i$OR$^{37}$, —(CH$_2$)$_n$CN(CH$_2$)$_n$OR$^{37}$, —(CH$_2$)$_n$CN(CH$_2$)$_n$R$^{37}$, and —(CH$_2$)$_n$OR$^{37}$, wherein n is an integer ranging from 0 to 6 and i is an integer ranging from 2 to 6, and the alkyl, aryl and heterocyclyl moieties of the foregoing $R^{36}$ and $R^{39}$ groups are optionally substituted by one or more substituents independently selected from —OH, halo, cyano, nitro, trifluoromethyl, azido, —C(O)R$^{40}$, —C(O)OR$^{40}$, —CO(O)R$^{40}$, —OC(O)OR$^{40}$, —NR$^{37}$C(O)R$^{41}$, —C(O)NR$^{37}$R$^{41}$, —NR$^{37}$R$^{41}$, —C$_1$-C$_6$ alkyl, —(CH$_2$)$_n$(C$_6$-C$_{10}$ aryl), —(CH$_2$)$_n$(5 to 10 membered heterocyclyl), —(CH$_2$)$_n$O(CH$_2$)$_i$OR$^{37}$, and —(CH$_2$)$_n$OR$^{37}$, wherein n is an integer ranging from 0 to 6 and i is an integer ranging from 2 to 6, with the proviso that when $R^{36}$ and $R^{39}$ are both attached to the same nitrogen, then $R^{36}$ and $R^{39}$ are not both bonded to the nitrogen directly through an oxygen;

each $R^{40}$ is independently selected from H, C$_1$-C$_{10}$ alkyl, —(CH$_2$)$_n$(C$_6$-C$_{10}$ aryl), C$_3$-C$_{10}$ cycloalkyl, and —(CH$_2$)$_n$(5-10 membered heterocyclyl), wherein n is an integer ranging from 0 to 6;

each $R^{37}$ and $R^{41}$ is independently selected from H, OR$^{36}$, C$_1$-C$_6$ alkyl and C$_3$-C$_{10}$ cycloalkyl;

$R^{42}$ and $R^{43}$ taken together with the nitrogen to which they are attached form a C$_5$-C$_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring, wherein said C$_5$-C$_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring are optionally substituted by 1 to 5 $R^{44}$ substituents, with the proviso that $R^{42}$ and $R^{43}$ are not both bonded to the nitrogen directly through an oxygen;

each $R^{44}$ is independently selected from the group consisting of halo, cyano, nitro, trifluoromethoxy, trifluoromethyl, azido, —C(O)R$^{40}$, —C(O)OR$^{40}$, —OC(O)R$^{40}$, —OC(O)OR$^{40}$, —NR$^{36}$C(O)R$^{39}$, —C(O)NR$^{36}$R$^{39}$, —NR$^{36}$R$^{39}$, —OR$^{37}$, —SO$_2$NR$^{36}$R$^{39}$, —SO$_2$R$^{36}$, —NR$^{36}$SO$_2$R$^{39}$, —NR$^{36}$SO$_2$NR$^{37}$R$^{41}$, C$_1$-C$_6$ alkyl, C$_2$-C$_6$ alkenyl, C$_2$-C$_6$ alkynyl, C$_3$-C$_{10}$ cycloalkyl, —C$_1$-C$_6$ alkylamino, —(CH$_2$)$_j$O(CH$_2$)$_i$NR$^{36}$R$^{39}$, —(CH$_2$)$_n$O(CH$_2$)$_i$OR$^{37}$, —(CH$_2$)$_n$OR$^{37}$, —S(O)$_j$(C$_1$-C$_6$ alkyl), —(CH$_2$)$_n$(C$_6$-C$_{10}$ aryl), —(CH$_2$)$_n$(5-10 membered heterocyclyl), —C(O)(CH$_2$)$_n$(C$_6$-C$_{10}$ aryl), —(CH$_2$)$_n$O(CH$_2$)$_j$(C$_6$-C$_{10}$ aryl), —(CH$_2$)$_n$O(CH$_2$)$_i$(5 to 10 membered heterocyclyl), —C(O)(CH$_2$)$_n$(5 to 10 membered heterocyclyl), —(CH$_2$)$_j$NR$^{39}$(CH$_2$)$_i$NR$^{36}$R$^{39}$, —(CH$_2$)$_j$NR$^{39}$CH$_2$C(O)NR$^{36}$R$^{39}$, —(CH$_2$)$_j$NR$^{39}$(CH$_2$)$_i$NR$^{37}$C(O)R$^{40}$, —(CH$_2$)$_j$NR$^{39}$(CH$_2$)$_n$O(CH$_2$)$_i$OR$^{37}$, —(CH$_2$)$_j$NR$^{39}$(CH$_2$)$_i$S(O)$_j$(C$_1$-C$_6$ alkyl), —(CH$_2$)$_j$NR$^{39}$(CH$_2$)$_n$R$^{36}$, —SO$_2$(CH$_2$)$_n$(C$_6$-C$_{10}$ aryl), and —SO$_2$(CH$_2$)$_n$(5 to 10 membered heterocyclyl) wherein, j is an integer from 0 to 2, n is an integer from 0 to 6 and i is an integer ranging from 2 to 6, and the alkyl, aryl and heterocyclyl moieties of the foregoing $R^{44}$ groups are optionally substituted by 1 or more substituents independently selected from the group consisting of halo, cyano, nitro, trifluoromethyl, azido, —OH, —C(O)R$^{40}$, —C(O)OR$^{40}$, —OC(O)R$^{40}$, —OC(O)OR$^{40}$, —NR$^{36}$C(O)R$^{39}$, —C(O)NR$^{36}$R$^{39}$, —(CH$_2$)$_n$NR$^{36}$R$^{39}$, —SO$_2$R$^{36}$, —SO$_2$NR$^{36}$R$^{39}$, C$_1$-C$_6$ alkyl, C$_3$-C$_{10}$ cycloalkyl, —(CH$_2$)$_n$(C$_6$-C$_{10}$ aryl), —(CH$_2$)$_n$(5 to 10 membered heterocyclyl), —(CH$_2$)$_n$O(CH$_2$)$_i$OR$^{37}$ and —(CH$_2$)$_n$OR$^{37}$, wherein n is an integer from 0 to 6 and i is an integer from 2 to 6; and Z is selected from the group consisting of —O— and —S(O)$_{0-2}$.

4. The method according to claim 1, wherein D is defined by the group $R^7$, wherein $R^7$ is -(5-10 membered heterocyclyl), -heteroaryl, —NR$^{42}$R$^{43}$, wherein the aforementioned $R^7$ groups are optionally substituted by 1 to 5 $R^{38}$.

5. The method according to claim 1, wherein $R^7$ is selected from the group consisting of

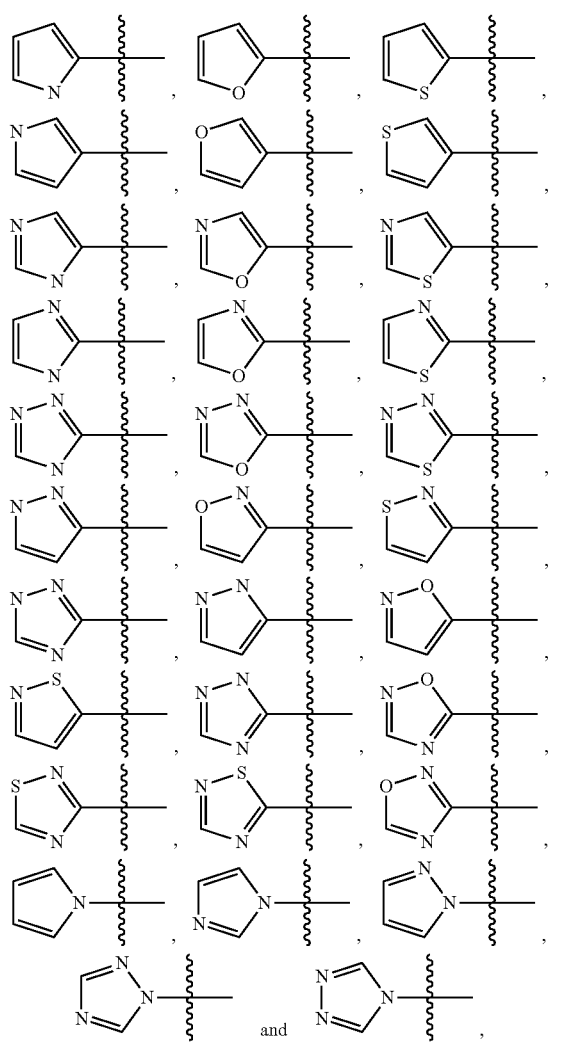
wherein the members of said group are substituted by 1 to 3 $R^{38}$.
6. The method according to claim 1, wherein $R^7$ is selected from the group consisting of
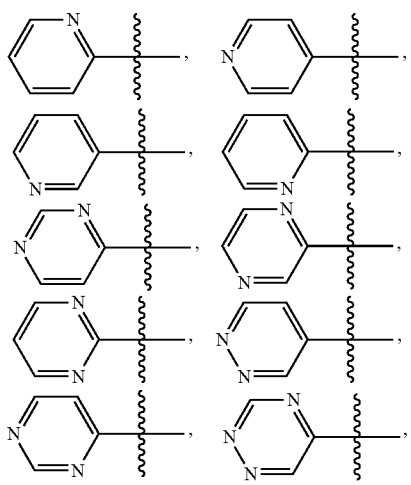
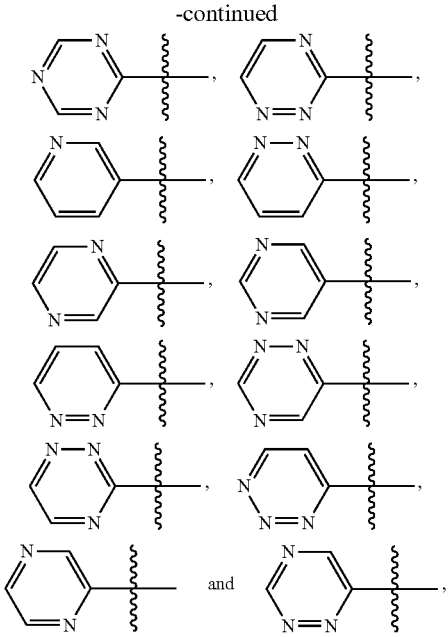
wherein the members of said group are substituted by 1 to 3 $R^{38}$.
7. The method according to claim 1, wherein $R^7$ is selected from the group consisting of
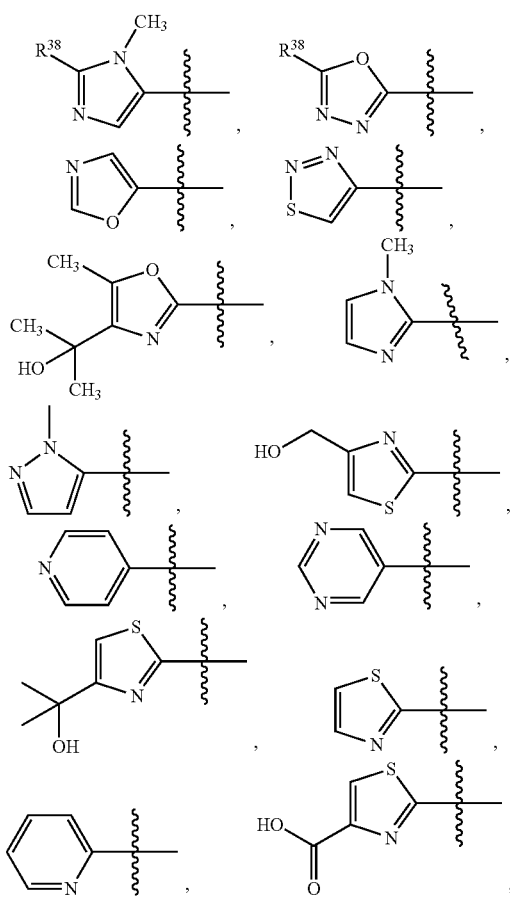

473
-continued
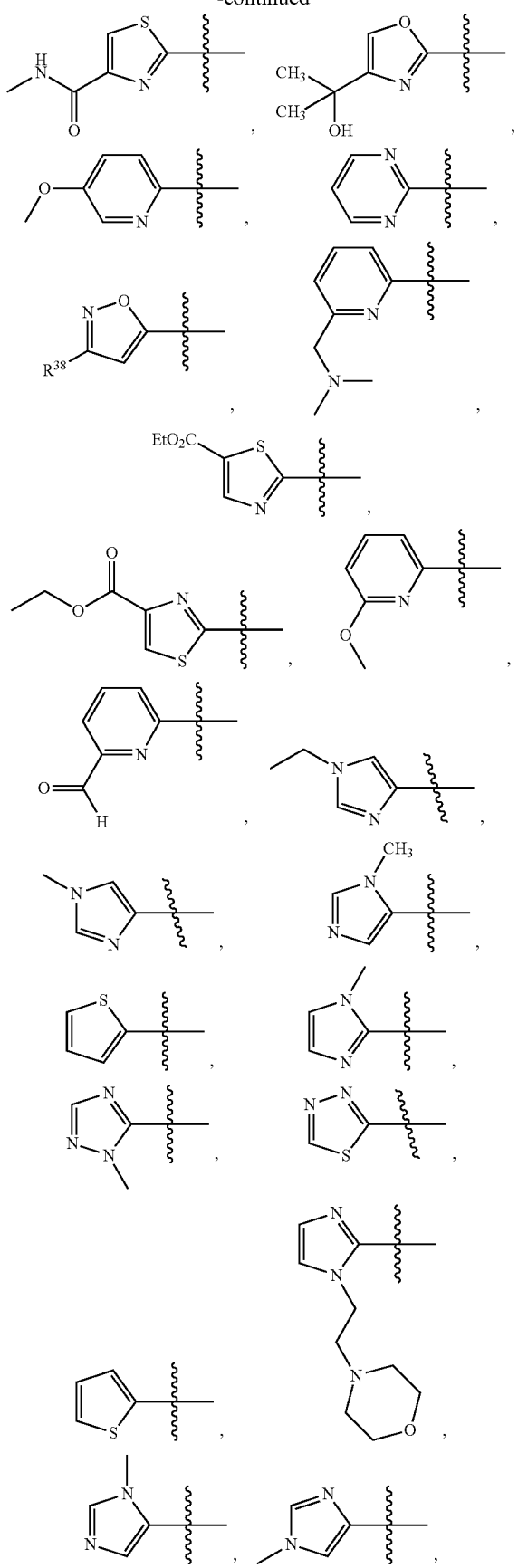
474
-continued
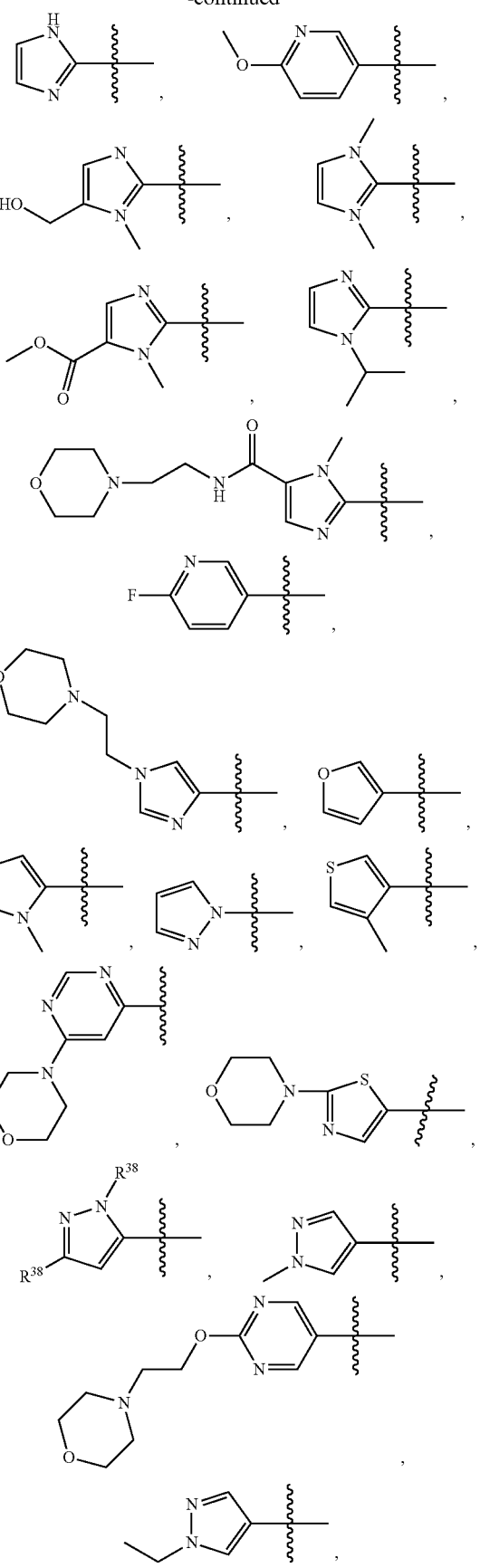

-continued

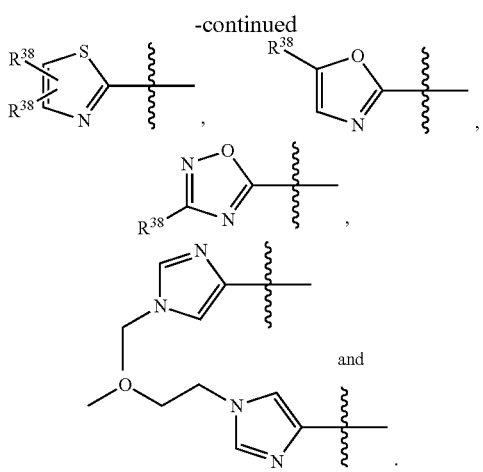

8. The method according to claim 1, wherein G is selected from the group consisting of:

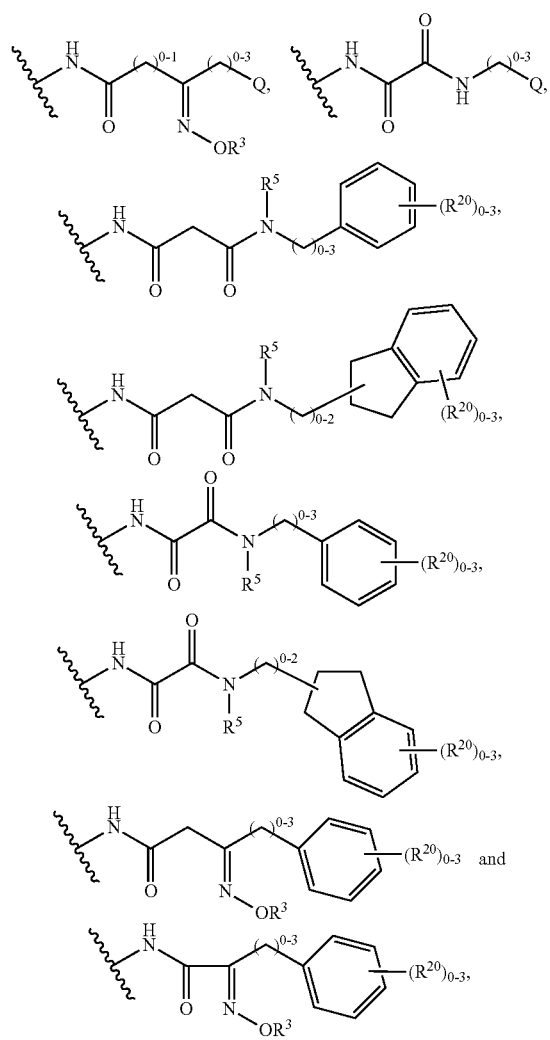

wherein each methylene in any of the above formulae, other than those in a depicted ring, is independently optionally substituted with $R^{25}$;

$R^{25}$ is selected from the group consisting of halogen, trihalomethyl, —CN, —NO$_2$, —NH$_2$, —OR$^3$, —NR$^3$R$^4$, —S(O)$_{0-2}$R$^3$, —SO$_2$NR$^3$R$^3$, —CO$_2$R$^3$, —C(O)NR$^3$R$^3$, —N(R$^3$)SO$_2$R$^3$, —N(R$^3$)C(O)R$^3$, —N(R$^3$)CO$_2$R$^3$, —C(O)R$^3$, an optionally substituted aryl, an optionally substituted arylalkyl, an optionally substituted heteroarylalkyl, and an optionally substituted (C$_1$-C$_6$)alkyl, two $R^{25}$, together with the carbon or carbons to which they are attached, can combine to form a three- to seven-membered alicyclic or heteroalicyclic;

$R^5$ is —H or an optionally substituted (C$_1$-C$_6$)alkyl.

9. The method according to claim 8, wherein a methylene group between two carbonyl groups is mono- or di-substituted with an optionally substituted (C$_1$-C$_6$)alkyl.

10. The method according to claim 1, wherein Q is selected from the group consisting of

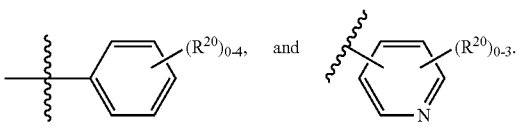

11. The method according to claim 1, wherein the compound is of formula A-1:

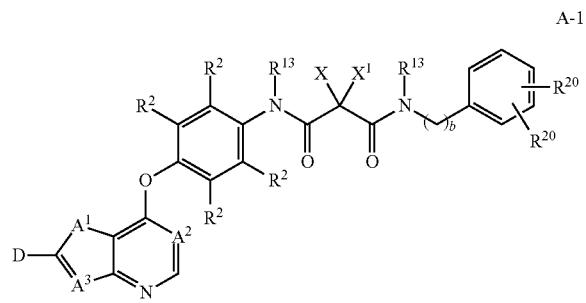

A-1 and pharmaceutically acceptable salts and hydrates thereof, wherein

X and $X^1$ are each independently selected from the group consisting of —H, halogen, cyano, nitro, C$_1$-C$_6$ alkyl, or X and $X^1$ taken together with the atom to which they are attached, form a C$_3$-C$_7$ cycloalkyl; and b is 0, 1, 2, or 3.

12. The method according to claim 1, wherein the compound is of formula A-2:

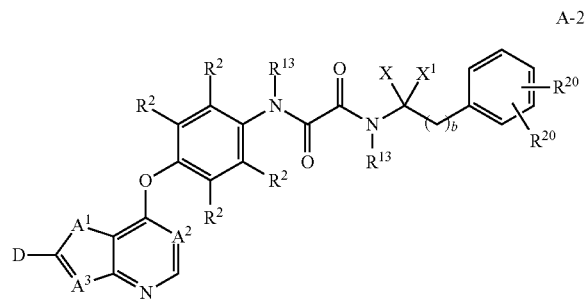

A-2 and pharmaceutically acceptable salts and hydrates thereof, wherein

X and $X^1$ are each independently selected from the group consisting of —H, halogen, cyano, nitro, $C_1$-$C_6$ alkyl, or X and $X^1$ taken together with the atom to which they are attached, form a $C_3$-$C_7$ cycloalkyl; and b is 0, 1, 2, or 3.

13. The method according to claim 1, wherein the compound is selected from the group consisting of $N^1$-(3-Fluoro-4-(2-(1-methyl-1H-imidazol-2-yl)thieno[3,2-b]pyridin-7-yloxy)phenyl)-$N^3$-phenylmalonamide, $N^1$-{3-Fluoro-4-[2-(1-methyl-1H-imidazol-4-yl)thieno[3,2-b]pyridin-7-yloxy]-phenyl}-$N^3$-phenylmalonamide, $N^1$-(4-(2-(1-ethyl-1H-imidazol-4-yl)thieno[3,2-b]pyridin-7-yloxy)-3-fluorophenyl)-$N^3$-phenylmalonamide, $N^1$-(3-fluoro-4-(2-(1-methyl-1H-imidazol-5-yl)thieno[3,2-b]pyridin-7-yloxy)phenyl)-$N^3$-phenylmalonamide, $N^1$-(3-Fluoro-4-(2-(1-methyl-1H-imidazol-2-yl)thieno[3,2-b]pyridin-7-yloxy)phenyl)-$N^3$-(2-methoxyphenyl)malonamide, $N^1$-(4-(2-(1-ethyl-1H-imidazol-4-yl)thieno[3,2-b]pyridin-7-yloxy)-3-fluorophenyl)-$N^3$-(2-methoxyphenyl)malonamide, $N^1$-(3-fluoro-4-(2-(1-methyl-1H-imidazol-5-yl)thieno[3,2-b]pyridin-7-yloxy)phenyl)-$N^3$-(2-methoxyphenyl)malonamide, $N^1$-(3-fluoro-4-(2-(1-methyl-1H-imidazol-2-yl)thieno[3,2-b]pyridin-7-yloxy)phenyl)-$N^3$-(2-fluoroxyphenyl)malonamide, $N^1$-(4-(2-(1-ethyl-1H-imidazol-4-yl)thieno[3,2-b]pyridin-7-yloxy)-3-fluorophenyl)-$N^3$-(2-fluorophenyl)-$N^3$-(2-fluorophenyl)malonamide, $N^1$-(3-fluoro-4-(2-(1-methyl-1H-imidazol-2-yl)thieno[3,2-b]pyridin-7-yloxy)phenyl)-$N^3$-methyl-$N^3$-phenylmalonamide, N-{3-Fluoro-4-[2-(1-methyl-1H-imidazol-2-yl)-thieno[3,2-b]pyridin-7-yloxy]-phenyl}-$N^1$-pyridin-4-yl-malonamide, $N^1$-(3-Fluoro-4-(2-(1-methyl-1H-imidazol-2-yl)thieno[3,2-b]pyridin-7-yloxy)phenyl)-2-methyl-$N^3$-phenylmalonamide, N-{3-Fluoro-4-[2-(3-methyl-3H-imidazol-4-yl)-thieno[3,2-b]pyridin-7-yloxy]-phenyl}-$N^1$-pyridin-3-yl-malonamide, $N^1$-(4-(2-(1-Ethyl-5-methyl-1H-imidazol-4-yl)thieno[3,2-b]pyridin-7-yloxy)-3-fluorophenyl)-$N^3$-phenylmalonamide, $N^1$-Cyclohexyl-$N^3$-(4-(2-(1-ethyl-1H-imidazol-4-yl)thieno[3,2-b]pyridin-7-yloxy)-3-fluorophenyl)malonamide, $N^1$-(3-fluoro-4-(2-(pyridin-4-yl)thieno[3,2-b]pyridin-7-yloxy)phenyl)-$N^3$-phenylmalonamide, $N^1$-(3-Fluoro-4-(2-(1-(2-hydroxyethyl)-1H-imidazol-4-yl)thieno[3,2-b]pyridin-7-yloxy)phenyl)-$N^3$-phenylmalonamide, $N^1$-(3-Fluoro-4-(2-(1-(methoxymethyl)-1H-imidazol-4-yl)thieno[3,2-b]pyridin-7-yloxy)phenyl)-$N^3$-(2-methoxyphenyl)malonamide, $N^1$-(3-Fluoro-4-(2-(1-(2-(methylamino)ethyl)-1H-imidazol-4-yl)thieno[3,2-b]pyridin-7-yloxy)phenyl)-$N^3$-(2-methoxyphenyl)malonamide, $N^1$-(4-(2-(1H-imidazol-4-yl)thieno[3,2-b]pyridin-7-yloxy)-3-fluorophenyl)-$N^3$-(2-methoxyphenyl)malonamide, $N^1$-(4-(2-(1-ethyl-2-methyl-1H-imidazol-4-yl)thieno[3,2-b]pyridin-7-yloxy)-3-fluorophenyl)-$N^3$-(2-methoxyphenyl)malonamide, $N^1$-(4-(2-(2-((Dimethylamino)methyl)-1-ethyl-1H-imidazol-4-yl)thieno[3,2-b]pyridin-7-yloxy)-3-fluorophenyl)-$N^3$-(2-methoxyphenyl)malonamide, $N^1$-(3-Fluoro-4-(2-(1-methyl-1H-imidazol-5-yl)thieno[3,2-b]pyridin-7-yloxy)phenyl)-$N^3$-(2-hydroxyphenyl)malonamide, $N^1$-(4-(2-(1-Ethyl-1H-imidazol-4-yl)thieno[3,2-b]pyridin-7-yloxy)-3-fluorophenyl)-$N^3$-(2-hydroxyphenyl)malonamide, $N^1$-(4-(2-(1-Ethyl-1H-imidazol-5-yl)thieno[3,2-b]pyridin-7-yloxy)-3-fluorophenyl)-$N^3$-(2-fluorophenyl)malonamide, $N^1$-(4-(2-(1-Ethyl-1H-imidazol-5-yl)thieno[3,2-b]pyridin-7-yloxy)-3-fluorophenyl)-$N^3$-(2-methoxyphenyl)malonamide, $N^1$-(3-Fluoro-4-(2-(1-isopropyl-1H-imidazol-4-yl)thieno[3,2-b]pyridin-7-yloxy)phenyl)-$N^3$-2-fluorophenyl)malonamide, $N^1$-(3-Fluoro-4-(2-(1-isopropyl-1H-imidazol-4-yl)thieno[3,2-b]pyridin-7-yloxy)phenyl)-$N^3$-(2-methoxyphenyl)malonamide, $N^1$-(3-Fluoro-4-(2-(1-isopropyl-1H-imidazol-4-yl)thieno[3,2-b]pyridin-7-yloxy)phenyl)-$N^3$-(thiazol-2-yl)malonamide, $N^1$-(3-Fluoro-4-(2-(1-propyl-1H-imidazol-4-yl)thieno[3,2-b]pyridin-7-yloxy)phenyl)-$N^3$-(2-fluorophenyl)malonamide, $N^1$-(3-fluoro-4-(2-(1-propyl-1H-imidazol-4-yl)thieno[3,2-b]pyridin-7-yloxy)phenyl)-$N^3$-(2-methoxyphenyl)malonamide, $N^1$-(4-(2-(1-Ethyl-1H-imidazol-4-yl)thieno[3,2-b]pyridin-7-yloxy)-3-fluorophenyl)-$N^2$-(2-methoxyphenethyl)oxalamide, $N^1$-(4-(2-(1-Ethyl-1H-imidazol-4-yl)thieno[3,2-b]pyridin-7-yloxy)-3-fluorophenyl)-$N^3$-(2-fluorophenethyl)oxalamide, $N^1$-(3-Fluoro-4-(2-(1-methyl-1H-imidazol-4-yl)thieno[3,2-b]pyridin-7-yloxy)phenyl)-$N^2$-(2-methoxyphenethyl)oxalamide, $N^1$-(4-(2-(1-ethyl-1H-imidazol-4-yl)thieno[3,2-b]pyridin-7-yloxy)-3-fluorophenyl)-$N^3$-(4-methoxyphenyl)malonamide, $N^1$-(3-fluoro-4-(2-(1-methyl-1H-imidazol-4-yl)thieno[3,2-b]pyridin-7-yloxy)phenyl)-$N^3$-phenylcyclopropane-1,1-dicarboxamide, N-(4-(2-(1-Ethyl-1H-imidazol-4-yl)thieno[3,2-b]pyridin-7-yloxy)-3-fluorophenyl)-$N^3$-phenylcyclopropane-1,1-dicarboxamide, $N^1$-(3-Fluoro-4-(2-(1-(2-(pyrrolidin-1-yl)ethyl)-1H-imidazol-4-yl)thieno[3,2-b]pyridin-7-yloxy)phenyl)-N3-methyl-N3-phenylmalonamide, N-(4-(2-(1-Ethyl-1H-imidazol-4-yl)thieno[3,2-b]pyridin-7-yloxy)-3-fluorophenyl)-N-(2-methoxyphenyl)cyclopropane-1,1-dicarboxamide, N-(3-Fluoro-4-(2-(1-(2-(pyrrolidin-1-yl)ethyl)-1H-imidazol-4-yl)thieno[3,2-b]pyridin-7-yloxy)phenyl)-N-(2-methoxyphenyl)cyclopropane-1,1-dicarboxamide, N-(3-Fluoro-4-(2-(1-methyl-1H-imidazol-4-yl)thieno[3,2-b]pyridin-7-yloxy)phenyl)-N-(4-methoxyphenyl)cyclopropane-1,1-dicarboxamide, N-(3-fluoro-4-(2-(1-methyl-1H-imidazol-4-yl)thieno[3,2-b]pyridin-7-yloxy)phenyl)-N-(2-fluorophenyl)cyclopropane-1,1-dicarboxamide, N-(4-(2-(1-ethyl-1H-imidazol-4-yl)thieno[3,2-b]pyridin-7-yloxy)-3-fluorophenyl)-N-(2-fluorophenyl)cyclopropane-1,1-dicarboxamide, N-(3-Fluoro-4-(2-(1-(2-(pyrrolidin-1-yl)ethyl)-1H-imidazol-4-yl)thieno[3,2-b]pyridin-7-yloxy)phenyl)-N-(2-fluorophenyl)cyclopropane-1,1-dicarboxamide, N-(3-Fluoro-4-(2-(1-methyl-1H-imidazol-4-yl)thieno[3,2-b]pyridin-7-yloxy)phenyl)-N-(4-fluorophenyl)cyclopropane-1,1-dicarboxamide, $N^1$-(4-(2-(1-(2-(Diethylamino)ethyl)-1H-imidazol-4-yl)thieno[3,2-b]pyridin-7-yloxy)-3-fluorophenyl)-$N^3$-methyl-$N^3$-phenylmalonamid, $N^1$-(4-(2-(1-ethyl-1H-imidazol-4-yl)thieno[3,2-b]pyridin-7-yloxy)-3-fluorophenyl)-$N^3$-(2-(trifluoromethyl)phenyl)malonamide, $N^1$-(4-(2-(1-(2-(Dimethylamino)ethyl)-1H-imidazol-4-yl)thieno[3,2-b]pyridin-7-yloxy)-3-fluorophenyl)-$N^3$-(2-fluorophenyl)malonamide, N-(4-(2-(1-ethyl-1H-imidazol-4-yl)thieno[3,2-b]pyridin-7-yloxy)-3-fluorophenyl)-N-(2-fluorophenyl)-N-methylcyclopropane-1,1-dicarboxamide, $N^1$-ethyl-$N^3$-(4-(2-(1-ethyl-1H-imidazol-4-yl)thieno[3,2-b]pyridin-7-yloxy)-3-fluorophenyl)-$N^1$-phenylmalonamide, $N^1$-(4-(2-(1-Ethyl-1H-imidazol-4-yl)thieno[3,2-b]pyridin-7-yloxy)-3-fluorophenyl)-$N^3$-isopropyl-$N^3$-phenylmalonamide, N-(4-(2-(1-Ethyl-1H-imidazol-4-yl)thieno[3,2-b]pyridin-7-yloxy)-3-fluorophenyl)-3-(indolin-1-yl)-3-oxopropanamide, $N^1$-(3-Fluoro-4-(2-(1-methyl-1,2,5,6-tetrahydropyridin-3-yl)thieno[3,2-b]pyridin-7-yloxy)phenyl)-$N^3$-(2-methoxyphenyl)malonamide, $N^1$-(3-fluoro-4-(2-(1-methyl-1H-imidazol-4-yl)thieno[3,2-b]pyridin-7-yloxy)phenyl)-$N^3$-(2-methoxyphenyl)malonamide, $N^1$-(3-fluoro-4-(2-(1-methyl-1H-imidazol-4-yl)thieno[3,2-b]pyridin-7-yloxy)phenyl)-$N^3$-(2-fluorophenyl)malonamide, N-(3-fluoro-4-(2-(1-methyl-1H-imidazol-4-yl)thieno[3,2-b]pyridin-7-yloxy)phenyl)-N-phenylcyclopropane-1,1-dicarboxamide, $N^1$-(3-fluoro-4-(2-(1-methyl-1H-imidazol-4-yl)thieno[3,2-b]pyridin-7-yloxy)phenyl)-$N^3$-methyl-$N^3$-phenylmalonamide, $N^1$-(3-fluoro-4-(2-(1-methyl-1H-imidazol-4-yl)thieno[3,2-b]pyridin-7-yloxy)phenyl)-$N^3$-(2-fluorophenyl)-$N^3$-methylmalonamide, N-(3-fluoro-4-(2-(1-methyl-1H-imidazol-4-yl)thieno[3,2-b]pyridin-7-yloxy)phenyl)-N-methyl-N-phenylcyclopropane-1,1-dicarboxamide, $N^1$-(4-(2-(1-Ethyl-1H-imidazol-4-yl)thieno[3,2-b]pyridin-7-yloxy)-3-fluorophenyl)-$N^3$-methyl-$N^3$-phenylmalonamide, $N^1$-(4-(2-(1-(2-(dimethylamino)ethyl)-1H-imidazol-4-yl)thieno[3,2-b]pyridin-7-yloxy)-3-fluorophenyl)-$N^3$-methyl-$N^3$-phenylmalonamide, $N^1$-(4-(2-(1-(2-(dimethylamino)ethyl)-1H-imidazol-4-yl)thieno[3,2-b]pyridin-7-yloxy)-3-fluorophenyl)-$N^3$-(2-methoxyphenyl)malonamide, $N^1$-(3-Fluoro-4-(2-(1-methyl-1,2,3,6-tetrahydropyridin-4-yl)thieno[3,2-b]pyridin-7-yloxy)phenyl)-$N^3$-methyl-$N^3$-phenylmalonamide, N-(3-Fluoro-4-(2-(1-methyl-1,2,3,6-tetrahydropyridin-4-yl)thieno[3,2-b]pyridin-7-yloxy)phenyl)-N-phenylcyclopropane-1,1-dicarboxamide, $N^1$-(3-Fluoro-4-(2-(1-methyl-1,2,3,6-tetrahydropyridin-4-yl)thieno[3,2-b]pyridin-7-yloxy)phenyl)-$N^3$-isopropyl-$N^3$-phenylmalonamide, $N^1$-(4-(2-(1-(2-(Dimethylamino)ethyl)-1H-imidazol-4-yl)thieno[3,2-b]pyridin-7-yloxy)-3-fluorophenyl)-$N^3$-phenylmalonamide, N-(4-(2-(1-(2-(dimethylamino)ethyl)-1H-imidazol-4-yl)thieno[3,2-b]pyridin-7-yloxy)-3-fluorophenyl)-N-phenylcyclopropane-1,1-dicarboxamide, N-(4-(2-(1-(2-(Dimethylamino)ethyl)-1H-imidazol-4-yl)thieno[3,2-b]pyridin-7-yloxy)-3-fluorophenyl)-N-(2-fluorophenyl)cyclopropane-1,1-dicarboxamide, N-(3-fluoro-4-(2-(1-(3-(pyrrolidin-1-yl)propyl)-1H-imidazol-4-yl)thieno[3,2-b]pyridin-7-yloxy)phenyl)-N-(2-fluorophenyl)cyclopropane-1,1-dicarboxamide, $N^1$-(3-fluoro-4-(2-(1-(3-(pyrrolidin-1-yl)propyl)-1H-imidazol-4-yl)thieno[3,2-b]pyridin-7-yloxy)phenyl)-$N^3$-methyl-$N^3$-phenylmalonamide, $N^1$-(4-(2-(1-(3-(Dimethylamino)propyl)-1H-imidazol-4-yl)thieno[3,2-b]pyridin-7-yloxy)-3-fluorophenyl)-$N^3$-methyl-$N^3$-phenylmalonamide, $N^1$-(3-Fluoro-4-(2-(2-morpholinopyrimidin-5-yl)thieno[3,2-b]pyridin-7-yloxy)phenyl)-$N^3$-(2-methoxyphenyl)malonamide, $N^1$-(4-(2-(1-Ethyl-1H-imidazol-4-yl)thieno[3,2-b]pyridin-7-yloxy)-3-fluorophenyl)-$N^3$-(3-fluorophenyl)malonamide, N1-(4-(2-(1-Ethyl-1H-imidazol-4-yl)thieno[3,2-b]pyridin-7-yloxy)-3-fluorophenyl)-N3-(3-methoxyphenyl)malonamide, N1-(4-(2-(1-Ethyl-1H-imidazol-4-yl)thieno[3,2-b]pyridin-7-yloxy)-3-fluorophenyl)-N3-(4-fluorophenyl)malonamide, N1-(3-Fluoro-4-(2-(1-propyl-1H-imidazol-4-yl)thieno[3,2-b]pyridin-7-yloxy)phenyl)-N3-(4-fluorophenyl)malonamide, N1-(3-Fluoro-4-(2-(1-propyl-1H-imidazol-4-yl)thieno[3,2-b]pyridin-7-yloxy)phenyl)-N3-(3-fluorophenyl)malonamide, 2-(4-(7-(2-Fluoro-4-(3-oxo-3-(phenylamino)propanamido)phenoxy)thieno[3,2-b]pyridin-2-yl)-1H-imidazol-1-yl)acetic acid, $N^1$-(3-Fluoro-4-(2-(1-(2-oxo-2-(3-(pyrrolidin-1-yl)propylamino)ethyl)-1H-imidazol-4-yl)thieno[3,2-b]pyridin-7-yloxy)phenyl)-$N^3$-phenylmalonamide, $N^1$-(4-(2-(6-(3-(Dimethylamino)propoxy)pyridin-3-yl)thieno[3,2-b]pyridin-7-yloxy)-3-fluorophenyl)-N3-(2-methoxyphenyl)malonamide, $N^1$-(3-Fluoro-4-(2-(5-((4-methylpiperazin-1-yl)methyl)pyridin-2-yl)thieno[3,2-b]pyridin-7-yloxy)phenyl)-N3-phenylmalonamide and $N^1$-(3-Fluoro-4-(2-(1-(2-methoxyethyl)-1H-imidazol-4-yl)thieno[3,2-b]pyridin-7-yloxy)phenyl)-N3-phenylmalonamide.

* * * * *